US011224181B2

(12) United States Patent
Shinozuka et al.

(10) Patent No.: US 11,224,181 B2
(45) Date of Patent: Jan. 18, 2022

(54) MANIPULATION OF SELF-INCOMPATIBILITY IN PLANTS

(71) Applicants: Agriculture Victoria Services Pty Ltd, Attwood (AU); Dairy Australia Limited, Southbank (AU)

(72) Inventors: Hiroshi Shinozuka, Kingsbury (AU); Noel Cogan, Macleod (AU); John White Forster, Diamond Creek (AU); German Carlos Spangenberg, Bundoora (AU); Nicola Patron, Norwich (GB); Yidong Ran, Bundoora (AU); Luke Pembleton, Diamond Creek (AU)

(73) Assignees: Agriculture Victoria Services PTY LTD, Bundoora (AU); Dairy Australia Limited, Southbank (AU)

( * ) Notice: Subject to any disclaimer, the term of this patent is extended or adjusted under 35 U.S.C. 154(b) by 0 days.

(21) Appl. No.: 16/394,796

(22) Filed: Apr. 25, 2019

(65) Prior Publication Data

US 2019/0246593 A1 Aug. 15, 2019

Related U.S. Application Data

(62) Division of application No. 14/769,423, filed as application No. PCT/AU2014/000146 on Feb. 19, 2014, now Pat. No. 10,306,858.

(30) Foreign Application Priority Data

Feb. 22, 2013 (AU) ................ 2013900597
Feb. 22, 2013 (AU) ................ 2013900601
Feb. 22, 2013 (AU) ................ 2013900602
Feb. 22, 2013 (AU) ................ 2013900603
Feb. 22, 2013 (AU) ................ 2013900604
Feb. 22, 2013 (AU) ................ 2013900606
Feb. 22, 2013 (AU) ................ 2013900608

(51) Int. Cl.
 *A01H 1/00* (2006.01)
 *A01H 6/46* (2018.01)
 *C07K 14/415* (2006.01)
 *A01H 1/02* (2006.01)
 *C12Q 1/6895* (2018.01)
 *C12N 15/82* (2006.01)

(52) U.S. Cl.
 CPC ............ *A01H 6/463* (2018.05); *A01H 1/00* (2013.01); *A01H 1/02* (2013.01); *C07K 14/415* (2013.01); *C12N 15/827* (2013.01); *C12N 15/8218* (2013.01); *C12N 15/8287* (2013.01); *C12Q 1/6895* (2013.01); *C12Q 2600/13* (2013.01); *C12Q 2600/156* (2013.01)

(58) Field of Classification Search
 None
 See application file for complete search history.

(56) References Cited

U.S. PATENT DOCUMENTS

| 5,585,543 | A  | * | 12/1996 | Kao ..................... C07K 14/415 435/320.1 |
| 7,214,786 | B2 |   | 5/2007  | Kovalic et al. |
| 8,362,325 | B2 | * | 1/2013  | Troukhan ............. C07K 14/415 800/295 |
| 2003/0204318 | A1 | | 10/2003 | Feldmann |
| 2007/0044171 | A1 | | 2/2007  | Kovalic et al. |

FOREIGN PATENT DOCUMENTS

| EP | 1466973 A1 | 10/2004 |
| WO | 2011/135527 A2 | 11/2011 |
| WO | 2012/085862 A2 | 6/2012 |
| WO | 2012/150598 A2 | 11/2012 |
| WO | 2014/127414 A1 | 8/2014 |

OTHER PUBLICATIONS

Bi et al. Molecular and General Genetics 263: 648-654 (2000).*
Supplemental Table 3 of Shinozuka et al, Plant Molecular Biology 72(3): 343-355 (2010).*
Translation of 1st Examination Report for Chilean Patent App. No. 00518-2019 (response due Jul. 28, 2020).*
Hai, H. Order Poales, updated Apr. 2015, pp. 1-2 from The Worldwide Vegetables website: the worldwidevegetables.weebly.com/order-poales.html.*
Shinozuka et al (2010, Plant Molecular Biology 72: 343-355). (Year: 2010).*
Cul, Y. et al. "Structual and Transcriptional Comparative Analysis of the S Locus Regions in Two Self-Incompatible *Brassica napus* Lines" The Plant Cell, 1999, pp. 2217-2231, vol. 11, No. 11.
Bai, Y. et al., "Genetic Transformation of Elite Turf-Type Cultivars of Tall Fescue", International Turfgrass Society Research Journal, 2001, pp. 129-136, vol. 9.
Baumann, U. et al., "Self-incompatibility in the Grasses", Annal of Botany, 2000, pp. 203-209, vol. 85.
Bevan, M., "Binary Agrobacterium vectors for plant transformation", Nucleic Acids Research, 1984, pp. 8711-8721, vol. 12, No. 22.
Bilang, R. et al., "The 3'-terminal region of the hygromycin-B-resistance gene is important for its activity in *Escherichia coli* and *Nicotiana tabacum*", Gene, 1991, pp. 247-250, vol. 100.

(Continued)

*Primary Examiner* — Russell Kallis
(74) *Attorney, Agent, or Firm* — Larson & Anderson, LLC

(57) ABSTRACT

The present invention relates to methods for controlling hybridization in plants and producing hybrid plants. The present invention also relates to nucleic acids encoding amino acid sequences for self-incompatibility (SI) proteins in plants, and the use thereof for the manipulation of SI, including seed production, in plants, particularly of the Poaceae family. The present invention also relates to kits, compositions, constructs and vectors including such nucleic acids, and related polypeptides, regulatory elements and methods. The present invention also relates to expression of self-gamete recognition genes in plants and to related nucleic acids, constructs, molecular markers and methods.

8 Claims, 144 Drawing Sheets

Figure 1:
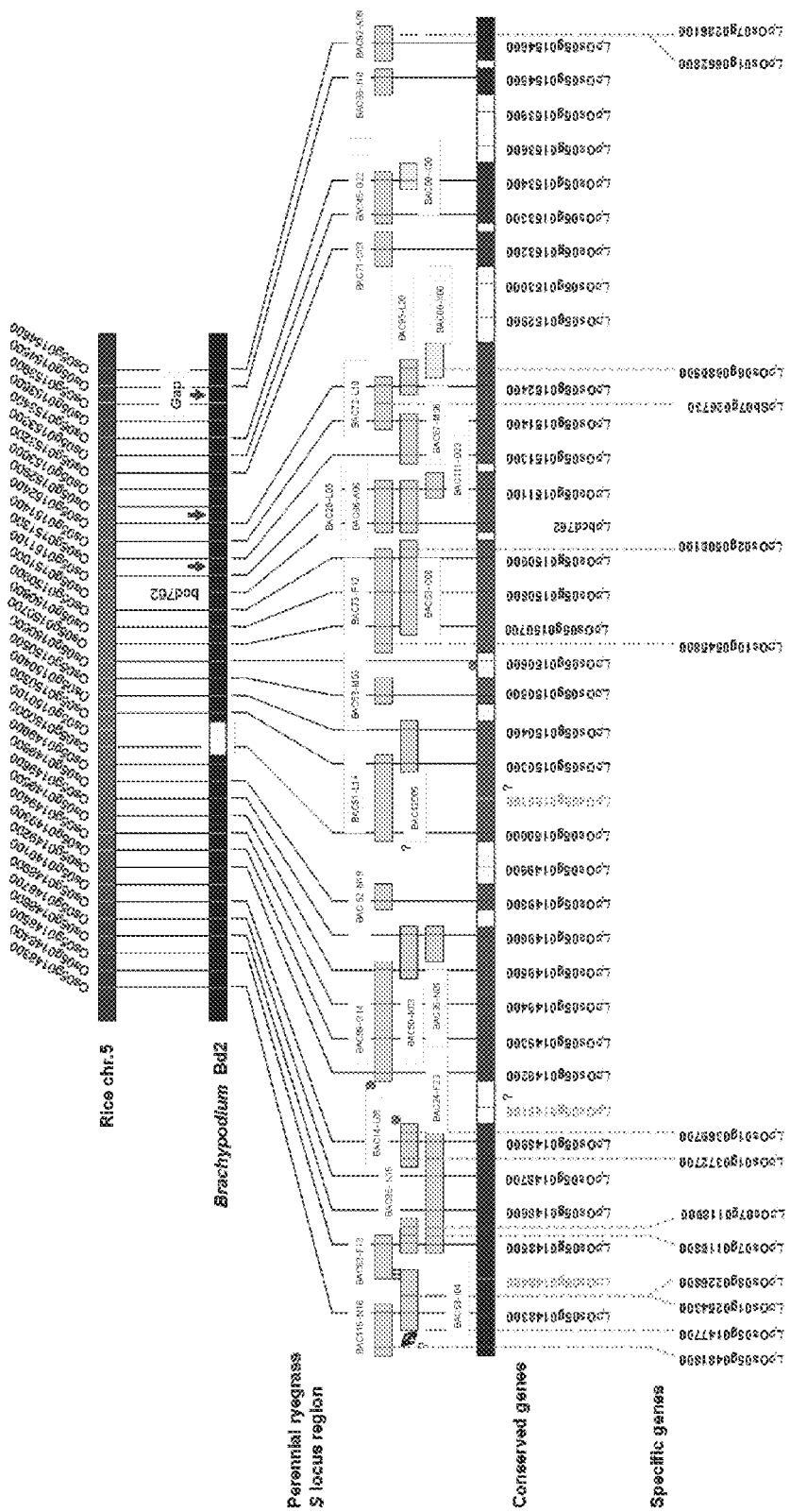

Specification includes a Sequence Listing.

(56) References Cited

OTHER PUBLICATIONS

Chenault, K.et al., "Cauliflower Mosaic Virus Isolate CMV-1", Plant Physiol, 1993, pp. 1395-1396, vol. 101.
Christensen, A. et al., "Maize polyubiquitin genes: structure, thermal perturbation of expression and transcript splicing, and promoter activity following transfer to protoplasts by electroporation", Plant Molecular Biology, 1992, pp. 675-689, vol. 18.
Cogan, N. et al., "Whole Genome Sequencing of Perennial Ryegrass (*Lolium perenne* L.) Supports Exome Assembly for Gene and SNP Catalogue Development", Molecular Breeding of Forage and Turf, 2012, p. 87.
Cogan, N. et al., "Development of a Transcriptome Atlas for Perennial Ryegrass (*Lolium perenne* L.)", Molecular Breeding of Forage and Turf, 2012, p. 86.
Den Herder, G. et al., "Seven in Absentia Proteins Affect Plant Growth and Nodulation in Medicago truncatula 1 [W] [OA]", Plant Physiology, Sep. 2008, pp. 369-382, vol. 148.
Doerks, T. et al., "GRAM, a novel domain in glucosyltransferases, myotubularins and other putative membrane-associated proteins", Trends Biochem. Sci, Oct. 2000, pp. 483-485.
Douchkov, D. et al., "A High-Throughput Gene-Silencing System for the Functional Assessment of Defense-Related Genes in Barley Epidermal Cells", The American Phytopathological Society, 2005, pp. 755-761, vol. 18, No. 8.
Forster, J.W. et al., "Functionally Associated Molecular Genetic Markers for Temperate Pasture Plant Improvement", Plant Genotyping II, 2008, pp. 154-186.
Forster, J.W. et al., "Next-Generation Solution for Genomics-Assisted Breeding of Outbreeding Forage Plant Species", Molecular Breeding of Forage and Turf, 2012, pp. 49-54.
Fraley, R. et al., "Expression of bacterial genes in plant cells", PNAS, 1983, pp. 4803-4807, vol. 80.
GenBank Accession: AK330766.1 "Triticum aestivum cDNA, clone: SE15_E01, cultivar: Chinese Spring", Jun. 25, 2009.
GenBank Accession: DT687279.1 "s13dFA29A01FM005_476430 Tall fescue, Festuca arundinacea Schreb, Floral meristem Festuca arundinacea cDNA, mRNA sequence", Sep. 12, 2005.
GenBank Accession: DV854332.1 "col1592 Colonial bentgrass EST Agrostis capillaris cDNA clone COL356T_F02 3-, mRNA sequence", Nov. 29, 2005.
GenBank Accession: GR357268 "CCOY1790.g1 CCOY Avena barbata root, pooled from different levels of rain and nitrogen (L) Avena barbata cDNA clone CCOY1790 3-, mRNA sequence", Jun. 19, 2009.
GenBank Accession: GR521673.1"ELPLPE1017C10-g1RSP_20001129 Perennial ryegrass etiolated seedling library (LPE) Lolium perenne cDNA 5-, mRNA sequence", Jul. 7, 2010.
GenBank Accession: GR522370.1 "ELPLPE1038A08-g1RSP_20011026 Perennial ryegrass etiolated seedlings library (LPE) Lolium perenne cDNA 5-, mRNA sequence", Jul. 7, 2010.
GenBank Accession: XM_003568881 "PREDICTED: Brachypodium distachyon serine/threonine-protein phosphatase 2A regulatory subunit B" subunit gamma-like (LOC100824191), mRNA, Nov. 15, 2011.
GenBank Accession: DV858816.1 "col6076 Colonial bentgrass EST Agrostis capillaris cDNA clone COL430T_G05 3-, mRNA sequence", Nov. 29, 2005.
Hackauf, B. et al., "Approaching the self-incompatibility locus Z in rye (*Secale cereale* L.) via comparative genetics", Theor. Appl. Genet., 2005, pp. 832-845, vol. 110.
Hayman, D.L. et al., "Mutations affecting self-incompatibility in Phalaris coerulescens Desf. (Poaceae)", Heredity, 1992, pp. 495-503, vol. 68.
Jiang, S. et al., "The Oryza sativa no pollen (Osnop) gene plays a role in male gametophyte development and most likely encodes a C2-GRAM domain-containing protein", Plant Molecular Biology, 2005, pp. 835-853, vol. 57.

Kaster, K. et al., "Analysis of a bacterial hygromycin B resistance gene by transcriptional and translational fusion and by DNA sequencing", Nucleic Acids Research, 1983, pp. 6895-6911, vol. 11, No. 19.
Klaas, M.et al., "Progress towards elucidating the mechanisms of self-incompatibility in the grasses: further insights from studies in Lolium", Annals of Botany, 2011, pp. 677-685, vol. 108.
Li, X. et al., "Cloning a Putative Self-Incompatibility Gene from the Pollen of the Grass Phalaris coerulescens", The Plant Cell, 1994, pp. 1923-1932, vol. 6.
McElroy, D. et al., "Isolation of an Efficient Actin Promoter for Use in Rice Transformation", The Plant Cell, 1990, pp. 163-171, vol. 2.
Rogers, S.G. et al., "Investigation of Factors Involved in Foreign Protein Expression in Transformed Plants", Biotechnology in Plant Science, 1985, pp. 219-226.
Shinozuka, H. et al., "Fine-scale comparative genetic and physical mapping supports map-based cloning strategies for the self-incompatibility loci of perennial ryegrass (*Lolium perenne* L.)", Plant MoL Biol., 2010, pp. 343-355 and Supplemental Tables 1 and 2a, vol. 72.
Spangenberg, G. et al., "Transgenic Tall Fescue (Festuca arundinacea) and Red Fescue (F. rubra) Plants from Microprojectile Bombardment of Embryogenic Suspension Cells", J. Plant. Physiol, 1995, pp. 693-701, vol. 145.
Spangenberg, G. et al., "Transgenic perennial ryegrass (*Lolium perenne*) plants from microprojectile bombardment of embryogenic suspension cells", Plant Science, 1995, pp. 209-217, vol. 108.
Spangenberg, G. et al., "Future directions in the molecular breeding of forage and turf", Molecular Breeding for the Genetic Improvement of Forage Crops and Turf, 2005, pp. 83-97.
Thorogood, D. et al., "Self-compatibility in *Lolium temulentum* L: its genetic control and transfer into *L. perenne* L. and *L. multiflorum* Lam" Heredity, 1992, pp. 71-78, vol. 68.
Toki, S. et al., "Expression of a Maize Ubiquitin Gene Promoter-bar Chimeric Gene in Transgenic Rice Plants", Plant Physiol, 1992, pp. 1503-1507, vol. 100.
Voylokov, A.V. et al., "Mapping of three self-fertility mutations in rye (*Secale cereale* L.) using RFLP, isozyme and morphological markers", Ther. Appl. Genet., 1997, pp. 147-153, vol. 97.
Ye, X. et al., "Transgenic Italian ryegrass (*Lolium multiflorum*) plants from microprojectile bombardment of embryogenic suspension cells" Plant Cell Reports, 1997, pp. 379-384, vol. 16.
Supplementary European Search Report dated Aug. 23, 2016 from related European Patent Application No. 14754321.9.
Thorogood, D. et al., "Identification and mode of action of self-compatibility loci in *Lolium perenne* L.", Heredity, 2005, pp. 356-363, vol. 94, No. 3.
Thorogood, D. et al., "Self-incompatibility in ryegrass 12. Genotyping and mapping the S and Z loci of *Lolium perenne* L ", Heredity, 2002, pp. 385-390, vol. 88, No. 5.
Yang, B et al., "Identification of genes expressed during the self-incompatibility response in perennial ryegrass (*Lolium perenne* L.)", Plant Mol Biol, 2009, pp. 709-723, vol. 70, No. 6.
Examination Report dated Mar. 24, 2017 from corresponding New Zealand Patent Application No. 630693.
Office Action dated Feb. 5, 2018 from related Japanese Patent Application No. 2015-558304.
Hua et al., "The Cullin-RING Ubiquitin-Protein Ligases", Annu. Rev. Plant Biol., 2011, pp. 299-334, vol. 62.
Kakeda, K., "S locus-linked F-box genes expressed in anthers of Hordeum bulbosum". Plant Cell Rep., 2009, pp. 1453-1460, vol. 28.
Hai, H., The Worldwide Vegetables, Subfamily Poodeae, last updated Mar. 2015, pp. 1-15, uploaded Aug. 20, 2018 from theworldwidevegetables.weebly.com/subfamily-pooideae.
Miyao, A. et al., "A large-scale collection of phenotypic data describing an insertional mutant population to facilitate functional analysis of rice genes", Plant Molecular Biology, 2007, pp. 625-635, vol. 63.
Wang, M. et al., "Genome-wide analysis of SINA family in plants and their phylogenetic relationships, DNA Sequence", 2008, pp. 206-216, vol. 19, No. 3.

* cited by examiner

FIG. 3

FIG. 3 (cont)

```
tgagctactc cctactgtcct aaaatgagtg tcccaactct ttctagattt ggaggtattt  6060
ataactaaaa tacatcatga tanatctgaa tctagacaaa gttgagtaac ttatttatgg  6120
acgaggag taccttctg cctacaagt aaggctatty tatgagcag tttattactc  6180
atcaggcag ttgtggaatg gcaacttctg tgtagaaact tcagaaatgt attaaacaa  6240
gacattgaaa agntgaagat ggttgtcact gattgcttgt ctaatattac ggcgtgcaca  6300
tgttttggtga tgtacttaat gtatctcctt ttaatgtgaa ttgtgctaa taagagtttt  6360
atgtgtaana agagagctct nctgcctata aaggtcaaga tgattatggc gacaaacgt  6420
cctgatgctc tggatcctgc actcttcgt cctggacgct tggacggaa gatagaaatt  6480
ccattgcaa atgacagtc gaggatgag gttctgaaaa tccangcagc tggtatcgcc  6540
aaacatggcg aaattgatta tgaggctgtt gttaagctcg ctgagcggct tcaatggtgc  6600
tgatctgcgc aatgtctgca ctgaagctgg catggctgaa gcttaacac ctatgcactg  6660
tcgttccagg gcttcaacgg tgccgatttg cgcaatgtct gcactgaagc tggcatggct  6720
gtattcgag cagagcgtga ctacgtcatc catgaagact tcatgaagca ggtgcggaag  6780
ctgaatgatg ccagaagct cgcgvcgarg ggcactaca ggcgkgactt ygccaaggaa  6840
agccagtact caccatttta gtttctgat gatgatgaca aaatgattgc aggcggtcg  6900
aaagctgaat gatgccaaga agctcgagtc tagcgccac tacagcgcag acttggcaa  6960
ggaataaga atcaaagtag gatacacg tctaacttg agacgattca gtgagccttc  7020
actttataca tcgcggagtt tgtcatcctg gcaataccag aggatcatg tacgtttctg  7080
cattgtctat gctttggat gtctgcctt gccgcacaag ttcgtctgg cttcgttgaa  7140
aacagattcc atgtacaage cggtcagtc tgaactggc ctactgagc cacagctatt  7200
cttagattta taacgttgc ttctcctagt tgcttggaat caagaaatgt tggaaaatg  7260
taacaattgc aacttgtgtt tctgtcttct gttactctac ctggaatcaa ggaatgtcca  7320
agaaggaaca tttgcagcgt gtgctcctcc ctattactct aacttggaat gtgcattgtt  7380
actttgcct gttgttaggg atatatcct tctgtgctga ttatgcttg attcatgg  7440
aatttctgat tcatgtgaaa tttctgtatt acaaattac tgtgctgaa cgaatattg  7500
ggttgcttgc ccaaactttc gctctatggc tctatcggta gatctgtta ttttgcaca  7560
ataattgt taggaaaatg ctattttc agacggtaa aaaggaaacg tggtcggag  7620
cgtcgcgcc acgcgttggg tcgaaacgcc ctgtcctctc cctatcgtcc atctccgttg  7680
cattattc gaggctgaag gcgcgatcaa aaccaaatt agtgagcacc tggccggacg  7740
cggggaaacc gccccatct ctcatctga ttggcacac aaggaaccaa accaaacatg  7800
gcaaccaac tttgatccat tccacttca atttctcgt gaattcttg ctcaacaaca  7860
cagattgga agatcgacg atcccaatt ctgcatttt tccatatata ccgttcttgat  7920
cgcatgacaa agctcaagag cgtggctcc acgtggggg cgcggagga gtgcggggg  7980
agccgtcgg agattgccc gtcgccgatg aagctgctgg tgcgtcgt ggaggcgg  8040
ggcctgctg cggtcagt aaacggac agcgaccct tcgtcaact gcagctcgg  8100
aagcgcggg ccaagacgc cgtcgtaag aagaactag cccccgtcg ggacgagga  8160
ttcagcttcc tgttgggga cgtcacgag gagctgccg tatccgtgct caacgaggac  8220
aagtacttca gcaacgacca cctggaagg gtcaagtgg ccctctcca ggtcatggac  8280
accgacggc tctcctgg cacagcatgg tacagctcc agccaaagag cagcaagtcc  8340
aagagaaat gcggcggtat cttctatct aatctatcta catcatgttt tggttttcct  8400
attttgtggt tctgtgatt cggttactgg ttgatctgt acagcaaat catgatatca  8460
tgcacaagaa aaaaagaca tattctggta atcttggaac catctaatta tctgcatct  8520
gcaggggaaa tctgctgcg catatccttg tctacaagaa cgcacagtgtc cgaagactg  8580
cacctctac cggcccaa ttggacgga gtatcatca gttcagacag gtcaatggg  8640
accaacgtg gagctgtc aaccaccaa agctacattg acctctcage ctgccccag  8700
ttggaccgag gatcgagag cagcttgaa cggtggcgg atagcttgt ggagcagcg  8760
cccaggagca gcatcaaca agcagtcact gagcctgaa gccgcctgga actgatgcg  8820
atgcccacca cgtcgtgat ggtagaggtc tgtctcgct atttcttcg gaaacctgtc  8880
gacgcgctg tgtgtcagt tgtctctgat gccagtcgg tcgtgacca gccccggag  8940
ccgaagcgt gcctctgaaga aagtgaaggt cctgagaatc gaacgccacc tgagtcgagc  9000
```

```
gagaccaaat aattgaatc gctccatcc taataagact aataagcgc ttaaacctaa   15060
aatccacgcc attgagccag ttgcaaata aattgacaat actacgtggt gggtataagg   15120
tataccctat ttggagact gaccatatag acctagcaaa cttacatgg aagaataagt   15180
gtttaatagt ctcgtcctgg gaagtctcc aacacctag cgatagtata gcttcgtgg    15240
cgaatatat tgacaagt cggatacggt tctcggagtg tggtattac taaccattta    15300
tcctcgcaga aacgaatttc cgaaggtc ttaatagaga aagatccata tggaagaaa    15360
tacttcttg ttccacaag accagccaa aatgtgtat ctcgggctt ccaaagaatt    15420
tgagatatag acttgagcc aatatacttc ctcttgagga gtgttttcca tatacccbct   15480
ttggtaagta acttggatag ccatttaccg agaagtgccc tattcttgac cggatgtct   15540
tggatgccaa gtcctccatg atctttggt cgacacagca cactccattt agtcagtcga   15600
tatttacgct tctcactatc cctgccaa tctgattgg aaatatcca atcttttaa     15660
gactcctcta ggaagttgga agaaaatat catgtatagt accatgttac ttagtatcg    15720
attatgagaa ctaatcttac tccaaagact agtaaataag cttccaact gcttaatcta    15780
atttgtagtc tttcctcaac ccatttcat taggcattgg tgagtctcct acaatgaatc    15840
cgaattccca agtacctaat tggaaatgg ccttgaccgt agctgaaaag ctcagcataa    15900
tctgaacat gatcttgggc ctcaccaaaa taaacaatt cactttatg gaaattaatt      15960
ttagacccg acaaatgctc gaatgctgaa agaatcagct ttagattccg agcattgtcg    16020
atgtcatgat ccataaaaag tattgtatcg tcggcatatt gaagaatgga taaacttcca    16080
tcacccagat gcggaatgac ccttcaatc tgaccatctg actttgcacg ttcaatcaat    16140
acatcaagca tatcagccac tatattaaat atcactggtg ctaatggta tccctgtgtt    16200
agtccttct tggtctggaa gtattgccc acgtcatcat tgactttaat ggcagcatc    16260
ccaccccgaga caaaactatt gatcaactac ttgattggc atgcacataa atcctttgc    16320
atatagctat ctccatgta gtccaatt ggcataaaga tcttgcatca ccgggtggat    16380
cagtggacac tttataagct atatatgttt ttatgttac actttgaga ttggcgcat    16440
gctagatttc tagccagaa ttgtcgagt gttcctggaa ggctgagggc gcgcaacgc    16500
ccttctacgtc atccttttg ttttatcca cttgaaggaa tgcatattta attagaaaa    16560
tatataatgg gggatgaact agatgttct tgagcaagga tgaacttaga cctcaaacac    16620
tatgtgtgtt tatttgatta attgacaata attacataaa tggaagtttg gaacacttca    16680
acatgaaaca cttggagaa ttcagaacaa tggagataaa agcacattat ttagcttgaa    16740
tttattccac ggaaactgcg gcaccagctt tactccttca ttagcataga ctggcagatg    16800
gcatcgatct ctacagcgca ttcatttagc ctgaatgac aagtaaaaca agtgtatttt    16860
tcttcagaaa atgcacgtgt ttgctgcaga gatccagtt taagagatcg aacgttgacg    16920
agttatatat acacatgtac ctctgcggtc tggtcatggt acttgccgg ggctttaaac    16980
tccagtttgt tgaagatact gttcatcaga atgtcagcag aatccgtgcc tgaaacgca    17040
atgcaaatta gttaagtacg tagtggaga tggcataata taacattgt cgatgggctg    17100
gaccgagacc tgcaaggtag gctagtcgta cttgcctga acgtgatact tgcacatctg    17160
gttctgcgcg cagtcgatca gaattccgc agagtcaata cctgcaagat aacctccatg    17220
gacatagcca ttgtagtgct cgctggtgtg ctccagtg aagtagacc gccccacgg    17280
cgcctgcagc aatcaaatt aaggacatca gactagccg gcggagcca ttaattggt    17340
gatggacatt tcaccatcgg tgtagttgag atctcgatca aaattcaat tcaatacag    17400
tgtcagtgtg tgtctgtggc taccgaagc tggtcgtatt cgtaggcgtt gacgccgatg    17460
ggccagttgg agtaggagct cttgagaag cggttggacc accactggg cagtagata    17520
tcgtcgcgt cgggacgtc ctcgtcggg aacatcctcc gcagcaccgc cacagcctcc    17580
gccatggtgg tgtgtccgg atgctgctcg atccgccgcg actcctggtc agtaccgtc    17640
acgagagca cgttgcccc cggtactcc tcctcgaagg actgcacat cccgtagtag    17700
cctgcctgg agctggcgta gacgaagaac tgcttgcctt cgccgcgtggg ccagaacttc    17760
cgaggaact tgaggaagat cttggtgtac actgccatgt cgaaccgta gatgcgata    17820
atttccatg cttgcaggtc gatcgacata gcaaatgtca agatatgat cgagtagtta    17880
gcagagtggt gtgttgggcg tcagatgcca agctggcaga gacctatgacg atagtctgcc    17940
tggtacactg agcgtcctc cgtcttgacg gtgatccga tcgaggagta ggagatctat    18000
```

FIG. 3 (cont)

FIG. 3 (cont)

```
tgtttcgtga ctcttgcaat ttaccagttg gaattacaat tgataccaa tgtctaacga  21060
tgagaatttc actccttaa ttttgtattt tttggtaatt caagctagaa aattcatgca  21120
attttgacca tctctcacc acaagttgt ttatattatt aattattagt atataaatt    21180
ttaaaatgtt tttctcttcg gggaaaatta gtaaagtttt aggttttcc gaaaatcagg  21240
tggagtacgt tgttgagttt taacctagga tctacgatgt tcccggcgtt gtccgtgctc  21300
agtactgtc cggcgatgtg atagacgagg gtctgaatc ccgctggta ggtgacgaag    21360
tgcgtgctt cccgaagtc ggcgaacgtg gcgtgggtt cagtattcg caggctggtg    21420
gacgtggcg gctcggcgaa atgtagtcg ttacctgaagt agtccagcgt catgtccacc  21480
gggtgcgg gcccgttcgg cgggctgcaa aaaacagaa gaggtctctc aggacatgg    21540
tcacctgatc gatgagtata taactgtata tacagctaa gaagacgcac gtactggttg  21600
aatatgcgct gcatggccaa gatggagatg tcgtgcggc cgctgggatc catctccgcg  21660
gcgagcttgc cgcccagctc ttccacttcg tcccacggt ccatttctt ctgcacgtac   21720
tcctcctcgt acagcggcc gctggttctc gtcaacaata gtacaaagca tgagattagg  21780
tttaacatgg atgctgttgg aacaaatctt gttattagta ctaagttcag agtttcagca  21840
tgtttcattt tgatttgtt gaagtatgca tgtagtagtc gtctcaggt aggaatgttt   21900
atgcatgtca acatggtgaa gtggacggat cgatcggcaa tgttgcgagc tgatcggcgg  21960
tcaagagaaa ccactagttg cgagtacatg ttgtattcag tcaagtccta cactagttg   22020
agtccacgt cagtgcatgt agctaaggat ctatacgttg ggcgagccga gagactagcg   22080
ctatatgagc tgagttagtt gtggcatata cgtgatgtty atccatagag tggctgcatg   22140
cgcgtgtggg cagttagtgt tagtggtcta ctagttagtt ggcacaagtg ctgaacgtgc  22200
gtgctgcag taagtgtgga gtagaagtcg gatcaaactg gtgtgtgtggct tgaccgtgtg  22260
tgcgtgggtt atgttataaa agcattgtaa cctcagctgt ttcagtcgag agaaatacag  22320
agaaagaggc agacgtgtgt tgccgagaat aacgtgtgt tcttctccac catatatgta   22380
tgtgtgttgt atcttggca atttcgtcag atgcaacgct tcgttcatca tcagtcctac   22440
aacgtatgtt ttcgatggag taattagaac cacgacgtca agatccggc gtcattacat   22500
taatttctga taatttttaa acttctcgtt cacgtcatca gtatatgact ctgtctgtag   22560
ttaattttgga ccctcttctt aatatcgtcc aatcattaga cccattcct gcgcgtgcgt   22620
gtcatttcca cgtggtttgg gcagcgtgcg ttgctgttca tcaatcatca gttattatta  22680
ggtgcggtaa tatcgacagt taccggcca tcgctaaat cttctgtctt cgttctcagc    22740
acgtgcatat atgttcatct gtttgggcat gcaggcatgc ctgtctaatg cctatgcata  22800
tttagataa tcagttttt cttcgaaagg tcttaatcgt cagtttgca gcatagatgt    22860
cttatatata cagtgaacgc acgtacttct ccttgtagac gctgctgacg acgccgtcga   22920
aatccgagta gaagttcctg agcttaagcg tggagttcac catggcag atcgggttga    22980
tcttgtccc gttgacgccc tccaccagt tggcgcgat atccacgttg acgccgctga    23040
agttgtgctt gtgcataaga acgccgatgc ggtccgtcgc ctccaggata agcaggtccc  23100
tcacgccggc gtcccacagc cgcttcccg ccgagatccc tgaggcaaa gatgtacaac    23160
accgacgaca tttcatgtga ccgtgtatggg tagcaaagac gtttccaccg aaggatccgt   23220
gcatgctgat taggtaccgg acatgccggc gccgactatg atgacccgg ggcctctgcc   23280
ggcggcgaga gaggcatgct gtgcagctac gagtatcaac actgctgta tagcagtgac   23340
acaggaagaa ggtttcatct ttcttctcac actaatctct ctggcttga cgcaatagc    23400
tagtttgctc cgatggacac tatctggtta agtgcgcat ctgctctccg gccgagccag   23460
tcagtgtgca cttatatagg gcagagagc agatggctac acaaaccaac tatgaattaa  23520
agacgcggga accaacacg ttccatatag agtaatacg attgcgacga aatcgaatgg    23580
tagctagaca ccgtggatgg aggacgtgg tggcgccgat ctatacat tgtcggctt     23640
cgccaaggtg tttcgaggcg ctctctgg atgagatatt gcgatcaat cttgtagtat    23700
aagttaacca gatttgctaa ctcccagtcg acgagaata atccttgtta acatgaaac    23760
cgttgatt tacgccaaga catgtgcgtg ccgattcgg aatcatgcgt gacgttgta     23820
tgtcgaaat atgatgcttg cgttgttggg cattctcact tgtttgtt tctgtttgc     23880
ccgtcaatg tgagtacgta gtagtgcaaga tggtcttca ccgcggatt cgtattttt     23940
gattattttt cttctatgc tcattttc gataaggg gatatacaa taccgcgaag         24000
```

FIG. 3 (cont)

FIG. 3 (cont)

```
ccgggtgcga aaatggagcc cttttctcca aacggctagt gctcctcctc ccatataaaa   27060
aggggcctto ttccccatcg agggctgct tcttctactc tctcctact ccattgttga    27120
ccttgagaag cttcctctcc ctaaatccc tccatgattc ttgctcatat ctaagggaaa   27180
gatagaggag atctagatct acatcttgac caaataaatt cctctctttg tgagggaatc  27240
cactagatct agatcttgga gaatttgt gtacctccta atatttgtc ttcctctctt    27300
attaccccaa tatcttttgt agcttgttg gaattgata gagaatgact tgagcatct    27360
tgtggtgttc tagacgttgc atttggtgca tcggtttgac ttctccacgg tgatacgtga   27420
aggtgaaagt tcgtgagaca tacacttcgg gagctgttc ccggagcttg ttcctcttgg  27480
gtctttgaac catgacggc ttagtggtct ttgtgtgtt cttggggcct ccaattaagt   27540
agcttgtgc tttggggctt agtggtattc tggggcctc ccattaagtt gggagattc    27600
ctcaaggcta aggcctttgt ggcaattat tggagcctc caattaagtt gtggagatag   27660
ccccaagctg tgtgcgggtt tggtgacgac cctaaggttc catagtggat cgaggacatc  27720
ccttttggtg ggaattctct agaagaatac ggtggccctc gtgcattgg agtgacttgt   27780
cctccacacc gatccaacgg agagtagcac tcgcaaaagt gtgaacttca ggatacatcg  27840
ttgtctccgc ctcacttcgg ttattcctat acccgagctc ttacttatg cattctactc  27900
tgtgataggcc ttagtgattg aagttatata tcttgctatc acatagttgc ttgaattgct 27960
tagcataagt cgttagtgca tataggtgaa tcctagttat ataggttttg tgttgacaa    28020
attaaagct agtttattc cgcatttgtt aagctatatt cgtaaaagtt ttaaaccgca    28080
tattaacccc ccctctagge ggcatccgtg tccttcagg tgcacctaa atacatgcat    28140
gttagaatga cctgtctcc atgttcttgg cattctcttc aagattgcc tttttgatat   28200
ttattgtt tccatgatg atcaactaa cgtctccgct ccaactacg gaatacagag      28260
tggtgatgat gcaatttct ctctctaatg ctaacacaa catcaaaggt tggcccaca    28320
cgaatcttgt agcaactcat cttgtggcag atcatgcatg cacagctacc ctactagaca  28380
ggagacaatt ttcgatatat atatatatat atatatata tatgcatgct tgttcataag  28440
agaaattata ttatatatgc atcaggtttt acaatatgta gtagctaga gtccgtatac   28500
gaaaatttgt ttgaaatgaa aataattgg agcacaaaat gcaaacacaa aataaagggg  28560
ctaaaacct aaacctagc gcttccttta gtcccggtta aagttaccaa acggtactaa    28620
aggttctcta ccccgagcgt gcttcaacca cgattattt aaactgagcc gttttctta   28680
cgtctgcacc tacataaggt tagatcgac acaattcatc ttgaagaag agttcataat   28740
atattggtc ttagaacgga gggaaaccaa ttaatgaaac atgggttccc ctccttttac   28800
aaaagaccat caatatatt tgggcattga tcggaagagc atcaatcaaa tatgattgcc  28860
cttcctgtta caaaaggtc ggcgtcaact tcacattaca tacatatata gggcctaaca  28920
aagttggtaa taactatgta atgtactaca catcctcctc ggcaccagag gacacgcgta  28980
gatgcgctg gtgtctgatg catctccatc gtcaaaagct acgccctctc cggagcatga   29040
tgccacggtg tcgttggcgc aatggcact aagcctgat gatttctgctt cgaaagcagc  29100
catgcgcctt tcagcgcagt tcatccacaa ctagcaagc tcgtcggcgg gaaattcag   29160
aacacgcact gcgcggccgg ccttcttaca ttttcttta acgcgtagca aagctgaagc   29220
cggtcctcgc ggagagtctc gaaggagtca tccaccacgc tatgcatagc ttcttcctca  29280
cgccacgtca actcgatgga ctactcgagc accatctcct cctctaagtc ctcttcaatc  29340
ctggctagat aatcctcgtc tgcagcgtgc ttctcctact ctagagggtg atcctcctcc  29400
gagtcatgcc ccgtgaggtc gatgatgctt ccccagcac tcatgtgttg tggaggaatg   29460
ctcgtcctcc gcatctgacg gtgaagtc gatgcaacct agagtggatt ggtagggagg   29520
catggtgcaa aggtgggtag gctgccagag agaagagtga gcgacgcatt tataggcgag   29580
gagctaaaca aggcgaacat tttgatttcg catttcaaac aaaatcagtt aactcgcgag   29640
aacatttgat gaccaaaata tcggcaaacg attctgcgga caaaactat tgcacagta   29700
tagctgacaa ccgtttgcgat acttcctac gcatacaatt ctatttgaac aaattgttc   29760
tgatattta tcgtgcacgt attggcagc cacatcattg cagcccatct ccgcgcgctc   29820
ttcatgtcc ttgaattca tttcacttc tcgtcgtct tggttgttag tcagtcgac       29880
ggactggtca tgctcctcct cggccatcag aggggcttgg ctctaaacgg cgacgttgtg  29940
cctgggtac ggccgcgacgc aagataggcg acgggtcttc ttggtgcgaa ccattacaaa  30000
```

FIG. 3 (cont)

```
gtaaactaca tgtgtaccgt aatggtgggg tgtgccaaac attgcggcgg tgtggggggg     30060
gggtctgtag cccggccaag gatccagctt gtcggcgatg tgtggcacgc cggaggaagg     30120
cgtagaagcc agtcgtcgac tgaaaattag acacacgact tttacatact gtaccatttg     30180
agtgcggcag aggagaagag acggtcaaga tttaaaactc ttcgcaaaat attcactatt     30240
cacacaggat aactttaccc atagtcgcgt gggatgaagg gcctattcgc tgaccattat     30300
ttttaaatag cccgtttgtg gactcttcct gactgcccgg aaataacttc agtgtgcttt     30360
catgcattcg tataggcctg cctggagacc aagcacacgg ttcgtggttt atggcgtcat     30420
cgttcggccg cacaatacac aaaaaggtct ttctatgtgc cactgagtcc ttaataggcc     30480
tgatctgtac tagtgatgcc ctgacatttt taaacgccga ggtatgcccg caatagctgt     30540
gctcgcacta gcccggcaaa acaaatccac cacggaaaac tacgttggaa aactgtaggc     30600
cctatttttt tcacacgaca tatccctatc cactacgcac gagacgacta aaactcctcg     30660
gtacattaac aaacaatatt ttttttgtcc atgcatagat aaggtggggc gcattccccc     30720
ccgtgtttcg tgcaactgtt ttcgatcgaa aagttaatcg caattcagta taaatatcag     30780
ttcatccatt ctgtttaaat tataatttcc atgtcattaa gattgataac tatatctcat     30840
tacataatat tagagtgcta ttgtttgact taatcaacat ctaactacct aattaacact     30900
aattagggaa aaaactccta tttctagttc tccatcaccg ctaatctctg gttgccttac     30960
accatgacct cgccgccata cgccatgacc tcgccggcga tcccatggac ctttgggagt     31020
tgtttttcca gccatattta tgtagggtct gaaatgaaga gaatcatgat tttagaagaa     31080
aatgaagagg gagtgtgaaa taaagtaagg gcctaatggt agtgatttag tgcgatgtga     31140
ggtggggatt atgaacattt accggtgtgg atttagcatg tcgggcaaac agagagaggg     31200
agtgcatgag atctagggtt cccagttgag tgtggagtgc ttgagatcta gggttcatag     31260
ttgaacgggg attgcgtgag atctagggtc catagttgag cggggagatc gtgatatcta     31320
aggttccttg ttgagtgtgg ggagtgcatg agtctagcgt tcatatttga gtgggggagt     31380
gcgatggtat catgggttgt tgggattgac catagctaaa gcatcactcg caatgttttg     31440
ggagcgatta atcttaaaga taatacacag tcgaacagtc cggcaaagtg ccttgatcta     31500
ggcaacaagg tgacccggag aagaacagtc cattgcagaa cttgtcacaa ggcgcggcac     31560
atcagcacta cctgttccaa tggtgattga gtcttggctc cattgcaagg caaagggcta     31620
tgccctccat acactcacac agctcagctt ctagagctaa ctagcagtgc tgcaaggccc     31680
cgcatgcaga gaagatgatg tttcctcaga atctcctaag atcttacctt tcccagttgc     31740
gctcgtctgc tccagaaagg agccatccac actgagtgac ataggcatcc ccaatgggcc     31800
taccgaagat ggtacccggg gtttacagaa ggcccacaag tcgaagaata tgaagttcgg     31860
aagcccagtt agtattaagg aaagttagag ttgtattagg aaatatagag acttgtaatt     31920
ttacgggacg ggttagaaac cctcccggac tctgtaactt gtgtattacg aatccctcgg     31980
ctccgcctcc tatataaggg ggagtcgagg gacaaagaga ggatcgaatc cattgtcaac     32040
ataaccctag ttttataatc gtcgagtact tttcggctaa aaccttcgag atctacttgc     32100
cctctacttc caacgaaacc ctagtctaca atacgtagac attgatcagt taataccttg     32160
tcaattggca ccgaccgtgg ggattagagg agacaaggag ctgatctcga tggcacgttc     32220
aagatcgtcg acttcgtcgg tagcaagcaa cgcattggat cgaggtaaat ggatcgaaac     32280
tgatctagtt gattttgttc ctcacccgcc ctcccgtttg gatgcatatg cgtatctgga     32340
ggagcccatg gagatgacgt tcggaaagtt ccgattctat gtcgagaaag aaggatcgta     32400
tcgtctcgaa gttccgatct cgtcgggatt atcggcggtc gattccgact tttcgtcagg     32460
cgaagaggag attttgtcgc cacgcttcat caacaccgtg gcaagcgaaa agctcgccaa     32520
gatcttcagc gacatgtcct tcgagtcgtc tgcggactct gatataagca gtgactcaga     32580
cagcgtcgac agcttcaatt tcatcgacag atctattgtt attgaaaggt cttcaccaat     32640
ctatacgatg gtgtcaccaa tcctgacaaa aatcaaaatt caaaatatca tcagatctac     32700
gcaattgagg aaaaaaaccg agcagagtcg gaaacatcag aggctttcga cgatgtggga     32760
aatccatatg tcgatcccgc tgatctcacg cgaggtctag gcactaaata tgttgggcct     32820
acaccacgtc taagggttca gctcccgcaa gaagcgtagg acagagccgc aagagccatg     32880
gatggtacag aaccaatgac cacaactgct acggtagaag aattgcaagc ttatcaatac     32940
agacttgctc gtgttagcag agagttagaa aaacagacag ccgcattaaa tagaagaaag     33000
```

FIG. 3 (cont)

```
gaggcagctt ccgcgtcaag caggcgaagg gcagattta gtcgacatc aggaaattcg    33060
ggagatagtg atacgtctca aacgtatcca taatttctta tgttccatgc tagtttatg    33120
acaatactca catattat acacactta catcattat acgcatttc cggcactac         33180
ctattaacga gatgccgaag cgccagttcc tgtttgtgt tgtttttggt ctcagaaatc    33240
ctacacagga aatattctcg gaattggacg aaattaacgc ccaggtctt atttttccac    33300
ggagattcca gagaccgaa ggggatacga agtgggcca cgaggtggcg acaccacaag    33360
gcggcgggc caaggagggg ccgtgctac cctatggtgt gggccctcg agcgcccc       33420
gactctgccc ttccgc                                                    33436
```

FIG. 3 (cont)

```
gagaagtagt tgtgcttgat acgacccct catacgtacg tacaggtgtc atccagccg       60
tccatcctca agtcggacgg ccccgatcac ccgtgcaac ggaagcgaac cttggtccg      120
tcaacgtc cctcgtacgc cagacggagt cctcctgca tctcataat acctgcatc        180
tccctctct cttctccca aacgaccaa acccacgtg ggacagaac ccagcctcct         240
ccagtcctcc tctagggttt gggccgacg gggcgaaca ctggaggcg gcgatgcgg        300
gccaggggca ggaccgaag acatcgatc tggaggaagg atgggcctac atggaggcg      360
gcatggcaa gccgtcaac atcctcgagg gcaagaacga gccgcagttc aactccgaga     420
actacatgat gctcacang taagcccgcc tcttcccacg ccgccggca aggttctaa      480
ctctgccggc ccgttcgat ccgaccgtt gtgatctag ggtttccgcc tcccccgcc       540
cgccatgatt tgtttcgtc tgttggcgca ggacgatata caacangcc acgacgaagc    600
cgcccaacga ctactgcag cagctctang acaagtaccg cgaggccttc gagaagtaca    660
tccgagacgc ggtaagcgc tggttcccc ttcttcccc tgttttgt ttttgttact       720
gttatgcggt tgctttggt tctctggtcc agcgaatga cccgaactcg actaggattt    780
gcttctgtt tcgaacgtgc acctatggt gtactagtac tggctgcgaa tgattagact   840
atgtctttc gattatatc tactaacgca cggtcagacc ctgcaaaaa tcgttccttg   900
actatttgaa acaagctgac tccagtacc tagtaactag taggtttagt tcagctagct  960
tcgcgtcgat gcatcggtaa gtttgcttt ttactgaca atgagtatg ctgtcagtt   1020
ccgttaaggt cctcctttt acggccaaag ctgttataga attcttttcg ccatcctaga  1080
tagaagctat aaaagtgaaa cctgtattgc acaacagttt gcagtgttt ccttgcttaa  1140
tttcttgagg tgaatattac tttcttgca ttgtacagct ggaacaatg gccttgata   1200
ggtgcatgat aacgcaaact gttagttcta tactactcg tcatgcatgc tgattatga   1260
aagtaacttg tattcttgca taatccattg gcctcgcttt agttttctcc cagtaatccc  1320
tttgttatt tgtgatactg tgcctgatt ggtgatcag gggattagga atccgggtc    1380
acaattatgt tatggttta tgaataagt caccacatc caacttttt tccaattatg    1440
ttgtactagt tgtgttacc tgtttcacg gtttacttg ttgttcaaac tactacaggt   1500
cttgccagca ataaagagc agcatgatga gtatatgcta aaacagctaa acgtaaggtg   1560
gaagaaccat aaagtcatgg ttcgctggct ttcacgttc ttccattacc ttgacggata  1620
cttcatcacc cggaggtctc ttactccact tcctgatgtt gggtttattt gcttccgacg  1680
cttggtaaac tgcctttta ttaacttcat cctccbgtt agtgcaccct aagtcttttt   1740
tttctcttct aatcagtcaa ctcatggtaa cagatatttc aagagatcaa aggaaggtg   1800
aaagatgcgg tgttagttct ggtgagtctt tgcatcccta gatgacccata tatcgaatga  1860
tttgacaaca tttacagac tttgcgaca actttcctct gcagataaat caagagctg    1920
aaggtgaaca gattgacaag acctgctga aggacgtcct ggatatattt gtgaaatcg   1980
ggttaactac catggagttt tgtgagaaag acttgaaga ttttcttgctt aaggacacta  2040
cagagtacta ttctgtcaag gctcaaact ggatcgttga ggattcttgt ccagattaca  2100
tgataaaggt acttcaata agacttttgc cctgcataat atttatgat gtatttctttt  2160
ttgttctatg taatagattt gctgatgct acttcattag gctgaggagt gcctgagaag  2220
agagaaggag cgagttagtc actacttgca tattacagt ggaccaaagt tgctggggt   2280
ctgttaaatg tttgctgtac ctattcaaa ctatttctcc actagtatat ccatatgta   2340
ttctgaatat gcatcatac ctttgtacc agaatatttct atgatcg ttcgagaaat    2400
gatgcaaaat agcgcagtct gtgaaatct tttatgtaat aatatttcct tttcttacag  2460
agagtgcaaa atgaattgct tgcaactat gcaacacaac ttctgcagaa ggaacattct  2520
ggatgttatg cattgctcg ggatgacaag gtttgctcag aacaaggcat atatatttct  2580
atacagtata cataatatt catgaacgca attgcccact cattcatctt ttgctatagg  2640
tggatgatct taaaggatg ttttcactct tctcaaaat caccgtggt ctggaactg    2700
tttctaacat gttcaaatcg gtattgacta tagtgcacat tatctcggct atcctttctg  2760
ttgcttgcag ttcactgtaa actataattcg aattaaacac tttgcagca cgttatgaat  2820
gcggtacaag cttttgtcaa gcaagcagaa gattctgcta taataaaa ggtgcagtat   2880
ttgctccgc cattgcttca tttctgcact tatttttat tgtggtaag ttttggcaca   2940
attcattca caatgtagtg tcatgtagct ccactgtcca gtgcaccat tctacatcta   3000
```

FIG. 5

FIG. 5 (cont)

```
gtttotacgg gottototty atggoattto otggttat oatgotgtgg ttacttgtoc    6060
accaaaattc ctgaagttt gagcgttg ccgctctatg ctcaaggt tctgctgcc       6120
tgtggttcct cgagcggtc cgttttagca tacatgcag tgcttaatg cttcatgttg    6180
tagctggacg gtggctaa gtggtgatt gtgtttgct gaggaagtat cctgtcgtta    6240
ccgacctagg aatagcattg ctgccgttct ccctcctgat cgtgccctt tgatactac    6300
aatccatgaa tttcctctgc cgtcaagcct gcctccgca ccttgctgga tttctcacaa    6360
aatctttgtc tgccctcc ccaagtcctg gagtgctgcc atcacatgcg ccaccactcc    6420
tctctgccgc tgtcttcctt cccaatgctc ctcacctcc cctctcgcca ttgatgcgac    6480
cccacacatg ctgactgcta gtgagcttgg cagcctgcc gtggagctg gggcgccac    6540
ggccagtcct caccaccatt gaaggtctga gacgccctcg accgctgaat ctgaagcca    6600
agtttccac gaggtggtct cctctctccg atgtgcgtc cgccatactc taggttgaac    6660
cggctggagc ctggaggtat ggtctcctct gatttctccc ttccatctt tgccttct    6720
gtaattatat ggtctagcac aagctgttgg actgaatgtt ttagtggad tgtgcgtgta    6780
atttgcatg ttttggtcta cccaagattt gagtcatat ttgtggtgat cattgattca    6840
tacaaaagctt gagtgagcat aaagtaaaga agataaatgt aaggcttcat cgttaatgat    6900
aaaaggttgc tatattctag tgtacctaga ctcaccgagc taatactgtc accaaagcaa    6960
acaaatttc agaagtagct ggtactgcca tttatttcat tccagtatga agtcaaggat    7020
tcctagaacc acaaatatgt atgaagtcaa ggattcctag aaccattaga aggtgtccaa    7080
tattacctaa agacacttaa tttatggcct aaattttga gccactttga accgcaaaaa    7140
tacttacttc ttatgcaaag tatgccattt cagttctgat tattgcaaca tgatcatgg    7200
tggtgaactt gttcatgtag cccaatcatt atgccttact gaaaaacaaa acacaagtat    7260
acttgttag tttcatctct tccgcagttc tcgtcgaatt gagtctagct ggtttcttac    7320
ctttactcat atacgggat aggtgtgtt gtaggtcca aaaacgggc caaattattt    7380
cctgtcaaaa aaactgcta gatttgctt ccgatctacc tttagattcg aaataataac    7440
caggaccgat cggcttcac gggtgaaaaa acccaggacc caaaggctt tgtatgcttc    7500
gttcgtacaa acaacaacaa cggtagtgt tcctttgct cgtcgttgag actttactct    7560
cgtcgtgaag gagttggcat cgaactcga ttcctaccaa atctatcgtg tcgtccaaga    7620
aacactccaa gtcgatcgct cgatcgtgtt taggtaaggt tctttctcgt tctataaaaa    7680
atatcagatg gcacggtat tacggctac cggaatgaa ataccagccg agatttttat    7740
tataaatttt aaatttatcc aaaattcgtc aaaattgaat agattacaaa aattcagta    7800
aataccggct gttattttct tatactggta ggtatgacaa aaccggttac cgccaagatt    7860
tcggaaatat cgggtgagga aaaacactag agcacattac cggtgcatgt ttacgacat    7920
gcatatttta attgatcatt ttacgtcat aactcttaaa tatatctaca tttatgaaca    7980
attagttacc cgtagcaacg cactgtatt gtcctagttc tagtatttcc taattctgta    8040
aatatttga gggattgtg ttggagaaca catcttcatc ctgtggtgag agccttgt    8100
tgggtttatt tgcattgtt ggtcattgct atgaaatttg tttcaggttc catgtggctg    8160
atgttccaat tgttgctggg cggacaggtt gaaacatgc aacacagcgg aagcacatct    8220
gccatttgca gaaaaaggc acgtaaaata cattgtgat gacatctgt tctgaatga    8280
taacatacca tttgcagaaa aaaggcaggt aaatactt gatgatccg tttactctg    8340
ggaatgcaga tgtgtttag agcattctac taatctgatg cctggacata catctgtccg    8400
gtccaacaa atgcattgct ttgaacttt gttccatacg ggaaaacgag aatatcaagg    8460
tatttgtaa tgtattttct gtgtcattc atagaatcat tccagcgtat acggtatag    8520
cttaatatga tgaattgat attactgat ccagcctgc tatatgatcg tgaaagctcc    8580
atgagttttt gattcctgat tttagcctat atattataac acagttgcct cggaacatat    8640
ttggccaaac agtgttttc tctgaaatgg tttgtatatt cactttcag ttaatttga    8700
gggtttaaag aaaacaaagc acgtactgt ttgactgtt tttaaggct gcagatgat    8760
aaccatttag tactcagca agaacactat gagttgact agtagaaaa ttacctaaac    8820
acctaaaacat gttcatcaga tcggcgcaga gctcatcaga agaatccaa aatttggatc    8880
ccttgaaaa aaaaatctgg aagtataat gcagtagt ttcatcaaag ctaaattat    8940
acactgcaat gcatatctgc cctttagataa cctgaatctt atgcaccgga gagctcattt    9000
```

FIG. 5 (cont)

FIG. 5 (cont)

```
cccccccccc cccacaattt tcaatcttgc atatgtgctt ccaaattgta agtttgtaac     13060
aaacgatct gccttttttg tgtgaaagca caagctagat attgcaaggt tcatgtgtgt     12120
tttgctattg tttgtgtttt cctcggatgt tttcaacgtt gtgtatgtgc tttcaaatgc    12180
ggcaaacaag cattggtttt gttgcattag tattttaaaa atgttgcaaa tatttttttg    12240
catttctttt taacatcgtc tgaatctttt tgtcgtgtaa tcattttcatt agttgcatta   12300
cctttttttt aactattgga aaactattac gtaggttgt aacatcttcc cgaagaaaat     12360
gttacgacaa gtatacccac agattgttg cattactatt ctataagatt gtgaaattg      12420
cttagtacta tttttgtaac atcttctaag aaatattgtg ttttcttgt tgcaaagcac     12480
ataaccgccc acatctgcct gctcgccgga tccgacgatg cgggatatgt ccgacccct    12540
tcctggacct gtttatcacc gaaggacac taacttaaca tgcattttct ctcacatggt    12600
agtgagccac tggaataatc aaattttctt tcttagagat cgatcaacac tagttccaca   12660
aaaaatcggc atcaaaattg agacgcgcg agaccactaa actaattcct ctatcgctgc     12720
atccatcct aacctcccaa tgagcatcgc ccacgtacga acgtgtacaa gtccaagcac    12780
ggccatgcac tttacgctgg acacaaggaa tgttcactct ccactccgat cgcagcttgg    12840
cgggctttga tcagtcagac tca                                           12863
```

FIG. 5 (cont)

```
ggctgtgtgc atccgtagtg ccattagggt ggtgcgttgt cgtagaggct gagtataatt      60
ggtatcttt  gatattaata tattccttt  atcgaaaaag aaactctcca caagagaacg     120
acaagtggcg cgtggcgaag caaccatacg cggagaattt tcttatgggc aacacctatc     180
gcatgtggaa gcactctcaa gagcgacctc tctataatga cgatttttct tgcgaattac     240
attccttttg ttgcaaaaag tattatcttg aaaaatcatt gttgtaattt caatcctcta     300
gattcctacg tctaggttgg tgtcccacag catattctca aatcaaaatc aaaccaaagc     360
tgaaaaatgt caaagaata  tttgaaaacc caaacctaac agtagccttg ctagagccag     420
ggtctacrga gagccaatt  gatcggctgt cggcatacat atgcagagcg gtccaatgtt     480
gcgttgcgaa ccaaaggaa  tatctcttg  gagagaaagc tatgcggaca aggccaagcc     540
cacaagccca catatgggag tgccacagaa attattccag cttcgtctc  caatctccat     600
cgccctcccc cttctctgtc gctcgatctg gtttctccat gtgtggacgt gaatcgaggg     660
gagcgcgcac ggcgcaccgc gtgctatata cggttcctgc gcggagaacc atgccactgg     720
ccgaagaatc cagtcctctg tgctctagcg ccgcgcgctt ccggagactc ggcagtttgg     780
ggtccaaatg ggggcggcgg agatgtgtc  tttgtgcttg gtactcgctg cggtggcatg     840
gacggagggg cagcggcccc gccggtgaa  agtggcgcg  ctcttcgact acgattccac     900
cattgccgc  gcgggcagc  tagccatcga gctcgacgtc gatgatgtca acgcggaccg     960
ctccgtgctc gcaggacca  agctggacct catcacggcg gacaccaact gcagccgttc    1020
tgttggaatc gtccaaggtt ggttgggttt tcattgtga  cttagctcc  atgcttgagg    1080
aactgcagtt tcttgctag  ctagtactaa tagttgagaa agatctgacg atagttaaat    1140
tcaagtaaat ttgatagagg aattgattt  ccaggatgca aggatgttag tatgggaagt    1200
tgctaattgt cgtattcta  aactagttta gttttttt   ttccgaatc  tgaactagtt    1260
tagtggtta  ataggtttgc ccctatgtcg gcataatcat ttcggaacaa caatgacaac    1320
aacaaaaacc ctttaatcac aagcaagttg cataatcttg agataaaacc aaagagtca    1360
cacaaccaa  cagagcaatg atattaggat aggactaata tagtactagt gatcgtaatt    1440
ctaatagtac agtcaatgtt agcacatgga ttattaattt taatcacacg tgtcaaaat    1500
cagatctgtt tgttggataa tgggcttatg cagtccgtgt taatatacgc tcaggttgaa    1560
tttaacatag attgggggact actctcaaaa cctttttgca tgcaaaaat  cctttgtgg    1620
gaaaatcaag ttgacacggt ggtatgcttt tttgaaatca agtttaagga aatggcacc    1680
aagccttttc actcgcactt cacatataat ctcataaagg gccaagactc ctcatgtaa    1740
gccgcgcc   ttaataaaag ccgattgtca tcggtctata atcagatggg ccgtttggga    1800
gatacgctc  acataggctt tagccatgat ttttattttt gttttttaa  acggagcaat    1860
caatttaaaa ttcattcat  tgggctggg  tggtatatgt gaccgtcaga ataagcacat    1920
tactgggac  tactcaccat atgttgcac  catatctata atgctgttg  gacactaaat    1980
ttgaacaga  agccaagtat tatgcttct  tgtcttgtga gatatggcaa taagattca    2040
gtttatcaac tacagttgtt gattgcttca acagttctaa tcaatgattt tttaccgc     2100
aaaaacaaac agttctgatc aatgaatttt attttgctg  cagcactgca actaatggag    2160
aaaatgtgg  ttgcagtgt  tggccgagg  tcctctgtga taggccatgt catctacat    2220
ttgttaatg  agctgcatgt tccgctccta tcattgcag  ccaatgatcc aactctttct    2280
gcatcggagt attcttactt tttaaggagc actgtcagcg attattcca  aatgcgtgcg    2340
atgctagca  ttgcttacta ctatcaatgg aaaaggtaa  ctgctatatt cgttgatgat    2400
gattatggga gagtggggt  gtctgccctt ggtgatgccc ttgcaacaaa gcctgccaga    2460
atttcatata aagcagtaat tcctccagat gcgaacaaag atgtgatcag tgatatactg    2520
tttaaagtta acatgatgga atcaagggtt ctgttgtgc atgtcaatcc cgatacaggg    2580
ctggattat  ttctatagc  taacgagctc cagtgatga  ccggtggta  tgtctggatt    2640
gtaactgatt ggctagctgc tgtcctggac tcctcaaagt ctggatatcc gaagagcatg    2700
agttatatgc aaggattaat tgccttcgt  cagcacattc ctgattctgc tgccaagaag    2760
aagttctatat caaatggaa tattrcgct  cgcaaaagga aattgcatc  tgtttgaat    2820
tcgtatgtt  tttatgctta tgattctact tggattgttg ccctatgcat cgataaattc    2880
ctcaatagtg ggcagcagat caattctct  gcagatacaa gattgcacga tcggataca    2940
agcattatca ctctgtcaac tctcaagata ttgatgggtg gtgaacattt gctacagcaa    3000
cttctgctca caaacttaa  aggctaaaca ggtatggttc aattgattc  agacgcaat    3060
ttggtacacc cagcatatga gatcctaac  atggtggtt  ctgttcatgg tttgattggc    3120
tattgtctat  attattggg  ccttcctgtt gctgctactg aaaatttgta tcagaagca    3180
ccaatatgt  cgtcaagtgc ccaacagttg agcactatgg tgtggtcagg tgctctacc    3240
actaaaccca  gggtgggt  tttccaaac  aatgccagc  ctctgagaat tggtgtttca    3300
aataatcaa  gttcaagga  attgtggca  agtggcaaag gtcctgataa cgtgacaggt    3360
tattgcattg atatattcaa tgcagcgtt  aaactgcttc cttacctgt  tccttccaaa    3420
```

FIG. 7

FIG. 7 (cont)

```
gtggtgtgg aaagagaagt aggttgtgga cccaaatgct agrggcttga gaagagatc    7020
ttctgctgag gcgggcttg cggaggaaga gggcactgaa cttgtgata caaccagcag    7080
ccctcttatg cttgtagctg aggaggcgga tgtcascct ggaaatca acacgaaga      7140
gcagttgttg cttgytcgg ctgtgaagt tgaggctgcg gataaggagg tgccatcgc    7200
gcctgcatat gtcacaccaa gggagcaaaa gaagcaaaat aagacagaca aggggtggagt 7260
tgagacaaga acacaagga agaatggagt aggctccgac tcggggggct gcagnttgc   7320
ggtcagtagt tcgggccgta agggtagtat tgtcatctat tggaataata aaataatgt   7380
taagatctta ccatatcac atatcatat cgtgccatt gtaactgaca aggagtga     7440
gccttggaga ctcacagtg tgtaggggga agacaaacc caactgcatt ttaagcatg    7500
ggatatgctc aaatttatca aatcggcgtg tccccatcca tggatgtgta tggtgattt   7560
caatgagttt ttacatcgat cggagcatat tggtgtgcaa gagcgcagtc tgacgcaaat  7620
tgcaggtttc gagaggtggt ggatgtatgc tgttgtgtg acttggttt aagggcgc    7680
agctggatgt atgagaagaa agtggccggc agaactttct accgggtgag gattgactag  7740
gacttgacca cggcggagtg atgctcgcgc tatccattag ccaggtcga gaacttgtg    7800
gccactagt cggaccaagg tcccattctt ctgcgttgag atccaaaaca agacacgagg   7860
ctgacgaggg atatgaagcg tacttcaag tctgaattca tatggaaaat cattctgatt   7920
ttccttctat gatggtgcag acctgtaaca acccaaaat ttcaaaacaa acaaattgaa   7980
ttttccctag tt                                                      7992
```

```
agaaaaaat gtcctaggag gtcagtcca tcgtaatgg ttcatctcta tagataaaca    7140
gtaactagta ctacctcgt tcttattaaa ttgacgcgat gtcaaggcta ggtagtacag    7200
attgtatgta catccagcgt cgattaaaca cggacggaag gagtacaatt ctaacgaata    7260
acttccaaaa atcattagtg ctgacacttg acaccattgc caatgcttg gctccgtcct    7320
tgtctgaact cgtcgtcact ctgctatgtg ctatgttaaa gcatttaacca tgtttattca    7380
acgcagttgg tagaagtttc aattaaagga aaactacatt ggaggttaaa taaatgagtt    7440
ctgcttctgt caataatgcc ctgatcctc cctttattg tcctgttat atataatata    7500
ggtataaaga aggccactca attaggcact ggaaagacac tcagcactgc tattctcttg    7560
attggaaac tcaacgtgtt tgggattatg tcggtgacag ctatgttcat cgtcttaatc    7620
actgaaaag cgatgcaaaa cattctaagc tcaggtcaaa gtgtgaattt tctgggaca    7680
acgatgactt ggatatggt ggagttatgt ttagcagaaa aactgataca gtaagagttc    7740
tggctctctt tgtgttgatt ctatgtaaca gcatcttagt aatcttgttc ttaaaatca    7800
tgtgctctgc tcttctcaac agatcgtgga tgaatacaac cgtcttctag caagccaact    7860
tgaaactcag agagaggtgc agtcctctct cctttgtact ccctccgtct catgaaactt    7920
gtctgagatt taactaaatt tggatgtgta tatcatact agatggtgta tagatacatc    7980
taaattttga caaatctaag acaacttag taggacgag ggagtgtat tttgtaccg    8040
tcactatcca acagctgta ctagagatca gcattttttt cggagttata gttgttata    8100
cagtgggcaa tgtagtatgt atctgaacca tatatatg cctatgttca tattgcagt    8160
attacgaggc tcttctgtca gagctaaga aagatggga acacatttct gttgctgtgg    8220
ataaagctgt aaatgataag cttcaagaga tgcaacttaa gcttgaaaat actatgttgg    8280
agaaaaagaa agttgcagaa gtgagcctct ttaaatcatg tatctttcag ttattaattca    8340
taaccagatt gagtcttggc ataactgata tcttttacctt atcctgtaga tgaatgaaaa    8400
actcatgaag agccaggata tctggtccaa gacagtaaaa ggaatagagg aaaggtatgt    8460
ttgttcattc caccagaaat tagtagcagc tcgtacatt catgatatgt aattgtgaaa    8520
gaagtcaagt aatgcaaatt tttttggggcg catcatggaa acagatactt gcagtgattt    8580
ggctaactgc ataaatacgt atcatgtaac agtctcatat ttaggatgtt aaagtaacat    8640
ttcgtatgaa ttccattcga aaatagcaca agattcatgt atcgttttctg ataaatcgc    8700
acgcacaggg agagagcca gttgaggctg aaggatgata caattctcga cctggaagaa    8760
cagtgtctta taatatttat tattgttat tgtaaagtt ccaccttaga ggggagtttc    8820
agtacagggg ctttctaaa cattccatgt gcaatccct gcagattaaa gactcaagt    8880
actgattac gttgcaaaaa tcgatagaga agagtacaca tcgtgatgat ctcaaggag    8940
gtatgctggt gccactggcc atggaatcag aatctggaaa gggtaaagaa tcgtccagaa    9000
gcaagaggag gaattacgg caggcatgca actggcctct tcgttaacta gcaagactgt    9060
tgctaaaaaa aatgaactag caagacagtc gtgactttgt gggagaagcc tccttactgt    9120
tagttttcta ctgctacact ctgatacatt gtccataacg aaactacaat cgggatacta    9180
catacacattt aaaaaaatac agaattcgga cattgtgtcg aaaatataagc caaaccaaat    9240
ccaagttcg tattactac ccagtgaagt gtcaggaagt tgtatcaatg tataagcaca    9300
cattagttta caatctgata aacacttcga aggtgcagag ttgagcatt atgtcaacat    9360
gtgtaaaaaa ggtaagcaaa ctatccatag tctacactac atcccagag tggaatttca    9420
gaaatccaag tggacataga cttaaacatt gagtacatac atgactggca gtttttctt    9480
ggacagatt acagctgag catgtcaaaa cgagaaccca acgtggccc aaacccaaaa    9540
tgccaacaca aacgcagcag ccctgatcac catgcgttc tcctgcttct tcctccacca    9600
caggatctgg agcggagca gcacacatgt tgccttgtgt aatcttgtga aggtttgtgt    9660
taggtagatc tccatgctga aagacctgat gatagctggg ttaactacca aggtatcggt    9720
ccactcaact catatgggga gaggtccaag cttttatata actccatgac gccaaaggta    9780
gtaggcattg tgccaacaaa aaattgttg cacagtgga tttcacatgt ctcagattc    9840
caagctccca aggaatcttt ccatccagca tctttggga tagattgatg ccagacatcg    9900
aaacgaaaaa actcaactag tgtgtagagt ttccttttcg tacaaagct gaagtcgtt    9960
aagccataga atgtacggta gcagtcaaag aaaaatctca tcgactgct gaataattc   10020
tatcatatgc ggcacctatg aagatatact tactcctacc aatacatgct ggtaacgaac   10080
ttgagagcct gttatgagac gagtcaatca tcctcaagta caggagttcg cacagttcg   10140
gaccccaatga aagtagctta atattgtcaa gataatgtac ccatggaagg ttcctgtga   10200
actgattgtg agtaatatcc aaagcaatca gactgatgc attagaatg agaagatat   10260
gtccaccagat aaggaattcc cagaaaaatt aacataattg agcagcaca aactacaatg   10320
tggtaaagat cctataaggt tgttgcttga tatatctaga agtcaaagac ttgtcaagcc   10380
gcaaatttct ggatgaactt tccctgttat acggttgcca gcaaggttca gtaccagca   10440
acaagcaata ttcacaaacg agttatcaag ttgccagaa agtcattat catgcaaatc   10500
gatgaccttt aaattccttt ctgatagatc acgagcgact atacaaaaa aatttattac   10560
```

```
catctaggaa aaactctgac tcaatggaaa aattactcat tccaccaaaa accacaccac    10620
caagctcgtt gtttgatacc gtcaaggtca agagcaaggg ataattagta aaaacacagg    10680
gcggacttto tccagaaagt tcattgtttg ataggtctaa tagcccacg attcccaa       10740
aaaactgtat tcaaata                                                   10757
```

FIG. 9 (cont)

FIG. 11

```
cgagtggata gcacgattaa gcgctaggag brttgcrgtc gcctagcact tagacatgcc  3540
ttttaaacc atgcttcga gattgcaatt gcctgaacag atcatgaaaa actagccaaa    3600
tgttattatg atgtccaggt ttagcactcc cggcaaacta ctgacttcac attctaaaca  3660
aataacagtt ccaacttttac catctcttgg aagtagccta acaaacaaat ggaccagaat 3720
aaccaccaaa cagaataggg caaacttctc aaagtatcgt caaacactca tcctgtcctg  3780
atctactatt aaaagtgaaa catgtaatgg agtgattttc gtctctgacc gacagtaaaa  3840
agattgaaat gtgtagtgtt ctcctatagt tcctttgatc tgtgtgtaat tacctctaga  3900
atctgcattt aatcttgtc aagtggactg actgggattg attactgac cactgtgcc    3960
tttgatatgc cattatgta ctgaactgg cacatgcata ataacttgtt caacctgcc    4020
tgttgtccac atgtgcaatg gtccctgctg gatcgttttt tagataanga ttttgttgaa  4080
ctatggatga cattattcac agttgttag atagctgttg tttgataagt ttacttattt   4140
atgtcagct agggagaacc taaaaaggc aaagaaagat tatgataaaa cagaagatga   4200
cttgaagtct ttgcagagtg tggccaaat cattggtgaa gtactagga catggacac    4260
tgaaagatgt aagtgaaag gttcttttt tggttttga aacaaaaatt tctctgtaca    4320
aacaatgata caagacatgc attctattct taacaatcaa tttcatcacc atattgcatg  4380
ttattctgtg tagcaacatg aaatgttttt actcatggta ataaactttt tgttcacaa   4440
attaacgact gaaacctgtt tttgttgaag ttatactcaa agccagtagt ggggcaacgtt 4500
atgtggttgg ctgcagaagc aaagttgaca aagaaaagct gacagtgga acgcgggttg   4560
ttcttgacat gacaacttta accattatgc gcactctacc acgcgaggta tatgggtatt  4620
ggcttttcat ctaggtttta gttgattatc ttttgaagtt cagttgtag catgacggt    4680
ttatttgcta actaaaaaac atgaacawat tckmaytct gccagtgag gttgatccdg    4740
tggtctataa catgctacat gaagaccctg gcaaagtcag ttaactcagct gtcaggtggat 4800
tctcggatca aataaggaaa ctgcgggcgt ctctcgagtt accgcttatg astcctgaac  4860
actttctccg tgttgggatt aaacgccaa aggtagtttg aagaaaattt gttcttttga   4920
gataacatac tatgctgtta gakmakmaak aagmatkcaa yytimwaat cywgarwtgt   4980
vtctwmtcy wgskattamw cmtycaaagg gtgttctgct ctaggccaa cctggaattg    5040
ggaagacatt gcttgctaga gctatgcta gaaccattga tgcaaacttt ttaaagaagg  5100
tttggttttt tctttaacgc tgttacatgt tgtcaatctc ttatttgac atctttacto  5160
taatattttg aactattttg cattgctaat gcagatgtt tcagtgcta tcattgacaa   5220
atatattggt gaaagtgcc gtcttataag agaaatgttc aactatgcac gcgagcatca   5280
agtatgtttg attatgcttt gttctatgt atatcttctt atcctaaaca ttcattttt   5340
gttggaaaac tattaaatc agaacaatgt aaacagtaaa ttgcatttct tgctctgtga  5400
ccaaatatat ttgcttcca agttttgtca tgaagtagct gcagaaagtc gattcattag  5460
gcgaacaaag caaagtaaaa aaattagcgt ctgatacttt gcgagaaaa tcaatggaaa  5520
catcttcact ttgaagttac tatgcatgtc tgaatgcac tctaagttct atrtctgttt   5580
cmagtaaagc atathattta gvcwastrtr tagtgtgwar tgwgstarta tcattcatgw  5640
kwtattttct ttyhmtgmwc atkwkswcya rccatgcctt attttcatgg atgaaatgga  5700
tgrcattggt ggcgaagat tcagtgaggg cactagtgcw gayogtgaaa tccaacggac  5760
attgatggag ctcctaaatc agttagatgg attttgatgag cttggaagg tacatgtttt  5820
ttcttttctg tgtgcacgtg tgttatgaca gcatgttatg gtaaaacata ttaacaacta  5880
tgaataggta ttatacagtg ataatgatac gatgcttact tgtaactaga tgattttttg  5940
gttgatcaat tgtaatgtg aactagttag ttagttatgg aatcaatcta acttgtctta  6000
tgagctactc ccacgcct aaaatgagtg tccaactct ttctagattt ggaggtattt     6060
ataactaaaa tactcatga tacatcgaa tctagacaaa gttgagtcac ttattatgg     6120
acggagggag tacttctg cctacaaggt aaggtatttg tatggagcag tttattacte    6180
atcagccag ttgtggaatg gcaacttctg tgtagaaact tcgaaatgt attaaaacaa    6240
gacattgaaa agttgacgat tgttgtcact gattgcttgt ctaatcttat gtgctgcaca  6300
tgtttgtga tgtacttaat gtctctcctt ttaatgtgaa ttacgcgtaa aaagagtttt   6360
atgtgtaaca agagagctct tctgcttata aagtcaaga tgattatgta gacbawagt    6420
actgatgtct tggatcctgc actcttcgt cctgaacgct tggacggaa gatagaaatt   6480
ccattgccaa atgagcagtc gaggatggag gtcctgaaaa tccagcagc tggtatcgcc  6540
aaacatggcg aaattgatta tgaggctgtb gttaagctcg ctgagcggct tcaatggtgc  6600
tgatctgcgc aatgtcgca ttgaagctgg catggttgaa gcctaacac ctatgcactg   6660
tcgttccagg gcttcaacgg tgcgattg cgcatgtct gcactgaagc tgcatggct    6720
gccttcgag cagcgcgtga ctacgtcatc catgaagact tcatgaagcg ggtgcbaag   6780
ctgaatgatg ccaagaagct cgwrwcyary gcgcactaca gcgakgactt yggcaaggaa 6840
agccagtact caccatttta gttttctgat gatgatgaca aaatgattgc aggggtggg   6900
```

```
aattbctgat  acggcttaa   ccagtcgcc   catagaagt   aagtagagt   tgtatacga   13960
cagctgacct  gtattcgaca  agtgttatag  taaaaggaag  ctaaattgt   ttcacaaagt  14040
tcttgtcaga  gttcgcgtgc  tgtaccgtga  aacaacaaa   caatatgcg   atatgcata   14100
catgtatact  attttgtagc  tgttcatttt  tctgtactcc  tgtcaaagct  ctaaacagtg  14160
gctgatccg   acatatttag  catatcttat  cttaagtatc  attttcacc   atatatggcc  14220
gatatagacg  atatatatca  gctgacatt   taccaatatt  ttgcctgaca  tcttggcaga  14280
tatggacaac  tgtgtattcc  ctccatccac  aaataagtgc  acgtttactt  gtcctttgtc  14340
aaacatttc   taagtttgat  cgattcata   gaaaaagta   gcaatatgcg  ttgcacaaaa  14400
ttaatatcgc  taattgtca   agctgaaca   aatttgatt   agggtaaagc  taaagtaca   14460
cttattcctc  aatggaggga  gtaggcaaca  cattttcaa   aatatttaag  aaatgcatat  14520
tgtcggttta  tatactgcc   taattactc   tcttctggta  tcatatatc   ttacatagac  14580
aaatcctact  acaagtcacg  tgtttcacac  aattgtttt   ccaaatctt   ttactactt   14640
ttcgaaaatg  ggcacttat   tacttaagc   aatagaccg   gcctgtcat   aactaagatg  14700
catacagccg  cacaaatatc  tgttacaaaa  ccacagtggt  gttcgacgac  aaaaacaaag  14760
tttgtggaag  acaaaaagac  tagctaggag  gatctagccg  aaggtcacac  tgccaccat   14820
gttgggagaa  aatatccctc  gccgtatcct  ccaacgtga   agacacctcc  gtaaagagt   14880
ctcggtgctc  cacacgctgc  agtggcaccc  atgaacaaag  cattgttgtg  caccgtgaa   14940
tgacctgcat  aaaggaggaa  gaaacattat  tgaaatctt   gtcatttcta  catagccaca  15000
gagaccaaat  aattgcaatc  gctccatcc   taataagact  aataagacgc  ttaaacctaa  15060
aatcacgcc   attgagccag  ttgcaaata   aattgacaat  actagtggt   gggtataagg  15120
tataccctat  tggacgact   gaccatatag  acctagcaaa  cttacattgg  aagaataagt  15180
gtttcatagt  ctcgtcctgg  gaaggtctcc  accccttag   cgatagtcatc qtttgtgg    15240
ggcactatat  tgtacaatgt  cggataccgt  tctccggagtg tggtattatc  taaccattta  15300
tcctcgcaga  aacgaattc   cgaccggtc   ttaatagaga  aagatccata  tggaaagaaa  15360
tacttcttg   ttttccattaag accagccaa  aaatgtggat  ctcgtggttt  ccaaagaatt  15420
tgagatatag  ccttttgagcc aatatacttc  ctcttgagga  gtgttgcca   tatacctct   15480
ttggtaagtc  acttggatag  ccattaccg   agaagtgccc  tattcttgac  ctggatgtct  15540
tggatgccaa  gtcctccatg  atatttgggt  cgacacagca  cactccattt  agtcagtcga  15600
tattttacgct tctcactatc  ccttgccaa   tcttgattgg  aaataatcca  atctctttaa  15660
gactcctcta  ggaagttgga  agaaaaatat  catgtatagt  accatgttaa  ttagtatcgc  15720
attatgagaa  ctaatcttcc  tccaaaggat  agtaatatac  cttccaact   gcttaatcta  15780
attgtagtc   ttttcctcaac caatttcat   taggcattgg  tgagtctcct  ataatgaatc  15840
ggaattccca  agtacctaat  tggaaattgg  cctgacgt    agctgaaag   ctcagcatac  15900
tctgcaacat  gatcttgggc  ctcaccaaa   taaacaatt   cactttatg   ggaattaatt  15960
tttagacccg  acaaatgctc  gaatgctgaa  agaattagct  ttagattcg   agcattgtcg  16020
atgtcatgat  ccataaaaag  tattgtatcg  tcgcatatt   gaagaatgga  taaacttcca  16080
tcaacaagat  gaggaatgac  ccattcaatc  tgaccatctg  actttgcacg  ttcaatcaat  16140
acatcaagca  tatcagccac  tatattaat   atcactggtg  ctaatgggtc  tccctgtgtt  16200
agtccttct   tggtatggaa  gtattgccc   acgtatcat   tgacttaat   ggcagcactc  16260
ccaccgaga   caaaactatt  gatcaactac  ttgattgggc  atgcacataa  atccctttgc  16320
atatagctat  cttccatgta  gttccaattt  ggcataaaga  tcttgcatca  ccgggtggat  16380
ccgtggacac  tttataagct  atatatgttt  ttatgttac   actttgaga   ttgcgcat    16440
gctagatttc  tagccagaa   ttgtcgagt   gttcctggaa  ggctgaggc   gcgaacgc    16500
cctctacgtc  ataccttg    ttttatccca  ttgaggaa    tgcatattta  attagaaaa   16560
tatataagg   gggatgaact  agatgttct   tgagcaagga  tgacttaga   cctcaaacac  16620
tatgtgtt    tatttgatta  atgacaata   attacataaa  tggaagttgg  gaacacttca  16680
acatgaaaca  cttggagaa   ttcagaacaa  tggagataaa  agcacattat  ttagcttgaa  16740
ttttcttccac ggaaactgcg  gcaccagctt  tactccttca  ttagcataga  ctggcagatg  16800
gcatcgtct   ctacagcgca  tcattagc    ctgcaatgac  aagtaaaaca  agtgtatttt  16860
tcttcagaaa  atgcacgtgt  ttgctcaga   gatccagtt   taagagtcg   aacgtgacg   16920
agttatatat  acacatgtac  ctctgcggtc  tggtcatggt  actgccgcg   gactttaac   16980
tccacgttgt  tgaagatact  gttcatcaga  atgtcagcag  aatccgtgcc  tgaaaccgca  17040
atgcaaatta  gttaagtacg  tagtggagaa  tggcataata  taactttga   cgatggctg   17100
gaccagacc   tgcaaggtag  gctagtcgta  cttgccctga  acctgatact  tgcacatctg  17160
gttctgcgcg  cagtcgacca  gaattccgc   agagtcaata  cctgcaagat  aaccccatg   17220
gacatagcca  ttgtagtgct  cgctggtgtg  ctcccagtg   aagtagaccc  gcccacccgg  17280
cgcctgcagc  aatcaaattt  aagacatca   gacctagccg  gccggagcca  ttaattggt   17340
gatggacatt  tcaacatcgg  tgtagttcag  atctagatca  aaattcaat   tcaactacag  17400
tgtgagtgtg  tgtctgtggc  taaccgaagc  tggtcgtatt  cgtagcgtt   gagccgatg   17460
```

```
ggcagtkgg agtaggagcc cttgaagaag cggtkggacc accactggg cacgtagata   17520
tcggtggcgt cgggagtc ctcgtcggg aacatcttcc gcagcaccga cacagcctcc   17580
gccatggtgg tgttgtcgg atgctgtcg atcgccgcg actcctgtc cgtcaccgtc   17640
acgaggagca cgttggccc cgggtactcc tcctcgaagg actgccacat ccgtagtag   17700
cctcgcctgg agctggcgta gacgaagac tgcttgcctt cgcccgtggg ccagaactta   17760
cgagggaact tgaggagat cttggtgtac actgccatgt cgaacggta gatggcgatg   17820
attttccatg cttgcaggtc gatcgacata gcaaatgtca agctatgat cgagtagtta   17880
gcagaggt gtgttggtg tgagatggca agctggcaga gaccatgacg atagtctgcc   17940
tggtacactg agcgtcctc cgtcttgacg gtgactcgc tcgaggagct ggagatctct   18000
cgcaccacct tgtgagctg caggagggg tggcgcagt tgccggagtc gtcggtgttg   18060
aggtactggc cggcgaggta gtggacgacg gactcgtagc cccgtttgtc gggcacgaag   18120
tagacgtcat ctccgaagtc gctgaaggtc ctctggggaa cgggttcg caggctggtc   18180
acgcgggcg gctcggcgta ctcgtagtca tacaggtagt agtctacac catgtaatta   18240
gcgatccgc ctccactatt ctcctctgc agaaacccat cgctcccct cccaggcacg   18300
catccgtccc cggcgccc atccactcct cctcgaggcg ccgcctcccc ctccgcctc   18360
ctgccacga cgtctcctac tccaccaca aacaacacgc agcctgcct gccatccg   18420
tccaccaac gacgtcgtcc agtcgccgcc acatcgtcgt cgtcggtat ccgccggct   18480
actcgccgcc tcccatccc gctaaaccg cgccgcctct ccggcgtc ataatccgc   18540
cgccgccaca tcatcgccgt gcccgatcct gccagccact acgctcgc gccacccgtc   18600
gtcctcctt ttgctggtga caatccaca ttcggcacca cgggatcct ctccaccgcg   18660
ccgccatgga tcctgcatct tccgctatcc ataagaaact agctagtagc tgattacgg   18720
gcagtcagg cttgaactgt atgagatcga tgtcaggac tcctaggctc gtggacaga   18780
tcagtcagtc cgcgctgtac gacgagttgt ctctgtgct cacgacgacg cgtctccggc   18840
tgtacgagat ctccgcacc acctgcagca ttgttcaaat ttatccaaaa aatattaaa   18900
gatgtggttt cttgatcac tcctacagta ctatgttgt atggagaaa attaattcat   18960
caggtttcaa ttattccagt atatgaatga attctggaaa gatagtgtgt ataggcatat   19020
agatgatgt tgcggcagaa attcatgatg aaaaagggt gctcaataagg gaaaaatgaagc   19080
atactggaat tgacgaggc ccattatttc gactgaaac tacaatgaaa atattccgat   19140
ttccatttgc agtatgatg agatgagctg gacgaaatat actcaatta ttgtgctaca   19200
taaatttatc tctgtagcac ctttattgca tgtatatctc aactgccaa gtcgagttca   19260
acaacactgt acagtgggca tcccgttga agaaagtgcc tcgagataac ttgtacttta   19330
tgtccggtga aaaccatga tctaacttgg gtgtttacac tcgtcgaga tggcgttgt   19380
acactactcc ttcctagat gtgccgtgt tggtggact cttcgcaag cttgtgtgt   19440
gattatttt aataatacc atttttaat catttcagg aataatgcgt ggttcaaaa   19500
aaaaaaatc aatcggcgga cggaggcg accgaggtc tcagaggyta ctgaagattg   19560
gaaccggtc gcggcaggg ctgccgatca gccagcagc ttccgatcgg caagcagtt   19620
gcgcgagg tgagctgtg gcagtacatc agtccataga ctccttctt cttattttc   19680
cctggtggcg gggtcctg atctctactg atgatgtgt gcccatgcta agatgagcc   19740
tggtggtaa ctattcatc ctcatgcacc aagcgatgtg tgcagcact gagaagagac   19800
gtgggcaag aaaagtgct cagatgcaa ggaaactgc tctatgcat tcgtagttct   19860
tgatttgca tgagcaag gctagtcact ttccgtgag cagacaagt ctaatcggcg   19920
tggctggca ttcgttcagg ccgatcaagt gattagttc actcgaccg atcggcacg   19980
gctgaaaacc gatcgtcga aagatggccg acgaagtcag aaaattgaaa ctttagaaa   20040
acgcgtatta ttcctgaaaa tgattagaa atttgttta tttttaaaaa tcgcccagct   20100
tggttttgcc aatggggtg gttgaccgct ttggcagagc catgcttct gtgtgcaaca   20160
ttcgcatctc aactaggct gaatttacg atggtatctt ttgatacta gtatatttc   20220
tttattaaaa atatacgtac aaatgagata aaataagaag attaattttc attagcttca   20280
ttacatgtg tttggccgg tgatggacta tagtaatctt gttagaaac cgtttatac   20340
acaacgatt gaatcaat tcatcaatt ttcaattttc agtgcatga attttagaag   20400
aatttacata ataatcta aagaggcg tatccaacaa gagaaataag ccatgtgcc   20460
cacatagttg gtgtttgta gtgagtgtat ctgttggtg gtagcgtgtg gtttgagta   20520
tgcattcaca ttcaatagg tgtgtcaaaa aaactagt tttgtctat caaaatcag   20580
ttattagtt ttacatattt tatttttat atataccaa tatgtcata actggatgc   20640
gttcgatat tatccgcctc cagtacaaca tcttgccat tagttttgt aagcacatcc   20700
taaaccatg gaaatcaaa atataaaga atattattc tcacaagaga tcttagggta   20760
ctattttatac ttgcaaaat taattaattt ctggtttg tgattctcg gctgagacta   20820
gtagatctta ggattgaat gtgatttgta atagctatga gttcatacg attgaaact   20880
aagatttat tcagctacag atgggattgt actgagaaa aatgcttgg gcagttgat   20940
ttcttatga ctgtgcaag ttaggttgc aattgagaaa aatgaacaa accgttggat   21000
```

FIG. 11 (cont)

```
tgtttcgtga ctcttgcaat tcaccagttg gaattacaat tgataaaaa tgtctcacga 21060
tgagaatttc acnccttaa tcttgtattt ttgggaatt caagctagaa aattaatgca 21120
atttgacca tctcctcacc acaagttgt ttatatcatt aattattagt atataaatt 21180
ttaaaatgtt tttctcttcg gggaaaatta gtaaagtttt aggcttttcc gaaaatcagg 21240
tggagtacat tgttgagttt taacttagga tctacgatgt tcccggcgtt gtccgtgctc 21300
aggtactgtc cggcgatgtg atagacgagg gtctcgaatc ccgctggtc ggcgacgaag 21360
tgccgtact cccgaagtc ggcgaacgtg gggtggct cagtattctg caggcggtg 21420
gcacgcggcg gctcggcgaa ctcgtagtcg tactgaagt agtccagcga catgtccacc 21480
ggcgtcgccg gccgttcgg ctggctgcaa aaaaacagaa gggtctctc atggacatgg 21540
tcaactgatc gatgagtata taactgtata tacagctaa gaagacgcac gtactggttg 21600
aatatcgct gcatggccaa gatggagatg tcgtcgcgc cgctgggatc catctccgcg 21660
gcgagcttgc cgccagctc ttccacttcg tcccacggt ccatttcttt ctgcacgtac 21720
tcctcctcgt acaggcgac gctggtctc gtcaacaata gtacaaagca tgagattagg 21780
tttaacatgg atgctgtgg aacaaatctt gtattagta ctaagtttag agtttcagca 21840
tgtttcattc tgattttgtt gaagtctgca tgtagtagtc gtctccgggt aggactgttt 21900
atgcatgtca tcatcgttgaa gtggacgat cgatcggcaa tgttgcgagc tgatcggcgg 21960
tcaagagaaa ccactagttg cgagtacatg ttgttattcag tcaagtccta cactagtttg 22020
agtccaccgt cagtgcatgt agtcaaggat ctatacgttg gggagcga gagactagcg 22080
ctatatgagc tgagttagtt gtggcatata cgtgatgttg atccatagag tggctgcatg 22140
cgcgtgtcgg cagttagtgt tagtggtcta ctagttagtt ggcacaagtg ctgaacgtgc 22200
gtgcgtgcag taagtgtgga gtagaagtcg gatcaaactg gtgtgtggct tgaccgtgtg 22260
tgcgtggtt atgtatataaa agcattgtaa cctcagtgt ttcagtcgag agaaatacag 22320
agaaagagc agacgtgtgt tgccgagaat acctgtgtgt tcttctcacc catatatgta 22380
tgtgtgttgt atcttgggca attctgtcag atgcaagct tcgttcatca tcagtcctac 22440
aacgatcgtt ttcgatggag ttaattagaac cacgacgtca aagatcgga gtcattacat 22500
ttaatttcga taatttttaa acttctcgtt cacgtcatca gtatatgact ctgtctgtag 22560
ttaatttgga ccctctttt aatatcgtcc aatcattaga cccatttct gccgtgcgt 22620
gtcattcca cgtggtttgg gcagcgtcg ttgctgttca tcaatcatca gttattatta 22680
ggtgcggtaa tatcgacagt tacccgccca tcagctaaat ctttgtttt cgttctcagc 22740
acgtgcatat atgttcatct gtttgggcat gcaggcatgc atgtataag tctatgcata 22800
ttctagataa tcagttttt cttcgaaagg tcttaatcgt cagtttggca gcatagatgt 22860
cttatctata cagtgaacgc acgtacttct cctgtagac gctgctgacg acgccgtcga 22920
agtggagta gaagttcctg agcttcagcg tggagttcac catggcccag atgggttga 22980
tattgtccc gttgacgccc tccacccagt tgcgccgat ctccacgttg acgccgctga 23040
agttgtgctt gtgcatccgc acgccgatgc ggtccgtcgc ctcaaggatc agcaggtccc 23100
tcacgccgg gtccacagc cgcttcccg ccgagatccc tgcagcaaa gatgtacaac 23160
accgacgaca tttcatgtga cgtgtatggg tagcaaagac gtttccgcca aggatcgt 23220
gcatgctgat taggtaccgg acatgccggc gccgactctg atgacccggg ggcctctgcc 23280
ggcggcgaga gaggcatgct gtgcagctat gagtatcaac actgctgcta tagcagtgac 23340
aaaggaagaa ggtttcatct ttcttctcac actaatctct ctggcttgc cgcgaatagc 23400
tagtttgctc cgatggacac tatctggtta agctgcgcat ctgctctcg gccgagccag 23460
tcagtgtgca cttatatagg gccgagagc agatggctac acaaaaccac tatgaattaa 23520
agacgcggga acccacccacg atccatatag agttaatacg attgcacga aatcgaatgg 23580
tgctagaca cggtggatgg agacgatgg tgcgccgat cttctcacat ttgttggctc 23640
cgccaaggtg tttgaggcg tttctctggg atgagatatt gcgatctaat ctgtagtat 23700
aagttaacca gattgctaa ctcccagtcg acgagaata atccttgtta acatgaaac 23760
cgttggattt tacgccaaga tatgtcgtg cggattgcgg aatcatgcgt gacgttgta 23820
ttgtcgaaat atgatgctg cgttgttcgg cattctcact ctgtttgtt ttatcgttgc 23880
cccgtcaatg tcagtactga gtagtgaga tcgtcttca acggcggatt cggtatttt 23940
gatttttt ctttctatgc tcattttc gataaaggg gatatactaa tacgcgaag 24000
ataccaatta caccagcat ctcgcacaac gtagtgtct aaatgcaata cggatgcaca 24060
caccaaaaa aagaaagatg aattacagaa aagaaagtc tcgattcagt gaccaattcc 24120
ttgcagtagc ggacgaacca ccaccagaat atccaccagaa atccatcaaa tccaaaagcg 24180
atgccttcca cgaaacattg cacagacgtc gacatcgcca taatcaaga ccatagtttt 24240
tcaccacgga gaagtcgc actccaaaa caatgccttt tcaacaagga cattgccatg 24300
cccacccaat taaggcaga cctggattt tcaccctgca agtttatca ctgaatttct 24360
cttgtgtgt tgccctcact tgctaattcc gctgccgaat tcacgaatca cgaagccaga 24420
ctcactgaac caccaggact tagaactcca ttgccaatcc ccagttctcg gattcaatgc 24480
cattatcgc gtgtcagttt ccaatgaac caacatgtcc catgatggca acagaccgca 24540
```

```
gagttcgca aagcctcttc tgaaacaaa cggtcagaat aaaacatggt tacgcgcgat    24600
agaaatggca tgaaaaacttg gcaaactcca ggcatggcgt ccattggaa tacgccggcg   24660
gattcgtatg gaactcagca tgcagcccta gatccaagac agctagtgac aacaaatct    24720
tcatcacggt gagagagag accaggacc gccacctta tttaatacg cgccggcagc       24780
cccacgcca ccagctagcg gctaagaaga aaactaatcc tagatgcgaa aacatgggca   24840
gacatcggca tagcaggtag gcaccaagca acaccgaggt agggaagat cgctcccaga    24900
atggcccacc ccgcctcag tgccatgccg ccgccaatc aatgcgcgc caccgccggc     24960
catgctgcc catgcctgcc ccactcat ccgtcctcc acgacagtc catggcccac        25020
caaagtcgta cctgccgct cgcggagatc aatcggaaa gccctctcat gccttagcc      25080
ttcagccgga cgggtgtcat cacccatgcc agcggaggca gcggcctggg aggccagag    25140
atggggggct aggcggcgga tggagacta cggatcgcc cgagcggagg cggcccggga    25200
ggttagaatt atgtgtgtg tcctgtctcg tttcgtcaac tttgtcgaa tgccctgaaa     25260
ggagacatac attctcatgc atcttcctct ctctcttct atctatcct ccctcctct      25320
ctctctctct ctcttcatt ttgcacgttg caaataatccg tgatctatt tatatctct    25380
aacaactaca atcattcgag caaaccaaga taggcataac acaagatata tgagtttag    25440
gagtagattt cattccttt ccttgaaaat ctaaaaatca tccaatagat atcaatacgc   25500
ctctaatacc aatacaagat ggtaacagat atgaatatag agaattaatt caaccatcac   25560
atagagatgg acaaagatgg ccagagttca ccatcaccac ctaattagag atatttaaaag  25620
ccattgttca tgaatagata gaataaagtt caaattaaga cactacaaga aaacgggctt   25680
ttaggctcgg gacggcctat agtcccggtt gcccaaccaa gactgcggaa tcgggactat   25740
atatcatggg ggagttggct ctatgtattc aacttcttg ttccttaaat tattttatata  25800
aactctctca aagagattat catccattac ccaaatgggg gagaatgaaa gtgcatagag   25860
tctccatgtg tggtttcggt aattaatgac aaatcctatg gaataatgtt tgcattgagt  25920
cataattgta ggagttgtcc ataggaaatg cttggacat atgttggctt caaggttgca    25980
ataagaagaa ataaatgaa agttcaagat gacccaacta gaagagatca tatgcttgaa    26040
gcttccttt catatggtga tcatggatat gtgaaaatat gccgaagaag aagctctccc   26100
atagtggagt atggggagc aattaagat acttcatcaa gccagcacaa tcaagaaagg    26160
tgttccatct tgttgcggtc aagatcatca tcatcgagct caagtggaat gtgcaaggtt   26220
aaggttatat cttataggg ttatttctt accggtctcg tcgtttagtt aggacacggg     26280
gttataggtt agttgccgca ctatcaaggg gctctctagt gagtaatcg atcgtatcgt   26340
tcggagagag ttcaaacctt tgcatcctg catatcttt cctggttgtt atttggatct    26400
tatccatatg gtgtttaga gcttgtactt attctcatga caatcctag ttcatcgaaa     26460
acacattcca catgaaatac ttgtcgtgtt ttcgatattg gagttttcc cggttttcg    26520
ttttgagagg ttcaccctct aaatgcatga aaaatctacc ccacttattc tttatatttt  26580
cactcttgt gcggtacctc gtctcatcc atttacaact aaattggtt tacctaaatc      26640
tgagttttct aactcaagtt gctgcaattt ccttattaga ggtgtagcg gtttagtct     26700
tatagataga ttaaactta cccatttga tcttatacac cgtagatgga ctatgattt     26760
tcctacatg atcttgtaga tattttgtt gtgattcaa tgagcccgag atcatcaaat     26820
ttggagtcca gatgtgaaaa tgacgacgtt tttggtgtgc ggtagctgc cagcgaagc    26880
ggtccggccc ccggtccgac gaaacggtcc cggctctcag attagtcgcc ggaatggggc  26940
tgggccggc cgacaagtc cggctgacca gaatgtccg gctaggcctg gaaggtccgg      27000
ccggtgcga aaatggagcc cttttctccc aacggctagt gctcatccto ccatataaaa  27060
agggcctttc ttccccattg agcggctgct tcttctactc tctctctact ccattgttga   27120
cttgagaag attcctctcc ctataatccc tccatgattc ttgtcatat tagggaaa      27180
gatagaggag atctagatct acatactgac caaataaatt cctctcttg tgagggatc    27240
cactagatct agatcttgga gaaattggt gtacctcctc ccattgtcc ttcctctctt    27300
attacccaa tatctttgt agtttgttg gaattgata gagaatgact tgagcatctt     27360
tgtggtgttc tagaagttgc atttggtgca tcgtttgac ttttccacgg tcatacctga  27420
agtgaaagt tgtgagaca tacacttcgg gagttgttc ccggagcttg ttcctcttgg    27480
gtcttgaac catagacggc ttagtggtct tgtgtgtt ctgggccttg ccaattaagt     27540
agcttgtgc ttggggctt agtggtattc ttgggcctc aattaagtt gtggagatta     27600
ctcaagggca aggccttgt gcaatttat tggagcctc cattaagtt gtggagatag      27660
ccccaagctg tgtcgggtt cgtgaccac cctaagttc catgtggat cgaggacatc      27720
ccttttgtg ggaattctct agaagaatac gtgggcctc gtgcattgg agtgacttgt     27780
cctcgaacc gctccacgg agagtagcac tcgcaaagt gtgaacttca ggatcatcg      27840
ttgtctcgc atcactggg ttattcctat atccgagtc ttatactatg catttactt      27900
tgtgataggc ttagtgattg aagttatata tcttgctatc acatagctgc ttgaattgct   27960
tagcataagt cgttagtgca cataggtgaa tcctagttat ataggtttg cgttgacaa    28020
attaacgct agttttattc cgcattgtc aagctatatt cgtaaagtt ttaaccgga     28080
```

FIG. 11 (cont)

FIG. 11 (cont)

```
tgcctccat acactcacac agctcagctt ctagagctaa ctagcagtgc tgcaagccc  31680
cgcatgcaga gaagatgatg ttcttcaga atctcctaag atcttacctt tcccagttgc  31740
gctcgtctgc tccagatagg agccatccac actgatcgac ataggcatcc ccaatggcc  31800
tacgaagat ggtacccggg gtttacagaa ggcccacaag tcgaagaata cgaagttcgg  31860
aagccagtt agtattaagg aaagtcagag ttgtattagg aaatatagag acttgtaatt  31920
ttacgggacg ggttagaaac cctcccggac tctgtaactt gtgtattacg aatccctcgg  31980
ctccgcctcc tatataaggg ggagtcgagg gacaagaga ggatcgaacc cattgtcaac  32040
ataacctag ttttataatc gtcgagtact ttcggctaa aaccttcgag atctacttgc  32100
cctctacttc caacgaaacc ctagtctaca atacgtagac attgataagt caatacctg  32160
tcaattggca ccgaccgtgg ggattagagg agacaaggag ctgatctcga tgccacgttc  32220
aagatcgtcg acttcgtcgg tagcaagcaa cgcattggat cgaggtaaat ggatcgaaac  32280
tgatctagtt gatttgttc ctcaccgcc ctcccgtttg gatgcatatg cgtatctgga  32340
ggagcccatg gagatgatgt tcggaagtt ccgattctat gtcgagaaag aaggatcgta  32400
tcgtctcgaa gttccgatct cgtcgggatt atcggcggtc gattcgact tttcgtcagg  32460
cgaagaggag attttgtcgc cacgttcct caacaccgtg gcaagcgaaa agctcgccaa  32520
gatcttcagc gacatgtcat tcgagtcgtc tcgggactct gatataagca gtgactcaga  32580
cagcgtcgac agcttcaatt tcatcgacag atctattgtt attgaaaggt ctcaccaat  32640
ctatacgatg gtgtcaaa tcctgacaaa aatcaaaatt caaatataa tcagatctac  32700
gcaattgagg aaaaaaccg agcagagtcg gaaacatcag aggcttcga cgatgtggga  32760
aatccatatg tcgatccgc tgatctcacg cgaggtctag gcactaaata tgttgggcct  32820
acaccacgtc taaggtttca gtccgcaa gaagcgtagg acagagccgc agagccatg  32880
gatcgtacag aacccaatgac cacaactgct acgtagaag aattgcaagc ctatcatac  32940
agacttgctc gtgttacag agagttcgaa cacagacag ccgcattaca tgaagacag  33000
gaggcagctt ccgcgtcaag caggcgaagg gcagattcaa gtcgacaatc aggaaattcg  33060
ggagatagtg ataggtctca aacgtatcca taattctta tgtccatgc tagttttatg  33120
acaatactca catattttat acacacttta catcattat acgcattttc aggcactaac  33180
ctattaagga gatgccgaag cgccagttcc tgtttgtgt tgttttggt ttcagaaatc  33240
ctacacagga aatattctcg gaattggcg aaattaacgc ccagggtctt atttttccac  33300
ggacttcca gaagccgaa gggatacga agtgggcca cagggtggcg acaccacaag  33360
gcggcggcc caaggaggg cccgtgctac cctatggtgt ggccccctcg agcgccccc  33420
gactctgcc ttccgc                                                    33436
```

FIG. 11 (cont)

```
gatgccgagt agcaagctgg ggttgttga gatcttccag aagtgcgtgc ctgcctgcct        60
ctcgttgtg cgtacttgat cttgaccaca ttctgctggg tcctggacag tcaagtagaa       120
acaatgggac cggcgtctac acgagaggca gcggcactcg atgacgtgac tttagacaac      180
accgacgccc tcgactgccg cctttgctgc ctaccactca agccgcccat cttcaagta       240
attaacatat gcaaaatgat gtcaaccatg cgaacaaggg ctcatcgact catgtctccg      300
cgcttgcagt gtaaggtggg gcaagtggta tgctcgacgt gccgagacaa gctggggcg      360
gctcggaggt gccatgtgtg tcgcacggcg acttccggcg gataccaccg gaaccacgac      420
atggagaagc tgctggagtc catccgggtg ccttgctcca acgacgccta cggctgcgcc      480
gccaagccgg tctactatga caggaacacc cacctccggt tgttctgcca gcaagagcac      540
tgcactgca atatagaagc atgtggcttc gttggctaga aattatcggc gctccttgac       600
cacgtcttcg ccgtgcatgt tgaataaacc ttatgcatca gttagttcac ttcagtta       660
tagctgtagt taggcatctg ttagtcgtgg tgttgagcc agtcatggga tggcatgaca      720
tgcggatcaa gaccgttgta ataggtgcct gtagatcacg atgccacga tcgtcttcgtg    780
ggatcgcgcg agtgtggttg ctggtcgcgt ggagcgtttt tagctgagat tgttacaccct    840
ctgtatctct gaataaatag acaaaaaaaa ccgaaaatgc agtaagtttt acactgcgcc     900
aaactgtgtc tcccctgcgt gtttttatcc acttgtattt gttcttcacg tgttcttcga     960
ggagatcgtgc cagagagtct tggtatacc gaggatcagg acaacagttg gtatcagage    1020
ccgtgtgctc gatcgctgag gcaatgtccg aatcccgac gaagaagtcc ggcgaggcga     1080
cgccgcgcgc caagatcccc gatggctgg aggaaggtgg aggccagatc gtgatccagt    1140
ggatggttag ggacggtgga tcggccaagt ggccgatgct caccagaacc aactatgccg   1200
actgggact actgatgc                                                    1218
```

```
acttattgc aagtttcaga ttagtcaggt aagtgtcttc tatatcctag ctgctgggca    10680
tgtgaggtg cctgagtcag tgacaagctg atcacgcgtg ttgaagatcc gtcggcctgt    10740
tggatgttgt tctcaagaa cggcatacat tcaaagatgc aagcctgtca aaattgccgt    10800
cattttcagc attgagggt aaggttgttt ctccaggagt ctgaagaga ggcaacatg     10860
cggattcctt tatatccgct tcactggaa gaacacctgt aactgaaagg aaaaggctca    10920
ggatcagatc cgatcaattc ctatggcta tgagttgtga cgataagatc ctgaaaacaa    10980
aaagcaaaca ctttttttt gtccaaaaa aaangggaac acaagtggc gatgcattat     11040
tagcttatca ggcactggaa agattatcta atgagtttc tgtgcttatt tgcccgata    11100
ataattttaac tacgaagcgt gaggcatga tcaaatggcg acccttttct gaaactggaa    11160
ggacagata acacactgta cgcgtgcac tttccaccac acttcgtg gtctgcccgc       11220
gtcagtggc cagtagctac tgtgctaagt ttgcttacca agtttgta cattctgg        11280
acaaatgcg tacctgaacc gggccagcc tatcagatc ggctccagca attgcaagtt      11340
gcttcagaa tgaaagttt tgccagatc tcacccaa ccagcaagta aacctcat         11400
tttctaaata aacagaagca ggcacatcac cgacgactg ctagttgctg cttatcagct    11460
gcattccttg actgtatccg cgtgcattc tgcttgtgt gcacgctgaa cgtgtgtcg      11520
cagtctcaa agtccacact agcactcaca tttaagcta gtcctactct cctaccagtc     11580
ggcagttgtt gacgttcat aatcgaagag aaggacttga cgatataact gcatatcttg    11640
tcatttatct tcgattgggt actgaaacaa tgatatattc atgtaacgct gaaagccca    11700
tcgtaccaga atcgtcttgc aattatatca ctgaacaaac tgggcacgag gtcggcatcc   11760
atatggagag cactggcgag gccatgttga tgtcgaatgc ttgatcgat ggaagcatat    11820
atacacgttg gtctaatgaa gtaaaggagg agtataagtg agcaaccgt cctattcaag    11880
ctcaggtta gctatagcta aggcgcacgt aactaatgct gtagaagca cgtcatggtc     11940
caccaatta tataacaaga taacaaagat aacaaactt gtctcgccca atgatccgcc     12000
aggtttagct tctttttgaga tttctattg ttattacttt ccgaaacgaa gattgtcttt    12060
tgttatgctt cagcaggct agtatgcta tgagtttgtt ttgcagtagc tatatcaagc     12120
aggacagcag tctgagaaaa gtgttgaat cattggccta gcaccatat gtattaacaa     12180
tagtttgtgc tgaaatctc aaaacccat ttgctcatt catgtgtggc aagaggtgag      12240
actaagttt agtgtgcat gttagttat aaggagtttg agctccatat aaggaaagct      12300
ctttccatg ttgtattagg catgcgaaaa gaagacctac acgtgtcct ccgctgctca     12360
cccgatcctc acgacgacg tcgctttcg agatgtgtg gggctgagga acacctata      12420
cacgtgtac gagttgtttt tccttcacc acacatgttg gagaatctga aaagttttt     12480
aaaaccaaa gttgcatcaa catacacga aggagggta gtaggcctct agagcctcgg     12540
ctgttgtaga tctatacggg tgaggggtga tcagattta aggpaggg gggggggg       12600
gaacgaaca gggtacgc ccccctatg atccaggctt ccttcacaa attagccatg       12660
attgcttctt atctatgtg tttttagctag attagccccc ntaatgaaca aagtagtatt   12720
agctcagcc accttagct aagatcctgg ctccgtccca gctaacagg ctactggcaa      12780
acaccagtc agaggagaac tcctccccg acaatggctt cttctggat gtcaacaacc    12840
tcttgggga acatgaatgc gcaggttgta ccatatgtga tcatgtcctc tctatttgag    12900
atttggtag agtttacttg atgagcaat tacattaaac gtgacatca tggtaatatt     12960
ttcatcttct attttctcga atacatatgt acatgcaat ttgcttatat attcaaacac    13020
aaagataaa aaaattggg actattgctc acttttgcaa gtcttggaat taaaggtgt     13080
tcaactaaat tcaactcac tcaagccgtt acgttctca agtcatca aatgcatgct      13140
gaatcgttca anatcccgtcc cgtatctccg tggaagcaa aatcgccatt aggtgatcc   13200
accaagctat cgattgctac caagtgacc accaccattg acttgtgtt actaaaaca    13260
cacaaacaat cattacttac tgtggaacg taatggcagc agcctaacc gaacccttt     13320
tcaacacgt gaccaggacg tctggcacca ccatgccact caagcactc ttccctgat    13380
cacaattccc atccgtgac acagctccc ccctcgaaac gggcggcac gtactctac      13440
cctcgggt aacctcttt atccctacgc acgcgcac cgctcaggcc aaagaatcc        13500
agtacgcatc gatcgaggcc ccgtccgcgt tcgtccggag acaaccgc cgtccgtat    13560
ccgaccac acgccaccg cgcgccacc tgcctgccg cggccagcc aaatactcc         13620
ccagcgcg cgcgagcac ctctcagtcc gtgagtcga agcccggaa gaactcgccg     13680
ggcagcgcg cctcgtctcc tctcgtcgt caagaccgca atagaaactt cgctggtag     13740
gtccggtcgc ccggcttca actccaccca ccaccacgg aatcctcga ccccaaacc    13800
gttctccttc actcttcccg cgcctctgct ctttccgtgg gcgggcacg gggcgagct    13860
caccaatcga gtccacgca agcatgtgct gagggcccgc gccactgcgg gactccacc    13920
ctctccctc cgcgaggtta aattgctgc ctttcacact gctcctgctc ctccggcgct   13980
ttgagagcac aacgtccgac gggtatggg ttccagcctc aagtaccgcg cgggcgtgt    14040
cctcatcggc gggtagagc tcatatgggt caactccgc gaggtcacgc aggtacacga    14100
aagactcagc ctccccccc cccaactctt cttcccctgc ctcgttcctt tctgttttaa    14160
```

FIG. 15 (cont)

FIG. 15 (cont)

```
tgaaatagaa tacagtaaaa gtaggatgcg aaggacatt atgctgtagc aaaactttgc   17760
actgtaaatt atgtagtagc ttgctgcaca atgctttctc aaccgtacac tgcatagcc   17820
tgttattctc agcagcctca atcgtcaatg cgttactttt gcaacatgaa ttgcatacag   17880
atgatgaatt gagtcgatgg aggcactctg agacgtgtta aagttatact atatgtccag   17940
ttgagctaca ttaaagtttc caaaactgaa atataaaatc atatataagg gttttgttgg   18000
agtatgcgca tgccataata ataggacggt aatactatat tgaaaattca aacttggtga   18060
tggattgatt aaagttgata atattccata cttgtcaac aatagatatt actagttcga   18120
aagaaaaaca atactcgatg ttacttactc ttatcagaaa gtcaattcgg cacacttgc   18180
cgcatgggac catatattcc tgccaccggt aaaaaaacat tccaacatgt caaaaaattc   18240
gacgaccct ttcaacatgt ccaaaaaact atcgaacgaa aatttgcgc tgtacgtatc   18300
gacattctat gtgcgaacat aagttctgtg aaaaacctat attttgtga atgtgtaaa   18360
aagacaaaaa aaaatgtaa cttgtgtgaa aagacaaaa agaaaacgtc aggtagataa   18420
actttttttt gtaccaaaat tcatattttt tacaaatgat aaaatgtggg ttttcggtg   18480
aaacgactttt ctgagcatgt agaatttcaa gatgaactcg tcaaatttg tgtcagaatt   18540
tttcaaaatt ttaaagagt atttaaaacg aaatttaaaa atcaggagct ctccggtct   18600
cttaattga attctaactt gttcctatgt caaactttgtt tacatttgac cgactatata   18660
gaaaattata ctaacatgta caccaaataa gtttttatta aattagtata ctgtagatta   18720
aactttaaga ctgacatgt ctgaagtgt agacattata atttggtac attcttcggc   18780
ccaaattaat tgagcagaa gtaacaaatg tgtggatcca tactatgata atagagcaca   18840
cgatttgtta atttgtacag cccaaaaaca atttgtattg cttatcatat ttaacacatg   18900
catagtggag catatacttg cgaacaacaa aaaaatctct accgttggg tgagtcaaaa   18960
agaatatttg tatgataaac ccgtgtaacg acgcggagtc agccctctg agaccgccgt   19020
aattcgatcg catacacgga gaagtcggg ttctacgatg gggcgcag cagcggccg   19080
gtgacctgt cgacctggc cacgtcgaag cctttcgc gcagcacgtc cacgcagtc   19140
tgcagcgcg accggacctc gctagcgc caacacacg tgccgtcccg ccacagcg   19200
cgcagcgtgg tagccattgc cggcatctcc tccggtcgt agaagacgtc cgacatgagc   19260
accccgtcca cgcacggac ctcacgatcg agcattacca gtccatctc ctccccag   19320
cgcagctccc gcagtcacgc ctgcgcgtg tcgagtaga gccttgc ctcggcgtt   19380
gctctaaggc ccgacggag cggcgcacg tcgtgacca ccagcgcgc ggcgccagg   19440
catgcacgg ccgcatgcc cggacgccc gtgcctgac cgagacgag cacgtggcg   19500
ccgaggagct gactggctc ggcgaccg aggtgttgg tgaggacag cgcggagtcc   19560
catagccagg agcccgtgag cgccggccg gtggccggt ctgccgcc gtccggtca   19620
accacggcca gggctcggcc ggcacatct acctgcacg gcgcatgat cacgtgtggg   19680
ttatctgctc gatcgacct gacggcgat cacgcgcgt gccgcagcg gggtctggac   19740
atcatattac ccagcttctat atgcaagctc ccgaacggat gatggaagt tcaggataat   19800
gccgggaccg cacctggct gtctcgatga tttgtaagct tacccttat ccatgacgy   19860
cttggccagc catgcgtgtt caactgttca tgcaccagct aaccgaacc ggcgattca   19920
caggcgcgcc ggtatgtgcc ggagtcgcat cgacccttca gctttgctt tagatgcgg   19980
ctccgttctc ggtataatg ggatgtaccg cttaccgttt ccgttcgat actactcgt   20040
cgaataccga aagcaacgac ctgacacctg tcagatacgc caagcatctg ggcccatcca   20100
cgcccacctt ccattgaaaa tatccgctct ctactcgcg attctctcgt tcatctagtc   20160
atggagagat cttgagcatg cgcgcggt catacagtca agataggacc tcctatacgt   20220
ctgcttcagg accggagtcg ccctgcagg tcgaccggt agcctcggt tccggcgcg   20280
gcgccgtcct caagatccgg tcagtacgct cccgatcgg agtcccagg tcaaacgtcc   20340
taccggcgg gcgggccacc tccagacacg catgcccgac gaaaaatacc cctggtatcc   20400
tttcatcgct aactgaccc ctgtccattg tctactgtcc acctccgatg ctgagctctc   20460
atgagaaga tcggtgcctg gagcgattg cttcctgctt cttttgattt aagttcatac   20520
agcaaatgta atgctgtta aatccattta tagttgtgta ttgttgcaaac tgaaattgaa   20580
atttgacaca ggattaaatg catgattaga tttgtaacta agttcatttt tgaaactgaa   20640
gtgactggt ttatcagatg aatttatgca atasaatagt atctaagtct tgtaattat   20700
cttccaaag accccgatct tcatgatttt ggattaatgg ttgttgaaat atcatcaagt   20760
cagtgccgt atttcaggat ttcaggattt tcagtataaa cagatgtttg ttcatcaaga   20820
atctatagta attccacac aaagtaggta gatgattcc ttctgatatt cagaatgtgc   20880
acttttctt gatttgatga agcggtttga gatttgtagc gtataacaaa tatgcatga   20940
acaatttca gaattcagct taagcgaaag ttgatttcat ttatggtgtc ctctcaata   21000
tcttgttggt aagaaataga tatttagttc tctttgaatt cctctactt gtgtattagt   21060
ggcttctcgt acctctaat cttcagtttc gcaaagaact tcatccaagc atctattttc   21120
cgaaattatt catggatctt gcgtgtctgaa tacttttgga actgaaactt cttaaacta   21180
gtgaaagttt attggaacac tttgaaacaa taaatgaagc ttaactcgta tatttatgaa   21240
```

FIG. 15 (cont)

FIG. 15 (cont)

```
ttccctttta ttttgcgtca atgcacaagc tctcggntcc aattgtttca aaanatttc    24840
aataaagnat gggctagtga aatgtgtttc acaagncac catggaatcc ttcaagcgtt    24900
tcacttggat gggcatgttc cacttcgtt tgaaatggat ggatggtgnt tcactttttt    24960
taaatgtaat atcttgtttc caattgtttc acattattca atcatccaag gcccattgca    25020
atgtatttca caagttcagc atcaatctt tctagtgttt caatggttc cacatgtttc    25080
ctattaatta caaaaatatg gagtgtattc cacttccttt gaatcaaatg tctgtagg     25138
```

FIG. 15 (cont)

LpOsO5g0148600

ATGGGG[A/G]GGCA[C/T]TTGGG[A/G][A/G]CGGAGTTGGG[A/G]GCGCT[C/T]GCTCT[C/G]AAGT
ACAC[C/G]GGC[A/G]TGTCCCTCTCGGTGTCGGACTACGACTCCAT[C/A]GTCGCCATGAACATCTTCGTC
GC[A/G]CTCCTCTGCGGCTGCATTGT[C/G]TTCGG[C/A]CACCTGCTGGAGGGGAACCGCTGGTCAACGA
GTCCACCACCGCGCT[C/A][A/G][G/T]C[C/A][A/T]GGTG[C/T]TTGCGGTTTTGTCTCGC[A/T]GG
GGC[C/T]GCCTCCCAT[C/G]GCT[C/G]AT[C/T]ACTGGAGCGGT[C/G]ATCCTGCTCGTCACCAATGGG
GTCAATTC[A/G]CGCATTCTGGT[C/A]TTCAGCGAGGATATATTCTTCATCTACTTGCTCCCGCC[C/A]AT
CATCTT[C/T]AACGCTGGGTTTCAAGTAAAGAAAAA[A/G]CA[A/G]TTCTTCCGCAATTT[C/T]GCAAC[
A/G]ATTACTTTCTT[C/T]GGGGCTATGGGACATTG[A/G]TATCCTTTGTAATAATCAGC[C/G]TTGGTG
CCATGGCATTCTTCAGCAAACTTGATGTTCATCCACTCCAGCTTGGGGACTATCTTGCAATTGG[G/T]GCTAT
GTTCTCAGCAACAGATTCTGTTTGCACCTT[A/G]CAGGTGCTTAACCAGGATGAAACACCCCTACTCTATAGT
CTGGTTTTTGGTGAAGGTGTTGTTAATGATGCTACATCTGTTGTGCT[C/A]TTCAATGCAATT[C/G]AAAC
ATTCATCTTCATCATTTCGATGC[G/T]TTTGTTCTACTACAACTTATTGGAAAATTCCTCTACCTACT[G/T]
TTCACCAGTAC[A/T]CTTCTTGGAATAGCT[C/T]TGCTGGATCT[A/G]AGTGGTATTCTCAC[C/T]GT[A
/G]TTCTTCTGTGGAATAGTAATGTCGCATTACAC[C/T]TGGCATAATGTGACAGAAAGCTCTAGGTTACTA
CCAAGCATACTTTTCCAACCTTATCATTCATTGCTCAA[C/T]TATTTCTTTTTCTCTACGTTGGGATGGATGC
ATTGGCATTCAAAAATGGAGATTAGCTAG[G/T]AGTAGGGAGCTAATAATATGGTGGGCAGGTCT[C/T]AT
GAGAGGAGCAGTTTC[A/G]ATTGCACTTGCTTA[C/T]AACAAGGTTTT[C/T]GGCTTGCTGACTAAGCCTC
TGATTAATCTCCTCATCCCACCAAGGCCTAG[C/T]AATACAGCTGATGGCTCAAGCCAGTCATTCCTTGACCC
[A/G]CTTCTGACTAGCTTATT[A/G]GGCTC[C/T]GACTTGGATATTGCCAATACCC[C/A]CCTCAAAC[
C/T]AACCTT[C/G]AGCTTCTTCTCAC[C/G]ATACAAACACGTTCTGTTCATCGTGTGGCC[C/T]AAGT
TCGATGAT

FIG. 17

LpOs01g0269700

ATC[A/G]GAATACACTGT[C/T]TT[C/G]TG[A/G]AAA[C/T]CTG[A/G]TTA[C/A]TATGATAGG[C/
T]GC[C/G]GTTCCTCGGATAAGGCA[C/T]CAGCTTGCATA[C/T]GCAACCACACTTTCTTCCA[C/T]AA
AGAGGATTTCTT[A/G]TATATCCATAC[A/T]CCATAATAACCACCAG[C/T]GA[C/T]TGTGAGGGTGC[
C/T]GG[C/T]GAGATGTTCCAAGTCAC[C/A]TCCTT[A/G]TTCAG[C/T]CAGTC[C/T]GAAAAGGTTGA
[C/T]AAGGAGCT[C/T]AAGGAGAACCCTGC[A/G]CC[A/G]TCTGAAGCTGAT[A/G]TTGAGGCTGCTAA
GCTTCTTGTCAACGAAAAGG[A/G]GATGC[A/G]GTTCC[A/G]CAACTTAAAGCA[A/G]CAAAAGCTAGC
AACCA[A/G]CACATAACTGCTGCTGTTTCCGACCTTACAAAGG[C/A]AAAAGAG[A/G][C/T]TCTCTTAA
GGCTGGAAGA[A/G]AGGTC[A/T]AAG[C/T]TGAAACCTGG[A/G]ATTCC[C/T]CA[C/T]A[A/G]AGA
TGATGG[C/G]TCCATTGCGTTTGAGAATGACTTCTTCAAGCGTGCAGCCTTTCT[A/G]ACTGTTTCAGGCCA
[A/G]CTTCAGGTTGAGACTTA[C/T]GCTTGTGCTCTCAGCAGTGTCTATACCTTTTGGACCCACATTCGGGC
AGAGAACTCACATGC[A/G]TCAAGACATTTGGCAGAATTTTGGATGGTTGAACC[A/G]GAAATTGCATATGC
AAACTTCCATCATCATATC[A/G]ACTAT[G/T]CAGAGACGTAC[A/G]TAAAATACCTCTGCAAATGGTTAC
T[C/T]GATCATTGCGTGAAGACATGGAATT[C/T]ATGGTGAAACATGTGGACAAGACTGCAATTGAGCG[C
/T]CTGGAGCTTGTTC[G/T]TC[C/T]ACACCCTTGAGCGCATCTCATATAC[A/T]AAGG[C/T][A/T]
GTGGAGATCTTAGAA[C/G]GTAC[A/G]GGTAA[A/G]AAATTTGAGAACAAGGTTGAATGGGGAATTGATTT
AGC[A/G]TCTGACCATGAG

FIG. 18

LpOs05g0149100

TCTCGGGAAACACGCATTGGCAATACCGGCCGATCGATCGACAGATCGGCACGGGTCCGGCGAGGCGCCGATGG
CGTATGGGTGCTGGAGGTGACGCTGATC[C/T]CGGCCAAGGACCTG[A/G]AGAAGGTGACGGTGT[C/T]C
[C/T]CCAAGATCCG[C/T]GTGTACGCGGT[A/G]GC[A/G]TCCA[C/T]CTCCGGCGGCGACCCGCGCACG
CCGAC[A/G]CACC[A/G]GACGCACTCGGAC[C/T]GGCA[C/A]GGCGGGCCGGCTGCGGTTCCCAAT[C/A]
CCGATCGC[C/T]GCCACCCCGCCGGGCTCGCACTGCACGTGCTCCTCCGCTCCGA[A/G]CGCTCCTTCGGC
GACCGCGACGT[C/T]GGCGAGGT[A/G]CTCGTCCCCGTCCAGGACCTTTTCGCCGCAGCGCCTC[C/T]CGC
CGGCGAGCATCGCCACCTCAGCTACCAGGTGCGACGCCCCATGAGCGGCCGGAAGCGCGGGGTGCTCCACATCT
CCTACAGCCTCACGGACGCGCCGGCGATAGGG

FIG. 19

LpOs05g0149500

ATGGCGGTCACCATCACCGGCGGCGG[C/G]A[C/A]G[C/A]GGCTGCACGT[A/G]GACCTCTACTACGCG[
C/T]GCGT[C/G]CAGAGCCGCGCGC[C/T]CTTCACGGT[A/G]TG[A/G]AGCCTCCTGCGGCT[C/G]ATG
CGGCGGCACC[C/G]CGGCCG[C/G]GTCCC[C/G]GAC[G/T]TGGACCTCATGTTCGACTGCA[C/T]GGAC
CG[C/G]CC[C/A]GCCATCAACCGCAC[C/T]GAGCA[C/T]A[C/G]CG[C/G]CGAGGGCGCGCC[C/G]C
C[G/T]CCGCC[A/G]CCGCTCTTCCGGTACTGCACCAC[C/T]CG[C/G]GACCACTT[C/G]GACATCCTGT
TCCC[G/T]GACTGGTCCTCTGGGG[C/A]TGGCCGGAGACGCAC[C/A]TCGAGCC[C/G]TGGAGCCG[C/
T]GAGTTCAA[A/G]AGCAT[C/T][C/A]GGCAGGGCGCCAAGAAGAACTGGGACGAGGAGGCGAGGTCCGG[
A/G]TACCAGAACTCGAAGCT[A/G]TCGAGCCAGTGCACGCACCGGTACAAGATCTACGCGGAGGGTTCGCG
TGGTCGGTGAGCCTGAA[A/G]TACAT[C/T]CTCTCCTGCGGCTC[C/G]ACGGCGCTCCTGATCGACCCG[C
/A]TGTACCAGGACTTCTTCAGCCGGGGGCTGGAGCCGCGGGTGAA[C/T]CACCTGCCGGTGAGC[A/G]CCG
T[C/G]GGGATGTCCGAGTCCATC[C/A]GGGACGCCGTGGAGTGGGGCAACGCGGACCCGGACGAGGCGGAGC
GCGTCGGGCC[A/G]GCGGGCAGCGGCTGATGCAGGACCT[C/G]GCCATGG[A/G]GGCC

FIG. 20

Lp0s05g0149800

ATGGCGGC[C/G]CAGGGGCAGGACCGCAACACCATCGATCTGGAGAAGGATGGGCTACATGGAGGCGGGCA
TCGGCAAGCTCCTCAACATCCTCGAGGGCAAGAACGAGCCGCAGTTCAACTCCGAGAACTACATGATGCTCTAC
ACGACGAT[A/T]TACAACATGTGCACGCAGAAGCCGCCCAACGACTACTC[C/G]CAGCAGCTCTACGACAAG
TACGGCGAGGC[C/A]TTCGAGAAGTACATCCCG[C/A]GACGCGGTCTTGCCAGCAAT[A/T]AAAGAGCAGCA
TGATCACTATATCCTAAAACAGCTAAA[C/A]GTAAGGTGGAAGAACCATAAAGTCATGGTTCGCTGGCTTTCA
CGTTTCTTCCAGTA[C/T]CTTGACCGATACTTCATCACCCGGAGGTCTCTTACTCCACTTAATGATGTTGG[C
/G]T[A/T]TATTGCTTCCGAGACTTGATATTTCAAGAGATCAAAGGAAGGTGAAAGATGC[A/G]GTG[C/
T]TACTTCTGATAAATCAAGAGCCTGAAGG[C/T]GAACAGATTGACAAGACCTTGCT[C/G]AAGCACGTC[C
/T]TGGATATATTTGTTGAAAT[C/T]GGGTTAACTAC[C/T]ATGAGTTTATGAGAATGACTTTGAAGATT
TCTTGCT[C/T]AAGGATACTACAGAGTACTATTCTGTCAAGGCTCAAAA[C/T]TGGATCGTTGAGGATTCTT
G[C/T]CCAGATTACATGATAAAGGCTGAGGAGTGCCTGA[A/G]AAGAGAAGGAGCGAGTT[A/G]GTCAC
TACTTCCATATTAACACTCAGCCAAAGTTGCT[C/G]GAGAGAGTGCAAAATGAATTGCT[C/T]GCCAACTAT
GCAAC[C/A]CAACTTCTGGAGAAGGAACATTCTGGATGTTATGCA[C/T]TGCTTCG[A/G]GATGACAAGGT
GGATGATCTTAAAAGGATGTTTC[A/G]CTCTTCTCAAAAATCACCCGTGG[A/T]CT[C/G]GAACCTGTTT
CTAACATGTTCAAATCCATGTTACGAATGAGGCTACAGGCTTTGGTCAAGCAAGCAGAAGATTCTGCTAG[C/T
]AATAA[A/G]AAGCCACAGAAGAAGGAGGATGGTTGGAATGCAGCAACAGGTTTTTGTCTGGAAAATCATTGCA
CTGCATGATAAGTATGTAGCATATGT[C/G]ACAGATTGTTTCCA[C/T]GGCCATACACTCTTCCACAAGGCA
CTTAAAGAAGCCTT[C/T]GAGGTCTTCTGCAATAAGGGTGTCTCTGGCAGTTC[A/G]AG[C/T]GCTGAATT
[A/G]CTCGCCACCTTCTCTGACAACATT[C/T]T[A/G]AAGAAAGGCTG[C/T]ACTGAAAAGCTCAGTGAT
CAACC[C/T]ATTCAACATCCCCTTGACAAGGTGCTGCC[C/G]CTGCT[C/T]GCATACATAAGTGATAAACA
[C/T]CTCTTTGCTGAGTTCT[A/G]CAGGAAGAA[A/G]CT[G/T]GCAAGGAG[A/G]TTGCT[A/T]TT[C
/T]GACAA[A/G]AGTGCTAATGATGA[A/G]CA[C/T]GAAACAAGCAT[C/T]CTGAC[A/G]AAGCT[A/T
]AA[A/G]CA[A/G]CAGTGTGGTGG[G/T]CA[A/G]TTTACTTCAAAAATGGA[A/G]GGCATGGT[C/T]A
CTGA[C/T]CTTACT[C/G]TTGCAAGAGATCATCAAACTAAGTGTGAAGAGTTTGTAGCTGAACATCAAGA[A
/G]TTG[C/A]ATCCTGGG[A/G]TAGACTTGGCTGT[C/T]ACTGT[C/T][C/T]TGACAACAGGATTCTGG
CCAAC[C/A]TA[C/T]AAA[A/T]C[A/T]TTTGA[C/A]ATAA[A/G]CCTTCCT[G/T]CTGA[A/G]ATG
GTAAATGTGTAGAGGTTTTCAAGGAGTT[C/T]TACCAAACAAGAACAAAGCACAGGAAGCTTACCTGGATAT
ACTCGTT[A/G]GGAAC[C/A]TGCAATATCAATGCAAAATTTGAAACCAAAACTATAGAGCTCATTGTTACAA
CATATCAGGCTGCGTTGCTGTTGTTATTCAATGGAGTTGATAGGCTTAGTTACTCTGAGATTGTAACACAGCTG
AACCTGTC[A/G]GATGATGATGTTGTGCGTTTGCTCCATTCTCTGTCTTGCGCTAAATACAAGATTCTTACCA
AAGAGCCAGCTGGTAGATCTATTTCTCCCAATGATGTTTT[C/T]GAGTTCAATTCAAAATT[C/T]AC[C/T]
GACAGGATGAGAAGAATCAAGATACCCCTGCCTCCTGTTGATGAGAAGAAAAAGGTTGTTGAAGATGTTGACAA
GGA[C/T]AGGAGGTA[C/T]GCAATTGATGC[A/G]TCGATTGT[C/G]CGTATCATGAAAAGCCGGCAAAGTC
ATGGCCCATACCCAGCTAGTTGCGGAATG[C/T]GTGGAGCAGCTCAGCCGCATGTTCAAGCC[C/T]GACTTC
AAAGC[A/T]ATCAAGAAGCGGATTGAGCATCTCATCACCAGGACTACCTGGAGCGTGACAAGGACAACGCCA
ACACATACAGATATCTGGCTTGA

FIG. 21

LpOs05g0150400

ATGGGGTTTGCTCCATCTCGCTGGACAGGCAGTACAGCACTGGTTATTAATTGCAGACCACTTCTCTACTGCAG
AAAACAGGATATCAATGGTCACAGTGGGCTGAGGAGAGATTTACCCGTTGCATCTTTGCTTCTTCGGCTGGATG
CAAGCATGTATAAGAACCAGCTCCAGGAGCTTGCACAGAGGAGCTGCTTCAACTTGCCATCCTATGCATGCATA
CGCGAGGGGCCGGATCATGCACCCCGGTTTAAGGCCACAGTTCATTTCAATGGGGAAGCATTTGAGAGCCCGAC
ATTCTGTTCCACCTTGCGGCTGCCGCAGCATGCGGCAGCTGAGGTACCACTCAATGAGTTGTCCAAGACGGGC
CTTCATCATCACTTGCTGCTAAAGTTCTGGATGAAACTGGATCTA[C/T]AAGAACCTGCTGCA[A/G]GAAA
CT[G/T][C/T]TCATGGGC[C/T]GGTTTAAAACTGCC[C/T]ATGTACTACTATTAG[A/G]TCCGGAC
CAGGGCATACACCAATGTTCACTTGTACAGTGGAGTT[A/G]GC[A/G]GGAAGGATCTTCAC[A/G]GGCAAT
CCTGCCAACACTAACAAACAAGCTCAAAAAAATGCTGC[G/T]ATGCTGCCTGGTCTGAATTAAA[A/G]GAA
TTGCCT[C/A]GAG[G/T]AGG[C/T][A/G]AGG[C/T]AGCATCTTCATCTTCTCCATCCGATCATGACAAT
G[A/G]GGAGCAGGAACAGGTCACAGTTGTCCGCACTCTTGAAA[A/G][C/T]TTGAACCAGAAAATGAAG[
C/T]CAAGCC[C/A][C/G]C[A/G]CATCAAAAGGAAAAGCAGCAACGCAATAACCGC[C/T]CGCAACCTCG
CAGATC[A/T]T[A/G]TCCTAAACCAAGTG[C/T]GTCATTTTA[C/T]GGATCACGCTTACAAAATCAG[A/
T]C[A/G]T[C/A]CCCAAATGT[C/T]GCACAA[A/G]AGCAAGCAATG[C/T]ACCATATGTGGCACCAGGT
GCA[A/G]CCAACACAGCAGAAG[C/A]CCCA[G/T]TTTCGGATGGTTCCAACT[A/T]TGGGCAACACAAGG
TTTCCACCCGCACCAAC[C/T]ATACT[C/T]TCCATGTACCCTCCACCTAGAGGACA[A/G]T[A/T]C[A/G
]C[C/T][A/G]TGC[C/A]AGCCA[A/G]CCAAGATGCTTTGCTCTA[C/A]TTC[C/A]ATGTTTCCTGA
A[C/G]CTGCTCCT[A/G]CCCTTCCACGGTA[C/T]TTCTC[A/G][C/T]CTTACCCTGCCTCATACGTACC
A[A/G]CAAGTCCA[C/T]TGCCA[A/G]CT[G/T]CA[A/G][C/T]TAACATGATGCATGGAGAAG[A/G]
CAAGGCTG[C/T]G[C/A]TGAAA[C/T]GGTTGAGCTTCCT[A/G]ATGC[A/G]CC[A/T]GTTTC[G/T]
[C/G]CAGATACACTGCTC[C/A]AGATT[A/G]CTCTA[C/G]TGCTCTGGAAAATGTTTGT[C/A]CAAGTG
AGGTTCAACA[A/G]TGGCCTAAAAATGGGAAGAGG[C/G]A[A/T][A/G]T[C/A]C[C/T][A/G]AGAG
[C/T]AGTG[C/G]TGC[C/T]ACCGAGGAA[A/G]AGAATAAAGCTCCCCAG[A/G]CTTC[G/T]TCAAGCT
CCACA[A/G][C/T][A/G]CATC[A/G]CCCATCACAAAA[G/T]TT[A/G]GAA[C/G][C/A]AAATGAAG
ATA[A/G]A[C/G]AGTC[G/T]AA[A/G]AA[A/G][C/G]CAGCAGAACA[A/G]CCACTTCT[C/T]GGTC
CATA[C/T]GTTGTACAAAGACCTG[C/T]CCAGC[A/G]ACAGA[A/G]TTATCCTA[G/T][C/T]CCC[A/
G]TGCAGCACAG[C/T]GAGCCT[A/G]TCCA[C/T]AGAAAT[A/G]ATCTTCC[A/G]TTCAGGA[C/T][A
/G]G[C/T]AACATCACCTG[A/G]CCCATGG[G/T][C/T]TT[C/T]GGACATGCA[A/G]ACTCCACCAAG
ATTTGG[C/T]ACTG[C/G][A/G]A[C/A]TCTTGCGAATTCAGCC[A/G]GT[C/T]TCTTATACCAGCAGC
G[A/G]CCTCCATGCTGGC[A/G]GCCCCAGTTACAGTT[C/A]GAACTTCTATCCTGTGTGTTCAGCTAGA
CCAAACGCAGCGGTGAACTCTAGCCCGGGAGCAGCAACTCGAGTCCGATCTACTGTCCAGATGCTCTCTAGAAA
TAACTCTGAGGCCCAGAGGAACACGAGAGACATGAGTGATGCTTCGACAGCAAGTTCAGAACTTAGTAAGCTCC
ATATCTGA

FIG. 22

LpOs05g0150500

CGGAACATTGACATTTGCTCCAATGCTTGTAATGTTTTTGCATATAATGGACCAGTCAATTTCACTCTACTTGA
GAGGCTAGTAAGCAGATGCCGCAACCTCAAGACTCTGAAGCTCAACAATGCAATCCTCTTGACAATGTTGCTA
GCTGCTTCGTAAGGCTCCGCA[C/A]ATA[A/G]TAGAACT[C/T]GGAACTGGCAAATT[C/T]TCTGC[G/
T]GA[C/T]TATCATCC[A/G]GATCT[C/T]TTTGC[A/G]AAG[C/G]TTGA[A/G]GC[A/G]GCATTTGC
AGCTTCTA[C/A]AAGCCTAACAAGGCT[A/T]TCTGGG[A/G]CTTGGA[C/T]GCTGTTCCAGATTACCTG
[C/T]CAGCATT[C/T]TAT[G/T]GTGTATG[C/T]GAA[A/G]GCCTCACATC[A/T]CTTAA[C/T]CTGA
GTTATGC[C/T]AC[C/T]GT[G/T]C[A/G]AGGCCCTGAGCTCAT[C/T]AAATT[C/T]ATTAGCAGATGC
AAGAATCGC[A/T]GCA[A/G]TTATGGTGATGGA[C/T]CTCATTGAGGACCATGGTCTA[G/T]CT[A/G]
]T[C/T]GTGGCATCAA[C/G]TTGCAGTAAACT[A/G]CAAGAGTTGCGGGTCTT[C/T]CCTTC[C/T]GA[
C/T]CCTTTTGGTCATAACG[C/G][C/T]GGGCA[A/G]GTTTT[C/G]TTGAC[A/T]GAAAG[A/G]GG[C
/T]CT[C/T]GTTGATGTTTCTGCCAG[C/T]TGTCCCA[A/T][A/G]TTGGA[A/G]TC[A/G]GT[C/T]C
T[C/T]TACTTCTGCAG[C/G]CGGATCACGAATGAGGCTCTT[A/G]TTA[C/T][A/G]ATTGCAAAGAACC
CTCC[C/A]AACTTCAC[C/T]TGCTTCCGC[C/T]TA[G/T][C/G]C[C/A]TCCTTGA[A/G]GC[C/T]C
GT[A/T]CTCC[A/G]GATTACAT[C/G]ACAC[A/G][A/G]CAG[C/T]CTCTTGATGC[A/T]GGTTTCAG
TGCCATTCT[G/T]CAATCATGCAAGGG[C/G]CTTAGGCGCCTCTCT[A/G]T[C/G]TC[C/T]GG[C/T]C
TTCTC[A/T]CAGATCTTCTATT[C/T]AAATCAAT[C/T]GGTG[C/A]ACATGCTGATCGTCTTGAGATGCT
[A/T]TCA[C/A]T[C/A]GC[C/A]TT[C/T]GCTGG[A/G][A/G]ACAG[C/T]GATCTAGGCCTG[C/A]
A[C/T][G/T]A[C/T]ATCCTCTC[A/T]GGCTGCAAGAGCCT[A/G]AAGAAGCT[A/G]GAGATCAGGGAC
TGCCC[A/G]TTTGGG[A/G]ATAA[A/G][C/G]CGTTGCTGGCAAATGCTGCCAAG[C/T]TCCAGACAATG
CCATCCCTTTGCATCAACTCCTCCTCGTTGACCGTGGCCGGTGCCGACTGCTTGCACTCAAGATGCCTCACCT
TACTGTGGAGATAATAAACGATCCTGGAGAGACATGTCCAGTGGAGTCACTCCCGTTTGATAGCCCTGTCGAGA
AATTCTATGTCTACCCGACTCTTGCAGGTCCTAGATCTAGACACCAGACTGTGTCCAGATTGTTTAG

FIG. 23

LpOs05g0151300

ATGGCGCACTCC[A/G]GCAGCGACGCCGC[C/A]CCGATCAGCAG[C/G]CACCCCACCGAGGAGCAGGAGGT
[C/G]ACGGTGGAG[C/A]GGACGCC[C/G]GAGGAGGAGG[C/A]GGCCAGGCTCAGGTACCTCGAGTTCGTG
CAGCAGGCGGC[C/G]GCGCAGGCGGT[C/G]GTGCT[C/G]GCCGC[C/T]GCGGCCTACGC[C/G]TACGC[
C/G]AAGCAGGGCGCGGGCCGCTCCGCCC[C/A]GG[C/A]GTCGACCACGTCGAGGGCACCGTCAAGGCCGT
CGTCGGCCCTGT[C/G]TA[C/T]GA[G/T]CG[C/G]TACCACGCC[A/G]T[C/G]CCGCTCGACCTCCTCA
AGTTCCT[C/A]GA[C/T]CGCAAGGTTGACGAGTCCGTCCAGGAGCTGGACCGCCGTGTCCCCCAGTTGTGA
AGGAGCTGCAACTTATGCCCGCTCTGCGGCGGCTGAGGTGCACAAGACCGGCTTAGTAGGCACAGCCAGGGC
CTGGCCAAGTCGGCCATTGCTCGTGCTGAGCCAAAGGCTCGCGACCTGTACACCGGCTACGAGCCTGTGGCGGA
GCGCAAGGCTCCCAAGCATGGGCTGCCCTCAACCGCCTCCGGCTTGTTCATCGGTGACCAGGCTGTCCTCC
CCACCGCTGCACAGCTCTCAGCCAAGTACAACTCTGCCGTGCTTGACGGGGCCAAGCGCGGGAACTCTGTTGCC
ACCTACCTCCCGCTTGTCCCCACGGAGCGCATCGCGAGGGTGTTCTCCTACCCGCCTACCGACGCTGCTGCCAC
CTCGGCTCCTGAGATGCAGCCCATCCCGACGCAGTAA

FIG. 24

Lp2x0bg0152400

ATCCTGCGCTGACCCTGCCCTGCCCTTCCACCTTGCTGATCTGGCAGGAAATTCTCTCATGGCACCGGATGAC
CTCCACACCACCACCCCACCGAGATATCCCTCACTGAATGGTGGATAGAAGCAAGACAACCCCTGCCCCCCGGA
CGCTGCTCATCCTGTGGATGACCTGGAAACACCGCAACAGTTGCGTGTTTGAGGGTGCACAACCTTTGATCAAT
GGTCTGATCTCCAGCATCAAAGATGAAACAATTCTCTGGGCTAAAGCCAGTGCCACTGGCCTAGGAGTAGTGAC
CCATCACCTGGATCTTCTCCATGCGTTATTCTAAATCCG[C/A]GGTTTATGAGTATTGTATTCTTGGCTGG
GAGAATCTTCCTCGGGTTCTTCTCATGTACTTCAACAACGTAGTGCTGCCTCAGGAAGGATA[C/T]TTCCACT
CAGTCATATGCAACTCGGTTGATTTCCGTAATTCCACTGTGAACAATGATTTGAGGTACAAGGTGTGGGATGAA
CCACCTCAGACACACCCCTATTTCTGAACATGGCACATTATGATGAGATGGTGAACAGCGG[A/G]CAGCCTT
TTCCAACGCCTTTTCAGAAGAAGGAAC[C/G]ATTGCTG[A/G]ACAAGAT[C/A]GATGACAAACTACTCAGG
CGTCCTGGGCATGGGCCTGTTCCTGGTGCCTGGTGCTCAGGCAGGAAGGGCTGGTTCGTTGACTCATGTTCCCA
GTGGAGTGACGTGAACGTTGTGAAACCTGGTCCTCAGGCCTTGAAGTTGCAGCAATATATCAATCGGACATGG
AAGAAGCAATTCTGGGCAAAATCATCCAGGCGATAG

FIG. 25

LpOsOsq0660500

ATGGGGGGGCCGCCGACCTGCTGTCTTTGCTGCTTGGTACTCGCTGCGGTGGCATGGACGGAGGGCAGCCGCCCCG
CGCCGTCAAAGTCGCCTCGCTCTTCGACTACGATTCCACCATTGCCCGCTGGCGCAGCTCTCCATCGAGCTCC
CCGTCGACGACGTCAACGCGGACCGCTCCTGCTCGCAGGGACCAAGCTGGACCTCATCACGGCGGACACCAAC
TGCAGCGG[C/T]TT[C/T]GTTGGAACCGTCCAAGCACTGCAACTAATGGAGAAAATGTGGTTGCAGTTGTT
GGCCC[A/G]CAGTCCTCTGTGATAGGCCATGTCATCTCACATTTTCTTAATGAGCTGCATGTTCCGCTCCTAT
CATTCGCAGCCACTGATCCAACTCTTTCTGCATC[A/G]GAGTATCTTACTTTTAAGGAGCACTGTCAGCGA
TTACTTCCAAATG[C/T]GTGC[A/G]ATTGCTAGCATTGCTT[C/A][C/T]TACTATCAATGGAAGAGGTA
ACTGCTATATTGTTCATGATCATTATGGCAGAGGTGGGGTGTCTGCCCTTGGTCATGCCCTTGCAACAAAGCG
TGCCAGAATTTCATATAAAGCAGT[C/A]ATTCCTC[C/T]AGATGC[G/T]AACAAAGATGTGATCAGTGATA
TACTGTTTAAAGTTAACATGATGGA[A/G]TCAAGGGTTCTGGTTGTGCATGTCAATCCTGATACAGGGCTGCG
A[A/T]TATTTCTATAGC[C/T]AACGAGCTCCAGATGATGA[C/G]CGGTGGCTATGTCTGGATTGTAACTG
ATTGCCTAGCTGCTGTCCTGGACTCCTCAAAGTC[A/T]CGATATCCGAAGA[A/G]CATGAGTTATATGCAAG
CATTAATTCCCCTTCCTCAGCACATTCCTCATTCTGCTGCCAAGAAGAAGTTCATATCAAAATGGAATA[C/T]
TG[C/T]GGCTCGCAAAAGGAAAATTGCATCTGGTTTGAATTC[C/G]TATGGTTTTATGCTTATGA[C/T]T
CT[A/G]TTTGGATTCTTGCCCATGCGATTGA[C/T]AAATTTCTCAA[C/T]AGTGGGCAG[C/A]AGATCAA
CTTCTCTGCAGATAC[A/T]AGATTGCACGATTCCGATACAAGCATTATCACTCTGTCAACTCTCAAGATATTT
GATGGTGGTGAACACTTGCTACAGCAACTTCTGCTCACAAACTTT[A/G][C/A]AGGCCTA[A/G]CAGGTCT
GGT[C/T]CAATTTGAT[C/T]CAGACCGCAATTTGGTACACCCAGCATATGAGATCCTTAACATTGGTGGTTC
TCTTCCTG[A/G][A/T]TTGATTGGCTATTGGTCTAATTA[C/T]TCTGGCCTTTCTCTTGCTGCTCCTGAAA
CTTTGTATCACAAGCCACCAAATATGTC[A/G]TCAAGTGCCCAACAGTTCACCACT[A/G]TGG[C/T]GTGG
TCAGGTG[A/G]CTCTACCACTAAACCCAGGGGGTGGGTTTTCCCAAACAATGGCCAGCCTCTGAGAATTGGTG
TTCCAAATAAACCAAG[C/T]TTCAAGGAATTTGTGGCAAGTGGCAAAGGTCCTGATAAC[A/G]TGACAGGTT
ATTCATTGATATATTCAATGCAGCAGTTAAACTGCTTCCTTACCCTGTTCCTTCCAAATTCATATCAATCGG[
C/T]GATGGTATACATAATCCTAAATATGATGACATCATTAATATGGTTGCAAACAA[G/T]ACCATTGA[C/T
]GTAGCTG[C/T]AGG[C/T]GACTTCGCTATTATCAAAAATAGAACAAGGATTGC[C/A]GAATTCAC[A/G]
CAGCCCTATATTGATCAGGGATGGTGATAGTAGCGCCAGTGAAACAGTCAACTTCAAGTGCATGGGCTTTCTT
TAA[A/G]CCATTCACATTAGAGATGTGGTGCGTAACTGGTGCTCTTTTTGTCTTTGTGGGAATAGTTGTTTGG
ATTCTGGAACATCGGACTAATGAGGAGTTCCGAGGCAC[A/T]CCACAGCAACAAGTCC[G/T]AACAATATTT
TGGTTTGCTTTCTCAACAATGTTCTTTGCACAC[C/A]GAGAAAACACCGTAAGTGGTCTTGGGCG[C/T]TTC
GT[C/T]CTGATCATATGGTTATTTGTGGTGCTGATCATCAACTCAAGTTACACTGCTAGTTTGACGTCAATCC
TCACAGTCCA[A/G]CAGCTTGTAACCGGAGT[A/T]ACTGGACTGGACAATTTGATTGCAAGCACTGTACCCA
TTGGACACCC[A/G]GCTGGAAAATTTATC[C/A]GAAATATCTGATTGAAGAGCTGAAT[A/G]TTCATGAA
TCCCGCCTGGTGCCA[C/T]TGAACACGATCCAGGACTATGCGGATGCCCTTAACCGTGGACCAAAAGCTGGTG
GTCTTCCTCAGTATTGATGAAATGCCGTGTGTTGAGCT[C/A]TTCCTGTCATACCACTGTAACTTCAGAAT
AGTAGGTCAGGAGTT[C/T]AC[A/G]AAGGAGGGAYGGGGATTGCATTTCAG[C/A]GAGATTCTGC[A/G]
CTTGCTGCAGACATGTCAACGGCCATCCTTCAACTTTCAGAGA[C/G]TGG[C/G]CAGCTCCAGAGAATTCAC
GACGAGTGGTTGACCGGCCAAGTTGCAGCTCTGATGATGTGGCTTGGACCAAGCAG[A/G]CT[A/G]GAT
CTTGGAAGCTTCTGGGTCTTTTCCTGCTGTGTGCTATGATCTGCCTCTTCTCTCTTGGGGCTTCTTTGTAAA
AATAAGCTGCCAGTACAGCAGGTACTCCA[C/G][C/T]TCTGTGGCTGCTGGCGAATCCAG[C/T]GAAGCTT
CTCCTACCTCCCCTGCTGTTTCTGAAGTACACCC[A/G]ACGAAA[C/G]CAAAGCCAAGACGTCTTGATAGCT
TCAAAGATCTGATG[C/T]ATTTTGTTGACAAGAAGGAGGAAGATGTTAAAAA[A/G]GAAATGAAAC[A/G]G
AGATCAAGCGATAAAGATAATCATGG[C/T]GTGGATCCTCAGATACACACTTGTCTCTTCAGCATAG

FIG. 26

LpOs05g0152900

ATGG[C/G]ACGGCGTCTACACGCCCGCAGCGGCACTC[C/G]A[C/T]G[A/G]CGTGACTTTAGACAACA
[C/A]CGACGGCCTCGACTGC[C/G]GC[C/A][C/T]TTGCTGCCTACC[C/A]CTCAAGCCGCCATCTTCC
AGTGTAAGGTGGGGCACGTGGTATGCTC[C/G][C/A]CGTGC[C/A]GA[C/G]ACAAGCTGGGGCGGCTC[
A/G]GAGGTGGCATGTGTGTCGCACG[A/G]CGAC[C/T]TCCGCGGATACCA[C/T]CGGAACCA[C/T]GA
CATGCACAAGCTCCTGGA[A/G]TC[C/G]AT[C/T]C[A/G]CGTGCCTGCTCCAACGCCCCTACGGCTC[
C/T]GC[C/T]GCCAAGCCGGCTACTA[C/T]GAC[A/G]GGGACACCCACCTCGGGTTGTTCTGCCAGCACG
CGCCTGCCACTGCAATATAGAAGCATGTGGCTTCGTTGGCTCGACATTATCGGCGCTCCTTGACCACGTCTTC
GCCGTGCATGTTGAATAA

FIG. 27

LpOs05q0153200

ATGGACTATACCTCGGATGGAGATTCTGAGCTTGAAGCTTATGGCTCAGACACTTATGCACTTCTGCTGTCAGG
AGATATACAAGTGATGAATGATGAGGGCTTGTACAAATGCCCTTTTGTTCGGATGAAAAGGATGACTATAACA
AATATGATTTACTGCAGCATGCCCTTGGTGTGGGGCTGCACATGATCAGCAAGTGAAAGAGAAGGTAGACCAT
CGAGCCCTTCCCAAGCATTTGAAGGATGATGAACCAGCTAAATCCCATAGCCCACTCCTGCAGCCAATTGTTAT
AGATGCACAGCCTCCTCAACATAACAGAGATGACCTGTTTGTCTGGCCTGGATGGGTATCATAGTCA[A/G]T
ATGGCT[C/T]CTGA[A/G]TATGTTGGAAAAAG[C/T][C/G]CAAACCGGCT[C/G]AAGG[A/G]GCATTT
CTCACGTTT[C/T]TATCC[C/T]GTGAAAGTGTACCATGT[C/G]TACAGTAAAG[C/G]TCGCCTACAGGA
AATGCTATTGTT[C/G]AGTTTGGGAAGGACTTGGTTGGTTTTAGAAATGCACTA[A/G]CATTTGA[C/G]AA
TCAATTTGAAGGAAGGG[C/T]ATGGGAAAAT[A/G][C/G]GCTGGCAGGAAAAA[C/G]AGCATGGAGGG
CCAGAGCCTTTTGGATGGATCGCTAGAG[C/G]AGAC[A/G]ATTACAAT[A/G]CTCCAGGAGCAA[C/T]AG
GGACTTTCTAAGAAAAATGGTGATCTGAAGACGGCTGACGGTGTTGAGGATGAAGAAACAATGAAAATAAC
AAACTTGTGGCCACTTTATCTTTAAAGTTATTGAAACTGATATGCATATAC[C/A]AGAACT[G/T]AAATCT
GTGTATCAGGA[C/G]AGAACTGC[C/A]TCACTGAAAGAATGATGGAGCAGAGGGAACAGCAGCTACAGTCA
TACAATCAAGAAATCCAAAAGATGCAACAGCTTTCTGTTGAACA[C/T]ACAA[A/G]AAC[A/G]ATTGTTGA
CGGACAAGAAGCTA[C/A]GCCTGGATCTTCAGTCTATGACGCATGAGCTTGATGCAGGTCCAAACAAATT
GATGAGTTGGC[C/T]GCACAGACTGATTGTGACAGAA[A/G]AAACCTTGAATTGGAGAAGCAAGGAATGC[
C/A]ATGAAGTTCAATCATCTTACGCTGGCAGAAC[A/G]GGAGTATCAGAAAGCTGATGAAAATGTTCTAAAG
CTTGTCGAACAACACAAGAGAGAAAAGAAACTGCTTTAAA[C/A]AATATTAAGAA[A/G]TTGAACGAAAAG
CTGCATCTGAC[A/G]CA[C/T]AAACTTCAA[C/T]TGGATATAAAGCACCTGAC[A/G]GGAAAATTGGAAG
TGATAAAGCTCACACCAGGCAATGAAACTTCAGAAT[C/T]GGGGAAAAGAATAGCGGAACTGACAGAGGAGCT
GGCTGATAAGATCGAGGAGATGGATTATACAGAAAACTACAACCAAGATCTAATCGTACAAGA[A/G]AAAAAG
ACTGCTGTTGACTTGCAAGAAGCTCGGAAACTGGCGATAGATGCAATACAGCGTTTTCCTGGCCAGAC[C/A]A
[G/T]TG[A/G]C[C/A]AAGCACACAT[C/A]GGCAT[C/G]AAGATGATTGCTGAGCTTGA[C/A]TTGAAA
GCATTTCAAATGTG[C/T]GCAGGCAAAAATTTCCAAA[A/G]GATGA[C/T]GC[C/T]GAAGTTGAAAGTG
TTAAGCTTTGTTCAAAGTGGCAGAATGAAATTAG[C/G]AATCCAAACTG[C/G]CATCCTTTGTGGCTGCTA
TG[G/T]TGAA[C/T]GGAAAA[C/G]AGTCGAAGTGATCAGGGAGGATGACAAGAAGCTCAGGAACTGAAA
GAGGAGTACGGTGAGGAAGCCTATGCTGCAGTTACGACGGCGCTGACCGAGCTCAATGAGCACAGTAGCAGCGG
CAGCAGGGTTCCTTTCCCCGAGATGTGGAACTACAAGGAGGGGAGGAAAGCGAAACAAAGGAAATTGTCCAGC
ATGTCATCAAGCTGGTCAAGGCGAGCAAAGGGGCGTTGA

FIG. 28

LpOs04g0645500

ATGGACAGGGGCCCAGGTAGCGATGAAATGATACCAGGGGTATTTTCGTCGGGCATCCGTGTCTGCAGGTGGC
CGCCGCCGCCGTAGCACCTTTGACCTGGGGACGCCGGATCTCGAGGCTACTGACCGGATCTTGAGGACGGCGC
CGCCGCCGGAACCGGAGGCTACCGGTCGGACCTGCAGGGGCGACGCCGGGCCTGAAGCAGACGTAGATGTGGCC
GGCCGAGCCCTGGCCGTGGTTGAGCGCGACGGCGCGCACGACCCGGCCACCGGCCGGCGCTCACCGGCTCCTG
GCTATGGACTC[C/G]GCG[C/A]TCGTCCTCACCA[A/G][C/T]C[A/G]CCTCGC[C/T]TC[A/G]GC[
C/T]G[A/T][A/G]CCCA[A/G][C/T]C[C/A]G[C/G]TCCT[C/G]GG[C/T]GCC[A/G]CCG[C/T]G
[C/G]TCGACCT[C/T]GG[C/T]G[C/T][C/A]GG[C/T]ACGGGCCT[C/T]CC[A/G]GGCATCGC[A/G
]GCCGT[C/T]GC[A/T]TGCCT[C/T]GGCGCCGCGCG[C/G]TG[C/T]GTGCTCA[C/T]GGA[C/T]GTG
C[A/G][A/G][C/G]C[G/T]CT[C/T]CTGCCGGCCT[C/T]AG[A/G]GC[C/G]AAC[A/G]CCGAGGC
[C/G]AACGG[A/G]CTCGACCTCG[C/A]C[A/G]C[C/G]G[C/T]G[C/T]AGG[C/T]GGACGTGCG[G/
T]GAGCTCCG[C/G]TGGCGGCAGGAG[G/T]A[A/T]GA[C/T][C/A]TGGT[A/G][C/A]TGCTCGATCG
TGAC[C/G]TC[C/G]C[A/G]TGCGT[G/T]GACGTGCTGCTCATGTCCGACGTCTTCTACGACCCGGAGGAG
ATGCCGGCAATGGCTACCACGCTGCGGCGGCTGTGGCGGACGGCACGGTGTGTTGGCGGCGAGCGAGGTGCG
GTGCGGCGTGCAGGACTGCGTGGACGTGCTGGCGGAAGAAGGCTTCGACGTGGCCGAGGTCGACAGGGTCACCA
GGCCGCTGCGCGGCCCCTCGCAGAACGCCGACTTCGCCGTGTATCGCATCGAATTACGGCGGTCTCGAGAG
GGCTCA

FIG. 29

LpOs04g0645600

ATGGGTTCCAG[C/T]CT[C/G]AAGTACCGCGCCGG[A/G]CTCGTCCTCATCGGCGCCGTCGTGCTCATATG
GGT[C/A]ACCTCCGCCGAGGTCACGCAGGAGAT[A/T]TTCGCTGACTA[C/T]AAGCAACC[A/G]TT[C/T
]GCGATCACTTACTTCGG[A/G]GCCTCCCTTATGGTCAT[C/T]TA[C/T]AT[C/T]CCC[C/T]TGGC[A/
G]TTTCT[A/G]AAGGATTC[A/T]TATACAAATTG[C/T]TGAGAAGGCA[G/T]TCTGGAAGCAGCAGAGC
[A/G]TCAAA[A/G]GTCG[C/T]GAGCAAATCTTCCTTTGG[C/T][A/G]GCAGCGCTCCTCTGAAGA[A/G
]C/T]GG[C/T]GAATT[C/T]GAGAAGATGCTGGAAATGGA[A/G]CC[G/T]CAGAA[A/G]ACCGTGGT[
C/G]ATA[A/G]ATTTAC[C/T]GA[C/T]GT[C/G][A/G]AC[C/A]TCCCTGT[A/G][C/A]TAGAAGA
GGC[A/G]AA[A/G]CC[A/G]CT[G/T]AT[C/T]TGTGGAATCGG[A/T]GA[A/G]TT[C/T]GGTGATGA
TGTTCT[C/G]AAGGAGCAACA[A/G]CTTTC[C/A]ACCAAGGAGATTGCAATTACGGATT[A/G]TATCTT
TG[C/T]CCCAT[A/T]TGGTTTGTCACAGAGTATTTATCAAATGCAGCCCTTGCAAGAACAAGTGTTGCCAGT
ACTAC[G/T]GTACTATCTTCAACTTCGGACTCTTCACACT[C/T]TTCATTAGTGTGCTCCTTGGCCAAGAT
TCCAT[A/T]AATGC[C/T]GCCAAAGTTAT[A/T]GCTGTTTTGTTAGCATGGCTGGTGTAGCAATGAC[A/
T]ACTATGGCCAGACTTGGCAAC[A/G]GATGAATC[A/T]GAAGTAAGCAAT[G/T]CAGGAA[C/T]T[C
/T]AT[C/T]G[C/T]CTTGCTAACC[A/G]TCTAATTC[A/T]TAAGC[C/A]T[C/T]AC[A/T]ACTGCAG
GGCCACACAGGACTCTTCTAGGTGATATGTTTGGTCTTCTGTCAGCTGT[G/T]TC[A/G]TATGGTCTCTT
[C/T]ACTGTGCT[C/T]CTCAAAAGTTGCTGG[C/A]GG[A/G]GAAGGATC[A/T]GAAAAGTTGATGT
CCA[A/G]AAA[C/T]T[C/G]TT[C/T]GGCTTTCTCGGACTTT[C/T]ACTCT[C/T]T[G/T]TCTTCTC
TGCTGGCT[C/T]GTCTGGCC[A/G][C/T]TAAC[A/T]GC[A/G]CTAGG[C/G]AT[C/T]GAGCCAAAGT
TTACAATGCC[C/T]CACTCAGC[C/T]AAAGTGGATGAAGT[G/T]GT[G/T]CTGGC[A/T]AATGG[C/T]
CT[A/T]ATTGGAGTGGCTATCAGACTATTTCTGGGCTCT[A/G]TC[C/T]GTGTTTGGACTAA[C/T]C
CC[C/T]TGGTGGCCACCTTAGGCATGTCACTCACAATTGGACTAGCGATGGTTGCTGACATGGTCATCCATGG
TCGACATTATTCAGCAGCTACATTATGGTTCTCTACAGGTATTCTTGGCTTTGTCATTGCCAATCTTGCCG
ATCGCTTTTCACGTTTTCTGGGTCTATAG

FIG. 30

Lp04g064730D

ATCACCAGCCCATCCCGCCGGCTCCCCTGCCCTCACCTCGCCGCCCACGGCTCACCTCGCGCCCGCTCGGCTT
CCCCCGCCGGTGCCTTCGCGTGCGTCCGCTCGGCCGCCCCGAGATCGGCCGCGACGGCCGCGAGGTGGCCCGCT
GCTCGCCCTGCGCGTTCTCCTCCCCGCCCGGGCCCGGCTCTACGGCTGGCTCTCCTGCGCCTCCGTCTTCTGC
CCCTGGCACGCCGCCTCCAACGCCTCCTCCTCCCGGGCGACCAGATCGCGGTCGACGTGGACGGCGCCAGCT
CTTCTGCCCGCCTGCGGGACCAGGTCTACGACCCGGACTTGACTACGCCGTCGTCCTCGCCAGTCCATGG
CGCTCAGCCCCCATCCACCTCCACCCCCTCACCCGCTCCCCGCAAGCGCCCGCGTCGACTACGCGCCTGG
CGGCCAGATCGCCCCGAATCGCCCCTGGTCAGCCCGGCCGCTGATCCCACCACTTCAGCGTCCACAACCGATCC
AGCGGGCCTGCGCGGGCTAAACAACCTCGGGCAACACCTGCTTCATGAACTCCGTGCTCCAGGCGCTCCTCCACG
CGGCGGCCGCTCCGGAACTACTTCCTCGGCGATCGCCACAACCGATTCCTCTGCCCGCGCCGCACGCCCATGAGG
CACCGCGCGACGATGCGGACGCCAAGGCCGCCTGCCTGGCTGCGATCTCGACGAGATCTACTCCGCCACCTT
CTCTGCGGAGCGTACGGCATACAGCCCCGCCAAGTTCCTCTATAGGTCCGCATCTCAA[C/G]CTC[G/T][A/
T]TTTGCATT[C/G][C/G]TT[C/G]ATG[C/T]C[A/G]CC[C/G]TCTCATTTC[A/G]C[C/A]A[A/G]
CCTGCTGTTCT[A/T]TTTAT[A/G]CT[G/T]GCTGGTGGCAGCAGCAACAAACCTTGCAAGCTA[C/T]G
AGCAACAGGATGC[C/A]CATGAATTTTTATCTCCATCCTTGA[C/T]CATATTCATGAAATATAAAGGATG
ATGAGCACAAATCACATGAACAAGGCCA[C/T]GGAGACTGTTGCATTGCACA[C/T]CGGGT[A/G]TTTTCT
GCTATCCTGACATCAGATCTCATCTGCACAAATTGTGGGTTCTCATCCACAACTTTTGAACCTTGCATGGACTT
[C/T]TCTTTACA[C/T][C/T]TGGATGCTGGATGTAA[C/T][A/G][G/T]TTCTCCTGGTCTTGCAAACC
CAAAAG[C/T]ACCCAATGGAGAGAGGAACTTAG[C/T]T[A/G]GCATGAATCCCAAGGTATCATCAACACTC
ATGAGATGTTTGGAGCGGCTTTACCAGGGCTGAGAGGCTAGATGCTGACCAGAAGTTCTTCTGTGAACGTTGCAA
GGAGGGCAAGAGTCCCTTAAGCAAATGTCCATTCGGAGGCTTCCACTAGTTCCTGCTTTCACATCAAGAGAT
TTCAGCATTCGACAGTTAAGAAGATCTCAAGCAAGGTTGATCACTCTTTGCAGTTCCTTTTTCTCTTGACATG
CCACCTTACCTGTC[A/G]TCCTCAATTCTCAGAAG[C/T]AGATA[C/T]GGGACCGCATATTCCATCACA
[A/T][G/T]CCAT[A/T]GATTCAGAAGCA[A/G]TT[C/T]C[A/G]GAATT[G/T]TCTTCAGAATTTGAA
ATATTTGC[A/G]GTGATCAC[A/T]CATAGTGGTAAG[C/T]AGATGCTGGCCACTA[C/T]GT[C/G][A/
G]CTTATCTCAGGTTAAACAATCAGTGGTACAGATGCGA[C/T]GATGCATGGTAACCAGAGTTGA[C/T]GA
GCATACTGTCAGGACTTCCCAAGCATATATGCTCTTCTATGTGCAGAAGAC[A/G]CTTT[A/T]CTATAAAGC
TTC[C/T]GAAA[A/G]GC[C/T]AGCTGCAGTCTGA

FIG. 31

Lpes03g0193400

ATGGGCAGGCGAGGCGGCGTGTTGTTTGTGGTGGGGGGAGGAGACGGCGTGGCGAGGAGGCGGGATGGGGAGGC
GGCGCCGCGAGGAGGAGGGGATGGGGGCGCCGGGGACGGATGCGTGCTGGGGAGGGGGAGCGATGGCTTTCTGC
GAGAGGAGAATACTGGAGGCGGGATCGCTAATTACATGGTGGTAGACTACTACCTGTATGACTACGAGTACGCC
GAGCCCCCCGCCTGACCAGCCTGCAGAACGCCGTTCCCAGAGGACCTTCAGCGACTTCGGAGATGACGTCTA
CTTCGTCGGCGACAAACGGGCTACGAGTCCGTCGTCCACTACCTCCCCGGCCAGTACCTCAACACCGACGACT
CCGGCAACGTCGCCGACCCCGCCCTGCAGCTCAACAAGGTGGTGCGAGAGATCTCCTACTCCTC[C/G]AG[C/
T]GGAGTC[A/G]C[C/G]GTCAAGACGGAGGACG[A/G]CTCAGTGGACC[A/G]GGCAGACTATGGTCAT[C
/G]GTCTCTGCCAGCTTGCCATCTCA[C/T]ACCCA[A/G]CA[C/G]ACCACTCT[A/G][C/G]TAA[C/T]
TACTCGATCATACTCTTGACA[C/T]TTGCTATGTCGATCGACCTGCA[A/G]GCATGGAA[A/G]ATCATCGC
CATCTAC[C/A]G[A/G]TT[C/T]GACATGGCAGT[C/G]TACACCAAGATCTTCCT[C/A]AA[A/G]TTCC
C[C/T]CGGAAGTTCTGGCCCACGGG[C/A]GA[C/A]GG[C/G]AAGCAGTTCTTCGT[C/G][C/T]ACGCC
AGCTC[C/T]AGGCAGGCTACTA[C/T]GGGATGTGGCAGTC[C/G]TT[C/T]GAGGAGGAGTACCCGGG[A
/G]GC[C/T]AACGTGCT[C/G]CT[C/G]GTGACGGTGACGGACCA[A/G]GAGTCGCGGCGGATCGAGCAGC
AGCCGGACAAC[A/G]C[C/G]AC[C/G]ATGGC[A/G]GAGGC[G/T]GTGGC[G/T]GTGCTGCG[C/G]AG
GATGTTCCCCG[A/G]CGAGGACGTCCC[C/A]GACGTCACCGA[C/T]ATCTACGTCCC[C/A]G[C/G]TG
GTGGTCCAACGGCTTCTTCAAGGGCTCCTACTCCAACTGGCC[C/T]ATGGCGTCAACCGCTACGAATA[C/T]
GACCAGCTTC[G/T]GGCGCCGGTGGG[A/G]CGGGTCTACTTCACT[G/T]GGGAGCACACCAG[C/A]GA[
A/G]CACTACAATGGCTATGTCCATGGAGGTTATCTTGCAGGCACGGATTCTGCTGACATTCTGATGAACAGTA
TCTTCAACAACGTGGAGTTAAAGTCCGCGCAAGTACCATGACCAGCGGCAGAGGCTAAATGA

FIG. 32

LgOs06g0607800

ATGCCCGAGCCCGACCATGCCGCGGCCGCCCGCCGACGCACCGTGGTCACCGACTACCGCAACAAGCTCCT[C/
G]AACTCCCGCCAGCTGGAGACGAGGGTCCGCACAGAATTAGAACTTGACAGAGGA[A/T]A[G/T]AAGAGTG
ACTACCCAGTATCT[C/T]GATCAGCTAGGGAGAACCT[A/T]AAAAGGCAAAGAAAGATTATGATAAAAC[A
/G]GAAGATGACTTGAAGTC[C/T]TTGCAGAGTGTGGGCAAATCATTGG[G/T]GAAGTACTTCGGCCATTG
GACACTGAAGATTTAT[C/T]GTCAA[A/G]GCCAG[C/T]AGTGGGCCAC[A/G]TTATGT[A/G]GTTGGC
TCCAG[A/G]AG[C/T]AAAGTTGACAAAGAAAAGCT[A/G]ACAGCTGGAACGCGGGTTGTTCTTGACA[C/T
]GACAACTTTAACCATTATG[C/A]G[C/A]ACTCTACC[A/G]CG[C/T]GAGG[C/T]TGATCCCGTGGTCT
ATAACATGCTACA[C/T]GAAGACCC[A/T]GGCAA[C/T]GTCAGTTA[C/T]TCAGCTGTAGGTGGATTATC
[A/G]GATCAAATAAGGGAACTGCGGGAGTCTATGGAGTTACCGCTTATGAATCCTGAACTCTTTCTGCGTGTT
GTGATTAAACCGCCAAAGGGTGTTCTGCTCTATGGCCCACCTGGAAC[G/T]GGGAAGACA[C/T]TGCTTGCT
ACAGCTAT[C/T]GCTAGCAACAT[C/T]GATGCAAACTTTTTAAA[A/G]AAGATTGTTTCAAGTGCTATCAT
TCACAAATATAT[C/T]GGTGA[A/G]AGTGCCCGTCTTATA[C/A]GAGAAATGTTCAACTATCCACGCCACC
ATCAACCATG[C/T]ATTATTTCATGGATGAAAT[C/T]GATGCCATTGGTGGCGAAGATT[C/T]AG[C/T
]GAGGG[C/A]AC[C/T]AG[C/T]GC[A/T]GA[C/T]CG[G/T]GA[A/G]ATCCAACGGACATTGATGGAG
CTCCTAAATCAGTTAGATGGATT[C/T]GATGAGCTTGGGAAGGTCAAGATGAT[C/T]ATGGC[A/G]ACCAA
G[C/A]G[G/T]CCTGATCT[C/G]TTGGATCCTGCACTCCTTCGTCTGGACGCTTGGACCGGAACATAGAAA
T[C/T]CCATTGCC[A/G]AATGAGCA[A/G]TC[C/G]AG[A/G]A[C/T][A/G]GAGGT[C/G]CT[A/G]
AAAATCCA[C/T]GC[A/G]GC[C/T]GGTAT[C/T]GCCAAACATGGCGA[A/G]ATTGATTATGAGGCT[A/
G]TTGTTAAGCT[C/T]GCTGAGGGCTTCAA[C/T]GG[C/T]GCCGATTTGCGCAATGTCTGCACTGAAGCTG
GCATGGCTGCCAT[C/T]CG[A/G]GCAGAGCGTGACTACGTCATCCATGA[A/G]GACTTCATGAAGGCGGTG
CGAAGGTGAATGATCCCAAGAAGCTCAGTCTAGCGCCCACTACAGCGCAGACTTTGCAAGGAATAA

FIG. 33

LpOs06g0607900

ATGACAAGCTCAAGAGCCTGGCGTCCACGGTGGGGCCCCGGAGGAGTCCGCGGGACGGCTCGGCAGATTGC
CCCGTCGCCGATGAAGCTGCTGGTGCGCTCGTGGAGGGCGGGGCCTGCTGGCGGTGCACGTCAACGGCACCA
GCCACGCCTTCGTCAAGCTGCAGCTCGGCAAGCGCCGGGCCAAGACCGGCGTCGTCAAGAAGAACCTGGCCGC
GTCTGGGACGAGGAGTTCAGCTTCCTCGTCGGCGACGTCACCGAGGAGCTCGCCGTATCCGTGCTCAACGAGGA
CAAGTACTTCAGCAACGACCACCTCGG[C/A]AGGGTCAAGGTGCC[C/A]CTCTC[C/A]CAGGTCATGGACA
CGGACGCCCTCTCCTCCG[C/T]ACCGCATGGTACCAGCTCCAGCCAAAGAGCAGCAAGTCCAAGAGGAAATG
GGG[C/T]CCCGAAATCTGC[C/T]TGCGCATATCCTTGTC[C/T]ACACG[A/G]ACGCAC[A/G]TGTCCG[
A/G]AGAA[C/T]TGCA[C/A]CCTCTACC[A/G]CGGCCGC[C/T]TC[A/G]GA[C/A]GGGTATGATCC
AGTTCAGCAGGTC[A/G]ATGGGACCAA[A/G]CG[C/T]GGAGCTCTGTCAACCACCAACAGCTACATTGA
CCT[C/G]TC[C/A]GC[C/T]GTGGCC[A/G]GCTTGGACCGAGG[A/G]TC[C/G]CAGAGCAGCTTCGA[A
/G]CG[A/G]TC[C/G]CC[A/G]GATAGCTTCGTGA[C/G]CAGCC[A/G]CCC[C/A]GGAGCAGC[A/G]
TCGA[A/G]CA[A/G]CCAG[C/T]C[A/G]CCGAGCCTGG[A/G]ACG[G/T]CCGCTCAAAC[C/T]GA[C/
T][A/G]CG[A/G][C/T]G[A/G]CCAACAC[A/G]TC[A/G]TCGATGGT[A/G]GAGGTCTTGTC[G/T]C
GCTA[C/T]TTCTTCGGAAACCTG[C/T]CGA[C/T]GC[C/T]G[C/T][G/T]GTG[C/G][C/T]TGC[A
/G]G[C/T]TGTCTC[C/T]GA[C/T]GCCGAGTCG[A/G]TGGTGGATCAGTC[C/G]CC[A/G]GAG[C/T]
CGAAAG[C/T][G/T]TGCTCTGAAGAACGTGAA[A/G]G[C/T]CCTGAGAA[C/T]CGC[A/G][C/T]GCC
ACCTCAG[A/T]C[A/G]AGCCTTGATGAGCTACT[A/G]AAAAT[C/T]ATCAGTCCAAAGATCA[A/G]GC
C[G/T]CTGAAATGCCAGC[C/T]AA[A/G]CTGTC[A/T]AA[C/T]GGCGT[G/T]CTGGT[C/T]GA[C/T
]GAATC[C/T]TA[C/T]GT[C/T]A[C/G]TGCACC[A/G]GC[C/T]GGACTGATA[C/G]GCT[C/A]TT
GTTTCTCCAAATTCAGA[C/T]TTCTGGCCGGC[A/T]GTAGCAGA[A/G]CTTCAAGGAACAAGTGG[A/G]
TTTCAGATTCA[A/G][C/T]C[A/G]TGGAAGATCGATAGCAA[C/T]GATGGTTGTTTGCGAAGAACATT[A
/G]A[C/G]TTACATAAAAGC[A/T]GCGAGTAAG[C/T]TGGTTAAAGCT[G/T][G/T][C/G]AA[A/G]G
C[C/T]ACAGAAGAGCACAA[A/G]TACTTGAA[A/G]GCAGCTGGGAATTCTTTTGCTGTT[C/T]TGTCTAT
TGTTAGCACTCCTGA[G/T]GT[C/T]CCTTG[C/T]GG[C/A]A[C/A][C/T]TGTTCAAGATAGAGATA[
C/T]TGTACT[C/G]TATAAC[A/G]CCAGGTCC[A/G]CA[G/T]TTATC[A/T]TC[A/T]GAAGA[A/G]C
AAACGGCACACCTTACTCTAAGTTGGCGGAT[C/A]AACTTTGT[C/T]CAGAGCACAATGATAAAGGAATCA
TTGAAAATGGGCAAACAAGGCATGTCAGAAGGTTATGCACAATTTCTGAAGTACT[A/G]TCCCAAAAGTT
TAA[A/G][A/G]TAGCTGAGCT[C/T]GATGATGCTAATGCAA[A/G]CAAAGCAAAGATTTT[A/G]GCTTC
[A/G]CTGCATACACAAAAGAACC[A/G]AGCTGGAGGCTGATTGTGCCGCTTCCT[C/T]GGGA[A/G]CTTC
ACATTCATAGTCTCTGTTATCGT[A/G]GGG[C/A]TATATATTATA[A/G]CACACCTTCATTT[A/G]TCAA
AGCCCAAAGCGATGAATGGGCT[C/T]GAGTATTTGGCATTGACCTTCC[C/A]GATTCAATTGGAGAGGTCG
TGGTTTGTGCTGTGTTGATCCTTCAGGACAGAATATCATGAAAGTAATGAAGCGCTTTT[C/T]GAATGCATG
GAAACAAGAGGTAGTGATCATGGAGTCAAAGCTCATGG[A/G]GATGGTTGGATACTGACTGTTGCACTTATT
GAGGGCA[C/G]TGGTATA[A/G]TA[A/G][C/T]TG[G/T][C/T]G[A/G]TTCCTCTGGCTTA[C/T]TT
GATCTTTATGCTGTTTTACTTGCAAT[A/G]CGAAGAGGAAAACAAGCTCAATTAAATTCCACACCTCTGATC
CAAAATGGAATGAGATATTCGAATTTGATGCAATGGATGATCCACCATCAAGGATGATGTGGCTATTCATGAT
TCTAATCGATC[C/T]GATGGAGATCC[C/T][A/G]TTGGTCA[C/T]GCTGAAGT[A/G]AACTTCTGA[C
/A][A/G]AGCAGTTTGTCAGATTTAACTGACATATGGGTTCCTCT[A/T]GATGGGAAGTGTGATCCAGCAAG
CAACCC[G/T]AAGCTACACTTA[C/A]GAAT[C/T]TT[C/T]TTGAACAA[C/T]TCAAGAGGAACTGAAGT
TGTCATGAATTACCTGTCAAAGATGGGGAAAGAAGTCGGTAAGAAGATAAAATTGCG[G/T]TCAGC[A/T]CA
AACAAATTC[C/A]GCATTCCGGAAGCTTTTTAACCTCCCTCCAGAAGAGTTTCTCATTGATGATTTCACCTGC
CATCTAAAACGGAAGATGCCACTGCAGGTTATCCCTC[C/A]TACACTGTCAATTGCAG[C/T]CCATCCTTG
ATGGTCATCCTGA[A/G]AAAGGATAGAGGGTCAGAAGCAAACATGGTGCCAAGGGAAC[C/A]GATAACAAT
GGAAGATTGAAGTTCCATTTTCAGTCCTTGGTTTCGTTCGGTGATGCTCACAGAATAATTATGGGGAT[C/T]T
GGAAAA[C/T]GCGGTCACCGGGTCCAGAACAGAAGGGGAGATAAT[G/T]GAGGAG[A/T]CTGAAC[C/T]
[A/G]AAAGAACTCCCGGC[C/T]GAAGAATC[A/G]GGGTCTTATTTAGCCATGAAGATGT[C/T]AAAATG
TCTGAAATATTCTC[A/G]TCAGTT[C/A]TCTCTGTGGACAATATATACCAG[C/A]GGCAAATCAAATCAA
CTACAAGTTTGACAAAGGATTGTCTCGATCTGGAGGAAAGCAAGCACCACTCAACAGAAGTATGCCCTAGTCA
ACCAAGATGG[C/G]TGGGCCATTGAAGAGGTGATGACACTCCAAGGTGTTCTACTTG[C/G]GGACTACTTTA
GTTTTGACAAACCATTCTCAAGATATGGAGGAAGCAACCACCACTCAGCAGACGTATGCTCTAGTGAACCAA
GACGGCTGGGCCATTGAAGAGGTGATGACCCTCCAAGGTGTTCTACTTGGGGACTGCTTCACTCTCCA[G/T]C
TCCAGCT[A/G]AAGTATCATATGGCGAA[C/T]GT[A/G]CC[A/G][C/G]C[A/G]AAACCAAACACCTGC
AGTGTCCAGGTTTTGTTGGGGATTGCCTGGTTAAAGAGCACCCAA[C/G]CA[A/G]CAAAAGAAGGTCACAAA
AATATCATGTCGAATACCTC[A/T]AATAGATTGAAGGAGCT[C/A]TTTTCTGAAGT[C/T]GAAAAGGATCT
TACGTCAAGAAACGGTACCCTTTTTAGCGGCATCTATTGATCCTTACCGTTCTTTA[C/T]ATGAT[C/T]CTAA
TATCACGTAA

FIG. 34

LpOs04g0648500

ATCAACAAGCTACGAGCTGCAGGCATACCACAAGATGCAGGTTTATCAGATTTTCTGAAGAACAGGCTACAGAA
GATACCAAGGATTCTGCCCCCACTCAGCTTTTCTTGGGTCCGCCCTGCATAGAAGTAGAACCGTAGAAACAC
CATGTGGAGGCAAAATCCCTTCATCAGAGGAGTTTT[C/G][C/G]TTGAT[A/T]TTACCCCTTCTTGCTGTC
TGCGTCTGTCCGTAGGAACTCTCTACGAACAGAGTCCGTCGAGT[C/T]ACC[C/T]GTGCCCGACGCCTTC
GC[C/T]G[C/T]CCTC[C/A]CC[A/G]CCGCCGACGCCGA[C/T]GAAG[C/T]GGAACCAGCAGCTCC[A
/G]CCG[C/G]CG[C/G]GGCGGCCA[A/G][C/A]CGCATCAAATCCCAT[C/A]TCCCC[A/G]CGCTCC
AGCAAC[C/T]CTCCCCTCC[A/G]CCACCTCGCCACAACCCCTCTCGAGCTGCCGGCGTA[C/A]C[C/
T]C[C/T]CGCCGC[C/G]TCCGC[A/G]CGAAACCCTAAGATCCACCGCACCC[A/G]CGG[C/T]GTCCTCC
ACCTCTACCGTCCTCCCC[C/A]TCC[C/T]TGCCCGC[C/T]TCATCCTACGGCTCGCCGTCGCCGTCGCC
G[C/T]CACCCCCTCCTC[C/T]TCCTCCTCCGGGCC[C/T][A/G]CC[C/G]CCCCACCGCTCCAAT[C/G]
CGA[C/C]TC[C/G]CT[A/G]CTCCCTCATGGCGCGGCACGGCCCTCCTTGTGCTCGC[C/T]GTCCCTACC
CGCGTCTCGC[C/G]GA[C/G]GACTTCGTCCG[C/T]TTTTGCGGCCCTACGT[C/T]GA[G/T]CACGCC
TCCGAGATCCGTCTCATCAGCCGACGA[C/T]GG[A/G]GTGGAGGACGG[C/G]TACAGC[G/T]TGCTTGTGG
AGTTTGAGGATCAAAGAGTGC[C/T]GA[C/T]GCATTCTACCTGGACCTCAATGGCTGGAGGTTCTCGTCCT
CAGAGGTTGTAATA[C/T]TGCCA[A/G]TTTGG[C/T]CCCAGTTGGTAGAGGTGTGCCATGTTCTGTTTATA
GTTGCTGTCCAATACATGGCATCCCCTCTGCCACCAGTTGGATCTAC[C/T]GAGCTTCCGAC[A/T]TGTCCT
GTTTGCAT[A/T]GAAAGCTTGGATCAAGACATCAGTGGAATTGTGGCAACCAATTGTGACCATTCTTTCCAGT
GTTCATGCGTTTCAATGTGGTCAGTTCATCTTGTCCGGTTTGTCAGTTTTG[C/T]CAGAAGCAGTCTGAAAC
TCCTACAAATCCTACATGTTCTGTTTGTCAGACCTCTGAAAACCT[C/T]TGGATCTGTGTGATATGTGGTTT
GTTGCATG[C/T]GGAAGGTATAAAGAAGGCCACTCAATTAGGCACTGGAAAGA[C/T]ACTCAGCA[C/T]TG
CTATTCTCT[C/T]GATTTGGAAACTCAAGGTGTTGGGATTATGTCGGTGACAGTTATGTTCATCGTCTTAAT
CACTCGAAAAGCGATGAAAACATTCTAAGCTCAGGTCAAAGTGTGAATTTTCTGGGGACAACGATGACT[C/T
]GGATATGGGTGGAGTTATGTTTAGCAGCAAAACTGATACAATGGTGGATGAATACAACCGTCTTCTTGCAAGC
CAACTTGAAACTCAGAGAGAGTATTACGAGGCTCTTCTGTCAGACGGTAAGAAAGATAGGGAACACATTTCTGT
TGCTGTGGATAAAGCTGTAAATGATAAGCTTCAAGAGATGCAACTTAAGCTTGAAAATACTATGTTGGAGAAAA
AGAAAGTTGCAGAAATGAATGAAAAACTCATGAAGAGCCAGGATATATGGTCCAAGACAGTAAAAGGAATAGAG
CAAAGGGAGAGACGCCAGTTGAGGCTGAAGGATGATACAATTCTTGACCTGGAAGAACAGATTAAAGACTTCAA
GTACTGGATTAAGTTGCAAAAATCGATAGAGAAGAGTACACATGCTGATGATCTCAAAGGAGGTATGCTGGTGC
CACTGGCCATGGAATCAGAATCTGGAAAGGGTGCAGAGTTTGAGCATTATGTCAACATGTGTAAAAAAGATCAT
GAGGCACGATACCAAAAAAATTTATTACCATCTAGGAAAAACTCTGACTCAATGGAAAAATTACTCATCCCACC
AAAAACCACACCACCAAGCTTTTTGTTTGATACCCTCAAGGTCAAGAACATGGGATAA

FIG. 35

LpOs04g0648500

ATGTCGA[A/G]GCTGACCGTGGGGGT[A/G][A/T]GCA[C/T]CATGGTGGCGCTCAG[C/T]CTGGCCGTC
TTC[C/T]TCACCATCGTC[A/G]TCCTCCTCCT[C/G]GCTGACCT[C/A]TTCTGCTCCCACCTCCGCC[G/
T]CGGCCG[C/A]CT[C/T]CGCGCTGACGC[C/G]G[C/A][C/G]ATGGC[A/G]CCGCACAAGAGGCC[A/
G]AAGC[A/T][C/T]GGCG[C/T]CCCGG[C/T]GTGTCCCC[A/G]CCG[C/T]ACACC[A/G]CCGACGA
[C/T]CCGTC[C/G]GTGGCCACCACCACCAC[C/G]ACGGCGACGCACGAGGCGCTCCAGCACCC[C/T]G
CCCTTCTACTAC[A/G]CGCACGG[C/T]GTCATGTGC[A/G]CGCCCACCCGCAA[G/T]GACCTCCTCG
CCATCCCC[A/G]AGCT[C/G]GAGGCC[A/G]CCGTG[C/T]GGAAGTGGTCTCCCGCG[C/T]GCCGCTCCT
CG[C/A]CGTCGCC[G/T]TCGCC[A/G]CC[G/T][C/T]GGTCCGAGCCCACCGCC[A/G]CGA[A/G]TC
CT[C/T]CTCC[C/T]CCGC[G/T]TACAGC[A/G]ACGGCTTCCTGCCA[C/T]CTCCAACCCCGT[A/G]T
ACGAGCGGGGCGC[C/T]A[C/T]GGCCG[C/G][C/G]CC[C/G]GGCG[A/G]G[C/T]ACGAAGAAGACA[
C/T]GC[C/T]GTTCGACACGCTG[A/G]C[A/G]C[A/G]TCGCC[A/G]TCCCGAATGGATTACAGAGG
AAGAGGGCTTTTGGACGTGTCAACCACACGCATCAGGGAGCCCGATCATGA

FIG. 36

LpOs04g0648900

ATGGCGCCTCTTCCGGGC[C/G]GC[A/G]GC[C/G]GC[C/G]GCCGTGGCCGC[C/G]AAGGAGGAGCTCGGC
GTGACGGTGGTC[A/G]TGGCGCCGCCGATGGCGCTGGCCCCGCTGAGCCAGCAGCA[G/T]CCGCGGCGG[C/
T]AGTACCGGCG[C/T]GTG[C/T]GCATGCG[C/G]AAGTGGGGCAAG[A/T]G[A/G]GTGGCGGATCC[
A/G]GGAGCCGCACAAG[C/T]G[C/T][A/T][C/T]GCG[C/T]ATCGGCTCGGCTCCTAC[A/G]CCACG
CCCG[C/T][C/G]GCCGCCGGCGG[C/T][A/G]CCTACGA[C/T]ACGG[C/T]CGT[C/G]TTCTACCTG[
C/T]GCCGCC[C/G]TCGGCAGGCTCAACTTCCCCGACGAGATCTCCGCGCT[C/G]GCCCGGCT[C/G]TC
CCCGCC[G/T]CCCGAGGAGCTGGAGGC[C/G]GACGGCGGCGCGCTGCGG[C/T]GGCGTCGATC[C/T]GG
AAGAAGGCTATCGAGGTCGGTGCCCGCGT[C/G]GAC[A/G]CGGT[C/G]CAGACCGG[C/G]ATGAC[C/G]
ATGGTCCCT[A/G]C[C/G]GCCGGCCGGCCG[A/G]CGAC[A/G]AACCA[C/G]CG[C/G]GAGCGGCAGAG
GCAGCA[C/G]CAC[A/G]C[A/G]CAGCAGCAGGC[G/T]GCCG[C/T]CA[C/T]GACGAGCTGCTCC[A/
T]GCTCCACCACCACAAGCAGC[A/G]GACGG[C/T]GTGGAACGGCGGCGCCAAGAACCCGGATCTGAAC
CAG[A/G]CGCCCGACCC[C/G]GACAGCTCCGACGCCGAGTGA

FIG. 37

LpOs05g0146600

MG[T/A]DLG[T/A]ELGALALKYTG[M/V]SLGVSCYDSIVAMNIFVALLCGCIVFGHLLECMWVNESTTAL
[S/I/C/V][F/M/Q/L]V[L/F]AVLSD[R/W]G[R/W]VA[S/W]LITGGVILLVTNGVNSRILVSGEDIPF
IYLLPPIIPRACFQVKKQFPRNFATITLPGAIGIL[I/V]SFVIIS[L/V]GAMSLFSKLDVSPLQLSDYLA
GAIFSATGSVCTLQVLNQDETPLLYSLVPGKGVVNDAFSVVLFNAI[Q/E]NIDLDSFDAFVLLQLIGKFLYLL
FTSTVLGIALLDLSGILTVPPCGIVMSHYTWHRVTESSRVTTRSTPATLSFIAKLFLFLYVGNDALDIERWRLA
[R/G]SRELLINVAGLMRGAVSIALAYSRVGLLTRPLINLLFPPRPSNTADGSSQSFLSPLLGSLLGSDLGIG
QYFPQTRL[Q/E]LLLTIQTDSVHPVWSRFDD

FIG. 38

LpOs01g0368700

MIGAVARIRHQLAYATNTFPDREDFLYINTPIITTSDCEGAGEMFQVTSLPSQAEKVDKELKSNPAPSEAD[I/
V]EAAKLVVKGKGDAVAQLKA[T/A]KASKQEITAAVSSLTK[E/A]KE[T/I/A/V]VLRLKERSKLEFSIPH
[K/R]DDGSIAPERDFFKRAAFLTVSGQLQVEIYACALSSVVTPGPFPRAESGFTSRELACFWWVRPKIAYANL
NDDM[N/D]Y[A/G]SRY[I/V]KYLCKWLLDHCREDMCFNVKIVCKTAIERLELVGSTFFSRISYTK[A/V]V
EILE[P/G]TGKKPEKKVENGIDLASEEE

FIG. 39

LpOs05g0143100

SRETNIGFTGRSIDRSARGPARRDGVSGAGGDAD[P/L]GQQP[E/G]ESDGV[P/L]QDA[G/C]VRG[S/G]
[I/V]SLRRPARAD[T/A]PDALG[P/L]ARRAAVPN[T/P]DR[P/C]KPPRARTAKAPPLR[T/A]LLKR
PRK[R/W]RG[T/A]RPRPGPFARSASRRASPPQLPGATPHEPPEARGAPSLLQPHGRAGDR

FIG. 40

LpOs05g0149500

MRVTITGGG[K/T]RLHVDLYYA[R/C]VQSSA[P/L]FTV[_/M]SLLQLHRRH[P/R]GRVPD[V/L]DLMF
DC[T/M]DRPAIHRTEH[T/S][A/G]EGAPPPPLERYCTTRDS[F/L]DIPFPGWSEVGWFSTS[I/L]EPW
SREFKSIRQGASKWDEEARSGYQNSKLSSQCTBRYKIYASGPAWSVSLKYILSCGSTALLIDP[N/L]YQDFF
SRGLEPRVNHLPVS[T/A]VGMCESIRDAVEWGKAHPDSAERVGPSSQPLMQDLAM[D/G]A

FIG. 41

LpOs05g0149600

MAQQGQDRKTIDLSSSWAYMEGGIGKLVNILSGKHEPQFNSENYPMLYTTIYNMCTQHPPNDYSQQLYDSYRSA
FESYIRDAVLPAIKEQSDEYMLKQL[R/H]VRWKHEKVMVRWLSRFPEYLDRYFITRRSLTPLHDVG[Y/F]EC
FRDLIPQEITKGKVKDAVLVLINQERSGEQIDKTLLKFVLDIFVEIGLTTMSFYENDFEDPLLKDTTEYYSVKAQ
NWIVEDSCPDYMIKAESCL[S/R]REKERV[S/G]HYLHINSSPKLLERVQNELLANYAIQLLESESSSGCYALL
RDDKVDSLKSMPSLFSKITRGLSPVSNMFXSSVTSEGTALVKQASDSASNKEFEKTSNVGMQECVFVWKIIALH
DKYVAYVTDCFSGRTLFHKALSEAFEVFCNKGVSGSSSASLLATFCDNILKKGCSERLSDSAIEDALEKVVSLL
AYISDKDLFAKF[Y/C]SKKLABRLLFDKGANDEHSRSILTKLKQCGSGFTSKNEGMVTDLT[L/V]ARGSQT
KFEEFVASHQEL[N/S]PG[I/V]DLAVTVLTTGPWPTYK[S/T]F[S/G]I[S/S]LP[A/S]ENVKCVEVPK
EFYQTRTKHRKLTWIYSLGTCNINAKFETKTIELIVTTYQAALLLLFNGVDRLSYSEIVTQLRLSDDDVVRLLS
SLSCAKYEILTKEPAGRSISPEDVFKPNSKFTHRMRRIKIPLPPVDSKKKVVEDVDKDRRYAIDASIVRIMKSR
KVNAHTQLVAECVEQLSRMFKPDFKAIKKRIEDLITRDYLERQRDNANTYRYLA

FIG. 42

LpOs05g0150400

MGFGSSRWTGSTALVINWRPLLYCRKEDIPSHSGLERQLPVASLLILPVEASMYKNQLQELAQRSCFRLPSYACI
REGPDHAPPKATVRFNGEAFKSPTPCSTLELAEHAAEVALNS[SKRGPSSSLAAKVLHSTGIYKNLLQST[A
/V/S/F]HKAGLKLPMYTTIRSGPGHTPSFTCTVRLAGRIFTGNPGKTKKQAQMNAAMAAWSRLKSLPR[G/V]
G[K/E][A/V]ASSSSPSDHGK[S/G]SQSQVTVRRTLR[N/S]LHQKNE[G/V]KA[P/A]HQKEPQQRSNR[
R/S]QPRRS[Y/C]PKPG[A/V]SFYGSRLQWQ[T/S][Y/S]PKVAQ[K/S]QAM[R/Y]HMWEQVQPTQQK[
T/P][Q/H]FRMVPT[M/L]GNTAPPPPPTILQWYPPRGQ[Y/F][T/A][M/V]Q/P]A[N/S]QDALAL[
I/L][Q/P]CFFE[P/A]AP[T/A]LPSYPS[P/S]YPASYVP[T/A]SPLP[T/A][A/S][S/I/G/V]NMM
HGRRQSC[D/A]E[T/M]VSLP[N/D]APVF[A/G/S/C]RYTA[Q/P]D[Y/C]S[T/S]ALENVC[T/P]SR
VQQPPRDGKS[A/G][N/S/Y/C][T/P][K/E]SS[A/G]ATEK[K/R]NRAPQ[T/A]SSSST[T/I/N/A/
V]H[H/R]PSQ[R/N]LE[Q/P/E/A]NED[R/R][Q/S]SRR[P/A]AEQPLLGPYVVQPF[A/V]Q[Q/P]Q
[N/S]YP[S/I]P[M/V]QSSSP[L/V]HRN[N/D]LPSF[T/I/M][A/V]TSP[D/G]PW[A/V/S/F][S/
L]DMQTPPRPGT[A/G][N/T]LANSA[S/G][L/F]LYQQRPPWLAAPVTVRTSIPVCSAKPNAAVRSSPGAA
TRVKSTVQMLSRNNSSAQRNTRDMSDASTASSHLSKLSI

FIG. 43

LpOs05g0150500

GNIDICSNARKVPAYMGPVNPTVLEKLVSRCRNLETLKLNNAIPLDNVASLLRKAP[Q/H]I[I/V]ELGTCKF
SADYSPDLFAK[L/V]SAAFAGC[K/T]SLRRLSG[T/A]MDAVPDYL[P/S]AFY[G/C]VCR[S/G]LTSLN
LGYATV[Q/R]GPELIKFISRCKNL[Q/L]QLWVMDLISDRGL[A/S][I/V]VAS[T/S]CSKLQELRVFFSD
PFGHN[A/G]GQV[F/L]DTERGLVDVSASCP[K/T/M]LESVLYPT[S/R]SMTNEAL[I/V][T/I/S]IAK
SRPNFTCFRL[A/G/S/C][I/L]LEPR[T/S]PDY[I/M]T[Q/R]Q[P/S]LDAGFSAIVESCRSLRRLS[I
/M/V]SCLL[T/S]DLVFKSIG[S/A]HADDLSMLS[I/L]APAG[N/D]SDLGL[N/H][D/Y]ILSGCKSLK
KLEIRDCPFC[N/D]K[P/A]LLASAAKLETMRSLWMMSCSLTVSGCRLLALKMPRLTVEIINDPGSTCPVEGL
PFDSPVEKLYVRTLAGPRSDTPDCVQIV

FIG. 44

LpOs05g0151300

MAQS[S/G]SDAAPISTSPTEEEVTVERTPEEE[S/A]ARLPYLSFVQQAAAQAVVLAAAAYAYAKQGAGFLR
PGVDHVEGTVRAVVGPVYDRYHA[I/M/V]PLDLLKFLDRKVOSGVQELDRRVPPVVKEVPTYARSAAASVERT
GLVETATGLAKSAIARAESSARDLYTRYEFVASRKAAEAWAALSRLPLVPSVTRAVLPTAAQLSASYSGAVLDG
AKRGNSVATYLPLVPTERIARVFSYPPTDAAATSAPEMQFIPTQ

FIG. 45

LpOs05g0152400

MLRLTLPCFSTLL[PQR]ILSWRNTCRPPAQEISLTEPH]SARQRLAPATLLIL*MTWKHRNGCVFSGAQPLIN
GLISS]KDETILSAKASATGLGVVTDDLGCSPWVILPPRFIKYCIL*MNLPRVLLRYFMNVVLPQSGYFHSVI
CRSVDFRNSTVRNDLRYKVWDEPPQTEPLFLNMAKYDEMVNSGQPFARRFQRKS[P/R]LL[N/D]KIDDKLLR
RPGHGPVPGANCSCRSGMFVDSCSQPSDVRVVKPGPQALKLQQYINRTLEEARSGAKSCRR

FIG. 46

LpOs06g0680500

MSAAELLSLCLVLAAVAWTEGQRPRAVKVGALFDYDSTIGRAAQLAIELAVDDVRADRSVLAGTKLDLITADFR
CSGFVGTQALQLMEYNVVAVVGPQSSVIGRVISRFVERLRVPLLSFAATDPTLSASRYSYFLRSTVSDYFQM[
R/C]AIASIA[Y/S]YY*WKEVTAIFVDDDYGRGGVSALSDALATKDARISYKAVIF[P/L]DANKKDVISDILF
KVMMESRVLVVRVNPQTGLR[I/L]FSIANELQ*DM[T/S]GGYWIVTDWLAAVLDSSRGSYPK[N/S]MGYM
QGLIALRQHIPDGAAKKKFISRWN[T/F][A/V]ARKRKIASGLNSYGFTAYDS[I/V]WIVAHAIDKFLNSGQ
[K/Q]IRFSADTRLHDGDTSIITLSTLKIFDGSERLLQQLLLTSF[K/T/E/A]GL[T/A]QLVQFD[P/S]DR
SLVRPAYEILRIGSSVP[E/G/D]LIGYWSRYSGLSVAAPETLYQKPPNMSSAGQLST[M/V][A/V]WSG[D
/G]STTKPRGWVFPNNGQPLRIGVPNKPSFKSFVASGKGPDN[M/V]TGYCIDIFNAAVKLLPYPVPSKFISIG
DGLHSPRYDDLIKMVAN[K/N]TIDVA[A/V]GDPAIIKNRTRIAEPTQPYIDS*MVIVAPVKQSTSSAWAFPK
PFTLEM*CVTGALFVFVGIVWIESRTNEEFPGTPQRDV[R/L]TIPWPAFSTMFFAJRRENTVSGLGPFVLII
WLFVVLIRSSYTASLTSILTVQQLVTGVTGLDWLIASTVPIGFPASKPIRRYLIEELN[I/V]HESRLVPLNY
IQDYADALNRGPKAGGVAAVIDEMPCVELFLSYWCKPRIVGQEPTKSGWGPAFQRUSPLAADMSTAILQLSH[T
/S]SQLQRISQSMLTRPGCSSODSGLGPSELDLGSFWGLFLLCAMICLPSLGAFFVKISCQYSRYS[T/S]SVA
AGESSEAGPTSPAVSEVEPTK[P/A]KPRELQSFKDLM[H/Y]PVDKKEEDVKKEMK[Q/D]RGSDRDKSGVGS
SDTSFVSGA

FIG. 47

LpOs05g0152900

M[A/C]PASTRAAAAL[S/D][D/G]VTLDN[N/T]GALDC[R/G][T/I/P/L]CCLPLRPPIEQCKVGHVC
S[T/P]CR[H/D]RLCAA[Q/R]RCHVCRT[T/A]TSGGYRNHDMEKLLESI[Q/R]VPCSHAAYCCAAKPVY
YD[R/G]DTSLRLPCQHAPCSCNIEACPVGSTLCALLDHVPAVEVE

FIG. 48

LpOs05g0153200

MDYTSDGDSELEAYGSDIYALLLSGDIQVMNDEGLYSCPFCSDEKDDYNRYDLLQHALGVGAARDQQVKESVDS
RALAKHLEDEPAKSHSPLLQFIVIDPQPPQSNRDDLFVWPRMGIIV[N/S]MP[P/S]SYVGRS[P/A]NPLK
[E/G]RFCRFTPVKVERVYSR[A/G]RPTGNAIV[Q/E]PGRDLVGFRNAL[T/A]F[D/E]NQFEKEG[K/Y]
GE[I/M][R/G]WQER[Q/E]HGGPEPFGWIAR[A/G]D[N/D]YN[T/A]PGA[T/I]GDFLRKNGDLRTADG
VECESTMSDNKLVASLSFKVISTDMH[Q/P]ELRSVYQ[D/E]RTASLKPMMEQDEQQLQSYNQEIQKMQQLS
VEHT[K/R]TIVDENKKL[S/S]LDLQSMTHSLDARSKQIGELAAQTDCDR[K/R]NLELEKQRNAMKFNHLTL
AE[Q/R]SYQKADENVLKLVEQRKREKETAL[K/N]EIKKLNERLRLTEKLQDIKRLTGKLEVIKLTPGSNETS
E[S/L]GKRIAELTESLRDKIEEMDYTSNYQDLIVQERKTAVELQEARKLAIDAIQRPFGQT[S/T][D/G]
K/Q]AHIG[I/M]KMIGEL[E/D]LKAFSEV[R/C]RQKFFKEDARESVKLCSSWQNEI[S/R]BPN[C/W]R
PFVAAM[V/L]NGK[Q/E]SEVIPEDDYYLQELREEYGEEAYAAVTTALTELNERSSSGSPVPFPEWMKYKEGR
KAETREIVQRVEKLASASKRGR

FIG. 49

LpOs04g0643600

MDRCRCSDEM]PGVFFVGRACLEVAAPAGRIFDLGTPDLRATDR]LRTAPPPSPEATGRTCRGDAGPEADVDVA
GRALAVVERDGAHDPATGRALTGSWLWDSA[I/L]VLT[N/S][S/R]LASA[E/V]P[N/S][Q/P][L/V]L
GA[T/A][A/V][L/V]KLG[A/V]GTGLPG]AAVACLGAARCVL[T/M]DV[Q/R][P/A]LLPGLRAN[T/A
]EENGLDL[D/A][T/A][A/V][Q/_][A/V]DVPELRWGEE[S/D/_/Y]D[N/L]V[M/L]LDRE[L/V][
P/A]CVDVVLMSDVFYDPEEMPAMATTLRRLMPDGTVCNAASEVPCSVGBCVDVLREEGFDVREVDRVTRPLLR
APSQRADFAVYR[S]LRRSPEQ

FIG. 50

LpOs04g0643600

MGSSLKYEAGLVLIGAVVLIWVTSAEVTQEIFADYKQFFAITYFGASLKVIYIPLAFLKDF[I/L]YKLLRR[Q
/R]SGSSRASKV[A/V]SKSSFG[S/G]SAPLK[R/S]GRFEKMLEKEPQKTVV[N/D]FTDV[N/D][I/L]
PV[I/L]EEAKPL]CSIGFFGDDVLKEQQLSTKE[IA]YGLYLCP]WFVTEYLSNAALAPTSVACTTVLSSTSGL
FTLPISVLLGQDSINAAKVIAFVSMAGVAMTTMGQTWATDESEVSN[A/S]G[T/I][S/T][R/C]LAN[S/
R]LI[S/L]K[H/P][S/Y][N/Y]CRATQSTLLGDMFGLLSAVGYSLPTVLLKKFAGGESSEKVDVQK[L/F]
PGFLGLFTL[C/F]LLMWLVWPLTALGIEFKFTRPESAKVGEVVLANGLIGSVLSDYFWALSVVWTNPLVATLG
MSLFFPLAMVAEKVFNGRHYSAVYIIGSLQVPSGFVIANLAGRFSRFLGL

FIG. 51

LpOs04g0647300

MTSPSAPPTCPSLAAHRLTSRPLRFPBBCLRVKPLQPPEIRSDAREVPPCSPCASSSPPPAPLYACLSCASVFC
PSHAASHASSSPCHQIAVGVGRAELFCAACGDQVYPDFDHAVVLAQSTALSPPSTSTPSPAPRKRSRVDYRAW
APDPAESALVSAAADPTTSASTIDPAGLRGLNNLGNTCFNNSVLQALLSAPPLRNYFLGDRSNRFLCPRSTPNR
HRATSADAKAACLACSLDEIYSATFSGERTPYSPAKFLYRSGSQ[P/A][R/L]FA[F/L][L/V][H/D][A/
V][T/A][L/V]GF[Q/R][K/Q]PAVLFY[T/A][G/C]WWQSATNLASYEQQDAHEFFISILDHIEENIRDD
SHKSHEQGHGSECIAMRVFSGILRSDVICTNCCFSSTTPFPCMDFSLDLDAGCM[S/I/G/V]SSGVANPK[A/
V]RKGERNL[A/V][S/G]MSPKVSSTLMPCLSRFTPAERLDADQKFFCEPCKSRQSSLKQMSIKELPLVSCFH
IKRFEHSTVKKSSRKVDHSLQFPFSLDMAPYLSSSILPSRYGNRIFPS[E/D][A/S]IDCEA[I/V][P/S]E
[L/F]SSEFEIPAVITHSGKLDAGHYV[T/A]YLRLNNQWYRCDDAKVTRVDSHTVPTSQAYNLFYVQRTL[Y/
F]YKACE[K/R][P/L]ARV

FIG. 52

LpOs03g0193400

MSSRCCVLFVVCSSDGVARSRCSSAAPSGGSCGAGDCCVLGPGSDGFLPEENSGGSIANYMVVCYYLYDYEYA
SPPRVTSLQNAVPQRTSGDFGDDVYFVADKRGYESVVRYLAGQYLXTDDSGNVADPRLQLNKVVRSISYSSGV
[T/A]VKTED[D/G]SVY[Q/R]ADYRS[R/G]LCQLAIS[R/Y]P[T/A][S/D]HS[T/S/A/G]RYSIILL
T[L/P]AMSIDLQAVKIIAIYRFDNAVYTKIFLKPPRKFWPTG[S/D]GKQFFV[H/Y]ASSPRGYYGSWQSFE
SEYPGARVLLVTVTDQESPPIEQQPDN[T/A]TMAEAVAVLRSMFP[D/G]EDVPDATDIYVP[S/R]WVSNPF
PRGSYSNWPIGVSRYEYDQL[R/L]APVGRVYPT[G/W]EPT[S/G]EHYNGYVSDGYLAGTDSAGILMNSIPN
NVEFKVPCKYSDQTASAK

FIG. 53

LpOs06g0607800

MASKDDAAAHRRWTVTDYREK[L]NCRELETSVFTSLSLDRG[K/N/_/Y]KSDYPVS[R/_]SAPENLKKAKK
DYEKFEDDLFSLQSVGQLIGEVLRPLDTEPPIVKASSGD[H/S]YVVGCPSKVDKSKLTAGTPVVLD[T/N]TT
LTIM[R/S]TLPRS[A/V]SPVVYKNLHEDPGNVSYSAVGGLSDQTRSLPSSIELPLKNPELFLSVGIKPPKGV
LLYGPPGTGKTLLARAIASNIDANFLKKIVSSAIIDKYIGESARLINEMFNYARSSQPCIIFMDSIDAIGGRRF
SRGTSADRSIQRTLMELLNQLDGFDELGKVKNISATN[R/S]PDVLDPALLRPGRLDPYIEIPLPKEQSR[T/I
/M]SVLKTHAAG[APRGSIDYIA[I/V]VKLAAGPSGADLRNVCTSAGMAAIRASRDYVISSDPNKAVRFLNDR
KRLESSAHYSADPGKS

FIG. 54

LpOs06g0607900 Inserted seq

MTKLKSVASTVCAAEECAGSARQIAPSPMKLLVSVVEAPGLLAVEVNGTSDPFVKLQLGKPRAKTAVVKKNLAP
VWDEEFSFLVCDVTEELAVSVLNEDKYFSNDHLGRVKVPLSQVMDTDGLSLGTAWYQLQPKSSKSKRKCPGEIC
LRISLSTRTH[M/V]S[E/G]EL[Q/S]PLPRPTS[E/D]GVSSSSDRSIGTKRGALSTTNSYIDLSAVA[S/G
]LDRGSQSSFEKSADSFV[D/E]QPPRDS[I/V]EQA[A/V][T/A]EPGT[A/S]AET[E/D][T/A][T/M/
A/V][T/A]NTSSMVEVLSRYFFRKP[A/V]DA[A/V]V[P/L/A/V]A[A/V]VSDAES[M/V]VDQSPE[P/
S]K[A/V]CEEERE[S/C]PENR[T/M/A/V]PPE[T/S]SLDSLLKIMESKDQG[A/S]EMPAKLSNGVLVDE
SYV[T/S]APACLE[T/R]LLFSPNSDFWPAVAELQGTSGPQIE[P/S]WKIDSNDGCLPRIL[T/S]YIKAAS
KLVKA[G/V/C/F/W/L]KATEEQKYLKAAGKSFAVLSIVSTP[E/D]VPCG[N/T]CFKIEILY[S/C]ITPG
P[Q/S]LSSEEQTASLTVSWRINFVQSTMIKGMIENGAKQGMSEGYAQFSEVLSQKFK[I/V]AELDDANA[N/
S]KASILASLHTQKEPSWRLIVRFLG[N/S]FTFIVSVIVG[I/L]YII[T/A]KLHLSKPKAMGLEYFGIDL
PDSIGEVVVCAVLILQGQNIMKVMKRF[S/L]NAWKQRGSDHGVKAHGDGWLLTVALIEG[T/S]GI[I/V][T
/I/A/V][G/V][D/G]SSGL[L/F]DLYAVFTCN[T/A]KRSTSSIKPHTGDFKWNEIFEFDAMDDPPSRMDV
AIHDSNRGDGDP[I/V]GHAEVNFL[K/T]SSLSDLTDIWVPLDGKCDPASNPKLHLRIFLNNSRGTEVVMNYL
SEMSKEVGKKINLRSAQTNSAFRKLFNLPPEEFLIDDFTCHLKRKMPLQVIP[E/P]TLSIGSPSLMVIL[K/R
]KDRGSEAKHGAKGTDNNGRLKFHFQSFVSFGDAHRIIMGIWK[T/M]RSPGPEQKGEI[M/I]EE[T/S]E[P
/L]KELPAEESGGLPSHEDVKMSEIFSSV[I/L]SVDKYIP[E/A]ANQINYKFDKALSRSGGEASTTQQKYAL
VNQDGWAIEEVMTLQGVLL[A/G]DYPSFDKPFSRYGGEATTTQQTYALVNQDGWAIEEVMTLQGVLLGDCPTL
[Q/H]LQLSYHMANVP[P/A]KPNTCSVQVLLGIAWLKST[N/K]QQKKVTKNIMGNTSNRLKELFSEVEKDLT
SRNGTLPSASIDPYRGL[H/Y]D[P/S]NIT_

FIG. 55

LpOs04g0646500

MKKLGGGGIPQDAGLSDPLKNNLQKIPRISAPTQLFLGPPLKPSRTVETPCSGKIPSSEEP[S/C/W]LTLPLL
AVSRLSETNSLRTESVE[S/L]PVPDAPA[A/V]L[T/P][T/A]ADADE[A/V]GTSSS[T/A][A/G][A/G
]GGA[N/T/D/A]ASNPISPRSSN[P/S]LPS[T/A]TSATTPLELPGV[T/P][P/L]AASAKNPKIHHT[H/
R]GVLHLYRSSPSLPASSYASAVAVA[A/V]TPSSSSSGP[T/A][P/A]PPLQ[S/C][D/E]SLLPSNPGTR
LLVLAVPTRVSP[D/E]DPVRFCGPYV[E/D]HASSIKVISDDGVSDRYS[V/L]LVSFSDQKSADGFYLDLNG
NRFSSSEVVI[V/L]P[I/V]W[R/C]QLVEVCHVLPIVAVQYNPSAVPFVGSTELPTCPVCIEPLDQDISGIV
ATKCDHSFQCSCVSMWVSSSCPVCQFCQKQSETPTNPTCSVCQTSENLWICVICGFVGCGRYKEGHSIRHWKDT
QHCYSLDLETQRVWDYVGDSYVHRLNHSKSDAKHSKLRSKCEFSGDNDD[S/L]DMGGVMFSSKTDTIVDEYNP
LLASQLETQREYYEALLSDAKKDREHISVAVDKAVNDKLQKMQLKLEKTMLEKKKVAKKNEKLMKSQDIWSKTV
KGIEEKEKRAQLRLKDDTILDLEEQIKDFKYSIKLQKSIKKSTHADDLKGGMLVPLAMESESGKGAKPEHYVNMC
KEDSEAPYQKNLLPSRKKSDSNEKLLIPPKTTPPSLLFDTLKVKSMG_

FIG. 56

LpOs04g0648600

MS[K/R]LTVGV[S/C][T/I]MVALSLAVF[L/F]TIV[I/V]LLLADLFCSHLR[R/L]RHLRADA[D/E/A
]MAPHKRPK[H/L]G[A/V]P[A/V]SSPP[H/Y]T[T/A]DDASVATTTTTATHEALSST[P/L]PFYY[T/A
]HGVMC[T/A]PTR[K/N]DLLLAIP[K/E]LEA[T/A]V[R/W]KKSPA[R/C]RSS[T/P]SPSPP[R/W]S
EPTA[S/R]ES[S/F]S[P/S]AYS[N/D]GFLR[T/I]SNPVYERSA[T/M]A[A/G]PG[E/G][H/Y]EED
[T/M][P/L]FDTP[D/G][T/A]SPSPNGITESSGAPGPVNHTEQGARS_

FIG. 57

Lp0a04q0648900

MAPLAAAAAVAAKEELGVTVA[M/V]APPMALAPLSQQ[Q/S]PRR[Q/_]YRGV[R/C]NRSPGK[R/_/W]
VAEL[Q/R]EPEK[D/C][T/M/S/L]RIWLGSY[T/A]TP[A/V]AAAR[T/A]YDT[A/V]VFYL[R/C]GR
SARLNFPDEISALAPLSPPPELLEADGGALS[A/V]ASI[R/N]KRALEVGCRVD[T

LpOs05g0148600

```
GGGGACAAGTTTGTACAAAAAAGCAGGCTGTGCAGCGTGACCCGGTCGTGCCCTCTCTAGAGATAA
TGAGCATTGCATGTCTAAGTTATAAAAATTACCACATATTTTTTGTCACAGTTGTTTGAAGTGC
AGTTTATCTATCTTTATACATATATTTAAACTTTACTCTACGAATAAATAATCTATAGTACTACAA
TAATATCAGTGTTTAGAGAATCATATAAATGAACAGTTAGACATGTCTAAAGGACAATTCAGTAT
TTTGCAACAGGACTCTACAGTTTTATCTTTTAGTGTGCATGTGTTCTCCTTTTTTTTGCAAATA
GCTTCACCTATATAATACTTCATCCATTTATTAGTACATCCATTTAGGGTTTAGGGTTAATGGTTT
TTATAGACTAATTTTTTTAGTACATCTATTTTATTCTATTTTACCCTCTAAATTAAGAAAACTAAAA
CTCTATTTTAGTTTTTTTATTTAATAATTTACATATAAAATAGAATAAAATAAAGTGCTAAAAATT
AAACAAATACCCTTTAAGAAATTAAAAAAACTAAGCAAACATTTTTCTTGTTTCGAGTAGATAATGC
CAGCCTGTTAAACGCCGTCGACGAGTCTAACGGACACCAACCAGCGAACCAGCAGCGTCGCGTCGGG
CCAACCGAAGCAGACGGCATGGCATCTCTGTCGCTGCCTCTGGACCCCTTTCGACAGTTCGCTCCA
CCGTTGCACTTGCTCCGCTGTCGGCATCCAGAAATTGCGTGGCGGAGCGGCAGACTGAGCCGGCAC
GGCAGGCGGCCTCCTCCTCCTCTCACGGCACGGCAGCTACGGGGATTCCTTTCCACCGCTCCTTC
GCTTTCCCTTCCTGCCGGCCGTAATAAATAGACACCCCCCTCCCACACCTTCTTTGTCCAACCTCGTG
TTGTTTGGAGCGCACACACACAACCGGATCTCCCCCCAAATCCACCCGTCGGCACCTCCGCTTCAA
GGTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGAATCCTGGGATGGCTCTAGCCGTTCCGCAGACGGGATCGATTTCATGATTTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTTT
CATACGCTATTTATTTGCTTGGTACTGTTTCTTTTGTCGATGCTCACCCTGTTGTTTGGTGTTACTT
CTGCAGGTCATGGTGTTTGCGGTTTTGTCTGCTGGGGCCGGGTGGCATGGCTCATACTGGAGGGG
TGATCCTGCTCGTCACCAATGGGGTCAAATTCGCGCATTCTGTCTTCAGCGAGGATATATTCTTCAT
CTACTTGCTCCGGCCCATCATCTTTAACGCTGCGTTTCAAGTAAAGAAAAGCAATTCTTCCGCAAT
TTTGCAACAATTACTTTGTTTGGGCTATTGGACATTGATATCCTTTGTAATAATCAGCCTTGGTG
CCATGGGATTGTTCAGCAAACTTGATGTTGATCCACTCCAGCTTGGGGACTATCTTGCAATTGGTGC
TATCTTCTCAGCAACAGATCTGTTTTGCACCTACAGGTGCTTAACCAGGATGAAACACCCTACTT
TATAGTCTGGTTTTTGGTGAAGGTGTTGTTAATGATGCTACATCTGTTGTGCTATTCAATGCAATTC
AAAACATTGATCTTGATCATTTCGATGCGTTTGGTTCTACTACAACTTATTGGAAAATCCTCTACCT
ACTTTTCACCAGTACTGTTCTTCGGAATAGCTAAAGGTATGGATAGTGTATCTTCATACTGCATTTGT
```

TTAATTTGAAAATGGTTATCTAGTTGCCTAACAAAATATAGCTGGGATATCTTATAACACATGTGCA
GGTGACATGGAAAAAAATGCCTATTTTTCTATGCACTAACTATTCATCATGTGACATACTTCCCCAA
AAAACTAAATAAGCCAAATTTTCCAGCTTCCGAGTCCTGAAAAAGAGTAGTGTACCTGATACAATTT
ATAGAGTTTTTTTTTTCGAAAAGAAGGGATAGCCCTCATAGATAGAGTACTAACTAAAAGTCTACTT
TTACCAATTTCAGGTTTTTGAGTTATTCCAAGAACAGTACTGGTGAAAAGTAGTAGAGGAATTTTC
CAATAAGTTGTAGTAGAACAAACGCATCGAAATGATCAAGATCATGTTTTGAATTGCATTGAATAG
CACAACAGATGTAGCATCATTAACAACACCTTCACCAAAAACCAGACTATAGAGTAGGGTGTTTCA
TCCTGGTTAGCACCTGTAAGGTGCAAACAGAATCTGTTGCTGAGAAGATAGCACCAATTGCAAGAT
AGTCCCCAAGCTGGAGTGGATCAACATCAAGTTTGCTGAACAATCCCATGGCACCAAGGCTGATTAT
TACAAAGGATATCAATGTCCCAATAGCCCCAAACAAAGTAATTGTTGCAAAATTGCGGAAGAATTGC
TTTTCTTTACTTGAAACCCAGCGTAAAGATGATGGGCGGGAGCAAGTAGATGAAGAATATATCCT
CGCTGAAGACCAGAATGCGCGAATTGACCCCATTGCTGACGAGCAGGATCACCCCTCCAGTGATGAG
CCATGCCACCCGGCCCCAGCGAGACAAACCGCAAACACCATGA*AGAAGGAGTGCGTCGAAGCAGAT*
*CGTTCAAACATTTGGCAATAAAGTTTCTTAAGATTGAATCCTGTTGCCGGTCTTGCGATGATTATCA*
*TATAATTTCTGTTGAATTACGTTAAGCATGTAATAATTAACATGTAATGCATGACGTTATTTATGAG*
*ATGGGTTTTTATGATTAGAGTCCCGCAATTATACATTTAATACGCGATAGAAAACAAAATATAGCGC*
*GCAAACTAGGATAAATTATCGCGCGCGGTGTCATCTATGTTACTAGATCGAACCCAGCTTTCTTGTA*
CAAAGTGGTCCCT

FIG. 59 (cont)

LpOs01g0369700

GGGGACAAGTTTGTACAAAAAAGCAGGCTGTGCAGCGTGACCCGGTCGTGCCCCTCTCTAGAGATAA
TGAGCATTGCATGTCTAAGTTATAAAAATTACCACATATTTTTTTGTCACACTTGTTTGAAGTGC
AGTTTATCTATCTTTATACATATATTTAAACTTTACTCTACCAATAATATAATCTATAGTACTACAA
TAATATCAGTGTTTAGAGAATCATATAAATGAACAGTTAGACATGGTCTAAAGACAATTGAGTAT
TTTGACAACAGGACTCTACAGTTTTATCTTTTTAGTGTGCATGTGTTCTCCTTTTTTTTTGCAAATA
GCTTCACCTATATAATACTTCATCCATTTTATTAGTACATCCATTTAGGTTTAGGGTTAATGCTTT
TTATAGACTAATTTTTTAGTACATCTATTTTATTCTATTTAGCCTCTAAATTAAGAAAACTAAAA
CTCTATTTTAGTTTTTTTATTTAATAATTTAGATATAAAATAGAATAAAATAAAGTGACTAAAAATT
AAACAAATACCCTTTAAGAAATTAAAAAAACTAAGGAAACATTTTTCTTGTTTCGAGTAGATAATGC
CAGCCTGTTAAACGCCGTCGACGAGTCTAACGGACACCAACCAGCGAACCAGCAGCGTCGCGTCGGG
CCAAGCGAAGCAGACGGCACGGCATCTCTGTCGCTGCCTCTGGACCCCTCTCGAGAGTTCCGCTCCA
CCGTTGGACTTGCTCCGCTGTCGGCATCCAGAAATTGCGTGGCGAGCGGCAGACGTGAGCCGGCAC
GGCAGGCGGCCTCCTCCTCCTCTCACGGCACGGCAGCTACGGGGATTCCTTTCCCACCGCTCCTTC
GCTTTCCCTTCCTCGCGCGGCCGTAATAAATAGACACCCCTCCACACCCTCTTTCCCCAACCTCGTG
TTGTTCGGAGCGCACAGACACACAACCAGATCTCCCCCAAATCCACCCGTCGGCACCTCCGCTTCAA
GGTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGGCGATTGTGAGGGTGCCGGTGAGATGCTTCCAAGTCACCTCCTTGTTCAGCCAGGCTGAAA
AGGTTGACAAGGAGCTTAAGGAGAACCCTGCACCATCTGAAGCTGATGTTGAGGCTGCTAAGCTTGT
TGTCAAGGGAAAAGGAGATGTAGTTGCGCAACTTAAAGCAGCAAAAGCTAGCAAGCAAGAGATAAGT
GTTGCTGTTTCGAGCTTACAAAGGCAAAAGAGGTTGTCTTAAGCCTGGAAGAGAGGTCTAAGTTGA
AACCTGGAATTCCCTACAAAGATGATGGGTCCATTGCCGTTGAGAATGACTTCTTCAAGCGTGCAGC
CTTTCTGACTGTTTCAGGCCAACTTCAGGTTGAGACTTATGCTTGTGCTCTCAGCAGTGTCTATACC
TTTGGACCCACATTCCGGGCAGAGAACTCACATACGTCAAGACATTTGGCAGAATTTTGATGGTTG
AACCAGAAATTGCATATGCAAACTTGCATAAAGGTATGGATAGTGTATCTTCATACTGCATTTGTTT
AATTTGAAAATGGTTATCTAGTTGCCTAACAAAATATAGCTGGGATATCTTATAACACATGTGCAGG
TGACATGGAAAAAAATGCCTATTTTTCTATGCACTAACTATTCATCATGTGACATACTTCCCCAAAA
AACTAAATAAGCCAAATTTTCCAGCTTCCGAGTCCTGAAAAAGAGTAGTGTACCTGATACAATTTAT

FIG. 60

AGAGTTTTTTTTTTCGAAAAGAAGGGATAGCCCTCATAGATAGAGTACTAACTAAAAGTCTACTTTT
ACCAATTTCAGGTTTTTGATGCAAGTTTGCATATGCAATTCTGGTTCAACCATCCAAAATTCTGCC
AAATGTCTTGACGTATGTGAGTTCTCTGCCCGGAATGTGGGTCCAAAGGTATAGACACTGCTGACAG
CACAAGCATAAGTCTCAACCTGAAGTTGGCCTGAAACAGTCAGAAAGGCTGCACGCTTGAAGAAGTC
ATTCTCAAACGCAATGGACCCATCATCTTTGTGGGAATTCCAGGTTTCAACTTAGACCTCTCTTCC
AGCCTTAAGACAACCTCTTTTGCCTTTGTAAGCTCCGAAACAGCAGCAGTTATCTCTTGCTTGCTAG
CTTTTGCTGCTTTAAGTTGCGCAACTGCATCTCCTTTTCCCTTGACAACAAGCTTAGCAGCCTCAAC
ATCAGCTTCAGATGGTGCAGGGTTCTCCTTAAGCTCCTTGTCAACCTTTTCAGCCTGGCTGAACAAG
GAGGTGACTTGAACATCTCACCGGCACCCTCACAATCGCAGAAGGAGTGCGTCGAAGCAGATCGTT
CAAACATTTGGCAATAAAGTTTCTTAAGATTGAATCCTGTTGCCGGTCTTGCGATGATTATCATATA
ATTTCTGTTGAATTACGTTAAGCATGTAATAATTAACATGTAATGCATGACGTTATTTATGAGATGG
GTTTTTATGATTAGAGTCCCGCAATTATACATTTAATACGCGATAGAAAACAAAATATAGCGCGCAA
ACTAGGATAAATTATCGCGCGCGGTGTCATCTATGTTACTAGATCGAACCCAGCTTTCTTGTACAAA
GTGGTCCCC

FIG. 60 (cont)

LpOs05g0149100

GGGGACAAGTTTGTACAAAAAAGCAGGCTGTGCAGCGTGACCCGGTCGTGCCCCTCTCTAGAGATAA
TCAGCAATGCAATGTCTAAGTTATAAAAAATTACCACATATTTTTTTGTCACACTTGTTTGAAGTGC
AGTTTATCTATCTTTATACATATATTTAAACTTTACTCTACGAATAATATAATCTATAGTACTACAA
TAATATCAGTGTTTAGAGAATCATATAAATGAACAGTTAGACATGGTCTAAAGGACAATTGAGTAT
TTGACAACAGCACTCTACAGTTTATCTTTTAGTGTGCATGTGTTCTCCTTTTTTTTGCAAATA
GCTTCACCTATATAATACTTCATCCATTTATTAGTACATCCATTTAGGGTTAGGGTTAATGGTTT
TTATAGACTAATTTTTTAGTACATCTATTTTATTCTATTTAGCCTCTAAATTAAGAAAACTAAAA
CTCTATTTAGTTTTTTATTTAATAATTTAGATATAAAATACAATAAAATAAAGTGACTAAAAATT
AAACAAATACCCTTTAAGAAATTAAAAAAACTAAGGAAACATTTTCTTGTTTCGAGTAGATAATGC
CAGCCTGTTAAACGCCGTCGACGAGTCTAACGGACACCAACCAGCGAACCAGCAGCGTCGCGTCGGG
CCAAGCGAAGCAGACGGCACGGCATCTCTGTCGCTGCTCTGGACCCCTCTCGAGAGTTCCGCTCCA
CCGTTGGACTTGCTCCGCTGTCGGCATCCAGAAATTGCGTGGCGGAGCGGCAGACGTGAGCCCGGCAC
GGCAGGCGGCCTCCTCCTCCTCTCACGGCACGGCAGCTACGGGGATTCCTTTCCCACCGCTCCTTC
GCTTTCCTTCCTCGGCCGCCGTAAGAAATAGACACCCCTCCACACCCTCTTTCCCCAACCTCGTG
TTGTTCGAGCGCACACAACACAATACCAGATCTCCCCCCAAATCCACCCGTCGGCACCTCCGCTTCAA
GGTACGCCGCTCGTCCTCCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGTTTCGGAAACACGGATTGGCAATACGGTCGATCGATCGACAGATCGGTACGGGGTTCG
GCGAGCGCGATGGCGTATCGGTGCTGGAAGTGACGCTGATCTCGCCAAGGACCTGAAGAAGGTG
ACGGTGTTCTCCAAGATGCGGGTGTACGCGGTGGCGTCCATCTCGGCGGCGACCCGCGCACGCCGA
CGCACCGGACGCACTCGGACCGGCACGGCGGGCCGCTGCGGTTCCCAATACCGATGGCCGCCGACCC
CCGCGGGCTGGCACTGCACGTGCTCTTCGCTTCCAGCGGCCTTCGGCGACCGGACGTCGGCGAG
GTGCTCGTCCCGTCCAGGACTTTTCGCCGGCAGCGGCTCTGCCGGCGAGCATCGCCACCTCAGCT
ACCAGGTGCGACGCCCATGAGCGGCCGGAAGCGCGGGTCCTCCACATCTCCTACAGCCTCACGGA
CGCGCGGCGGATAGGGAAAGGTATGGATAGTGTATCTTCATACTGCATTTGTTTAATTTGAAAATGG
TTATCTAGTTGCCTAACAAAATATAGCTGGGATATCTTATAACACATGTGCAGGTGACATGGAAAAA
AATGCCTATTTTTCTATGCACTAACTATTCATCATGTGACATACTTCCCCAAAAAACTAAATAAGCC
AAATTTTCCAGCTTCCGAGTCCTGAAAAAGAGTAGTGTACCTGATACAATTTATAGAGTTTTTTTTT

FIG. 61

TCGAAAAGAAGGGATAGCCCTCATAGATAGAGTACTAACTAAAAGTCTACTTTTACCAATTTCAGGT
TTTTGCCCTATCGCCGGCGCGTCCGTGAGGCTGTAGGAGATGTGGAGCACCCCGCGCTTCCGGCCGC
TCATGGGGCGTCGCACCTGGTAGCTGAGGTGGCGATGCTCGCCGGCGAGAGGCGCTGCGGCGAAAAG
GTCCTGGACGGGGACGAGCACCTCGCCGACGTCGCGGTCGCCGAAGGAGCGCTCGGAGCGGAGGAGC
ACGTGCAGTGCGAGCCCGCGGCGGTCGGCGGCCATCGGTATTCGGAACCGCAGCGGCCCGCCGTGCC
GGTCCGAGTGCGTCCGGTGCGTCGGCGTCGCGCGGCTGCCGGCCGGAGATGGACGCCACCGCGTACAC
CCGCATCTTGGAGAACACCGTCACCTTCTTCAGGTCCTTGGCCGAGATCAGCGTCACCTCCAGCACC
CGATACGCCATCGCGCCTCGCCGGACCCCGTGCCGATCTGTCGATCGATCGGCCGGTATTGCCAATC
CGTGTTCCCCGAGAAGAAGGAGTGCGTCGAAGCAGATCGTTCAAACATTTGGCAATAAAGTTTCTTA
AGATTGAATCCTGTTGCCGGTCTTGCGATGATTATCATATAATTTCTGTTGAATTACGTTAAGCATG
TAATAATTAACATGTAATGCATGACGTTATTTATGAGATGGTTTTTATGATTAGAGTCCCGCAATT
ATACATTTAATACGCGATAGAAAACAAAATATAGCGCGCAAACTAGGATAAATTATCGCGCGCGGTG
TCATCTATGTTACTAGATCGAACCCAGCTTTCTTGTACAAAGTGGTCCCC

FIG. 61 (cont)

LpOs05g0149500

GGGGACAAGTTTGTACAAAAAAGCAGGCTGTGCAGCGTGACCCGGTCGTGCCCCTCTCTAGAGATAA
TGAGCATTGCATGTCTAAGTTATAAAAATTACCACATATTTTTTTGTCACAGTTGTTGAAGTGC
AGTTTATCTATCTTTATACATATATTTAAACTTTACTCTACGAATAATATAATCTATAGTACTACAA
TAATATCAGTGTTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTGCAAATA
GCTTCACCTATATAATACTTCATCCATTTATTAGTACATCCATTTAGGGTTTAGGGTTAATGGTTT
TTATAGACTAATTTTTTAGTACATCTATTTTATTCTATTTAGCCTCTAAATTAAGAAAACTAAAA
CTCTATTTAGTTTTTTATTTAATAATTTACATATAAAATAGAATAAAATAAAGTGACTAAAAATT
AAACAAATACCCTTTAAGAAATTAAAAAAACTAAGGAAACATTTTCTTGTTTCGAGTAGATAATGC
CAGCCTGTTAAACGCCGTCGACGAGTCTAACGGACACCAACCAGCGAACCAGCAGCGTCGCGTCGGG
CCAAGCGAAGCAGACGGCACGGCATCTCTGTGCTGCCTCTGACCCTCTGAGAGTTCCGCTCCA
CCGTTGGACTTGCTCGCTGTCGGCATCCAGAAATTGCGTGGCGGAGCGGCAGACGTGAGCCGGCAC
GGCAGGCGGCCTCCTCCTCCTCTCACGGCACGGCAGCTACGGGGATTCCTTTCCTACTGCTCCTTC
GCTTTCCTTCCTGCCGCCGTAATAAATAGACACCCCTCCACACCCTCTTCCCCAACCTCGTG
TTGTTCGAGCGCACACACACAACCAGATCTCCCCCAAATCCACCCGTCGGCACCTCCGTTCAA
GGTACGCCGCTCGTCCTCCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTAGCCCTGCCTT
CATACGCTATTTATTTGCTTGGTACTGTTTCTTTTGTCGATGCTCACCCTGTTGTTTGGTGTTACTT
CTGCAGGATGGCGTCACCATCACCGGCGGCGGGATGAGGCTGCACGTGGACCTCTACTACGCGTGC
GTGCAGAGCCGGCGCTCTTCACGGTGTGGAGCCTCCTGCAGCTGATGCGGCGGCACCGCGGCCGCC
TGCCGGACGTGGACCTCATGTTCGATTGCATGGACCCGGCCGGCATCAACGCACCGAGCACAGCGG
CGAGGCGCGCCGCCCTTCGCCGCCGCTGTTCGGTACTGCACCACTGCGACCACTTCGACATCCCG
TTCCCGGACTGGTCCTTCTGGGCTGGCCGGAGAGCACCTCGAGCCCTGCAGCCGCGAGTTCAAGA
GCATCCGGCAGGGCGCCAAGAAGAACTGGGACGAGGAGGCGAGGTCGGGTACCAGAACTCGAAGCT
GTCGAGCCAGTGCACGTACAGGTACAAGATCTACGCGGAGGGGTCGCGTGGTCGGTGAGCCTGAAA
TACATTCTCTCCTGCGGCTCTACGGCGTCCTCGATCGACCCGCTGTACCAGGACTCTTCAGCCGGG
GCTCGGAGCCGCGGGTGAACCACCTGCCGGTGAGCACCGTGGCGATGTGCGAGTCCATCAGGGACGC
CGTGGAGTGGGGCAACGCGCACCCGGACGACGCGGAGCGCGTCGGGCGGCGGGCAGCGGCTGATG
CAGGATCTGGCCATGGACCGCAAAGGTATGGATAGTGTATCTTCATACTGCATTTGTTTAATTTGAA

FIG. 62

AATGGTTATCTAGTTGCCTAACAAAATATAGCTGGGATATCTTATAACACATGTGCAGGTGACATGG
AAAAAAATGCCTATTTTTCTATGCACTAACTATTCATCATGTGACATACTTCCCCAAAAAACTAAAT
AAGCCAAATTTTCCAGCTTCCGAGTCCTGAAAAAGAGTAGTGTACCTGATACAATTTATAGAGTTTT
TTTTTTCGAAAAGAAGGGATAGCCCTCATAGATAGAGTACTAACTAAAAGTCTACTTTTACCAATTT
CAGGTTTTTGGCCTCCATGGCCAGGTCCTGCATCAGCCGCTGCCCGCGCCGCCCGACGCGCTCCGC
CTCGTCCGGGTGCGCGTTGCCCCACTCCACGGCGTCCCTGATGGACTCGCACATCCCCACGGTGCTC
ACCGGCAGGTGGTTCACCCGCGGCTCCAGCCCCCGGCTGAAGAAGTCCTGGTACAGCGGGTCGATCA
GGAGCGCCGTGGAGCGCCAGGAGAGGATGTATTTCAGGCTCACCGACCACGCGAACTCCTCCGCGTA
GATCTTGTACCGGTGCGTGCACTGGCTGGACAGCTTCGAGTTCTGGTACCCGGACCTCGCCTCCTCG
TCCCAGTTCTTCTTGGCGCCCTGCCGGATGCTCTTGAACTCGCGGCTCCAGGGCTCGAGGTGCGTCT
CCGGCCAGCCCAGAAGGACCAGTCCGGCAACCGGATGTCGAAGTGGTCGCGAGTGGTGCAGTACCG
GAACAGCGGCGGCGGAGGGGCGCGCGCCCTCGCCGCTGTGCTCGGTGCCGTTGATGCCGGCCGGTCC
ATGCAGTCGACATGAGGTCCACGTCGGGGACGCGGCCGCGGTGCCGCCGCATCAGCTGCAGGAGGC
TCCACACCGTGAAGAGCGCGCGGCTCTGCACGCACGCGTAGTAGAGGTCCACGTGCAGCCTCGTCCC
GCGGCGGTGATGGTCACGCGCAT*AGAAGGAGTGCGTCGAAGCAGATCGTTCAAACATTTGGCAATA
AAGTTTCTTAAGATTGAATCCTGTTGCCGGTCTTGCGATGATTATCATATAATTTCTGTTGAATTAC
GTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATC
GCGCGCGGTGTCATCTATGTTACTAGATCGAACCCAGCTTTCTTGTACAAAGTGGT*CCCC

FIG. 62 (cont)

LpOs05g0149600 - CULLIN

```
GGGGACAAGT TTGTACAAAA AAGCAGGCTG TGCAGCGTGA CCCGGTCGTG CCCCTCTCTA
GAGATAATCA GCATTCCATC TCTAAGTTAT AAAAAATTAC CACATATTTT TTTTGTCACA
CTTGTTCAA GTGCAGTTTA TCTATCTTTA TACATATATT TAAACTTTAC TCTACGAATA
ATATAATCTA TAGTACTACA ATAATATCAG TGTTTTAGAG AATCATATAA ATGAACAGTT
ACACATGGTC TAAGGACAA TTGACTATTT TCACAACAGG ACTCTACAGT TTTATCTTTT
TAGTGTGCAT GTGTTCTCCT TTTTTTTGC AAATAGCTTC ACTTATATAA TACTTCATCC
ATTTTATTAG TACATCCATT TAGGGTTTAG GGTTAATGGT TTTTATAGAC TAATTTTTTT
AGTACATCTA TTTTATTCTA TTTTAGCCTC TAAATTAAGA AAACTAAAAC TCTATTTTAG
TTTTTTTATT TAATAATTTA CATATAAAAT ACAATAAAAT AAACTGACTA AAAATTAAAC
AAATCCCTT TAAGAAATTA AAAAAACTAA GGAAACATTT TTCTTCTTTC GACTAGATAA
TGCCATCTG TTAAACGGCG TCGACGATTC TAACTGACAC CAACCAGCGA ACCAGTAGCG
TCGCTCGGG CCAAGCGAAG CAGACGGCAC GGCATCTCTG TCGCTGCCTC TGGACCCCTC
TCAGCAGTTC CGCTCCACCG TTGACTTGC TCCCTCGTTG GCATCCAGAA ATTGCGTCGC
GGAGCGGCAG ACGTGAGCCG GCAGGCAGG CGCCCTCCTC CTCCTCTCAC GGCACGGCAG
CTACGGCGGA TTCCTTTCCC ACGGCTCCTT CGCTTTCCCT TCCTCGCCCG CCGTAATAAA
TAGATATCCC CTCCACAGCT TCTTTTCACA ACCTGTGTT GTTCCAGCTT CACACACACA
CAACCAGATC TCCCCTAAAT CCACCCGTCG GCACCTCGGC TTCAAGTAC GCCGCTCGTC
CTCCCCCCCC CCCCCTCTCT ACCTTCTCTA GATCGGCGTT CCGGTCCATG GTTAGGGCCC
GGTAGTTCTA CTTCTGTTCA TGTTTGTGTT AGATCCGTGT TTGTGTTAGA TCCGTGCTGC
TAGCGTTCGT ACACGGATGC GACCTGTACG TCAGACACGT TCTGATTGCT AACTTGCCAG
TGTTTCTCTT TGGGAATCC TGGGATGGCT CTAGCCGTTC CGCAGACGGG ATCGATTTCA
TGATTTTTTT TGTTTCGTTG CATAGGGTTT GGTTTGCCCT TTTCCTTTAT TTCAATATAT
GCCGTGCACT TGTTTGTCGG GTCATCTTTT CATGCTTTTT TTTGTCTTGG TTGTGATGAT
GTGGTCTGGT TGGGCGGTCG TTCTAGATCG GAGTAGAATT CTGTTTCAAA CTACCTGGTG
GATTTATTAA TTTTGGATCT GTATGTGTGT GCCATACATA TTCATAGTTA CGAATTGAAG
ATGATGGATG GAAATATCGA TCTAGGATAG GTATACATGT TGATGCGGGT TTTACTGATG
CATATACAGA GATGCTTTTT GTTCGCTTGG TTGTGATGAT GTGGTGTGGT TGGGCGGTCG
TTCATTCGTT CTAGATCGGA GTAGAATACT GTTTCAAACT ACCTGGTGTA TTTATTAATT
TTGGAACTGT ATGTGTGTGT CATACATCTT CATAGTTACG AGTTTAAGAT GGATGGAAAT
ATCGATCTAG GATAGGTATA CATGTTGATG TGGGTTTTAC TGATGCATAT ACATGATGGC
ATATGCAGCA TCTATTCATA TGCTCTAACC TTGAGTACCT ATCTATTATA ATAAACAAGT
ATGTTTATA ATTATTTGA TCTTGATATA CTTGGATGAT GGCATATGCA GCAGCTATAT
GTGGATTTTT TTAGCCCTGC CTTCATACGC TATTTATTTG CTTGGTACTG TTTCTTTTGT
CGATGCTCAC CCTGTTGTTT GGTGTTACTT CTGCAGGGGA GAAGGAACAT TCTGGATGTT
ATGCATTGCT TGGGATGAC AAGGTGGATG ATCTTAAAAG GATGTTTTCG CTCTTCTCAA
AAATCACCCG TGGCTGGAA CCTGTTTCTA ACATGTTCAA ATGGCATGTT ACGAATGACG
GTACAGCTTT GGTCAAGCAA GCAGAAGATT CTGCTAGTAA TAAAAAGCCA GAGAAGAACG
AGATGGTTGG AATGCAGGAA CAGGTTTTTC TCGGAAAAT CATTGCACTG CATGATAAGT
ATGTAGCATA TGTGACAGAT TGTTTCCACG GCCATACACT CTTCACAAG GCACTTAAAG
AAGCTTTGA GTCTTCTGC AATAAGGATG TCTCTGGCAG TTGGAGTGCT GAATTGCTCG
CCAGCTTCTG TGACAACATT CTGAAGAAAG GCTGCAGTGA AAAGCTCAGT GATGAAGCCA
TTGAAGATGC CGTTGAGAAG GTGGTGCGC TGCTTGCATA CATAAGTGAT AAAGACCAAA
GGTATGGATA GTGTATCTTC ATACTGCATT TGTTTAATTT GAAAATGGTT ATCTAGTTGC
CTAACAAAAT ATAGCTGGGA TATCTTATAA CACATGTGCA GGTGACATGG AAAAAAATGC
CTATTTTCT ATGCACTAAC TATTCATCAT GTGACATACT TCCCAAAAA ACTAAATAAG
CCAAATTTTC CAGCTTCCGA GTCCTGAAAA AGAGTAGTGT ACCTGATACA ATTTATAGAG
```

FIG. 63

TTTTTTTTTT GTACTAACTA AAAGTCTACT TTTACCAATT TCAGGTTTTT GGGTCTTTAT
CACTTATGTA TGCAAGCAGG GCGACCACCT TCTCAAGGGC ATGTTCAATG GCTTCATCAC
TCAGCTTTTC ACTGCAGCCT TTGTTCAGAA TGTTGTCACA GAAGGTGGCG AGCAATTCAG
CACTCGAACT GCCAAGACA CCCTTATTGC AGAAGACCTC AAAGGCTTCT TTAAGTGCCT
TGTGGAAGAG TGTATGGGCG TGGAAACAAT CTGTCACATA TGTACAATAC TTATCATGCA
GTGGAATGAT TTTCCACACA AAAACCTGTT CCTGCATTCC AAGCATCTCC TTCTTCTCTG
CCTTTTATT ACTAGCAGAA TGTTCTGCTT GCTTCACCAA AGCTGTACCC TCATTCGTAA
CATGCGATTT GAACATGTTA GAAACAGGTT CCAGACCACG GGTGATTTTT GAGAAGAGCG
AAAACATCCT TTTAAGATCA TCCAGCTTGT CATCCGCAAG CAATGCAGAA CATCCAGAAT
GTTCCTTCTC CAGAAGGAGT GCGTCGAAGC AGATCGTTCA AACATTGGC AATAAAGTTT
CTTAAGATTG AATCCTGTTG CCGGTCTTGC GATGATTATC ATATAATTTC TGTTGAATTA
CGTTAAGCAT GTAATAATTA ACATGTAATG CATGACGTTA TTTATGAGAT GGGTTTTTAT
GATTAGAGTC CCGCAATTAT ACATTTAATA CGCGATAGAA AACAAAATAT AGCGCGCAAA
CTAGGATAAA TTATCGCGCG CGGTGTCATC TATGTTACTA GATCGAACCC AGCTTCTTG
TACAAAGTGG TCCCC

FIG. 63 (cont)

LpOs05g0150400

GGGGACAAGTTTGTACAAAAAAGCAGGCTGTGCAGCGTGACCGGTCGTGCCCCTCTCTAGAGATAA
TGAGCATTGCATGTCTAAGTTATAAAAATTACCACATATTTTTTGTCACACTTGTTTGAAGTGC
AGTTTATCTATCTTTATACATATATTTAAACTTTACTCTACGAATAAATAATCTATAGTACTACAA
TAATATCAGTGTTTAGAGAATCATATAAATGAACAGTTAGACATGGTCTAAAGGACAATTCAGTAT
TTTGCAACAGGACTCTACAGTTTTATCTTTTAGTGTGCATGTGTTCTCCTTTTTTTTGCAAATA
GCTTCACCTATATAAAACTTCATCCATTTATTAGTACATCCATTTAGGGTTTAGGGTTAATGGTTT
TTATAGACTAATTTTTTAGTACATCTATTTTATTCTATTTACCCTCTAAATTAAGAAAACTAAAA
CTCTATTTAGTTTTTTTATTTAATAATTTACATATAAATAGAATAAAATAAAGTGACTAAAAATT
AAACAAATAGCCCTTTAAGAAATTAAAAAAACTAAGCAAACATTTTTCTTGTTTCGAGTAGATAATGC
CAGCCTGTTAAACGCCGTCGACGAGTCTAACGGACACCAACCAGCGAACCAGCAGCGTCGCGTCGGG
CCAAGCGAAGCAGACGGCAGGCATCTCTGTCGCTGCCTCTGGACCCCTTTCGACAGTTTCGCTCCA
CCGTTGGACTTGCTCCGCTGTCGGCATCCAGAAATTGCGTGGCGGAGCGGCAGACGTGAGCCGGCAC
GGCAGGCGGCTCCTCCTCCTCTCACGGCACGGCAGCTACGGGGATTCCTTTCCACCGCTCCTTC
GCTTTCCCTTCCTCGCCCGCCGTAAAAAATAGACACTCCCTCCACACCCTCTTTCTCCAACCTCGTG
TTGTTTGGAGCGCACACACACAACCAGATCTCCCCCAAATCCACCCGTCGCACCTCCGCTTCAA
GGTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGTGCCTCGAGTAGGTGAGGTAGCATCTTCATCTTCTCCATCCGATCATGACAATGAGGAGT
AGGAACAGGTACAGTTGTCCGCACTCTTGAAAGCTTGAACCAGAAAAATGAAGGCAAGGCACCACA
TCAAAAGGAAAGCAGTAACGCAATAACCGGCCGCAACCTGGAGATCTTATCCTAAACCAGTGCC
TCATTTTACGGATCACGCTTACAAAATCAGACATACCCAAATGTTGCACAAGAGCAAGCAATGTACC
ATATGTGGCACCAGGTGCAACCAACACAGCAGAAGTCGCCATTTTCGGATGGTTCCAACTATGGGCAA
CACAAGGTTTCCACCGCCATCAACTATACTCTCCATGTACCTTCTACCTAGAGGACAGTTCGCCGTG
CTAGCCAGCCAAGATGCTTTGGCTCTAATTCCATGTTTCCTGAAGCTGCTCCTGCCTTCCACGGT
ACTTCTCGCCTTACCCTGCCTCATACGTACCAGCAAGTCCACTGCCAGCTGCAGTTAACATGATGCA
TGGAGAAGGCAAGGGTGTGCTGAAACGGTTGAGCTTCCTGATGCACCAGTTTCGCCAGATACACT
GCTCAAAGGTATGGATAGTGTATCTTCATACTGCATTTGTTTAATTTGAAAATGGTTATCTAGTTGC
CTAACAAAATATAGCTGGGATATCTTATAACACATGTGCAGGTGACATGGAAAAAAATGCCTATTTT
TCTATGCACTAACTATTCATCATGTGACATACTTCCCCAAAAAACTAAATAAGCCAAATTTTCCAGC

FIG. 64

TTCCGAGTCCTGAAAAAGAGTAGTGTACCTGATACAATTTATAGAGTTTTTTTTTTCGAAAAGAAGG
GATAGCCCTCATAGATAGAGTACTAACTAAAAGTCTACTTTTACCAATTTCAGGTTTTTGGAGCAGT
GTATCTGGCGAAAACTGGTGCATCAGGAAGCTCAACCGTTTCAGCACACCCTTGCCTTCTCCCATGC
ATCATGTTAACTGCAGCTGGCAGTGGACTTGCTGGTACGTATGAGGCAGGGTAAGGCGAGAAGTACC
GTGGAAGGGCAGGAGCAGCTTCAGGAAAACATGGAATTAGAGCCAAAGCATCTTGGCTGGCTGGCAC
GGCGAACTGTCCTCTAGGTGGAGGGTACATGGAGAGTATAGTTGGTGGCGGTGGAAACCTTGTGTTG
CCCATAGTTGGAACCATCCGAAAATGGGGCTTCTGCTGTGTTGGTTGCACCTGGTGCCACATATGGT
ACATTGCTTGCTCTTGTGCAACATTTGGGTATGTCTCATTTCTAAGCGTGATCCGTAAAATGACGC
ACTTGGTTTAGGATAAGATCTCCGAGGGTTGCGGGCGGTTATTGCGTTGCTGCTTTTCCTTTTGAGGT
GGTGCCTTGCCTTCATTTTTCTGGGTCAAGCTTTCAAGAGTGCGGACAACTGTGACCTGTTCCTGCT
CCTCATTGTCATGATCGGATGGAGAAGATGAAGATGCTACCTCACCTACTCGAGGCA*AGAAGGAGTG*
*CGTCGAAGCAGATCGTTCAAACATTTGGCAATAAAGTTTCTTAAGATTGAATCCTGTTGCCGGTCTT*
*GCGATGATTATCATATAATTTCTGTTGAATTACGTTAAGCATGTAATAATTAACATGTAATGCATGA*
*CGTTATTTATGAGATGGGTTTTTATGATTAGAGTCCCGCAATTATACATTTAATACGCGATAGAAAA*
*CAAAATATAGCGCGCAAACTAGGATAAATTATCGCGCGCGGTGTCATCTATGTTACTAGATCGA*ACC
CAGCTTTCTTGTACAAAGTGGTCCCC

FIG. 64 (cont)

LpOs05g0150500

GGGGACAAGTTTGTACAAAAAAGCAGGCTGTGCAGCGTGACCGGTCGTGCCCCTCTCTAGAGATAA
TGAGCATTCATGTCTAGTTATAAAAATTACCACATATTTTTTTGTCACACTTGTTTGAAGTGC
AGTTTATCTATCTTTATACATATATTTAAACTTACTCTACGAATAATATAATCTATAGTACTACAA
TAATATCAGTGTTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTGCAAATA
GCTTCAGCTATATAATACTTCATCCATTTTATTAGTACATCCATTTAGGGTTTAGGGTTAATGGTTT
TTATAGACTAATTTTTTTAGTACATCTATTTTATTCTATTTTAGCCTCTAAATTAAGAAAACTAAAA
CTCTATTTTAGTTTTTTTATTTAATAATTTAGATATAAAATAGAATAAAATAAAGTGACTAAAAATT
AAACAAATACCCTTTAAGAAAGTAAAAAAACTAAGGAAACATTTTCTTGTTTGAGTAGATAATGC
CAGCCTGTTAAACGCCGTCGACGAGTCTAACGGACACCAACCAGCGAACCAGCAGCGTCGCGTCGGG
CCAAGGGAAGCAGACGGCACGGCATCTCTGTCGCTGCCTCTGGACCCCTCTCGAGAGTTCCGCTCCA
CCGTTGGACTTGCTCCGCTGTCGGCATCCAGAAATTGCGTGGCGGAGCGGCAGACGTGAGCCGGCAC
GGCAGCCGGCCTTCCTCCTCTCACGGCACGGCAGCTACGGGGATTCCTTTCCCACCGCTCCTTC
GCTTTCCTTCCTCGCCGGCCGTAATAAATAGACACCCCCTCCACACCCTCTTTCCCCAACCTCGTG
TTGTTCGGAGCGCACACACACAACCAGATCTCCCCCAAATTCACCCGTCGGCACCTCCGCTTCAA
GTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGTTTCACTGTACTTGAGAGGCTAGTAAGCAGAGCCGGAACCTCAAGACTCTGAAGCTCAA
CAATGCAATCCCTCTTAACAATGTTGCTAGCCTGCTTCGTAAGCTTCGCAAATAATAGAACTCGGA
ACTGGCAAATTCTCTGCTGACTACATCCAGATCTTTTTGCAAAGGTTGAAGCAGCATTGCAGGTT
GTACAAGCCTAAGAAGGCTTTCTGGGACTTGGGACGCTGTTCCAGATTACCTGCCAGCATTCTATTG
TGTATGTGAAGGCTCACATCTCTTAATCTGAGTTATGCCACCGTGCAGGCCCTGAGCTCATCAAA
TTCATTACAGATGCAAGATCTGCTGCAGTTATGGCTGATGGACTCATTGAGGACCAGGTCTAT
CTGTTGTGCATCAAGTTGCAGTAAACTGCAAGAGTTGCGGGTCTTCCCTTCCGATCCTTTGGTCA
TAACGGCGGGCAAGTTTTCTTGACAGAAAGAGGTCTTGAAAGGTATGGATAGTGTATCTTCATACTG
CATTTGTTTAATTTGAAAATGGTTATCTAGTTGCCTAACAAAATATAGCTGGGATATCTTATAACAC
ATGTGCAGGTGACATGGAAAAAATGCCTATTTTCTATGCACTAACTATTCATCATGTGACATACT

FIG. 65

TCCCCAAAAAACTAAATAAGCCAAATTTTCCAGCTTCCGAGTCCTGAAAAAGAGTAGTGTACCTGAT
ACAATTTATAGAGTTTTTTTTTTCGAAAAGAAGGGATAGCCCTCATAGATAGAGTACTAACTAAAAG
TCTACTTTTACCAATTTCAGGTTTTTGCAAGACCTCTTTCTGTCAAGAAAACTTGCCCGCCGTTATG
ACCAAAAGGATCGGAAGGGAAGACCCGCAACTCTTGCAGTTTACTGCAACTTGATGCCACAACAGAT
AGACCATGGTCCTCAATGAGGTCCATCACCCATAACTGCAGCAGATTCTTGCATCTGCTAATGAATT
TGATGAGCTCAGGGCCTTGCACGGTGGCATAACTCAGATTAAGAGATGTGAGGCCTTCACATACACA
ATAGAATGCTGCAGGTAATCTGGAACAGCGTTCCAAGTCCCAGAAAGCCTTCTTAGGCTTGTACAA
CCTGCAAATGCTGCTTCAACCTTTGCAAAAGATCTGGATGATAGTCAGCAGAGAATTTGCCAGTTC
CGAGTTCTATTATTTGCGGAGCCTTACGAAGCAGGCTAGCAACATTGTCAAGAGGGATTGCATTGTT
GAGCTTCAGAGTCTTGAGGTTGCGGCATCTGCTTACTAGCCTCTCAATACAGTGAAA*AGAAGGAGT*
*GCGTCGAAGCAGATCGTTCAAACATTTGGCAATAAAGTTTCTTAAGATTGAATCCTGTTGCCGGTCT*
*TGCGATGATTATCATATAATTTCTGTTGAATTACGTTAAGCATGTAATAATTAACATGTAATGCATG*
*ACGTTATTTATGAGATGGGTTTTTATGATTAGAGTCCCGCAATTATACATTTAATACGCGATAGAAA*
*ACAAAATATAGCGCGCAAACTAGGATAAATTATCGCGCGCGGTGTCATCTATGTTACTAGATCGAAC*
*CCAGCTTTCTTGTACAAAGTGGT*CCCC

FIG. 65 (cont)

LpOs05g0151300

GGGGACAAGTTTGTACAAAAAAGCAGGCTGTGCAGCGTGACTCGGTCGTGCCCCTCTCTAGAGATAA
TGAGCATTGCATGTCTAAGTTATAAAAATTACCATATTTTTTTGTCACAGTTGTTTGAAGTGC
AGTTTATCGATCTTTATACATATATTTAAACTTTACTCTACGAATAATATAATCTATAGTACTACAA
TAATATCAGTGTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTGCAAATA
GCTTCACCTATATAATACTTCATCCATTTTATTAGTACATCCATTTAGGGTTTAGGGTTAATGGTTT
TTATAGACTAATGTTTTAGTACATCTATTTTATTCTATTTAGCCTCTAAATTAAGAAAACTAAAA
CTCATTTTAGTTTTTTATTTAATAATTTACATATAAAATAGAATAAAATAAAGTGACTAAAAATT
AAACAAATACCCTTTAAGAAATTAAAAAAACTAAGGAAACATTTTCTTGTTTCGAGTAGATAATGC
CAGCCTGTTAAACGCCGTCGACGAGTCTAACGGACACCAACCAGCGAACCAGCAGCGTCGCGTCGGG
CCAGCGAAGCAGACGGCACGGCATCTCTCTGTGCTGCCTCTGGACCCCTGTCGACAGTTCCGCTCCA
CCGTTGGACTTGCTCCGCTGTCGGCATCCAGAAATTGCGTGGCGAGCGGCAGACTGAGCCGGCAC
GGCAGCGGCCTCCTCCTCCTCTCACGGCACGGCAGCTACGGGGATCCTTTCCTACCGCTCCTTC
GCTTTCCCGTCCTCGCCCGTCCGTAATAAATAGACACCCCTCCACACCCTCTTTCCCAACCTCGTG
TTGTTCGGAGCGCACACACACAACCAGATCTCCCCCAAATCCACCCGTCGGCACCTCCGCTTCAA
GGTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGATGGCGCAGTCGGCAGCGACGCCGCACCGATCAGCACGGCATCCACCGAGGAGGAGGAG
GTGACGGTGGAGAGGACGCCGGAGGAGGAGGCGGCCAGGCTCAGGTACCTCGAGTTCGTGCAGCAGG
CGGCGGCGGCAGCGGCGTGTGCTGGCGCCGCGCCTACGCCTACGGCAAGTAGGGCGCGGGGCCGCT
CTGGCCCGGCGTCGACCACGTTGAGGGCACGTCAAGGCGTGTCGGCCCTGTGTATGATCGGTAC
CACGGCGTGCCGGTCGACCTCTTCAAGTTCCTCGACCGCAAGAAAGGTATGGATAGTGTATCTTCAT
ACTGCATTTGTTTAATTTGAAAATGGTTATCTAGTTGCCTAACAAAATATAGCTGGGATATCTTATA
ACACATGTGCAGGTGACATGGAAAAAAATGCCTATTTTTCTATGCACTAACTATTCATCATGTGACA
TACTTCCCCAAAAAACTAAATAAGCCAAATTTTCCAGCTTCCGAGTCCTGAAAAAGAGTAGTGTACC
TGATACAATTTATAGAGTTTTTTTTTTCGAAAAGAAGGGATAGCCCTCATAGATAGAGTACTAACTA
AAAGTCTACTTTTACCAATTTCAGGTTTTTGCTTGCCGTCGAGGAACTTGAGGAGGTCGAGCCGGCAC
GGCCGTGGTACCGATCATACACAGGGCCGACGACGGCCTTGACGGTGCCCTCGAGGTGGTCGACGCCG

FIG. 66

GGGCGGAGCGGCCCCGCGCCCTGCTTGGCGTAGGCGTAGGCCCGGCGGCCAGCACGATCGCCTGCG
CCGCCGCCTGCTGCACGAACTCGAGGTACCTGAGCCTGGCCGCCTCCTCCTCCGGCGTCCTCTCCAC
CGTCAACTCCTCCTCCTCGGTGGGGTGCGTGCTGATCGGTGCGGCGGTCGCTGCCGGACTGCGCCATA
GAAGGAGTGCGTCGAAGCAGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATACGC
GATAGAAAACAAAATATAGCGCGCAAACTAGGATAAATTATCGCGCGCGGTGTCATCTATGTTACTA
GATCGAACCCAGCTTTCTTGTACAAAGTGGTCCCC

FIG. 66 (cont)

LpOs05g0152400

GGGGACAAGTTTGTACAAAAAAGCAGGCTGTGCAGCGTGACCCGGTCGTGCCCCTCTCTAGAGATAA
TGAGCATTGCATGTCTAAGTTATAAAAATTACCACATATTTTTTTGTCACACTTGTTGAAGTGC
AGTTTATCTATCTTTATACATATATTAAAGTTACTCTACCAATAATATAATCTAGAGTACTACAA
TAATATCAGTGTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTGCAAATA
GCTTCACCTATATAATACTTCATCCATTTATTAGTACATCCATTTAGGGTTTAGGGTTAATGGTTT
TTATAGACTAATTTTTAGTACATCTATTTATTCTATTTAGCCTCTAAATTAGAAAACTAAAA
CTCTATTTTAGTTTTTTATTTAATAATTTACATATAAATAGAATAAAATAAAGTGACTAAAATT
AAACAAATACCCTTTAAGAAATTAAAAAAACTAAGGAAACATTTTCTTGTTTGAGTAGATAATGC
CAGCCTGTTAAACGCCGTCGACGAGTCTAACGACACCAACCAGCGAACCAGCAGCGTCGCGTCGGG
CCAAGCGAAGCAGACGGCACGGCATCTCTGTCCTGCCTCTGCACCCTCTCGAGAGTTCCGCTCCA
CCGTTGGACTTGCTCCGCTGTCGGCATCCAGAAATTGCGTGGCGGAGCGGCAGACTGAGCCGGCAC
GGCAGGCGGCCTCCTCCTCCTCTCACGGCACGGCAGCTACGGGGATTCCTTTCCTACTGCTCCTTC
GCTTTCCCTTCCTGGCCGCCGTAATAAATAGACACCCCCTCCACACCCTCTTCCCCAACCCTCGTG
TTGTTCGAGCGCACACACACAACCAGATCTCCCCCAAATCCACCCGTCGGCACTTCCGTTCAA
GGTACGCCGCTCGTCCTCCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGAATCCTGGGATGGCTCTAGCCGTTCCGCAGACGGGATCGATTTCATGATTTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTAGCCCTGCCTT
CATACGCTATTTATTTGCTTGGTACTGTTTCTTTTGTCGATGCTCACCCTGTTGTTTGGTGTTACTT
CTGCAGGTCTCCATGGGTTATTCTAAATCGGCGGTTTATAGAGTATTGTATTCTTGGCTGGGAGAAT
CTTCCTCGGGTTCTTCTCATGTACTTCAACAACGTAGTGCTGCCTCAGGAAGGATACTTCCACTCAG
TCATATGCAACTCGGTTGATTTCCGTAATTCCACTGTGAACAATGATTGAGGTACAAGGTGTGGA
TGACCACCTCAGACAGAGCCCCTATTTCTGAACATGCACATTATGATGAGATGGTGAACAGCCGA
CAGCCTTTTGCAAGGCGTTTTCAGAAGAAGGAACCATTGCTGGACAAGATCGATGACAAATACTCA
GGCGTCCTGGGCATGGGCCTGTTCCTGGTGCCAAAGGTATGGATAGTGTATCTTCATACTGCATTTG
TTTAATTTGAAAATGGTTATCTAGTTGCCTAACAAAATATAGCTGGGATATCTTATAACACATGTGC
AGGTGACATGGAAAAAATGCCTATTTTTCTATGCACTAACTATTCATCATGTGACATACTTCCCCA
AAAAACTAAATAAGCCAAATTTTCCAGCTTCCGAGTCCTGAAAAAGAGTAGTGTACCTGATACAATT
TATAGAGTTTTTTTTTTCGAAAAGAAGGGATAGCCCTCATAGATAGAGTACTAACTAAAAGTCTACT
TTTACCAATTTCAGGTTTTTGGGCACCAGGAACAGGCCCATGCCCAGGACGCCTGAGTAGTTTGTCA

FIG. 67

TGATCTTGTCCAGCAATGGTTCCTTCTTCTGAAAACGGCTTGCAAAAGGGTGTGCGGCTGTTCACCA
TCTCATCATAATGTGCCATGTTCAGAAATAGGCGCTCTGTCTGAGGTGGTTCATCCACACGTTGTA
CCTCAAATCATTGTTCACAGTGGAATTACGGAAATCAACCGAGTTGCATATGACTGAGTGGAAGTAT
CCTTCCTGAGGCAGCACTACGTTGTTGAAGTACATGAGAAGAACCGAGGAAGATTCTCCCAGCCAA
GAATACAATACTCTATAAACCGCCGATTAGAATAACCCATGGAGAAGAAGGAGTGCGTCGAAGCAG
ATCGTTCAAACATTTGGCAATAAAGTTTCTTAAGATTGAATCCTGTTGCCGGTCTTGCGATGATTAT
CATATAATTTCTGTTGAATTACGTTAAGCATGTAATAATTAACATGTAATGCATGACGTTATTTATG
AGATGGTTTTTATGATTAGAGTCCCGCAATTATACATTTAATACGCGATAGAAAACAAAATATAGC
GCGCAAACTAGGATAAATTATCGCGCGGGTGTCATCTATGTTACTAGATCGAACCCAGCTTTCTTG
TACAAAGTGGTCCCC

FIG. 67 (cont)

LpOs06g0680500 - Glutamate

```
GGGACAAGT TTGTACAAAA AAGCAGGCTG TGCAGCCTCA CCCGGTCCTG
CCCCTCTCTA GAGATAATGA GCATGCATG TCTAAGTTAT AAAAATTAC
CACATATTT TTTGTCACA CTTGTTGAA GTCAGTTTA TCTATCTTA
TACATATATT TAAACTTAC TCTACGAATA ATATAAGCTA TAGTACTACA
ATATATCAG TGTTTTAGAG AATCATATAA ATAACAGTT AGACATGGTC
TAAAGCACAA TTGAGTATTT TGACAACAGG ACTCTACAGT TTTATCTTTT
TAGTGTGCAT GTGTTCTCCT TTTTTTTGC AAATAGCTTC ACCTATATAA
TACTGCATCC ATTTTATTAG TACATCCATT TAGGGTTAG GGTTAATGGT
CTTTATACAC TAATTTTTTT AGTACATCTA TTTATTCTA TTTAGCCTC
TAAATTAAGA AAAGTAAAAC TCTATTTAG GTTTTTATT TAATAAGTTA
GATATAAAAT ACAATAAAAT AAAGTGACTA AAAATTAAAC AAATACCGTT
TAAGAAATTA AAAAAACTAA GGAAACAATT TTCTTGTTTC GAGTACATAG
TGCCAGCCTG TTAAACCCG TCACGAGTC TAACGACAC CAACTAGCGA
ACCGCAGCG TGTGTGGG CCAAGCGAAG CAGACGGCAG GGCATCTCTG
TGCTGCTC TGGACCCTC TGAGAGTTC CGCTCCACCG TTGGACTTGC
TCCGCTGTCG GCATCCAGAA ATTGCGTGGC GGAGCGGCAG ACGTGAGCCG
GCAGGCAGG CGCGCTCCTC CTCCTCTCAC GGCACGGCAG CTACGGGCGA
TTGTTTTCCC ACGGCTCTTT CGCTTTCCCT TCCTCCCCCG CCGTAATAAA
TAGACACCCG CTCCACCCG TGTTCCCCA ACCTCGTGTT GTTCGGACCG
GACACACACA CAACCAGATC TCCCAAAT CCACCGGTCG GGACCTCCGC
TTCAAGTAC GCCGCTCGTC CTCCCCCCCC CCCCCTCTCT ACCTTCTCTA
GATCGGCGTT CCGGTCCATG GTTAGGGCCC GGTAGTTCTA CTTCTGTTCA
TGTTTGTGTT AGATCCGTGT TTGTGTTAGA TCCGTGCTGC TAGCGTTCGT
ACACGGATGC GACCTGTACG TCAGACACGT TCTGATTGCT AACTTGCCAG
TGTTTCTCTT TGGGAATCC TGGGATGGCT CTAGCCGTTC CGCAGACGGG
ATCGATTTCA TGATTTTTTT TGTTTCGTTG CATAGGGTTT GGTTTGCCCT
TTCCTTTAT TTCAATATAT GCCGTGCACT TGTTTGTCGG GTCATCTTTT
CATGCTTTTT TTGTCTTGG TTGTGATGAT GTGGTCTGGT TGGGCGGTCG
TTCTAGATCG GAGTAGAATT CTGTTTCAAA CTACCTGCTG GATTTATTAA
TTTTGGATCT GTATGTGTGT GCCATACATA TTCATAGTTA CGAATTGAAG
ATGATGGATG GAAATATCGA TCTAGGATAG GTATACATGT TGATGCGGGT
TTACTGATG CATATACAGA GATGCTTTTT GTTCGCTTGG TTGTGATGAT
GTGGTGTGGT TGGGCGGTCG TTCATTCGTT CTAGATCGGA GTAGAATACT
GTTTCAAACT ACCTGGTGTA TTTATTAATT TTGGAACTGT ATGTGTGTGT
CATACATCTT CATAGTTACG AGTTAAGAT GGATGGAAAT ATCGATCTAG
GATAGGTATA CATGTTGATG TGGGTTTTAC TGATGCATAT ACATGATGGC
ATATGCAGCA TCTATTCATA TGCTCTAACC TTGAGTACCT ATCTATTATA
ATAAACAAGT ATGTTTTATA ATTATTTTGA TCTTGATATA CTTGGATGAT
GGCATATGCA GCAGCTATAT GTGGATTTTT TTAGCCCTGC CTTCATACGC
TATTTATTTG CTTGGTACTG TTTCTTTTGT CGATGCTCAC CCTGTTGTTT
GGTGTTACTT CTGCAGGCAA TCCAGACATA GCCACGGGTC ATCATCTGGA
GCCCGTTAGC TATACAAAT AATCGCAGCC CTGTATCAGG ATTGACATGC
```

FIG. 68

```
ACAACCAGAA CCCTTGATTC CATCATGTTA ACTTTAAACA GTATATCACT
GATCGCATCT TTGTTCCTAT CTGGAAGGAT TACTGCTTTA TATGAAATTC
TGGCAGGCTT TGTTGCAAGG GCATCACCAA GGGCAGCAC CCACTTTC
CCATAATCAT CATCACAAA TATAGAGTT ACTGTTCC ATGATAGTA
GTAACCAATG CTAGCAATCG CACCGATTTG GAAGTAATCG CTGACAGTGC
TCCTTAAAAA GTAAGAATAC TCCGATGCAG AAAGAGTTCG ATCAGTGGT
GCGAATGATA GGAGCGGAAC ATGCAGCTCA TTAACAAAAT GTGAGATGAC
ATGGCCTATC ACAGAGGACT GCGGGCCAAC AACTGCAACC AGATTTTCT
CAAAGGTATG GATAGTGTAT CTTCATACTG CATTGTTTA ATTTGAAAAT
GGTTATCTAG TTGCCTAACA AAATATAGCT GGGATATCTT ATAACACATG
TGCAGGTGAC ATGGAAAAAA ATGCCTATTT TTCTATGCAC TAACTATTCA
TCATGTGACA TACTTCCCCA AAAAACTAAA TAAGCCAAAT TTTCCAGCTT
CCGAGTCCTG AAAAAGAGTA GTGTACCTGA TACAATTTAT AGAGTTTTTT
TTTTCGAAAA GAAGGGATAG CCCTCATAGA TAGAGTACTA ACTAAAGTC
TACTTTTACC AATTTCAGGT TTTGAAGAA AAATGTGGTT GTAGTTGTTG
GCCCGCGCTC CTCTGTGATA GGCCATGTCA TCTCACATTT TGTTAATGAG
GTCCATGTTC CCCTCCTATC ATGGCAGCC ACTGATCCAA CTCTTTCTGC
ATGGAGTAT TCTTACTTTT TAGGAGCAC TGTCAGCGAT TACTTCCAAA
TGCGTGCGAT TGTAGCATT GTTACTACT ATCAATGGAA AGAGGTAACT
GCTATATTTG TTGATGATGA TTATGGGAGA GGTGGGTGT TTGTCCTTGG
TGATGCCTT GCAACAAAGT GTGCCAGAAT TTCATAAAA GCAGTAATTC
CTCCAGATGC GAACAAAGAT GTGATCAGTG ATATACTGTT TAAAGTTAAC
ATAATGAAT CAAGAATTCT GGTTGTGCAT CTCAATCCTG ATACAGGGT
GGGATTAATC TCTATAGCTA ACGAGCTCCA GATGATAGCC GTGGCTATG
TCTGGATTCA GAAGGAGTGC GTCGAAGCAG ATCGTTCAAA CATTGGCAA
TAAAGTTTCT TAAGATTGAA TCCTGTTGCC GGTCTTGCGA TGATTATCAT
ATAATTTCTG TTGAATTACG TTAAGCATGT AATAATTAAC ATGTAATGCA
TGACGTTATT TATGAGATGG GTTTTATGA TTAGAGTCCC GCAATTATAC
ATTTAATACG CGATAGAAAA CAAATATAG CGCGCAAACT AGGATAAATT
ATCGCGCGCG GTGTCATCTA TGTTACTAGA TCGAACCCAG CTTTCTTGTA
CAAAGTGGTC CCC
```

FIG. 68 (cont)

LpOs05g0152900-SIAH

```
    ACAAGT TTGTACAAAA AAGCAGGCT
```

```
TCAA GTAC GCCGCTCGTC CTCCCCCCCC CCCCCTCTCT ACCTTCTCTA
GATCGGCGTT CCGGTCCATG GTTAGGGCCC GGTAGTTCTA CTTCTGTTCA
TGTTTGTGTT AGATCCGTGT TTGTGTTAGA TCCGTGCTGC TAGCGTTCGT
ACACGGATGC GACCTGTACG TCAGACACGT TCTGATTGCT AACTTGCCAG
TGTTTCTCTT TGGGGAATCC TGGGATGGCT CTAGCCGTTC CGCAGACGGG
ATCGATTTCA TGATTTTTTT TGTTTCGTTG CATAGGGTTT GGTTTGCCCT
TTTCCTTTAT TTCAATATAT GCCGTGCACT TGTTTGTCGG GTCATCTTTT
CATGCTTTTT TTGTCTTGG TTGTGATGAT GTGGTCTGGT TGGGCGGTCG
TTCTAGATCG GAGTAGAATT CTGTTTCAAA CTACCTGGTG GATTTATTAA
TTTGGATCT GTATGTGTGT GCCATACATA TTCATAGTTA CGAATTGAAG
ATGATGGATG GAAATATCGA TCTAGGATAG GTATACATGT TGATGCGGGT
TTTACTGATG CATATACAGA GATGCTTTTT GTTCGTTGG TTGTGATGAT
GTGGTGTGGT TGGGCGGTCG TTCATTCGTT CTAGATCGGA GTAGAATACT
GTTCAAACT ACCTGGTGTA TTTATTAATT TTGGAACTGT ATGTGTGTGT
CATACATCTT CATAGTTACG AGTTTAAGAT GGATGGAAAT ATCGATCTAG
GATAGGTATA CATGTTGATG TGGGTTTTAC TGATGCATAT ACATGATGGC
ATATGCAGCA TCTATTCATA TGCTCTAACC TTGAGTACCT ATCTATTATA
ATAAACAAGT ATGTTTATA ATTATTTGA TCTTGATATA CTTGGATGAT
GGCATATGCA GCAGCTATAT GTGGATTTTT TTAGCCCTGC CTTCATACGC
TATTTATTTG CTTGGTACTG TTTCTTTTGT CGATGCTCAC CCTGTTGTTT
GGTGTTACTT CTGCAGGTCA
```

FIG. 69

```
GTGGTAGGCA GCAAGGCGG CAGCCAGGG GGTCGGTGT GTCTAAAGTC
ACGCGTGGA GTCCGCTGC CGCGCGTGTA GACGCCGTG CGTTCTTC
TACTTGACTG TCCAGGAAAA GGTATGGATA GTGTATCTTC ATACTGCATT
TGTTTAATTT GAAAATGGTT ATCTAGTTGC CTAACAAAAT ATAGCTGGGA
TATCTTATAA CACATGTGCA GGTGACATGG AAAAAAATGC CTATTTTTCT
ATGCACTAAC TATTCATCAT GTGACATACT TCCCCAAAAA ACTAAATAAG
CCAAATTTTC CAGCTTCCGA GTCCTGAAAA AGAGTAGTGT ACCTGATACA
ATTTATAGAG TTTTTTTTTT CGAAAAGAAG GGATAGCCCT CATAGATAGA
GTACTAACTA AAAGTCTACT TTTACCAATT TCAGGTTTTT GTCTGGACA
GTCAAGTAGA AACAATGCTA CCGCGTCTA CACGCGTGGC AGCGCGACTC
CACGCGTGA CTTTAGACAA CACCGACGCC CTCGACTGCC GCCTTCCTG
CCTACCACTC AAGCCGCCA TCTTCCAGGT AATTAACATA TCCAAATCA
TGTCACCAT GCGGACAAGG GTCATCGTC TTATGTCTCC GCGCTTCCAG
TGTAGGTGG GCCACGTGGT GTCCTCGACG TGCGAGACA AGCTGGGCGC
GGTTCGGAGG TCCCATGTGT GTCGCACGGC GACTTCCCGC GATACCACC
GGAACTACTA CATGGAGAAC CTGCTGGAGT CCATCCGGT GCTTCCTCC
AACGCTGCCT ACGGCTGCCT CGCCAAGCCG GTCTACTATG AGAAGGAGT
GCGTCGAAGC AGATCGTTCA AACATTTGGC AATAAAGTTT CTTAAGATTG
AATCCTGTTG CCGGTCTTGC GATGATTATC ATATAATTTC TGTTGAATTA
CGTTAAGCAT GTAATAATTA ACATGTAATG CATGACGTTA TTTATGAGAT
GGGTTTTTAT GATTAGAGTC CCGCAATTAT ACATTAATA CGCGATAGAA
AACAAAATAT AGCGCGCAAA CTAGGATAAA TTATCGCGCG CGGTGTCATC
TATGTTACTA GATCGAACCC AGCTTTCTTG TACAAAGTGG TCCCC
```

FIG. 69 (cont)

LpOs05g0153200

GGGGACAAGTTTGTACAAAAAAGCAGGCTGTGCAGCGTGACCCGGTCGTGCCCTCTCTAGAGATAA
TGAGCATTGCATGTCTAAGTTATAAAAATTACCACAGATTTTTTTGTCACACTTGTTTGAAGTGC
AGTTTATCTATCTTTATACATATATTTAAACTTTACTCTACGAATAATATAATCTATAGTACTACAA
TAATATCAGTGTTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTTGCAAATA
GCTTCACCTATATAATACTTCATCCATTTTATTAGTACATCCATTTAGGGTTTAGGGTTAATGCTTT
TTATAGACTAATTTTTTAGTACATCTATTTTATTCTATTTAGCCTCTAAATTAAGAAAACTAAAA
CTCTATTTTAGTTTTTTTATTAATAATTTAGATATAAAATAGAATAAAATAAAGTGACTAAAAATT
AAACAAATACCCTTTAAGAAATTAAAAAAACTAAGGAAACATTTTTCTTGTTTCGAGTAGATAATGC
CAGCCTGTTAAACGCCGTTGACGAGTCTAACGGACACCAACCAGCGAACCAGCAGCGTCGCGTCGGG
CCAAGCGAAGCAGACGGCACGGCATCTCTGTCGCTGCCTCTGGACCCCTCGAGAGTTCCGCTCCA
CCGTTGGACTTGCTCCGCTGTCGGCATCCAGAAATTGCGTGGCGGAGCGGCAGACGTGAGCCGGCAC
GGCAGGCGCCTCCTCCTCCTCTCACGGCACGGCAGCTACGGGGGATTCCTTCCCACCGCTCCTTC
GCTTTCCCTTCCTCGGCGGCCGTAATAAATAGACACCCCCTCCACACCCTCTTTCCCCAACCTCGTC
TTGTTCGAGGGCACACACACAACCAGATCTCCTCCAAATCCACCCGTGGCACTTCCGTTCAA
GGTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTAGCCCTGCCTT
CATACGCTATTTATTTGCTTGGTACTGTTTCTTTTGTCGATGCTCACCCTGTTGTTTGGTGTTACTT
CTGCAGGATGGGTATCATAGTCAATATGCCTTCTGAATATGTTGGAAAAAGTGCAAACCGGCTGAAG
GAGCATTTCTACGGTTTTATCCTGTGAAAGTGCACCATGTGTACAGTAAAGGTCGCCTACAGGAA
ATGCTATGTTGAGTTTGGGAGGACTTGGTGGCTTTAGAAATGCACTAACATTTGAGAATCAATT
TGAGAAGGAGGGCATGGAAAATAGCTGGCAGGAAAAACAGCATGGAGGGCCAGAGCTTTTTGGA
TGGATCGCTAGAGCAGACGATTACAATGCTCCAGGAGCAATAGGGGACTTCTAAGAAAAATGGTG
ATCTGAAGACGGCTGACGGTGTTGAGGATGAACAAATAATGAAAATAACAAACTTGTGGCCAGTTT
ATCTTTTAAAGTTATTGAAACTGATATGCATATACCAGAACTTAAATCTGTGTATCAGGAGAGAACT
GCCTCACTGAAAGAATGATGGAGCAGAGGGAACAGCAGCTACAGTCATACAATCAGTGCGTCCTA
ATCTTCTAAAGGTATGGATAGTGTATCTTCATACTGCATTTGTTTAATTTGAAAATGGTTATCTAGT
TGCCTAACAAAATATAGCTGGGATATCTTATAACACATGTGCAGGTGACATGGAAAAAAATGCCTAT
TTTTCTATGCACTAACTATTCATCATGTGACATACTTCCCCAAAAAACTAAATAAGCCAAATTTTCC

FIG. 70

AGCTTCCGAGTCCTGAAAAAGAGTAGTGTACCTGATACAATTTATAGAGTTTTTTTTTTCGAAAAGA
AGGGATAGCCCTCATAGATAGAGTACTAACTAAAAGTCTACTTTTACCAATTTCAGGTTTTTGAGAA
GATTAGGACGCACTTGATTGTATGACTGTAGCTGCTGTTCCCTCTGCTCCATCATTCTTTCAGTGA
GGCAGTTCTCCTGATACACAGATTTAAGTTCTGGTATATGCATATCAGTTTCAATAACTTTAAAA
GATAAACTGGCCAGAAGTTTGTTATTTTCATTGTTTCTCATCCTCAACACCGTCAGCCGTCTTCA
GATCACTATTTTTCTTAGAAAGTCCCTATTGCTCCTGAGCATTGTAATCGTCTGCTCTAGCGAT
CCATCCAAAAGGCTCTGGCCCTCCATGCTGTTTTCCTGCCAGCCTATTTTCCATGCCCTTCCTTC
TCAAATTGATTCTCAAATGTTAGTGCATTCTAAAACCAACCAAGTCCTTCCCAAACTCAACAATAG
CATTCCTGTAGGGCGACCTTTACTGTACACATGCTGCACTTTCACAGGATAAAAACGTGAGAAATC
CTCCTTCAGCCGGTTTGCACTTTTTCCAACATATTCAGAAGGCATATTGACTATGATACCCATAGAA
GGAGTGCGTCGAAGCAGATCGTTCAAACATTTGGCAATAAAGTTTCTTAAGATTGAATCCTGTTGCC
GGTCTTGCGATGATTATCATATAATTTCTGTTGAATTACGTTAAGCATGTAATAATTAACATGTAAT
GCATGACGTTATTTATGAGATGGGTTTTTATGATTAGAGTCCCGCAATTATACATTTAATACGCGAT
AGAAAACAAAATATAGCGCGCAAACTAGGATAAATTATCGCGCGCGGTGTCATCTATGTTACTAGAT
CGAACCCAGCTTTCTTGTACAAAGTGGTCCCC

FIG. 70 (cont)

LpOs04g0645500

GGGGACAAGTTTGTACAAAAAAGCAGGCTGTGCAGCGTGACCGGTCGTGCCCTCTCTAGAGATAA
TGAGCTTGCATGTCTAGTTAPAAAAATTACCACATATTTTTTTGTCACACTTGTTTGAAGTGC
AGTTTATCTATCTTTATACATATATTTAAACTTTACTCTACGAATAATATAATCTATAGTACTACAA
TAATATCAGTGTTTTAGAGAATCATATAAATGAACAGTTAGACATGGTCTAAAGGACAATTGAGTAT
TTGACAACAGGACTCTACAGTTTTATCTTTTTAGTGTGCATGTGTTCTCCTTTTTTTTGCAAATA
GCTTCACCTATATAATACTTCATCCATTTTATTAGTACATCCATTTAGGGTTTAGGGTTAATGCTTT
TTATAGACTAATTTTTTAGTACATCTATTTATTCTATTTAGCCTCTAAATTAAGAAAACTAAAA
CTCTATTTTAGTTTTTTTATTTAATAATTTAGATATAAAATAGAATAAAATAAAGTGACTAAAAATT
AAACAAATACCCTTTAAGAAATTAAAAAAACTAAGGAAACATTTTCTTGTTTCGAGTAGATAATGC
CAGCCTGTAAACGCCGTCGACGAGTCTAACGGACACCAACCAGCCAACCAGCAGGTCGCGTCGGG
CCAAGCGAAGCAGACGGCACGGCATCTCTGTCGCTGCTCTGGACTCCTCTCGAGAGTTCCGCTCCA
CCGTTGGACTTGCTCCGCTGTCGGCATCCAGAAATTGCGTGGCGGAGCGGAGACGTGAGCTGGCAC
GGCAGGCGGCCTCCTCCTCCTCTCACGGCACGGCAGCTACGGGGATTCCTTTCCCACGGTCCTTC
GCTTTCCCTTCCTCGCCCGCCGTAATAAATAGACACCCCCTCCACACCCTCTTGCCCCAACTTGGTG
TTGTTCGGAGCGCACACACACAACCAGATCTCCCCCAAATCCACCCGTGGCACTCCGCTTCAA
GGTACGCCGCTCGTCCTCCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTAGCCCTGCCTT
CATACGCTATTTATTTGCTTGGTACTGTTTCTTTTGTCGATGCTCACCCTGTTGTTGGTGTTACTT
CTGCAGGGTCGTGAGCAAATCTTCCTTTGGCGGCAGCGCTCCTCTGAAGAATGGTGAATTTGAGAAG
ATGCTGGAAATGGAACCGCAGAAAACCGTGGTCAGAGATTTACTGATGTGACATCCTGTTCTAG
AAGAGGCAAAACCGCTTATTTGTGGAATCGGTGAGTTGGTGATGATGTTCTGAAGGAGCAACAGCT
TTCCACCAAGGAGATTGCAATTTACGGATTATATCTTTGCCCCATTTGGTTTGTCACAGAGTATTTA
TCAAATGCAGCCCTTGCAAGAACAAGTGTTGCAGTACTACGGTACTATCTTCAACTTCGGACTCT
TCTCACTCTTCATTAGTGTGCTCCTTGGCCAAGATTCCATAAATGCTGCCAAAGTTATTGCTGTTTT
TGTTAGCATGGCTGGTGTAGCAATGACAACTATGGGCCAGACTTGGGCAACAGATGAATCTGAAGTA
AGCAATTCAG**AAAGGTATGGATAGTGTATCTTCATACTGCATTTGTTTAATTTGAAAATGGTTATCT
AGTTGCCTAACAAAATATAGCTGGGATATCTTATAACACATGTGCAGGTGACATGGAAAAAATGCC
TATTTTCTATGCACTAACTATTCATCATGTGACATACTTCCCCAAAAAACTAAATAAGCCAAATTT
TCCAGCTTCCGAGTCCTGAAAAAGAGTAGTGTACCTGATACAATTTATAGAGTTTTTTTTTTCGAAA**

FIG. 71

AGAAGGGATAGCCCTCATAGATAGAGTACTAACTAAAAGTCTACTTTTACCAATTTCAGGTTTTTGC
TGAATTGCTTACTTCAGATTCATCTGTTGCCCAAGTCTGGCCCAAAGTTGTCATTGCTACACCAGCC
ATGCTAACAAAAACAGCAATAACTTTGGCAGCATTTATGGAATCTTGGCCAAGGAGCACACTAATGA
AGAGTGTGAAGAGTCCCGAAGTTGAAGATAGTACCGTAGTACTGGCAACACTTGTTCTTGCAAGGGC
TGCATTTGTAAATACTCTGTGACAAACCAAATGGGGCAAAGATATAATCCGTAAATTGGAATCTCC
TTGGTGGAAAGCTGTTGCTCCTTCAGAACATCATCACCAAACTCACCGATTCCACAAATAAGCGGTT
TTGCCTCTTCTAGCACAGGATGTCCACATCAGTAAAATCTATGACTACGGTTTTCTGCGGTTCCAT
TTCCAGCATCTTCTCAAATTCACCATTCTTCAGAGGAGCGCTCCGGCAAAGGAAGATTTGCTCACG
ACAGAAGGAGTGCGTCGAAGCAGATCGTTCAAACATTTGGCAATAAAGTTTCTTAAGATTGAATCCT
GTTGCCGGTCTTGCGATGATTATCATATAATTTCTGTTGAATTACGTTAAGCATGTAATAATTAACA
TGTAATGCATGACGTTATTTATGAGATGGGTTTTTATGATTAGAGTCCCGCAATTATACATTTAATA
CGCGATAGAAAACAAAATATAGCGCGCAAACTAGGATAAATTATCGCGCGGTGTCATCTATGTTA
CTAGATCGAACCCAGCTTTCTTGTACAAAGTGGTCCCC

FIG. 71 (cont)

LpOs04g0645600

GGGGACAAGTTTGTACAAAAAAGCAGGCTGTGCAGCGTGACCCGTCGTGCCCCTCTCTAGAGATAA
TCAGCATTGCATGTCTAAGTTATAAAAATTACCACATATTTTTTTGTCACACTTGTTTGAAGTGC
AGTTTATCTATCTTTATACATATATTTAAACTTACTCTACGAATAATATAATCTATAGTACTACAA
TAATATCAGTGTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTGCAAATA
GCTTCACCTATATAATACTTCATCCATTTTATTAGTACATCCATTTAGGGTTTAGGGTTAATGCTTT
TTATAGACTAATTTTTTAGTACATCTATTTTATTCTATTTAGCCTCTAAATTAAGAAAACTAAAA
CTCTATTTTAGTTTTTTATTTAATAATTTAGATATAAAATAGAATAAAATAAAGTGACTAAAAATT
AAACAAATACCCTTTAAGAAATTAAAAAAACTAAGGAAACATTTTTCTTGTTTCGAGTAGATAATGC
CAGCCTGTTAAACGCCGTCGACGAGTCTAACGGACACCAACCAGCGAACCAGCAGCTTCGCGTCGGG
CCAAGCGAAGCAGACGGCACGGCATCTCTGTCGCTGCTTCTGGACTCCCTCTCGAGAGTTCCGCTCCA
CCGTTGGACTTGCTCCGCTGTCGGCATCCAGAAATGCGTGGCGGAGCGCAGACGTGAGCCGGCAC
GGCAGCGGCCTCCTCCTCCTCTCACGGCACGGCAGCTACGGGGATTCCTTCCCACCGCTCCTTC
GCTTTCCCTTCCTGCCCGCCGTAATAAATAGACACCCCCTCCACACCCTCTTTCCCAACCTCGTG
TTGTTCGGAGCGCACACACACAACCAGATCTCCCCAAATCCACCGTCGGCACCTCCGCTTCAA
GTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTGCTTGGTACTGTTTCTTTTGTCGATGCTCACCCTGTTGTTTGGTGTTACTT
CTGCAGGCACACTGTTCATTAGTGTGCTCCTTGGCCAAGATTCCATAAATGCTGCCAAAGTTATTGC
TGTTTTTGTTAGCATGGCTGGTGTAGCAATGACAACTATGGGCCAGACTTGGGCAACAGATGAATCT
GAAGTAAGCAATTCAGGAACTTATCGCCTTGCTAACCATCTAATTCTTAAGCCTTACTACTGCAGGG
CCACACAGAGGACTCTTCTAGGTGATATGTTTGGTCTTCTGTCAGCTGTGTCATATGGTCTCTTCAC
TGTGCTTCTCAAAAGTTTGCTGGAGGAGAAGGATCTGAAAAGTTGATGTCAAAAACTGTTCGGC
TTTCTCGGACTTTCACTCTTTGTCTTCTCTGGTGGCTTGTCTGGCCATTAACTGCGCTAGGCATTG
AGCCAAAGTTTACAATGCCCACTCAGCTAAAGTGGATGAAGTTGTTCTGGCAAATGGCCTTATTGG
GAGTGTGCTATCAGCTATTTCTGGGCTCTATCGTTGAAAGGTATGGATAGTGTATCTTCATACTG
CATTTGTTTAATTTGAAAATGGTTATCTAGTTGCCTAACAAAATATAGCTGGGATATCTTATAACAC
ATGTGCAGGTGACATGGAAAAAATGCCTATTTTCTATGCACTAACTATTCATCATGTGACATACT
TCCCCAAAAAACTAAATAAGCCAAATTTTCCAGCTTCCGAGTCCTGAAAAAGAGTAGTGTACCTGAT
ACAATTTATAGAGTTTTTTTTTTCGAAAAGAAGGGATAGCCCTCATAGATAGAGTACTAACTAAAAG

FIG. 72

TCTACTTTTACCAATTTCAGGTTTTTGCAACAGATAGAGCCCAGAAATAGTCTGATAGCACTCCC
AATAAGGCCATTTGCCAGAACAACTTCATCCACTTTAGCTGAGTGGGGCATTGTAAACTTTGGCTCA
ATGCCTAGCGCAGTTAATGGCCAGACAAGCCACCAGAGAAGACAAAGAGTGAAAAGTCCGAGAAAGC
CGAACAGTTTTGGACATCAACCTTTTCAGATCCTTCTCCTCCAGCAAACTTTTTGAGAAGCACAGT
GAAGAGACCATATGACACAGCTGACAGAAGACCAAACATATCACTTAGAAGAGTCCTCTGTGTGTGCCC
CTGCAGTAGTAAGGCTTAAGAATTAGATGGTTAGCAAGGCGATAAGTTCCTGAATTGCTTACTTCAG
ATTCATCTGTTGCCAAGTCTGGCCCATAGTTGTCATTGCTACACCAGCCATGCTAACAAAACAGC
AATAACTTTGGTAGCATTTATGGAATCTTGCCAAGGAGCACACTAATGAAGAGTGTG*AGAAGGAGT*
*GCGTCGAAGCAGATCGTTCAAACATTTGGCAATAAAGTTTCTTAAGATTGAATCCTGTTGCCGGTCT*
*TGCGATGATTATCATATAATTTCTGTTGAATTACGTTAAGCATGTAATAATTAACATGTAATGCATG*
*ACGTTATTTATGAGATGGGTTTTTATGATTAGAGTCCCGCAATTATACATTTAATACGCGATAGAAA*
*ACAAAATATAGCGCGCAAACTAGGATAAATTATCGCGCGCGGTGTCATCTATGTTACTAGATCGAAC*
*CCAGCTTTCTTGTACAAAGTGGT*CCCC

FIG. 72 (cont)

LpOs04g0647300 – TC116908

```
gggACAAGT TTGTACAAAA AAGCAGGCTg tcagcgtca ccggtcgtg ccctctcta
gagataatga gcattgcatc tctaagttat aaaaattac cacatatttt tttgtcaca
cttgtttgaa gtgcagttta tctatcttta tacatatatt taaactttac tctacgaata
atataatcta tagtactaca atatatcag tgtttagag aatcatataa atgaacactt
agacatggtc taaggacaa ttgagtattt tgacacagg actctacagt tttatctttt
tagtgtgcat gtgttctcct tttttttgc aaatagctc actatatca tacttcatcc
atttattac tacatccatt tagggttag ggtaatggt tttatagac taattttttt
agtacatcta tttattcta ttagccctc taaattaaga aactaaaac tctattttag
tttttatt taataattta gatacaaat agaataaat aaagtcacta aaaattaaac
aatacccct taagaaatta aaaaactaa ccaacatt ttcttcttc gagtacataa
tgctacctg ttaaaggca tcgacgagtc taaggacac caaccagga accagcagcg
tcggtcggg ccaagcgaag cagacggcac ggcatctg tcctgcctc tggacccctc
tcgagagttc cgctccaccg ttgacttgc tccgctgtcg ggatccagaa attggtgcc
ggagcggcag acgtcagccc gcacggcagg ccgtcctc ctcctcac gccacggcag
ctacgggca ttcctttcct accgtctt cgctttccct tcctgcccg cctaataaa
tagacaccc ctccacacc tctttcccca acctcgtgtt gttcggagcg cacacacaca
aaccagatc tccccaaat caaccgtcg gcaccctcc ttcaaGTAC GCCGCTCGTC
CTCCCCCCCC CCCCCTCTCT ACCTTCTCTA GATCGGCGTT CCGGTCCATG GTTAGGGCCC
GGTAGTTCTA CTTCTGTTCA TGTTTGTGTT AGATCCGTGT TTGTGTTAGA TCCGTGCTGC
TAGCGTTCGT ACACGGATGC GACCTGTACG TCAGACACGT TCTGATTGCT AACTTGCCAG
TGTTTCTCTT TGGGGAATCC TGGGATGGCT CTAGCCGTTC CGCAGACGGG ATCGATTTCA
TGATTTTTTT TGTTTCGTTG CATAGGGTTT GGTTTGCCCT TTTCCTTTAT TTCAATATAT
GCCGTGCACT TGTTTGTCGG GTCATCTTTT CATGCTTTTT TTGTCTTGG TTGTGATGAT
GTGGTCTGGT TGGGCGGTCG TTCTAGATCG GAGTAGAATT CTGTTTCAAA CTACCTGGTG
GATTATTAA TTTTGGATCT GTATGTGTGT GCCATACATA TTCATAGTTA CGAATTGAAG
ATGATGGATG GAAATATCGA TCTAGGATAG GTATACATGT TGATGCGGGT TTTACTGATG
CATATACAGA GATGCTTTTT GTTCGCTTGG TTGTGATGAT GTGGTGTGGT TGGGCGGTCG
TTCATTCGTT CTAGATCGGA GTAGAATACT GTTTCAAACT ACCTGGTGTA TTTATTAATT
TTGGAACTGT ATGTGTGTGT CATACATCTT CATAGTTACG AGTTTAAGAT GGATGGAAAT
ATCGATCTAG GATAGGTATA CATGTTGATG TGGGTTTTAC TGATGCATAT ACATGATGGC
ATATGCAGCA TCTATTCATA TGCTCTAACC TTGAGTACCT ATCTATTATA ATAAACAAGT
ATGTTTTATA ATTATTTTGA TCTTGATATA CTTGGATGAT GGCATATGCA GCAGCTATAT
GTGGATTTTT TTAGCCCTGC CTTCATACGC TATTTATTTG CTTGGTACTG TTTCTTTTGT
CGATGCTCAC CCTGTTGTTT GGTGTTACTT CTGCAGgga gctcagcca taagcccg
ccaagttcct ctagggtcc ggatcaag ctctattgc attgttgat gcagccgtgt
gattcagca acgtgctgtt tttttcaa tgctgggttc gtgcgtatt aggaagtta
gccgttagtt aaatggctgt gtcaagtatt gtaactgtgg gaagcaggtc ttgtttgaga
cagtatactg tatattctct cctgcaaag atagagtaat ctttcatgc tattccatgg
aactaagtta gatcatgcag attgcaagtc tacttaacat gatatggaat gatgtgaaca
gagatatatc actaaaacgg gcaaggtttg ctagtggga gctgctactg ggggaaatg
gtgcacgtt tgcatttcta tgcctgttt gaggaaatcc cctgtatat aaagcatgta
tagagttaag ttctatattt tcatttgat tctgcaagta cttttgcca AAGGTATGGA
TAGTGTATCT TCATACTGCA TTTGTTAAAT TTGAAAATGG TTATCTAGTT GCCTAACAAA
ATATAGCTGG GATATCTTAT AACACATGTG CAGGTGACAT GGAAAAAAAT GCCTATTTTT
CTATGCACTA ACTATTCATC ATGTGACATA CTTCCCCAAA AAACTAAATA AGCCAAATTT
```

FIG. 73

```
TCCAGCTTCC GAGTCCTGAA AAAGAGTAGT GTACCTGATA CAATTTATAG AGTTTTTTTT
TTCGAAAAGA AGGGATAGCC CTCATAGATA GAGTACTAAC TAAAAGTCTA CTTTTACCAA
TTCAGGTTT TTGTGCCAAC AGTACTTGCA GAATCAAATG AAAACATAAG AACTTAACTC
TATACATGCT TTATATACGA GGGGATTTCC TCAAACAGGC CATGAAATG CAAACGTGCA
ACCATTTCCC CCCAGTAGGA GCTCCCACTA AGCAAACCTT GCCCTTTA GTGATATATC
TCTGTTCACA TCATTCCATA TCATGTTAAG TAGACTTGCA ATCTGCATGA TCTAACTTAG
TTCATCGAA TACCATAGAA ACATTACTCT ATCTTTGCA GGACAGAATA TACAGTATAC
TGTCTAAAC AAGACCTGCT TCCCACAGTT ACAATACTTG ACACAGCCAT TTAACTAACG
GCTAACTTCC CTAATACGCA ACGAACCCAG CATTGAAAAA AAAACAGCAC GTTGCTGAAA
TCACAGCGCT GCATCAACCA ATGCAAATAG AGCTTCAGAT GCCCACCTAT AGAGGAACTT
GCGCCAGCTG TATGGCGTGC GCTCCAGAAG GAGTGCGTCG AAGCAGATCG TTCAAACATT
TGGCAATAAA GTTTCTTAAG ATTGAATCCT GTTGCCGGTC TTGCGATGAT TATCATATAA
TTTCTGTTGA ATTACGTTAA GCATGTAATA ATTAACATGT AATGCATGAC GTTATTTATG
AGATGGGTTT TTATGATTAG AGTCCCGCAA TTATACATTT AATACGCGAT AGAAAACAAA
ATATAGCGCG CAAACTAGGA TAAATTATCG CGCGCGGTGT CATCTATGTT ACTAGATCGA
ACCCAGCTTT CTTGTACAAA GTGGTCCCC
```

FIG. 73 (cont)

LpOs03g0193400

GGGGACAAGTTTGTACAAAAAAGCAGGCTGTGCAGCGTGACCCGGTCGTGCCCCTCTCTAGAGATAA
TGAGCATTGCATGTCTAAGTTATAAAAATTACCACATATTTTTTTGTCACACTTGTTTGAAGTGC
AGTTTATCTATCTTTATACATATATTTAAACTTTACTCTACCAATAATATAATCTATAGTACTACAA
TAATATCAGTGTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTTGCAAATA
GCTTCACCTATATAATACTTCATCCATTTTATTAGTACATCCATTTAGGGTTTAGGGTTAATGGTTT
TTATAGACTAATTTTTTAGTACATCTATTTATTCTATTTAGCTCTAAATTAAGAAAACTAAA
GTCTATTTTAGTTTTTTATTTAATAATTTAGATATAAAATAGAATAAAATAAAGTGACTAAAAATT
AAACAAATACCCTTTAAGAAATTAAAAAAACTAAGGAAACATTTTCTTGTTTCGAGTAGATAATGC
CAGCCTGTTAAACGCCGTCGACGAGTCTAACGGACACCAACCAGCGAACCAGCAGCGTCGCGTCGGG
CCAAGCGAAGCAGACGGCACGGCATCTCTGTCGCTGCCTCTGGACCCCTCTCGAGAGTTCCGCTCCA
CCGTTGGACTTGCTCCGCTGTCGGCATCCAGAAATTGCGTGGCGGAGCGGCAGACGTGAGCCGGCAC
GGCAGGCGGCCTCCTCCTCCTCTCACGGCACGCAGCTACGGGGATTCCTTTCCCACCGCTCCTTC
GCTTTCCCTTCCTCGCCCGCCGTAATAAATAGACACCCCCTCCACACCCTCTTTCCCCAACCTCGTG
TTGTTCGAGCGCACAGACACAACCAGATCTCCCCCAAATCCACCCGTCGGCACCTCCGTTCAA
GTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGATGGGCAGGCGAGCCGGCGTGTTGTGGTGGGGAGGAGACGGCGTGGCGAGGAGG
CGGGATGGGGAGGCGGCGCGTCAGGAGGAGGGATGGGGGCCCGGGACGGATGCGTGCTGGGGA
GGGGAGCGATGGGTTTCTGCGAGAGGAGAATAGTGGACGCGGATCGCTAATTACATGGTGGTAGA
CTACTACCTGTATGACTACGAGTACGCCGAGCCGCGCGCGTGACCAGCCTGCAGAACGCCGTTCCT
CAGAGGACCTTCAGCGACTTCGGAGATGACGTCTACTTCGTCGCCGACAAACGGGCTACGAGTCCG
TCGTCCACTACCTCGCCGGCCAGTACCTCAACACCGACGACTCGGCAACGTCGCCGACCCCGGCT
GCAGTTCAACAAGGTGGTGGCGAGAGATCTCCTACTCCTCGAGCGGAGTCACCGTCAAGACGGAGGAC
GGCTCAGTGTACCAGCAGACTATCGTCATGCATGGAAAATCATCGCCATCTACCGTTCGACATGG
CAGTGTACACCAAGATCTTCCTCAAGTTCCCTCGAAGTTCTGGCCTACGGGCGAAGGCAAGCACTTT
CTTCGTCTACGCCAGCTGCAGGCGAGGCTACTACGGGATGTGGCAGTCCTTCGAGGAGGATACCCG
GGGCCAACGTGGTCCTTCGTGACGGTGACGGACCAGGAGTCGCGGCGGATCGAGCAGCAGTCGGACA

ACACCACCATGGCGGAGGCTGTGGCGGTGCTGCGGAGGATGTTCCCCGACGAGGACGTCCCGACGC
CACCGATATCTACGTGCCCAGGTGGTGGTCCAACCGCTTCTTCAAGGGCTCCTACTCCAACCGGCCC
ATCGGCGTCAACCGCTACGAATACGACCAGCTTCGGAAAGGTATGGATAGTGTATCTTCATACTGCA
TTTGTTTAATTTGAAAATGGTTATCTAGTTGCCTAACAAAATATAGCTGGGATATCTTATAACACAT
GTGCAGGTGACATGGAAAAAAATGCCTATTTTTCTATGCACTAACTATTCATCATGTGACATACTTC
CCCAAAAAACTAAATAAGCCAAATTTTCCAGCTTCCGAGTCCTGAAAAAGAGTAGTGTACCTGATAC
AATTTATAGAGTTTTTTTTTTCGAAAAGAAGGGATAGCCCTCATAGATAGAGTACTAACTAAAAGTC
TACTTTTACCAATTTCAGGTTTTTGCCGAAGCTGGTCGTATTCGTAGCGGTTGACGCCGATGGGCCA
GTTGGAGTAGGACCCTTGAAGAGCGGTTGGACCACCACTTGGCACGTAGATATCGGTGGCGTCG
GGGACGTCCTCGTCGGGAACATCCTCCGCAGCACCGCCACAGCCTCCGCCATGGTGGTGTTGTCCG
GCTGCTGCTCGATCCGCCGCGACTCCTGGTCCGTCACCGTCACGAGGAGCACGTTGGCCCCCGGGTA
CTCCTCCTCGAAGGACTGCCACATCCCGTAGTAGCCTTGCCTGGAGCTGGCGTAGACGAAGAACTGC
TTGCCTTCGCCGGTGGCCAGAACTTCCGAGGGAACTTGAGGAAGATCTTGGTGTACACTGCCATGT
CGAACCGGTAGATGGCGATGATTTTCCATGCATGACGATAGTCTGCCTGGTACACTGAGCCGTCCTC
CGTCTTGACGGTGACTCCGCTCGAGGAGTAGGAGATCTCTCGCACCACCTTGTTGAGCTGCAGGCGG
GGGTCGGCGACGTTGCCGGAGTCGTCGGTGTTCAGGTACTGGCCGGCGAGGTAGTGAGGACGGACT
CGTAGCCCCGTTTGTCGGCGACGAAGTAGACGTCATCTCCGAAGTCGCTGAAGGTCCTCTGGGGAAC
GGCGTTCTGCAGGCTGGTCACGCGCGGCGGCTCGGCGTACTCGTAGTCATACAGGTAGTAGTCTACC
ACCATGTAATTAGCGATCCCGCCTCCACTATTCTCCTCTCGCAGAAACCCATCGGTCCGCCCTCCCA
GCACGCATCGGTCCCCGGCGCCCCCATCCCCTCCTCCTCGCGGCGCCGCCTCCCCATCCCGCTTCCT
CGCCACGCCGTCTCCTTCCCTCCACCACAAACAACACCGCGCTCGCTGCCCATAGAAGGAGTGCGT
CGAAGCAGATCGTTCAAACATTTGGCAATAAAGTTTCTTAAGATTGAATCCTGTTGCCGGTCTTGCG
ATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAA
AATATAGCGCGCAAACTAGGATAAATTATCGCGCGCGGTGTCATCTATGTTACTAGATCGAACCCAG
CTTTCTTGTACAAAGTGGTCCCC

FIG. 74 (cont)

LpOs06g0607800 - 26S prot

GGGGACAAGT TTGTACAAAA AAGCAGGCTG TGCAGCGTGA CCCGGTCGTG CCCCTCTCTA
GAGATAATGA GCATTGCATG TCTAAGTTAT AAAAAATTAC CACATATTTT TTTTGTCACA
CTTGTTTGAA GTGCAGTTTA TCTATCTTTA TACATATATT TAAACTTTAC TCTACGAATA
ATATAATCTA TAGTACTACA ATAATATCAG TGTTTTAGAG AATCATATAA ATGAACAGTT
AGACATGGTC TAAGGACAA TTGAGTATTT TGACAACAGG ACTCTACAGT TTTATCTTTT
TAGTGTGCAT GTGTTCTCCT TTTTTTTGC AAATAGCTTC ACCTATATAA TACTTCATCC
ATTTATTAG TACATCCATT TAGGGTTAG GGTAATGGT TTTATAGAC TAATTTTTT
AGTACATCTA TTTTATTCTA TTTAGCCTC TAAATTAAGA AAACTAAAAC TCTATTTTAG
TTTTTTATT TAATAATTTA GATATAAAAT AGAATAAAAT AAGTGACTA AAATTAAAC
AAATACCCTT TAAGAAATTA AAAAACTAA GGAACATTT TTCTTGTTTC GAGTAGATAA
TGCCAGCCTG TTAAACGCCG TCGACGAGTT TAACGACAC CAACCAGCGA ACCAGCAGCG
TCGCGTCGGG CCAAGCGAAG CAGACGGCAC GGCATCTG
TCGCTGCCTC TGGACCCCTC TCGAGAGTTC CGTCCACCG TTGGACTTGC TCCGTGTCG
GCATCGAGAA ATTGCGTGGC GGAGCGGCAG ACGTGAGCCG GCACGGCAGG CGGCCTCCTC
CTCCTCTCAC GGTACGGCAG CTACGGGGA TTCTTTCCC ACCGCTCCTT CGCTTTCCCT
TCCTCGCCCG CCGTAATAAA TAGACACCCC CTCCACACCC TCTTCCCCA ACTCGTGTT
GTTCGGAGCG CACACACACA CAACCAGATC TCCCCAAAT CCACCCGTCG GCACCTCCGC
TTCAACGTAC GCCGCTCGTC CTCCCCCCCC CCCCTCTCT ACCTTCTCTA GATCGGCGTT
CCGGTCCATG GTTAGGGCCC GGTAGTTCTA CTTCTGTTCA TGTTTGTGTT AGATCCGTGT
TTGTGTTAGA TCCGTGCTGC TAGCGTTCGT ACACGGATGC GACCTGTACG TCAGACACGT
TCTGATTGCT AACTTGCCAG TGTTTCTCTT TGGGGAATCC TGGATGGCT CTAGCCGTTC
CGCAGACGGG ATCGATTTCA TGATTTTTT TGTTTCGTTG CATAGGGTTT GGTTTGCCCT
TTTCCTTTAT TTCAATATAT GCCGTGCACT TGTTTGTCGG GTCATCTTTT CATGCTTTTT
TTTGTCTTGG TTGTGATGAT GTGGTCTGGT TGGGCGGTCG
TTCTAGATCG GAGTAGAATT CTGTTTCAAA CTACCTGGTG GATTTATTAA TTTTGGATCT
GTATGTGTGT GCCATACATA TTCATAGTTA CGAATTGAAG ATGATGGATG GAAATATCGA
TCTAGGATAG GTATACATGT TGATGCGGGT TTTACTGATG CATATACAGA GATGCTTTTT
GTTCGCTTGG TTGTGATGAT GTGGTGTGGT TGGGCGGTCG TTCATTCGTT CTAGATCGGA
GTAGAATACT GTTTCAAACT ACCTGGTGTA TTATTAATT TTGGAACTGT ATGTGTGTGT
CATACATCTT CATAGTTACG AGTTTAAGAT GGATGGAAAT ATCGATCTAG GATAGGTATA
CATGTTGATG TGGGTTTTAC TGATGCATAT ACATGATGGC ATATGCAGCA TCTATTCATA
TGCTCTAACC TTGAGTACCT ATCTATTATA ATAAACAAGT ATGTTTTATA ATTATTTTGA
TCTTGATATA CTTGGATGAT GGCATATGCA GCAGCTATAT GTGGATTTTT TTAGCCCTGC
CTTCATACGC TATTTATTTG CTTGGTACTG TTTCTTTTGT CGATGCTCAC CCTGTTGTTT
GGTGTTACTT CTGCAGGCCA ATGGCATCGA TTCATCCAT GAAATAATA CATGGTTGAT
GCTCACGTGC ATAGTTGAAC ATTTCTCTTA TAAGACGGGC
ACTTTCACCA ATATATTGT CAATGATAGC ACTTGAAACA ATCTTTAAAA AGTTTGCATC
GATGTTGCTA GCATAGCTC TAGCAAGCAA TGTCTTCCCC GTCCAGGTG GGCATAGAG
CAGAACACCC TTTGGCGGTT TGATTCCAAC ACGGAGAAAC AGTTCAGGAT TCATAAGCGG
TAACTCGATG GACTCCCGCA GTTCCTTAT TTGATCTGAT AATCCACCTA CAGCTGACTA
ACTGACGTTG CCTGGGTCTT CATGTAGCAT GTTATAGACC ACCGGATCAA CCTCACGCGG

FIG. 75

TAGAGTTCTC ATAATGGTTA AAGTTGTCAT GTCAAGAACA ACCCGCGTTC CAGCTGTCAG
CTTTCTTTG TCAACTTTAC TCCTGCAGCC AACCACATAA CGTGCCCAC TACTGGCAAA
GGTATGGATA GTGTATCTTC ATACTGCATT TGTTTAATTT GAAAATGGTT ATCTAGTTGC
CTAACAAAAT ATAGCTGGGA TATCTTATAA CACATGTGCA GGTGACATGG AAAAAAATGC
CTATTTTTCT ATGCACTAAC TATTCATCAT GTGACATACT TCCCCAAAAA ACTAAATAAG
CCAAATTTTC CAGCTTCCGA GTCCTGAAAA AGAGTAGTGT ACCTGATACA ATTTATAGAG
TTTTTTTTT CGAAAAGAAG GGATAGCCCT CATAGATAGA GTACTAACTA AAAGTCTACT
TTTACCAATT TCAGGTTTTT GCCAGTAGT GGCCACGTT ATGTGGTTGG CTGCAGGAGT
AAAGTTGACA AGAAAAGCT GACAGCTGGA ACGCGGGTTG TTCTTGACAT GACAACTTTA
ACCATTATGA GAACTCTACC GCGTGAGGTT GATCCGGTGC TCTATAACAT GCTACATGAA
GACCCAGGCA ACGTCAGTTA CTCAGCTGTA GGTGGATTAT CAGATCAAAT AAGGGAACTG
CGGGAGTCCA TCGAGTTACC GCTTATGAAT CCTGAACTGT TTCTCCGTGT TGGAATCAAA
CCGCCAAAGG GTGTTCTGCT CTATGGCCCA CCTGGAACGG GGAAGACATT GCTTGCTAGA
GCTATTGCTA GCAACATCGA TGCAAACTTT TTAAAGATTC TTCAAGTGC TATCATTGAC
AAATATATTG GTGAAAGTGC CCGTCTTATA AGAGAAATGT TCAACTATGC ACGTGAGCAT
CAAGCATGTA TTATTTTCAT GGATGAAATC GATCCATTG *AGAAGGAGT GCGTCGAAGC*
*AGATCGTTCA AACATTTGGC AATAAAGTTT CTTAAGATTG AATCCTGTTG CCGGTCTTGC*
*GATGATTATC ATATAATTTC TGTTGAATTA CGTTAAGCAT GTAATAATTA ACATGTAATG*
*CATGACGTTA TTTATGAGAT*
*GGGTTTTTAT GATTAGAGTC CCGCAATTAT ACATTTAATA CGCGATAGAA AACAAAATAT*
*AGCGCGCAAA CTAGGATAAA TTATCGCGCG CGGTGTCATC TATGTTACTA GATCGAACCC*
*AGCTTTCTTG TACAAAGTGG* TCCCC

FIG. 75 (cont)

LpOs06g0507900 - NOP Gram domain

```
GGGGACAAGT TTGTACAAAA AAGCAGGCTC ...
...
(illegible lowercase sequence block)
...
TTCAAGTAC GCCGCTCGTC CTCCCCCCCC CCCCCTCTCT ACCTTCTCTA
GATCGGCGTT CCGGTCCATG GTTAGGGCCC GGTAGTTCTA CTTCTGTTCA
TGTTTGTGTT AGATCCGTGT TTGTGTTAGA TCCGTGCTGC TAGCGTTCGT
ACACGGATGC GACCTGTACG TCAGACACGT TCTGATTGCT AACTTGCCAG
TGTTTCTCTT TGGGAATCC TGGGATGGCT CTAGCCGTTC CGCAGACGGG
ATCGATTTCA TGATTTTTTT TGTTTCGTTG CATAGGGTTT GGTTTGCCCT
TTTCCTTTAT TTCAATATAT GCCGTGCACT TGTTTGTCGG GTCATCTTTT
CATGCTTTTT TTTGTCTTGG TTGTGATGAT GTGGTCTGGT TGGGCGGTCG
TTCTAGATCG GAGTAGAATT CTGTTTCAAA CTACCTGGTG GATTTATTAA
TTTTGGATCT GTATGTGTGT GCCATACATA TTCATAGTTA CGAATTGAAG
ATGATGGATG GAAATATCGA TCTAGGATAG GTATACATGT TGATGCGGGT
TTTACTGATG CATATACAGA GATGCTTTTT GTTCGCTTGG TTGTGATGAT
GTGGTGTGGT TGGGCGGTCG TTCATTCGTT CTAGATCGGA GTAGAATACT
GTTCAAACT ACCTGGTGTA TTTATTAATT TTGGAACTGT ATGTGTGTGT
CATACATCTT CATAGTTACG AGTTTAAGAT GGATGGAAAT ATCGATCTAG
GATAGGTATA CATGTTGATG TGGGTTTTAC TGATGCATAT ACATGATGGC
ATATGCAGCA TCTATTCATA TGCTCTAACC TTGAGTACCT ATCTATTATA
ATAAACAAGT ATGTTTTATA ATTATTTTGA TCTTGATATA CTTGGATGAT
GGCATATGCA GCAGCTATAT GTGGATTTTT TTAGCCCTGC CTTCATACGC
TATTTATTTG CTTGGTACTG TTTCTTTTGT CGATGCTCAC CCTGTTGTTT
```

FIG. 76

```
GGTGTTACTT CTGCAGG... ......... ......... .........
......... ......... ......... ......... .........
......... ......... ......... ......... .........
......... ......... ......... ......... .........
......... ......... ......... ......... .........
......... ......... ......... ......... .........
......... ......... ......... ......... .........
......... ......... ......... ......... .........
.........  ......AAA GGTATGGATA GTGTATCTTC ATACTGCATT
TGTTTAATTT GAAAATGGTT ATCTAGTTGC CTAACAAAAT ATAGCTGGGA
TATCTTATAA CACATGTGCA GGTGACATGG AAAAAAATGC CTATTTTTCT
ATGCACTAAC TATTCATCAT GTGACATACT TCCCCAAAAA ACTAAATAAG
CCAAATTTTC CAGCTTCCGA GTCCTGAAAA AGAGTAGTGT ACCTGATACA
ATTTATAGAG TTTTTTTTTT CGAAAAGAAG GGATAGCCCT CATAGATAGA
GTACTAACTA AAAGTCTACT TTTACCAATT TCAGGTTTTT .........
......... ......... ......... ......... .........
......... ......... ......... ......... .........
......... ......... ......... ......... .........
......... ......... ......... ......... .........
......... ......... ......... ......... .........
......... ......... ......... ......... .........
......... ......... ......... ......... .........
......... ......... ......... ......... AGAAGGAGT
GCGTCGAAGC AGATCGTTCA AACATTTGGC AATAAAGTTT CTTAAGATTG
AATCCTGTTG CCGGTCTTGC GATGATTATC ATATAATTTC TGTTGAATTA
CGTTAAGCAT GTAATAATTA ACATGTAATG CATGACGTTA TTTATGAGAT
GGGTTTTTAT GATTAGAGTC CCGCAATTAT ACATTTAATA CGCGATAGAA
AACAAAATAT AGCGCGCAAA CTAGGATAAA TTATCGCGCG CGGTGTCATC
TATGTTACTA GATCGAACCC AGCTTCTTG TACAAAGTGG T....
```

FIG. 76 (cont)

LpOs04g0648500 - ubi

```
CGGGACAAGT TTGTACAAAA AAGCAGGCTG TGCAGCGTCA CCCCGTCGTC CCCCTCTCTA
GAGATAATGA GCATTGCATG TCTAAGTTAT AAAAAATTAC CACATATTTT TTTTGTCACA
CTTGTTCAA  GTGCAGTTTA TCTATCTTTA TACATATATT TAAACTTTAC TCTACGAATA
ATATAATCTA TAGTACTACA ATAATATCAG TGTTTAGAG  AATCATATAA ATGAACAGTT
AGACATGGTC TAAAGGACAA TTAGTATTT  TGACAACAGG ACTCTACAGT TTTATCTTT
TAGTGTGCAT GTGTTCTGCT TTTTTTTTGC AAATAGCTTC ACCTATATAA TACTTCATCC
ATTTATTAG  TACATCCATT TAGGGTTTAG GTTAATGGT  TTTATAGAC  TAATTTTTTT
AGTACATCTA TTTATTCTA  TTTTAGGCTC TAAATTAAGA AAACTAAAAT TCTATTTTAG
TTTTTTTATT TAATAATTTA CATATAAAAT AGAATAAAAT AAACTCACTA AAAATTAAAC
AAATCCCTT  TAAGAAATTA AAAAAACTAA GGAAACATTT TTCTTGTTTC GAGTAGATAA
TGGCAGCCTG TTAAAGGCGG TCTACGAGTC TAACGGACAC CTACCAGCGA ACCAGCAGCG
TTGCGTCGGG GTAAGCGAAG CAGAGGGTAC GGTATCTCTG TGTCTGCCTT TGGACCCGTC
TCAGAGTTC  CCGTTCCACCC TTCGACTTGC TCCGCTGTCG GCATCCAGAA ATTCCGTCGC
GGAGCGGTAG ACGTTAGCCG GTACGGCAGT CGGCCTCCTC CTCCTCTCAC GGTACGGCAG
CTACGGGGGA TTCCTTTCCC ACCGCTCCTT CGCTTTCCCT TCCTCGTCCG CCGTAATAAA
TAGACACCCC CTCCACGCC  TCTTTCCCA  ACTCGTGTT  GTTGGCAGCC CACACACACA
CAACCGGATC TCCCCAAAT  CCACCCGTCG GCACCTCCGC TTCAA GTAC GCCGCTCGTC
CTCCCCCCCC CCCCCTCTCT ACCTTCTCTA GATCGGCGTT CCGGTCCATG GTTAGGGCCC
GGTAGTTCTA CTTCTGTTCA TGTTTGTGTT AGATCCGTGT TTGTGTTAGA TCCGTGCTGC
TAGCGTTCGT ACACGGATGC GACCTGTACG TCAGACACGT TCTGATTGCT AACTTGCCAG
TGTTTCTCTT TGGGGAATCC TGGGATGGCT CTAGCCGTTC CGCAGACGGG ATCGATTTCA
TGATTTTTTT TGTTTCGTTG CATAGGGTTT GGTTTGCCCT TTTCCTTTAT TTCAATATAT
GCCGTGCACT TGTTTGTCGG GTCATCTTTT CATGCTTTTT TTTGTCTTGG TTGTGATGAT
GTGGTCTGGT TGGGCGGTCG TTCTAGATCG GAGTAGAATT CTGTTTCAAA CTACCTGGTG
GATTTATTAA TTTTGGATCT GTATGTGTGT GCCATACATA TTCATAGTTA CGAATTGAAG
ATGATGGATG GAAATATCGA TCTAGGATAG GTATACATGT TGATGCGGGT TTTACTGATG
CATATACAGA GATGCTTTTT GTTCGCTTGG TTGTGATGAT GTGGTGTGGT TGGGCGGTCG
TTCATTCGTT CTAGATCGGA GTAGAATACT GTTTCAAACT ACCTGGTGTA TTTATTAATT
TTGGAACTGT ATGTGTGTGT CATACATCTT CATAGTTACG AGTTTAAGAT GGATGGAAAT
ATCGATCTAG GATAGGTATA CATGTTGATG TGGGTTTTAC TGATGCATAT ACATGATGGC
ATATGCAGCA TCTATTCATA TGCTCTAACC TTGAGTACCT ATCTATTATA ATAAACAAGT
ATGTTTTATA ATTATTTTGA TCTTGATATA CTTGGATGAT GGCATATGCA GCAGCTATAT
GTGGATTTTT TTAGCCCTGC CTTCATACGC TATTTATTTG CTTGGTACTG TTTCTTTTGT
CGATGCTCAC CCTGTTGTTT GGTGTTACTT CTGCAGGCCT TTCGCTATT  CCTTTACTG
TCTTGGACCA TATATCTGG  CTCTTCATGA GTTTTCATT  CATTCTGCA  ACTTTCTTT

TCTCCAACAT AGTATTTTCA AGCTTAAGTT GCATCTCTTG AAGCTATCA  TTACAGCTT
TATCACAGC  AACAGAAATG TGTTCCCTAT CTTTTTTAGC GTCTGACAGA AAGCTGGTA
ATACTCTCT  TGAGTTTCAA GTTGGCTTGC AAGAAGACGG TTGTACTCAT CCACGATTGT
ATCAGTTTG  CTGCTAAACA TAACTCCACC CATATCGAG  TCATCGTTGT CCCAGAAAA
TTCACACTTT GACCTGACCT TAGAATGTTT TGCATCGCTT TTGAGTGAT  TAAGACGATG
AAGATAACTG TCACGACAT  AATCCCAAAC ACGTTGAGTT TCAAATCAA  GAGAATAGCA
GTGCTGAGTG TCTTTCCAGT GCCTAATGA  GTGGCTTCT  TTATACCTTC CGCATCCAAC
AAAACCACAT ATCACAGA   TCCAGAGGTT TTCAGAGGTC TGACAAACAG AACATGTAGG
ATTTGTAGGA GTTTCAAAGG TATGGATAGT GTATCTTCAT ACTGCATTTG TTTAATTTGA
AAATGGTTAT CTAGTTGCCT AACAAAATAT AGCTGGGATA TCTTATAACA CATGTGCAGG
TGACATGGAA AAAAATGCCT ATTTTTCTAT GCACTAACTA TTCATCATGT GACATACTTC
```

FIG. 77

```
CCCAAAAAAC TAAATAAGCC AAATTTTCCA GCTTCCGAGT CCTGAAAAAG AGTAGTGTAC
CTGATACAAT TTATAGAGTT TTTTTTTTCG AAAAGAAGGG ATAGCCCTCA TAGATAGAGT
ACTAACTAAA AGTCTACTTT TACCAATTTC AGGTTTTTGC AAACTCCTAC AAATCCTACA
TGTCTGTTT GTCAGACCTC TGAAAACCTC TGGATCTGTG TGATATGTGG TTTTGTTGGA
TGGGGAGGT ATAAGAAGG CCACTCAATT AGGCACTGGA AAGACACTCA GCACTGCTAT
TCTTCTTGATT TCCAAACTCA ACGTGTTGG CATTATGTCC GTGACAGTTA TGTTCATCCT
CTAATCACT CGAAAACCGA TGCAAACAT TCTAAGCTCA GGTCAAAGTC TGAATTTCT
GGGCACAACG ATGACTCGGA TATGGGTGGA GTTATGTTTA GCAGCAAAAC TGTATACAATC
GTGATGAGT ACAACCGTCT TCTTGCAAGC CAACTTGAAA CTCAGAGAGA GTATTACGAG
GCTTTCTCTC ACACGCTAAG AAAGATAGGG AACACATTTC TGTTGCTGTG GATAAAGCTG
TAAATGATAA GGTTCAAGAG ATGCAACTTA AGCTTGAAAA TACTATGTTG GAGAAAAGA
AAGTTGCAGA AATGAATGAA AAACTCATGA AGAAGCCAGGA TATATGGTCC AAGACAGTAA
AAGGAATACA GGAAAGGAGA AGGAGTGCGT CGAAGCAGAT CGTTCAAACA TTTGGCAATA
AAGTTTCTTA AGATTGAATC CTGTTGCCGG TCTTGCGATG ATTATCATAT AATTTCTGTT
GAATTACGTT AAGCATGTAA TAATTAACAT GTAATGCATG ACGTTATTTA TGAGATGGGT
TTTTATGATT AGAGTCCCGC AATTATACAT TTAATACGCG ATAGAAAACA AAATATAGCG
CGCAAACTAG GATAAATTAT CGCGCGCGGT GTCATCTATG TTACTAGATC GAACCCAGCT
TTCTTGTACA AAGTGGTCCCC
```

FIG. 77 (cont)

LpOs04g0648600

GGGGACAAGTTTGTACAAAAAAGCAGGCTGTGCAGCGTGACCCGGTCGTGCCCCTCTCTAGAGATAA
TGAGCATTGCATGTCTAAGTTATAAAAATTACCACATATTTTTTTGTCACACTTGTTTCAAGTGC
AGTTTATCTATCTTATACATATATTTAAACTTTACTCTACGAATAATATAATCTATAGTACTACAA
TAATATCAGTGTTTAGAGAATCATATAAATGAACAGTTAGACATGGTCTAAAGGACAATTGAGTAT
TTTGACAACAGGACTCTACAGTTTTATCTTTTTAGTGTGCATGTGTTCTCCTTTTTTTTTGCAAATA
GCTTCACCTATATAATACTTCATCCATTTTATTAGTACATCCATTTAGGTTTAGGGTTAATGCTTT
TTATAGACTAATTTTTTAGTACATCTATTTTATTCTATTTAGCCTCTAAATTAAGAAAACTAAAA
CTCTATTTAGTTTTTTATTAATAATTAGATATAAAATAGAATAAAATAAAGTGACTAAAAATT
AAACAAATACCCTTTAAGAAATTAAAAAAACTAAGGAAACATTTTCTTGTTTGAGTAGATAATGC
CAGCCTGTTAAACGCCGTGACGAGTCTAACGGACACCAACCAGCGAACCAGCAGCGTCGCGTCGGG
CCAAGCGAAGCAGACGGCACGGCATCTCTGTCGCTGCCTCTGGACCCCTCTGAGAGTTCCGCTCCA
CCGTTGGACTTGCTCCGCTGTGGCATCCAGAAATTGCGTGGCGAGCGGCAGACCTGAGCCGGCAC
GGCAGCGGCCTCCTCCTCCTCTCACGGCACGGCAGCTACGGGGATCCTTTCCCACCGCTCCTTC
GCTTTCCCTTCCTCGCCCGCCGTAATAAATAGACACCCCCCTCCACACCCTCTTTCCCCAACCTCGTC
TTGTTCGGAGCGCACACACACAACCAGATCTCCCCAAATCCACCCGTCGGACCTCCGGTTCAA
GTACGCCGCTCGTCCTCCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGGTCAGCCTGGCCGTCTTCCTCACCATCGTCGTCCTCCTCCTGGCCGACCTCTTCTGCTCCC
AGCTCCGTCTCCGCCCATCGTCGTGACGCCGACATGGCCGTGCACAAGAGGCCAAGCTGGCGT
CCCGGCGTCGTCCCGCTGCACAACGGCCGACGACGCGTCGGTGGCCACCACCACCACCACGGCGACG
CACGAGGCGTCTCTAGCACCTCGGCCTTTACTACGGCACGGCGTCATGTGGCGCCTACCGGCA
AGGACCTCCTCCTCGGCATCCCAAGCTGGAGGCCGCCGTGTGGAAGTGGTCTCCGCGCGCGCTC
CTCGCCGTGGCTTCGCGGCCGCGGTCGAGCGTACGCCCGCGAGTCCTCCTCCTCCGCGTACGC
GACGGCTTCCTGGCGCATCTCCAACCCGTGTACGAGCGGCGCCACGGCGCGCCGGGCGGGTACG
AAGAAGACACGCCGTTCGACACGCCTGACGTATCGTCGAAAGGTATGGATAGTGTATCTTCATACTG
CATTTGTTTAATTTGAAAATGGTTATCTAGTTGCCTAACAAAATATAGCTGGGATATCTTATAACAC
ATGTGCAGGTGACATGGAAAAAAATGCCTATTTTTCTATGCACTAACTATTCATCATGTGACATACT
TCCCCAAAAAACTAAATAAGCCAAATTTTCCAGCTTCCGAGTCCTGAAAAGAGTAGTGTACCTGAT

FIG. 78

ACAATTTATAGAGTTTTTTTTTTCGAAAAGAAGGGATAGCCCTCATAGATAGAGTACTAACTAAAAG
TCTACTTTTACCAATTTCAGGTTTTTGCGGCGATGCGTCAGGCGTGTCGAACGGCGTGTTTCTTCG
TACCCGCCCGGCGCGGCCGTGGCGCCCCGGCTCGTACACGGGGTTGGAGATGCGCAGGAAGCCGTCGC
TGTACGCGGAGGAGGAGGACTCGCGGCGGTGGCTCGGACCCGGCGGCGAAGCGACGGCGAGGA
GCGGCGCGGGAGACCACTTCCACACGGCGGCCTCCAGCTTGGGGATGGCGAGGAGGAGGTCCTTG
CGGGTGGGCGCGCACATGACGCCGTGCGCGTAGTAGAAGGGCGGGGTGCTGGAGAGCGCCTCGTGCG
TCGCCGTGGTGGTGGTGGTGGCCACCGACGGTTCGTCGGCGGTGTGGCGGGGACGCGCCGGGAC
GCCAAGCTGCGGCCTCTTGTGCGGCGCCATCTCGGCGTCAGCGCGGAGGCGGCGGAGCGGAGGTGG
GAGCAGAAGAGGTCGGCCAGGAGGAGGACGACGATGGTGAGGAGACGGCCAGGCTGA*AGAAGGAGT*
*GCGTCGAAGCAGATCGTTCAAACATTTGGCAATAAAGTTTCTTAAGATTGAATCCTGTTGCCGGTCT*
*TGCGATGATTATCATATAATTTCTGTTGAATTACGTTAAGCATGTAATAATTAACATGTAATGCATG*
*ACGTTATTTATGAGATGGGTTTTTATGATTAGAGTCCCGCAATTATACATTTAATACGCGATAGAAA*
*ACAAAATATAGCGCGCAAACTAGGATAAATTATCGCGCGCGGTGTCATCTATGTTACTAGATCGAAC*
*CCAGCTTTCTTGTACAAAGTGGT*CCCC

FIG. 78 (cont)

LpOs04g0648900

<u>ACAAGTTTGTACAAAAAAGCAGGCT</u>GTGCAGCGTGACCCGGTCGTCCCCTCTCTAGACATAA
TCAGCATTGCATGCTAAGTTATAAAAATTACCACATATTTTTTTGTCACACTTGTTTGAACTGC
AGTTTATCTATCTTTATACATATATTAAACTTACTCTACGAATAAATAACTATAGTACTACAA
TAATATCAGTGTTTACACAATCATATAAATGAACAGTTAGACATGGTCTAAAGGACAATTCAGTAT
TTTGACAACAGGACTCTACAGTTTTATCTTTTAGTGTGCATGTGTTCTCCTTTTTTTTTGCAAATA
GCTCACCTATATAATACTTCATCCATTTATTAGTACATCCATTTAGGGTTTAGGGTAATGGTTT
TTATAGACTAATTTTTTAGTACATCTATTTATTCTATTTAGCCTCTAAATTAAGAAAACTAAAA
CTCTATTTAGTTTTTTATTTAATAATTTAGATATAAATACAATAAAATAAAGTGACTAAAAATT
AAACAAATACCCTTTAAGAAATTAAAAAAACTAAGGAAACATTTTTCTTGTTTGAGTAGATAATGC
CATCCTGTTAAACGCCGTCGACGAGTCTAACGGACACCAACCAGCGAACCAGCAGCGTCGCGTCGG
CCAAGCGAAGCAGACGGCACGGCATCTCTGTCGCTGCCTCTGGACCCCTCTCGAGAGTTCCGCTCCA
CCGTTGGACTTGCTCCGCTGTCGGCATCCAGAAATTGCGTGGCGGACGGCAGACGTGAGCCGGCAC
GGCAGGCGGCCTCCTCCTCTTCTACGGCACGGCAGCTACGGGGATTCCTTCCCACCGCTCCTTC
GCTTTCCCTTCCTCGCCCGCCGTAATAAATAGACACCCCTCCACACCCTCTTCCCCAACCTCGTG
TTGTTCGGAGCGCACACACACAACCAGATCTCTCCCCAAATCCACCCGTCGGCACCTCCGCTTCAA
<u>G</u>TACGCCGCTCGTCCTCCCCCCCCCCCTCTCTACCTTCTCTAGATCGGCGTTCCGGTCCATGGT
TAGGGCCCGGTAGTTCTACTTCTGTTCATGTTTGTGTTAGATCCGTGTTTGTGTTAGATCCGTGCTG
CTAGCGTTCGTACACGGATGCGACCTGTACGTCAGACACGTTCTGATTGCTAACTTGCCAGTGTTTC
TCTTTGGGGAATCCTGGGATGGCTCTAGCCGTTCCGCAGACGGGATCGATTTCATGATTTTTTTGT
TTCGTTGCATAGGGTTTGGTTTGCCCTTTTCCTTTATTTCAATATATGCCGTGCACTTGTTTGTCGG
GTCATCTTTTCATGCTTTTTTTTGTCTTGGTTGTGATGATGTGGTCTGGTTGGGCGGTCGTTCTAGA
TCGGAGTAGAATTCTGTTTCAAACTACCTGGTGGATTTATTAATTTTGGATCTGTATGTGTGTGCCA
TACATATTCATAGTTACGAATTGAAGATGATGGATGGAAATATCGATCTAGGATAGGTATACATGTT
GATGCGGGTTTTACTGATGCATATACAGAGATGCTTTTTGTTCGCTTGGTTGTGATGATGTGGTGTG
GTTGGGCGGTCGTTCATTCGTTCTAGATCGGAGTAGAATACTGTTTCAAACTACCTGGTGTATTTAT
TAATTTTGGAACTGTATGTGTGTGTCATACATCTTCATAGTTACGAGTTTAAGATGGATGGAAATAT
CGATCTAGGATAGGTATACATGTTGATGTGGGTTTTACTGATGCATATACATGATGGCATATGCAGC
ATCTATTCATATGCTCTAACCTTGAGTACCTATCTATTATAATAAACAAGTATGTTTTATAATTATT
TTGATCTTGATATACTTGGATGATGGCATATGCAGCAGCTATATGTGGATTTTTTTAGCCCTGCCTT
CATACGCTATTTATTTGCTTGGTACTGTTTCTTTTGTCGATGCTCACCCTGTTGTTTGGTGTTACTT
CTGCAGG<u>ATGGCGCCTCTTGCCGCCGCGGCCGCGGCCGTGGCCGCGAAGGAGGAGCTGGGCGTGACG
GTGCGCGTTGCGCGGCGCGATGGCGCTGCCCCGGTGAGCCAGCAGCAGCCGCGGCGGCAGTACCGGC
GGCGTGCGCATGCGGAAGTGGGGCAAGTGGTGGCGGAGATCCGGAGCCGCAAGCGCACGCGCAT
CTGGCTCGGCTCTTACGCCACGCCCGTCGGCGCGGTGCGGCTACGACATGGCCGTCTTCTACCTG
CGCGGCCTGGTCGGCTAGGCTCAACTTCCCGACGAGATCTCCGCGCTGGCGCTGTCCCGCCGC
CCGAGGAGCTGGAGGCGACGGCGGCGGCTGTCGGCGGCGTCGATCCGGAAGAAGGCCATCGAGGT
CGGGTCCCGCGTCGACGCGCTCCAGACCGGGATGACCATGGCTGCCACCGCGCCGCGGCGGACA
AACCACCGGGAGCGGCAGAGGCAGCATCACGCGCAGCAGCAGGCTGGCGCGACGACGAGGACCTGCTCC
AGCTCCACCACCAGAAGCAGCAGCCGACGGCGTGGAACGGCCGGCCAAGAACCCGGATCTCAACCA
GGGCGCTCGACCCCGACAGCTCCCGACGCCGAGTGA</u>AAAGGTATGGATAGTGTATCTTCATACTGCATT

TGTTTAATTTGAAAATGGTTATCTAGTTGCCTAACAAAATATAGCTGGGATATCTTATAACACATGT
GCAGGTGACATGGAAAAAAATGCCTATTTTTCTATGCACTAACTATTCATCATGTGACATACTTCCC
CAAAAAACTAAATAAGCCAAATTTTCCAGCTTCCGAGTCCTGAAAAAGAGTAGTGTACCTGATACAA
TTTATAGAGTTTTTTTTTTCGAAAAGAAGGGATAGCCCTCATAGATAGAGTACTAACTAAAAGTCTA
CTTTTACCAATTTCAGGTTTTTG CCACTCGCCGTCGGAGCTGTCGGGTCGGCGCCTGGTTGAGAT
CGGGTTCTTGGCCGCCGTTCCACGCCGTCCGCTGCTGCTTCTGGTGGTGGAGCTGAGCAGCTC
CTCGTCGCGCGCAGCTGCTGCTGCGCGTGGTGCTGCCTCTGCCGGTCCGGTGGTTTGTCGTCGGC
GGGCGGCGGTGGCGACCATGGCATTCCGTCTCGAGCGCGTCGATGCGGGACCGACCTCGATGG
CCTTCTTCCGGATCGACGCCGCCGACAGCGCGCCGCCGTCGGCCTCCAGCTCCTCGGGCGGCGGGGA
CAGCGGCGCCAGCGCGGAGATCTCGTCGGGAAGTTGAGCCTGGCCGACCGGCCGCGCAGGTAGAAG
ACGGCCGTGTCGTAGCGCGCGCGGCGGCGACGGCGCTGGCGTAGGAGCCGAGCCAGATGCGCGTGC
GCTGTGCGGCTCCCGGATCTCCGCCACCCACTTGCCCACTTCCGCATGCGTACGCGCGGTACTG
CCGCCGCGGCTGCTGCTGGCTCAGCGGGGCCAGCGCCATCGGCGGCGCCACGGCCACGGTCACGCCC
AGCTTCTCCTTGCGTGCCACCGCCGCAGCCGCGGCGCAAGAGCGCCAT AGAAGGAGTGCGTCGAA
GCAGATCGTTCAAACATTTGGCAATAAAGTTTCTTAAGATTGAATCCTGTTGCCGGTCTTGCGATGA
TTATCATATAATTTCTGTTGAATTACGTTAAGCATGTAATAATTAACATGTAATGCATGACGTTATT
TATGAGATGGGTTTTTATGATTAGAGTCCCGCAATTATACATTTAATACGCGATAGAAAACAAAATA
TAGCGCGCAAACTAGGATAAATTATCGCGCGCGGTGTCATCTATGTTACTAGATCGAACCCAGCTTT
CTTGTACAAAGTGGTCCCC

FIG. 79 (cont)

A
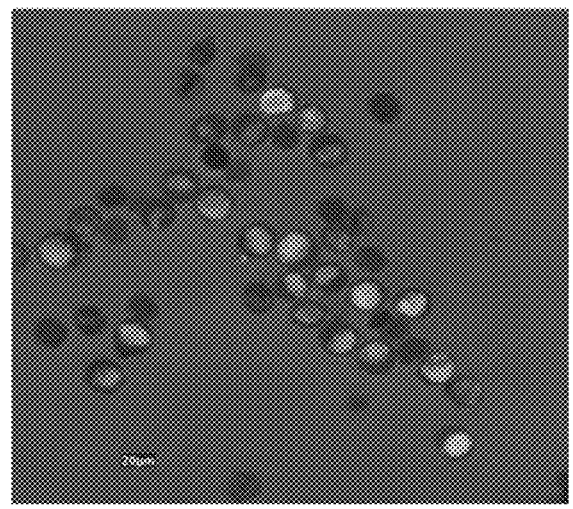
B
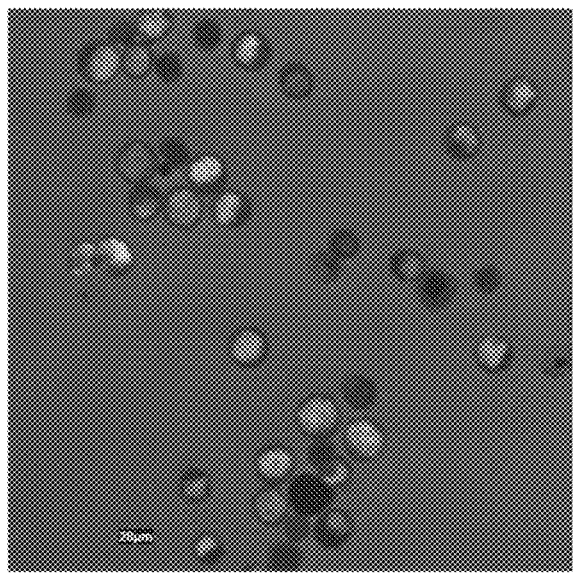
FIG. 82

A
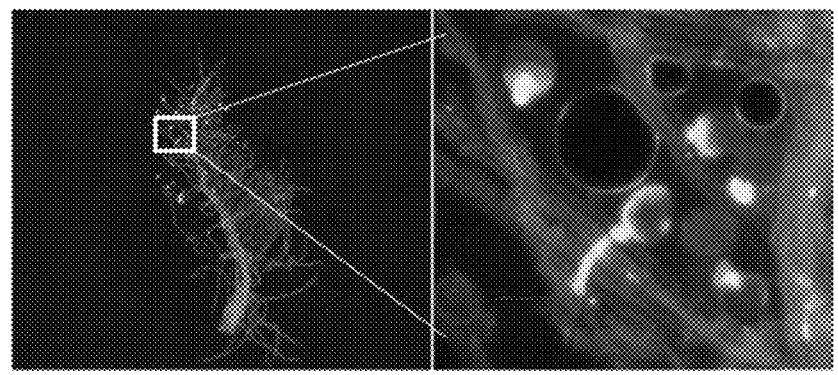
B
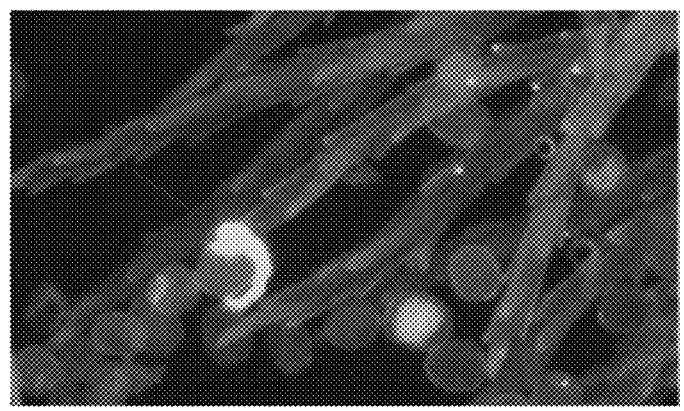
C
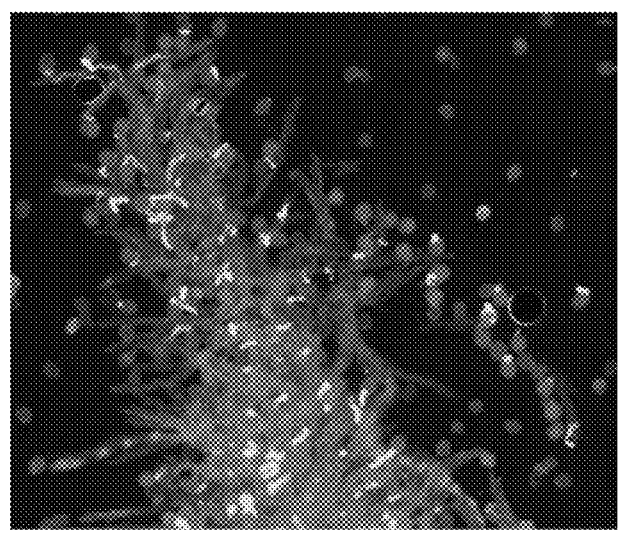
FIG. 84

```
                          SEQUENCE LISTING

<160> NUMBER OF SEQ ID NOS: 161

<210> SEQ ID NO 1
<211> LENGTH: 810
<212> TYPE: DNA
<213> ORGANISM: Lolium perenne

<400> SEQUENCE: 1
atgctcctcc taatccgccg cctcaccgcc gttccttccc gcctagccgc cctcgcactc         60
cggcaacccc acggtcgagc cgcaacgacg acgtccacga cacccgcggt atcctcctcc        120
catctcgcgg gttcgccgcc tgcagaggat ccagcagctg atccggggtg cgagtcggaa        180
cccctcgatc gcgactgggg ctccacgctg tcccgagcgg atccggcaga ggtggccggg        240
attctccggc gtctgcacga cgagacgatt catttaggcc tgggcaccta caatctgctg        300
ctggagcgag cgtgcgaggc agaggacttc gcgctcttcg ccaaggtatt cagataccct        360
ctgctctcca aagccgctcc tgacttgacc tcttacatgc atgtcgccag ggccatcggg        420
gatttagatg accctgaacc gatgctcagg tttgttagag aggtattgga ggtcacgcag        480
ggtagagatc ccacggtggt gaatcgcatt gttttcgcca cgggtaaata cggtcacatc        540
gataaaagct tgatcatatt cgaagagctg aagaaagata agaagtgctt ggatgtcgtc        600
acgttcaaca ccgtcttgga catgcttggg aaagccggcc agattgaccg aatgctccga        660
gaggtgaagc tgatggagga gctcggcatt tcccctgaca tcgtgacata taatacggtg        720
ataaactgcc tgcgtaggct tggaaggttg gatatgtgca agagctttgc aacggagatg        780
gttgagaggg gcatcggtcc agatttgaga                                         810

<210> SEQ ID NO 2
<211> LENGTH: 1158
<212> TYPE: DNA
<213> ORGANISM: Lolium perenne

<400> SEQUENCE: 2
atggctccgc ccgccgccac cgtcgccgtc ctcggcgacg acctcctgcg ggaggtcttc         60
atcctcctcc ccaccccac cgacctcctc cgcgccgcgc tcgcctgcaa gcccttcctc        120
cgcgccgccc gcagcgcccc tttcctccgc cgcttccgcc gccgccaccc cttcacctgc        180
ccgctcctcc tcggctgcct cctccacggc cccaccgacc gccgccgcac caccgcctcc        240
cacctgctcc cggcctaccc cgacgccgcc acgcgccgcc tcatcgacgg cgccgacttc        300
accttctcct tcctccccg ccgcggctgg cccaagccg ccggcagcgc gtggcagctc        360
ctcgactgcc gcaacggccg cgccctcttg ctcagccggg cttcgagggc gctcgccgtc        420
```

```
gccgatccgc tcacccggcg ctcggtcacc ctccccgcga tccgcggcct agggtacgcc    480
ctcgtcgccg acgacggcga ctcgtcgctg ttcaaggcgg tctgcatttc cgacgcgtc     540 ggagccccgg ggctgcgcgc cttcctcctc tcctccgccg acctccgatg ggtccaagtc    600
gccgtcgctg gcctcgacga tgtgcagccc gatctcgccg gctcccgcgc gatgcaagcc    660
aacggatcgc tctactggaa gctagtgggc ggggagcaca tggtggcgct caacacggag    720
accatggagt tcgccgtgct ggagctcccg cctttcttga gggagatcag tttcgacatc    780
attgagaagg gggaggacgc cgcagctggg ctctacctgc tcaccatgcg cggattctgc    840
attgaggttt gggccggtgt gaaggacggc gccgacggcg ggctgacctg gacgctggtg    900
gagaagtctg tcatgttcca cagggccatg gccgagatgc ttggttccga attcctttac    960
cagaacaggc tggatgtcat cggggtggtt gccggtgttg tgttcttgcg caatggcgaa   1020
tgtctcttct ccattgatct ccagaccatg aagatgacca gggtgtctcc caaggagaat   1080
tgcccatccc atctgattta tccttgcacg atagcgtggc cgccttcttt cctgaaccct   1140
actgaacaag gtgcttga                                                 1158

<210> SEQ ID NO 3
<211> LENGTH: 315
<212> TYPE: DNA
<213> ORGANISM: Lolium perenne

<400> SEQUENCE: 3
atgagcgcgg cggcgggcgg gctgcggcag ctactgacgg cggcggtgac ggcgggcgca     60
gcggaggcgc gcgccgcggt gttcggccac gcggtcaacc cgtcggggaa gcgcgcggcg    120
acgaagctgc tgcggaggaa gttcatcgga gagcagctcg cgcagtggta tccctacgac    180
atcaagcggg acgaccccat cgtcatggca cgcgaggaga aagagcgtct taccaagctt    240
gaaatgctca gcgtcgcgg aaagggtccg ccgaagaagg ccagggaag cgtgcggtc     300 aagagaacca agtag                                                    315

<210> SEQ ID NO 4
<211> LENGTH: 240
<212> TYPE: DNA
<213> ORGANISM: Lolium perenne

<400> SEQUENCE: 4
atggcggtgt cggcggacct gagcaaggaa gaggctctca agctggccgc tggaatggcc     60
ttgtcatcca ctgcggcagt ccgcgctagc gcagggaagg ccggtgatgc ggccaataac    120
tcctatgcgc gcagcggatc catctcccgcc cgcaccagca gctgcgccac caccacctcc   180
ttcggctctg cccgcaccaa caccgtcagc gccacactag ccctggccgt cagcgcctaa    240

<210> SEQ ID NO 5
<211> LENGTH: 879
<212> TYPE: DNA
<213> ORGANISM: Lolium perenne

<400> SEQUENCE: 5
atggagatga agaacgggga ctacgcctcc gtctccctcg agctcgtcac cgcccacgcc     60
caggccaggg ccaccttcga ggtcaggctg ctcgaccagg ccggcaagct gccgccctcc    120
gtcgtgctcg cccggtacaa gcccctgctg ttccgctcca acccgcccac ctacatgagc    180
gaggacttcc tgcagccatt gccctacctg cacgctgacg acagcctcgt ggtcgagtgc    240
gacatcacag tcatcaaaga atccgagctg gccctggttc actctaccct cgacatcaaa    300
```

```
gtgcctccct ccgacttgtc acagaacctc agacaactgc tggaggccgg ggatgaatca    360
gacgtcgcct tcgaggtccg aggggaggtt ttccccgcgc acaagctcgt gctcgcgatg    420
cggtcgcggg tcttcaaagc cgacctcttt ggcccgatgg gcgacaggac aaggaagacc    480
atacccatag aggatatgca gcccgctgtc ttcggcgcgc tgctccactt catctacacg    540
gattcgctgc cttccatgga gcatcttcac ggagatgatg ctgaggaaat ggtgaagcac    600
ctgctcgtgg ctgcagatag gtatgccatg gaaaggatga aggtgatgtg cgagagcatc    660
ctttgcaaga ctcttaatgt ccgtaatgtc accactactc tagctctagc cgaccagcat    720
cagtgcagcc acctcaaaga tgcttgcctt gactttatcg cttctccgga cagaacagat    780
gatgtggtgg caagcgaagg ctatgcttgc ctcaaaagat cttgccctgc tgtcatagca    840
gatatcttcg agagggcaac caagtctcgc aaaatctag                           879

<210> SEQ ID NO 6
<211> LENGTH: 276
<212> TYPE: DNA
<213> ORGANISM: Lolium perenne

<400> SEQUENCE: 6
atggcggcgg tggcgcagcg gaagacgaag ggttcatcgg cggcgagcac cggcggcgcc     60
aagacgaaga ggaggaggaa gacgaaggtg ctcccgccgc tgctgtcgcc ggggacggcc    120
gtggaggtgc tccggaacgg gaagtggtgg ggcggcggca cggtgacgat ccggaacgac    180
cgcacctaca tggtcagcct ccccgagggc atgaccgtgc tcatgacacg ggggagggtc    240
cggcccaccg ccggatacgg cacgctttat tcgtag                              276

<210> SEQ ID NO 7
<211> LENGTH: 1002
<212> TYPE: DNA
<213> ORGANISM: Lolium perenne

<400> SEQUENCE: 7
atgagaattg cttcaagaag ggttaacagt gcaagctgtg atgagattac agcccttcga     60
tcagaagcaa aggttgctag cgagttggtc acatctgtat ctcggcgtgt aaaaggtgct    120
ggatcagaac agagatctct tcatgcaaca tccaatagaa tgatgctgtc acaagaagaa    180
atgttcaatt acagcacaaa aaagcaacag gcaacacata tattttcaaa ccttagaaag    240
caaatatcct ccatttttaat tgctgacatt gaggaactaa gggctaaagg atgcattatt    300
tcccttgctt gttctgacca tacgagttca gaagctaatg ttgccataaa catttcacat    360
agtttgtctt ttaaagagtg tcctctagca ttatctcctg tttcaagtga attgtgttta    420
ggtatacatt ctgatatagc tgagcaaaaa ttagaacact ggtcctcagt tgcaccactt    480
gcacttgaag ttgtcctatc aattggacaa aaggctagag atggaacttt atcagataat    540
gacgtaaatg atacgctgg agacggaaat attgaaagca tgcttctagt tgagaaagga    600
ctgcgcgaat tagcttcgct caagataaat gtagccattt ttatgattac taagcttcct    660
tctgcaggcc cagtttatcc cgctgaaaat cacagctctt cagagccact cgagttaagt    720
gaggaagagc gggaagatgt acgcttcaag caggcatggt tgacatactt ttggaggcgg    780
gccaaaaatc atgatgtaga ggaagatata gctgacgagc ggctacaatt ttggatagag    840
caaggcaatc atccagttac tacaagcgat gtcatcgaag ttgatagagg acttcatgag    900
ctgaagaagc tgggagtcga gtctcagctg tgggaggcga cgaggagatc tctcgacgat    960
```

```
gatttcagta atcatgggag tccatttgga tctgaagttt ag                    1002
```

<210> SEQ ID NO 8
<211> LENGTH: 510
<212> TYPE: DNA
<213> ORGANISM: Lolium perenne

<400> SEQUENCE: 8

```
atggagcaat gcgacgcgga gatcccatcc agtggacgcg ggctttccta cggcggcgac    60
agctgcaggg aggaccgcct cagcgcgctt cccgacgact tgcttatcca tatccttctc   120
aagatcctcg acgccgccgg cgccgcgcgg accagcgtcc tctcccgccg ctggcgccgc   180
ctctggaccc tcctgccgga gctcctcttc cccaacagta accccatca catacgcctc    240
gccctcaccg cccatgaagc gccggcccta cgcaagctcg ccgtcaccgt cacagacccc   300
aaccctgagt ccgtggcggc ctggcttccc atcgccgcgc ccgcctctc tggcgatctt    360
ttcctcttta acatggctca gcggaacgaa tcggaggacg aggccgggga aagaggcgcc   420
tttgagctcc cctgcttcga gagggccacc gcaatcgtgc tcccctgcca aggggccct    480
tgccccttga cggtctccat cgccgcctgc                                   510
```

<210> SEQ ID NO 9
<211> LENGTH: 489
<212> TYPE: DNA
<213> ORGANISM: Lolium perenne

<400> SEQUENCE: 9

```
atggagcaat gcgacgcgga gatcccatcc agggaacgcg ggctttccta cggcggcgac    60
ggctacaggg aggaccgcct cagcgcgctt cccgacgact tgcttatcca tatccttctc   120
aagatcctcg acgccgccgg cgccgcgcgg accagcgtcc tctcccgccg ctggcgccgc   180
ctctggaccc tcctgccgga gctcctcttc cccaacagta accccatca catacgcctc    240
gccctcaccg cccatggagc gccggcccta cgcaagctcg ccgtcaccgt cacagacccc   300
aaccctgagt ccgtggcggc ctggcttccc atcgccgcgc ccgcctctc tggcgatctt    360
ttcctcttta acatggctca gcggaacgaa tcggaggacg aggccgggga aagaggcgcc   420
tttgagctcc cctgcttcga gagggccacc gcaatcgtgc tcccctgcca agggccctt    480
gccccttga                                                          489
```

<210> SEQ ID NO 10
<211> LENGTH: 1236
<212> TYPE: DNA
<213> ORGANISM: Lolium perenne

<400> SEQUENCE: 10

```
atgggggcgg atttgggggc ggagttgggg gcgctcgctc tgaagtacac cggggtgtcg    60
ctctcggtgt cggactacga ctccatcgtc gccatgaaca tcttcgtcgc gctcctctgc   120
ggctgcattg tcttcggcca cctgctcgag ggaaccgct gggtcaacga gtccaccacc    180
gcgctcgtca tggtgtttgc ggttttgtct cgctgggcc gggtggcatg gctcatcact    240
ggaggggtga tcctgctcgt caccaatggg gtcaattcgc gcattctggt cttcagcgag   300
gatatattct tcatctactt gctcccgccc atcatcttta acgctgggtt tcaagtaaag   360
aaaaagcaat tcttccgcaa ttttgcaaca attactttgt ttggggctat tgggacattg   420
atatcctttg taataatcag ccttggtgcc atggattgt tcagcaaact tgatgttgat   480
ccactccagc ttggggacta tcttgcaatt ggtgctatct tctcagcaac agattctgtt   540
```

-continued

```
tgcaccttac aggtgcttaa ccaggatgaa acacccctac tctatagtct ggttttggt      600 gaaggtgttg ttaatgatgc tacatctgtt gtgctattca atgcaattca aaacattgat      660
cttgatcatt tcgatgcgtt tgttctacta caacttattg gaaaattcct ctacctactt      720
ttcaccagta ctgttcttgg aatagctctg ctggatctga gtggtattct caccgtgttc      780
ttctgtggaa tagtaatgtc gcattacact tggcataatg tgacagaaag ctctagggtt      840
actaccaagc atacttttgc aaccttatca ttcattgctg aactatttct ttttctctac      900
gttgggatgg atgcattgga cattgaaaaa tggagattag ctaggagtag ggagctaata      960
atatggtggg caggtctcat gagaggagca gtttcaattg cacttgctta caacaaggtt     1020
tttggcttgc tgactaagcc tctgattaat ctcctcatcc caccaaggcc tagcaataca     1080
gctgatggct caagccagtc attccttgac ccgcttctga gtagcttatt gggctccgac     1140
ttggatattg ccaatacccc ccctcaaacc aaccttcagc ttcttctcac catacaaaca     1200
cgttctgttc atcgtgtgtg gcgcaagttc gatgat                              1236
```

<210> SEQ ID NO 11
<211> LENGTH: 1254
<212> TYPE: DNA
<213> ORGANISM: Lolium perenne

<400> SEQUENCE: 11

```
atggctagcc aaatctctgg tactgtagca tctagtgggg tgggctataa tgatcaatac       60
ggaatgccct gtaagatgaa aggactacat tgtgtatcat tgaattgtat accccccaaat     120 ttagaggcaa ggaaggggat gagtggatat cacttagtcg tcaggttctg ttcaaatgat     180
agatatgggc aaaccactct taagtccaac agttccatgc tcagacaagg tcagagtgtt     240
tggtgccgtt cttatgggcc tcgtggtagc agtgaaacta agagcgcga gagttctgaa     300 gatgacaatg atgcttacag ggattttaaa gagcagccaa gaggaaattc gcaattttca     360
gatgatcaag ttgcggctca gaaaaaatca ctctactcta ttcaagggct atctaaagct     420
tgccaatttg tttacaatga tgcaaagttt gtgaatgaaa gagctcagag tgatattctt     480
ttgctttcac gtggcatcac aaggctaaac aaacgggcat ctcaggatgt tgctgtatta     540
gggttgggat ttctcaagct tgatgctcgc gcaaggaagg acactcaaaa gattgataac     600
agtgtgaagg agcgagcagc ccacctgacc aatttttgcta gaatactgaa ggagcgcgct     660
gaatcagact tgaagaaagc agcagatcag cattggagtg atggtgcttt agaggcagat     720
ctgcggcgag ctgacatggt tgttaggcga cgtgccatgg aggacgcttt catggctcta     780
aagtttgtac gggatatcca tgacatgatg gcaaacaaat tacaggatca gattccaaag     840
gatgcttcat tttcacagga tgcatacctg agtatggcat ctgccttgtc tgaggctgat     900
ggtatcgact acacagatcc tgaggagctt gaattattag tagcggctct tattgatctg     960
gatgccatgg atgggaaaag gagtgtttcc ttattagctg aatgttcaag ctctccagat    1020
gttaatacca ggaaagcttt ggctaacgca ttggctggca gctccatcta tgtggactct    1080
agggaatgct gggatgggtg cattacagct agctctgcag caagagccat tgatgaactc    1140
agaaagcagt gggagcttga gagggtgac agtctgaggt tgtcgtgaa ccaaaacttg    1200 gataccaaag agactggtga tgacagttca gcagaagatg atacaacccc gtga         1254
```

<210> SEQ ID NO 12
<211> LENGTH: 1686
<212> TYPE: DNA

<213> ORGANISM: Lolium perenne

<400> SEQUENCE: 12

```
atggggcagc cgacagaccg tgtggatgat ttctcatcga gaggcaaggt ggctagggtt      60
tggtgtatgc gtgaaagaaa ttcaactttc aggaaaatcc tcggaattta tgtcgaaggg     120
cttatttttc cagaagaatc acggagccag aagggcaggc ctgggggagg cccaggcccc     180
ccaaacaata ggctggcgcg gcctgtaggg tggcgcgccg ccctagcgtg tggcccactc     240
ggccagcctc tgacgccccc ctctggacta cttaagggtt ttgatctaaa acgcgagac      300
gggaagtcaa agtcgcgaga aaccatccag tacgccgcca ccgtcgcgaa actccgtctc     360
gggaccagaa actccgttct ggcacctcgc cgggatgggg aattggagga gatcatcgcc     420
atcatcacca ccgacgcctc tccatcgacc agccatgttt cccccatcca taggcgcg      480
gttgctcgga taaggcatca gcttgcatac gcaacccaca ctttcttcga taagaggat     540
ttcttgtata ccatacacc cataataacc accagcgatt gtgagggtgc cggtgagatg     600
ttccaagtca cctccttgtt cagccaggct gaaaaggttg acaaggagct taaggagaac     660
cctgcaccat ctgaagctga tgttgaggct gctaagcttg ttgtcaaggg aaaaggagat     720
gcagttgcgc aacttaaagc agcaaaagct agcaagcaag agataactgc tgctgtttcg     780
gagcttacaa aggcaaaaga ggttgtctta aggctggaag agaggtctaa gttgaaacct     840
ggaattcccc acaaagatga tgggtccatt gcgtttgaga atgacttctt caagcgtgca     900
gcctttctga ctgtttcagg ccaacttcag gttgagactt atgcttgtgc tctcagcagt     960
gtctatacct ttgacccac attccgggca gagaactcac atacgtcaag acatttggca    1020
gaattttgga tggttgaacc agaaattgca tatgcaaact gcatgatga tatgaactat    1080
gcagagaggt acgtaaaata cctctgcaaa tggttactcg atcattgccg tgaagacatg    1140
gaattcatgg tgaaacatgt ggacaagact gcaattgagc gtctggagct gtttcttcc    1200
acacccttttg agcgcatctc atatacaaag gctgtggaga tcttagaagg tacgggtaag    1260
aaatttgaga caaggttga tgggaatt gatttagcgt ctgagcatga gaggtatttg     1320
actgaggtga tatttaagaa gccagttatt gtttataact acccgaaagg aataaaggca    1380
ttttacatga ggctgaatga tgaccagaag acggtggctg caatggatgt acttgttccc    1440
aaggttggtg aattaattgg tggaagccaa agggaggagc gtcttgatgt ctctcacacaa    1500
agaatactcg acgcagatct gcccttggag ccttatgagt ggtacttgga cctcaggcgc    1560
tttggatctg tgaagcacag cgggtttggc cttggcttcg agaggatgat cctttcgcc     1620
actggtctcg acaacatcag agacgtcatc ccattcccaa gatatcccgg tagggctgat    1680
ctttga                                                                1686
```

<210> SEQ ID NO 13
<211> LENGTH: 678
<212> TYPE: DNA
<213> ORGANISM: Lolium perenne

<400> SEQUENCE: 13

```
atggcgccgg cggccgtgaa ggtgtacggg tgggcgatgt cgccgttcgt tgcgcgcgcg      60
ctgctgtgcc tggaggaggc cggcgtcgag tacgagctcg tccccatgag ccgccaggcc     120
ggcgaccacc tccagccgga ctttctcgcc aggaacccgt tcgcccaggt gcctgtcctc     180
gaggacggcg aactcacact cttcgagtcg cgcgcgatcg cgaggcacgt gctgcgcaag     240
cacaagccgg agctgctggt gggcgacggc tcaccggagg cggcggcgat ggtggacgtg     300
```

```
tggctggagg tggaggcgca tcagcaccac gccccgacgg ccgccatcat ggtgcagtgc    360
atcctcgccc cgctcctcgg cggcgcgcgc gaccaggccg tcatcgacga gaacgtcccc    420
aagctgaaga aggtgctgga ggtgtacgag gcgcggctat cgaagtcgag gtacctcgcc    480
ggggaatcgg tgagcctcgc cgacctcagc cacttcccga tgctgcgcta cttcatggag    540
accgagtaca aggcgctggt ggaggagctc ccgcacgtga aggcgtggtg gaggagctc     600 aaggccaggc cggcggcgag gaaggttacc gagttcatgc cggtggactt tggtctggga    660
aagaaggcag agcagtga                                                  678
```

<210> SEQ ID NO 14
<211> LENGTH: 687
<212> TYPE: DNA
<213> ORGANISM: Lolium perenne

<400> SEQUENCE: 14

```
atggcgcaga cggcggtgaa ggtgtacggg tgggcagtgt caccgttcgt ggcgcgtgcg     60
ctgctgtgcc tcgaggaggc cggcgtcgat tacgagctcg ttcccatgag ccgcgaggct    120
ggcgatcacc tccgcccgga cttcttggcc cgtaaccccct cgcccaggt gcccgtcctc    180 caggacggtg acctcacact gttcgagtcg cgcgcgatcg cgaggcacgt gctgcgcaag    240
cacaagccgg agctgctggt cggggacggc tcgccggagg cggcggcgtt ggtggacgtg    300
tggctggagg tggaggcgca tcagcaccac cccccaacgg gtgccatcat ggtgcagtgc    360
atcctcaccc cgctcctcgg cggcgtgcgc gaccaggccg tcgtggacga gaacgtcgcc    420
aagctgaaga aggtgttggc ggtgtacgag gcgcggctct cggcgtcgag gtacctcgcc    480
ggggagtccc tcacgctcgc cgatctcagc catttcccca tgatgcgcta cttcatggag    540
accgagtacg cggcgctggt ggaggagctc ccgcatgtca aggcctggtg gaggagctc     600 aatgccaggc ccgcggcgag gaaggtcacg gagcacgccg tcaatgccgc caaactttgg    660
gctctggaaa aggcagagca gcagtga                                        687
```

<210> SEQ ID NO 15
<211> LENGTH: 478
<212> TYPE: DNA
<213> ORGANISM: Lolium perenne

<400> SEQUENCE: 15

```
tctcgggaaa cacgcattgg caataccggc cgatcgatcg acagatcggc acggggtccg     60
gcgaggcgcg atggcgtatc gggtgctgga ggtgacgctg atctcggcca aggacctgaa    120
gaaggtgacg gtgttctcca agatgcgggt gtacgcggtg gcgtccatct ccggcggcga    180
cccgcgcacg ccgacgcacc ggacgcactc ggaccggcac ggcgggccgc tgcggttccc    240
aataccgatc gccgccgacc cccgcgggct cgcactgcac gtgctcctcc gctccgagcg    300
ctccttcggc gaccgcgacg tcggcgaggt gctcgtcccc gtccaggacc ttttcgccgc    360
agcgcctctc gccggcgagc atcgccacct cagctaccag gtgcgacgcc ccatgagcgg    420
ccggaagcgc ggggtgctcc acatctccta cagcctcacg gacgcgccgg cgatagggg    478
```

<210> SEQ ID NO 16
<211> LENGTH: 2445
<212> TYPE: DNA
<213> ORGANISM: Lolium perenne

<400> SEQUENCE: 16

-continued

| | |
|---|---|
| atggtcttgt caatagacac cggcgaggta acggcggagt gtgaacgaat ggaggtggtt | 60 |
| agggttcggg gtgaggcatg gggattggga attggagagg atgtgaagat ggtctggtcg | 120 |
| aggatgcggc gggtcaagtg tcgaggaggg gctcggccgc tcaagggccg gcagagggtg | 180 |
| ccggagaagg agaacgcccc ggcagccaag ggcggaggg gcgccgccgg cgcggcggcg | 240 |
| aggctcatgg agaagatcgt gcccggcgcg ccggccatca agctcaaggc gagcaagaag | 300 |
| gaccagtacc tgctcaagcg ccgggacgac gcccgtgctc cggcactgcc gccggtcgtg | 360 |
| ctcccggacg cgacccccgc accggacgac ggcgggccgc cgcctggctt cccgtcggcg | 420 |
| gagccgcaga cgccgccgtt gcccagcagt gctggaggtg cgacgatga ggagttcatg | 480 |
| ctgcagagac gcacgctccc gtccgccggt caggcgagcg acggcggcgc aactgcggac | 540 |
| gacgccacag ccgccgcgcc caagaaggca gcgaagccca agaaggcccg caagcgcgag | 600 |
| agggaggtgg cggcggaagc caccgccgac gagtccgccg ccgccggcga gccaaagacg | 660 |
| aagaagaaaa agaagaagct cgctgagctc aacagcggcg cgccctctgc cgaccccctcc | 720 |
| ggcggcggcg caaagccagc cgcttctctcg cccccaagg tcgacctcga tggcctggat | 780 |
| ctgaaacagg taatatcgga ccttgagaac ctcccgctgc ttccctccta cggcgccggc | 840 |
| agatccatct ctgacggatc tcactccttc ctcctcgcct tccgctcgaa acactacaag | 900 |
| aagagctatg agaacgatcc tagcgaggag tccaagaaga gtctggatac taaacccaat | 960 |
| gccgccgtcg ctgccgctgt tgacggcagc cgcccaagc cggtcaaaaa gaagccggtc | 1020 |
| atgagaccca ttgaccccac cattgccggc gtgaagcgcg ggccctctga ccggcaggag | 1080 |
| gagatggcca ccaagaagaa aataaagctc gagaagatta agacactggc agccgagaag | 1140 |
| aaggccgggc tggagccgaa agtcgtcact gcccctgcct cagctgtggg aggcgttacg | 1200 |
| ccggcggctc agcagccacg tgctggcatg aaggagaagg ctctggggtt agtcaagaag | 1260 |
| aaggtgccag cggcggcgcc ggcgaggagg atggcgtcgc ccacggcgct gatgatgaag | 1320 |
| ttcccgccca atagcacgct gccgtcggtg gcctccctca aggcgaggtt cgcgcgcttc | 1380 |
| gggccgctag acatcgacgg catccggtg tactggaagt cctacatgtg ccgggtcatc | 1440 |
| tacaagtaca agtccgacgc cgagatggcg ctcaagtcag ccaagtccac agccatgttc | 1500 |
| ggccaggtgg tccccaacta ccacctccgc ggcatcgagt cgtcgtcggc cggcgctgac | 1560 |
| atggggcctg agccggctcc tcctgcgcag cagcgctccg agttgcggct catggagacc | 1620 |
| acgccgttca ggcctgggag ctctggcaat ggcgctcctc tgacgctgtc aagggcggcg | 1680 |
| ccagcgcgcg cagtcgtcgg gcagcccaag tcaatcctca agaagaacaa cgacgatggt | 1740 |
| ggggccagcg cgctccggga ctcccctcgg gtgaagttca tgttggacgg tggcgacagc | 1800 |
| aagctcgagc cacctgcaat tccggcgagc ggcaatagcc cggacgctgc tgcaccggtg | 1860 |
| agcaaggtcg cgaggtcggt cggcttcgca cagccgcctc tacagccact ggcacgccct | 1920 |
| gcacagccca acatgcaacc ggccatgcgt gcacagcaac agcagctgca gcctccacgc | 1980 |
| gcactggata cgcaggcact tccaccgcca ccgccgctgc cgtaccagcc tcgtgccagt | 2040 |
| gagccgttgc cgtaccagcc tcgcgtcagc gaggcatcac catatcagcc ccgtcacaca | 2100 |
| gacgcgccgc catcttttcaa caacatgcag ctgccgtacc aggctcgcca catcgacgtg | 2160 |
| ccgctcatgc tctctggaca gccgacgctg ccataccccgc ctcgtgccag ctttgcccgc | 2220 |
| tccgacgaca tgccgccgcc gtctcacttt gacaacaatg cagccaacgc catgccggct | 2280 |
| cccctttgaca ggaacgctgt gaacgccatg cccgtgtgga agaggggaga gaaggagttc | 2340 |
| agtgaggagc tgatgagggt gatgcttggg atcgccaagc tggtggagcc attgatggac | 2400 |

```
aagaacggca acttccccta ccacctcttc ggcaggtcag cttga           2445
```

<210> SEQ ID NO 17
<211> LENGTH: 936
<212> TYPE: DNA
<213> ORGANISM: Lolium perenne

<400> SEQUENCE: 17

```
atggtagtgc cagtgatcga cttctccaag ctggacggcg ccgagagggc cgagaccatg    60
gcgcagatcg ccgacggctg cgagaactgg ggcttcttcc agctggtgaa ccacggcatc   120
ccactggagc tcctcgatcg cgtcaagaag gtgtgctccg agagctaccg tctccgggag   180
gcggcgttcc ggcagtcgga gccggtgcag acgctggagg ctctgttgga ggcggagcgg   240
cgcggcgagg ccgtggcgcc ggtggacgac atggactggg aggacatctt ctacctccac   300
gacgacaacc agtggccatc cgacccgccg gcgttcaagg agaccatgcg cgagtaccgc   360
gccgagctga agaagctggc ggagcgggtc atggaagcca tggacgagaa tcttggcctg   420
gacaagggtc gcatgaaggc ggccttcact tgcgacggca tccacgcgcc gaccttcggc   480
accaaggtga gccactaccc gccgtgcccg cgcccggacc tcgtcacggg cctccgcgcg   540
cacaccgacg ccggcggcgt catcctgctc ttccaggacg acaaggtcgg tggcctggag   600
gtgctcaagg acggtgagtg gctcgacgtg cagccgctcg ccgacgccat cgtggtcaac   660
accggcgacc aggtggaggt gctcagcaac gggcggtatc gcagcgcgtg gcaccgcgtc   720
ttgcccatgc gcaacggcaa ccgccgctcc atcgcgtcct tctacaaccc ggcgttcgag   780
gcggccatct cgccggccgt ggccgagggc ggcgccgccg cgtcgtaccc ggagttcgtg   840
ttcggggact acatggacgt gtacagcaag cacaagttcg aggccaagga accgaggttc   900
gaggccgtca aggccccaaa cacacctcaa gcttaa                             936
```

<210> SEQ ID NO 18
<211> LENGTH: 936
<212> TYPE: DNA
<213> ORGANISM: Lolium perenne

<400> SEQUENCE: 18

```
atggtagtgc cagtgatcga cttctccaag ctggacggcg ccgagagggc cgagaccatg    60
gcgcagatcg ccgatggctg cgagaactgg ggcttcttcc agctggtgaa ccacggcatc   120
ccactggagc tcctcgatcg cgtcaagaag gtgtgctccg agagctaccg tctccgggag   180
gcggcgtttc ggtcgtcgga gccggtgcgg acgctggagg cgctggtgga ggcggagcgg   240
cgcggcgagg ccgtggcgcc cgtggacgac atggactggg aggatatctt ctacctccac   300
gacgacaaca cgtggccgtc cgaccctcca gcgttcaagg agaccatgcg cgagtaccgc   360
gccgagctca agaagctggc ggagcgggtc atggaggcca tggacgagaa cctcggcctg   420
gacaagggcc gcatgaaggc ggccttcacc tgcgacggca tccgcgcgcc gaccttcggc   480
accaaggtga gccactaccc gccgtgcccg cgcccggacc tcgtcacggg cctccgcgcg   540
cacaccgacg ccggcggcgt gatcctgctg ttccaggacg acaaggtcgg tggcctggag   600
gtgctcaagg acggtgagtg gctggacgtg cagccgctcg ccgatgccat cgtggtcaac   660
accggcgacc aggtggaggt gctcagcaac gggcggtacc gcagcgcgtg gcaccgcgtc   720
ctgcccatgc gcaacggcaa ccgccgctcc atcgcgtcct tctacaaccc ggcgttcgag   780
gcggccatct cgccggccgt ggccgagggc ggcgccgccg cgtcgtaccc gaagtttgtg   840
```

```
ttcggggact acatggacgt gtacagcaag cacaagttcg aggccaagga accgaggttc    900
gaggccgtca aggctccaaa gacacctcaa gcttaa                              936

<210> SEQ ID NO 19
<211> LENGTH: 684
<212> TYPE: DNA
<213> ORGANISM: Lolium perenne

<400> SEQUENCE: 19
atgcgcgtca ccatcaccgg cggcgggacg aggctgcacg tggacctcta ctacgcgtgc     60
gtgcagagcc gcgcgctctt cacggtgtgg agcctcctgc agctgatgcg gcggcaccgc    120
ggccgcgtcc ccgacgtgga cctcatgttc gactgcatgg accggcccgc catcaaccgc    180
accgagcaca cgcgcgaggg cgcgccccct ccgccgccgc tgttccggta ctgcaccact    240
cgcgaccact tcgacatccc gttcccggac tggtccttct ggggctggcc ggagacgcac    300
ctcgagccct ggagccgcga gttcaagagc atccggcagg cgccaagaa gaactgggac     360 gaggaggcga ggtccgggta ccagaactcg aagctgtcga ccagtgcac gcaccggtac     420 aagatctacg cggaggggtt cgcgtggtcg gtgagcctga atacatcct ctcctgcggc     480 tccacggcgc tcctgatcga cccgctgtac caggacttct tcagccgggg gctggagccg    540
cgggtgaacc acctgccggt gagcaccgtg gggatgtgcg agtccatcag ggacgccgtg    600
gagtggggca acgcgcaccc ggacgaggcg gagcgcgtcg ggcggcgcgg gcagcggctg    660
atgcaggacc tggccatgga cgcc                                          684

<210> SEQ ID NO 20
<211> LENGTH: 2241
<212> TYPE: DNA
<213> ORGANISM: Lolium perenne

<400> SEQUENCE: 20
atggcgggcc aggggcagga ccgcaagacc atcgatctgg aggaaggatg ggcctacatg     60
gagggcggca tcggcaagct cgtcaacatc ctcgagggca agaacgagcc gcagttcaac    120
tccgagaact acatgatgct ctacacgacg atatacaaca tgtgcacgca gaagccgccc    180
aacgactact cgcagcagct ctacgacaag taccgcgagg ccttcgagaa gtacatccga    240
gacgcggtct tgccagcaat aaaagagcag catgatgagt atatgctaaa acagctaaac    300
gtaaggtgga agaaccataa agtcatggtt cgctggcttt cacgtttctt ccattacctt    360
gaccgatact tcatcacccg gaggtctctt actccactta atgatgttgg gtttatttgc    420
ttccgagact tgatatttca agagatcaaa ggaaaggtga agatgcggt gttagttctg    480 ataaatcaag agcgtgaagg tgaacagatt gacaagacct tgctgaagga cgtcctggat    540
atatttgttg aaatcgggtt aactaccatg gagttttatg agaatgactt tgaagatttc    600
ttgcttaagg atactacaga gtactattct gtcaaggctc aaaactggat cgttgaggat    660
tcttgtccag attacatgat aaaggctgag gagtgcctga agagagaa ggagcgagtt      720 agtcactact tgcatattaa cagtgagcca agttgctgg agagagtgca aaatgaattg    780
cttgccaact atgcaacaca acttctggag aaggaacatt ctggatgtta tgcattgctt    840
cgggatgaca aggtggatga tcttaaaagg atgttttcac tcttctcaaa aatcacccgt    900
ggtctggaac ctgttttctaa catgttcaaa tcgcatgtta cgaatgaggg tacagctttg    960
gtcaagcaag cagaagattc tgctagtaat aaaaagccag agaagaagga gatggttgga   1020
atgcaggaac aggtttttgt ctggaaaatc attgcactgc atgataagta tgtagcatat   1080
```

```
gtgacagatt gtttccacgg ccatacactc ttccacaagg cacttaaaga agcctttgag    1140
gtcttctgca ataagggtgt ctctggcagt tcgagtgctg aattgctcgc caccttctgt    1200
gacaacattc tgaagaaagg ctgcagtgaa aagctcagtg atgaagccat tgaagatgcc    1260
cttgagaagg tggtgcgcct gcttgcatac ataagtgata agacctcttt gctgagttc     1320 tacaggaaga aacttgcaag gagattgctt tttgacaaga gtgctaatga tgaacatgaa    1380
agaagcatcc tgacaaagct taagcagcag tgtggtgggc agtttacttc aaaaatggaa    1440
ggcatggtta ctgaccttac tcttgcaaga gatcatcaaa ctaagtttga gagtttgta     1500 gctgaacatc aagagttgca tcctggggta gacttggctg ttactgtctt gacaacagga    1560
ttctggccaa cctacaaaac ttttgaaata gccttcctt ctgagatggt taaatgtgta     1620
gaggttttca aggagttcta ccaaacaaga acaaagcaca ggaagcttac ctggatatac    1680
tcgttgggaa cctgcaatat caatgcaaaa tttgaaacca aaactataga gctcattgtt    1740
acaacatatc aggctgcgtt gctgttgtta ttcaatggag ttgataggct tagttactct    1800
gagattgtaa cacagctgaa cctgtcagat gatgatgttg tgcgtttgct ccattctctg    1860
tcttgcgcta atacaagat tcttaccaaa gagccagctg gtagatctat ttctcccaat     1920
gatgttttcg agttcaattc aaaatttacc gacaggatga aagaatcaa gatacccctg     1980 cctcctgttg atgagaagaa aaaggttgtt gaagatgttg acaaggacag gaggtatgca    2040
attgatgcat cgattgtgcg tatcatgaaa agccgcaaag tcatggccca tacccagcta    2100
gttgcggaat gtgtggagca gctcagccgc atgttcaagc ccgacttcaa agcaatcaag    2160
aagcggattg aggatctcat caccagggac tacctggagc gtgacaagga caacgccaac    2220
acatacagat atctggcttg a                                              2241
```

<210> SEQ ID NO 21
<211> LENGTH: 1350
<212> TYPE: DNA
<213> ORGANISM: Lolium perenne

<400> SEQUENCE: 21

```
atggcgcctc ctctgccggg gccgcgcccg ccggcaggcg gatcccgccg gcctcgtcca     60
tgccctgggt ccgcaacctc cgccgcttcg ttggtacggg cgccggcctc ggatccgagg    120
ccctcatgga tgcttaaatc agagacaaaa cctgaagatg gatctattag caatagagtt    180
cagaggctgg caaaatacag gtttctaaag aaacaatcag agcttctact taatgccgac    240
gatcttgatg ccatgtgggt ttgtctcagg gaaaattgtg ttatagacga tgtgactggc    300
tctgaaaaga tgaattatga agatttctgc catattgcca cagtgtgcac agagcagatt    360
ggccagaaat gcaacgtttt ctttagccct tcaaacttta tgaagttcga gaggatgat    420 tctgggagaa ttgcaatctt accattctat ctttatgtta tgcgaacagt ttctcttact    480
caagcaagaa ttgatatgag tgaacttgat gaggattctg atggtttcct tcaacctcat    540
gaaatggaag catacatcag agggctcatt cccaatttgg cacaattgcg cgacatgcca    600
tcggcgtttg ttcaaatgta ctgccgcata gctgcacgga agttcttttt cttctgtgat    660
ccacacagac gggggaaagc atgtataaag aaagtattgt tgagcaattg tcttcaagaa    720
ctgatggaat tgcatcagga gagcgaggaa gaggtaactg atactgagca ggctgaaaat    780
tggttttcct tgacttcagc tcagcgcata tgtgatatgt tcttgcact agataaagat    840 acaaatggca cattgagcaa acaagagctt aaggaatatg ctgatggcac actaacagaa    900
```

| | |
|---|---|
| atcttcatcg aaagagttttt tgacgaacat gtacgccgga gcaaagttgg aggtggcaac | 960 |
| agtcgtgaga tggatttttga aagctttctt gattttgttt tggctctaga aaacaaagat | 1020 |
| acccctgaag ggttgacata cttatttaga tgccttgatc ttaacggaag gggattcctg | 1080 |
| acgactgctg atatccatac tctgttcaga gatgtacacc agaaatggat cgagggtggg | 1140 |
| aactacgagc tttgcatcga agacgtaagg gatgaaatct gggacatggt gaaaccagct | 1200 |
| gatcctctga ggatcgcact cacggatctc ctttcgtgca agcaaggtgg gacgatcgcc | 1260 |
| agcatgctta tagacgtccg cggcttctgg gcccacgaca acagagagaa cctcctccag | 1320 |
| gaagaggaag aacaagtgga agaggcttga | 1350 |

<210> SEQ ID NO 22
<211> LENGTH: 1776
<212> TYPE: DNA
<213> ORGANISM: Lolium perenne
<220> FEATURE:
<221> NAME/KEY: misc_feature
<222> LOCATION: (36)..(42)
<223> OTHER INFORMATION: n is a, c, g, or t
<220> FEATURE:
<221> NAME/KEY: misc_feature
<222> LOCATION: (201)..(204)
<223> OTHER INFORMATION: n is a, c, g, or t
<220> FEATURE:
<221> NAME/KEY: misc_feature
<222> LOCATION: (386)..(414)
<223> OTHER INFORMATION: n is a, c, g, or t
<220> FEATURE:
<221> NAME/KEY: misc_feature
<222> LOCATION: (557)..(608)
<223> OTHER INFORMATION: n is a, c, g, or t
<220> FEATURE:
<221> NAME/KEY: misc_feature
<222> LOCATION: (917)..(917)
<223> OTHER INFORMATION: n is a, c, g, or t
<220> FEATURE:
<221> NAME/KEY: misc_feature
<222> LOCATION: (1147)..(1147)
<223> OTHER INFORMATION: n is a, c, g, or t
<220> FEATURE:
<221> NAME/KEY: misc_feature
<222> LOCATION: (1531)..(1589)
<223> OTHER INFORMATION: n is a, c, g, or t

<400> SEQUENCE: 22

| | |
|---|---|
| atgttccgtt ccatgacgaa ccgggtttgc agaacnnnnn nnggtcacct cctatcctag | 60 |
| ccagttttca tagagtatac cagatcacct cctatcctag ccagttttca tagagtacat | 120 |
| tgcacaacca ttctgagacc cacgcactac atcggcacac ggcagtgcgc cgcgcaatcc | 180 |
| accccttcaaa cctccatccg nnnnccataa agcccagcgt gctgccttcc atcagggttg | 240 |
| tcacatttca gcttcggcat tcactgcaca ttcggtgttc agatatgtga cgttgttttg | 300 |
| aacccatggt ccctaaagca gctcggcatc atcctggtca ccatcgtcgt cggcttcgtt | 360 |
| ctcgtcctcg tcttcgggtg catccnnnnn nnnnnnnnnn nnnnnnnnnn nnngcgctc | 420 |
| caatcctttc ttagcggctt cattgtatgg gtttatcctt agtgcagctt gatagtggga | 480 |
| gagtgcatca gagagaagat ttgtcgccgc aaatacttga gccaacttga tatgtagaga | 540 |
| atcatctgcc cattgcnnnn nnnnnnnnnn nnnnnnnnnn nnnnnnnnnn nnnnnnnnnn | 600 |
| nnnnnnnntc agccagtgcc aatgctgctc caagaaatcc aggttcgaga cgaatggcag | 660 |
| attcatagaa ctttcttgcc ttctctcttc cactggaact tatagcatgc acatcaccaa | 720 |
| ctaacttaag ggctttcgca gactgatgca taaccttcat tgcttcacgt gcagtgaata | 780 |
| atgcatcttt acatttagaa agtgctagat aagcacgtac caaaccttga taagagcgaa | 840 |

-continued

```
gatcagccct tagctcctga gctgccctga agtctgttac tgccagatct ggccgattcg      900
atgaaagatg caaattntcc cttcataata tagccagtta tatgcctatc gtcaactcgg      960
aggctctttt cagcatatat caaagctttt ctttcatctt ttctttccca aaatgctgcc     1020 agagcaaatac atgtttctgg tcttgcggga tcaatatgca gcatatcatg taccaacttg    1080
tttagcctag tgtaatccga tttaaatttt aggagaattg catactcatc catatatgtc    1140
ataatgnttt ggatcaatta accgagcctt ctcaaaattc atgattgctt catcattctt    1200
gccaatgatg gtttcaacct ttgcaatttc cagcaagatg tgcacattat ggggaatcg     1260 ttgcaatagt tccacgtata tatcaaggcc acctttataa tcatgtgaag caatgcaaca    1320
ctgcgcctct acatacctat tccaccaacg ttgtgcatct acaaaatcac ctggtggctt    1380
gcctcctcta tttggtgctt gaagaaataa taaagaaaac tccttcgaag aaagccccat    1440
ttcagccaaa gctgcaatag cctcaaatac ataagggcat tgcctcaaac actctttata    1500
acatatggcc gaagcacggt tatttctgga nnnnnnnnnn nnnnnnnnnn nnnnnnnnnn    1560
nnnnnnnnnn nnnnnnnnnn nnnnnnnnnt tcattgaagg gcgttgcatt tgaagaattt    1620
ggagagggtg agcggcctgt agtggaaact gagattctgg tggaacttgt tgcttgttta    1680
gggatacttt tgctacattg cacagcttgc ttgtaggcac ccagagccct ccgaaattcc    1740
ttctccccgt acaacgcatc accgtgcagg accaag                              1776
```

<210> SEQ ID NO 23
<211> LENGTH: 854
<212> TYPE: DNA
<213> ORGANISM: Lolium perenne
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (671)..(676)
<223> OTHER INFORMATION: n is a, c, g, or t

<400> SEQUENCE: 23

```
ccccaggtta tcgcccccac gaaaaatgct cgaaactttt ccccccttc tggctgtgtg       60 aagaaactgc tgaccgaaac atgactgaaa gcaagttgct aatgaaaccc atccagtacc     120
tacaaaacct atatgtatat aattagcatt tgagctgtgg aggtcagttc attcttgatt     180
tgatcccgcg caacacaacc gaattttgtg catttcaccg gatgtgcttc gtaacagttc     240
aaaacactta gttgtctaag caagtgttct tctcgttgca gctccccgag gatattgagt     300
ggcatttcat tgggaacctg caanacgctg cttcggcgag aactacgtgc aggagctcat    360
cgacaaggcc cccagctcc ccgaggatat tgagtggcat tcattggga acctgcaaag     420 caacaaagcc aaagctctcc tagctggtgt accaaatctt gacatggttg agagcgtaga    480
tgatgagnat aatttgagac acaaacttag ttggactgat ctgcttcata gtgctaatgt    540
actatgtttg ttgatcgcat aggcactggc tagttgtcgg aaggaggtat gcgacgagct    600
tggaatacca gaagagcaat gtgagttgtc aatgggcatg tctgctgatt ttgagcaagc    660
gattgaaatg nnnnnngcac aaatatcaga gttggatcaa ctatatttgg tgcaagagaa    720 taccccgaaga agaactagga taactatata ttcaggtttt gttgcggcag tgcctgcgta    780
```

| | |
|---|---|
| gaatatgtac tattctcgtc tgcaaataaa atattggtga taaatatgta tccagttcct | 840 |
| ccaacattcc gctt | 854 |

<210> SEQ ID NO 24
<211> LENGTH: 3195
<212> TYPE: DNA
<213> ORGANISM: Lolium perenne

<400> SEQUENCE: 24

| | |
|---|---|
| atggggaagc cggcggagta cgaggacgac gacgaggagg tgtccacctc cgtcggcgac | 60 |
| gagcagccgg acgaggagga gcaggagtcg gacggatccg aggaggagga ggatgagccg | 120 |
| gaggggagc aggcggcggg ggacgccgag gacgaggagg aagaggtgga cgaggaggag | 180 |
| atcgtggctg ccaccacggg cgccggcgcc gacgacgacg acgacgccgg cgacggcgcg | 240 |
| ggcgaggcgg agtctaccga ggacgacgag gccgtcgccc cgaggaggg cggcgaggaa | 300 |
| gacgccgacg agtctgaaga cgccgccgga acgcagagg ttggcaagcg ggagcgcgcc | 360 |
| aagctcaggc agatgcagaa gctcaagaag cagaagatcc aagagatact ggatagccaa | 420 |
| aacgccacca tcgatgctga catgaacaag aaggggaagg ggcgtctcaa atacctcctg | 480 |
| cagcagactg aaatatttgc tcatttcgcc aagggagcc aatctgcgga gaaaagtct | 540 |
| cgcggaagcg tctgccttct ctgttttgct aatgtggtta gaacttatag gggtcgtcat | 600 |
| gaatcaaagg tgacagagga ggaggaagat gaagaatacc tcaaggagga gatgcccctt | 660 |
| gctagtgcag gaggaacacg cttgcttata caaccatcat gcataaatgg gaagatgaga | 720 |
| gattaccaac tagctggact taactggctc atacgtttgt atgagaatgg catcaatggg | 780 |
| atattggctg atgaaatgaa tcatatacgg gaaaatttgt tagctccagg gaagtttgat | 840 |
| gtctgtgtta ctagttttga aatggcaata aagaaaaaa ctgcattgag gcgttttagc | 900 |
| tggcgctata ttattattga tgaagctcat cgaataaaaa atgagaactc ccttctttct | 960 |
| aagacaatga ggcttttcag caccaattat cgcctgctca ttacgggaac tccactgcag | 1020 |
| aataatcttc atgagctttg gtctcttctc aacttcttgt taccagaaat atttagctcc | 1080 |
| gctgagactt tgatgaatg gttccagatc tcagggaaa atgatcaaca tgaggttgtt | 1140 |
| cagcagcttc ataaggtttt gcgtcccttt ctccttcgaa ggcttaaatc tgatgttgag | 1200 |
| aaaggtttac ctccaaagaa ggagactata cttaaagttg gaatgtctga gatgcaaaaa | 1260 |
| cagtattatc gtgctttact tcaaaaggat ctggaggtta ttaatgctgg tggtgagcgc | 1320 |
| aagcgccttc ttaacatagc catgcaactg cgcaagtgct gcaatcatcc atatttattc | 1380 |
| caaggcgctg agcctggccc accttacaca actggggacc atctaattga gaatgcagga | 1440 |
| aaaatggttc tgttagataa attgcttccc aagctaaagg cccgtgactc tagagtacta | 1500 |
| atattctccc agatgacccg tcttttggac atcttggaag attatctcat gtacagaggg | 1560 |
| tatcagtatt gccggattga tggtaatact ggtggcgatg atcgtgatgc ttccattgaa | 1620 |
| gctttcaaca agccagggag tgaaaagttc atcttcttgc tttcaactag gcaggtggt | 1680 |
| cttgggatca atcttgcaac agctgacatt gtggttcttt atgatagtga ctggaaccct | 1740 |
| caagtggatt gcaagctca agaccgtgca catagaattg tcaaaagaa agaagttcaa | 1800 |
| gtcttccgtt tctgcactga gtataccatt gaggaaaaag taattgagag agcatataag | 1860 |
| aagcttgcct tggatgcttt ggtcatacag caaggccgat tggcagaaca gaaagctgtc | 1920 |
| aataaggatg agttgttgca aatggtgaga tttggtgctg aaatggtatt cagttccaag | 1980 |
| gatagtacaa taacagatga agatattgac cgcattatcg ctagaggaga agaagcgaca | 2040 |

```
gcacagcttg atgcaaaaat gaagaaattc acagaagatg ccattaaatt taaaatggac    2100
gacactgcgg aactttatga ttttgatgat gacaaggagg aggacaagcc tgattttaaa    2160
aagctagtca gcgataactg gatagaacct cctagaagag aaagaaagcg aaactactcg    2220
gagtctgaat atttcaagca agcacttcgc caaggtgcac cagcaaaacc tagggaacca    2280
agaattcccc gaatgccaaa cttgcatgat ttccagttct tcaacactca gaggctcaat    2340
gaattatatg aaaaggaagt caaatacccta gtgcaaacga atcagaaaaa ggatacaatt    2400
ggtgatgggg atgggatga tgaagatcaa ctggaaccac tgaccgagga ggagcaagag    2460
gagaaggagc agctgctgga agagggcttt tcaacatgga caaggaggga cttcaacaca    2520
ttcattcgag cttgtgagaa atatggtcgt gacgacataa agagtatatt ctctgaaatg    2580
gaagggaaaa cagaggagga agttcagcgg tatgccgaag ttttcaaaga agatacacac    2640
gaattgaatg attatgaccg aattatcaag aacattgaga aaggagaatc aaagatctct    2700
cggaaggatg agattatgaa agccattgcg aaaaagatgg accgctataa gaacccatgg    2760
ttggagttga aaattcagta tggccagaac aaagggaagt tgtacaatga agaatgtgac    2820
agattcctgt tatgcatggt gcacaaactt ggctatggaa actgggaaga actgaagtcg    2880
gccttccgca tgtctcccctt gttccgtttc gattggtttg tgaagtccag aaccacccaa    2940
gagttgtcta aagatgtga cactctcatt cgtctggtgg agaaggagaa ccaagagtgt    3000
gatgagcgtg atagacaggc taggaaagat aagaagaaca tgacatcctc aaagcgtcct    3060
gcggcaagta gtccagcatt tgagtctccc atccagagct cttccaagag agggcgccgg    3120
gatggcagtg cagcctcgtg ttcatgggtc aaccagatta ttgaactggt taaagctttt    3180
ggtgatctat cgtaa                                                     3195

<210> SEQ ID NO 25
<211> LENGTH: 1848
<212> TYPE: DNA
<213> ORGANISM: Lolium perenne

<400> SEQUENCE: 25
atggggtttg gtcgatctcg ctggacaggc agtacagcac tggttattaa ttggagacca     60
cttctctact gcagaaaaga ggatatcaat ggtcacagtg ggctgaggag agatttaccg    120
gttgcatctt tgcttcttcg ggtggatgca agcatgtata agaaccagct ccaggagctt    180
gcacagagga gctgcttcaa cttgccatcc tatgcatgca tacgcgaggg gccggatcat    240
gcaccccggt ttaaggccac agttcatttc aatggggaag catttgagag cccgacattc    300
tgttccacct gcggctggc ggagcatgcg gcagctgagg tagcactcaa tgagttgtcc    360 aagaggggc cttcatcatc acttgctgct aaagttctgg atgaaactgg gatctacaag    420
aacctgctgc aagaaactgc tcatcgggcc ggtttaaaac tgcctatgta cactactatt    480
agatccggac cagggcatac accaatgttc acttgtacag tggagttagc aggaaggatc    540
ttcacgggca atcctggcaa gactaagaaa caagctcaaa aaaatgctgc tatggctgcc    600
tggtctgaat taaggaatt gcctcgagta ggtgaggtag catcttcatc ttctccatcc    660
gatcatgaca atgaggagca ggaacaggtc acagttgtcc gcactcttga aagcttgaac    720
cagaaaaatg aaggcaaggc accacatcaa aaggaaaagc agcaacgcaa taaccgcccg    780
caacctcgga gatcttatcc taaaccaagt gcgtcatttt acggatcacg cttacaaaat    840
cagacatacc caaatgttgc acaagagcaa gcaatgtacc atatgtggca ccaggtgcaa    900
```

```
ccaacacagc agaagcccca ttttcggatg gttccaacta tgggcaacac aaggtttcca      960
ccgccaccaa ctatactctc catgtaccct ccacctagag gacagttcgc cgtgccagcc     1020
agccaagatg ctttggctct aattccatgt tttcctgaag ctgctcctgc ccttccacgg     1080
tacttctcgc cttaccctgc ctcatacgta ccagcaagtc cactgccagc tgcagttaac     1140
atgatgcatg ggagaaggca agggtgtgct gaaacggttg agcttcctga tgcaccagtt     1200
ttcgccagat acactgctcc agattactct agtgctctgg aaaatgtttg tccaagtgag     1260
gttcaacaat ggcctaaaaa tgggaaagag gcatataccg agagcagtgc tgccaccgag     1320
gaaaagaata aagctcccca gacttcttca agctccacaa cgcatcaccc atcacaaaag     1380
ttggaaccaa atgaagatag agagtcgaaa aagccagcag aacaaccact tcttggtcca     1440
tatgttgtac aaagacctgt ccagcgacag agttatccta gtcccgtgca gcacagcgag     1500
cctatccaca gaaataatct tccgttcagg acggcaacat cacctggccc atggtcttcg     1560
gacatgcaaa ctccaccaag atttggtact gcgactcttg cgaattcagc cagtttctta     1620
taccagcagc ggcctccatg gctggcggcc ccagttacag ttcgaacttc tatccctgtg     1680
tgttcagcta gaccaaacgc agcggtgaac tctagcccgg gagcagcaac tcgagtccga     1740
tctactgtcc agatgctctc tagaaataac tctgaggccc agaggaacac gagagacatg     1800
agtgatgctt cgacagcaag ttcagaactt agtaagctcc atatctga                  1848
```

<210> SEQ ID NO 26
<211> LENGTH: 1206
<212> TYPE: DNA
<213> ORGANISM: Lolium perenne

<400> SEQUENCE: 26

```
gggaacattg acatttgctc caatgctcgt aatgtttttg catataatgg accagtcaat       60
ttcactgtac ttgagaggct agtaagcaga tgccgcaacc tcaagactct gaagctcaac      120
aatgcaatcc ctcttgacaa tgttgctagc ctgcttcgta aggctccgca ataatagaaa      180
ctcggaactg gcaaattctc tgctgactat catccagatc tttttgcaaa ggttgaagca      240
gcatttgcag gttgtacaag cctaagaagg ctttctggga cttgggacgc tgttccagat      300
tacctgccag cattctattg tgtatgtgaa ggcctcacat ctcttaatct gagttatgcc      360
accgtgcaag gccctgagct catcaaattc attagcagat gcaagaatct gctgcagtta      420
tgggtgatgg acctcattga ggaccatggt ctatctgttg tggcatcaag ttgcagtaaa      480
ctgcaagagt tgcgggtctt cccttccgat ccttttggtc ataacggcgg gcaagttttc      540
ttgacagaaa gaggtcttgt tgatgtttct gccagttgtc ccaaattgga gtcagttctt      600
tacttctgca gccggatgac gaatgaggct cttgttatga ttgcaaagaa ccgtccaaac      660
ttcacttgct tccgcttagc cctccttgag ccccgttctc cggattacat gacacggcag      720
cctcttgatg ctggtttcag tgccattgtt gaatcatgca aggggcttag gcgcctctct      780
atgtctggtc ttctcacaga tcttgtattc aaatcaattg gtgcacatgc tgatcgtctt      840
gagatgctat cactcgcatt tgctggagac agcgatctag gcctgaatga catcctctct      900
ggctgcaaga gcctgaagaa gctagagatc agggactgcc cgtttgggga taaagcgttg      960
ctggcaaatg ctgccaagct ggagacaatg cgatcccttt ggatgaactc gtgctcgttg     1020
accgtgggcg ggtgccgact gcttgcactc aagatgcctc accttactgt ggagataata     1080
aacgatcctg gagagacatg tccagtggag tcactcccgt ttgatagccc tgtcgagaaa     1140
ttgtatgtct accggactct tgcaggtcct agatctgaca caccagactg tgtccagatt     1200
```

-continued gtttag                                                                     1206

<210> SEQ ID NO 27
<211> LENGTH: 2011
<212> TYPE: DNA
<213> ORGANISM: Lolium perenne
<220> FEATURE:
<221> NAME/KEY: misc_feature
<222> LOCATION: (427)..(436)
<223> OTHER INFORMATION: n is a, c, g, or t
<220> FEATURE:
<221> NAME/KEY: misc_feature
<222> LOCATION: (847)..(867)
<223> OTHER INFORMATION: n is a, c, g, or t
<220> FEATURE:
<221> NAME/KEY: misc_feature
<222> LOCATION: (1234)..(1240)
<223> OTHER INFORMATION: n is a, c, g, or t
<220> FEATURE:
<221> NAME/KEY: misc_feature
<222> LOCATION: (1560)..(1583)
<223> OTHER INFORMATION: n is a, c, g, or t
<220> FEATURE:
<221> NAME/KEY: misc_feature
<222> LOCATION: (1878)..(1886)
<223> OTHER INFORMATION: n is a, c, g, or t

<400> SEQUENCE: 27
gcttctctcc ccggagccgc gagcagcagg cggcggcgga gggcgcaaac cgagcggcgg      60
gaggctgagg gcgcaaaccg agcggcggga ggctgagggc gcggaacaaa gtcccgattc     120
catcagttgc tcaaggatat tgttgaccca caagtcgaac aacccaggcg tatttgtac     180
cagcctaaca gcctggagga tctggtattc agctgggag caccaagctt ggtctgaaag     240
cacacttcac tggttctaac catggaagcc agttccgtcg gcgctgacgt atctgccgac     300
catgtcatcg ccgagttgct cgaaatgggg ttcgagttcg acaagatcag cgaggcgatt     360
ggggtcgtgg gaccatgccg tgctgatgtg gtggagttta tgctgaatgg gtctgggggt     420
gagcagnnnn nnnnnngtgg ggggtcgcaa agacgctgtc ctgacaggag cactaggctg     480
gctaatccca gggggaaatt taagcagtct agtattaccg atcacatcgc ctcaaccact     540
ggcagtaaaa cggtgtctcg tggcgggaa ccgagtacct cgtattcttg tttatcagcc      600
tccatcgacc cttcattgac tgctgctatc tgttctaaat caaagcctga acctcagtct     660
tcgcttgtga attcaagagg cgagtttgac cgcactggaa aaattagtgc tgttttgcaa     720
aagcatttcg gcttctcctg cgtcaagggt ttccaaaagg aagccctgga tgcttggttt     780
gctcgcaagg attgtcttgt tctagcggca actggatcag gaaagtccct ttgcttccag     840
atcccannnn nnnnnnnnn nnnnnnngct cttttgacta ccaagattgt ggtcgtcatc      900
tcacccttga ttagtctaat gcacgatcag tgccttaaac ttgcaaaaca tgggatatca     960
gcatgcttcc ttggatcagg gcaaccagat aatcgtgttg agggcaaagc gatggctggc    1020
atgtataaga ttgtttatgt ttgccctgag acaattttga gactgatgga accgttgaag    1080
aaacttgcag aaaagccagg gattgcactt tttgccattg atgaagttca ttgtgtttct    1140
aagtggggtc atgatttccg acctgactat aggagattgt ctgtgcttcg agaaaacttc    1200
tgttccagca aattgaagtt cttgaacat gatnnnnnnn attcctttga tggcattgac     1260
tgctactgca actttccatg tacgagaaga cattctcaag tccttgaaaa tgtcagaaca    1320
tacagtggtt gtcttgacgt cctttttccg gccaaacctt cgatttactg taaagcacag    1380
taaaacctct gcctcatcat atggacagga cttttcaagaa cttatggga cttacaatgc    1440

| | |
|---|---|
| ttcaaggaat tcaggggga aaggccagaa aattcttcat gaagttgagc ctgagtctga | 1500 |
| aagcagttca tatgactctc tggatgatag tgcatcagac gacgaaaagg aagttcctgn | 1560 |
| nnnnnnnnnn nnnnnnnnnn nnnacattaa aaaaaataaa cttgccaagt ctctggtaaa | 1620 |
| agaaaacacc gaacatgagc tggatcagta tccaggagta gatgattttg atgtttcatg | 1680 |
| tggggagttc cttgaaagct cgcggcctga gatctttgca cctcctgtgc catcccatga | 1740 |
| aactagttca tcagaaagtt ttgatcaagg tcctacaatt gtgtatgtac ccacgaggaa | 1800 |
| aggaactgtg gaactagcta actatctgtg taaatcaggc ctcaaagctg cagcgtataa | 1860 |
| tgcaaagatg cctagagnnn nnnnnnaaca tttgaggcag gtgcatgagc agttccattg | 1920 |
| caatgcctta gaggtagttg tggctacaat agcatttggt atgggaattg acaagtcaaa | 1980 |
| tgtcaggaga attattcact atggtttacc a | 2011 |

<210> SEQ ID NO 28
<211> LENGTH: 717
<212> TYPE: DNA
<213> ORGANISM: Lolium perenne

<400> SEQUENCE: 28

| | |
|---|---|
| atggccttct cgcgccttct cccctcccgc cgcctcctct ccaccctcct ccacaccccc | 60 |
| accccgaccc ccgccgcgcc cgccaccgac gccaccacca ccaccccgtt cgcccacaat | 120 |
| ctccaccccg cccgcttctt ctccgcgaca cggcgggccg gaccgggcgc cccgcgggag | 180 |
| ccccgcgcgg cggacatcgg cgcgcgggcg cggcagctgc agagccggcg cctctggacc | 240 |
| tacgcgctca ccttcggctg cgcggcgggg ttcgtggtca ccatgctggc cacgtcccag | 300 |
| gaccagctcg tcttctacct cacgcccacg gacgcgctcg cgcgcttcgc caccgacccc | 360 |
| tccaagaccc gctgccggct cggcgggctc gtcctcgagg gctccatcgc ccaccccctcc | 420 |
| tcctccgcct ccgagatcga gttcgtcgag ggcgccctcc ccgacctctt ccgcgagggc | 480 |
| cactccgtcg tcgtcgaggg cttcctcaag ccctctcccg acgacctccg cctcgacggc | 540 |
| gccggcagga aggtctccga caaggcgcgg gaggggcagt acttcctgca gggcaccgag | 600 |
| gcgcttcttc cttcgctcgc gccgcatttt ttttgctacc atgtctccgg tgaggttttcc | 660 |
| ggcgagttct tttgcgaggt ctccgatgag gttttttcga taagggatt atattaa | 717 |

<210> SEQ ID NO 29
<211> LENGTH: 738
<212> TYPE: DNA
<213> ORGANISM: Lolium perenne

<400> SEQUENCE: 29

| | |
|---|---|
| atggccggag ccggctcctc cccctcggc ggacaactgt cccggcagcg cgggtggcaa | 60 |
| cagcggcaag aagaagaaga aaggaaaac aagaacaagc ccgcggcgcc ggtgccggcg | 120 |
| cagggtaacg ccacagtgga aggcagcggt ggcggcggat ccattcccct ggagaatcag | 180 |
| gacaacggcg gcacctgtga tgaagcatcc ggcgacgagc aacctcaaaa gcctgaaggt | 240 |
| ggtagcggcg gaggcccgca cgtggttgcc ccattcgcca tgacgccgca cggcatacag | 300 |
| cccatggcac ccaccgccaa tgccaatgcc gccgtggcg gtgtaaagaa aaagaagaag | 360 |
| ggcaagggag gtggcaacgg cagtgccaat gccaacgcag acggcgccgg tgcaacggcg | 420 |
| gagatgattc acacgacgc aaccgcggga aacgccggtc agcacgccgc ggctgccgtc | 480 |
| gatgccgggg cctaccgcc cgccacgacg atgagctacc cggggtacta cgccggcgga | 540 |
| gggcaaatgc cgccgccgta cgccatgagc tacagcaccg cgcacccgct ccggagcagc | 600 |

```
gcgtactacc acccgatggt cggcgccgcg tacacgggcg gcgccgagta cttccactcg    660
acggcgccga tatcagcggc accgaggtcg tattacatgt tcagcgagga gaacgccaac    720
gcatgcagcg tcatgtga                                                  738
```

<210> SEQ ID NO 30
<211> LENGTH: 1902
<212> TYPE: DNA
<213> ORGANISM: Lolium perenne

<400> SEQUENCE: 30

```
atggctctga gcatggtgct ggcgcattat tctgaagggt tcgacgtgga ggaggtcacc     60
gctggcttcc cctcggagac tggggagttc gatgttgccg aagtgctgcg gctgatggat    120
gcggtgcgcc ccttcgccga ccgagtactg gcgaccgcgg acttggagac tcatatcccc    180
agccaagcgg ctcctggtga cgcggagaag gagccgggcc cggtggacta ccccgcggag    240
cgcctcttcc atgctgctgc cgccggctcg ctgtctacat atccggtcgt ggtcagtcgc    300
cttgcgaccc caatgaaggc tatcgacttg actgttttcc ttttcgagct gggcgtcccc    360
agtcgcacct tctcggcggc atccttctcg gattcggcca ccgcacgccg gaaggccgcc    420
tcctcctctg ccgcctccgc ttccttctcg ccggctcgcg gatctcctcc gcttcctccg    480
ccgctcaccg cttatacccc tgccgggcag ttacagagcc agcacctgaa cagcctgctg    540
tctgaccgcg attacacctg gaacgacaac ggcgaactca tccgcatcag cagcccgcgc    600
cagacccgga gttacagcta cagcaccacc ggcaggctga ccggcgttca caccaccgca    660
gcgaatctgg atatccgcat cccgtatacc acagacccgg caggtaaccg cctgcccgac    720
ccggagctgc acccggacag cgccctcagc atgtggccgg ataaccgtat cgcccgtgac    780
gcgcactatc tttaccggta tgaccgtcac ggcaggctga cagagaaaac cgacctcatc    840
ccggaagggg ttatccgcac ggatgatgag cggactcacc ggtaccatta ctacagtcag    900
caccggctgg tgcactacac gcggacacaa tatgaagagc cgctggtcga aagtcgctat    960
ctttacgacc cgctgggccg cagggtggca aaacgggtgt ggcggcgtga acgggacctg   1020
acgggctgga tgtcgctgtc acggaaaccg caagtgacct ggtacggctg ggacggcgac   1080
cggctgacca cgatacagaa cgacaggagc cgcatccaga cgatttatca gccggggagc   1140
ttcacgccac tcatcagggt cgaaactgcc accggtgagc tggcgaaaac gcagcgccgc   1200
agcctggcgg atgcccttca gcagtccggc ggcgaagacg gtggcagtgt ggtgttcccg   1260
ccggtgctgg tgcagatgct cgaccggctg gaaagtgaaa tcctggctga ccggcttcca   1320
ttgcccaagc atatcaatga agaaaatata ttaaacgaga tctccattga gaaagatgtt   1380
gatggttttc atcctctgaa cattggtaag ctcgcaatga aggtagaga tcctctgttc   1440 ctaccttgca cgccaaaggg atgcatggag ctcctatcac gaagtggagt cactgttaaa   1500
ggaaaaaatg cagttgtggt agggcgtagc aacattgtgg gtttaccagt atcccttctt   1560
cttctgaaag cagatgcaac cgtgtcaatc gtgcattcac ggacccctaa tcctgaagta   1620
attgtgcggc aagcagacat catcattgca gcagctgggc aggctatgat gatcaaggga   1680
gactggatca aacctggtgc tgcggtcatc gatgtcggga caaattccat cgacgaccca   1740
acaaggaagt ctggatacag gcttgtcggt gatgtggatt tcacggaggc aagcaaggtc   1800
gcaggtcacc tgactccagt tccaggaggc gttgggccaa tgaccgtggc gatgctgctg   1860
aagaacacag tggacggcgc caagagggga atagtctcat ag                      1902
```

<210> SEQ ID NO 31
<211> LENGTH: 3576
<212> TYPE: DNA
<213> ORGANISM: Lolium perenne

<400> SEQUENCE: 31

| | | | | | | |
|---|---|---|---|---|---|---|
| atggcaacac | cccttgcttc | cgcccctcca | cccttatcc | ccgttcagct | ggatccttcg | 60 |
| aaggattccg | acaagaacgt | cgagggaaca | tctgctcacc | cggagaaaac | ctccggagca | 120 |
| gatcaagcag | agcagaaggc | ggaagaagtg | gccgccaaaa | aatccaaagc | tcgccagcgg | 180 |
| gacagtgaag | ccaaggggaa | atggtggccc | tgcaccacca | ccgaaacaga | actcaacaac | 240 |
| ctcgaggcgg | agggcttcct | aaggcccgga | tcctggcgga | cagtttcggg | ttctctggtt | 300 |
| ccagctcccg | aggccggaga | aatggtggtg | accaaggcgc | tggtggagcg | cgacttctca | 360 |
| tttccgccat | gtgatttctt | ctcggaaatc | ttgaaggcgt | atgggctcca | gccccacaac | 420 |
| atctccccaa | acagcgtcct | ggccatcagc | aatcacgtca | ctctttgtga | aggccatctc | 480 |
| cgggacgttt | ccgacccggc | gagcgagagg | gtgctgccgc | ccttcaagaa | cagccccacc | 540 |
| agcgagaatc | cggcctggat | gcaatgtcct | catcttttcg | agtcgcctca | gctgactcgc | 600 |
| gcagttaggc | ggatctgcaa | gctgacgagg | aaggtctgt | cggggaagga | cctcacaatg | 660 |
| tcctggttca | ccaagtggat | ccaaccactt | caacatcggg | acagcctgat | gttccaatac | 720 |
| acgggacgcg | atgatcctat | gcgcgcctct | aaggacaacc | tttctgctga | cgccatcgat | 780 |
| aagcggatcc | aactcctcat | caagattccg | cgtgatcttc | ggattcacgt | gtgtaacaag | 840 |
| gacatccaca | ccaacggctc | cgggaccacg | ctcgaagccc | tcgaggaggg | tgaactcgga | 900 |
| actctcctcc | gggttccgca | cgcgggcaac | actgacccgg | aagccgtatc | ggaggcggaa | 960 |
| gctcccgagg | ctccgcgccc | ctccaagaga | acgagggctg | ctccctccag | cccgcagcc | 1020 |
| aaatgtgccc | gcgaagtgcc | cagcaccgcg | gctacccgca | aggcggaggc | ggagaagaag | 1080 |
| cgcctcaagc | ttatcgacac | cagcaaccgc | gcacaacctg | acatgaacca | ttttttcaag | 1140 |
| ccttccggaa | gttccggaag | ccagccctcc | aagatcctga | agaaaagaac | gaagccgtct | 1200 |
| cctgcttcca | ttccagtcac | accgaaagtt | gaggttccgc | ccaaggcctc | ttctaccgca | 1260 |
| tggccggatc | ccaaggacgt | catcaatctt | gatgaccttc | ccgaagaacc | aactgctgag | 1320 |
| accggccacg | cgcaatccgg | caagggcgcc | tcctcgtctg | ctcctccacc | tgagaagcca | 1380 |
| accgccacct | ccactgaagc | tccggctgag | gaggttgaaa | agaaattctt | gctaagtcgt | 1440 |
| gccaccggca | cgccccagac | ccatcctcat | ctttttccaa | ctttgcaaaa | gcccccctc | 1500 |
| tcacagcgcc | acgcggagat | atccgccatg | atggaccaag | tgtgggggcc | tgcgaacacg | 1560 |
| gaaatgaagg | agctctcaga | tctcgagagt | gatctcaaga | ttttctttgc | taagcacaag | 1620 |
| aacgtgcgcc | agaggtgtgt | tgcttttacc | ataagagatc | ttaaccttgg | tgccaaccgg | 1680 |
| gcagctctcc | cgttcacact | tcctatggtg | gatctccatg | acagactaga | gaggcccgag | 1740 |
| tatgtgagct | ttcctgtttt | actttcaccc | cttctagata | acctaagtgc | aatcaagaga | 1800 |
| taccagatag | caaaagtata | caggagggat | aacccatcaa | agggaagata | tcgagaattc | 1860 |
| taccaatgcg | acttcgacat | tgctggagta | tatgagccaa | tggaaccaga | tttcgaggtt | 1920 |
| atcaaagtat | tgactgaatt | gctggataag | ctggatattg | tgtgtatga | ggtaaaatta | 1980 |
| aatcacagaa | agttgcttga | tggaatgttg | gagatctgtg | gcgtgcctgc | tgagaagttc | 2040 |
| agaacagttt | gctcaagtat | tgataagcta | gacaaacttg | cctttgaaga | ggtgaaaaag | 2100 |
| gaactggtgg | aagataaagg | ggtatcggat | gaaaccgctg | aaaatattgg | cagtttagtg | 2160 |

| | |
|---|---|
| aagacaaaag ggccaccact ggaagttttg ctggaattga gaaaggaggg tagcaagttc | 2220 |
| atgcaagaac gagaagttac agcccccgtg accgatctcc aaggcgtcgc agtgtttctc | 2280 |
| cagcgccagc ccgtgggcgc agctacagca agtcaccacc acacaaccgt ggccgtgatg | 2340 |
| attctcctga tgctaaaggt gatggaggtg ccaggtaccg acgcagcagg agttaggcct | 2400 |
| gaagcctttg ccccatgcat gctcttcaag agaacttacc atttgccctg cgtgctagga | 2460 |
| atactaagac ctgacgtcaa cttcttgact tcggttaaga tggatcccaa gagaatattc | 2520 |
| aagaagatgc aaatatctaa gcttggggat gcccaaggca tccccctatt catcaaccaa | 2580 |
| catgaggttg tctccttcaa actcaatatt acccatccac atattgagga gatgagaagg | 2640 |
| attcgagagg atccatttct tcaatgtgaa ggtgacacca atattaaaga tagctatgta | 2700 |
| cttccagatt tgaatgaaca tgagaatgaa gtagctaacg aacctgaacc tgaacttgaa | 2760 |
| catgtgaaga aaaagcagaa gacggttaaa agaggacccg aaccagcaac gagatgtcat | 2820 |
| tcctttgtgc aaattgatga catactagac tacataccat catcaaatga atatgagttc | 2880 |
| catggttttc taaaggatga agatgatgat tattttcaac caatcacgat ggtgccacca | 2940 |
| aagggtagaa agagtcgaag gaagaaaatc cccccaagaa aatggtatga tgagaagagg | 3000 |
| ctgcaaccac atgaacaatt gtgtttgaaa atgtgtttta ccaatgtgca acaatttaga | 3060 |
| aatgctttga ttgatttgta cattgcacaa agccgaaact acatgtacca caggaactcc | 3120 |
| aacataagga tcattgtgaa gtgcataaag cagaggtgtt cctttctaca taaccttgca | 3180 |
| aaagcctata aaggccgtcg cgtggtagaa gacgtcagcc tgaccgtcaa ctccggggaa | 3240 |
| attgtcggtc tgctggggcc aaacggtgcc ggtaagacca ccactttcta catggttgta | 3300 |
| ggcattgtgc cgcgcgatgc gggcaacatc attattgatg atgacgatat cagtctgctg | 3360 |
| cctctgcatg cacgcgcgcg ccgcggtatc ggctatctgc cacaggaagc ctccattttc | 3420 |
| cgtcgcctca gcgtttacga taacctgatg gcggtactgc aaattcgtga ctacttgtct | 3480 |
| gctgaacaac gtgaagaccg cgctaacgag cttatggaag agtttcacat tgagcacctg | 3540 |
| cgtgacagca tggggcagtc actcgtccgg gggtga | 3576 |

<210> SEQ ID NO 32
<211> LENGTH: 840
<212> TYPE: DNA
<213> ORGANISM: Lolium perenne

<400> SEQUENCE: 32

| | |
|---|---|
| atggggtggt tcgcgtcatg gcgaataaag tggcccgagc tcgcccccca tctcgccggc | 60 |
| aacggcgacg agtttctggg tcctctgggt ctcgcgggtg gcgtcctggc gaggtggatg | 120 |
| tcatccttcg tcgagctttt gtcctccagg cctcttcctc gcgctaccgt cggcgtctcc | 180 |
| ttgggcggtg gcaggcctgt ggtggtggat ggcgccgggc ctggttctcc agttcctcgt | 240 |
| cgtcgtcttt gtgcaggagt caaggtgtct cgatctgggg tcgacgagcg acggtgctcg | 300 |
| tgcccggatc tggttgttct tcagctgttt cctcctctga atcaagcaga tgcagaccat | 360 |
| ggtgtgtgct ctggctggct ttggtggtct gacagccgga gtgaatcggg gcgtgtcccc | 420 |
| cgccgatgcg tgttcattct ccatcagatc tcggcgtccg cgtcgggtgg tttttgcggc | 480 |
| gacatcaacg aggtttactc ctcaaaagtt tctctccggc aacacagctg cggcctgcga | 540 |
| ggcctcttct cgttctccgg cgaggttgag gcattggcga aggcggtggc cgatcacgga | 600 |
| gaaagagaga tccaggagga gctagcggag atggcggact ggggtccggt ggtcatcgcg | 660 |

| | |
|---|---|
| acggtgctct tcgtgctgct cacgccgggg ctgctcttcc agctgccggg gcacggccgg | 720 |
| gtcgtggcct tcggcagcat gcacaccagc ggcctcgcca tcctcgtcca cgccgtcatc | 780 |
| tacttcgccc tcatcaccat cttcctcatc gccatcgggg tacacatcta cgccggatag | 840 |

<210> SEQ ID NO 33
<211> LENGTH: 5091
<212> TYPE: DNA
<213> ORGANISM: Lolium perenne

<400> SEQUENCE: 33

| | |
|---|---|
| atggccgagt gtccaggaca ttttggtcac cttgagctcg caaagccaat gttccacatt | 60 |
| ggattcatca agactgtgct ctccataatg cgctgtgtgt gcttcaactg ttccaagatc | 120 |
| ctcgtgcctg aggaggaccc caagttcaag caggctctga aaatcaagaa tccaaagaac | 180 |
| agattaagac gaatctatga tgcttgcaag agcaaaaaga cttgcgatgg tggtgatgaa | 240 |
| cttgaggctc aggatcagca ggacactgat gaaccagtaa agaaaagaag tggttgtggt | 300 |
| gctcagcagc caaatatcac agttgatggt atgaagatgg ttgcagaatt taaagcaaca | 360 |
| aagaagaaaa atgatgatca agatcaactc cctgagccag tggagcggaa gcaaattctc | 420 |
| tctgccgaga gggtacttaa tgttctcaag cgtatcagtg acgaggactg tcttttattg | 480 |
| ggcctgagtg ctaaatatgc tcgacctgac tggatgatac ttcaagtact tccgattcct | 540 |
| ccaccacctg tgagaccatc tgtcatgatg gatacttcct ccagaagtga ggatgatttg | 600 |
| actcatcaat tagcgatgat aattcgacat aatgagaatt tgaggaggca agagagaaat | 660 |
| ggagcaccag ctcatattat aacagagttt gctcagttgt tgcagtttca catcgcaaca | 720 |
| tactttgaca atgatcttcc tggacaacca agggcaactc agcgttctgg aaggcctatt | 780 |
| aagtcaattt gcagcaggct gaaagcaaaa gaaggtcgga ttagaggaaa tttgatgggg | 840 |
| aagcgtgttg atttctcagc tcgtacggtc atcacaccag atcccaatat caacattgat | 900 |
| cagttggggg tgccatggag tattgcattg aatctgacat acccagaaac tgtaaccccca | 960 |
| tacaacattg agaggttgaa agagctagta gaatatgggc ctcaccctcc ccctgggaag | 1020 |
| acaggtgcca agtacattat cagggaagat ggtcagaggc ttgatctacg ctatgtgaag | 1080 |
| aaaagtagtg atcagcattt ggagctgggc tacaaggttg aaaggcacct caatgatgga | 1140 |
| gattttgttc ttttcaatcg acaacccagt cttcacaaaa tgtctattat ggggcatcgc | 1200 |
| attaaaatta tgccctactc aactttccgg ctaaacttgt ctgtcacatc accatacaat | 1260 |
| gctgattttg acggggatga atgaatatg catgttcctc agtcatttga gaccagggct | 1320 |
| gaagttctag agctgatgat ggtgccaaaa tgtattgtgt cacctcaagc aaataggcct | 1380 |
| gttatgggca ttgtccagga cacgcttctt gggtgtcgga aaatcaccaa aagggatact | 1440 |
| cttattgaaa aggatgtatt tatgaacatc ttaatgtggt gggaagattt tgatgggaag | 1500 |
| gttcctgccc ctgccatttt gaaaccaagg ccaatttgga ctggcaaaca gttttcaac | 1560 |
| ttgattatcc ccaagctaat caatttgatt agattttcag cctggcatgc tgaaacagaa | 1620 |
| actggattta ttactcctgg tgataccatg gtccggatag agaagggaga gcttctgtct | 1680 |
| ggtacacttt gcaaaaaaac tcttgggaca ggaactggga gtcttattca tgttatttgg | 1740 |
| gaggaagtag ggccagatgc tgcacggaag ttcttgggtc acacacagtg gctggtcaac | 1800 |
| tattggctcc tgcaaaatgg gttcagtatt ggaattgggg atacaattgc agatgcaagt | 1860 |
| accatggaaa agattaatga gactatcgga aaagctaaga atgacgtgaa ggagcttatt | 1920 |
| aaacaagcac aagaaaaaag tttggaacct gagccaggac gcacaatgat ggagtctttt | 1980 |

```
gaaaacagag taaaccaggt tcttaacaag gctcgtgatg atgctgggag tagtgctcag    2040
aagagtttat ctgagagtaa caatttgaaa gctatggtca ctgcaggctc aaaaggaagt    2100
ttcattaata tttcacaaat gactgcttgt gtcggacaac agaatgttga gggcaagcgg    2160
atcccatttg gttttgttga tcgtacattg ccccacttca caaaagatga ctatggtcct    2220
gaaagccgtg gatttgtgga gaactcttac cttcgaggtc taacaccaca ggaattttc     2280 ttccatgcta tgggtggtag agaaggtctt attgatactg ccgtgaaaac ttctgaaact    2340
ggctatattc agcggcggct tgtgaaggct atggaggaca tcatggtcaa gtatgatggt    2400
acagtgagaa attctttagg tgatgtcatt cagttcttgt atggagaaga tggcatggat    2460
gctgtgtgga ttgaatcaca gaaattggac tccctgaaga tgaaaagaa tgagttcgat     2520 aatgtatatc ggtatgaact ggatgatgag aactggaggc ctacgtacat gatgcctgaa    2580
tatgttgatg atttgaagac cattcgagaa ttcagaaatg tgtttgaggc agaggttcag    2640
aaattagaag ctgaccgttt acagcttggg actgagatta ccacaactgg cgacaacaca    2700
tggcctatgc ctgtgaatct caagcggctg atctggaatg ctcaaaagac attcaagatt    2760
gatttaagaa gaccttctga catgcacccg atggaaattt ttgaagcaat agataagctg    2820
caagaaagac ttaaggttgt ccctggtgat gatgcaatga gcattgaagc tcagaagaac    2880
gctactttgt tcttcaatat cctgcttcgt agcacatttg ctagcaagag ggtcttgaaa    2940
gaatacaggc ttacaaagga atcttttgaa tgggtcattg gtgagattga atcgagattc    3000
cttcagtctt tggtagctcc tggggaaatg attgggtgtg tggctgcaca gtccattgga    3060
gaaccagcaa ctcagatgac gctgaatact ttccattatg ctggtgtcag tgcaaagaat    3120
gttacccttg gtgttcccag gttgagagag atcattaacg ttgccaagaa gataaagact    3180
ccatcactgt ctgttttcct gaagcctgag gtgggcaaga agaaagaatt ggccaagaat    3240
gtccaatgtg ccctggagta cactacacta cgtagtgtga cgcatgccac tgagatatgg    3300
tacgatcctg atcctctggg aaccatcatt gaagaggatg tggaatttgt cagatcatac    3360
tatgagatgc ctgatgagga tattgacccg gataagatct ctccttggct gctgcgtatt    3420
gaactgaacc gtgagatgat ggttgataag aagttgagca tggctgatat cgcagagaag    3480
atcaatcatg aatttgatga tgacttatca tgcatattca atgatgataa cgcagataag    3540
ctcatcctcc gtgtccgtat aacaaatgat gaagctccaa agggagaaat acaggatgaa    3600
tctgccgagg atgatgtctt tctcaagaag atcgaaggta acatgttgac cgagatggcc    3660
cttcgaggca ttccagacat taacaaggtc ttcatcaaat acgggaaggt caataaatt     3720 gaggaaaatg aaggtttcaa acccgataac gagtggatgc ttgatacaga aggcgtcaac    3780
ctcttggcgg tgatgtgtca tgaggatgtt gatgctacaa ggacaacaag taatcattta    3840
attgaagtca ttgaagttct tgggattgag gctgtccgca ggtctctctt ggatgagctg    3900
agggtggtca tatcttttga tggatcttat gtgaattaca gcatctggc cattctatgt     3960 gatacaatga catacagagg tcatctgatg gccattacta ggcacggcat aaatcgtaat    4020
gacacagggc ctcttatgag atgttccttt gaagaaactg tggatatctt gcttgatgct    4080
tctgtatatg ccgaatccga ctacctgaga ggtgtcactg agaacattat ggttggccag    4140
cttgctccta ttggtacagg aggctgtgga ttgtatctga atgacaagat gctacagcag    4200
gccattgagc ttcaactccc gagctatgtt gacggtcttg actatggcat gacaccaggg    4260
cgttcaccca tctctgggac accttacatt gatggaggaa tgatgtcacc aatgctgagt    4320
```

| | | |
|---|---|---|
| ccgaatttca gggcttcccc cattacagat gctcagttct ctccgtatgt tggtggcatg | 4380 | |
| tcgttctcgc ctattccgtc aaactacagc ccatcctctg ggggtggtta cagtccatct | 4440 | |
| tctcctgttt tcagcccagg gccagggcaa gcatatagcc cgacatctcc tgcatacagc | 4500 | |
| ccgacgtcgc catcttacag cccaacatca ccatcttata gcccgacgtc gccatcatac | 4560 | |
| agtcctacat ctccttcata cagccccacg tcaccatcat acagccccac gtctccttca | 4620 | |
| tacagcccta catctccatc atacagccct acatcgccct catacagccc aacatcgcct | 4680 | |
| gcatacagcc ctacatcgcc cggctacagc ccgacgtctc ccagctatag cccaacttcg | 4740 | |
| ccgaattaca gtccaacttc accgagctac aatccttctt cggccaagta cagtccttca | 4800 | |
| catgcttact ctccaagcag cccaaggatg atgagccctt atagccaaac ttctccaaac | 4860 | |
| tacagcccca cctcaccgtc ttactcgccc acctcaccgt cgtatgcaca accaagcccg | 4920 | |
| tcatatagcc caaccagccc gcacactacc tccggaggac ctagcccaga ttacagccca | 4980 | |
| acttctccaa attacagccc tagcgcaagc tactcccca ctgcaccagg ctactccccg | 5040 | |
| tcatccaccg ggccgcaaac tactgacaag gacgacgaga ttgctccttg a | 5091 | |

<210> SEQ ID NO 34
<211> LENGTH: 405
<212> TYPE: DNA
<213> ORGANISM: Lolium perenne

<400> SEQUENCE: 34

| | | |
|---|---|---|
| atggggtact cctccaagcg cctccacgcc agcatcctgg cggtggaggc cgggcaggac | 60 | |
| gcggtgatca ggatgctgct gtaccagcgc gccgacgaga cggtggcgcc gtacaggggc | 120 | |
| cacacggtgg cggagttcac gcggcggatc tccgactggc ggaacggcat gtccgggtgc | 180 | |
| ggcgccaagg acgaggggt caaggtgctg accggcggc aggggcgga gcggaggacc | 240 | |
| atcagcaaca tcctcggcgc gggggtggac tcgctcgggt accagcgcac gccggcggag | 300 | |
| gcgctgcgca tcctctacgg ctcgcgcaac gagcaggtgc ccggcgggtt cctgccccat | 360 | |
| ggcgctaatg gcaccatcgc cagaggattc ttccagctcg cgtag | 405 | |

<210> SEQ ID NO 35
<211> LENGTH: 759
<212> TYPE: DNA
<213> ORGANISM: Lolium perenne

<400> SEQUENCE: 35

| | | |
|---|---|---|
| atggcgcagt ccggcagcga cgccgcaccg atcagcacgc accccaccga ggaggaggag | 60 | |
| gtgacggtgg agaggacgcc ggaggaggag gcggccaggc tcaggtacct cgagttcgtg | 120 | |
| cagcaggcgg cggcgcaggc ggtcgtgctg ccgccgcgg cctacgccta cgccaagcag | 180 | |
| ggcgcgggc cgctccgccc cggcgtcgac cacgtcgagg gcaccgtcaa ggccgtcgtc | 240 | |
| ggccctgtgt atgatcggta ccacgccgtg ccgctcgacc tcctcaagtt cctcgaccgc | 300 | |
| aaggttgacg agtccgtcca ggagctggac cgccgtgtcc ccccagttgt gaaggaggtg | 360 | |
| ccaacttatg cccgctctgc ggcggctgag gtgcacaaga ccggcttagt aggcacagcc | 420 | |
| acgggcctgg ccaagtcggc cattgctcgt gctgagccaa aggctcgcga cctgtacacc | 480 | |
| cgctacgagc ctgtggcgga gcgcaaggct gccgaagcat gggctgccct caaccgcctc | 540 | |
| ccgcttgttc catcggtgac cagggctgtc ctccccaccg ctgcacagct tcagccaag | 600 | |
| tacaactctg ccgtgcttga cggggccaag cgcgggaact ctgttgccac ctacctcccg | 660 | |
| cttgtcccca cggagcgcat cgcgagggtg ttctcctacc cgcctaccga cgctgctgcc | 720 | |

```
acctcggctc ctgagatgca gcccatcccg acgcagtaa              759
```

<210> SEQ ID NO 36
<211> LENGTH: 2109
<212> TYPE: DNA
<213> ORGANISM: Lolium perenne

<400> SEQUENCE: 36

```
atgcaggagg gcggcggcgg ccgtgcggtc cgagcaggac ggtacccgcc cctcgcctcc    60
ctcgtcgtct ccaccatcgc cgccttctcc gccgtcatcg tcatcgccgt cctccactcg   120
gcgtacgacg acgctctgtc ccggacgcgg acgctgctgg ggcacaacct ggagccgacg   180
ccgtggcacc cgttcccgca cgacaagggc cgcccgccgc cgcgcgccgc gctccggtgc   240
gcctcctacc tcgcctgcct cccgccgctc tcgcagccgc ggccggctgc ggcggcgctg   300
gcacccaaca acgcgtcgac gaggccgcgg cggcagtgcc cgtcctactt ctccgccatc   360
caccgcgacc tcgcgccctg gaagcgccgc gccgatggcg ttggcggcgt cacgcgcgct   420
ctgctcgagt cagcccgcgc cagggcatcc atgcgcgtca ccatcaccgg cggcgggacg   480
aggctgcacg tggacctcta ctacgcgtgc gtgcagagcc gcgcgctctt cacggtgtgg   540
agcctcctgc agctgatgcg gcggcacccc ggccgggtcc ccgacgtgga cctcatgttc   600
gactgcatgg accggcccgc catcaaccgc accgagcaca cgccgagggg cgcgcccccg   660
ccgccgccgc tgttccggta ctgcaccacc cgcgaccact tcgacatccc gttcccggac   720
tggtccttct ggggctggcc ggagacgcac atcgagccgt ggagccgcga gttcaagagc   780
atcaggcagg gcgccaagaa ggtgcggtgg ccggaccggg tgcccaccgc gtactggaag   840
ggcaacccgg acgtggcgtc gccgctccgg ctagctctcc tcgcctgcaa cgacaccaac   900
ctctggcgag ccgagatcat cgccagaaag aaacagtgga aggacgagct ccgcaggttg   960
aaggagatga agaagagggg caagtctgat atggacgctt atgggtatgc tagtattgca  1020
ggagaaaacg atcaggatcc tcctccagaa aatgtttcag tcccttttacc tgacatggtg  1080
ctgcctcctt catttgattg tgacaatccg acataccggt accgctttct ggaaccaacc  1140
tctactgtcc ttgctaggcc tgttttagat gcgcatgggt gggatcatga ctgcggttat  1200
gatggagtaa gtgttgaaga gtcactcgcg ctccttagca agttcccagg gactgtggca  1260
gttcaggtta ccaaggacaa gaaggaattt agcatccatc tagattcttc catctcagca  1320
aagcatggag aggatgcgtc ttcccttgct ggttttgaca tccagactgt tgggcggcag  1380
cttgcgtata ttcttcgtgg tgagaccaaa ttcaagagta tcaagaagaa caagactact  1440
ggaggattct ctgtgacttt cttgggtgac attgtggcaa ctgggctgaa ggttgaggac  1500
cagctctctg ttggtaagag gctggcatta gttgcaagta caggagcaat gcgagctcaa  1560
ggggatactg cttatggagc taacttggaa atgcgcttga aggacaaaga ctatccaatt  1620
ggccaatcct tgtcaacctt gggcctgtcc ctcatgaagt ggcgccgcga ccttgccctt  1680
ggcgctaacc tgcagtccca gttctcgatc ggaagggggtt caaagatggc ggtccgcctt  1740
gggctgaaca acaagctgag tgggcagatc accgtcagga caagcaccct cagagcagatg  1800
cccccctaatc ccatggagga agaggatccg gagtccggag agagtgatcc agatcacatg  1860
cacgttatag ggcagcaatg gagcggcggc gtggatcggc tcgccggcgg tgagtcgccg  1920
tcgtcggagg tttattcgtg tgcgtctgtt atggcgacga aaactacagt ggcaacgtca  1980
gatcttgcag catctgggtc gggcaccgtc ggtgtagatg accgagaagt tttgatggtg  2040
```

```
aagctcggac ttcgcgagga ggaccttgat gacattgtgt tagaggaaga aggaagccaa    2100
catgagtag                                                            2109

<210> SEQ ID NO 37
<211> LENGTH: 1023
<212> TYPE: DNA
<213> ORGANISM: Lolium perenne

<400> SEQUENCE: 37
atgtcagagc cggatgcgaa gacaaccatt ctgggttctt ctgtctttca gttcagagtc      60
gactacgagc aaagtaagca gcttcccatc gggaaggccg tccggtccga cgttgtctcg     120 gcaggggac acctctggag ggttgatttt tccccgcgtg agagactga cgaagacaat       180 ggcgagtata cttctatctt cctcagccac atgagcaaat cctgtagtgt caaggccgtc    240
ttcgaggctt tcatgatggg tgggaacagc aaactgtcta cgtccttgaa cgcaggaagg    300
acattggaaa ccttcgaaat cttgggagat aaagacttcg ttgacacctg gggatggact    360
cgtttcatca agaggacttc tgttcaggaa aatttcttaa cagagggtca catcacactt    420
gtgtgcgccg tcatggtcat cgatgacagt cctattcctg tgccgccttc agacattggg    480
acccatattg gccgcctgct agatgagact gacgggacag atgtggcatt catcgtcgac    540
gacaagacat tccctgctca ccgagcagtg cttgctgccc gctcaccggt tttcaaagca    600
gagctattcg gttccatggc cgagtctaca atgttgtcca tcacgctgca cgacatcaca    660
cctgcaacat ttaaaacttt gctacggttc atatacacag atgaattgcc cgcagaagat    720
gaccatcagg actcttccac tgagatgatt cagaatctac taattgcagc cgatcggtat    780
gcgcttgaca ggctgaagat catctgtgct cagaagctat gggataaagt gtcggtagat    840
acagttgcag ctatcttagg tttcgccgaa acatacaatt gtcaggagtt gaaaaacaag    900
tgcatcgact tctttgcagt ggagaataat ttcaaacagg tcatgttcac cgatggttac    960
gcaatgttgc ttctgaagtt cccattgatc attgctgagc tgaagaagag ggttggggca   1020
taa                                                                 1023

<210> SEQ ID NO 38
<211> LENGTH: 828
<212> TYPE: DNA
<213> ORGANISM: Lolium perenne

<400> SEQUENCE: 38
atgctgcgcc tgaccctgcc tgcccttcc accttgctga tctggcagga aattctctca       60
tggcaccgga tgacctgcag accaccagcc caggagatat ccctcactga atggtggata    120
gaagcaagac aacgcctggc ccccgcgacg ctgctcatcc tgtggatgac ctggaaacac    180
cgcaacagtt gcgtgtttga gggtgcacaa cctttgatca atggtctgat ctccagcatc    240
aaagatgaaa caattctctg gctaaagcc agtgccactg gcctaggagt agtgaccgat     300
gacctgggat gttctccatg ggttattcta aatcggcggt ttatagagta ttgtattctt    360
ggctgggaga atcttcctcg ggttcttctc atgtacttca caacgtagt gctgcctcag     420 gaaggatact ccactcagt catatgcaac tcggttgatt ccgtaattc cactgtgaac      480 aatgatttga ggtacaaggt gtgggatgaa ccacctcaga cagagcccct atttctgaac    540
atggcacatt atgatgagat ggtgaacagc ggacagcctt tgcaaggcg ttttcagaag     600 aaggaaccat tgctggacaa gatcgatgac aaactactca ggcgtcctgg gcatgggcct    660
gttcctggtg cctggtgctc aggcaggaag ggctggttcg ttgactcatg ttcccagtgg    720
```

-continued

| | | |
|---|---|---|
| agtgacgtga acgttgtgaa acctggtcct caggccttga agttgcagca atatatcaat | | 780 |
| cggacattgg aagaagcaaa ttctggcgca aaatcatgca ggcgatag | | 828 |

<210> SEQ ID NO 39
<211> LENGTH: 2796
<212> TYPE: DNA
<213> ORGANISM: Lolium perenne

<400> SEQUENCE: 39

| | | |
|---|---|---|
| atgggggcgg cggagctgct gtctttgtgc ttggtactcg ctgcggtggc atggacggag | | 60 |
| gggcagcggc cccgcgcggt gaaagtgggc gcgctcttcg actacgattc caccattggc | | 120 |
| cgcgcggcgc agctcgccat cgagctcgcc gtcgacgacg tcaacgcgga ccgctccgtg | | 180 |
| ctcgcaggga ccaagctgga cctcatcacg gcggacacca actgcagcgg tttttgttgga | | 240 |
| accgtccaag cactgcaact aatggagaaa aatgtggttg cagttgttgg cccgcagtcc | | 300 |
| tctgtgatag gccatgtcat ctcacatttt gttaatgagc tgcatgttcc gctcctatca | | 360 |
| ttcgcagcca ctgatccaac tctttctgca tcggagtatt cttactttt aaggagcact | | 420 |
| gtcagcgatt acttccaaat gcgtgcgatt gctagcattg cttactacta tcaatggaaa | | 480 |
| gaggtaactg ctatatttgt tgatgatgat tatgggagag gtggggtgtc tgcccttggt | | 540 |
| gatgcccttg caacaaagcg tgccagaatt tcatataaag cagtaattcc tccagatgcg | | 600 |
| aacaaagatg tgatcagtga tatactgttt aaagttaaca tgatggaatc aagggttctg | | 660 |
| gttgtgcatg tcaatcctga tacagggctg cgattatttt ctatagctaa cgagctccag | | 720 |
| atgatgaccg gtggctatgt ctggattgta actgattggc tagctgctgt cctggactcc | | 780 |
| tcaaagtctg gatatccgaa gagcatgagt tatatgcaag gattaattgc ccttcgtcag | | 840 |
| cacattcctg attctgctgc caagaagaag ttcatatcaa aatggaatat tgcggctcgc | | 900 |
| aaaaggaaaa ttgcatctgg tttgaattcg tatggttttt atgcttatga ttctatttgg | | 960 |
| attgttgccc atgcgattga taaatttctc aatagtgggc agcagatcaa cttctctgca | | 1020 |
| gatacaagat tgcacgattc ggatacaagc attatcactc tgtcaactct caagatattt | | 1080 |
| gatggtggtg aacacttgct acagcaactt ctgctcacaa actttaaagg cctaacaggt | | 1140 |
| ctggttcaat ttgattcaga ccgcaatttg gtacacccag catatgagat ccttaacatt | | 1200 |
| ggtggttctg ttcctggttt gattggctat tggtctaatt attctggcct ttctgttgct | | 1260 |
| gctcctgaaa ctttgtatca gaagccacca aatatgtcgt caagtgccca acagttgagc | | 1320 |
| actatggtgt ggtcaggtgg ctctaccact aaacccaggg ggtgggtttt cccaaacaat | | 1380 |
| ggccagcctc tgagaattgg tgttccaaat aaaccaagtt tcaaggaatt tgtggcaagt | | 1440 |
| ggcaaaggtc ctgataacgt gacaggttat tgcattgata tattcaatgc agcagttaaa | | 1500 |
| ctgcttcctt accctgttcc ttccaaattc atatcaatcg gcgatggtat acataatcct | | 1560 |
| aaatatgatg acatcattaa tatggttgca acaataccat tgatgtagc tgtaggcgac | | 1620 |
| ttcgctatta tcaaaaatag aacaaggatt gcagaattca cacagcccta tattgagtca | | 1680 |
| gggatggtga tagtagcgcc agtgaaacag tcaacttcaa gtgcatgggc tttcttttaaa | | 1740 |
| ccattcacat tagagatgtg gtgcgtaact ggtgctcttt ttgtctttgt gggaatagtt | | 1800 |
| gtttggattc tggaacatcg gactaatgag gagttccgag gcactccaca gcaacaagtc | | 1860 |
| cgaacaatat tttggtttgc tttctcaaca atgttctttg cacaccgaga aaacaccgta | | 1920 |
| agtggtcttg ggcgtttcgt cctgatcata tggttatttg tggtgctgat catcaactca | | 1980 |

| | |
|---|---|
| agttacactg ctagtttgac gtcaatcctc acagtccagc agcttgtaac cggagttact | 2040 |
| ggactggaca atttgattgc aagcactgta cccattggac acccggctgg aaaatttatc | 2100 |
| cgaaattatc tgattgaaga gctgaatatt catgaatccc gcctggtgcc actgaacacg | 2160 |
| atccaggact atgcggatgc ccttaaccgt ggaccaaaag ctggtggtgt tgctgcagtt | 2220 |
| attgatgaaa tgccgtgtgt tgagctcttc ctgtcatacc actgtaactt cagaatagta | 2280 |
| ggtcaggagt tcacaaagga gggatgggga tttgcatttc agagagattc tccgcttgct | 2340 |
| gcagacatgt caacggccat ccttcaactt tcagagactg gccagctcca gagaattcac | 2400 |
| gacgagtggt tgacgcggcc aagttgcagc tctgatgata gtgggttggg accaagcagg | 2460 |
| ctagatcttg gaagcttctg gggtcttttc ctgctgtgtg ctatgatctg cctcttctct | 2520 |
| cttggggcgt tctttgtaaa ataagctgc cagtacagca ggtactccag ttctgtggct | 2580 |
| gctggcgaat ccagtgaagc ttctcctacc tcccctgctg tttctgaagt acacccgacg | 2640 |
| aaaccaaagc caagacgtct tgatagcttc aaagatctga tgcattttgt tgacaagaag | 2700 |
| gaggaagatg ttaaaaagga aatgaaacag agatcaagcg ataaagataa tcatggcgtg | 2760 |
| ggatcctcag atacacactt tgtctcttca gcatag | 2796 |

<210> SEQ ID NO 40
<211> LENGTH: 432
<212> TYPE: DNA
<213> ORGANISM: Lolium perenne

<400> SEQUENCE: 40

| | |
|---|---|
| atggcaccgg cgtctacacg cgcggcagcg gcactccacg gcgtgacttt agacaacacc | 60 |
| gacgccctcg actgccgcct ttgctgccta ccactcaagc cgcccatctt ccagtgtaag | 120 |
| gtggggcacg tggtatgctc gccgtgccga gacaagctgg gggcggctcg gaggtgccat | 180 |
| gtgtgtcgca cggcgacttc cggcggatac caccggaacc acgacatgga gaagctgctg | 240 |
| gagtccatcc gggtgccttg ctccaacgcc gcctacggct cgccgccaa gccggtctac | 300 |
| tatgacaggg acacccacct ccggttgttc tgccagcacg cgccctgcca ctgcaatata | 360 |
| gaagcatgtg gcttcgttgg ctcgacatta tcggcgctcc ttgaccacgt cttcgccgtg | 420 |
| catgttgaat aa | 432 |

<210> SEQ ID NO 41
<211> LENGTH: 2553
<212> TYPE: DNA
<213> ORGANISM: Lolium perenne

<400> SEQUENCE: 41

| | |
|---|---|
| atgtcgacaa tgaagggcgt cgacgacgcg ttcctcggcg tcggcgacaa gccagggctg | 60 |
| gacatctggt gcattatggg caccagtgta gtcccaattg caaagaattt gcatggcaaa | 120 |
| ttctacactg ggaactgcta tattgtactc agtacagctg agctcaagag gggaagtcgg | 180 |
| caacacagtg tgcattactg ggtaggggaa gaagcgaaag aggaacactg tgtgatggct | 240 |
| tccgacaagg cctttgagtt ggatgcggca ctgggctccc aagctgtcca gtacagggaa | 300 |
| atgcaaggtg aagaatctga caagttcttg tcatacttca ggccatgcat aatccctgtg | 360 |
| caaggcagct tctcttcgca ctggagaaga tctgcggagg aatgcgacca gaccacaatg | 420 |
| tttcggtgtg aaggagagca tgtagctcgt gtcacagaag ttccgttttc gcgtacctcc | 480 |
| ctggatcata aggcagcgtt tatagttgac actccgttga agatcttcct tttcagcggt | 540 |
| tgtaattcta gtgtgaaaac aagggcaaag gcattagatg tcattaagta cctgagagaa | 600 |

```
aaccgacatt ccggtagatg tgaaattggg acaatagagg atggaaagct tgttggtgat    660
tctgatgctg gtgagttttg gaacctgttt ggaggctatg cacctattcc ccgtgatgta    720
ccagatgcag ccaatgggga gctgatgact accacatcca agaaactttt ttggattaat    780
aagagaaaac ttgttcctat ggatgcacac ttgttagata gagaaatgct gaagtctgac    840
agaagttaca tactggactg tggaactgaa atatacttgt ggttagggat ggcaacactg    900
gtttcagaga ggaagatatc cattactgtc ttagaggatt atgtacgaag tcaaggaaga    960
tcatcaattg gtcaaactgt tataacgact gaaggtcatg aaattgccga ctttaagctg   1020
cagtttcagc attggccgaa gaatgtcgtc caaaagttat atgaggcagg agagagaaa    1080 gtggcagcaa ttttcaagca tcaggggtat gatgttgcag aaattccaga agataaacct   1140
caacagtcca tcagtagtaa tggttctctg aaggtatggc tggtggaccg tggttctgta   1200
accctccttt gcactgagga gcaggaggaa ctgtataatg gggattgcta tattgtacag   1260
tacagctatg ttgaagatgg aaaagattat aatctgttct tttcttggtc tggacaaaat   1320
agcgtacagg aagacagact tgcttcagtt tcattgatgt caagcatgtc tgattcagtc   1380
aaaggtcctg cagttgtggg gcaagtgtct gaggccagag aaccagagct gttttttccta   1440 gtattcaagt ccttgatcat attcaagggt ggtaggagtg ctgcatataa gaactctgtt   1500
ctgcagaaaa gcaatagaac tgaagggtac cagaaagacg gggctgcatt attccgggtt   1560
caagggctga gacatgattg cgcaagagcc gttcaggttg atctgattgc aagctcgctt   1620
aattcctcgc actgctatat tttgcaagac ggtccttctt tctttacctg gactggaagc   1680 cttttcttcac caactgaaca tgttatactt gacaggatga tgaataagtt gtttccacta   1740
aagcaatcgt ttctattaaa agaaggttct gaacctgatc acttctggaa aacattagaa   1800
ggaagatcag agtactccaa agagaagtgt gtcaagagtt ggccggcaga tccacgtctg   1860
tatacctgta ctttccagca atgtctgttc aaggcaaagg aggtatttac cttctgtcag   1920
gatgatctgg caactgagga gaccttgata ctggactgcg gcgaggaaat ttatgtctgg   1980
gttggacttc actcaggtgt cacgtccaaa gagcatgccc tcgacatcgg caagatgttc   2040
cttcaggcag gcaatgctga ggatgggcga cggtccatct tgacacaac tgtttatgct    2100 gtcgcggaag gggatgagcc tgcatttttc accagcttct tcaactggga taactcaaaa   2160
caagttgcat ccgttctggg caactcattt gagaggaagc tggcgatact gaagggatt    2220 tcaccaaaac tggaggcacc ggacaggagc ttgcgcagat catcctcgag aaggccaggg   2280
acatcgtcgg agccgaccac gccggaacag caccagccag cagcgaggag gacgttcggc   2340
cctgcctctg cctctgtcgg gagggtagcc aaggagagat caggagcatc tccggcactg   2400
tcgccgtcgc cggtaacacc atcctggtct tgcgaggagc cgcgcctcgt cctcgccgtc   2460
gtcgccatcc acaccgttgg tagcgcggcg gctcttcccg tccacgctgc acgcccctc    2520 cgctacagcc actgcgagcc ccgctcgacg acg                                2553
```

<210> SEQ ID NO 42
<211> LENGTH: 1881
<212> TYPE: DNA
<213> ORGANISM: Lolium perenne

<400> SEQUENCE: 42

```
atggactata cctcggatgg agattctgag cttgaagctt atgggtcaga cacttatgca     60
cttctgctgt caggagatat acaagtgatg aatgatgagg gcttgtacaa atgccccttt    120
```

```
tgttcggatg aaaaggatga ctataacaaa tatgatttac tgcagcatgc ccttggtgtg    180
ggggctgcac atgatcagca agtgaaagag aaggtagacc atcgagccct tgccaagcat    240
ttgaaggatg atgaaccagc taaatcccat agcccactcc tgcagccaat tgttatagat    300
ccacagcctc ctcaacataa cagagatgac ctgtttgtct ggccctggat gggtatcata    360
gtcaatatgc cttctgaata tgttggaaaa agtgcaaacc ggctgaagga gcatttctca    420
cgtttttatc ctgtgaaagt gcaccatgtg tacagtaaag gtcgccctac aggaaatgct    480
attgttgagt ttgggaagga cttggttggt tttagaaatg cactaacatt tgagaatcaa    540
tttgagaagg aagggcatgg gaaaataggc tggcaggaaa acagcatgg agggccagag    600 cctttggat ggatcgctag agcagacgat tacaatgctc caggagcaat aggggacttt    660
ctaagaaaaa atggtgatct gaagacggct gacggtgttg aggatgaaga aacaatgaaa    720
aataacaaac ttgtggccag tttatctttt aaagttattg aaactgatat gcatatacaa    780
gaacttaaat ctgtgtatca ggagagaact gcatcactga aaagaatgat ggagcagagg    840
gaacagcagc tacagtcata caatcaagaa atccaaaaga tgcaacagct ttctgttgaa    900
cacacaaaaa cgattgttga cgagaacaag aagctaagcc tggatcttca gtctatgacg    960
catgagcttg atgcaaggtc caaacaaatt gatgagttgg ctgcacagac tgattgtgac   1020
agaaaaaacc ttgaattgga gaagcaaagg aatgcaatga agttcaatca tcttacgctg   1080
gcagaacggg agtatcagaa agctgatgaa atgttctaa agcttgtcga acaacacaag   1140
agagaaaaag aaactgcttt aaacaatatt aagaagttga cgaaaagct gcatctgacg   1200 cacaaacttc aattggatat aaagcacctg acgggaaaat tggaagtgat aaagctcaca   1260
ccaggcaatg aaacttcaga atcggggaaa agaatagcgg aactgacaga ggagctgcgt   1320
gataagatcg aggagatgga ttatacgaaa aactacaacc aagatctaat cgtacaagaa   1380
aaaaagactg ctgttgagtt gcaagaagct cggaaactgg cgatagatgc aatacagcgt   1440
tttcctggcc agaccattga caaagcacac ataggcatca agatgattgg tgagcttgac   1500
ttgaaagcat tttcaaatgt gtgcaggcaa aaatttccaa aagatgatgc tgaagttgaa   1560
agtgttaagc tttgttcaaa gtggcagaat gaaattagca atccaaactg gcatcctttt   1620
gtggctgcta tgttgaacgg aaaagagtcg gaagtgatca gggaggatga caagaagctc   1680
caggaactga agaggagta cggtgaggaa gcctatgctg cagttacgac ggcgctgacc   1740
gagctcaatg agcacagtag cagcggcagc agggttcctt tccccgagat gtggaactac   1800 aaggaggga ggaaagcgaa aacaaaggaa attgtccagc atgtcatcaa gctggccaag   1860
gcgagcaaaa gggggcgttg a                                              1881

<210> SEQ ID NO 43
<211> LENGTH: 252
<212> TYPE: DNA
<213> ORGANISM: Lolium perenne

<400> SEQUENCE: 43
atgatcggca tgattgacgg gcggacggag ctgaaaccgg cgccggagac gtccgccggc     60
gacatgaggc agctacaggt gctcaacgtc ctggtctccg gcgaggtcgc cgacctggag    120
agcgggtacg tgacggacgg gacgccccct catcgtgcgga cgtacctgat cctcgagatc    180
accgtcatgg cggccaagat cgcctacgag aacgccgcct tcgtcgagaa cgtggtcaac    240
aatgtctgga ag                                                        252
```

```
<210> SEQ ID NO 44
<211> LENGTH: 1296
<212> TYPE: DNA
<213> ORGANISM: Lolium perenne

<400> SEQUENCE: 44
atggcggagc tgaattacat tcccaaccgc gtggcacaac aactggcggg caaacagtcg      60
ttgctgattg gcgttgccac ctccagtctg gccctgcacg cgccgtcgca aattgtcgcg     120
gcgattaaat ctcgcgccga tcaactgggt gccagcgtgg tggtgtcgat ggtagaacga     180
agcggcgtcg aagcctgtaa agcggcggtg cacaatcttc tcgcgcaacg cgtcagtggg     240
ctgatcatta actatccgct ggatgaccag gatgccattg ctgtggaagc tgcctgcact     300
aatgttccgg cgttatttct tgatgtctct gaccagacac ccatcaacag tattattttc     360
tcccatgaag acgagcaccg tcatgcactg ggacgcagat tagagacctg gaaagatgtt     420
gtcgccgtcc tcgccgccgt cgaggtagtt gaacggcgcg tccccctcgt agcggaagtc     480
cgggccgacg tagcacttca tctcgtggaa caggttcagg ttgtccacca gtttgtggaa     540
aatgttgcag ccgcagcact gaacgaagac ggtgccgtcg gtgtaggcgt gcgggttgat     600
ggcgcgggtg gtgcgctgcc cgcacacgtt gcaggtcgat gcgtgcgggg agctggcatt     660
gttgaagcag gggatgcagc agagcttgtc tttaaggctg caacatcact ggactctgtt     720
ctgtggacta cgatgatctc agcttatgga aagtctggcc gtgcgcaaga tgcagtatct     780
atgtttgata gaatggcaca tttgggcata aaaagagatg gagtagcata ccttgcggtg     840
ttgtcagctt gtagccatgg cggacttgtt cgggaaggtt ggcactactt caaggttctg     900
tttgatggcc agagctcggt taagctgcag cctgagcact acggttgcat ggcagatctt     960
atttgcagga gaggttgcct acaagatgct cttgaattca ttgagagcat gccatttgac    1020
tccagtgttg ctgcctggag tgcattgctt aattcatgtc gaatctatag ggatgctaag    1080
ttgggtcagc ttgcagcatc tcgtctactc aagcttgatc cggggaacca cagtaactgg    1140
gttgctctat caagtataca tgctttggag ggagattggc atgagacctg gatgatcagg    1200
gagaacatga acaaagagtg ggtaaacttc ttcttcatca tcatcatttc tttttacagt    1260
acagccatgg tgattacata catggcggcg agatga                              1296

<210> SEQ ID NO 45
<211> LENGTH: 2075
<212> TYPE: DNA
<213> ORGANISM: Lolium perenne
<220> FEATURE:
<221> NAME/KEY: misc_feature
<222> LOCATION: (400)..(474)
<223> OTHER INFORMATION: n is a, c, g, or t
<220> FEATURE:
<221> NAME/KEY: misc_feature
<222> LOCATION: (603)..(638)
<223> OTHER INFORMATION: n is a, c, g, or t
<220> FEATURE:
<221> NAME/KEY: misc_feature
<222> LOCATION: (1091)..(1148)
<223> OTHER INFORMATION: n is a, c, g, or t
<220> FEATURE:
<221> NAME/KEY: misc_feature
<222> LOCATION: (1263)..(1280)
<223> OTHER INFORMATION: n is a, c, g, or t
<220> FEATURE:
<221> NAME/KEY: misc_feature
<222> LOCATION: (1536)..(1536)
<223> OTHER INFORMATION: n is a, c, g, or t
<220> FEATURE:
<221> NAME/KEY: misc_feature
<222> LOCATION: (1666)..(1696)
```

<223> OTHER INFORMATION: n is a, c, g, or t
<220> FEATURE:
<221> NAME/KEY: misc_feature
<222> LOCATION: (1908)..(1908)
<223> OTHER INFORMATION: n is a, c, g, or t

<400> SEQUENCE: 45

```
ccgccccacg agcctccacc taccggcccc gtcgccgtcg ccgtcgccgc ctccaacatc      60
cgccccaaa  accctagccc cgccacctcc acagccgccc cacgccatgg ccaccaacgg     120
cagctccccg agggttagag acgcggagag cagcctggac aaggtgaagc ggcagctgtc     180
cacggggtcc gggaggtacc tgctgcaggg tccctgctg  aaacgatctg agacgctacg     240
gaaatggaat gaaagatgga taatattgga cccaacatct ggaaagatgg aatacaaact     300
tcggaggaat gaaactgctg tgaagggatc cattttattt gatgctgcaa gcaccattac     360
tttgtctcct gtaaattttc acggaatgcc aaagtatgan nnnnnnnnnn nnnnnnnnnn     420
nnnnnnnnnn nnnnnnnnnn nnnnnnnnnn nnnnnnnnnn nnnnnnnnnn nnntccttg      480
aacacaaact ttgatttgca tattctttct aagttttgaa gtttgtttaa ctaacacttc     540
aaacctcgca gcgggatgcc aaagtatgac ggctgctgtt tctacattgg aactcctcag     600
aannnnnnnn nnnnnnnnnn nnnnnnnnnn nnnnnnnnga ttactttctt tgcgctgaaa     660
ctcctggtgc tgccaaagct tgggtatcta cattgcatgc aacacagtta gtactacaag     720
cacataaaga ggcagtaaat tcgttggctg ggaatggctc tccttctaca ttaggcacgg     780
ttgcgacggc agttgctaat gctaacgcaa ctgctttgga ggccatgaag gaggtagatg     840
ctgcactgaa ggtttcaatg agggcagctc ttgggttggg tacaaataat ccaaatgagg     900
gtcaacttga tgatttaacc atcatgaagg agacgctccg agtgaaagat gaggagttgc     960
agcatttggc taaggacatc cgtgctcggg actctacaat tcgggaaata gcagacaaat    1020
taacagagac tgcagaggct gcagaggcag cagcttctgc agctcataca ctggatgaac    1080
agagacgact nnnnnnnnnn nnnnnnnnnn nnnnnnnnnn nnnnnnnnnn nnnnnnnnnn    1140
nnnnnnnngg aagctcatat gtggcgcact gaactaggaa aagctagaga gcaagcggtg    1200
atacaggaag caactattgc acgagcagag gagaaggtaa gggtgtctga agcggatgct    1260
gcnnnnnnnn nnnnnnnnnn cgttcggata aggaagctg  ctgaaaattt gcatgctgtt    1320
gagaaagaaa aggaggaact tttagcccctt attggtgttc tccaatcaca agtgcagaga    1380
gaccaaagca gcacaaaaca agtatgtgaa gagagatctg aatcatgctc tggtgccgac    1440
aactcccctc cattgacaaa gcacgtcgat gcatcagatg atgatgtgga caaagcatgt    1500
gtaagtgatt caagatcagt cctggtttct agcgantagc accgaagtcc agcttgctgt    1560
ggatggggtg gacatccgtc caattggcga tgcagaatgg ggtgacttcc agcggccaga    1620
agcattgatc gctgatgtcc gggaagtctc cccggaagga gaaggnnnnn nnnnnnnnnn    1680
nnnnnnnnnn nnnnnnccac cagtccctga tcatatgcag ggaggggcaa cacatccttg    1740
aaggtcttgg agctcccaca tactttcttg ggggttgtg  attattgagg aaactgccaa    1800
ggatttgaat cctctcgaga attactgtcg caggttttg  cactgcttcc gggttgtatg    1860
tccattgtat ttaagtatgc aactcaataa aagatgttac gggtttgnct gtgtgattgt    1920
aaattgttca cttcatctcc ttctgccatc atctggcttt cagttcatga ttgaaactgc    1980
gatgtgaaag tctgtttgga agttcagcaa ttagatatat ctctatggaa caaaagaaaa    2040
agtaaaagtt gtgcctgtct cgtttggatg ctcct                              2075
```

<210> SEQ ID NO 46
<211> LENGTH: 2157
<212> TYPE: DNA
<213> ORGANISM: Lolium perenne

<400> SEQUENCE: 46

```
atgctgcacg agctcctcct cgccctcctc ggcttcaccg gcgacttcgt catcgacaac      60
tcctcctcct cctccgcccg ccgccggccc tctcccgccg aatccgtggc cgccggagac     120
gcggacgcgg gccccgcctt ccgcctcgcc cccgacctca ccttcctcca gccttccgag     180
aggagcgcta ttgaaaggct catttctctg gcttttact ataganaact gaaccgtttt     240
gcaaccgagt ctcgagatct gagctggatt cagtcttctg tagatgtttc atcacctaat     300
gctgatataa ctctgaaggg caaagtgaga aagggagtg cataccggag agcaattggc     360
aatggtattg ccgagatttt atcagtttat aggtcagctg ttctgcaggt tgagcaaaac     420
ctattgtctg atccattgcc tatcctggcg acagtaaccc atgggctaaa taagtttgag     480
gttctcctgc ctccacttta tgagcttgtt atggaaatcg agcagaaaga catcaaggga     540
ggacagcttc ttaacctgtt gcataaacga tgccattgtg gggttccaga actgcaaagc     600
tgtattcaga gacaggttga cagggatgag gagaatgaat cagctcagtc agatgttgct     660
gataagtttg cgcagaaatt agctaaagac acatccctga ctagttggca ttcaggattt     720
catgtatcat tggacatgct acctgagtat atccacatgc gagttgcaga tcaattctc      780
tttgccggaa aagcaataag ggtccttaga atcctagtc ctggtgctac attgcaggaa     840
cctgctaacc aaagtcagat cttgaaagga tctcatagaa tgcaaacttt cacagggggt     900
tccggtgctc tgaaggagct accaaacttc tctaacatta gcgcagaaga attattaccc     960
caagttgaag cagataaagt tgatgcgatg ctcaaacagc taaagcattc ttccgagttc    1020
cataaaaggt tgtttgagtc tgctgttagc tcaatacgaa caattgcagc taatcatctt    1080
tggcagctag tggttgtacg ggctgatctc aatggtcact tgaaggcact taagagattat   1140
ttccttttag caaaaggtga tttttccag tgtttctcg aggaaagccg tcaattaatg    1200
cgcttaccac ctcgtcaatc tacagctgaa gcagatctca ttgttccttt tcagttggct    1260
gcgctgaaga ctataggtga tgaagacaaa tacttcacca gggtatccct aaggatgccg    1320
ttgtttggta tgaaatcaag cacctcgcag aaagatcttc aaaagtccaa tactccagat    1380
cttcctctc aaggaaaagc tagctcagag ttggcacttg atggatggca tagtattgct    1440
ctagaatatt ctgtcgattg gccactacaa ctcttcttta ctcctgatgt tctttctaag    1500
tatcgcaaag ttttccagta tctcatccga ttgaagagga cacaaatgga attggagaaa    1560
tcttggacag ctgtaatgca tcaagatcat gttgatttt ctgattattg caaggatcgg    1620
aaaaattctt ctgcaaccca actgcgccgg ttacgcacta agcctttctg gcgagtaagg    1680
gagcatatgg ctttcttgat cagaaaccta cagttctaca tccaggttga tgtaattgag    1740
tcacaatgga atgtcttaca aactcatgta caagattcac acgatttac agaactagtg     1800
acctttcatc aagactattt gtcagcgttg atttcacaat ccttcttgga tataggatca    1860
gtgtccagga tactgacag tataatgaag ctctgcttgc agttctgttg gagtatcgag    1920
cattatgaaa ccggcgcaaa catgtttgag attgatcaca taactgagga gttcaacaag    1980
aaatcaaatt cgctgtacac tatcctaagg agtagtcgac ttgcggggag tcagagagca    2040
cctttcctca ggcagttcct gatgagacta aacttcaact cttctcttga cacaactgcg    2100
agaggggtga tgaactcggg caggcttcgg ccaaacacag cggcaccca gctataa        2157
```

<210> SEQ ID NO 47
<211> LENGTH: 2457
<212> TYPE: DNA
<213> ORGANISM: Lolium perenne

<400> SEQUENCE: 47

```
atgggccagc aggtgtttgc ggagcatcca cctgtatctg cggcaccagg ggcacatcct      60
tgcccgtatg ttgcgtactt gcaacctctt ccatcattgg cctcatcatc aagcgcccat     120
gtccctgaga gaactatgga tgggtctgtg tatcatgatc attggaatca cctggctggc     180
ccatcagatg ggaggccctt gcacacggtg ccacccactg atttccatca taaccattgg     240
gcacatctgc cgcattccta tgcccaaccc aacagtaata atgggttgac tgagcagcca     300
ggggtcccctt tcggaacaat gagagctgca agggctgacg tgatatcca acgccgaggg    360
tctgttattt ctccatcata cttcagcaat ggatctggct ctagatctag agctcctaat     420
gttcccctc tggtacctca attcatgagg gggcatggca acatcaacga gcagtaccag     480
cagaatccat catctagcct ttttgcgggg gctcatagat cgggaggcat gcgatctgcc     540
cctccacctc aaccagagaa cccaacattt tgcctgttcc cgcctggttc gtctggccat     600
agttcaatgg agactgatga cgctggagga agccgattct acgcctggga gcgtgatcgc     660
ttcgcgccat acccattaat gccagtcgac tgcgagacaa gctggtggag ctcgcagcag     720
tctcacgggg catcagaatc cacagcagca ccagcaccag cacccgcgcc gaggagacta     780
ttcgggcaat ggatcggtct cggcaggggc gccgccactc tgggcatact gcaacagctg     840
caccccctggc ggatgatccc catgatttcc atctatgctg aagatatcat ggcgatcaaa     900
gagattctca atcttttttg gcgtacatca gggctacagg tgaacttctc aaagagctct     960
gccacccttaa tcactgcag tgaggaagac accgatgcca tcggccaaca ctttagatgc    1020
ccatctgtgc aattccctat catctacctg gcatttcgc tcactgcccg caaatcaaca    1080
gccgcccaga tgcagccgct gattgagaag gcgcgagaca atctaccaac atggaaggca    1140
cgtcttatga caagtctgg tcgccttgag cttatcaaat ctgttctcag tgcaataccc    1200
atgcatcagc tgcttgtcct tgcgccaccg aagaaaagca ccaagcaatt agaaaaaaat    1260
cgagcgtgga tttctctgga ctgcgatctg gagcgcgccg gcctcactct gcgcctccgg    1320
tggctctggt atagccacac cgacatgaac agggcctgga gcaaccttga actccaattc    1380
tcggcagaag aacacaccct cttcttcact tccacttcga tgtcagcggg caatggccag    1440
accgcgctgt tctgggacga tcgctggatc agcggccgct caatcagcga gattgcacca    1500
caactccatg cctgcagacc aaaaagaagg tggaaagccc ctgagacaat gctgcgcctg    1560
accctgccct gccttccac cttgctgatc tggcaggaaa ttctctcatg caccggatg     1620
acctgcagac caccagccca ggagatatcc ctcactgaat ggtggataga agcaagacaa    1680
cgcctggccc ccgcgacgct gctcatcctg tggatgaccc ggaaacaccg caacagttgc    1740
gtgtttgagg gtgcacaacc tttgatcaat ggtctgatct ccagcatcaa agatgaaaca    1800
attctctggg ctaaagccag tgccactggc ctaggagtag tgaccgatga cctgggatgt    1860
acattagtta gttttcctct ttttttttca agaacccgca ggaaatctcc gagtcatttc    1920
attaagctcg aaaaggaggg ttctccatgg gttattctaa atcggcggtt tatagagtat    1980
tgtattcttg gctgggagaa tcttcctcgg gttcttctca tgtacttcaa caacgtagtg    2040
ctgcctcagg aaggatactt ccactcagtc atatgcaact cggttgattt ccgtaattcc    2100
actgtgaaca atgatttgag gtacaaggtg tgggatgaac cacctcagac agagccccta    2160
```

| | |
|---|---|
| tttctgaaca tggcacatta tgatgagatg gtgaacagcg acagcctttt gcaaggcgt | 2220 |
| tttcagaaga aggaaccatt gctggacaag atcgatgaca aactactcag gcgtcctggg | 2280 |
| catgggcctg ttcctggtgc ctggtgctca ggcaggaagg gctggttcgt tgactcatgt | 2340 |
| tcccagtgga gtgacgtgaa cgttgtgaaa cctggtcctc aggccttgaa gttgcagcaa | 2400 |
| tatatcaatc ggacattgga agaagcaaat tctggcgcaa aatcatgcag gcgatag | 2457 |

<210> SEQ ID NO 48
<211> LENGTH: 1224
<212> TYPE: DNA
<213> ORGANISM: Lolium perenne

<400> SEQUENCE: 48

| | |
|---|---|
| atgaaggtcc atttctcggc gaagctgcta tccggcccgg tgccggtcta cttgctggcg | 60 |
| ctggccgtcc tcatcctcct cacccacgcg cactacatgg ggcacgtcgg cgtcggcgtg | 120 |
| ccgcccgccg ccaagctgga ggagccggtg gtgagcgtga tgaagcagtg cgacatcttc | 180 |
| cgcggcgagt gggtgccgga cacggcggcg cccgcctaca gccacaagac gtgcggcatg | 240 |
| atccaggagc accagaactg cctcaagtac ggccgcccg acctcggctt cctcaaatgg | 300 |
| cggtggaggc cgtcgggctg cgagctgccg cggttcgacc cggcgcagtt cctgcgattc | 360 |
| gcccgccaca ggtcgctcgc cttcgtgggg gactccctgg ctcgcaacca catgcagtct | 420 |
| ctgctctgcc tcctcgcgca ggtcgcgtct cccaaggaca tatcgccgga tccatcggac | 480 |
| cagcagaaca aggtgtacca ctacagggcg tacaacttca ccgtcgccat gttctggtcg | 540 |
| ccgttcctgg tgcgggcgcg ggagcccgcc cacgacgacc ccgcgcacac cgcccactac | 600 |
| agcctctacc tggacgagcc ggacgagagg tgggtgtccc aggtcccag gttcgactac | 660 |
| gtgctcgtct ccgccgccaa ctggttctcc cgcccctcgc tcttctacga aagcgccgc | 720 |
| ctcgtcggat gcagcttctg cagccgccag tacggcgtgc cggacctgac actgcactac | 780 |
| tcgcaccgca aggcctggcg cgtggcgctg cgggcgatca acgccctgga caacgtcacg | 840 |
| gggcgggtga tcgtgcggac gctgtcgccc atgtcgcact tcgacaacgg gacctgggac | 900 |
| cagggcggcg actgcaggcg gacggagccg ctccggagca accagacctc catgatggac | 960 |
| ggccgggggcc ccgaccaccg gttctacgcg gcgcagatgg aggagtaccg ggcggcggag | 1020 |
| aaggccgcgc gggccaaggg gacgatgcgg ctcatgctca tggacgccac cgccgcgatg | 1080 |
| ctcatgcggc cggatggaca ccccagccgc tacggccacc gccccaacga caaggtgcag | 1140 |
| ctctacaacg actgcgtgca ctggtgcctg ccagggccca ttgacatctg gaacgacatg | 1200 |
| ctattccaga tgatcctcgt ctag | 1224 |

<210> SEQ ID NO 49
<211> LENGTH: 5064
<212> TYPE: DNA
<213> ORGANISM: Lolium perenne

<400> SEQUENCE: 49

| | |
|---|---|
| atggccccca aggccggccg cggcaagggc aggggcggcg gcggcaaggg agaccgcaag | 60 |
| aagaaggagg agaaagtggt gccgaccgtg gtagacctca cggtaaccac cccctacgat | 120 |
| tcccaggtga cactcaaggg gatctcgacg gatcgcgtgc tggacgtgag gaggctgttg | 180 |
| gggtccaacg tcgagacgtg ccacctcacc aattactcgc tctcccatgt ggtgcgtggt | 240 |
| catcggctgg acgacggcgt ggaaatcgtg gccctcaaac catgcgctct gaccatcgcc | 300 |

-continued

| | |
|---|---|
| gaagaggagt acgcgacgga ggaggccgcc gtggcgcacg tccgccgcct gctggacatc | 360 |
| gtcgcctgca ccaccgcctt cgccaagcac aagcacaagt cctcgcccaa gcacgcgcgc | 420 |
| cccgcgacgc cccgtctcc gcccgccaca gcctcctccc ccgcggccaa tggcggcaaa | 480 |
| ggcgacggtg ccgaggcgcc tgcgatatcg gaggcgcacg acatggcggc catcgggccg | 540 |
| ccgccgaagc tcggcgagtt ctacgacttc ttctccttcg cgcacctcac accgcccctc | 600 |
| cactttatca ggaggaagga gaagaatggt gctgcccagg aaggcgatta cttcgaaatc | 660 |
| gaggtgaagg tctgcaacgg gaagcttctg cacattgttg cttcggtcaa ggggttctac | 720 |
| ctggtgggga agccgcacac cgcgtacgag gcactgatga aagcttttgt ggatcacaac | 780 |
| aagttcggga atctgccgtt cggcttccgt gcaaacacat ggcttgttcc tcctgtatac | 840 |
| atggactctg ctgcaagggg cccagcgttg cctgttgagg atgagagctg ggcgggcat | 900 |
| ggaggcggca gaggacgaga cggaaagcat gaccggagac ggtgggcaaa agagttttct | 960 |
| attttggcta gaatgccgtg caaaacggag gaagagaggg tggtcagaga ccgcaaggct | 1020 |
| ttccttttgc acaatctgtt tgtagataca gcgattttca gagctgcttc gacaatacgg | 1080 |
| cggctgattg ataccagtgt gcgaactggt tctgatggtt cgttagtgtt tgaggaacgc | 1140 |
| gttgggggaca tgcatgtaac tgtaaagaag gacgatgctg atgctagtgt gaagttgggg | 1200 |
| gataaagttg atgcagctgc cgtctaccag acggatgcta tggatatatc tcaaaggaat | 1260 |
| cttcttaaag gtttaacttc tgatgagagc gtcgtcgcta aggactcttc cacgctaggt | 1320 |
| gtggtgattg ttaagcattg tggatatacg gcaacggtga aggtttcggg tcgtacaaag | 1380 |
| aatagcactg atagcaaaca acccagtgat atctctgatc atcttgatgg agtgctgaac | 1440 |
| atcgatgtag atgatcatcc cgatggaggt tccaatgcct tgaatgttca cagtctaaga | 1500 |
| ataccactgc caaaaattat taacccagaa gtggctgcca gtaaccagca ccttagctct | 1560 |
| aagactcatg ttgataatta tgcgagaaaa ctagcacgta cagtacttga agccagcttg | 1620 |
| atgaagctgg agaacatgca gaaagaaaat cctagactta tcagatggga acttgggtcg | 1680 |
| tcctggctgc aacatttgca gaaaaaggat tcttcagctt ctggggatag tgagaagagc | 1740 |
| accaaaaaag ttgaaaaaga ttcatctgtc aaaggtcttg gcaagcactt tgaacaatta | 1800 |
| aggaaactta aaaagaatgt tgaaggtgct aagactgaga aggaagactc tgatagcaac | 1860 |
| tgctcactga caaatggtat ggaagaatca gataataaag catttgacga aaccagtgag | 1920 |
| gctgaattaa ggaagctgat gacagaagat gctttctgtc gcttaaagag tttggaagct | 1980 |
| ggccttcatc aaaagtccct tgaagagctc acaaagatgg cccataagtt ttatgatgat | 2040 |
| actgcactcc cgaagctggt ggccgatttt gcttctcttg agctttctcc agtggatgga | 2100 |
| agaactatga ctgatttcat gcacacaagg ggacttaata tgtgctcatt aggtcgtgtg | 2160 |
| gttgacctag cagagaagct cccacacatc cagtcaatat gcatacatga aatggtcatt | 2220 |
| cgatccttta gcatgtcat tcgagctgtt attgcaagtg tcgatgacat gcaaaatatg | 2280 |
| tctgctgtta tagctgagac tttgaacatt ttattgggat ctccaagatt agataatgat | 2340 |
| cttgatacag atgcccataa tgagcataac ttacgactga atggatagag agcttccta | 2400 |
| tctaaaagat actgttggaa attgaaagat gaatatgaac acttgcggaa gtccatcatt | 2460 |
| ttgagaggcc tttgcagcaa ggttggcctt gagttggttg caagagacta tgatatgaat | 2520 |
| agcccaaacc cgtttgacaa atccgatatt gtcaatatag ttcctatatg caagcatgtc | 2580 |
| gtttactcat ctattgatag taggaactta ctagaatcat cgaagatggc tttgataaaa | 2640 |
| ggaaaacttg atgatgctgt taactatgga gcaaaggcct tgtccaaagt tatagcagtt | 2700 |

```
tgtggtccat accatcggct aactgctaat gcctacagtc ttcttgctgt agttctttac   2760
catactggag attttaatca ggcaactata tatcagcaga aggcactcga catcaatgaa   2820
agggagctag gtcttgacca tcctgaaact atgaagagct atggggattt atctgttttc   2880
tactaccgtc tccaacacat tgagatggct ctgaagtatg tcaaccgcgc actttatcta   2940
cttcaatttt cttgtgggct ttcacatcca aattcagctg ccacctacat aaatgtggct   3000
atgatggaag aaggtatggg aaatgttcat gttgctctaa ggtatttgca tgaagcgctg   3060
aagtgcaaca aaagattgct tggagctgat catatacaga ctgctgcaag ctaccatgcc   3120
atagccatag ccctctccat gatggatgca tactccctaa gcgtgcaaca tgaacaaacc   3180
accttacaga tacttcagga gaaactagga gaagatgacc ttcgtactca ggatgctgct   3240
gcttggctgg agtatttcga ttcaaaagca ttagaacagc aagaggccgc tcggagaggc   3300
attccaaaac ctgattcttc tattgcaagt aaaggacatc ttagtgtatc agatctactt   3360
gactacataa gcccggacca ggaaagaaaa gagagggaca tgcaaaggaa gtgcaggcgc   3420
gcaaagaata ataccagagc ccaacaaggt gaatcagttg aagaaaagga gaacttccag   3480
gatgactcag gatctcttct tgaagcagtc aaaaatgatt tccaagaagc aaaactagaa   3540
ccgcaggctc ctgttgtatc agtagtaaca gaagaaattt gtgcagtcca tgatgagctg   3600
aagcaggtag aggctttatc acctgaagag tattctgatg agggttggca agcagctact   3660
ttaagaggga ggtctgcaaa tgtgcggaag aaaagcatcc gcagaaggcc agctcttact   3720
aaattagcag ttggtcgcat agaagatggc cgcactgctt ctgctcaaag gactgatgta   3780
cagccacaga caaaagagca taagaggaa gctacatact cccctagcca actatcattt   3840
ggcaactttt tcaacagtga caagttgaat ggtgatcccg tccttactga agacaagtct   3900
tgtaatgcta cgtccaaatc agaacagagc ataaaaccta caggaattaa caggccaact   3960
agcatagctt ccaagttggt atcatacaaa gacgtggcag cgtcaccgcc tgcacagta   4020 tggaaaccaa ttttggagca gaaggaagca aaggagaagg atactgaaga agttattgat   4080
gtaacacctt cgtccgagga agatgggaag gttacagatg aagttgagaa gtcgagtgat   4140
gagggaagca aagagattgt ctcaagtcag ccagagggag gcagtcattc agagaaagct   4200
tctgacagtg acggaagcac atctccgaac aagaaaacaa gtggaagcaa actttcagct   4260
tcagcacctc cgttcaatcc tggatcactc ttatcagttt cccatcctta cagcacagta   4320
gcaatatatg atgctagtgt tgttcttcag acaatcccaa gtcaggcaat ggagattttt   4380
cctcatgctg ttgatactag agtgcctcgt ggtcctcggt ccaccttgta ctaccgtact   4440
gggcattctt tccaaaggaa gcagggttat acacagagcc agagcaccat tgtgagaggt   4500
agcacctccc ctccagccat gaatccccat gctgctgagt tgtgcctgg aaaggctgtg   4560 caacaaacgg attttggctaa tgggaaacat gtggccgatt cagcggatca gcagttgacg   4620
ccgcagacct cagatgaagt gaaagccgat attcatgctg cagacaaggc aggccaagtg   4680
gagaagataa ctccaggtaa agggaaggaa aaccgaggga aagatgcgat gagagattcg   4740
tacaaggcag agctggcaag gcagatcctg ctcagtttca ttgtcaagtc ggtgcatgac   4800
agtttaggtt cgactcgagc tcagccagac agaaagccaa gtgcaccgga tgaaccaagt   4860
aacgaacaga gcagcaacat aaccaagccc gcttcagctc gcaaggagtt cgataaacaa   4920
cccaaggcag ctgaggtgct gaaaagcgag aaggatacag agggcttcac agtagtttca   4980
aagcgaagaa gaagcaagca acacttcatg aacccccataa atggtctcta ctctcagcag   5040
```

```
tccatctgca cttcggtcag ctga                                          5064
```

<210> SEQ ID NO 50
<211> LENGTH: 621
<212> TYPE: DNA
<213> ORGANISM: Lolium perenne

<400> SEQUENCE: 50

```
atgtcgtcgt cctcgtctcg ccctccgacg acgccgaggg gcgctgcagc ggcggcggcg    60
ggatgcgcgg acccgaacac gacgttcgtg caggccgacc cggcgaccct ccgcgcgctc   120
gtgcagaagc tgactggcgc gcctggggga gcgccggcgg cgtcggtaga aagcagcag   180
gtttctggca ctatcttccc ggcggtgccg ctgcctttga ggcggccgaa gctgcaggag   240
aggcggcgcg cggcgccggc caggctggag ctcgcgcggc cgcagccgtt ctactaccac   300
cctcatcatc acaaccacca ccaccaccac caccaccacg gcatcatgca gtactcgccg   360
gtgtcgacca tggactacgc ccacgccctg gcggcctcct cctccgcctc ttcgccgtca   420
ccatcgccgc actcgtcgtg ctcctgcggg gtggtcataa gcaaggagga ggaggagagg   480
gaggagaagg ccatcgcctc caaggccttc tacctgcact cctcgcccag gagctccgcg   540
gtcgccggag gcgactccga gaggcccaag ctgctgccgt tgttccccgt ccactcccca   600
cggagctcct ccttcgccta g                                             621
```

<210> SEQ ID NO 51
<211> LENGTH: 681
<212> TYPE: DNA
<213> ORGANISM: Lolium perenne

<400> SEQUENCE: 51

```
atgtcctcgg ctcccctcc tccggcaccg ccttcgcggt cgtctaaccc ggaggcgccg    60
ccgcgtgtcg tccgcccgcc gccgaggcgt ccccgaggg cgcccggacc gccgccgtgg   120
gctgagcggc ggccctctgt ttccgtcgac tacgaccgcg gccgccgcac cgcccgggtc   180
gaggtggacg gcgtcggcgc cgacgcgctt ccctcgcggc accgcctgcg cgtggagggg   240
agccggtggc aacgggactg gaaggtgtcc caagttgccg cgcgcgtgct cgcgctcccg   300
ccagccgacg cccatgccgt cgacgccgtg ctcaactgct gggccgggcg cttcgcgcgc   360
cgtaacttcc cgctccttat tcgtgaaatc acatttaccg ggtccttgca acacgctgta   420
catgtgttcc gctggatgaa aaatcaggag aattactgtg ctcgtaatga catttacggt   480
atgatgatac gattacatgg cagacacaat ctggttgatc aagcacgtgg cctcttcttt   540
gagatgcaag aatggcggtg cactccagat gctgacatat tcaactctct aatccatgtg   600
catgctcggg ctggtcaatg gcgctgggcc atcaacatta tggatgatat gcttcgtgct   660
gctgttagta ttgttctttg a                                             681
```

<210> SEQ ID NO 52
<211> LENGTH: 864
<212> TYPE: DNA
<213> ORGANISM: Lolium perenne

<400> SEQUENCE: 52

```
atggacaggg ggcgaggtag cgatgaaatg ataccagggg tattttttcgt cgggcatgcg    60
tgtctggagg tggccgcccc cgccggtagg acgtttgacc tggggacgcc ggatctggag   120
gctactgacc ggatcttgag gacggcgccg ccgccggaac cggaggctac cggtcggacc   180
tgcaggggcg acgccgggcc tgaagcagac gtagatgtgg ccggccgagc cctggccgtg   240
```

```
gttgagcgcg acggcgcgca cgacccggcc accggccgcg cgctcaccgg ctcctggcta    300
tgggactccg cgctcgtcct caccaaccac ctcgcctcgg ccgagcccag tcagctcctc    360
ggcgccaccg tgctcgagct cggcgcaggc acgggcctcc cgggcatcgc ggccgtcgca    420
tgcctcggcg ccgcgcgctg cgtgctcacg gacgtgcggc cgctcctgcc gggccttaga    480
gccaacgccg aggccaacgg gctcgacctc gacacggcgc aggcggacgt gcgggagctg    540
cgctgggggg aggagtatga cctggtaatg ctcgatcgtg aggtcccgtg cgtggacgtg    600
gtgctcatgt cggacgtctt ctacgacccg gaggagatgc cggcaatggc taccacgctg    660
cggcggctgt ggcgggacgg cacggtgtgt ggggcggcga gcgaggtgcg gtgcggcgtg    720
caggactgcg tggacgtgct gcgggaagaa ggcttcgacg tggccgaggt cgacagggtc    780
accaggccgc tgctgcgcgc ccctcgcag aacgccgact cgccgtgta tcgcatcgaa     840 ttacggcggt ctcgagaggg ctga                                          864

<210> SEQ ID NO 53
<211> LENGTH: 1245
<212> TYPE: DNA
<213> ORGANISM: Lolium perenne

<400> SEQUENCE: 53
atgggttcca gcctcaagta ccgcgccggg ctcgtcctca tcggcgccgt cgtgctcata     60
tgggtcacct ccgccgaggt cacgcaggag atattcgctg actacaagca accgttcgcg    120
atcacttact tcggggcctc ccttatggtc atctacattc ccttggcgtt tctgaaggat    180
ttcatataca aattgttgag aaggcattct ggaagcagca gagcgtcaaa agtcgtgagc    240
aaatcttcct ttggcggcag cgctcctctg aagaatggtg aatttgagaa gatgctggaa    300
atggaaccgc agaaaaccgt ggtcatagat tttactgatg tggacatccc tgtgctagaa    360
gaggcaaaac cgcttatttg tggaatcggt gagtttggtg atgatgttct gaaggagcaa    420 cagcttttcca ccaaggagat tgcaatttac ggattatatc tttgccccat ttggtttgtc    480
acagagtatt tatcaaatgc agcccttgca agaacaagtg ttgccagtac tacggtacta    540
tcttcaactt cgggactctt cacactcttc attagtgtgc tccttggcca agattccata    600
aatgctgcca agttattgc tgttttttgtt agcatggctg tgtagcaat gacaactatg      660 ggccagactt gggcaacaga tgaatctgaa gtaagcaatt caggaactta tcgccttgct    720
aaccatctaa ttcttaagcc ttactactgc agggccacac agaggactct tctaggtgat    780
atgtttggtc ttctgtcagc tgtgtcatat ggtctcttca ctgtgcttct caaaaagttt    840
gctggaggag aaggatctga aaaggttgat gtccaaaaac tgttcggctt tctcggactt    900 ttcactctttt gtcttctctg gtggcttgtc tggccattaa ctgcgctagg cattgagcca    960
aagtttacaa tgccccactc agctaaagtg gatgaagttg ttctggcaaa tggccttatt   1020
gggagtgtgc tatcagacta tttctgggct ctatctgttg tttggactaa tcccttggtg   1080
gccaccttag gcatgtcact cacaattcca ctagcgatgg ttgctgacat ggtcatccat   1140
ggtcgacatt attcagcagt ctacattatt ggttctctac aggtattctc tggctttgtc   1200
attgccaatc ttgccgatcg cttttcacgt tttctgggtc tatag                   1245

<210> SEQ ID NO 54
<211> LENGTH: 1749
<212> TYPE: DNA
<213> ORGANISM: Lolium perenne
```

<400> SEQUENCE: 54

```
atgaccagcc catccgcgcc gccgccctgc cctcacctcg ccgcgcaccg cctcacctcg      60
cgcccgctcc gcttccccg ccgctgcctg cgcgtgcgtc cgctcggccg ccccgagatc     120
cgccgcgacg cgcgcgaggt gccccgctgc tccccctgcg cgtcctcctc cccgcccccc     180
gcccgcctct acgcctgcct ctcctgcgcc tccgtcttct gccctcgca cgccgcctcc     240
cacgcctcct cctccccggg ccaccagatc gcggtcgacg tggaccgcgc cgagctcttc     300
tgcgccgcct gcggggacca ggtctacgac ccggacttcg accacgccgt cgtcctcgcc     360
cagtccaccg cgctcagccc cccatccacc tccaccccct cacccgctcc ccgcaagcgc     420
cgccgcgtcg actaccgcgc ctgggcgcca gatccggccg aatccgcgct ggtcagcgcg     480
gccgccgatc ccaccacttc agcgtccaca accgatccag cgggcctgcg cgggctaaac     540
aacctcggca cacctgcttc catgaactcc gtgctccagg cgctcctcca cgcgccgccg     600
ctccggaact acttcctcgg cgatcgccac aaccgattcc tctgcccgcg ccgcacgccc     660
atgaggcacc gcgcgaccga tgcggacgcc aaggccgcct gcctcgcctg cgatctcgac     720
gagatctact cggccacctt ctctggggag cgtacgccat acagccccgc caagttcctc     780
tataggtccg gatctcaagc tctatttgca ttggttcatg tcgcgctgtc atttcagcag     840
cctgctgttc tattttatgc tggctggtgg cagcatgcaa caaaccttgc aagctacgag     900
caacaggatg cacatgaatt ttttatctcc atccttgacc atattcatga aaatataaag     960
gatgatgagc acaaatcaca tgaacaaggc cacggagact gttgcattgc acaccgggtg    1020
ttttctggta tcctgagatc agatgtcatc tgcacaaatt gtgggttctc atccacaact    1080
tttgaacctt gcatggactt ctctttagac ttggatgctg gatgtaacgg ttctcgtggt    1140
gttgcaaacc caaaagcacg caatggagag aggaacttag ctggcatgaa tcccaaggta    1200
tcatcaacac tcatgagatg tttggagcgg tttaccaggg ctgagaggct agatgctgac    1260
cagaagttct tctgtgaacg ttgcaaggag aggcaagagt cccttaagca aatgtccatt    1320
cggaggcttc cactagtttc ctgctttcac atcaagagat ttgagcattc gacagttaag    1380
aagatgtcaa ggaaggttga tcactctttg cagttcccctt tttctcttga catggcacct    1440
tacctgtcat cctcaattct cagaagcaga tatgggaacc gcatatttcc atcagaatcc    1500
atagattcag aagcagtttc ggaattgtct tcagaatttg aaatatttgc ggtgatcact    1560
catagtggta agctagatgc tggccactac gtgacttatc tcaggttaaa caatcagtgg    1620
tacagatgcg atgatgcatg ggtaaccaga gttgacgagc atactgtcag gacttcccaa    1680
gcatatatgc tcttctatgt gcagaagaca ctttactata aagcttgtga aaagccagct    1740
gcagtctga                                                           1749
```

<210> SEQ ID NO 55
<211> LENGTH: 888
<212> TYPE: DNA
<213> ORGANISM: Lolium perenne

<400> SEQUENCE: 55

```
atggtccgtg ctctttcgtc cagccccgtc tcttcgttcg caaacgcact ccctggcgtc      60
cccgcccgca gatcacgcca tggattgggc cacccggaat cccagatgcc gaacatcaat     120
gacgaggacg aggacaccgg ccccttcgta cccaccgcac ctcgccatcc gcccgatcga     180
tccatgcagc cgccaactcc cctcaaatca gccccacttg gacgaggacg agggcacccc     240
atcatgcccg ccgcacctcg ccatagcccc atcatcctga gcttgacgga gagccctaac     300
```

```
ggcgagcttg aaccccgccg tcgccgatgt tctgtatccc cgcgatttcg agcaggagaa       360
gcaaaccaca ggctcacggt ggaccgggag tttgaggatc tggaggcgca ctctgggca        420 acagatttag agtccggggc tgatgaggag gatcaagatc aagccgccca ccgccggggc       480
tgttgccgct gctgcatggt tccaggttcg gcctcctcct cttgggctgc tggtgaagca       540
aaaaatagta catacggaac tggtggcttc atccttctca acacacggga cgaggttaca       600
cagccttccc atggtcttct tagcaccatt gcttacaaga ttgcccata tgtaaccacc        660 aattatgttc tcgaaagctc aattgcaatt gctggtccag tagttaagtg gttgagagac       720
agccttgaaa tcattagcgc agccgtagaa attgaaattt tggctggaag tgtgcaggat       780
tcagattcag ggttcatcgg agatggactt cttcaggatg ctaacagata caatattcag       840
gaagtcatca acaaagggaa gttacaatgt cgtttgttca gacattga                   888
```

<210> SEQ ID NO 56
<211> LENGTH: 1566
<212> TYPE: DNA
<213> ORGANISM: Lolium perenne
<220> FEATURE:
<221> NAME/KEY: misc_feature
<222> LOCATION: (1415)..(1415)
<223> OTHER INFORMATION: n is a, c, g, or t

<400> SEQUENCE: 56

```
atgaggtgtg aacttgatta ttactggtca ctgggtgaag tctctgacaa tgggggagtt        60
tcatgtgtca tctacaaagt ccaagaacac attcgcatgg ctgacaagct ctccttacgaa      120 ccttgtgtgc tatcaattgg cccttatcat catggagctc cagccctaca gaccttgcag       180
aaagacaaat ggagctattt agattttatt ctgaacttga atacagataa aaccttgcag       240
gattacctac ttgcacttga aagcctatca aaggtagcaa ggagctgcta ctcggaggat       300
atcgaaatgg acgctgagga gttcctgcaa atgcttttac tcgatgggtg ctttgtttta       360
gtagctcttg gaggaaccaa agaaattttg gcagccgcaa acatataaa gttggacaaa        420 ttgaagtctg aagatacgcc agagaacata tctaatccca acgatgcttt taatgggaca       480
gatgaaacaa ataacgaaag tatgaaccaa gaaggtggag aagatggtaa attgcaggca      540
gaacaccgca ctcaatacca agatgaattc gggcaatggt tctatagatt tttagttcat      600
gatttgttct tgttagagaa ccaaatacca ttctttattg tgaagaagat attcaatgta      660
gtcgccagtg acaacatctt ggatgattca ccgtttactc atgaaatatc gagatatgtg      720
gacgctgctt tgcggtggtt tccaaaatca attcaagagt ctgatatgcc gaaagacttc      780
gacaatttac ttcagctgtg ccacatgtac tttcggccaa gccgtacggc agaggattat      840
agctatcaat taggaaagca atatttcaac agatttttaa gtttcggcct caaatacttg      900
aaaattggac agtatcatga cgatactgaa gaatattcat catacaatct tgagatacca      960
tacttacaag atggccagca gttgagtcgc tggcgtcgag ctgcacaata ccttgaagct     1020
ggagtcaagt ttaagaaacg ggagcatgat caattgcatc ctcattcact attagacgta     1080
aaatttagca atggtacaat ggaagttcca tgtattgttc ttgatgagtt cacggggggct   1140 ctctttagga accttattgc atttgaacaa acttgtcctc agtttggaga tgactttaca     1200
gcatacattg ttttcttatc ccagctcata gtatgcctg aagatgtcac actacttgct      1260
cggagagaga tcattgtgca tcatctcgac agcgacgaaa cggtgtcaga tctgttcacc     1320
atgctcagta aggatgtggt ctttgatttt aatggtcagt attatctgaa atctttatgc     1380
```

```
cagatgatgg agacttacta ccagagtcgt ctgantaggt ggatggcatg gctttggcta    1440
aatcacttca gaaacccatg gttggtttta gctgcatttg ccacagctgt tgttctcgta    1500
tgtacagtag tacagacagt ttatggagta ctggcctaca ttcacccacc aggatccaac    1560
aagtaa                                                               1566
```

<210> SEQ ID NO 57
<211> LENGTH: 1173
<212> TYPE: DNA
<213> ORGANISM: Lolium perenne

<400> SEQUENCE: 57

```
atgggcaggc gaggcggcgt gttgtttgtg gtgggggag gagacggcgt ggcgaggagg      60
cgggatgggg aggcggcgcc gcgaggagga ggggatgggg gcgccgggga cggatgcgtg    120
ctggggaggg ggagcgatgg gtttctgcga gaggagaata gtggaggcgg gatcgctaat    180
tacatggtgg tagactacta cctgtatgac tacgagtacg ccgagccgcc gcgcgtgacc    240
agcctgcaga acgccgttcc ccagaggacc ttcagcgact cggagatga cgtctacttc     300 gtcgccgaca acggggcta cgagtccgtc gtccactacc tcgccggcca gtacctcaac    360
accgacgact ccggcaacgt cgccgacccc cgcctgcagc tcaacaaggt ggtgcgagag    420
atctcctact cctcgagcgg agtcaccgtc aagacggagg acggctcagt gtaccaggca    480
gactatcgtc atggtctctg ccagcttgcc atctcacacc caacacacca ctctgctaac    540
tactcgatca tactcttgac atttgctatg tcgatcgacc tgcaagcatg gaaaatcatc    600
gccatctacc ggttcgacat ggcagtgtac accaagatct tcctcaagtt ccctcggaag    660
ttctggccca cgggcgaagg caagcagttc ttcgtctacg ccagctccag gcgaggctac    720
tacgggatgt ggcagtcctt cgaggaggag taccgggggg ccaacgtgct cctcgtgacg    780
gtgacggacc aggagtcgcg gcggatcgag cagcagccgg acaacaccac catggcggag    840
gctgtggcgg tgctgcggag gatgttcccc gacgaggacg tccccgacgc caccgatatc    900
tacgtgccca ggtggtggtc caaccgcttc ttcaagggct cctactccaa ctggcccatc    960
ggcgtcaacc gctacgaata cgaccagctt cgggcgccgg tggggcgggt ctacttcact   1020
ggggagcaca ccagcgagca ctacaatggc tatgtccatg gaggttatct tgcaggcacg   1080
gattctgctg acattctgat gaacagtatc ttcaacaacg tggagtttaa agtccgcggc   1140
aagtaccatg accagaccgc agaggctaaa tga                                 1173
```

<210> SEQ ID NO 58
<211> LENGTH: 795
<212> TYPE: DNA
<213> ORGANISM: Lolium perenne

<400> SEQUENCE: 58

```
atggccgagg ccgacgatgc cgcggccgcc cgccgacgca ccgtggtcac cgactaccgc     60
aacaagctcc tgaactgccg cgagctggag acgagggtcc gcacagaatt agaacttgac    120
agaggaaaga gagtgactac cccagtatct cgatcagcta gggagaacct aaaaaaggca    180
aagaaagatt atgataaaac agaagatgac ttgaagtctt tgcagagtgt gggccaaatc    240
attggtgaag tacttcggcc attggacact gaaagattta tcgtcaaagc cagcagtggg    300
ccacgttatg tggttggctg cagaagcaaa gttgacaaag aaaagctgac agctggaacg    360
cgggttgttc ttgacatgac aactttaacc attatgcgca ctctaccacg cgagattgtt    420
tcaagtgcta tcattgacaa atatattggt gaaagtgccc gtcttataag agaaatgttc    480
```

| | |
|---|---|
| aactatgcac gcgagcatca agtcaagatg attatggcga ccaaccgtcc tgatgtcttg | 540 |
| gatcctgcac tccttcgtcc tggacgcttg gaccggaaga tagaaattcc attgccaaat | 600 |
| gagcagtcga ggatggaggg cttcaacggt gccgatttgc gcaatgtctg cactgaagct | 660 |
| ggcatggctg ccattcgagc agagcgtgac tacgtcatcc atgaagactt catgaaggcg | 720 |
| gcggtgcgaa agctgaatga tgccaagaag ctcgagtcta gcgcccacta cagcgcagac | 780 |
| tttggcaagg aataa | 795 |

<210> SEQ ID NO 59
<211> LENGTH: 3264
<212> TYPE: DNA
<213> ORGANISM: Lolium perenne

<400> SEQUENCE: 59

| | |
|---|---|
| atgacaaagc tcaagagcgt ggcgtccacg gtggggcgg cggaggagtg cgcggggagc | 60 |
| gctcggcaga ttgccccgtc gccgatgaag ctgctggtgc gcgtcgtgga ggcgcggggc | 120 |
| ctgctggcgg tgcacgtcaa cggcaccagc gaccccttcg tcaagctgca gctcggcaag | 180 |
| cgccgggcca agaccgccgt cgtcaagaag aacctcgccc cgtctgggga cgaggagttc | 240 |
| agcttcctcg tcggcgacgt caccgaggag ctcgccgtat ccgtgctcaa cgaggacaag | 300 |
| tacttcagca acgaccacct cggaagggtc aaggtgcccc tctcccaggt catggacacc | 360 |
| gacggcctct ccctcggcac cgcatggtac cagctccagc caaagagcag caagtccaag | 420 |
| aggaaatgcc gcggggaaat ctgcttgcgc atatccttgt ctacacgaac gcacgtgtcc | 480 |
| gaagaactgc accctctacc gcgcccact tcggacggcg tatcatccag ttcagacagg | 540 |
| tcaatcggga ccaagcgtgg agctctgtca accaccaaca gctacattga cctctcagcc | 600 |
| gtggccagct tggaccgagg atcgcagagc agcttcgaac ggtcggcgga tagcttcgtg | 660 |
| gagcagccgc ccaggagcag catcgaacaa gcagtcaccg agcctggaac ggccgctgaa | 720 |
| actgatgcga tggccaacac gtcgtcgatg gtagaggtct tgtctcgcta tttctttcgg | 780 |
| aaacctgtcg acgccgctgt ggctgcagtt gtctctgatg ccgagtcggt ggtggatcag | 840 |
| tccccggagc cgaaagcgtg ctctgaagaa cgtgaaggtc ctgagaatcg cacgccacct | 900 |
| gagtcgagcc ttgatgagct actgaaaaat atggagtcca agatcaagg cgctgaaatg | 960 |
| ccagctaaac tgtctaatgg cgttctggtt gacgaatctt atgttactgc accagccgga | 1020 |
| ctgaatacgc tcttgttttc tccaaattca gatttctggc cggctgtagc agagcttcaa | 1080 |
| ggaacaagtg gatttcagat tgaatcgtgg aagatcgata gcaacgatgg ttgtttgcga | 1140 |
| agaacattaa gttacataaa agctgcgagt aagctggtta agcttgcaa ggccacagaa | 1200 |
| gagcagaaat acttgaaagc agctgggaat tcttttgctg ttttgtctat tgttagcact | 1260 |
| cctgatgttc cttgtggaac ttgtttcaag atagagatat tgtactctat aacgccaggt | 1320 |
| ccccagttat catctgaaga gcaaacggca caccttactg taagttggcg gatcaacttt | 1380 |
| gttcagagca caatgataaa aggaatgatt gaaaatgggg caaaacaagg catgtcagaa | 1440 |
| ggttatgcac aattttctga agtactgtcc caaaagttta agtagctga gcttgatgat | 1500 |
| gctaatgcaa gcaaagcaaa gattttggct tcactgcata cacaaaaaga accgagctgg | 1560 |
| aggctgattg tccgcttcct tgggaacttc acattcatag tctctgttat cgtagggata | 1620 |
| tatattatag cacaccttca tttgtcaaag cccaaagcga tgaatgggct tgagtatttt | 1680 |
| ggcattgacc ttcccgattc aattggagag gtcgtggttt gtgctgtgtt gatccttcag | 1740 |

```
ggacagaata tcatgaaagt aatgaagcgc ttttcgaatg catggaaaca aagaggtagt    1800
gatcatggag tcaaagctca tggagatggt tggatactga ctgttgcact tattgagggc    1860
agtggtatag tagctggtga ttcctctggc ttatttgatc tttatgctgt ttttacttgc    1920
aatgcgaaga ggaaaacaag ctcaattaaa ttccacacct ctgatccaaa atggaatgag    1980
atattcgaat tgatgcaat ggatgatcca ccatcaagga tggatgtggc tattcatgat    2040
tctaatcgat ccgatggaga tcccattggt cacgctgaag tgaactttct gacaagcagt    2100
ttgtcagatt taactgacat atgggttcct cttgatggga agtgtgatcc agcaagcaac    2160
cctaagctac acttaagaat cttttttgaac aactcaagag gaactgaagt tgtcatgaat    2220
tacctgtcaa agatggggaa agaagtcggt aagaagataa atttgcggtc agcacaaaca    2280
aattcagcat tccggaagct ttttaacctc cctccagaag agtttctcat tgatgatttc    2340
acctgccatc taaaacggaa gatgccactg caggttatcc ctcctacact gtcaattggc    2400
agcccatcct tgatggtcat cctgagaaag gatagagggt cagaagcaaa acatggtgcc    2460
aagggaaccg ataacaatgg aagattgaag ttccattttc agtcctttgt ttcgttcggt    2520
gatgctcaca gaataattat ggggatttgg aaaatgcggt caccgggtcc agaacagaag    2580
ggggagataa tggaggagtc tgaactgaaa gaactcccgg ccgaagaatc agggtcctta    2640
tttagccatg aagatgtcaa aatgtctgaa atattctcat cagttctctc tgtggacaaa    2700
tatataccag cggcaaatca aatcaactac aagtttgaca aagcattgtc tcgatctgga    2760
ggagaagcaa gcaccactca acagaagtat gccctagtga accaagatgg gtgggccatt    2820
gaagaggtga tgacactcca aggtgttcta cttggggact actttagttt tgacaaacca    2880
ttctcaagat atggaggaga agcaaccacc actcagcaga cgtatgctct agtgaaccaa    2940
gacggctggg ccattgaaga ggtgatgacc ctccaaggtg ttctacttgg ggactgcttc    3000
actctccagc tccagctgaa gtatcatatg gcgaacgtac cgccaaaacc aaacacctgc    3060
agtgtgcagg ttttgttggg gattgcctgg ttaaagagca ccaagcaaca aaagaaggtc    3120
acaaaaaata tcatgtcgaa tacctctaat agattgaagg agctattttc tgaagtcgaa    3180
aaggatctta cgtcaagaaa cggtacccctt tttagcgcat ctattgatcc ttaccgttct    3240
ttacatgatc ctaatatcac gtaa                                           3264
```

<210> SEQ ID NO 60
<211> LENGTH: 819
<212> TYPE: DNA
<213> ORGANISM: Lolium perenne

<400> SEQUENCE: 60

```
atggcggcca tcaccaccac aaccgcgccc tcctccttcc gcatctcctc ctcaccacca     60
ccaacaacct ctaccccccg tagcaacctc accttccacg cgcgcaaccg ctgccactcc    120
aggctcgcct gccgtgccac cgatgtgtcc ggggccgagc cctccgcgcc gcccgaggcc    180
ggaggcggcc gcacctgggt accggtcgtg ccgctcgcgg cgctcccgcg cggggagcgc    240
cgggtgatcg tgcaggacgg ggacgagatc ctgcttctct ggtacaaaga tgaagtcttc    300
gccatcgaga accgctcccc ggccgagggc gcatactcgg agggcctcct caacgccaag    360
ctcacgcagg acggttgcat catgtgccca tcaacagata gtacatttga tcttcgcact    420
ggggaaataa aagaatggta ccccaaaaac cctgttttaa gggctctaac acctgttctg    480
cgaaaactat tcgtctaccc tgcgaaaacc gatggagaaa atatatacat cagcattagg    540
ggagatggtg cctctgttgg atcagctgag attttgttca gtgggaaagc tcaacctggc    600
```

```
agtacagcat ctgatgttaa catcgaagag gtgagaatgg tagttgatga aggtgttgga    660
ggttttggtt tcaccccta caatgaactt atcaacggaa gagctgccat aattggcttt     720
ctattgctga tagattttga acttttaact ggtaaaggcc ttctcagggg aactggtttg    780
ttggacttca tctatgcaat ttcaagagct ttcagctga                           819

<210> SEQ ID NO 61
<211> LENGTH: 3045
<212> TYPE: DNA
<213> ORGANISM: Lolium perenne

<400> SEQUENCE: 61
atgggtagcc tctcgccatg gggacagttc tccctggtcc catttctact gttacagttc     60
atgcttcacg tgtcctatgg ctgctccgtg gaggagaggg ctgccctact ggagatccgg    120
tcttctctga tgagagcgca ctccctggag gtgcctgatt catggaggaa ggatgatcat    180
gattgctgct cgtggaagca tgtcaaatgc aacaataaaa cacagcgagt gtcccatctt    240 gaccttcct ccgtatatgc aacaacagag ggagatggcc attggttttt gaactcgact     300
gtgttttctg tattccatga gcttcagtac ctagatctat catacaattc cccttgttcc    360
ttaagcttga aaggattagt tgggttagcc aagcttcgat atctcgacct cagtggcact    420
atgtggggag tgggtttccc agaatttatc ggagaaattg tttcactgga agtattagcg    480
ctcaacgata acaacatcac cggaggtctt cccggcacag ctgttaaaaa tcttaggaac    540
ttgcgacaat tgaatatgac ttcgaatagc tgcgatggaa acctcccgga atcactattt    600
tcacttcctc acctaaagat cctagatctc tcagcaaata tctttggtgg gcatattcca    660
attagctcag cgtcacaacc aatttcactt gaagtcttgg atcttagctc taatcacctc    720
aatggaactc tacctgttgc tgcctttcaa aacatcagga acttgaattt gtctggcaac    780
cagttcagag gatctctcca tgtatcatta tttgcacttc ctcatctgaa gttcctagat    840
ctctcataca ataattttga gggacgtttt cctgttagtt tgtctccaga accagttcca    900
cttgaagtat aaatctcca ttataataac atgagtgggg ctcttccgtc tgaacaagca    960
tttgaaaatt tcaagaaact acgagggttg tatttgagtt ccaaccaatt cagcggaaac   1020
attccagcat tcttgtttta tcttccacat attgaacggt tgaatctctc aacaaatatc   1080
ttcagcggac caattccgat aaatccatct ttgaatcttc cattgtcgct taagagtctg   1140
cggttttccc aaaacaattt gagtggtagg atttctttca tttggcttgg aaacctgaca   1200
aaactagaag tgatagacct ttcaggcaat gctaacctag ttgttgatgt caatattcct   1260
ggatggacac ctcagttcca gttgaaacag ctattactct ctggttgtga tcttgacaag   1320
agcattattg cagaaccacg ttttttacac acacagcatc atctagaggt ggttgattta   1380
tccaacaata acttgtcagg tagcatgccg aattggctgt ttacaaagga agcaacacta   1440
cagtatctaa atcttggaaa taactcgcta actggattgt tggacccaat atggcatacc   1500
caatcttttc tctatgttat caacatacac atgaaccata ttgcaggaca gctgccggct   1560
aacatcagct caatgtttcc atgtttgtct gttctggatt tttctaataa taacctcctt   1620
gggcacatac catcttcact gtgcgagatc agcttaatgc aacatttaga cctatcgaac   1680
aacaaacttt ctggggaagt tcctgcttgt gtgttcacta attatcccat gctaatgacc   1740
ttgaaggtat caaacaacaa gcttggtggt gtgattttg gtgggatgaa taatctgtcc   1800
attatgtcag aattgtgcct ggacggtaac aaatttgaag gacaatatc tcatgatctg   1860
```

```
tcaggggttt tagaaatcat ggatttgcat gataacgagc tgtctggcag acttgatacg    1920
tcattgtgga atctgtcttc tttggtggtc ctgaatcttt caggcaaccg tctgaccggc    1980
aaaatttatc ctcaaatttg tggcttggca ggaattcgac ttttagatct atctagcaac    2040
aaccttgcag gatctgtgcc aaactgtagc tttctattgc tcaattttct taacttgtct    2100
ggaaactcct tatctggcga tatctcgtat tccttttttca acacatcaag tctggttgct    2160
ttggatataa gacacaatca gttcacgggc aaccttcact gggtacgcta tgttggtaac    2220
accaggctac ttttcttgag tggaaacaag tttgaagggc agatcagtcc aaacctgtgc    2280
aaactcctgt acttgaggat aattgatttg tcacataaca gctttcagg ttcattacca    2340 gcatgtattg gtaatatctc tttcaaaggc gagacagatg atcagatttt tcagccagtc    2400
cacaggttta tatcgtactt ctacagaaat ttctatgccc cccaaaagta tagtaattcc    2460
tatgacttca aaagcttcgc ctttgctaca aaagggaatc tgtacatata tggtcgcagt    2520
ttctttcttt cgatgtctgg catcgacctg tctgcaaaca tgctggatgg agaaaattcct    2580 tgggagctag gaaatctaag ccgtatcaaa tcccttaacc tgtcatacaa tttctttgtt    2640
ggccctatcc cagcaacctt cggtggcatg aaggagatag aaagcttgga cctctcccac    2700
aatgagttga gcggactgat acctcagcag ctaacccagt tatcatcatt aggggtcttc    2760
tccgtggcat acaacaactt gtcaggatgc ataccgaact ctggtcagct cgggtcgttc    2820
ggcatacaga gctacctagc aaacaccaac cttcacaaga tcacacatgg caacatgtgc    2880
actgctcccg gtctagatcc agcgccggag gaagatgtgg gagagatgtt tggtgatccg    2940
gtgctatacg tggtcaccgc tgccacgttt gtgttggcat tttgggccac cattggattc    3000
tcattttgcc atccctacgg aaggtctgta atgctcaagc tgtag                   3045
```

<210> SEQ ID NO 62  
<211> LENGTH: 2022  
<212> TYPE: DNA  
<213> ORGANISM: Lolium perenne

<400> SEQUENCE: 62

```
atgaagaagc taggaggtgg aggcatacca caagatgcag gtttatcaga ttttctgaag      60
aacaggctac agaagatacc aaggatttct gccccactc agcttttctt gggtccgccc     120
ctgcatagaa gtagaaccgt agaaacacca tgtggaggca aaatccctc atcagaggag     180 ttttccttga ttttacccct tcttgctgtc tcgcgtctgt cccgtacgaa ctctctacga     240
acagagtccg tcgagtcacc tgtgcccgac gccttcgccg cctcccccac cgccgacgcc     300
gacgaagtcg gaaccagcag ctccaccgcc ggcggcggcg caaccgcatc aaatcccatc     360
tccccgcgct ccagcaaccc tctcccctcc accacctccg ccacaacccc tctcgagctg     420
cccggcgtac ccccgccgc gtccgcacga aaccctaaga tccaccacac ccgcggcgtc     480
ctccacctct accgctcctc cccctcccctg cccgcttcat cctacgcctc cgccgtcgcc     540
gtcgccgcca cccctcctc ttcctcctcc gggcccaccg ccccaccgct ccaatgcgac     600
tcgctgctcc cgtcatggcg cggcacgcgc ctccttgtgc tcgccgtccc tacccgcgtc     660
tcgccggagg acttcgtccg ctttttgcgg ccctacgttg agcacgcctc cgagatccgt     720
gtcatcagcg acgatggggt ggaggaccgg tacagcgtgc ttgtggagtt tgaggatcaa     780
aagagtgccg acggattcta cctggaccte aatggctgga ggttctcgtc ctcagaggtt     840
gtaatattgc caatttggtg ccagttggta gaggtgtgcc atgttctgtt tatagttgct     900
gtgcaataca tgccatccgc tgtgccacca gttggatcta ctgagcttcc gacatgtcct     960
```

```
gtttgcattg aaaggttgga tcaagacatc agtggaattg tggcaaccaa ttgtgaccat    1020
tctttccagt gttcatgcgt ttcaatgtgg gtcagttcat cttgtccggt ttgtcagttt    1080
tgtcagaagc agtctgaaac tcctacaaat cctacatgtt ctgtttgtca gacctctgaa    1140
aacctctgga tctgtgtgat atgtggtttt gttggatgcg gaaggtataa agaaggccac    1200
tcaattaggc actggaaaga cactcagcac tgctattctc ttgatttgga aactcaacgt    1260
gtttgggatt atgtcggtga cagttatgtt catcgtctta atcactcgaa aagcgatgca    1320
aaacattcta agctcaggtc aaagtgtgaa ttttctgggg acaacgatga cttggatatg    1380
ggtggagtta tgtttagcag caaaactgat acaatcgtgg atgaatacaa ccgtcttctt    1440
gcaagccaac ttgaaactca gagagagtat tacgaggctc ttctgtcaga cgctaagaaa    1500
gatagggaac acatttctgt tgctgtggat aaagctgtaa atgataagct tcaagagatg    1560
caacttaagc ttgaaaatac tatgttggag aaaagaaag ttgcagaaat gaatgaaaaa    1620
ctcatgaaga gccaggatat atggtccaag acagtaaaag gaatagagga aagggagaga    1680
gcgcagttga ggctgaagga tgatacaatt cttgacctgg aagaacagat taaagacttc    1740
aagtactcga ttaagttgca aaaatcgata gagaagagta cacatgctga tgatctcaaa    1800
ggaggtatgc tggtgccact ggccatggaa tcagaatctg gaaagggtgc agagtttgag    1860
cattatgtca acatgtgtaa aaaagatcat gaggcaccat accaaaaaaa tttattacca    1920
tctaggaaaa actctgactc aatggaaaaa ttactcatcc caccaaaaac cacaccacca    1980
agcttgttgt tgatacccct caaggtcaag agcatgggat aa                      2022

<210> SEQ ID NO 63
<211> LENGTH: 615
<212> TYPE: DNA
<213> ORGANISM: Lolium perenne

<400> SEQUENCE: 63
atgtcgaagc tgaccgtggg ggtgtgcatc atggtggcgc tcagcctggc cgtcttcctc     60
accatcgtcg tcctcctcct ggccgacctc ttctgctccc acctccgcct ccgccgcctc    120
cgcgctgacg ccgagatggc gccgcacaag aggccgaagc ttggcgtccc ggcgtcgtcc    180
ccgccgcaca ccgccgacga cgcgtcggtg gccaccacca ccaccacggc gacgcacgag    240
gcgctctcca gcaccccgcc cttctactac gcgcacggcg tcatgtgcgc gcccacccgc    300
aaggacctcc tcctcgccat ccccaagctg gaggccgccg tgtggaagtg gtctcccgcg    360
cgccgctcct cgccgtcgcc ttcgccgccg cggtccgagc ccaccgcccg cgagtcctcc    420
tcctccgcgt acagcgacgg cttcctgcgc atctccaacc ccgtgtacga gcgggcgcc    480 acggccgcgc cggcgggta cgaagaagac acgccgttcg acacgcctga cgcatcgccg    540
tccccgaatg ggattacaga ggaagagggg gcttttggac gtgtcaacca cacgcatcag    600
ggagcccgat catga                                                    615

<210> SEQ ID NO 64
<211> LENGTH: 579
<212> TYPE: DNA
<213> ORGANISM: Lolium perenne

<400> SEQUENCE: 64 atgagggat ctctcagtta ccaggtgtcc atctccgggc acagccgcgg cggcaaggtg     60
gccttcgcgc tcgcgctggg ccacgccaag acctccctgc cactcgcggc cctgatcgcc    120
```

| | |
|---|---|
| gtcgaccccg tggacggcac cggcctcggc aaccagacgc ccccgcccat cctcacctac | 180 |
| aaagaaaccc cgctgcacgt cccggcgccc atcatggtca tcggcacggg cctcggcgag | 240 |
| gtgccccgca acttcctgtg cccgccgtgc gcgccgctgg gcgtgagcca tgccgcgttc | 300 |
| taccgcgagt gcgcggcgcc ggcgtgccac ctcgtggcca gggactacgg gcacaccgac | 360 |
| atgatggacg acgtgacgac cggcgccaag ggcctggcga cgcgcgccgt ctgcaagagc | 420 |
| ggcgaggcca gggagcccat gaggcggttc gtcggcgggg ccatggtggc gttcctcaag | 480 |
| aaatgggtgg agggccggcc agagtggttg acggcatca gggagcggcc ggaggtggcg | 540 |
| cccgtggtgc tgtccgtcgt tgagttccgc gatgaatag | 579 |

<210> SEQ ID NO 65
<211> LENGTH: 243
<212> TYPE: DNA
<213> ORGANISM: Lolium perenne

<400> SEQUENCE: 65

| | |
|---|---|
| gagcgaactc agtataggaa cccatcctgt tctaatagtt ggaaacgccc gccagtggaa | 60 |
| gaggttttct gcaaattagt aacacactat gctagagttc actcaaggca atgcttagat | 120 |
| gaagctgaag tagcagagca tgttgttggc cttacatcca gtcttgcaaa ttgcaaattc | 180 |
| agttactctg tcccgtcatt gctatttaga catttaaacc atttctatca cagtagggta | 240 |
| taa | 243 |

<210> SEQ ID NO 66
<211> LENGTH: 306
<212> TYPE: DNA
<213> ORGANISM: Lolium perenne

<400> SEQUENCE: 66

| | |
|---|---|
| atggcgttca agaaggtgca gatggcggac aagtacccca agggccagtc ccgtggccgc | 60 |
| cagtggaagc acctgcgctt cctcctccag gccgccgacg ccacctcgct tcccccggac | 120 |
| cgccccaact atctaaatat tcagtcaccg ccatccattt atccaccaaa gagatactgt | 180 |
| gacgtaacag gttttgaggg gtgtatttta ggtaccaagg ggattcagga tgggagggga | 240 |
| tttgttgaat tcctcctctt cacccaatcc cctctatata aatgtggttt ggtaatcagg | 300 |
| gattaa | 306 |

<210> SEQ ID NO 67
<211> LENGTH: 5946
<212> TYPE: DNA
<213> ORGANISM: Lolium perenne

<400> SEQUENCE: 67

| | |
|---|---|
| atggctttgg agaaagaaag catcagaaag gacagtttta gcaaagaaca aatccaatat | 60 |
| actagagagg gaacaggagg tacaccatct acacatttag atttacaagc tcatttggag | 120 |
| aagattgcac gattggagag atccttgcaa ggtttacaag aacaactttc atttgctcag | 180 |
| gctgaatgct ttgacaaaga tgttattta gccaagcaag caaaagtagc tgaagaagcc | 240 |
| atactaggct gggagaaagc agaagcagaa gctatagcta ccaagacaga acttgatgac | 300 |
| actctacacc agaaagccac agttgagcaa aggatttgtc agcttgatga ggctctaaat | 360 |
| gttacaatgg tagagaggga gttattgata aaggatactg ctaaaataat ttcttgtgag | 420 |
| aaggataaag ttcataagct ggaagaaaat ttagaagaga acaaaacat aattgctagt | 480 |
| ttggacgatg agtatagcag actatctgaa atcctcttag caaaagagaa agtcatctta | 540 |

```
gatctaactg aattaaatgc agtgaaagag tcagacttaa aggaccttgt ggtaaagcta      600
gagtcaacag agagatcaaa ttcttctctt agatatgagg tttgtatgct gcagaagcaa      660
cttgatattc gaagtgagga aaggaagtgc aatctcaaat cagctgatgc ttcacacaag      720
caacatctcg aaaatgtaag gaagattacg aagctagaag aagaatgcaa gagattgcgt      780
tcaatggtac gtaaaaggct accaggacca gctgccattg caaaaatgag aagtgaagtt      840
gaaacactgg gcaacaatat agctcagaca aggatgggga gttaaaattc tccggcatca      900
tccaattcat atgatccggt acagaatttt tctgacgcat cacattcaag ttcttctttg      960
cttgcaaggc tacatgtgat ggaagatcaa aataaatcca tgaaggaatc actttctaga     1020
aaggatggtg aacttcaatt ttctcgtact atgcttgctc gtgcaaactc taaactttcc     1080
caagttgaag ctcaacttga agaattatca ggcgatcagg ctgccacaga actggtaaaa     1140
agaagtcctg cactggctga aaccctctt tcatctatct ctgaaaatgg ttgcaatgaa      1200
gataacgtca gctgttcagg ttcatgggcg tcagccttaa tttctgaact tgaacatttc     1260
aagaagggga agctgaccac accttcttgt cagagcacag gagtatcaga catgagtttc     1320
atggatgact tgaagaaat agaaaggcta gcgatggtat gtgacaataa accttcaaaa      1380
ttgtatgatg caaagagaga ggcaatagaa tcagcaggca aagagctggt tccagttgat     1440
ggtccgaatg aaacaaacga tcaagttcat caatacaaga ttcagaaggg actcgttaag     1500
ttaattgaac ttgtcgaggg agttattcag agatcgtcaa aggatcacaa tagcaaattc     1560
gtgcaatctg gtgacaacat gggtgatcag tccacagcta tagatggtta ttttgctcat     1620
gcgttcttgt ggaaaacatc agaacttact tgtgtactgc gacatttcat tgttgtatgc     1680
aatgagctca tgtatgggaa taccgatgcc gaaagatttg ttcttgaagt gaacctcaca     1740
ctggattgga taatcaacca ctgcttttcg ctccaagatg taccagacat gagggaaact     1800
atcataaatc atttggagtt agatagcagc gacgggcttg acgccgttgc agccaagcaa     1860
atagcaatcc aaaccacaaa gggcgtacat gaacccagca ccccaaatag cgtgcagatg     1920
tcactaattt ctgttttcaag ccacgtggat attggactta aagctgataa tgacacgcgc     1980
agtataacga atgaagtgcc agtctctaat ccccacgaat ggaaggaaa atcttcaagt     2040 ttgcgagcag aacttaatgc attgaaggaa acaggaaaaa taatgcaca agtgttaac      2100 tgtgaatcaa cagtgagtga cctgacaaa cacaaaccca tctgtaactc tgaggaagga     2160
aagccatatt ttgaattcac cattattcta caacccgtag gcattgacaa gttaatacct     2220
tgtcaattgg cgccgtttgt gggaactaga ggcgtcaagg atccgatctc gatggcacgt     2280
ttaagatcgt cgacttcatc aaccgcaagc aacgcgatgg atcgaggtaa acagatcgca     2340
actggtcttg tcgattttgt tcctcacccg ccctcccgtt tggatgcata tgcgtatctg     2400
gaggagccta tggagatgac gttcggaaga tttcactttc gcgtcgagaa agagggatcg     2460
tatcgtgtcg aaattccgat ttcgtcggga tcgtcggcgg tcgattccga ttttccaagc     2520
tatacatcgt caaccgaatc aggagaggaa gaaacttcat cgtcacgctt catcagcacc     2580
agggcaagag aaaaacttgc caagatcttc agcgacatgt cgtttgagtc atctgcggac     2640
tcctatataa gcgatggctc aagcagtgtc aacagctacg acttcatcga caatctcact     2700
acagtgggca aggtcttcgc caatcttcat gatggtgtca ccaaacccaa catgatctg      2760 aatacaaagt atcatcatat ttatgtcatc ggagagccaa gtcgtgatca ggaggaaaca     2820
tctgaggctt tcgatgattt gggaaatcca tacgtcgatc cctctgattt gcgacgaggc     2880
```

```
ctaggcaata aatatatcgg gccacagccg cgagacagag tccaacttcc gcaagcagca   2940
tgggatagag ccgcaagggc tatggatggc tcagaaccaa tggccaccac agccacgcca   3000
gaagaattac aagcatatca atataggctc gcacgagctg caagggaatt ggaaaaacag   3060
acagctgaat taaacagaag aaaggaggca gcctctgcat caaacaagac cttgctggat   3120
acttcttgtt ctggatcatt tacacgcaac aaagaagagt ttaaaaggga ccttcttgat   3180
cggatccaag aaaatactga aggttgggag aacgacaagg atagagaatc aggttttatg   3240
gatactgata aatttcgtaa tatgagtgct acatatggtc ttgattctca agttgctgca   3300
aatctttata aagcttttgc ctctcattat gaattgccta agaagaattt tgataagtat   3360
catgaaccgt ataaagataa aattgattca tctattaata aatgcgttgt agttgaaact   3420
gctgatcatg ttattcctga agcttatatt gaaaaaactc cttccctgc taaaatgaag   3480
gagtactctg ttataaatag tgcggttcat aaaagtgaaa agaaacctgt agaacctgaa   3540
gaacaaataa aagttgaacc tgctgttgca atagttaaag atcttgtgac tgaaaatgtg   3600
gaggatggtc atattatttt ctgtgaagat gcttctaata ttgtttcaca tcctaataaa   3660
cccaaacaag ttagtgttcc tatgctatct gttagaattg gtgatcattg ctattatggt   3720
ttatgtgata ttggtgcaag tgttagtgct attccttatg agctttacac ggagattatg   3780
cacgaaattg attcttgtga acttgaagat attgatgtgg ttattcagct ggctaataga   3840
gaaactattt ctccaattgg tattgttcga gatgtagaag ttctatgtgg taagattaaa   3900
tatcctgctg acttttttggt acttggttct gctgctagtg attattgtcc tatcattttt   3960
ggtagacctt ttctaaatac ttgtggagct attatagatt gcaagaaaga gaaaattttg   4020
actaaatttg ctggtgaatc ttatgagttt aacttctcta aatttaccaa aactccttat   4080
aaagctgatt tgcctagtga tgattttaaa atggagcagt gtgcatctat tattcttgtt   4140
cctaataatc ctttgcagca acatttggag aatagcgaga gtgaagtttt taggaaagaa   4200
agagatgagc ttgaggaaat ttttcttcgc caacctattc tcaagcatga tttaccggtg   4260
gaagatttgg gtacaacacc gccaccaaag gaagatcctg tttttgattt aaagcctta   4320
cctgataatc ttaaatatgc tcatattgat gataagaaaa tatatcctgt tattattagt   4380
tctaagcttt cagagattga ggaagaaagg ttattggaaa tattgaagaa acaccgagga   4440
gctattggct atactcttga tgatttgaag gggattctc cttctatttg ccaacatgct   4500
attaatatgg aagatgatgc aaagcctgtt gttgaacatc agcgtcgtct aattccgaag   4560
atgaaggagg tggtaaggaa tgaggtatta aaacttcttg aagctggtat tatatatcct   4620
attgctgata gtagatgggt tagtcctgtg cattgcgttc ccaagaaagg aggaatgact   4680
gttgtgccta atgataatga tgagctcatc cctcaaagag tagttgtagg ttgcttgcga   4740
aaccttgata aagttttgca gagatgtgaa gaaactaacc ttgttcttaa ttgtgagaaa   4800
tgccactta tggttaatga aggaattgta ttgggacata aaattctga gagagctatt   4860
gaagttgata gagctaaagt tgaagcaatt gagaagatgc cctatccgag ggatgttaaa   4920
ggtattcgta gtgttcttgg tcatgctgag ttttataggagatttattaa agatttctcc   4980
aagatttcaa agcctcttac taatcttctt caaaaaggcg taccttttgt ttttgatgat   5040
gattgtaagg aagcttttga aactctaaaa aaagccttaa caactgctcc tatagttgaa   5100
cctcctgatt ggaatttgcc ttttgaaatt atgtgtgatg ctagtgattt tgctgtaggc   5160
gctgttcttg gacagcgagt agataaaaaa ctgaatgtta ttcattatgc tagtaaaact   5220
cttgatgctg ctcaaagaaa ttatgctaca actgaaaaag aattattagc tgtagtcttt   5280
```

```
gcttgtgata aatttagatc ttatattgtt gattcaaaag ttacgattca tactgatcat     5340
gctgcaatta gataccttat gacaaagaaa gatgctaagc cgaggcttat tagatgggta     5400
cttcttttgc aagaatttga tttacatatt gtagatagga aaggtgctga taatcctgtt     5460
gctgataatt tgtctagatt ggaaaatatt gcttatgatc ctgttcctgt taatgatagt     5520
tttccaaata aacaattggc tgtaataaag gtgagctcgc gagacagtcc ttggtatgct     5580
gattatgcta actttattgt ttccaagtac ttgcctccaa cctttttcagc tcagcaaagg     5640 aggaaattct tttatgactt gaggcattat ttctgggatg acccacactt atataaagaa     5700
ggagtggatg gtattctgcg aagtagtcgt ctcagggtag gactgtttat gcatgtcatc     5760
atggtgaagt ggacggatcg atcggcaatg ttgcgagctg atcggcggtc aagagaaacc     5820
actagttgcg agtacatgtt gtattcagtc aagtcctaca ctagtttgag tccaccgtca     5880
gtgcatgtag ctaaggatct atacgttggg cgagccgaga gactagcgct atatgagctg     5940
agttag                                                                5946

<210> SEQ ID NO 68
<211> LENGTH: 1536
<212> TYPE: DNA
<213> ORGANISM: Lolium perenne

<400> SEQUENCE: 68
atggacatgg atagaataag atacactaat aatattgatg atggtgggga gatcaaagca       60
ccaataccat atgacgagca gccagagtcg ttcccttctt tgaatgcttc cttgggtaat      120
tttccactaa tgccagagga cattgatcaa agatcaggca gttctctgga tggccgtcgt      180
ttagcgtgca agaggaaaac cattgaggga gcccatggga tattttcagc aggtgctagc      240
actagttttt cccacagaaa tgataatgtc ttccataaca ttccttcaac aagtttcagt      300
cctgctccta ccatgaatgt gccctctcat aatttttgt tacctccaag ttctatcgag      360
gaacaactcc cccactatgg agcaactaca ggactgccat ctagtagcta caatcatcct      420
agtggaggca attataattc tggaaactca caaagaagtt tccgggtaag aactaccacc      480
gctcagcagg ttaacccata cggtgtatgg ccttcttcaa gtaccatgag tcattccagt      540
tcatggaacc accaggcgcc tgcccttcag agcgcgtttg atgaaatgca agagggtatt      600
cccatggtca gtggaatcaa cttgcaatac caacatcctg caaatgtagt tcctggcatt      660
ccacaaatag cacaccgttt tgcttgccat ggagcttcat catctagagc gggcagtttg      720
gataacagaa ttcttggtag tgaggacgtt actggggagga gtgttgcagc tcccaacttc      780
tctaatgcag cgcctcttgc tggaatagac atgagacctt tggttccaga accatctacc      840
tggaattctg atctccgtgg cactgccatc cctggaaatg tttcttctgt atctagagct      900
aatcctagtt caatagttaa tcgaccagca ggctcaccat ctgtcgctca tccaaccctg      960
catagacgac atcctagaaa tttatcagag gagataggtc gtctatctgg agcccttcgt     1020
ggtcagcagc aaccacgttt aaggtcgggg tttctattgg aacgtcaggg tgatggtgtt     1080
tggggtgttc cattaccaat gaggagtagt agggaaggaa gaaggttaat agagatacgg     1140
aatgcactag aaatgattca aagaggggaa aatgtcagat tgagtctat tttctatggc     1200 ggtgtcgaca ttcatgatag acacagggat atgcgtcttg acatagacaa tatgtcttat     1260
gaggagctat tagcactgga ggaaagaata ggaaatgtta gcactggcat cagcgaggac     1320
gatgtgatga agctcctgaa gcaaagaaag ttctcgtcct ggagattagc atcaatggaa     1380
```

```
tatgagccat gttgtatttg tcaggaagag tacgtcgacg gagacgatct cgggacgctc    1440
cactgtggtc acgacttcca tgcgggctgc atcaggcagt ggctggtggt gaagaacctg    1500
tgcccgattt gcaagaacac cgccttgaag acctaa                              1536

<210> SEQ ID NO 69
<211> LENGTH: 630
<212> TYPE: DNA
<213> ORGANISM: Lolium perenne

<400> SEQUENCE: 69
atggcgcctc ttgccgccgc ggccgcggcg gtggcggcga aggaggagct gggcgtgacg      60
gtggccgtgg cgccgccgat ggcgctggcc ccgctgagcc agcagcagcc gcggcggcag     120
taccgcggcg tgcgcatgcg gaagtggggc aagtgggtgg cggagatccg ggagccgcac     180
aagcgcacgc gcatctggct cggctcctac gccacgcccg tcgccgccgc gcgcgcctac     240
gacacggccg tcttctacct cgcggccgg tcggccaggc tcaacttccc cgacgagatc      300
tccgcgctgg cgccgctgtc cccgccgccc gaggagctgg aggccgacgg cggcgcgctg     360
tcggcggcgt cgatccggaa gaaggccatc gaggtcgggt cccgcgtcga cgcgctccag     420
accgggatga ccatggtcgc caccgccgcc gcgccggcga caaaccaccg ggagcggcag     480
aggcagcacc acgcgcagca gcaggctgcg cgcgacgagg agctgctcca gctccaccac     540
cagaagcagc agcggacggc gtggaacggg cgggccaaga cccggatct caaccaggcg      600 cccgaccccg acagctccga cgccgagtga                                     630

<210> SEQ ID NO 70
<211> LENGTH: 1950
<212> TYPE: DNA
<213> ORGANISM: Lolium perenne

<400> SEQUENCE: 70
atgaggaaat ctaactggtg ttggcctcgc agattttgta tgttcgttgc caagaaaaaa     60
cactgtcagg cactcaaact ggaaaatcca gctggcaatg atagccctgt ggtcctatg     120 cagggagaac atacagaaac cttcgtggcc attttcgctg cgaagaaaga acactatgtg     180
tgttcaatcg tcgtccactt tgtcgtcacc gtggtagtgc ctgcggcagg atgtgtcgtc     240
aaacaccttc acgctcatca cctcgacgcc ttggtaggag aatgtgagta cgcggctagc     300
cgacttggag gtcgtggaac cgggagaact tctcccggcc gatgtggagt ggagccagaa     360
gaggtggggg aacgaccgag acaccagaca cggcaagaac cggaggaagg cggcagctcg     420
ccagccatgt gggatctcaa tgactcgccg gccgccgacg cgccgcacgc gccgccgctc     480
tccccgtccg tcgacgactc cggcgcctcc tcctcctccg ccgccgcggt cgtcgagata     540
cacgacgacg gtgacgacgc ctccgccgcc gcagccgcgg aagagcccat gttcacccgc     600
cagttcttcc cccgccgt cccggcgac cccgccccgg caacggccg cgcggcctgg        660 ctccgcctcg ccggcgctcc ccctcccgcc gcggccgccc cttctgcggc agcacccggt     720
gccggcgcag gacccgccgc cgcagcggca tcagcagcaa acaagaagag ccggcgcggg     780
ccgaggtccc gcagctcgca gtaccgcggc gtcaccttct accgccggac gggccgctgg     840
gagtcgcaca tatgggattg tggcaagcag gtctatttgg gaggatttga cactgctcat     900
gcggcggcca gggcgtacga tcgggcggcg atcaagttcc gcggcatgga ggccgacatc     960
aatttcagcc tcgaggacta cgaggacatc aagcagatgg gcaatctgac caaggaggag    1020
ttcgtccacg tgctccggcg ccagagcacc ggcttcccgc gcggcagctc caagtacagg    1080
```

-continued

```
ggagtcaccc tccacaagtg cggcagatgg gaggccagga tgggccagtt cctcggcaag   1140
aagtacgtct acttgggcct gttcgatacc gaggaggaag ccgccaggtc ctacgaccgc   1200
gctgccatca agtgcaacgg caaggacgcc gtcacaaact tcgatcccag cacttacgcc   1260
gaggagttcg agctgcccgc ggctgcttcg acgggcgacg acggcgagca gaacctggac   1320
ctgtcgctgg gcagctcggc gggctccaac aaacggggca gcctcgacgg cggcgacgac   1380
gacggcacgg cggggtccga ccagcgcgtc cccatggcgt tcgagctcga ctggcagacg   1440
gcggcgcgga gcaccaaggc caagttcgac caaaactcga cgcatcacca gatgccccct   1500
cccgtcctgc aggcctccca cctgccgttc agcccaggc attccaagt gggtactttc   1560 gccatgccat tttcgaggga attttctcga attagcagcc tgttcttgtt cgcgagcaac   1620
ggcgatccgg ggacagcggg aggcctgtcg ctgacggtcg gtggcgccag cggcggaggc   1680
ggcgggcact ggctgcctca tcagtaccac caccagcaac cgccgcagca gcagcaacag   1740
aggctgcacc acggtggctg gggcaacggc gcgcccggca cgagctggcc gccgccgccg   1800
caaccgcacc tgccgacggc gccaccgtcc aacgctgccg tcgccgccgc ggcagctgca   1860
gcatcatcac gattcccacc ctacgtcgct acgcaagccc acagctggct gcagaagaac   1920
gggttccact ccctcgccag acccacctag                                    1950
```

<210> SEQ ID NO 71
<211> LENGTH: 270
<212> TYPE: PRT
<213> ORGANISM: Lolium perenne

<400> SEQUENCE: 71

```
Met Leu Leu Leu Ile Arg Arg Leu Thr Ala Val Pro Ser Arg Leu Ala
1               5                   10                  15

Ala Leu Ala Leu Arg Gln Pro His Gly Arg Ala Ala Thr Thr Thr Ser
                20                  25                  30

Thr Thr Pro Ala Val Ser Ser His Leu Ala Gly Ser Pro Pro Ala
            35                  40                  45

Glu Asp Pro Ala Ala Asp Pro Gly Cys Glu Ser Glu Pro Leu Asp Arg
50                  55                  60

Asp Trp Gly Ser Thr Leu Ser Arg Ala Asp Pro Ala Glu Val Ala Gly
65                  70                  75                  80

Ile Leu Arg Arg Leu His Asp Glu Thr Ile His Leu Gly Leu Gly Thr
                85                  90                  95

Tyr Asn Leu Leu Leu Glu Arg Ala Cys Glu Ala Glu Asp Phe Ala Leu
            100                 105                 110

Phe Ala Lys Val Phe Arg Tyr Leu Leu Leu Ser Lys Ala Ala Pro Asp
        115                 120                 125

Leu Thr Ser Tyr Met His Val Ala Arg Ala Ile Gly Asp Leu Asp Asp
    130                 135                 140

Pro Glu Pro Met Leu Arg Phe Val Arg Glu Val Leu Glu Val Thr Gln
145                 150                 155                 160

Gly Arg Asp Pro Thr Val Val Asn Arg Ile Val Phe Ala Thr Gly Lys
                165                 170                 175

Tyr Gly His Ile Asp Lys Ser Leu Ile Ile Phe Glu Glu Leu Lys Lys
            180                 185                 190

Asp Lys Lys Cys Leu Asp Val Val Thr Phe Asn Thr Val Leu Asp Met
        195                 200                 205

Leu Gly Lys Ala Gly Gln Ile Asp Arg Met Leu Arg Glu Val Lys Leu
```

```
            210                 215                 220
Met Glu Glu Leu Gly Ile Ser Pro Asp Ile Val Thr Tyr Asn Thr Val
225                 230                 235                 240

Ile Asn Cys Leu Arg Arg Leu Gly Arg Leu Asp Met Cys Lys Ser Phe
                245                 250                 255

Ala Thr Glu Met Val Glu Arg Gly Ile Gly Pro Asp Leu Arg
                260                 265                 270
```

<210> SEQ ID NO 72
<211> LENGTH: 385
<212> TYPE: PRT
<213> ORGANISM: Lolium perenne

<400> SEQUENCE: 72

```
Met Ala Pro Pro Ala Ala Thr Val Ala Leu Gly Asp Asp Leu Leu
1               5                  10                  15

Arg Glu Val Phe Ile Leu Leu Pro Thr Pro Thr Asp Leu Leu Arg Ala
                20                  25                  30

Ala Leu Ala Cys Lys Pro Phe Leu Arg Ala Ala Arg Ser Ala Pro Phe
                35                  40                  45

Leu Arg Arg Phe Arg Arg Arg His Pro Phe Thr Cys Pro Leu Leu Leu
50                  55                  60

Gly Cys Leu Leu His Gly Pro Thr Asp Arg Arg Thr Thr Ala Ser
65                  70                  75                  80

His Leu Leu Pro Ala Tyr Pro Asp Ala Ala Thr Arg Arg Leu Ile Asp
                85                  90                  95

Gly Ala Asp Phe Thr Phe Ser Phe Leu Pro Arg Arg Gly Trp Pro Gln
                100                 105                 110

Ala Ala Gly Ser Ala Trp Gln Leu Leu Asp Cys Arg Asn Gly Arg Ala
                115                 120                 125

Leu Leu Leu Ser Arg Ala Ser Arg Ala Leu Ala Val Ala Asp Pro Leu
130                 135                 140

Thr Arg Arg Ser Val Thr Leu Pro Ala Ile Arg Gly Leu Gly Tyr Ala
145                 150                 155                 160

Leu Val Ala Asp Asp Gly Asp Ser Ser Leu Phe Lys Ala Val Cys Ile
                165                 170                 175

Ser Arg Arg Val Gly Ala Pro Gly Leu Arg Ala Phe Leu Leu Ser Ser
                180                 185                 190

Ala Asp Leu Arg Trp Val Gln Val Ala Val Ala Gly Leu Asp Asp Val
                195                 200                 205

Gln Pro Asp Leu Ala Gly Ser Arg Ala Met Gln Ala Asn Gly Ser Leu
210                 215                 220

Tyr Trp Lys Leu Val Gly Gly Glu His Met Val Ala Leu Asn Thr Glu
225                 230                 235                 240

Thr Met Glu Phe Ala Val Leu Glu Leu Pro Pro Phe Leu Arg Glu Ile
                245                 250                 255

Ser Phe Asp Ile Ile Glu Lys Gly Glu Asp Ala Ala Gly Leu Tyr
                260                 265                 270

Leu Leu Thr Met Arg Gly Phe Cys Ile Glu Val Trp Ala Gly Val Lys
                275                 280                 285

Asp Gly Ala Asp Gly Gly Leu Thr Trp Thr Leu Val Glu Lys Ser Val
                290                 295                 300

Met Phe His Arg Ala Met Ala Glu Met Leu Gly Ser Glu Phe Leu Tyr
305                 310                 315                 320
```

-continued

```
Gln Asn Arg Leu Asp Val Ile Gly Val Val Ala Gly Val Val Phe Leu
            325                 330                 335

Arg Asn Gly Glu Cys Leu Phe Ser Ile Asp Leu Gln Thr Met Lys Met
            340                 345                 350

Thr Arg Val Ser Pro Lys Glu Asn Cys Pro Ser His Leu Ile Tyr Pro
            355                 360                 365

Cys Thr Ile Ala Trp Pro Pro Ser Phe Leu Asn Pro Thr Glu Gln Gly
            370                 375                 380

Ala
385

<210> SEQ ID NO 73
<211> LENGTH: 104
<212> TYPE: PRT
<213> ORGANISM: Lolium perenne

<400> SEQUENCE: 73

Met Ser Ala Ala Ala Gly Gly Leu Arg Gln Leu Leu Thr Ala Ala Val
1               5                   10                  15

Thr Ala Gly Ala Ala Glu Ala Arg Ala Ala Val Phe Gly His Ala Val
            20                  25                  30

Asn Pro Ser Gly Lys Arg Ala Ala Thr Lys Leu Leu Arg Arg Lys Phe
        35                  40                  45

Ile Gly Glu Gln Leu Ala Gln Trp Tyr Pro Tyr Asp Ile Lys Arg Asp
    50                  55                  60

Asp Pro Ile Val Met Ala Arg Glu Lys Glu Arg Leu Thr Lys Leu
65                  70                  75                  80

Glu Met Leu Lys Arg Arg Gly Lys Gly Pro Lys Lys Gly Gln Gly
                85                  90                  95

Arg Arg Ala Val Lys Arg Thr Lys
            100

<210> SEQ ID NO 74
<211> LENGTH: 79
<212> TYPE: PRT
<213> ORGANISM: Lolium perenne

<400> SEQUENCE: 74

Met Ala Val Ser Ala Asp Leu Ser Lys Glu Glu Ala Leu Lys Leu Ala
1               5                   10                  15

Ala Gly Met Ala Leu Ser Ser Thr Ala Ala Val Arg Ala Ser Ala Gly
            20                  25                  30

Lys Ala Gly Asp Ala Ala Asn Asn Ser Tyr Ala Arg Ser Gly Ser Ile
        35                  40                  45

Ser Ala Arg Thr Ser Ser Cys Ala Thr Thr Thr Ser Phe Gly Ser Ala
    50                  55                  60

Arg Thr Asn Thr Val Ser Ala Thr Leu Ala Leu Ala Val Ser Ala
65                  70                  75

<210> SEQ ID NO 75
<211> LENGTH: 292
<212> TYPE: PRT
<213> ORGANISM: Lolium perenne

<400> SEQUENCE: 75

Met Glu Met Lys Asn Gly Asp Tyr Ala Ser Val Ser Leu Glu Leu Val
1               5                   10                  15

Thr Ala His Ala Gln Ala Arg Ala Thr Phe Glu Val Arg Leu Leu Asp
```

```
            20                  25                  30
Gln Ala Gly Lys Leu Pro Pro Ser Val Val Leu Ala Arg Tyr Lys Pro
        35                  40                  45
Leu Leu Phe Arg Ser Asn Pro Thr Tyr Met Ser Glu Asp Phe Leu
 50                  55                  60
Gln Pro Leu Pro Tyr Leu His Ala Asp Asp Ser Leu Val Val Glu Cys
 65                  70                  75                  80
Asp Ile Thr Val Ile Lys Glu Ser Glu Leu Ala Leu Val His Ser Thr
                85                  90                  95
Phe Asp Ile Lys Val Pro Pro Ser Asp Leu Ser Gln Asn Leu Arg Gln
            100                 105                 110
Leu Leu Glu Ala Gly Asp Glu Ser Asp Val Ala Phe Glu Val Arg Gly
            115                 120                 125
Glu Val Phe Pro Ala His Lys Leu Val Leu Ala Met Arg Ser Arg Val
            130                 135                 140
Phe Lys Ala Asp Leu Phe Gly Pro Met Gly Asp Arg Thr Arg Lys Thr
145                 150                 155                 160
Ile Pro Ile Glu Asp Met Gln Pro Ala Val Phe Gly Ala Leu Leu His
                165                 170                 175
Phe Ile Tyr Thr Asp Ser Leu Pro Ser Met Glu His Leu His Gly Asp
                180                 185                 190
Asp Ala Glu Glu Met Val Lys His Leu Leu Val Ala Ala Asp Arg Tyr
            195                 200                 205
Ala Met Glu Arg Met Lys Val Met Cys Glu Ser Ile Leu Cys Lys Thr
            210                 215                 220
Leu Asn Val Arg Asn Val Thr Thr Thr Leu Ala Leu Ala Asp Gln His
225                 230                 235                 240
Gln Cys Ser His Leu Lys Asp Ala Cys Leu Asp Phe Ile Ala Ser Pro
                245                 250                 255
Asp Arg Thr Asp Asp Val Val Ala Ser Glu Gly Tyr Ala Cys Leu Lys
                260                 265                 270
Arg Ser Cys Pro Ala Val Ile Ala Asp Ile Phe Glu Arg Ala Thr Lys
            275                 280                 285
Ser Arg Lys Ile
            290

<210> SEQ ID NO 76
<211> LENGTH: 91
<212> TYPE: PRT
<213> ORGANISM: Lolium perenne

<400> SEQUENCE: 76

Met Ala Ala Val Ala Gln Arg Lys Thr Lys Gly Ser Ser Ala Ala Ser
 1               5                  10                  15
Thr Gly Gly Ala Lys Thr Lys Arg Arg Arg Lys Thr Lys Val Leu Pro
             20                  25                  30
Pro Leu Leu Ser Pro Gly Thr Ala Val Glu Val Leu Arg Asn Gly Lys
             35                  40                  45
Trp Val Gly Gly Gly Thr Val Thr Ile Arg Asn Asp Arg Thr Tyr Met
         50                  55                  60
Val Ser Leu Pro Glu Gly Met Thr Val Leu Met Thr Arg Gly Arg Val
 65                  70                  75                  80
Arg Pro Thr Ala Gly Tyr Gly Thr Leu Tyr Ser
                 85                  90
```

```
<210> SEQ ID NO 77
<211> LENGTH: 333
<212> TYPE: PRT
<213> ORGANISM: Lolium perenne

<400> SEQUENCE: 77

Met Arg Ile Ala Ser Arg Arg Val Asn Ser Ala Ser Cys Asp Glu Ile
1               5                   10                  15

Thr Ala Leu Arg Ser Glu Ala Lys Val Ala Ser Glu Leu Val Thr Ser
            20                  25                  30

Val Ser Arg Arg Val Lys Gly Ala Gly Ser Glu Gln Arg Ser Leu His
        35                  40                  45

Ala Thr Ser Asn Arg Met Met Leu Ser Gln Glu Glu Met Phe Asn Tyr
    50                  55                  60

Ser Thr Lys Lys Gln Gln Ala Thr His Ile Phe Ser Asn Leu Arg Lys
65                  70                  75                  80

Gln Ile Ser Ser Ile Leu Ile Ala Asp Ile Glu Glu Leu Arg Ala Lys
                85                  90                  95

Gly Cys Ile Ile Ser Leu Ala Cys Ser Asp His Thr Ser Ser Glu Ala
            100                 105                 110

Asn Val Ala Ile Asn Ile Ser His Ser Leu Ser Phe Lys Glu Cys Pro
        115                 120                 125

Leu Ala Leu Ser Pro Val Ser Ser Glu Leu Cys Leu Gly Ile His Ser
    130                 135                 140

Asp Ile Ala Glu Gln Lys Leu Glu His Trp Ser Ser Val Ala Pro Leu
145                 150                 155                 160

Ala Leu Glu Val Val Leu Ser Ile Gly Gln Lys Ala Arg Asp Gly Thr
                165                 170                 175

Leu Ser Asp Asn Asp Val Asn Asp Thr Ala Gly Asp Gly Asn Ile Glu
            180                 185                 190

Ser Met Leu Leu Val Glu Lys Gly Leu Arg Glu Leu Ala Ser Leu Lys
        195                 200                 205

Ile Asn Val Ala Ile Phe Met Ile Thr Lys Leu Pro Ser Ala Gly Pro
    210                 215                 220

Val Tyr Pro Ala Glu Asn His Ser Ser Ser Glu Pro Leu Glu Leu Ser
225                 230                 235                 240

Glu Glu Glu Arg Glu Asp Val Arg Phe Lys Gln Ala Trp Leu Thr Tyr
                245                 250                 255

Phe Trp Arg Arg Ala Lys Asn His Asp Val Glu Glu Asp Ile Ala Asp
            260                 265                 270

Glu Arg Leu Gln Phe Trp Ile Glu Gln Gly Asn His Pro Val Thr Thr
        275                 280                 285

Ser Asp Val Ile Glu Val Asp Arg Gly Leu His Glu Leu Lys Lys Leu
    290                 295                 300

Gly Val Glu Ser Gln Leu Trp Glu Ala Thr Arg Arg Ser Leu Asp Asp
305                 310                 315                 320

Asp Phe Ser Asn His Gly Ser Pro Phe Gly Ser Glu Val
                325                 330

<210> SEQ ID NO 78
<211> LENGTH: 170
<212> TYPE: PRT
<213> ORGANISM: Lolium perenne

<400> SEQUENCE: 78
```

```
Met Gln Cys Asp Ala Glu Ile Pro Ser Gly Arg Gly Leu Ser
1               5                   10                  15

Tyr Gly Gly Asp Ser Cys Arg Glu Asp Arg Leu Ser Ala Leu Pro Asp
                20                  25                  30

Asp Leu Leu Ile His Ile Leu Leu Lys Ile Leu Asp Ala Ala Gly Ala
            35                  40                  45

Ala Arg Thr Ser Val Leu Ser Arg Arg Trp Arg Arg Leu Trp Thr Leu
    50                  55                  60

Leu Pro Glu Leu Leu Phe Pro Asn Ser Asn Pro His His Ile Arg Leu
65                  70                  75                  80

Ala Leu Thr Ala His Glu Ala Pro Ala Leu Arg Lys Leu Ala Val Thr
                85                  90                  95

Val Thr Asp Pro Asn Pro Glu Ser Val Ala Ala Trp Leu Pro Ile Ala
            100                 105                 110

Ala Arg Arg Leu Ser Gly Asp Leu Phe Leu Phe Asn Met Ala Gln Arg
            115                 120                 125

Asn Glu Ser Glu Asp Glu Ala Gly Glu Arg Gly Ala Phe Glu Leu Pro
            130                 135                 140

Cys Phe Glu Arg Ala Thr Ala Ile Val Leu Pro Cys Gln Gly Ala Pro
145                 150                 155                 160

Cys Pro Leu Thr Val Ser Ile Ala Ala Cys
                165                 170

<210> SEQ ID NO 79
<211> LENGTH: 162
<212> TYPE: PRT
<213> ORGANISM: Lolium perenne

<400> SEQUENCE: 79

Met Glu Gln Cys Asp Ala Glu Ile Pro Ser Arg Glu Arg Gly Leu Ser
1               5                   10                  15

Tyr Gly Gly Asp Gly Tyr Arg Glu Asp Arg Leu Ser Ala Leu Pro Asp
                20                  25                  30

Asp Leu Leu Ile His Ile Leu Leu Lys Ile Leu Asp Ala Ala Gly Ala
            35                  40                  45

Ala Arg Thr Ser Val Leu Ser Arg Arg Trp Arg Arg Leu Trp Thr Leu
    50                  55                  60

Leu Pro Glu Leu Leu Phe Pro Asn Ser Asn Pro His His Ile Arg Leu
65                  70                  75                  80

Ala Leu Thr Ala His Gly Ala Pro Ala Leu Arg Lys Leu Ala Val Thr
                85                  90                  95

Val Thr Asp Pro Asn Pro Glu Ser Val Ala Ala Trp Leu Pro Ile Ala
            100                 105                 110

Ala Arg Arg Leu Ser Gly Asp Leu Phe Leu Phe Asn Met Ala Gln Arg
            115                 120                 125

Asn Glu Ser Glu Asp Glu Ala Gly Glu Arg Gly Ala Phe Glu Leu Pro
            130                 135                 140

Cys Phe Glu Arg Ala Thr Ala Ile Val Leu Pro Cys Gln Gly Pro Leu
145                 150                 155                 160

Ala Pro

<210> SEQ ID NO 80
<211> LENGTH: 412
<212> TYPE: PRT
<213> ORGANISM: Lolium perenne
```

<400> SEQUENCE: 80

```
Met Gly Ala Asp Leu Gly Ala Glu Leu Gly Ala Leu Ala Leu Lys Tyr
1               5                   10                  15
Thr Gly Val Ser Leu Ser Val Ser Asp Tyr Asp Ser Ile Val Ala Met
            20                  25                  30
Asn Ile Phe Val Ala Leu Leu Cys Gly Cys Ile Val Phe Gly His Leu
        35                  40                  45
Leu Glu Gly Asn Arg Trp Val Asn Glu Ser Thr Thr Ala Leu Val Met
    50                  55                  60
Val Phe Ala Val Leu Ser Arg Trp Gly Arg Val Ala Trp Leu Ile Thr
65                  70                  75                  80
Gly Gly Val Ile Leu Leu Val Thr Asn Gly Val Asn Ser Arg Ile Leu
                85                  90                  95
Val Phe Ser Glu Asp Ile Phe Phe Ile Tyr Leu Leu Pro Pro Ile Ile
            100                 105                 110
Phe Asn Ala Gly Phe Gln Val Lys Lys Lys Gln Phe Phe Arg Asn Phe
        115                 120                 125
Ala Thr Ile Thr Leu Phe Gly Ala Ile Gly Thr Leu Ile Ser Phe Val
    130                 135                 140
Ile Ile Ser Leu Gly Ala Met Gly Leu Phe Ser Lys Leu Asp Val Asp
145                 150                 155                 160
Pro Leu Gln Leu Gly Asp Tyr Leu Ala Ile Gly Ala Ile Phe Ser Ala
                165                 170                 175
Thr Asp Ser Val Cys Thr Leu Gln Val Leu Asn Gln Asp Glu Thr Pro
            180                 185                 190
Leu Leu Tyr Ser Leu Val Phe Gly Glu Gly Val Val Asn Asp Ala Thr
        195                 200                 205
Ser Val Val Leu Phe Asn Ala Ile Gln Asn Ile Asp Leu Asp His Phe
    210                 215                 220
Asp Ala Phe Val Leu Leu Gln Leu Ile Gly Lys Phe Leu Tyr Leu Leu
225                 230                 235                 240
Phe Thr Ser Thr Val Leu Gly Ile Ala Leu Leu Asp Leu Ser Gly Ile
                245                 250                 255
Leu Thr Val Phe Phe Cys Gly Ile Val Met Ser His Tyr Thr Trp His
            260                 265                 270
Asn Val Thr Glu Ser Ser Arg Val Thr Thr Lys His Thr Phe Ala Thr
        275                 280                 285
Leu Ser Phe Ile Ala Glu Leu Phe Leu Phe Leu Tyr Val Gly Met Asp
    290                 295                 300
Ala Leu Asp Ile Glu Lys Trp Arg Leu Ala Arg Ser Arg Glu Leu Ile
305                 310                 315                 320
Ile Trp Trp Ala Gly Leu Met Arg Gly Ala Val Ser Ile Ala Leu Ala
                325                 330                 335
Tyr Asn Lys Val Phe Gly Leu Leu Thr Lys Pro Leu Ile Asn Leu Leu
            340                 345                 350
Ile Pro Pro Arg Pro Ser Asn Thr Ala Asp Gly Ser Ser Gln Ser Phe
        355                 360                 365
Leu Asp Pro Leu Leu Ser Leu Leu Gly Ser Asp Leu Asp Ile Gly
    370                 375                 380
Gln Tyr Pro Pro Gln Thr Asn Leu Gln Leu Leu Thr Ile Gln Thr
385                 390                 395                 400
Arg Ser Val His Arg Val Trp Arg Lys Phe Asp Asp
                405                 410
```

<210> SEQ ID NO 81
<211> LENGTH: 417
<212> TYPE: PRT
<213> ORGANISM: Lolium perenne

<400> SEQUENCE: 81

Met Ala Ser Gln Ile Ser Gly Thr Val Ala Ser Ser Gly Val Gly Tyr
1               5                   10                  15

Asn Asp Gln Tyr Gly Met Pro Cys Lys Met Lys Gly Leu His Cys Val
            20                  25                  30

Ser Leu Asn Cys Ile Pro Pro Asn Leu Glu Ala Arg Lys Gly Met Ser
        35                  40                  45

Gly Tyr His Leu Val Val Arg Phe Cys Ser Asn Asp Arg Tyr Gly Gln
    50                  55                  60

Thr Thr Leu Lys Ser Asn Ser Ser Met Leu Arg Gln Gly Gln Ser Val
65                  70                  75                  80

Trp Cys Arg Ser Tyr Gly Pro Arg Gly Ser Ser Glu Thr Lys Glu Arg
                85                  90                  95

Glu Ser Ser Glu Asp Asp Asn Asp Ala Tyr Arg Asp Phe Lys Glu Gln
            100                 105                 110

Pro Arg Gly Asn Ser Gln Phe Ser Asp Asp Gln Val Ala Ala Gln Lys
        115                 120                 125

Lys Ser Leu Tyr Ser Ile Gln Gly Leu Ser Lys Ala Cys Gln Phe Val
130                 135                 140

Tyr Asn Asp Ala Lys Phe Val Asn Glu Arg Ala Gln Ser Asp Ile Leu
145                 150                 155                 160

Leu Leu Ser Arg Gly Ile Thr Arg Leu Asn Lys Arg Ala Ser Gln Asp
                165                 170                 175

Val Ala Val Leu Gly Leu Gly Phe Leu Lys Leu Asp Ala Arg Ala Arg
            180                 185                 190

Lys Asp Thr Gln Lys Ile Asp Asn Ser Val Lys Glu Arg Ala Ala His
        195                 200                 205

Leu Thr Asn Phe Ala Arg Ile Leu Lys Glu Arg Ala Glu Ser Asp Leu
    210                 215                 220

Lys Lys Ala Ala Asp Gln His Trp Ser Asp Gly Ala Leu Glu Ala Asp
225                 230                 235                 240

Leu Arg Arg Ala Asp Met Val Val Arg Arg Ala Met Glu Asp Ala
                245                 250                 255

Phe Met Ala Leu Lys Phe Val Arg Asp Ile His Asp Met Met Ala Asn
            260                 265                 270

Lys Leu Gln Asp Gln Ile Pro Lys Asp Ala Ser Phe Ser Gln Asp Ala
        275                 280                 285

Tyr Leu Ser Met Ala Ser Ala Leu Ser Glu Ala Asp Gly Ile Asp Tyr
    290                 295                 300

Thr Asp Pro Glu Glu Leu Glu Leu Leu Val Ala Ala Leu Ile Asp Leu
305                 310                 315                 320

Asp Ala Met Asp Gly Lys Arg Ser Val Ser Leu Leu Ala Glu Cys Ser
                325                 330                 335

Ser Ser Pro Asp Val Asn Thr Arg Lys Ala Leu Ala Asn Ala Leu Ala
            340                 345                 350

Gly Ser Ser Ile Tyr Val Asp Ser Arg Glu Cys Trp Asp Gly Cys Ile
        355                 360                 365

Thr Ala Ser Ser Ala Ala Arg Ala Ile Asp Glu Leu Arg Lys Gln Trp

```
                 370                 375                 380
Glu Leu Glu Glu Gly Asp Ser Leu Arg Phe Val Val Asn Gln Asn Leu
385                 390                 395                 400

Asp Thr Lys Glu Thr Gly Asp Ser Ser Ala Glu Asp Asp Thr Thr
                405                 410                 415

Pro

<210> SEQ ID NO 82
<211> LENGTH: 561
<212> TYPE: PRT
<213> ORGANISM: Lolium perenne

<400> SEQUENCE: 82

Met Gly Gln Pro Thr Asp Arg Val Asp Asp Phe Ser Ser Arg Gly Lys
1               5                   10                  15

Val Ala Arg Val Trp Cys Met Arg Glu Arg Asn Ser Thr Phe Arg Lys
                20                  25                  30

Ile Leu Gly Ile Tyr Val Glu Gly Leu Ile Phe Pro Glu Glu Ser Arg
            35                  40                  45

Ser Gln Lys Gly Arg Pro Gly Gly Pro Gly Pro Pro Asn Asn Arg
50                  55                  60

Leu Ala Arg Pro Val Gly Trp Arg Ala Ala Leu Ala Cys Gly Pro Leu
65                  70                  75                  80

Gly Gln Pro Leu Thr Pro Pro Ser Gly Leu Lys Gly Phe Asp Leu
                85                  90                  95

Lys Thr Arg Asp Gly Lys Ser Lys Ser Arg Glu Thr Ile Gln Tyr Ala
            100                 105                 110

Ala Thr Val Ala Lys Leu Arg Leu Gly Thr Arg Asn Ser Val Leu Ala
                115                 120                 125

Pro Arg Arg Asp Gly Glu Leu Glu Glu Ile Ile Ala Ile Thr Thr
130                 135                 140

Asp Ala Ser Pro Ser Thr Ser His Val Ser Pro Ile His Ile Gly Ala
145                 150                 155                 160

Val Ala Arg Ile Arg His Gln Leu Ala Tyr Ala Thr His Thr Phe Phe
                165                 170                 175

Asp Lys Glu Asp Phe Leu Tyr Ile His Thr Pro Ile Ile Thr Thr Ser
            180                 185                 190

Asp Cys Glu Gly Ala Gly Glu Met Phe Gln Val Thr Ser Leu Phe Ser
                195                 200                 205

Gln Ala Glu Lys Val Asp Lys Glu Leu Lys Glu Asn Pro Ala Pro Ser
210                 215                 220

Glu Ala Asp Val Glu Ala Ala Lys Leu Val Val Lys Gly Lys Gly Asp
225                 230                 235                 240

Ala Val Ala Gln Leu Lys Ala Ala Lys Ala Ser Lys Gln Glu Ile Thr
                245                 250                 255

Ala Ala Val Ser Glu Leu Thr Lys Ala Lys Glu Val Val Leu Arg Leu
            260                 265                 270

Glu Glu Arg Ser Lys Leu Lys Pro Gly Ile Pro His Lys Asp Asp Gly
                275                 280                 285

Ser Ile Ala Phe Glu Asn Asp Phe Phe Lys Arg Ala Ala Phe Leu Thr
290                 295                 300

Val Ser Gly Gln Leu Gln Val Glu Thr Tyr Ala Cys Ala Leu Ser Ser
305                 310                 315                 320

Val Tyr Thr Phe Gly Pro Thr Phe Arg Ala Glu Asn Ser His Thr Ser
```

```
            325                 330                 335
Arg His Leu Ala Glu Phe Trp Met Val Glu Pro Glu Ile Ala Tyr Ala
            340                 345                 350
Asn Leu His Asp Asp Met Asn Tyr Ala Glu Arg Tyr Val Lys Tyr Leu
            355                 360                 365
Cys Lys Trp Leu Leu Asp His Cys Arg Glu Asp Met Glu Phe Met Val
            370                 375                 380
Lys His Val Asp Lys Thr Ala Ile Glu Arg Leu Glu Leu Val Ser Ser
385                 390                 395                 400
Thr Pro Phe Glu Arg Ile Ser Tyr Thr Lys Ala Val Glu Ile Leu Glu
            405                 410                 415
Gly Thr Gly Lys Lys Phe Glu Asn Lys Val Glu Trp Gly Ile Asp Leu
            420                 425                 430
Ala Ser Glu His Glu Arg Tyr Leu Thr Glu Val Ile Phe Lys Lys Pro
            435                 440                 445
Val Ile Val Tyr Asn Tyr Pro Lys Gly Ile Lys Ala Phe Tyr Met Arg
            450                 455                 460
Leu Asn Asp Asp Gln Lys Thr Val Ala Ala Met Asp Val Leu Val Pro
465                 470                 475                 480
Lys Val Gly Glu Leu Ile Gly Gly Ser Gln Arg Glu Arg Leu Asp
            485                 490                 495
Val Leu Thr Gln Arg Ile Leu Asp Ala Asp Leu Pro Leu Glu Pro Tyr
            500                 505                 510
Glu Trp Tyr Leu Asp Leu Arg Arg Phe Gly Ser Val Lys His Ser Gly
            515                 520                 525
Phe Gly Leu Gly Phe Glu Arg Met Ile Leu Phe Ala Thr Gly Leu Asp
            530                 535                 540
Asn Ile Arg Asp Val Ile Pro Phe Pro Arg Tyr Pro Gly Arg Ala Asp
545                 550                 555                 560
Leu

<210> SEQ ID NO 83
<211> LENGTH: 225
<212> TYPE: PRT
<213> ORGANISM: Lolium perenne

<400> SEQUENCE: 83

Met Ala Pro Ala Ala Val Lys Val Tyr Gly Trp Ala Met Ser Pro Phe
1               5                   10                  15
Val Ala Arg Ala Leu Leu Cys Leu Glu Glu Ala Gly Val Glu Tyr Glu
            20                  25                  30
Leu Val Pro Met Ser Arg Gln Ala Gly Asp His Leu Gln Pro Asp Phe
            35                  40                  45
Leu Ala Arg Asn Pro Phe Ala Gln Val Pro Val Leu Glu Asp Gly Asp
        50                  55                  60
Leu Thr Leu Phe Glu Ser Arg Ala Ile Ala Arg His Val Leu Arg Lys
65                  70                  75                  80
His Lys Pro Glu Leu Leu Val Gly Asp Gly Ser Pro Glu Ala Ala Ala
                85                  90                  95
Met Val Asp Val Trp Leu Glu Val Glu Ala His Gln His Ala Pro
            100                 105                 110
Thr Ala Ala Ile Met Val Gln Cys Ile Leu Ala Pro Leu Leu Gly Gly
            115                 120                 125
Ala Arg Asp Gln Ala Val Ile Asp Glu Asn Val Pro Lys Leu Lys Lys
```

```
        130                 135                 140
Val Leu Glu Val Tyr Glu Ala Arg Leu Ser Lys Ser Arg Tyr Leu Ala
145                 150                 155                 160

Gly Glu Ser Val Ser Leu Ala Asp Leu Ser His Phe Pro Met Leu Arg
                165                 170                 175

Tyr Phe Met Glu Thr Glu Tyr Lys Ala Leu Val Glu Glu Leu Pro His
                180                 185                 190

Val Lys Ala Trp Trp Glu Glu Leu Lys Ala Arg Pro Ala Ala Arg Lys
                195                 200                 205

Val Thr Glu Phe Met Pro Val Asp Phe Gly Leu Gly Lys Lys Ala Glu
                210                 215                 220

Gln
225

<210> SEQ ID NO 84
<211> LENGTH: 228
<212> TYPE: PRT
<213> ORGANISM: Lolium perenne

<400> SEQUENCE: 84

Met Ala Gln Thr Ala Val Lys Val Tyr Gly Trp Ala Val Ser Pro Phe
1               5                   10                  15

Val Ala Arg Ala Leu Leu Cys Leu Glu Glu Ala Gly Val Asp Tyr Glu
                20                  25                  30

Leu Val Pro Met Ser Arg Glu Ala Gly Asp His Leu Arg Pro Asp Phe
                35                  40                  45

Leu Ala Arg Asn Pro Phe Ala Gln Val Pro Val Leu Gln Asp Gly Asp
            50                  55                  60

Leu Thr Leu Phe Glu Ser Arg Ala Ile Ala Arg His Val Leu Arg Lys
65                  70                  75                  80

His Lys Pro Glu Leu Leu Val Gly Asp Gly Ser Pro Glu Ala Ala Ala
                85                  90                  95

Leu Val Asp Val Trp Leu Glu Val Glu Ala His Gln His His Pro Pro
                100                 105                 110

Thr Gly Ala Ile Met Val Gln Cys Ile Leu Thr Pro Leu Leu Gly Gly
                115                 120                 125

Val Arg Asp Gln Ala Val Val Asp Glu Asn Val Ala Lys Leu Lys Lys
            130                 135                 140

Val Leu Ala Val Tyr Glu Ala Arg Leu Ser Ala Ser Arg Tyr Leu Ala
145                 150                 155                 160

Gly Glu Ser Leu Thr Leu Ala Asp Leu Ser His Phe Pro Met Met Arg
                165                 170                 175

Tyr Phe Met Glu Thr Glu Tyr Ala Ala Leu Val Glu Glu Leu Pro His
                180                 185                 190

Val Lys Ala Trp Trp Glu Glu Leu Asn Ala Arg Pro Ala Ala Arg Lys
                195                 200                 205

Val Thr Glu His Ala Val Asn Ala Lys Leu Trp Ala Leu Glu Lys
                210                 215                 220

Ala Glu Gln Gln
225

<210> SEQ ID NO 85
<211> LENGTH: 159
<212> TYPE: PRT
<213> ORGANISM: Lolium perenne
```

```
<400> SEQUENCE: 85

Ser Arg Glu Thr Arg Ile Gly Asn Thr Gly Arg Ser Ile Asp Arg Ser
1               5                   10                  15

Ala Arg Gly Pro Ala Arg Arg Asp Gly Val Ser Gly Ala Gly Gly Asp
            20                  25                  30

Ala Asp Leu Gly Gln Gly Pro Glu Glu Gly Asp Gly Val Leu Gln Asp
        35                  40                  45

Ala Gly Val Arg Gly Val His Leu Arg Arg Pro Ala His Ala
    50                  55                  60

Asp Ala Pro Asp Ala Leu Gly Pro Ala Arg Ala Ala Val Pro
65                  70                  75                  80

Asn Thr Asp Arg Arg Arg Pro Pro Arg Ala Arg Thr Ala Arg Ala Pro
                85                  90                  95

Pro Leu Arg Ala Leu Leu Arg Arg Pro Arg Arg Arg Gly Ala Arg
                100                 105                 110

Pro Arg Pro Gly Pro Phe Arg Arg Ser Ala Ser Arg Arg Ala Ser
            115                 120                 125

Pro Pro Gln Leu Pro Gly Ala Thr Pro His Glu Arg Pro Glu Ala Arg
        130                 135                 140

Gly Ala Pro His Leu Leu Gln Pro His Gly Arg Ala Gly Asp Arg
145                 150                 155

<210> SEQ ID NO 86
<211> LENGTH: 814
<212> TYPE: PRT
<213> ORGANISM: Lolium perenne

<400> SEQUENCE: 86

Met Val Leu Ser Ile Asp Thr Gly Glu Val Thr Ala Glu Cys Glu Arg
1               5                   10                  15

Met Glu Val Val Arg Val Arg Gly Glu Ala Trp Gly Leu Gly Ile Gly
            20                  25                  30

Glu Asp Val Lys Met Val Trp Ser Arg Met Arg Arg Val Lys Cys Arg
        35                  40                  45

Gly Gly Ala Arg Pro Leu Lys Gly Arg Gln Arg Val Pro Glu Lys Glu
    50                  55                  60

Asn Ala Pro Ala Ala Lys Gly Arg Arg Gly Ala Ala Gly Ala Ala Ala
65                  70                  75                  80

Arg Leu Met Glu Lys Ile Val Pro Gly Ala Pro Ala Ile Lys Leu Lys
                85                  90                  95

Ala Ser Lys Lys Asp Gln Tyr Leu Leu Lys Arg Arg Asp Asp Ala Arg
            100                 105                 110

Ala Pro Ala Leu Pro Pro Val Val Leu Pro Asp Ala Thr Pro Ala Pro
        115                 120                 125

Asp Asp Gly Gly Pro Pro Gly Phe Pro Ser Ala Glu Pro Gln Thr
    130                 135                 140

Pro Pro Leu Pro Ser Ser Ala Gly Gly Gly Asp Glu Glu Phe Met
145                 150                 155                 160

Leu Gln Arg Arg Thr Leu Pro Ser Ala Gln Ala Ser Asp Gly Gly
                165                 170                 175

Ala Thr Ala Asp Asp Ala Thr Ala Ala Pro Lys Lys Ala Ala Lys
            180                 185                 190

Pro Lys Lys Ala Arg Lys Arg Glu Arg Glu Val Ala Ala Glu Ala Thr
        195                 200                 205
```

```
Ala Asp Glu Ser Ala Ala Ala Gly Glu Pro Lys Thr Lys Lys Lys
    210                 215                 220
Lys Lys Leu Ala Glu Leu Asn Ser Gly Ala Pro Ser Ala Asp Pro Ser
225                 230                 235                 240
Gly Gly Gly Ala Lys Pro Ala Ala Phe Ser Pro Lys Val Asp Leu
                245                 250                 255
Asp Gly Leu Asp Leu Lys Gln Val Ile Ser Asp Leu Glu Asn Leu Pro
        260                 265                 270
Leu Leu Pro Ser Tyr Gly Ala Gly Arg Ser Ile Ser Asp Gly Ser His
            275                 280                 285
Ser Phe Leu Leu Ala Phe Arg Ser Lys His Tyr Lys Lys Ser Tyr Glu
    290                 295                 300
Asn Asp Pro Ser Glu Glu Ser Lys Lys Ser Leu Asp Thr Lys Pro Asn
305                 310                 315                 320
Ala Ala Val Ala Ala Ala Val Asp Gly Gln Pro Lys Pro Val Lys
                325                 330                 335
Lys Lys Pro Val Met Arg Pro Ile Asp Pro Thr Ile Ala Gly Val Lys
                340                 345                 350
Arg Gly Pro Ser Asp Arg Gln Glu Glu Met Ala Thr Lys Lys Ile
            355                 360                 365
Lys Leu Glu Lys Ile Lys Thr Leu Ala Ala Glu Lys Lys Ala Gly Leu
    370                 375                 380
Glu Pro Lys Val Val Thr Ala Pro Ala Ser Ala Val Gly Gly Val Thr
385                 390                 395                 400
Pro Ala Ala Gln Gln Pro Arg Ala Gly Met Lys Glu Lys Ala Leu Gly
                405                 410                 415
Leu Val Lys Lys Lys Val Pro Ala Ala Ala Pro Ala Arg Arg Met Ala
                420                 425                 430
Ser Pro Thr Ala Leu Met Met Lys Phe Pro Pro Asn Ser Thr Leu Pro
            435                 440                 445
Ser Val Ala Ser Leu Lys Ala Arg Phe Ala Arg Phe Gly Pro Leu Asp
    450                 455                 460
Ile Asp Gly Ile Arg Val Tyr Trp Lys Ser Tyr Met Cys Arg Val Ile
465                 470                 475                 480
Tyr Lys Tyr Lys Ser Asp Ala Glu Met Ala Leu Lys Ser Ala Lys Ser
                485                 490                 495
Thr Ala Met Phe Gly Gln Val Val Pro Asn Tyr His Leu Arg Gly Ile
            500                 505                 510
Glu Ser Ser Ser Ala Gly Ala Asp Met Gly Pro Glu Pro Ala Pro Pro
    515                 520                 525
Ala Gln Gln Arg Ser Glu Leu Arg Leu Met Glu Thr Thr Pro Phe Arg
    530                 535                 540
Pro Gly Ser Ser Gly Asn Gly Ala Pro Leu Thr Leu Ser Arg Ala Ala
545                 550                 555                 560
Pro Ala Arg Ala Val Val Gly Gln Pro Lys Ser Ile Leu Lys Lys Asn
                565                 570                 575
Asn Asp Asp Gly Gly Ala Ser Ala Leu Arg Asp Ser Pro Arg Val Lys
            580                 585                 590
Phe Met Leu Asp Gly Gly Asp Ser Lys Leu Glu Pro Pro Ala Ile Pro
            595                 600                 605
Ala Ser Gly Asn Ser Pro Asp Ala Ala Ala Pro Val Ser Lys Val Ala
    610                 615                 620
Arg Ser Val Gly Phe Ala Gln Pro Pro Leu Gln Pro Leu Ala Arg Pro
```

```
                625                 630                 635                 640
Ala Gln Pro Asn Met Gln Pro Ala Met Arg Ala Gln Gln Gln Leu
                    645                 650                 655

Gln Pro Pro Arg Ala Leu Asp Thr Gln Ala Leu Pro Pro Pro Pro
                660                 665                 670

Leu Pro Tyr Gln Pro Arg Ala Ser Glu Pro Leu Pro Tyr Gln Pro Arg
            675                 680                 685

Val Ser Glu Ala Ser Pro Tyr Gln Pro Arg His Thr Asp Ala Pro Pro
690                 695                 700

Ser Phe Asn Asn Met Gln Leu Pro Tyr Gln Ala Arg His Ile Asp Val
705                 710                 715                 720

Pro Leu Met Leu Ser Gly Gln Pro Thr Leu Pro Tyr Pro Pro Arg Ala
                725                 730                 735

Ser Phe Ala Arg Ser Asp Asp Met Pro Pro Ser His Phe Asp Asn
            740                 745                 750

Asn Ala Ala Asn Ala Met Pro Ala Pro Phe Asp Arg Asn Ala Val Asn
            755                 760                 765

Ala Met Pro Val Trp Lys Arg Gly Glu Lys Glu Phe Ser Glu Glu Leu
        770                 775                 780

Met Arg Val Met Leu Gly Ile Ala Lys Leu Val Glu Pro Leu Met Asp
785                 790                 795                 800

Lys Asn Gly Asn Phe Pro Tyr His Leu Phe Gly Arg Ser Ala
                805                 810

<210> SEQ ID NO 87
<211> LENGTH: 311
<212> TYPE: PRT
<213> ORGANISM: Lolium perenne

<400> SEQUENCE: 87

Met Val Val Pro Val Ile Asp Phe Ser Lys Leu Asp Gly Ala Glu Arg
1               5                   10                  15

Ala Glu Thr Met Ala Gln Ile Ala Asp Gly Cys Glu Asn Trp Gly Phe
            20                  25                  30

Phe Gln Leu Val Asn His Gly Ile Pro Leu Glu Leu Leu Asp Arg Val
        35                  40                  45

Lys Lys Val Cys Ser Glu Ser Tyr Arg Leu Arg Glu Ala Ala Phe Arg
    50                  55                  60

Gln Ser Glu Pro Val Gln Thr Leu Glu Ala Leu Leu Glu Ala Glu Arg
65                  70                  75                  80

Arg Gly Glu Ala Val Ala Pro Val Asp Asp Met Asp Trp Glu Asp Ile
                85                  90                  95

Phe Tyr Leu His Asp Asp Asn Gln Trp Pro Ser Asp Pro Pro Ala Phe
            100                 105                 110

Lys Glu Thr Met Arg Glu Tyr Arg Ala Glu Leu Lys Lys Leu Ala Glu
        115                 120                 125

Arg Val Met Glu Ala Met Asp Glu Asn Leu Gly Leu Asp Lys Gly Arg
    130                 135                 140

Met Lys Ala Ala Phe Thr Cys Asp Gly Ile His Ala Pro Thr Phe Gly
145                 150                 155                 160

Thr Lys Val Ser His Tyr Pro Pro Cys Pro Arg Pro Asp Leu Val Thr
                165                 170                 175

Gly Leu Arg Ala His Thr Asp Ala Gly Gly Val Ile Leu Leu Phe Gln
            180                 185                 190
```

```
Asp Asp Lys Val Gly Gly Leu Glu Val Leu Lys Asp Gly Glu Trp Leu
        195                 200                 205

Asp Val Gln Pro Leu Ala Asp Ala Ile Val Val Asn Thr Gly Asp Gln
        210                 215                 220

Val Glu Val Leu Ser Asn Gly Arg Tyr Arg Ser Ala Trp His Arg Val
225                 230                 235                 240

Leu Pro Met Arg Asn Gly Asn Arg Arg Ser Ile Ala Ser Phe Tyr Asn
                245                 250                 255

Pro Ala Phe Glu Ala Ala Ile Ser Pro Val Ala Glu Gly Ala
            260                 265                 270

Ala Ala Ser Tyr Pro Glu Phe Val Phe Gly Asp Tyr Met Asp Val Tyr
        275                 280                 285

Ser Lys His Lys Phe Glu Ala Lys Glu Pro Arg Phe Glu Ala Val Lys
        290                 295                 300

Ala Pro Asn Thr Pro Gln Ala
305                 310

<210> SEQ ID NO 88
<211> LENGTH: 311
<212> TYPE: PRT
<213> ORGANISM: Lolium perenne

<400> SEQUENCE: 88

Met Val Val Pro Val Ile Asp Phe Ser Lys Leu Asp Gly Ala Glu Arg
1               5                   10                  15

Ala Glu Thr Met Ala Gln Ile Ala Asp Gly Cys Glu Asn Trp Gly Phe
            20                  25                  30

Phe Gln Leu Val Asn His Gly Ile Pro Leu Glu Leu Leu Asp Arg Val
        35                  40                  45

Lys Lys Val Cys Ser Glu Ser Tyr Arg Leu Arg Glu Ala Ala Phe Arg
    50                  55                  60

Ser Ser Glu Pro Val Arg Thr Leu Glu Ala Leu Val Glu Ala Glu Arg
65                  70                  75                  80

Arg Gly Glu Ala Val Ala Pro Val Asp Asp Met Asp Trp Glu Asp Ile
                85                  90                  95

Phe Tyr Leu His Asp Asp Asn Thr Trp Pro Ser Asp Pro Pro Ala Phe
                100                 105                 110

Lys Glu Thr Met Arg Glu Tyr Arg Ala Glu Leu Lys Lys Leu Ala Glu
            115                 120                 125

Arg Val Met Glu Ala Met Asp Glu Asn Leu Gly Leu Asp Lys Gly Arg
        130                 135                 140

Met Lys Ala Ala Phe Thr Cys Asp Gly Ile Arg Ala Pro Thr Phe Gly
145                 150                 155                 160

Thr Lys Val Ser His Tyr Pro Pro Cys Pro Arg Pro Asp Leu Val Thr
                165                 170                 175

Gly Leu Arg Ala His Thr Asp Ala Gly Gly Val Ile Leu Leu Phe Gln
            180                 185                 190

Asp Asp Lys Val Gly Gly Leu Glu Val Leu Lys Asp Gly Glu Trp Leu
        195                 200                 205

Asp Val Gln Pro Leu Ala Asp Ala Ile Val Val Asn Thr Gly Asp Gln
        210                 215                 220

Val Glu Val Leu Ser Asn Gly Arg Tyr Arg Ser Ala Trp His Arg Val
225                 230                 235                 240

Leu Pro Met Arg Asn Gly Asn Arg Arg Ser Ile Ala Ser Phe Tyr Asn
                245                 250                 255
```

```
Pro Ala Phe Glu Ala Ala Ile Ser Pro Ala Val Ala Glu Gly Ala Ala
                260                 265                 270

Ala Ala Ser Tyr Pro Lys Phe Val Phe Gly Asp Tyr Met Asp Val Tyr
            275                 280                 285

Ser Lys His Lys Phe Glu Ala Lys Glu Pro Arg Phe Glu Ala Val Lys
        290                 295                 300

Ala Pro Lys Thr Pro Gln Ala
305                 310

<210> SEQ ID NO 89
<211> LENGTH: 228
<212> TYPE: PRT
<213> ORGANISM: Lolium perenne

<400> SEQUENCE: 89

Met Arg Val Thr Ile Thr Gly Gly Gly Thr Arg Leu His Val Asp Leu
1               5                   10                  15

Tyr Tyr Ala Cys Val Gln Ser Arg Ala Leu Phe Thr Val Trp Ser Leu
            20                  25                  30

Leu Gln Leu Met Arg Arg His Arg Gly Arg Val Pro Asp Val Asp Leu
        35                  40                  45

Met Phe Asp Cys Met Asp Arg Pro Ala Ile Asn Arg Thr Glu His Ser
50                  55                  60

Gly Glu Gly Ala Pro Pro Pro Pro Leu Phe Arg Tyr Cys Thr Thr
65                  70                  75                  80

Arg Asp His Phe Asp Ile Pro Phe Pro Asp Trp Ser Phe Trp Gly Trp
                85                  90                  95

Pro Glu Thr His Leu Glu Pro Trp Ser Arg Glu Phe Lys Ser Ile Arg
                100                 105                 110

Gln Gly Ala Lys Lys Asn Trp Asp Glu Glu Ala Arg Ser Gly Tyr Gln
            115                 120                 125

Asn Ser Lys Leu Ser Ser Gln Cys Thr His Arg Tyr Lys Ile Tyr Ala
        130                 135                 140

Glu Gly Phe Ala Trp Ser Val Ser Leu Lys Tyr Ile Leu Ser Cys Gly
145                 150                 155                 160

Ser Thr Ala Leu Leu Ile Asp Pro Leu Tyr Gln Asp Phe Phe Ser Arg
                165                 170                 175

Gly Leu Glu Pro Arg Val Asn His Leu Pro Val Ser Thr Val Gly Met
                180                 185                 190

Cys Glu Ser Ile Arg Asp Ala Val Glu Trp Gly Asn Ala His Pro Asp
            195                 200                 205

Glu Ala Glu Arg Val Gly Arg Arg Gly Gln Arg Leu Met Gln Asp Leu
        210                 215                 220

Ala Met Asp Ala
225

<210> SEQ ID NO 90
<211> LENGTH: 746
<212> TYPE: PRT
<213> ORGANISM: Lolium perenne

<400> SEQUENCE: 90

Met Ala Gly Gln Gly Gln Asp Arg Lys Thr Ile Asp Leu Glu Glu Gly
1               5                   10                  15

Trp Ala Tyr Met Glu Gly Gly Ile Gly Lys Leu Val Asn Ile Leu Glu
            20                  25                  30
```

```
Gly Lys Asn Glu Pro Gln Phe Asn Ser Glu Asn Tyr Met Met Leu Tyr
     35                  40                  45

Thr Thr Ile Tyr Asn Met Cys Thr Gln Lys Pro Pro Asn Asp Tyr Ser
 50                  55                  60

Gln Gln Leu Tyr Asp Lys Tyr Arg Glu Ala Phe Glu Lys Tyr Ile Arg
 65                  70                  75                  80

Asp Ala Val Leu Pro Ala Ile Lys Glu Gln His Asp Glu Tyr Met Leu
                 85                  90                  95

Lys Gln Leu Asn Val Arg Trp Lys Asn His Lys Val Met Val Arg Trp
                100                 105                 110

Leu Ser Arg Phe Phe His Tyr Leu Asp Arg Tyr Phe Ile Thr Arg Arg
                115                 120                 125

Ser Leu Thr Pro Leu Asn Asp Val Gly Phe Ile Cys Phe Arg Asp Leu
         130                 135                 140

Ile Phe Gln Glu Ile Lys Gly Lys Val Lys Asp Ala Val Leu Val Leu
145                 150                 155                 160

Ile Asn Gln Glu Arg Glu Gly Glu Gln Ile Asp Lys Thr Leu Leu Lys
                 165                 170                 175

Asp Val Leu Asp Ile Phe Val Glu Ile Gly Leu Thr Thr Met Glu Phe
             180                 185                 190

Tyr Glu Asn Asp Phe Glu Asp Phe Leu Leu Lys Asp Thr Thr Glu Tyr
             195                 200                 205

Tyr Ser Val Lys Ala Gln Asn Trp Ile Val Glu Asp Ser Cys Pro Asp
         210                 215                 220

Tyr Met Ile Lys Ala Glu Cys Leu Arg Arg Glu Lys Glu Arg Val
225                 230                 235                 240

Ser His Tyr Leu His Ile Asn Ser Glu Pro Lys Leu Leu Glu Arg Val
                 245                 250                 255

Gln Asn Glu Leu Leu Ala Asn Tyr Ala Thr Gln Leu Leu Glu Lys Glu
             260                 265                 270

His Ser Gly Cys Tyr Ala Leu Leu Arg Asp Asp Lys Val Asp Asp Leu
         275                 280                 285

Lys Arg Met Phe Ser Leu Phe Ser Lys Ile Thr Arg Gly Leu Glu Pro
     290                 295                 300

Val Ser Asn Met Phe Lys Ser His Val Thr Asn Glu Gly Thr Ala Leu
305                 310                 315                 320

Val Lys Gln Ala Glu Asp Ser Ala Ser Asn Lys Lys Pro Glu Lys Lys
                 325                 330                 335

Glu Met Val Gly Met Gln Glu Gln Val Phe Val Trp Lys Ile Ile Ala
             340                 345                 350

Leu His Asp Lys Tyr Val Ala Tyr Val Thr Asp Cys Phe His Gly His
         355                 360                 365

Thr Leu Phe His Lys Ala Leu Lys Glu Ala Phe Glu Val Phe Cys Asn
     370                 375                 380

Lys Gly Val Ser Gly Ser Ser Ala Glu Leu Leu Ala Thr Phe Cys
385                 390                 395                 400

Asp Asn Ile Leu Lys Lys Gly Cys Ser Glu Lys Leu Ser Asp Glu Ala
                 405                 410                 415

Ile Glu Asp Ala Leu Glu Lys Val Val Arg Leu Leu Ala Tyr Ile Ser
             420                 425                 430

Asp Lys Asp Leu Phe Ala Glu Phe Tyr Arg Lys Lys Leu Ala Arg Arg
         435                 440                 445
```

Leu Leu Phe Asp Lys Ser Ala Asn Asp Glu His Glu Arg Ser Ile Leu
          450                 455                 460
Thr Lys Leu Lys Gln Gln Cys Gly Gly Gln Phe Thr Ser Lys Met Glu
465                 470                 475                 480
Gly Met Val Thr Asp Leu Thr Leu Ala Arg Asp His Gln Thr Lys Phe
                    485                 490                 495
Glu Glu Phe Val Ala Glu His Gln Glu Leu His Pro Gly Val Asp Leu
                500                 505                 510
Ala Val Thr Val Leu Thr Thr Gly Phe Trp Pro Thr Tyr Lys Thr Phe
                515                 520                 525
Glu Ile Ser Leu Pro Ser Glu Met Val Lys Cys Val Glu Val Phe Lys
530                 535                 540
Glu Phe Tyr Gln Thr Arg Thr Lys His Arg Lys Leu Thr Trp Ile Tyr
545                 550                 555                 560
Ser Leu Gly Thr Cys Asn Ile Asn Ala Lys Phe Glu Thr Lys Thr Ile
                    565                 570                 575
Glu Leu Ile Val Thr Thr Tyr Gln Ala Ala Leu Leu Leu Leu Phe Asn
                580                 585                 590
Gly Val Asp Arg Leu Ser Tyr Ser Glu Ile Val Thr Gln Leu Asn Leu
                595                 600                 605
Ser Asp Asp Asp Val Val Arg Leu Leu His Ser Leu Ser Cys Ala Lys
610                 615                 620
Tyr Lys Ile Leu Thr Lys Glu Pro Ala Gly Arg Ser Ile Ser Pro Asn
625                 630                 635                 640
Asp Val Phe Glu Phe Asn Ser Lys Phe Thr Asp Arg Met Arg Arg Ile
                    645                 650                 655
Lys Ile Pro Leu Pro Pro Val Asp Glu Lys Lys Val Val Glu Asp
                660                 665                 670
Val Asp Lys Asp Arg Arg Tyr Ala Ile Asp Ala Ser Ile Val Arg Ile
                675                 680                 685
Met Lys Ser Arg Lys Val Met Ala His Thr Gln Leu Val Ala Glu Cys
                690                 695                 700
Val Glu Gln Leu Ser Arg Met Phe Lys Pro Asp Phe Lys Ala Ile Lys
705                 710                 715                 720
Lys Arg Ile Glu Asp Leu Ile Thr Arg Asp Tyr Leu Glu Arg Asp Lys
                725                 730                 735
Asp Asn Ala Asn Thr Tyr Arg Tyr Leu Ala
                740                 745

<210> SEQ ID NO 91
<211> LENGTH: 449
<212> TYPE: PRT
<213> ORGANISM: Lolium perenne

<400> SEQUENCE: 91

Met Ala Pro Pro Leu Pro Gly Pro Arg Pro Ala Gly Gly Ser Arg
1               5                   10                  15
Arg Pro Arg Pro Cys Pro Gly Ser Ala Thr Ser Ala Ala Ser Leu Val
                20                  25                  30
Arg Ala Pro Ala Ser Asp Pro Arg Pro Ser Trp Met Leu Lys Ser Glu
            35                  40                  45
Thr Lys Pro Glu Asp Gly Ser Ile Ser Asn Arg Val Gln Arg Leu Ala
        50                  55                  60
Lys Tyr Arg Phe Leu Lys Lys Gln Ser Glu Leu Leu Leu Asn Ala Asp
65                  70                  75                  80

Asp Leu Asp Ala Met Trp Val Cys Leu Arg Glu Asn Cys Val Ile Asp
            85                  90                  95

Asp Val Thr Gly Ser Glu Lys Met Asn Tyr Glu Asp Phe Cys His Ile
        100                 105                 110

Ala Thr Val Cys Thr Glu Gln Ile Gly Gln Lys Cys Lys Arg Phe Phe
        115                 120                 125

Ser Pro Ser Asn Phe Met Lys Phe Glu Lys Asp Asp Ser Gly Arg Ile
130                 135                 140

Ala Ile Leu Pro Phe Tyr Leu Tyr Val Met Arg Thr Val Ser Leu Thr
145                 150                 155                 160

Gln Ala Arg Ile Asp Met Ser Glu Leu Asp Glu Asp Ser Asp Gly Phe
                165                 170                 175

Leu Gln Pro His Glu Met Glu Ala Tyr Ile Arg Gly Leu Ile Pro Asn
            180                 185                 190

Leu Ala Gln Leu Arg Asp Met Pro Ser Ala Phe Val Gln Met Tyr Cys
        195                 200                 205

Arg Ile Ala Ala Arg Lys Phe Phe Phe Cys Asp Pro His Arg Arg
210                 215                 220

Gly Lys Ala Cys Ile Lys Lys Val Leu Leu Ser Asn Cys Leu Gln Glu
225                 230                 235                 240

Leu Met Glu Leu His Gln Glu Ser Glu Glu Val Thr Asp Thr Glu
                245                 250                 255

Gln Ala Glu Asn Trp Phe Ser Leu Thr Ser Ala Gln Arg Ile Cys Asp
                260                 265                 270

Met Phe Leu Ala Leu Asp Lys Asp Thr Asn Gly Thr Leu Ser Lys Gln
            275                 280                 285

Glu Leu Lys Glu Tyr Ala Asp Gly Thr Leu Thr Glu Ile Phe Ile Glu
        290                 295                 300

Arg Val Phe Asp Glu His Val Arg Arg Ser Lys Val Gly Gly Gly Asn
305                 310                 315                 320

Ser Arg Glu Met Asp Phe Glu Ser Phe Leu Asp Phe Val Leu Ala Leu
                325                 330                 335

Glu Asn Lys Asp Thr Pro Glu Gly Leu Thr Tyr Leu Phe Arg Cys Leu
            340                 345                 350

Asp Leu Asn Gly Arg Gly Phe Leu Thr Thr Ala Asp Ile His Thr Leu
        355                 360                 365

Phe Arg Asp Val His Gln Lys Trp Ile Glu Gly Gly Asn Tyr Glu Leu
370                 375                 380

Cys Ile Glu Asp Val Arg Asp Glu Ile Trp Asp Met Val Lys Pro Ala
385                 390                 395                 400

Asp Pro Leu Arg Ile Ala Leu Thr Asp Leu Leu Ser Cys Lys Gln Gly
                405                 410                 415

Gly Thr Ile Ala Ser Met Leu Ile Asp Val Arg Gly Phe Trp Ala His
            420                 425                 430

Asp Asn Arg Glu Asn Leu Leu Gln Glu Glu Glu Gln Val Glu Glu
        435                 440                 445

Ala

<210> SEQ ID NO 92
<211> LENGTH: 574
<212> TYPE: PRT
<213> ORGANISM: Lolium perenne
<220> FEATURE:
<221> NAME/KEY: misc_feature

```
<222> LOCATION: (12)..(14)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (127)..(136)
<223> OTHER INFORMATION: Xaa can be any naturally occurring amino acid
<220> FEATURE:
<221> NAME/KEY: misc_feature
<222> LOCATION: (182)..(199)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (494)..(513)
<223> OTHER INFORMATION: Xaa can be any naturally occurring amino acid

<400> SEQUENCE: 92

Met Phe Arg Ser Met Thr Asn Arg Val Cys Arg Xaa Xaa Xaa Gly His
1               5                   10                  15

Leu Leu Ser Pro Val Phe Ile Glu Tyr Thr Arg Ser Pro Pro Ile Leu
            20                  25                  30

Ala Ser Phe His Arg Val His Cys Thr Thr Ile Leu Arg Pro Thr His
        35                  40                  45

Tyr Ile Gly Thr Arg Gln Cys Ala Ala Gln Ser Thr Leu Gln Thr Ser
    50                  55                  60

Ile Xaa Xaa Pro Ser Pro Ala Cys Cys Leu Pro Ser Gly Leu Ser His
65                  70                  75                  80

Phe Ser Phe Gly Ile His Cys Thr Phe Gly Val Gln Ile Cys Asp Val
                85                  90                  95

Val Leu Asn Pro Trp Ser Leu Lys Gln Leu Gly Ile Ile Leu Val Thr
            100                 105                 110

Ile Val Val Gly Phe Val Leu Val Phe Gly Cys Ile Xaa Xaa
        115                 120                 125

Xaa Xaa Xaa Xaa Xaa Xaa Xaa Xaa Ala Leu Gln Ser Phe Leu Ser Gly
    130                 135                 140

Phe Ile Val Trp Val Tyr Pro Cys Ser Leu Ile Val Gly Glu Cys Ile
145                 150                 155                 160

Arg Glu Lys Ile Cys Arg Arg Lys Tyr Leu Ser Gln Leu Asp Met Arg
                165                 170                 175

Ile Ile Cys Pro Leu Xaa Xaa Xaa Xaa Xaa Xaa Xaa Xaa Xaa
            180                 185                 190

Xaa Xaa Xaa Xaa Xaa Xaa Xaa Gln Pro Val Pro Met Leu Leu Gln Glu
    195                 200                 205

Ile Gln Val Arg Asp Glu Trp Gln Ile His Arg Thr Phe Leu Pro Ser
210                 215                 220

Leu Phe His Trp Asn Leu His Ala His Gln Leu Thr Gly Leu Ser
225                 230                 235                 240

Gln Thr Asp Ala Pro Ser Leu Leu His Val Gln Ile Met His Leu Tyr
            245                 250                 255

Ile Lys Val Leu Asp Lys His Val Pro Asn Leu Asp Lys Ser Glu Asp
        260                 265                 270
```

```
Gln Pro Leu Ala Pro Glu Leu Pro Ser Leu Leu Pro Asp Leu Ala
        275                 280                 285

Asp Ser Met Lys Asp Ala Asn Xaa Pro Phe Ile Ile Pro Val Ile Cys
    290                 295                 300

Leu Ser Ser Thr Arg Arg Leu Phe Ser Ala Tyr Ile Lys Ala Phe Leu
305                 310                 315                 320

Ser Ser Phe Leu Ser Gln Asn Ala Ala Arg Ala Ile His Val Ser Gly
            325                 330                 335

Leu Ala Gly Ser Ile Cys Ser Ile Ser Cys Thr Asn Leu Phe Ser Leu
        340                 345                 350

Val Ser Asp Leu Asn Phe Arg Arg Ile Ala Tyr Ser Ser Ile Tyr Val
    355                 360                 365

Ile Met Xaa Trp Ile Asn Pro Ser Leu Leu Lys Ile His Asp Cys Phe
370                 375                 380

Ile Ile Leu Ala Asn Asp Gly Phe Asn Leu Cys Asn Phe Gln Gln Asp
385                 390                 395                 400

Val His Ile Ile Gly Glu Ser Leu Gln Phe His Val Tyr Ile Lys Ala
            405                 410                 415

Thr Phe Ile Ile Met Ser Asn Ala Thr Leu Arg Leu Tyr Ile Pro Ile
        420                 425                 430

Pro Pro Thr Leu Cys Ile Tyr Lys Ile Thr Trp Trp Leu Ala Ser Ser
    435                 440                 445

Ile Trp Cys Leu Lys Lys Arg Lys Leu Leu Arg Arg Lys Pro His Phe
450                 455                 460

Ser Gln Ser Cys Asn Ser Leu Lys Tyr Ile Arg Ala Leu Pro Gln Thr
465                 470                 475                 480

Leu Phe Ile Thr Tyr Gly Arg Ser Thr Val Ile Ser Gly Xaa Xaa Xaa
            485                 490                 495

Xaa Xaa Xaa Xaa Xaa Xaa Xaa Xaa Xaa Xaa Xaa Xaa Xaa Xaa
        500                 505                 510

Xaa Ser Leu Lys Gly Val Ala Phe Glu Glu Phe Gly Glu Gly Glu Arg
    515                 520                 525

Pro Val Val Glu Thr Glu Ile Leu Val Glu Leu Val Ala Cys Leu Gly
    530                 535                 540

Ile Leu Leu Leu His Cys Thr Ala Cys Leu Ala Pro Arg Ala Leu Arg
545                 550                 555                 560

Asn Ser Phe Ser Pro Tyr Asn Ala Ser Pro Cys Arg Thr Lys
            565                 570

<210> SEQ ID NO 93
<211> LENGTH: 273
<212> TYPE: PRT
<213> ORGANISM: Lolium perenne
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid

<400> SEQUENCE: 93

Pro Arg Leu Ser Pro Pro Arg Lys Met Leu Glu Thr Phe Pro Pro Phe
```

```
            1               5                  10                 15
        Leu Ala Val Arg Asn Cys Pro Lys His Asp Lys Gln Val Ala Asn Glu
                        20                  25                  30

Thr His Pro Val Pro Thr Lys Pro Ile Cys Ile Leu Ala Phe Glu Leu
                        35                  40                  45

Trp Arg Ser Val His Ser Phe Asp Pro Ala Gln His Asn Arg Ile Leu
                        50                  55                  60

Cys Ile Ser Pro Asp Val Leu Arg Asn Ser Ser Lys His Leu Val Val
         65                  70                  75                  80

Ala Ser Val Leu Leu Val Ala Ala Pro Arg Gly Tyr Val Ala Phe His
                        85                  90                  95

Trp Glu Pro Ala Xaa Arg Cys Phe Gly Glu Asn Tyr Val Gln Leu Leu
                       100                 105                 110

Ile Asp Lys Ala Pro Gln Leu Pro Glu Asp Ile Glu Trp His Phe Ile
                       115                 120                 125

Gly Asn Leu Gln Ser Asn Lys Ala Lys Ala Leu Leu Ala Gly Val Pro
        130                 135                 140

Asn Leu Asp Met Val Glu Ser Val Asp Asp Glu Xaa Asn Leu Arg His
        145                 150                 155                 160

Lys Leu Ser Trp Thr Asp Leu Leu His Ser Ala Asn Val Leu Cys Leu
                       165                 170                 175

Leu Ile Ala Ala Leu Ala Ser Cys Arg Lys Glu Val Cys Asp Glu Leu
                       180                 185                 190

Gly Ile Pro Glu Glu Gln Cys Glu Leu Ser Met Gly Met Ser Ala Asp
                       195                 200                 205

Phe Glu Gln Ala Ile Glu Met Xaa Xaa Ala Gln Ile Ser Glu Leu Asp
                       210                 215                 220

Gln Leu Tyr Leu Val Gln Glu Asn Thr Arg Arg Thr Arg Ile Thr
        225                 230                 235                 240

Ile Tyr Ser Gly Phe Val Ala Ala Val Pro Ala Asn Met Tyr Tyr Ser
                       245                 250                 255

Arg Leu Gln Ile Lys Tyr Trp Ile Cys Ile Gln Phe Leu Gln His Ser
                       260                 265                 270

Ala

<210> SEQ ID NO 94
<211> LENGTH: 1064
<212> TYPE: PRT
<213> ORGANISM: Lolium perenne

<400> SEQUENCE: 94

Met Gly Lys Pro Ala Glu Tyr Glu Asp Asp Glu Glu Val Ser Thr
         1               5                  10                 15

Ser Val Gly Asp Glu Gln Pro Asp Glu Glu Gln Glu Ser Asp Gly
                        20                  25                  30

Ser Glu Glu Glu Glu Asp Glu Pro Glu Gly Glu Gln Ala Ala Gly Asp
                        35                  40                  45

Ala Glu Asp Glu Glu Glu Val Ala Glu Glu Ile Val Ala Ala
                        50                  55                  60

Thr Thr Gly Ala Gly Ala Asp Asp Asp Asp Ala Gly Asp Gly Ala
         65                  70                  75                  80

Gly Glu Ala Glu Ser Thr Glu Asp Asp Glu Ala Val Ala Pro Glu Glu
                        85                  90                  95

Gly Gly Glu Glu Asp Ala Asp Glu Ser Glu Asp Ala Ala Gly Asn Ala
```

-continued

```
                100                 105                 110
Glu Val Gly Lys Arg Glu Arg Ala Lys Leu Arg Gln Met Gln Lys Leu
            115                 120                 125

Lys Lys Gln Lys Ile Gln Glu Ile Leu Asp Ser Gln Asn Ala Thr Ile
130                 135                 140

Asp Ala Asp Met Asn Lys Lys Gly Lys Gly Arg Leu Lys Tyr Leu Leu
145                 150                 155                 160

Gln Gln Thr Glu Ile Phe Ala His Phe Ala Lys Gly Ser Gln Ser Ala
                165                 170                 175

Glu Lys Lys Ser Arg Gly Ser Val Cys Leu Leu Cys Phe Ala Asn Val
            180                 185                 190

Val Arg Thr Tyr Arg Gly Arg His Glu Ser Lys Val Thr Glu Glu Glu
            195                 200                 205

Glu Asp Glu Glu Tyr Leu Lys Glu Asp Ala Leu Ala Ser Ala Gly
            210                 215                 220

Gly Thr Arg Leu Leu Ile Gln Pro Ser Cys Ile Asn Gly Lys Met Arg
225                 230                 235                 240

Asp Tyr Gln Leu Ala Gly Leu Asn Trp Leu Ile Arg Leu Tyr Glu Asn
                245                 250                 255

Gly Ile Asn Gly Ile Leu Ala Asp Glu Met Asn His Ile Arg Glu Asn
                260                 265                 270

Leu Leu Ala Pro Gly Lys Phe Asp Val Cys Val Thr Ser Phe Glu Met
            275                 280                 285

Ala Ile Lys Glu Lys Thr Ala Leu Arg Arg Phe Ser Trp Arg Tyr Ile
            290                 295                 300

Ile Ile Asp Glu Ala His Arg Ile Lys Asn Glu Asn Ser Leu Leu Ser
305                 310                 315                 320

Lys Thr Met Arg Leu Phe Ser Thr Asn Tyr Arg Leu Leu Ile Thr Gly
                325                 330                 335

Thr Pro Leu Gln Asn Asn Leu His Glu Leu Trp Ser Leu Leu Asn Phe
            340                 345                 350

Leu Leu Pro Glu Ile Phe Ser Ser Ala Glu Thr Phe Asp Glu Trp Phe
            355                 360                 365

Gln Ile Ser Gly Glu Asn Asp Gln His Glu Val Val Gln Gln Leu His
            370                 375                 380

Lys Val Leu Arg Pro Phe Leu Leu Arg Arg Leu Lys Ser Asp Val Glu
385                 390                 395                 400

Lys Gly Leu Pro Pro Lys Lys Glu Thr Ile Leu Lys Val Gly Met Ser
            405                 410                 415

Glu Met Gln Lys Gln Tyr Tyr Arg Ala Leu Leu Gln Lys Asp Leu Glu
            420                 425                 430

Val Ile Asn Ala Gly Gly Glu Arg Lys Arg Leu Leu Asn Ile Ala Met
            435                 440                 445

Gln Leu Arg Lys Cys Cys Asn His Pro Tyr Leu Phe Gln Gly Ala Glu
            450                 455                 460

Pro Gly Pro Pro Tyr Thr Thr Gly Asp His Leu Ile Glu Asn Ala Gly
465                 470                 475                 480

Lys Met Val Leu Leu Asp Lys Leu Leu Pro Lys Leu Lys Ala Arg Asp
                485                 490                 495

Ser Arg Val Leu Ile Phe Ser Gln Met Thr Arg Leu Leu Asp Ile Leu
            500                 505                 510

Glu Asp Tyr Leu Met Tyr Arg Gly Tyr Gln Tyr Cys Arg Ile Asp Gly
            515                 520                 525
```

```
Asn Thr Gly Gly Asp Asp Arg Asp Ala Ser Ile Glu Ala Phe Asn Lys
            530                 535                 540

Pro Gly Ser Glu Lys Phe Ile Phe Leu Leu Ser Thr Arg Ala Gly Gly
545                 550                 555                 560

Leu Gly Ile Asn Leu Ala Thr Ala Asp Ile Val Val Leu Tyr Asp Ser
                565                 570                 575

Asp Trp Asn Pro Gln Val Asp Leu Gln Ala Gln Asp Arg Ala His Arg
            580                 585                 590

Ile Gly Gln Lys Lys Glu Val Gln Val Phe Arg Phe Cys Thr Glu Tyr
            595                 600                 605

Thr Ile Glu Glu Lys Val Ile Glu Arg Ala Tyr Lys Lys Leu Ala Leu
        610                 615                 620

Asp Ala Leu Val Ile Gln Gln Gly Arg Leu Ala Glu Gln Lys Ala Val
625                 630                 635                 640

Asn Lys Asp Glu Leu Leu Gln Met Val Arg Phe Gly Ala Glu Met Val
                645                 650                 655

Phe Ser Ser Lys Asp Ser Thr Ile Thr Asp Glu Asp Ile Asp Arg Ile
            660                 665                 670

Ile Ala Arg Gly Glu Glu Ala Thr Ala Gln Leu Asp Ala Lys Met Lys
        675                 680                 685

Lys Phe Thr Glu Asp Ala Ile Lys Phe Lys Met Asp Asp Thr Ala Glu
690                 695                 700

Leu Tyr Asp Phe Asp Asp Lys Glu Glu Asp Lys Pro Asp Phe Lys
705                 710                 715                 720

Lys Leu Val Ser Asp Asn Trp Ile Glu Pro Pro Arg Glu Arg Lys
                725                 730                 735

Arg Asn Tyr Ser Glu Ser Glu Tyr Phe Lys Gln Ala Leu Arg Gln Gly
            740                 745                 750

Ala Pro Ala Lys Pro Arg Glu Pro Arg Ile Pro Arg Met Pro Asn Leu
            755                 760                 765

His Asp Phe Gln Phe Phe Asn Thr Gln Arg Leu Asn Glu Leu Tyr Glu
    770                 775                 780

Lys Glu Val Lys Tyr Leu Val Gln Thr Asn Gln Lys Lys Asp Thr Ile
785                 790                 795                 800

Gly Asp Gly Asp Gly Asp Glu Asp Gln Leu Glu Pro Leu Thr Glu
                805                 810                 815

Glu Glu Gln Glu Lys Glu Gln Leu Leu Glu Gly Phe Ser Thr
                820                 825                 830

Trp Thr Arg Arg Asp Phe Asn Thr Phe Ile Arg Ala Cys Glu Lys Tyr
            835                 840                 845

Gly Arg Asp Asp Ile Lys Ser Ile Phe Ser Glu Met Glu Gly Lys Thr
850                 855                 860

Glu Glu Glu Val Gln Arg Tyr Ala Glu Val Phe Lys Glu Arg Tyr Thr
865                 870                 875                 880

Glu Leu Asn Asp Tyr Asp Arg Ile Ile Lys Asn Ile Glu Lys Gly Glu
                885                 890                 895

Ser Lys Ile Ser Arg Lys Asp Glu Ile Met Lys Ala Ile Ala Lys Lys
            900                 905                 910

Met Asp Arg Tyr Lys Asn Pro Trp Leu Glu Leu Lys Ile Gln Tyr Gly
        915                 920                 925

Gln Asn Lys Gly Lys Leu Tyr Asn Glu Glu Cys Asp Arg Phe Leu Leu
930                 935                 940
```

```
Cys Met Val His Lys Leu Gly Tyr Gly Asn Trp Glu Glu Leu Lys Ser
945                 950                 955                 960

Ala Phe Arg Met Ser Pro Leu Phe Arg Phe Asp Trp Val Lys Ser
                965                 970                 975

Arg Thr Thr Gln Glu Leu Ser Arg Arg Cys Asp Thr Leu Ile Arg Leu
                980                 985                 990

Val Glu Lys Glu Asn Gln Glu Cys Asp Glu Arg Asp Arg Gln Ala Arg
            995                1000                1005

Lys Asp Lys Lys Asn Met Thr Ser Ser Lys Arg Pro Ala Ala Ser
        1010                1015                1020

Ser Pro Ala Phe Glu Ser Pro Ile Gln Ser Ser Ser Lys Arg Gly
        1025                1030                1035

Arg Arg Asp Gly Ser Ala Ala Ser Cys Ser Trp Val Asn Gln Ile
        1040                1045                1050

Ile Glu Leu Val Lys Ala Phe Gly Asp Leu Ser
        1055                1060

<210> SEQ ID NO 95
<211> LENGTH: 615
<212> TYPE: PRT
<213> ORGANISM: Lolium perenne

<400> SEQUENCE: 95

Met Gly Phe Gly Arg Ser Arg Trp Thr Gly Ser Thr Ala Leu Val Ile
1               5                   10                  15

Asn Trp Arg Pro Leu Leu Tyr Cys Arg Lys Glu Asp Ile Asn Gly His
            20                  25                  30

Ser Gly Leu Arg Arg Asp Leu Pro Val Ala Ser Leu Leu Leu Arg Val
        35                  40                  45

Asp Ala Ser Met Tyr Lys Asn Gln Leu Gln Glu Leu Ala Gln Arg Ser
    50                  55                  60

Cys Phe Asn Leu Pro Ser Tyr Ala Cys Ile Arg Glu Gly Pro Asp His
65                  70                  75                  80

Ala Pro Arg Phe Lys Ala Thr Val His Phe Asn Gly Glu Ala Phe Glu
                85                  90                  95

Ser Pro Thr Phe Cys Ser Thr Leu Arg Leu Ala Glu His Ala Ala Ala
            100                 105                 110

Glu Val Ala Leu Asn Glu Leu Ser Lys Arg Gly Pro Ser Ser Ser Leu
        115                 120                 125

Ala Ala Lys Val Leu Asp Glu Thr Gly Ile Tyr Lys Asn Leu Leu Gln
    130                 135                 140

Glu Thr Ala His Arg Ala Gly Leu Lys Leu Pro Met Tyr Thr Thr Ile
145                 150                 155                 160

Arg Ser Gly Pro Gly His Thr Pro Met Phe Thr Cys Thr Val Glu Leu
                165                 170                 175

Ala Gly Arg Ile Phe Thr Gly Asn Pro Gly Lys Thr Lys Lys Gln Ala
            180                 185                 190

Gln Lys Asn Ala Ala Met Ala Ala Trp Ser Glu Leu Lys Glu Leu Pro
        195                 200                 205

Arg Val Gly Glu Val Ala Ser Ser Ser Pro Ser Asp His Asp Asn
    210                 215                 220

Glu Glu Gln Gly Gln Val Thr Val Val Arg Thr Leu Glu Ser Leu Asn
225                 230                 235                 240

Gln Lys Asn Glu Gly Lys Ala Pro His Gln Lys Glu Lys Gln Gln Arg
                245                 250                 255
```

Asn Asn Arg Pro Gln Pro Arg Ser Tyr Pro Lys Pro Ser Ala Ser
        260                 265                 270

Phe Tyr Gly Ser Arg Leu Gln Asn Gln Thr Tyr Pro Asn Val Ala Gln
            275                 280                 285

Glu Gln Ala Met Tyr His Met Trp His Gln Val Gln Pro Thr Gln Gln
290                 295                 300

Lys Pro His Phe Arg Met Val Pro Thr Met Gly Asn Thr Arg Phe Pro
305                 310                 315                 320

Pro Pro Pro Thr Ile Leu Ser Met Tyr Pro Pro Arg Gly Gln Phe
                325                 330                 335

Ala Val Pro Ala Ser Gln Asp Ala Leu Ala Leu Ile Pro Cys Phe Pro
            340                 345                 350

Glu Ala Ala Pro Ala Leu Pro Arg Tyr Phe Ser Pro Tyr Pro Ala Ser
            355                 360                 365

Tyr Val Pro Ala Ser Pro Leu Pro Ala Ala Val Asn Met Met His Gly
        370                 375                 380

Arg Arg Gln Gly Cys Ala Glu Thr Val Glu Leu Pro Asp Ala Pro Val
385                 390                 395                 400

Phe Ala Arg Tyr Thr Ala Pro Asp Tyr Ser Ser Ala Leu Glu Asn Val
                405                 410                 415

Cys Pro Ser Glu Val Gln Gln Trp Pro Lys Asn Gly Lys Glu Ala Tyr
            420                 425                 430

Thr Glu Ser Ser Ala Ala Thr Glu Glu Lys Asn Lys Ala Pro Gln Thr
            435                 440                 445

Ser Ser Ser Ser Thr Thr His His Pro Ser Gln Lys Leu Glu Pro Asn
        450                 455                 460

Glu Asp Arg Glu Ser Lys Lys Pro Ala Glu Gln Pro Leu Leu Gly Pro
465                 470                 475                 480

Tyr Val Val Gln Arg Pro Val Gln Arg Ser Tyr Pro Ser Pro Val
                485                 490                 495

Gln His Ser Glu Pro Ile His Arg Asn Asn Leu Pro Phe Arg Thr Ala
            500                 505                 510

Thr Ser Pro Gly Pro Trp Ser Ser Asp Met Gln Thr Pro Pro Arg Phe
        515                 520                 525

Gly Thr Ala Thr Leu Ala Asn Ser Ala Ser Phe Leu Tyr Gln Gln Arg
        530                 535                 540

Pro Pro Trp Leu Ala Ala Pro Val Thr Val Arg Thr Ser Ile Pro Val
545                 550                 555                 560

Cys Ser Ala Arg Pro Asn Ala Ala Val Asn Ser Ser Pro Gly Ala Ala
                565                 570                 575

Thr Arg Val Arg Ser Thr Val Gln Met Leu Ser Arg Asn Asn Ser Glu
            580                 585                 590

Ala Gln Arg Asn Thr Arg Asp Met Ser Asp Ala Ser Thr Ala Ser Ser
        595                 600                 605

Glu Leu Ser Lys Leu His Ile
    610                 615

<210> SEQ ID NO 96
<211> LENGTH: 401
<212> TYPE: PRT
<213> ORGANISM: Lolium perenne

<400> SEQUENCE: 96

Gly Asn Ile Asp Ile Cys Ser Asn Ala Arg Asn Val Phe Ala Tyr Asn

```
  1               5                  10                  15
Gly Pro Val Asn Phe Thr Val Leu Glu Arg Leu Val Ser Arg Cys Arg
                 20                  25                  30

Asn Leu Lys Thr Leu Lys Leu Asn Asn Ala Ile Pro Leu Asp Asn Val
             35                  40                  45

Ala Ser Leu Leu Arg Lys Ala Pro Gln Ile Ile Glu Leu Gly Thr Gly
         50                  55                  60

Lys Phe Ser Ala Asp Tyr His Pro Asp Leu Phe Ala Lys Val Glu Ala
 65                  70                  75                  80

Ala Phe Ala Gly Cys Thr Ser Leu Arg Arg Leu Ser Gly Thr Trp Asp
                 85                  90                  95

Ala Val Pro Asp Tyr Leu Pro Ala Phe Tyr Cys Val Cys Glu Gly Leu
                100                 105                 110

Thr Ser Leu Asn Leu Ser Tyr Ala Thr Val Gln Gly Pro Glu Leu Ile
                115                 120                 125

Lys Phe Ile Ser Arg Cys Lys Asn Leu Leu Gln Leu Trp Val Met Asp
            130                 135                 140

Leu Ile Glu Asp His Gly Leu Ser Val Val Ala Ser Cys Ser Lys
145                 150                 155                 160

Leu Gln Glu Leu Arg Val Phe Pro Ser Asp Pro Phe Gly His Asn Gly
                165                 170                 175

Gly Gln Val Phe Leu Thr Glu Arg Gly Leu Val Asp Val Ser Ala Ser
                180                 185                 190

Cys Pro Lys Leu Glu Ser Val Leu Tyr Phe Cys Ser Arg Met Thr Asn
            195                 200                 205

Glu Ala Leu Val Met Ile Ala Lys Asn Arg Pro Asn Phe Thr Cys Phe
210                 215                 220

Arg Leu Ala Leu Leu Glu Pro Arg Ser Pro Asp Tyr Met Thr Arg Gln
225                 230                 235                 240

Pro Leu Asp Ala Gly Phe Ser Ala Ile Val Glu Ser Cys Lys Gly Leu
                245                 250                 255

Arg Arg Leu Ser Met Ser Gly Leu Leu Thr Asp Leu Val Phe Lys Ser
            260                 265                 270

Ile Gly Ala His Ala Asp Arg Leu Glu Met Leu Ser Leu Ala Phe Ala
            275                 280                 285

Gly Asp Ser Asp Leu Gly Leu Asn Asp Ile Leu Ser Gly Cys Lys Ser
            290                 295                 300

Leu Lys Lys Leu Glu Ile Arg Asp Cys Pro Phe Gly Asp Lys Ala Leu
305                 310                 315                 320

Leu Ala Asn Ala Ala Lys Leu Glu Thr Met Arg Ser Leu Trp Met Asn
                325                 330                 335

Ser Cys Ser Leu Thr Val Gly Gly Cys Arg Leu Leu Ala Leu Lys Met
            340                 345                 350

Pro His Leu Thr Val Glu Ile Ile Asn Asp Pro Gly Glu Thr Cys Pro
            355                 360                 365

Val Glu Ser Leu Pro Phe Asp Ser Pro Val Glu Lys Leu Tyr Val Tyr
            370                 375                 380

Arg Thr Leu Ala Gly Pro Arg Ser Asp Thr Pro Asp Cys Val Gln Ile
385                 390                 395                 400

Val

<210> SEQ ID NO 97
<211> LENGTH: 373
```

```
<212> TYPE: PRT
<213> ORGANISM: Lolium perenne
<220> FEATURE:
<221> NAME/KEY: misc_feature
<222> LOCATION: (56)..(59)
<223> OTHER INFORMATION: Xaa can be any naturally occurring amino acid
<220> FEATURE:
<221> NAME/KEY: misc_feature
<222> LOCATION: (196)..(202)
<223> OTHER INFORMATION: Xaa can be any naturally occurring amino acid
<220> FEATURE:
<221> NAME/KEY: misc_feature
<222> LOCATION: (325)..(327)
<223> OTHER INFORMATION: Xaa can be any naturally occurring amino acid

<400> SEQUENCE: 97
```

Met Glu Ala Ser Ser Val Gly Ala Asp Val Ser Ala Asp His Val Ile
1               5                   10                  15

Ala Glu Leu Leu Glu Met Gly Phe Glu Phe Asp Lys Ile Ser Glu Ala
            20                  25                  30

Ile Gly Val Val Gly Pro Cys Arg Ala Asp Val Val Glu Phe Met Leu
        35                  40                  45

Asn Gly Ser Gly Gly Glu Gln Xaa Xaa Xaa Xaa Gly Gly Ser Gln Arg
    50                  55                  60

Arg Cys Pro Asp Arg Ser Thr Arg Leu Ala Asn Pro Arg Gly Lys Phe
65                  70                  75                  80

Lys Gln Ser Ser Ile Thr Asp His Ile Ala Ser Thr Thr Gly Ser Lys
                85                  90                  95

Thr Val Ser Arg Gly Gly Glu Pro Ser Thr Ser Tyr Ser Cys Leu Ser
            100                 105                 110

Ala Ser Ile Asp Pro Ser Leu Thr Ala Ala Ile Cys Ser Lys Ser Lys
        115                 120                 125

Pro Glu Pro Gln Ser Ser Leu Val Asn Ser Arg Gly Glu Phe Asp Arg
    130                 135                 140

Thr Gly Lys Ile Ser Ala Val Leu Gln Lys His Phe Gly Phe Ser Cys
145                 150                 155                 160

Val Lys Gly Phe Gln Lys Glu Ala Leu Asp Ala Trp Phe Ala Arg Lys
                165                 170                 175

Asp Cys Leu Val Leu Ala Ala Thr Gly Ser Gly Lys Ser Leu Cys Phe
            180                 185                 190

Gln Ile Pro Xaa Xaa Xaa Xaa Xaa Xaa Ala Leu Leu Thr Thr Lys
        195                 200                 205

Ile Val Val Val Ile Ser Pro Leu Ile Ser Leu Met His Asp Gln Cys
    210                 215                 220

Leu Lys Leu Ala Lys His Gly Ile Ser Ala Cys Phe Leu Gly Ser Gly
225                 230                 235                 240

Gln Pro Asp Asn Arg Val Glu Gly Lys Ala Met Ala Gly Met Tyr Lys
                245                 250                 255

Ile Val Tyr Val Cys Pro Glu Thr Ile Leu Arg Leu Met Glu Pro Leu
            260                 265                 270

Lys Lys Leu Ala Glu Lys Pro Gly Ile Ala Leu Phe Ala Ile Asp Glu
        275                 280                 285

Val His Cys Val Ser Lys Trp Gly His Asp Phe Arg Pro Asp Tyr Arg
    290                 295                 300

Arg Leu Ser Val Leu Arg Glu Asn Phe Cys Ser Ser Lys Leu Lys Phe
305                 310                 315                 320

Leu Glu His Asp Xaa Xaa Xaa Ser Phe Asp Gly Ile Asp Cys Tyr Cys
                325                 330                 335

Asn Phe Pro Cys Thr Arg Arg His Ser Gln Val Leu Glu Asn Val Arg
            340                 345                 350

Thr Tyr Ser Gly Cys Leu Asp Val Leu Phe Pro Ala Lys Pro Ser Ile
            355                 360                 365

Tyr Cys Lys Ala Gln
            370

<210> SEQ ID NO 98
<211> LENGTH: 238
<212> TYPE: PRT
<213> ORGANISM: Lolium perenne

<400> SEQUENCE: 98

Met Ala Phe Ser Arg Leu Leu Pro Ser Arg Arg Leu Leu Ser Thr Leu
1               5                   10                  15

Leu His Thr Pro Thr Pro Thr Pro Ala Ala Pro Ala Thr Asp Ala Thr
                20                  25                  30

Thr Thr Thr Pro Phe Ala His Asn Leu His Pro Ala Arg Phe Phe Ser
            35                  40                  45

Ala Thr Arg Arg Ala Gly Pro Gly Ala Pro Arg Glu Pro Arg Ala Ala
50                  55                  60

Asp Ile Gly Ala Arg Ala Arg Gln Leu Gln Ser Arg Arg Leu Trp Thr
65                  70                  75                  80

Tyr Ala Leu Thr Phe Gly Cys Ala Ala Gly Phe Val Val Thr Met Leu
                85                  90                  95

Ala Thr Ser Gln Asp Gln Leu Val Phe Tyr Leu Thr Pro Thr Asp Ala
            100                 105                 110

Leu Ala Arg Phe Ala Thr Asp Pro Ser Lys Thr Arg Cys Arg Leu Gly
            115                 120                 125

Gly Leu Val Leu Glu Gly Ser Ile Ala His Pro Ser Ser Ser Ala Ser
            130                 135                 140

Glu Ile Glu Phe Val Glu Gly Ala Leu Pro Asp Leu Phe Arg Glu Gly
145                 150                 155                 160

His Ser Val Val Val Glu Gly Phe Leu Lys Pro Leu Ser Asp Asp Leu
                165                 170                 175

Arg Leu Asp Gly Ala Gly Arg Lys Val Ser Asp Lys Ala Arg Glu Gly
            180                 185                 190

Gln Tyr Phe Leu Gln Gly Thr Glu Ala Leu Leu Pro Ser Leu Ala Pro
            195                 200                 205

His Phe Phe Cys Tyr His Val Ser Gly Glu Val Ser Gly Glu Phe Phe
            210                 215                 220

Cys Glu Val Ser Asp Glu Val Phe Ser Ile Lys Gly Leu Tyr
225                 230                 235

<210> SEQ ID NO 99
<211> LENGTH: 245
<212> TYPE: PRT
<213> ORGANISM: Lolium perenne

<400> SEQUENCE: 99

Met Ala Gly Ala Gly Ser Ser Pro Leu Gly Gly Gln Leu Ser Arg Gln
1               5                   10                  15

Arg Gly Trp Gln Gln Arg Gln Glu Glu Glu Lys Glu Asn Lys Asn
                20                  25                  30

Lys Pro Ala Ala Pro Val Pro Gln Gly Asn Ala Thr Val Glu Gly
            35                  40                  45

```
Ser Gly Gly Gly Gly Ser Ile Pro Leu Glu Asn Gln Asp Asn Gly Gly
    50                  55                  60

Thr Cys Asp Glu Ala Ser Gly Asp Glu Gln Pro Gln Lys Pro Glu Gly
65                  70                  75                  80

Gly Ser Gly Gly Gly Pro His Val Val Ala Pro Phe Ala Met Thr Pro
                85                  90                  95

His Gly Ile Gln Pro Met Ala Pro Thr Ala Asn Ala Asn Ala Ala Gly
            100                 105                 110

Gly Gly Val Lys Lys Lys Lys Gly Lys Gly Gly Asn Gly Ser
        115                 120                 125

Ala Asn Ala Asn Ala Asp Gly Ala Gly Ala Thr Ala Glu Met Ile Pro
    130                 135                 140

His Asp Ala Thr Ala Gly Asn Ala Gly Gln His Ala Ala Ala Val
145                 150                 155                 160

Asp Ala Gly Ala Tyr Pro Pro Ala Thr Thr Met Ser Tyr Pro Gly Tyr
                165                 170                 175

Tyr Ala Gly Gly Gly Gln Met Pro Pro Tyr Ala Met Ser Tyr Ser
                180                 185                 190

Thr Ala His Pro Leu Arg Ser Ser Ala Tyr Tyr His Pro Met Val Gly
            195                 200                 205

Ala Ala Tyr Thr Gly Gly Ala Glu Tyr Phe His Ser Thr Ala Pro Ile
    210                 215                 220

Ser Ala Ala Pro Arg Ser Tyr Tyr Met Phe Ser Glu Glu Asn Ala Asn
225                 230                 235                 240

Ala Cys Ser Val Met
            245

<210> SEQ ID NO 100
<211> LENGTH: 633
<212> TYPE: PRT
<213> ORGANISM: Lolium perenne

<400> SEQUENCE: 100

Met Ala Leu Ser Met Val Leu Ala His Tyr Ser Glu Gly Phe Asp Val
1               5                   10                  15

Glu Glu Val Thr Ala Gly Phe Pro Ser Glu Thr Gly Glu Phe Asp Val
                20                  25                  30

Ala Glu Val Leu Arg Leu Met Asp Ala Val Arg Pro Phe Ala Asp Arg
            35                  40                  45

Val Leu Ala Thr Ala Asp Leu Glu Thr His Ile Pro Ser Gln Ala Ala
    50                  55                  60

Pro Gly Asp Ala Glu Lys Glu Pro Gly Pro Val Asp Tyr Pro Ala Glu
65                  70                  75                  80

Arg Leu Phe His Ala Ala Ala Ala Gly Ser Leu Ser Thr Tyr Pro Val
                85                  90                  95

Val Val Ser Arg Leu Ala Thr Pro Met Lys Ala Ile Asp Leu Thr Val
                100                 105                 110

Phe Leu Phe Glu Leu Gly Val Pro Ser Arg Thr Phe Ser Ala Ala Ser
            115                 120                 125

Phe Ser Asp Ser Ala Thr Ala Arg Arg Lys Ala Ser Ser Ala
    130                 135                 140

Ala Ser Ala Ser Phe Ser Pro Ala Arg Gly Ser Pro Pro Leu Pro Pro
145                 150                 155                 160

Pro Leu Thr Ala Tyr Thr Pro Ala Gly Gln Leu Gln Ser Gln His Leu
```

```
                165                 170                 175
Asn Ser Leu Leu Ser Asp Arg Asp Tyr Thr Trp Asn Asp Asn Gly Glu
            180                 185                 190

Leu Ile Arg Ile Ser Ser Pro Arg Gln Thr Arg Ser Tyr Ser Tyr Ser
            195                 200                 205

Thr Thr Gly Arg Leu Thr Gly Val His Thr Thr Ala Ala Asn Leu Asp
            210                 215                 220

Ile Arg Ile Pro Tyr Thr Thr Asp Pro Ala Gly Asn Arg Leu Pro Asp
225                 230                 235                 240

Pro Glu Leu His Pro Asp Ser Ala Leu Ser Met Trp Pro Asp Asn Arg
                245                 250                 255

Ile Ala Arg Asp Ala His Tyr Leu Tyr Arg Tyr Asp Arg His Gly Arg
                260                 265                 270

Leu Thr Glu Lys Thr Asp Leu Ile Pro Glu Gly Val Ile Arg Thr Asp
            275                 280                 285

Asp Glu Arg Thr His Arg Tyr His Tyr Tyr Ser Gln His Arg Leu Val
            290                 295                 300

His Tyr Thr Arg Thr Gln Tyr Glu Glu Pro Leu Val Glu Ser Arg Tyr
305                 310                 315                 320

Leu Tyr Asp Pro Leu Gly Arg Arg Val Ala Lys Arg Val Trp Arg Arg
                325                 330                 335

Glu Arg Asp Leu Thr Gly Trp Met Ser Leu Ser Arg Lys Pro Gln Val
            340                 345                 350

Thr Trp Tyr Gly Trp Asp Gly Asp Arg Leu Thr Thr Ile Gln Asn Asp
            355                 360                 365

Arg Ser Arg Ile Gln Thr Ile Tyr Gln Pro Gly Ser Phe Thr Pro Leu
370                 375                 380

Ile Arg Val Glu Thr Ala Thr Gly Glu Leu Ala Lys Thr Gln Arg Arg
385                 390                 395                 400

Ser Leu Ala Asp Ala Leu Gln Gln Ser Gly Gly Glu Asp Gly Gly Ser
                405                 410                 415

Val Val Phe Pro Pro Val Leu Val Gln Met Leu Asp Arg Leu Glu Ser
                420                 425                 430

Glu Ile Leu Ala Asp Arg Leu Pro Leu Pro Lys His Ile Asn Glu Glu
            435                 440                 445

Asn Ile Leu Asn Glu Ile Ser Ile Glu Lys Asp Val Asp Gly Phe His
            450                 455                 460

Pro Leu Asn Ile Gly Lys Leu Ala Met Lys Gly Arg Asp Pro Leu Phe
465                 470                 475                 480

Leu Pro Cys Thr Pro Lys Gly Cys Met Glu Leu Leu Ser Arg Ser Gly
                485                 490                 495

Val Thr Val Lys Gly Lys Asn Ala Val Val Gly Arg Ser Asn Ile
            500                 505                 510

Val Gly Leu Pro Val Ser Leu Leu Leu Lys Ala Asp Ala Thr Val
            515                 520                 525

Ser Ile Val His Ser Arg Thr Pro Asn Pro Glu Val Ile Val Arg Gln
            530                 535                 540

Ala Asp Ile Ile Ile Ala Ala Ala Gly Gln Ala Met Met Ile Lys Gly
545                 550                 555                 560

Asp Trp Ile Lys Pro Gly Ala Ala Val Ile Asp Val Gly Thr Asn Ser
                565                 570                 575

Ile Asp Asp Pro Thr Arg Lys Ser Gly Tyr Arg Leu Val Gly Asp Val
                580                 585                 590
```

```
Asp Phe Thr Glu Ala Ser Lys Val Ala Gly His Leu Thr Pro Val Pro
        595                 600                 605

Gly Gly Val Gly Pro Met Thr Val Ala Met Leu Leu Lys Asn Thr Val
610                 615                 620

Asp Gly Ala Lys Arg Gly Ile Val Ser
625                 630

<210> SEQ ID NO 101
<211> LENGTH: 1191
<212> TYPE: PRT
<213> ORGANISM: Lolium perenne

<400> SEQUENCE: 101

Met Ala Thr Pro Leu Ala Ser Ala Pro Pro Phe Ile Pro Val Gln
1               5                   10                  15

Leu Asp Pro Ser Lys Asp Ser Asp Lys Asn Val Glu Gly Thr Ser Ala
                20                  25                  30

His Pro Glu Lys Thr Ser Gly Ala Asp Gln Ala Glu Gln Lys Ala Glu
            35                  40                  45

Glu Val Ala Ala Lys Lys Ser Lys Ala Arg Gln Arg Asp Ser Glu Ala
50                  55                  60

Lys Gly Lys Trp Trp Pro Cys Thr Thr Thr Glu Thr Glu Leu Asn Asn
65                  70                  75                  80

Leu Glu Ala Glu Gly Phe Leu Arg Pro Gly Ser Trp Arg Thr Val Ser
                85                  90                  95

Gly Ser Leu Val Pro Ala Pro Glu Ala Gly Glu Met Val Val Thr Lys
            100                 105                 110

Ala Leu Val Glu Arg Asp Phe Ser Phe Pro Pro Cys Asp Phe Phe Ser
        115                 120                 125

Glu Ile Leu Lys Ala Tyr Gly Leu Gln Pro His Asn Ile Ser Pro Asn
130                 135                 140

Ser Val Leu Ala Ile Ser Asn His Val Thr Leu Cys Glu Gly His Leu
145                 150                 155                 160

Arg Asp Val Ser Asp Pro Ala Ser Glu Arg Val Leu Pro Pro Phe Lys
                165                 170                 175

Asn Ser Pro Thr Ser Glu Asn Pro Ala Trp Met Gln Cys Pro His Leu
            180                 185                 190

Phe Glu Ser Pro Gln Leu Thr Arg Ala Val Arg Arg Ile Cys Lys Leu
        195                 200                 205

Thr Glu Glu Gly Leu Ser Gly Lys Asp Leu Thr Met Ser Trp Phe Thr
210                 215                 220

Lys Trp Ile Gln Pro Leu Gln His Arg Asp Ser Leu Met Phe Gln Tyr
225                 230                 235                 240

Thr Gly Arg Asp Asp Pro Met Arg Ala Ser Lys Asp Asn Leu Ser Ala
                245                 250                 255

Asp Ala Ile Asp Lys Arg Ile Gln Leu Leu Ile Lys Ile Pro Arg Asp
            260                 265                 270

Leu Arg Ile His Val Cys Asn Lys Asp Ile His Thr Asn Gly Ser Gly
        275                 280                 285

Thr Thr Leu Glu Ala Leu Glu Glu Gly Leu Gly Thr Leu Leu Arg
290                 295                 300

Val Pro His Ala Gly Asn Thr Asp Pro Glu Ala Val Ser Glu Ala Glu
305                 310                 315                 320

Ala Pro Glu Ala Pro Arg Pro Ser Lys Arg Thr Arg Ala Ala Pro Ser
```

-continued

```
                325                 330                 335
Ser Pro Ala Ala Lys Cys Ala Arg Glu Val Pro Ser Thr Ala Ala Thr
                340                 345                 350
Arg Lys Ala Glu Ala Lys Lys Arg Leu Lys Leu Ile Asp Thr Ser
                355                 360                 365
Asn Arg Ala Gln Pro Asp Met Asn His Phe Phe Lys Pro Ser Gly Ser
            370                 375                 380
Ser Gly Ser Gln Pro Ser Lys Ile Leu Lys Lys Arg Thr Lys Pro Ser
385                 390                 395                 400
Pro Ala Ser Ile Pro Val Thr Pro Lys Val Glu Val Pro Lys Ala
                405                 410                 415
Ser Ser Thr Ala Trp Pro Asp Pro Lys Asp Val Ile Asn Leu Asp Asp
                420                 425                 430
Leu Pro Glu Glu Pro Thr Ala Glu Thr Gly His Gly Glu Ser Gly Lys
                435                 440                 445
Gly Ala Ser Ser Ser Ala Pro Pro Glu Lys Pro Thr Ala Thr Ser
450                 455                 460
Thr Glu Ala Pro Ala Glu Val Glu Lys Lys Phe Leu Leu Ser Arg
465                 470                 475                 480
Ala Thr Gly Thr Pro Gln Thr His Pro His Leu Phe Pro Thr Leu Gln
                485                 490                 495
Lys Pro Pro Leu Ser Gln Arg His Ala Glu Ile Ser Ala Met Met Asp
                500                 505                 510
Gln Val Trp Gly Pro Ala Asn Thr Glu Met Lys Glu Leu Ser Asp Leu
                515                 520                 525
Glu Ser Asp Leu Lys Ile Phe Phe Ala Lys His Lys Asn Val Arg Gln
                530                 535                 540
Arg Cys Val Ala Leu Pro Ile Arg Asp Leu Asn Leu Gly Ala Asn Arg
545                 550                 555                 560
Ala Ala Leu Pro Phe Thr Leu Pro Met Val Asp Leu His Asp Arg Leu
                565                 570                 575
Glu Arg Pro Glu Tyr Val Ser Phe Pro Val Leu Leu Ser Pro Leu Leu
                580                 585                 590
Asp Asn Leu Ser Ala Ile Lys Arg Tyr Gln Ile Ala Lys Val Tyr Arg
                595                 600                 605
Arg Asp Asn Pro Ser Lys Gly Arg Tyr Arg Glu Phe Tyr Gln Cys Asp
                610                 615                 620
Phe Asp Ile Ala Gly Val Tyr Glu Pro Met Glu Pro Asp Phe Glu Val
625                 630                 635                 640
Ile Lys Val Leu Thr Glu Leu Leu Asp Lys Leu Asp Ile Gly Val Tyr
                645                 650                 655
Glu Val Lys Leu Asn His Arg Lys Leu Leu Asp Gly Met Leu Glu Ile
                660                 665                 670
Cys Gly Val Pro Ala Glu Lys Phe Arg Thr Val Cys Ser Ser Ile Asp
                675                 680                 685
Lys Leu Asp Lys Leu Thr Phe Glu Glu Val Lys Lys Glu Leu Val Glu
                690                 695                 700
Asp Lys Gly Val Ser Asp Glu Thr Ala Glu Asn Ile Gly Ser Leu Val
705                 710                 715                 720
Lys Thr Lys Gly Pro Pro Leu Glu Val Leu Leu Glu Leu Arg Lys Glu
                725                 730                 735
Gly Ser Lys Phe Met Gln Glu Arg Glu Val Thr Ala Pro Val Thr Asp
                740                 745                 750
```

```
Leu Gln Gly Val Ala Val Phe Leu Gln Arg Gln Pro Val Gly Ala Ala
        755                 760                 765

Thr Ala Ser His His His Thr Thr Val Ala Val Met Ile Leu Leu Met
770                 775                 780

Leu Lys Val Met Glu Val Pro Gly Thr Asp Ala Ala Gly Val Arg Pro
785                 790                 795                 800

Glu Ala Phe Ala Pro Cys Met Leu Phe Lys Arg Thr Tyr His Leu Pro
                805                 810                 815

Cys Val Leu Gly Ile Leu Arg Pro Asp Val Asn Phe Leu Thr Ser Val
                820                 825                 830

Lys Met Asp Pro Lys Arg Ile Phe Lys Lys Met Gln Ile Ser Lys Leu
                835                 840                 845

Gly Asp Ala Gln Gly Ile Pro Leu Phe Ile Asn Gln His Glu Val Val
850                 855                 860

Ser Phe Lys Leu Asn Ile Thr His Pro His Ile Glu Glu Met Arg Arg
865                 870                 875                 880

Ile Arg Glu Asp Pro Phe Leu Gln Cys Glu Gly Asp Thr Asn Ile Lys
                885                 890                 895

Asp Ser Tyr Val Leu Pro Asp Leu Asn Glu His Glu Asn Glu Val Ala
                900                 905                 910

Asn Glu Pro Glu Pro Glu Leu Glu His Val Lys Lys Lys Gln Lys Thr
                915                 920                 925

Val Lys Arg Gly Pro Glu Pro Ala Thr Arg Cys His Ser Phe Val Gln
930                 935                 940

Ile Asp Asp Ile Leu Asp Tyr Ile Pro Ser Ser Asn Glu Tyr Glu Phe
945                 950                 955                 960

His Gly Phe Leu Lys Asp Glu Asp Asp Tyr Phe Gln Pro Ile Thr
                965                 970                 975

Met Val Pro Pro Lys Gly Arg Lys Ser Arg Arg Lys Lys Ile Pro Pro
                980                 985                 990

Arg Lys Trp Tyr Asp Glu Lys Arg Leu Gln Pro His Glu Gln Leu Cys
                995                 1000                1005

Leu Lys Met Cys Phe Thr Asn Val Gln Gln Phe Arg Asn Ala Leu
    1010                1015                1020

Ile Asp Leu Tyr Ile Ala Gln Ser Arg Asn Tyr Met Tyr His Arg
    1025                1030                1035

Asn Ser Asn Ile Arg Ile Ile Val Lys Cys Ile Lys Gln Arg Cys
    1040                1045                1050

Ser Phe Leu His Asn Leu Ala Lys Ala Tyr Lys Gly Arg Arg Val
    1055                1060                1065

Val Glu Asp Val Ser Leu Thr Val Asn Ser Gly Glu Ile Val Gly
    1070                1075                1080

Leu Leu Gly Pro Asn Gly Ala Gly Lys Thr Thr Thr Phe Tyr Met
    1085                1090                1095

Val Val Gly Ile Val Pro Arg Asp Ala Gly Asn Ile Ile Ile Asp
    1100                1105                1110

Asp Asp Asp Ile Ser Leu Leu Pro Leu His Ala Arg Ala Arg Arg
    1115                1120                1125

Gly Ile Gly Tyr Leu Pro Gln Glu Ala Ser Ile Phe Arg Arg Leu
    1130                1135                1140

Ser Val Tyr Asp Asn Leu Met Ala Val Leu Gln Ile Arg Asp Tyr
    1145                1150                1155
```

Leu Ser Ala Glu Gln Arg Glu Asp Arg Ala Asn Glu Leu Met Glu
    1160                1165                1170

Glu Phe His Ile Glu His Leu Arg Asp Ser Met Gly Gln Ser Leu
    1175                1180                1185

Val Arg Gly
    1190

<210> SEQ ID NO 102
<211> LENGTH: 279
<212> TYPE: PRT
<213> ORGANISM: Lolium perenne

<400> SEQUENCE: 102

Met Gly Trp Phe Ala Ser Trp Arg Ile Lys Trp Pro Glu Leu Ala Pro
1               5                   10                  15

His Leu Ala Gly Asn Gly Asp Glu Phe Leu Gly Pro Leu Gly Leu Ala
            20                  25                  30

Gly Gly Val Leu Ala Arg Trp Met Ser Ser Phe Val Glu Leu Leu Ser
        35                  40                  45

Ser Arg Pro Leu Pro Arg Ala Thr Val Gly Val Ser Leu Gly Gly Gly
    50                  55                  60

Arg Pro Val Val Val Asp Gly Ala Gly Pro Gly Ser Pro Val Pro Arg
65                  70                  75                  80

Arg Arg Leu Cys Ala Gly Val Lys Val Ser Arg Ser Gly Val Asp Glu
                85                  90                  95

Arg Arg Cys Ser Cys Pro Asp Leu Val Val Leu Gln Leu Phe Pro Pro
            100                 105                 110

Leu Asn Gln Ala Asp Ala Asp His Gly Val Cys Ser Gly Trp Leu Trp
        115                 120                 125

Trp Ser Asp Ser Arg Ser Glu Ser Gly Arg Val Pro Arg Arg Cys Val
130                 135                 140

Phe Ile Leu His Gln Ile Ser Ala Ser Ala Ser Gly Gly Phe Cys Gly
145                 150                 155                 160

Asp Ile Asn Glu Val Tyr Ser Ser Lys Val Ser Leu Arg Gln His Ser
                165                 170                 175

Cys Gly Leu Arg Gly Leu Phe Ser Phe Ser Gly Glu Val Glu Ala Leu
            180                 185                 190

Ala Lys Ala Val Ala Asp His Gly Glu Arg Glu Ile Gln Glu Glu Leu
        195                 200                 205

Ala Glu Met Ala Asp Trp Gly Pro Val Val Ile Ala Thr Val Leu Phe
    210                 215                 220

Val Leu Leu Thr Pro Gly Leu Leu Phe Gln Leu Pro Gly His Gly Arg
225                 230                 235                 240

Val Val Ala Phe Gly Ser Met His Thr Ser Gly Leu Ala Ile Leu Val
                245                 250                 255

His Ala Val Ile Tyr Phe Ala Leu Ile Thr Ile Phe Leu Ile Ala Ile
            260                 265                 270

Gly Val His Ile Tyr Ala Gly
        275

<210> SEQ ID NO 103
<211> LENGTH: 1696
<212> TYPE: PRT
<213> ORGANISM: Lolium perenne

<400> SEQUENCE: 103

-continued

```
Met Ala Glu Cys Pro Gly His Phe Gly His Leu Glu Leu Ala Lys Pro
1               5                   10                  15

Met Phe His Ile Gly Phe Ile Lys Thr Val Leu Ser Ile Met Arg Cys
            20                  25                  30

Val Cys Phe Asn Cys Ser Lys Ile Leu Val Pro Glu Glu Asp Pro Lys
        35                  40                  45

Phe Lys Gln Ala Leu Lys Ile Lys Asn Pro Lys Asn Arg Leu Arg Arg
    50                  55                  60

Ile Tyr Asp Ala Cys Lys Ser Lys Lys Thr Cys Asp Gly Gly Asp Glu
65                  70                  75                  80

Leu Glu Ala Gln Asp Gln Gln Asp Thr Asp Glu Pro Val Lys Lys Arg
                85                  90                  95

Ser Gly Cys Gly Ala Gln Gln Pro Asn Ile Thr Val Asp Gly Met Lys
            100                 105                 110

Met Val Ala Glu Phe Lys Ala Thr Lys Lys Asn Asp Asp Gln Asp
                115                 120                 125

Gln Leu Pro Glu Pro Val Glu Arg Lys Gln Ile Leu Ser Ala Glu Arg
        130                 135                 140

Val Leu Asn Val Leu Lys Arg Ile Ser Asp Glu Asp Cys Leu Leu Leu
145                 150                 155                 160

Gly Leu Ser Ala Lys Tyr Ala Arg Pro Asp Trp Met Ile Leu Gln Val
                165                 170                 175

Leu Pro Ile Pro Pro Pro Val Arg Pro Ser Val Met Met Asp Thr
        180                 185                 190

Ser Ser Arg Ser Glu Asp Asp Leu Thr His Gln Leu Ala Met Ile Ile
        195                 200                 205

Arg His Asn Glu Asn Leu Arg Arg Gln Glu Arg Asn Gly Ala Pro Ala
        210                 215                 220

His Ile Ile Thr Glu Phe Ala Gln Leu Leu Gln Phe His Ile Ala Thr
225                 230                 235                 240

Tyr Phe Asp Asn Asp Leu Pro Gly Gln Pro Arg Ala Thr Gln Arg Ser
                245                 250                 255

Gly Arg Pro Ile Lys Ser Ile Cys Ser Arg Leu Lys Ala Lys Glu Gly
            260                 265                 270

Arg Ile Arg Gly Asn Leu Met Gly Lys Arg Val Asp Phe Ser Ala Arg
        275                 280                 285

Thr Val Ile Thr Pro Asp Pro Asn Ile Asn Ile Asp Gln Leu Gly Val
        290                 295                 300

Pro Trp Ser Ile Ala Leu Asn Leu Thr Tyr Pro Glu Thr Val Thr Pro
305                 310                 315                 320

Tyr Asn Ile Glu Arg Leu Lys Glu Leu Val Glu Tyr Gly Pro His Pro
                325                 330                 335

Pro Pro Gly Lys Thr Gly Ala Lys Tyr Ile Ile Arg Glu Asp Gly Gln
            340                 345                 350

Arg Leu Asp Leu Arg Tyr Val Lys Lys Ser Ser Asp Gln His Leu Glu
        355                 360                 365

Leu Gly Tyr Lys Val Glu Arg His Leu Asn Asp Gly Asp Phe Val Leu
    370                 375                 380

Phe Asn Arg Gln Pro Ser Leu His Lys Met Ser Ile Met Gly His Arg
385                 390                 395                 400

Ile Lys Ile Met Pro Tyr Ser Thr Phe Arg Leu Asn Leu Ser Val Thr
                405                 410                 415

Ser Pro Tyr Asn Ala Asp Phe Asp Gly Asp Glu Met Asn Met His Val
```

-continued

```
            420                 425                 430
Pro Gln Ser Phe Glu Thr Arg Ala Glu Val Leu Glu Leu Met Met Val
            435                 440                 445
Pro Lys Cys Ile Val Ser Pro Gln Ala Asn Arg Pro Val Met Gly Ile
            450                 455                 460
Val Gln Asp Thr Leu Leu Gly Cys Arg Lys Ile Thr Lys Arg Asp Thr
465                 470                 475                 480
Leu Ile Glu Lys Asp Val Phe Met Asn Ile Leu Met Trp Trp Glu Asp
                485                 490                 495
Phe Asp Gly Lys Val Pro Ala Pro Ala Ile Leu Lys Pro Arg Pro Ile
            500                 505                 510
Trp Thr Gly Lys Gln Val Phe Asn Leu Ile Ile Pro Lys Leu Ile Asn
            515                 520                 525
Leu Ile Arg Phe Ser Ala Trp His Ala Glu Thr Glu Thr Gly Phe Ile
            530                 535                 540
Thr Pro Gly Asp Thr Met Val Arg Ile Glu Lys Gly Glu Leu Leu Ser
545                 550                 555                 560
Gly Thr Leu Cys Lys Lys Thr Leu Gly Thr Gly Thr Gly Ser Leu Ile
                565                 570                 575
His Val Ile Trp Glu Glu Val Gly Pro Asp Ala Ala Arg Lys Phe Leu
            580                 585                 590
Gly His Thr Gln Trp Leu Val Asn Tyr Trp Leu Leu Gln Asn Gly Phe
            595                 600                 605
Ser Ile Gly Ile Gly Asp Thr Ile Ala Asp Ala Ser Thr Met Glu Lys
            610                 615                 620
Ile Asn Glu Thr Ile Gly Lys Ala Lys Asn Asp Val Lys Glu Leu Ile
625                 630                 635                 640
Lys Gln Ala Gln Glu Lys Ser Leu Glu Pro Glu Pro Gly Arg Thr Met
                645                 650                 655
Met Glu Ser Phe Glu Asn Arg Val Asn Gln Val Leu Asn Lys Ala Arg
            660                 665                 670
Asp Asp Ala Gly Ser Ser Ala Gln Lys Ser Leu Ser Glu Ser Asn Asn
            675                 680                 685
Leu Lys Ala Met Val Thr Ala Gly Ser Lys Gly Ser Phe Ile Asn Ile
            690                 695                 700
Ser Gln Met Thr Ala Cys Val Gly Gln Gln Asn Val Glu Gly Lys Arg
705                 710                 715                 720
Ile Pro Phe Gly Phe Val Asp Arg Thr Leu Pro His Phe Thr Lys Asp
                725                 730                 735
Asp Tyr Gly Pro Glu Ser Arg Gly Phe Val Glu Asn Ser Tyr Leu Arg
            740                 745                 750
Gly Leu Thr Pro Gln Glu Phe Phe Phe His Ala Met Gly Gly Arg Glu
            755                 760                 765
Gly Leu Ile Asp Thr Ala Val Lys Thr Ser Glu Thr Gly Tyr Ile Gln
            770                 775                 780
Arg Arg Leu Val Lys Ala Met Glu Asp Ile Met Val Lys Tyr Asp Gly
785                 790                 795                 800
Thr Val Arg Asn Ser Leu Gly Asp Val Ile Gln Phe Leu Tyr Gly Glu
                805                 810                 815
Asp Gly Met Asp Ala Val Trp Ile Glu Ser Gln Lys Leu Asp Ser Leu
            820                 825                 830
Lys Met Lys Lys Asn Glu Phe Asp Asn Val Tyr Arg Tyr Glu Leu Asp
            835                 840                 845
```

```
Asp Glu Asn Trp Arg Pro Thr Tyr Met Met Pro Glu Tyr Val Asp Asp
850                     855                 860

Leu Lys Thr Ile Arg Glu Phe Arg Asn Val Phe Glu Ala Glu Val Gln
865                 870                 875                 880

Lys Leu Glu Ala Asp Arg Leu Gln Leu Gly Thr Glu Ile Thr Thr Thr
                885                 890                 895

Gly Asp Asn Thr Trp Pro Met Pro Val Asn Leu Lys Arg Leu Ile Trp
            900                 905                 910

Asn Ala Gln Lys Thr Phe Lys Ile Asp Leu Arg Arg Pro Ser Asp Met
        915                 920                 925

His Pro Met Glu Ile Val Glu Ala Ile Asp Lys Leu Gln Glu Arg Leu
    930                 935                 940

Lys Val Val Pro Gly Asp Asp Ala Met Ser Ile Glu Ala Gln Lys Asn
945                 950                 955                 960

Ala Thr Leu Phe Phe Asn Ile Leu Leu Arg Ser Thr Phe Ala Ser Lys
                965                 970                 975

Arg Val Leu Lys Glu Tyr Arg Leu Thr Lys Glu Ser Phe Glu Trp Val
                980                 985                 990

Ile Gly Glu Ile Glu Ser Arg Phe Leu Gln Ser Leu Val Ala Pro Gly
            995                 1000                1005

Glu Met Ile Gly Cys Val Ala Ala Gln Ser Ile Gly Glu Pro Ala
    1010            1015                1020

Thr Gln Met Thr Leu Asn Thr Phe His Tyr Ala Gly Val Ser Ala
    1025            1030                1035

Lys Asn Val Thr Leu Gly Val Pro Arg Leu Arg Glu Ile Ile Asn
    1040            1045                1050

Val Ala Lys Lys Ile Lys Thr Pro Ser Leu Ser Val Phe Leu Lys
    1055            1060                1065

Pro Glu Val Gly Lys Lys Glu Leu Ala Lys Asn Val Gln Cys
    1070            1075                1080

Ala Leu Glu Tyr Thr Thr Leu Arg Ser Val Thr His Ala Thr Glu
    1085            1090                1095

Ile Trp Tyr Asp Pro Asp Pro Leu Gly Thr Ile Ile Glu Glu Asp
    1100            1105                1110

Val Glu Phe Val Arg Ser Tyr Tyr Glu Met Pro Asp Glu Asp Ile
    1115            1120                1125

Asp Pro Asp Lys Ile Ser Pro Trp Leu Leu Arg Ile Glu Leu Asn
    1130            1135                1140

Arg Glu Met Met Val Asp Lys Lys Leu Ser Met Ala Asp Ile Ala
    1145            1150                1155

Glu Lys Ile Asn His Glu Phe Asp Asp Asp Leu Ser Cys Ile Phe
    1160            1165                1170

Asn Asp Asp Asn Ala Asp Lys Leu Ile Leu Arg Val Arg Ile Thr
    1175            1180                1185

Asn Asp Glu Ala Pro Lys Gly Glu Ile Gln Asp Glu Ser Ala Glu
    1190            1195                1200

Asp Asp Val Phe Leu Lys Lys Ile Glu Gly Asn Met Leu Thr Glu
    1205            1210                1215

Met Ala Leu Arg Gly Ile Pro Asp Ile Asn Lys Val Phe Ile Lys
    1220            1225                1230

Tyr Gly Lys Val Asn Lys Phe Glu Glu Asn Glu Gly Phe Lys Pro
    1235            1240                1245
```

-continued

Asp Asn Glu Trp Met Leu Asp Thr Glu Gly Val Asn Leu Leu Ala
1250                1255                1260

Val Met Cys His Glu Asp Val Asp Ala Thr Arg Thr Thr Ser Asn
1265                1270                1275

His Leu Ile Glu Val Ile Glu Val Leu Gly Ile Glu Ala Val Arg
1280                1285                1290

Arg Ser Leu Leu Asp Glu Leu Arg Val Val Ile Ser Phe Asp Gly
1295                1300                1305

Ser Tyr Val Asn Tyr Arg His Leu Ala Ile Leu Cys Asp Thr Met
1310                1315                1320

Thr Tyr Arg Gly His Leu Met Ala Ile Thr Arg His Gly Ile Asn
1325                1330                1335

Arg Asn Asp Thr Gly Pro Leu Met Arg Cys Ser Phe Glu Glu Thr
1340                1345                1350

Val Asp Ile Leu Leu Asp Ala Ser Val Tyr Ala Glu Ser Asp Tyr
1355                1360                1365

Leu Arg Gly Val Thr Glu Asn Ile Met Val Gly Gln Leu Ala Pro
1370                1375                1380

Ile Gly Thr Gly Gly Cys Gly Leu Tyr Leu Asn Asp Lys Met Leu
1385                1390                1395

Gln Gln Ala Ile Glu Leu Gln Leu Pro Ser Tyr Val Asp Gly Leu
1400                1405                1410

Asp Tyr Gly Met Thr Pro Gly Arg Ser Pro Ile Ser Gly Thr Pro
1415                1420                1425

Tyr Ile Asp Gly Gly Met Met Ser Pro Met Leu Ser Pro Asn Phe
1430                1435                1440

Arg Ala Ser Pro Ile Thr Asp Ala Gln Phe Ser Pro Tyr Val Gly
1445                1450                1455

Gly Met Ser Phe Ser Pro Ile Pro Ser Asn Tyr Ser Pro Ser Ser
1460                1465                1470

Gly Gly Gly Tyr Ser Pro Ser Ser Pro Val Phe Ser Pro Gly Pro
1475                1480                1485

Gly Gln Ala Tyr Ser Pro Thr Ser Pro Ala Tyr Ser Pro Thr Ser
1490                1495                1500

Pro Ser Tyr Ser Pro Thr Ser Pro Ser Tyr Ser Pro Thr Ser Pro
1505                1510                1515

Ser Tyr Ser Pro Thr Ser Pro Ser Tyr Ser Pro Thr Ser Pro Ser
1520                1525                1530

Tyr Ser Pro Thr Ser Pro Ser Tyr Ser Pro Thr Ser Pro Ser Tyr
1535                1540                1545

Ser Pro Thr Ser Pro Ser Tyr Ser Pro Thr Ser Pro Ala Tyr Ser
1550                1555                1560

Pro Thr Ser Pro Gly Tyr Ser Pro Thr Ser Pro Ser Tyr Ser Pro
1565                1570                1575

Thr Ser Pro Asn Tyr Ser Pro Thr Ser Pro Ser Tyr Asn Pro Ser
1580                1585                1590

Ser Ala Lys Tyr Ser Pro Ser His Ala Tyr Ser Pro Ser Ser Pro
1595                1600                1605

Arg Met Met Ser Pro Tyr Ser Gln Thr Ser Pro Asn Tyr Ser Pro
1610                1615                1620

Thr Ser Pro Ser Tyr Ser Pro Thr Ser Pro Ser Tyr Ala Gln Pro
1625                1630                1635

Ser Pro Ser Tyr Ser Pro Thr Ser Pro His Thr Thr Ser Gly Gly

```
              1640                1645                1650

Pro  Ser  Pro  Asp  Tyr  Ser  Pro  Thr  Ser  Pro  Asn  Tyr  Ser  Pro  Ser
         1655                1660                1665

Ala  Ser  Tyr  Ser  Pro  Thr  Ala  Pro  Gly  Tyr  Ser  Pro  Ser  Ser  Thr
         1670                1675                1680

Gly  Pro  Gln  Thr  Thr  Asp  Lys  Asp  Asp  Glu  Ile  Ala  Pro
         1685                1690                1695

<210> SEQ ID NO 104
<211> LENGTH: 134
<212> TYPE: PRT
<213> ORGANISM: Lolium perenne

<400> SEQUENCE: 104

Met  Gly  Tyr  Ser  Ser  Lys  Arg  Leu  His  Ala  Ser  Ile  Leu  Ala  Val  Glu
 1                 5                  10                  15

Ala  Gly  Gln  Asp  Ala  Val  Ile  Arg  Met  Leu  Leu  Tyr  Gln  Arg  Ala  Asp
             20                  25                  30

Glu  Thr  Val  Ala  Pro  Tyr  Arg  Gly  His  Thr  Val  Ala  Glu  Phe  Thr  Arg
         35                  40                  45

Arg  Ile  Ser  Asp  Trp  Arg  Asn  Gly  Met  Ser  Gly  Cys  Gly  Ala  Lys  Asp
     50                  55                  60

Glu  Gly  Val  Lys  Val  Leu  Asp  Arg  Arg  Gln  Gly  Ala  Glu  Arg  Arg  Thr
 65                 70                  75                  80

Ile  Ser  Asn  Ile  Leu  Gly  Ala  Gly  Val  Asp  Ser  Leu  Gly  Tyr  Gln  Arg
                 85                  90                  95

Thr  Pro  Ala  Glu  Ala  Leu  Arg  Ile  Leu  Tyr  Gly  Ser  Arg  Asn  Glu  Gln
            100                 105                 110

Val  Pro  Gly  Gly  Phe  Leu  Pro  His  Gly  Ala  Asn  Gly  Thr  Ile  Ala  Arg
        115                 120                 125

Gly  Phe  Phe  Gln  Leu  Ala
        130

<210> SEQ ID NO 105
<211> LENGTH: 252
<212> TYPE: PRT
<213> ORGANISM: Lolium perenne

<400> SEQUENCE: 105

Met  Ala  Gln  Ser  Gly  Ser  Asp  Ala  Ala  Pro  Ile  Ser  Thr  His  Pro  Thr
 1                  5                  10                  15

Glu  Glu  Glu  Glu  Val  Thr  Val  Glu  Arg  Thr  Pro  Glu  Glu  Glu  Ala  Ala
             20                  25                  30

Arg  Leu  Arg  Tyr  Leu  Glu  Phe  Val  Gln  Gln  Ala  Ala  Ala  Gln  Ala  Val
         35                  40                  45

Val  Leu  Ala  Ala  Ala  Tyr  Ala  Tyr  Ala  Lys  Gln  Gly  Ala  Gly  Pro
     50                  55                  60

Leu  Arg  Pro  Gly  Val  Asp  His  Val  Glu  Gly  Thr  Val  Lys  Ala  Val  Val
 65                  70                  75                  80

Gly  Pro  Val  Tyr  Asp  Arg  Tyr  His  Ala  Val  Pro  Leu  Asp  Leu  Leu  Lys
             85                  90                  95

Phe  Leu  Asp  Arg  Lys  Val  Asp  Glu  Ser  Val  Gln  Glu  Leu  Asp  Arg  Arg
            100                 105                 110

Val  Pro  Pro  Val  Val  Lys  Glu  Val  Pro  Thr  Tyr  Ala  Arg  Ser  Ala  Ala
            115                 120                 125

Ala  Glu  Val  His  Lys  Thr  Gly  Leu  Val  Gly  Thr  Ala  Thr  Gly  Leu  Ala
```

```
            130                 135                 140
Lys Ser Ala Ile Ala Arg Ala Glu Pro Lys Ala Arg Asp Leu Tyr Thr
145                 150                 155                 160

Arg Tyr Glu Pro Val Ala Glu Arg Lys Ala Ala Glu Ala Trp Ala Ala
                165                 170                 175

Leu Asn Arg Leu Pro Leu Val Pro Ser Val Thr Arg Ala Val Leu Pro
                180                 185                 190

Thr Ala Ala Gln Leu Ser Ala Lys Tyr Asn Ser Ala Val Leu Asp Gly
                195                 200                 205

Ala Lys Arg Gly Asn Ser Val Ala Thr Tyr Leu Pro Leu Val Pro Thr
                210                 215                 220

Glu Arg Ile Ala Arg Val Phe Ser Tyr Pro Pro Thr Asp Ala Ala Ala
225                 230                 235                 240

Thr Ser Ala Pro Glu Met Gln Pro Ile Pro Thr Gln
                245                 250

<210> SEQ ID NO 106
<211> LENGTH: 702
<212> TYPE: PRT
<213> ORGANISM: Lolium perenne

<400> SEQUENCE: 106

Met Gln Glu Gly Gly Gly Gly Arg Ala Val Arg Ala Gly Arg Tyr Pro
1               5                   10                  15

Pro Leu Ala Ser Leu Val Val Ser Thr Ile Ala Ala Phe Ser Ala Val
                20                  25                  30

Ile Val Ile Ala Val Leu His Ser Ala Tyr Asp Asp Ala Leu Ser Arg
            35                  40                  45

Thr Arg Thr Leu Leu Gly His Asn Leu Glu Pro Thr Pro Trp His Pro
        50                  55                  60

Phe Pro His Asp Lys Gly Arg Pro Pro Arg Ala Ala Leu Arg Cys
65                  70                  75                  80

Ala Ser Tyr Leu Ala Cys Leu Pro Pro Leu Ser Gln Pro Arg Pro Ala
                85                  90                  95

Ala Ala Ala Leu Ala Pro Asn Asn Ala Ser Thr Arg Pro Arg Arg Gln
                100                 105                 110

Cys Pro Ser Tyr Phe Ser Ala Ile His Arg Asp Leu Ala Pro Trp Lys
            115                 120                 125

Arg Arg Ala Asp Gly Val Gly Gly Val Thr Arg Ala Leu Leu Glu Ser
        130                 135                 140

Ala Arg Ala Arg Ala Ser Met Arg Val Thr Ile Thr Gly Gly Gly Thr
145                 150                 155                 160

Arg Leu His Val Asp Leu Tyr Tyr Ala Cys Val Gln Ser Arg Ala Leu
                165                 170                 175

Phe Thr Val Trp Ser Leu Leu Gln Leu Met Arg Arg His Pro Gly Arg
                180                 185                 190

Val Pro Asp Val Asp Leu Met Phe Asp Cys Met Asp Arg Pro Ala Ile
                195                 200                 205

Asn Arg Thr Glu His Ser Ala Glu Gly Ala Pro Pro Pro Pro Pro Leu
                210                 215                 220

Phe Arg Tyr Cys Thr Thr Arg Asp His Phe Asp Ile Pro Phe Pro Asp
225                 230                 235                 240

Trp Ser Phe Trp Gly Trp Pro Glu Thr His Ile Glu Pro Trp Ser Arg
                245                 250                 255
```

```
Glu Phe Lys Ser Ile Arg Gln Gly Ala Lys Lys Val Arg Trp Pro Asp
                260                 265                 270

Arg Val Pro Thr Ala Tyr Trp Lys Gly Asn Pro Asp Val Ala Ser Pro
            275                 280                 285

Leu Arg Leu Ala Leu Leu Ala Cys Asn Asp Thr Asn Leu Trp Arg Ala
        290                 295                 300

Glu Ile Met Arg Gln Lys Lys Gln Trp Lys Asp Glu Leu Arg Arg Leu
305                 310                 315                 320

Lys Glu Met Lys Lys Arg Gly Lys Ser Asp Met Asp Ala Tyr Gly Tyr
                325                 330                 335

Ala Ser Ile Ala Gly Glu Asn Asp Gln Asp Pro Pro Glu Asn Val
            340                 345                 350

Ser Val Pro Leu Pro Asp Met Val Leu Pro Ser Phe Asp Cys Asp
                355                 360                 365

Asn Pro Thr Tyr Arg Tyr Arg Phe Leu Glu Pro Thr Ser Val Leu
            370                 375                 380

Ala Arg Pro Val Leu Asp Ala His Gly Trp Asp His Asp Cys Gly Tyr
385                 390                 395                 400

Asp Gly Val Ser Val Glu Glu Ser Leu Ala Leu Leu Ser Lys Phe Pro
                405                 410                 415

Gly Thr Val Ala Val Gln Val Thr Lys Asp Lys Lys Glu Phe Ser Ile
            420                 425                 430

His Leu Asp Ser Ser Ile Ser Ala Lys His Gly Glu Asp Ala Ser Ser
                435                 440                 445

Leu Ala Gly Phe Asp Ile Gln Thr Val Gly Arg Gln Leu Ala Tyr Ile
            450                 455                 460

Leu Arg Gly Glu Thr Lys Phe Lys Ser Ile Lys Lys Asn Lys Thr Thr
465                 470                 475                 480

Gly Gly Phe Ser Val Thr Phe Leu Gly Asp Ile Val Ala Thr Gly Leu
                485                 490                 495

Lys Val Glu Asp Gln Leu Ser Val Gly Lys Arg Leu Ala Leu Val Ala
            500                 505                 510

Ser Thr Gly Ala Met Arg Ala Gln Gly Asp Thr Ala Tyr Gly Ala Asn
        515                 520                 525

Leu Glu Met Arg Leu Lys Asp Lys Asp Tyr Pro Ile Gly Gln Ser Leu
530                 535                 540

Ser Thr Leu Gly Leu Ser Leu Met Lys Trp Arg Arg Asp Leu Ala Leu
545                 550                 555                 560

Gly Ala Asn Leu Gln Ser Gln Phe Ser Ile Gly Arg Gly Ser Lys Met
                565                 570                 575

Ala Val Arg Leu Gly Leu Asn Asn Lys Leu Ser Gly Gln Ile Thr Val
            580                 585                 590

Arg Thr Ser Thr Ser Glu Gln Met Pro Pro Asn Pro Met Glu Glu Glu
        595                 600                 605

Asp Pro Glu Ser Gly Glu Ser Asp Pro Asp His Met His Val Ile Gly
610                 615                 620

Gln Gln Trp Ser Gly Gly Val Asp Arg Leu Ala Gly Gly Glu Ser Pro
625                 630                 635                 640

Ser Ser Glu Val Tyr Ser Cys Ala Ser Val Met Ala Thr Lys Thr Thr
                645                 650                 655

Val Ala Thr Ser Asp Leu Ala Ser Gly Ser Gly Thr Val Gly Val
            660                 665                 670

Asp Asp Arg Glu Val Leu Met Val Lys Leu Gly Leu Arg Glu Glu Asp
```

```
                675                 680                 685
Leu Asp Asp Ile Val Leu Glu Glu Glu Gly Ser Gln His Glu
        690                 695                 700

<210> SEQ ID NO 107
<211> LENGTH: 340
<212> TYPE: PRT
<213> ORGANISM: Lolium perenne

<400> SEQUENCE: 107

Met Ser Glu Pro Asp Ala Lys Thr Thr Ile Leu Gly Ser Ser Val Phe
 1               5                  10                  15

Gln Phe Arg Val Asp Tyr Glu Gln Ser Lys Gln Leu Pro Ile Gly Lys
            20                  25                  30

Ala Val Arg Ser Asp Val Val Ser Ala Gly Gly His Leu Trp Arg Val
        35                  40                  45

Asp Phe Phe Pro Arg Gly Glu Thr Asp Glu Asp Asn Gly Glu Tyr Thr
    50                  55                  60

Ser Ile Phe Leu Ser His Met Ser Lys Ser Cys Ser Val Lys Ala Val
65                  70                  75                  80

Phe Glu Ala Phe Met Met Gly Gly Asn Ser Lys Leu Ser Thr Ser Leu
                85                  90                  95

Asn Ala Gly Arg Thr Leu Glu Thr Phe Glu Ile Leu Gly Asp Lys Asp
            100                 105                 110

Phe Val Asp Thr Trp Gly Trp Thr Arg Phe Ile Lys Arg Thr Ser Val
        115                 120                 125

Gln Glu Asn Phe Leu Thr Glu Gly His Ile Thr Leu Val Cys Ala Val
    130                 135                 140

Met Val Ile Asp Asp Ser Pro Ile Pro Val Pro Pro Ser Asp Ile Gly
145                 150                 155                 160

Thr His Ile Gly Arg Leu Leu Asp Glu Thr Asp Gly Thr Asp Val Ala
                165                 170                 175

Phe Ile Val Asp Asp Lys Thr Phe Pro Ala His Arg Ala Val Leu Ala
            180                 185                 190

Ala Arg Ser Pro Val Phe Lys Ala Glu Leu Phe Gly Ser Met Ala Glu
        195                 200                 205

Ser Thr Met Leu Ser Ile Thr Leu His Asp Ile Thr Pro Ala Thr Phe
    210                 215                 220

Lys Thr Leu Leu Arg Phe Ile Tyr Thr Asp Glu Leu Pro Ala Glu Asp
225                 230                 235                 240

Asp His Gln Asp Ser Ser Thr Glu Met Ile Gln Asn Leu Leu Ile Ala
                245                 250                 255

Ala Asp Arg Tyr Ala Leu Asp Arg Leu Lys Ile Ile Cys Ala Gln Lys
            260                 265                 270

Leu Trp Asp Lys Val Ser Val Asp Thr Val Ala Ala Ile Leu Gly Phe
        275                 280                 285

Ala Glu Thr Tyr Asn Cys Gln Glu Leu Lys Asn Lys Cys Ile Asp Phe
    290                 295                 300

Phe Ala Val Glu Asn Asn Phe Lys Gln Val Met Phe Thr Asp Gly Tyr
305                 310                 315                 320

Ala Met Leu Leu Leu Lys Phe Pro Leu Ile Ile Ala Glu Leu Lys Lys
                325                 330                 335

Arg Val Gly Ala
            340
```

<210> SEQ ID NO 108
<211> LENGTH: 275
<212> TYPE: PRT
<213> ORGANISM: Lolium perenne

<400> SEQUENCE: 108

Met Leu Arg Leu Thr Leu Pro Cys Pro Ser Thr Leu Ile Trp Gln
1               5                   10                  15

Glu Ile Leu Ser Trp His Arg Met Thr Cys Arg Pro Ala Gln Glu
            20                  25                  30

Ile Ser Leu Thr Glu Trp Trp Ile Glu Ala Arg Gln Arg Leu Ala Pro
        35                  40                  45

Ala Thr Leu Leu Ile Leu Trp Met Thr Trp Lys His Arg Asn Ser Cys
    50                  55                  60

Val Phe Glu Gly Ala Gln Pro Leu Ile Asn Gly Leu Ile Ser Ser Ile
65                  70                  75                  80

Lys Asp Glu Thr Ile Leu Trp Ala Lys Ala Ser Ala Thr Gly Leu Gly
                85                  90                  95

Val Val Thr Asp Asp Leu Gly Cys Ser Pro Trp Val Ile Leu Asn Arg
            100                 105                 110

Arg Phe Ile Glu Tyr Cys Ile Leu Gly Trp Glu Asn Leu Pro Arg Val
        115                 120                 125

Leu Leu Met Tyr Phe Asn Asn Val Val Leu Pro Gln Glu Gly Tyr Phe
    130                 135                 140

His Ser Val Ile Cys Asn Ser Val Asp Phe Arg Asn Ser Thr Val Asn
145                 150                 155                 160

Asn Asp Leu Arg Tyr Lys Val Trp Asp Glu Pro Pro Gln Thr Glu Pro
                165                 170                 175

Leu Phe Leu Asn Met Ala His Tyr Asp Glu Met Val Asn Ser Gly Gln
            180                 185                 190

Pro Phe Ala Arg Arg Phe Gln Lys Lys Glu Pro Leu Leu Asp Lys Ile
        195                 200                 205

Asp Asp Lys Leu Leu Arg Arg Pro Gly His Gly Pro Val Pro Gly Ala
    210                 215                 220

Trp Cys Ser Gly Arg Lys Gly Trp Phe Val Asp Ser Cys Ser Gln Trp
225                 230                 235                 240

Ser Asp Val Asn Val Val Lys Pro Gly Pro Gln Ala Leu Lys Leu Gln
                245                 250                 255

Gln Tyr Ile Asn Arg Thr Leu Glu Glu Ala Asn Ser Gly Ala Lys Ser
            260                 265                 270

Cys Arg Arg
        275

<210> SEQ ID NO 109
<211> LENGTH: 931
<212> TYPE: PRT
<213> ORGANISM: Lolium perenne

<400> SEQUENCE: 109

Met Gly Ala Ala Glu Leu Leu Ser Leu Cys Leu Val Leu Ala Ala Val
1               5                   10                  15

Ala Trp Thr Glu Gly Gln Arg Pro Arg Ala Val Lys Val Gly Ala Leu
            20                  25                  30

Phe Asp Tyr Asp Ser Thr Ile Gly Arg Ala Ala Gln Leu Ala Ile Glu
        35                  40                  45

```
Leu Ala Val Asp Asp Val Asn Ala Asp Arg Ser Val Leu Ala Gly Thr
 50                  55                  60
Lys Leu Asp Leu Ile Thr Ala Asp Thr Asn Cys Ser Gly Phe Val Gly
 65                  70                  75                  80
Thr Val Gln Ala Leu Gln Leu Met Glu Lys Asn Val Val Ala Val Val
                     85                  90                  95
Gly Pro Gln Ser Ser Val Ile Gly His Val Ile Ser His Phe Val Asn
                100                 105                 110
Glu Leu His Val Pro Leu Leu Ser Phe Ala Ala Thr Asp Pro Thr Leu
                115                 120                 125
Ser Ala Ser Glu Tyr Ser Tyr Phe Leu Arg Ser Thr Val Ser Asp Tyr
130                 135                 140
Phe Gln Met Arg Ala Ile Ala Ser Ile Ala Tyr Tyr Gln Trp Lys
145                 150                 155                 160
Glu Val Thr Ala Ile Phe Val Asp Asp Asp Tyr Gly Arg Gly Gly Val
                165                 170                 175
Ser Ala Leu Gly Asp Ala Leu Ala Thr Lys Arg Ala Arg Ile Ser Tyr
                180                 185                 190
Lys Ala Val Ile Pro Pro Asp Ala Asn Lys Asp Val Ile Ser Asp Ile
                195                 200                 205
Leu Phe Lys Val Asn Met Met Glu Ser Arg Val Leu Val Val His Val
210                 215                 220
Asn Pro Asp Thr Gly Leu Arg Leu Phe Ser Ile Ala Asn Glu Leu Gln
225                 230                 235                 240
Met Met Thr Gly Gly Tyr Val Trp Ile Val Thr Asp Trp Leu Ala Ala
                245                 250                 255
Val Leu Asp Ser Ser Lys Ser Gly Tyr Pro Lys Ser Met Ser Tyr Met
                260                 265                 270
Gln Gly Leu Ile Ala Leu Arg Gln His Ile Pro Asp Ser Ala Ala Lys
                275                 280                 285
Lys Lys Phe Ile Ser Lys Trp Asn Ile Ala Ala Arg Lys Arg Lys Ile
290                 295                 300
Ala Ser Gly Leu Asn Ser Tyr Gly Phe Tyr Ala Tyr Asp Ser Ile Trp
305                 310                 315                 320
Ile Val Ala His Ala Ile Asp Lys Phe Leu Asn Ser Gly Gln Gln Ile
                325                 330                 335
Asn Phe Ser Ala Asp Thr Arg Leu His Asp Ser Asp Thr Ser Ile Ile
                340                 345                 350
Thr Leu Ser Thr Leu Lys Ile Phe Asp Gly Gly Glu His Leu Leu Gln
                355                 360                 365
Gln Leu Leu Leu Thr Asn Phe Lys Gly Leu Thr Gly Leu Val Gln Phe
                370                 375                 380
Asp Ser Asp Arg Asn Leu Val His Pro Ala Tyr Glu Ile Leu Asn Ile
385                 390                 395                 400
Gly Gly Ser Val Pro Gly Leu Ile Gly Tyr Trp Ser Asn Tyr Ser Gly
                405                 410                 415
Leu Ser Val Ala Ala Pro Glu Thr Leu Tyr Gln Lys Pro Pro Asn Met
                420                 425                 430
Ser Ser Ser Ala Gln Gln Leu Ser Thr Met Val Trp Ser Gly Gly Ser
                435                 440                 445
Thr Thr Lys Pro Arg Gly Trp Val Phe Pro Asn Asn Gly Gln Pro Leu
450                 455                 460
Arg Ile Gly Val Pro Asn Lys Pro Ser Phe Lys Glu Phe Val Ala Ser
```

```
              465                 470                 475                 480
        Gly Lys Gly Pro Asp Asn Val Thr Gly Tyr Cys Ile Asp Ile Phe Asn
                        485                 490                 495
        Ala Ala Val Lys Leu Pro Tyr Pro Val Pro Ser Lys Phe Ile Ser
                    500                 505                 510
        Ile Gly Asp Gly Ile His Asn Pro Lys Tyr Asp Asp Ile Asn Met
                    515                 520                 525
        Val Ala Asn Asn Thr Ile Asp Val Ala Val Gly Asp Phe Ala Ile Ile
                    530                 535                 540
        Lys Asn Arg Thr Arg Ile Ala Glu Phe Thr Gln Pro Tyr Ile Glu Ser
        545                 550                 555                 560
        Gly Met Val Ile Val Ala Pro Val Lys Gln Ser Thr Ser Ser Ala Trp
                        565                 570                 575
        Ala Phe Phe Lys Pro Phe Thr Leu Glu Met Trp Cys Val Thr Gly Ala
                        580                 585                 590
        Leu Phe Val Phe Val Gly Ile Val Val Trp Ile Leu Glu His Arg Thr
                        595                 600                 605
        Asn Glu Glu Phe Arg Gly Thr Pro Gln Gln Val Arg Thr Ile Phe
            610                 615                 620
        Trp Phe Ala Phe Ser Thr Met Phe Phe Ala His Arg Glu Asn Thr Val
        625                 630                 635                 640
        Ser Gly Leu Gly Arg Phe Val Leu Ile Ile Trp Leu Phe Val Val Leu
                        645                 650                 655
        Ile Ile Asn Ser Ser Tyr Thr Ala Ser Leu Thr Ser Ile Leu Thr Val
                        660                 665                 670
        Gln Gln Leu Val Thr Gly Val Thr Gly Leu Asp Asn Leu Ile Ala Ser
                    675                 680                 685
        Thr Val Pro Ile Gly His Pro Ala Gly Lys Phe Ile Arg Asn Tyr Leu
                    690                 695                 700
        Ile Glu Glu Leu Asn Ile His Glu Ser Arg Leu Val Pro Leu Asn Thr
        705                 710                 715                 720
        Ile Gln Asp Tyr Ala Asp Ala Leu Asn Arg Gly Pro Lys Ala Gly Gly
                    725                 730                 735
        Val Ala Ala Val Ile Asp Glu Met Pro Cys Val Glu Leu Phe Leu Ser
                    740                 745                 750
        Tyr His Cys Asn Phe Arg Ile Val Gly Gln Glu Phe Thr Lys Glu Gly
                    755                 760                 765
        Trp Gly Phe Ala Phe Gln Arg Asp Ser Pro Leu Ala Ala Asp Met Ser
                    770                 775                 780
        Thr Ala Ile Leu Gln Leu Ser Glu Thr Gly Gln Leu Gln Arg Ile His
        785                 790                 795                 800
        Asp Glu Trp Leu Thr Arg Pro Ser Cys Ser Ser Asp Asp Ser Gly Leu
                        805                 810                 815
        Gly Pro Ser Arg Leu Asp Leu Gly Ser Phe Trp Gly Leu Phe Leu Leu
                        820                 825                 830
        Cys Ala Met Ile Cys Leu Phe Ser Leu Gly Ala Phe Phe Val Lys Ile
                        835                 840                 845
        Ser Cys Gln Tyr Ser Arg Tyr Ser Ser Ser Val Ala Ala Gly Glu Ser
                    850                 855                 860
        Ser Glu Ala Ser Pro Thr Ser Pro Ala Val Ser Glu Val His Pro Thr
        865                 870                 875                 880
        Lys Pro Lys Pro Arg Arg Leu Asp Ser Phe Lys Asp Leu Met His Phe
                        885                 890                 895
```

-continued

```
Val Asp Lys Lys Glu Glu Asp Val Lys Lys Glu Met Lys Gln Arg Ser
            900                 905                 910
Ser Asp Lys Asp Asn His Gly Val Gly Ser Ser Asp Thr His Phe Val
            915                 920                 925
Ser Ser Ala
        930

<210> SEQ ID NO 110
<211> LENGTH: 143
<212> TYPE: PRT
<213> ORGANISM: Lolium perenne

<400> SEQUENCE: 110

Met Ala Pro Ala Ser Thr Arg Ala Ala Ala Leu His Gly Val Thr
1               5                   10                  15
Leu Asp Asn Thr Asp Ala Leu Asp Cys Arg Leu Cys Cys Leu Pro Leu
                20                  25                  30
Lys Pro Pro Ile Phe Gln Cys Lys Val Gly His Val Val Cys Ser Pro
            35                  40                  45
Cys Arg Asp Lys Leu Gly Ala Ala Arg Arg Cys His Val Cys Arg Thr
50                  55                  60
Ala Thr Ser Gly Gly Tyr His Arg Asn His Asp Met Glu Lys Leu Leu
65                  70                  75                  80
Glu Ser Ile Arg Val Pro Cys Ser Asn Ala Ala Tyr Gly Cys Ala Ala
                85                  90                  95
Lys Pro Val Tyr Tyr Asp Arg Asp Thr His Leu Arg Leu Phe Cys Gln
            100                 105                 110
His Ala Pro Cys His Cys Asn Ile Glu Ala Cys Gly Phe Val Gly Ser
        115                 120                 125
Thr Leu Ser Ala Leu Leu Asp His Val Phe Ala Val His Val Glu
    130                 135                 140

<210> SEQ ID NO 111
<211> LENGTH: 851
<212> TYPE: PRT
<213> ORGANISM: Lolium perenne

<400> SEQUENCE: 111

Met Ser Thr Met Lys Gly Val Asp Asp Ala Phe Leu Gly Val Gly Asp
1               5                   10                  15
Lys Pro Gly Leu Asp Ile Trp Cys Ile Met Gly Thr Ser Val Val Pro
            20                  25                  30
Ile Ala Lys Asn Leu His Gly Lys Phe Tyr Thr Gly Asn Cys Tyr Ile
        35                  40                  45
Val Leu Ser Thr Ala Glu Leu Lys Arg Gly Ser Arg Gln His Ser Val
50                  55                  60
His Tyr Trp Val Gly Glu Glu Ala Lys Glu Glu His Cys Val Met Ala
65                  70                  75                  80
Ser Asp Lys Ala Phe Glu Leu Asp Ala Ala Leu Gly Ser Gln Ala Val
                85                  90                  95
Gln Tyr Arg Glu Met Gln Gly Glu Glu Ser Asp Lys Phe Leu Ser Tyr
            100                 105                 110
Phe Arg Pro Cys Ile Ile Pro Val Gln Gly Ser Phe Ser Ser His Trp
        115                 120                 125
Arg Arg Ser Ala Glu Glu Cys Asp Gln Thr Thr Met Phe Arg Cys Glu
    130                 135                 140
```

```
Gly Glu His Val Ala Arg Val Thr Glu Val Pro Phe Ser Arg Thr Ser
145                 150                 155                 160

Leu Asp His Lys Ala Ala Phe Ile Val Asp Thr Pro Leu Lys Ile Phe
            165                 170                 175

Leu Phe Ser Gly Cys Asn Ser Val Lys Thr Arg Ala Lys Ala Leu
            180                 185                 190

Asp Val Ile Lys Tyr Leu Arg Glu Asn Arg His Ser Gly Arg Cys Glu
            195                 200                 205

Ile Gly Thr Ile Glu Asp Gly Lys Leu Val Gly Asp Ser Asp Ala Gly
            210                 215                 220

Glu Phe Trp Asn Leu Phe Gly Gly Tyr Ala Pro Ile Pro Arg Asp Val
225                 230                 235                 240

Pro Asp Ala Ala Asn Gly Glu Leu Met Thr Thr Thr Ser Lys Lys Leu
            245                 250                 255

Phe Trp Ile Asn Lys Arg Lys Leu Val Pro Met Asp Ala His Leu Leu
            260                 265                 270

Asp Arg Glu Met Leu Lys Ser Asp Arg Ser Tyr Ile Leu Asp Cys Gly
            275                 280                 285

Thr Glu Ile Tyr Leu Trp Leu Gly Met Ala Thr Leu Val Ser Glu Arg
            290                 295                 300

Lys Ile Ser Ile Thr Val Leu Glu Asp Tyr Val Arg Ser Gln Gly Arg
305                 310                 315                 320

Ser Ser Ile Gly Gln Thr Val Ile Thr Thr Glu Gly His Glu Ile Ala
            325                 330                 335

Asp Phe Lys Leu Gln Phe Gln His Trp Pro Lys Asn Val Val Gln Lys
            340                 345                 350

Leu Tyr Glu Ala Gly Arg Glu Lys Val Ala Ala Ile Phe Lys His Gln
            355                 360                 365

Gly Tyr Asp Val Ala Glu Ile Pro Glu Asp Lys Pro Gln Gln Ser Ile
            370                 375                 380

Ser Ser Asn Gly Ser Leu Lys Val Trp Leu Val Asp Arg Gly Ser Val
385                 390                 395                 400

Thr Leu Leu Cys Thr Glu Glu Gln Glu Glu Leu Tyr Asn Gly Asp Cys
            405                 410                 415

Tyr Ile Val Gln Tyr Ser Tyr Val Glu Asp Gly Lys Asp Tyr Asn Leu
            420                 425                 430

Phe Phe Ser Trp Ser Gly Gln Asn Ser Val Gln Glu Asp Arg Leu Ala
            435                 440                 445

Ser Val Ser Leu Met Ser Ser Met Ser Asp Ser Val Lys Gly Pro Ala
            450                 455                 460

Val Val Gly Gln Val Ser Glu Ala Arg Glu Pro Glu Leu Phe Phe Leu
465                 470                 475                 480

Val Phe Lys Ser Leu Ile Ile Phe Lys Gly Gly Arg Ser Ala Ala Tyr
            485                 490                 495

Lys Asn Ser Val Leu Gln Lys Ser Asn Arg Thr Glu Gly Tyr Gln Lys
            500                 505                 510

Asp Gly Ala Ala Leu Phe Arg Val Gln Gly Leu Arg His Asp Cys Ala
            515                 520                 525

Arg Ala Val Gln Val Asp Leu Ile Ala Ser Ser Leu Asn Ser Ser His
            530                 535                 540

Cys Tyr Ile Leu Gln Asp Gly Pro Ser Phe Phe Thr Trp Thr Gly Ser
545                 550                 555                 560
```

Leu Ser Ser Pro Thr Glu His Val Ile Leu Asp Arg Met Met Asn Lys
            565                 570                 575

Leu Phe Pro Leu Lys Gln Ser Phe Leu Leu Lys Glu Gly Ser Glu Pro
            580                 585                 590

Asp His Phe Trp Lys Thr Leu Glu Gly Arg Ser Glu Tyr Ser Lys Glu
            595                 600                 605

Lys Cys Val Lys Ser Trp Pro Ala Asp Pro Arg Leu Tyr Thr Cys Thr
            610                 615                 620

Phe Gln Gln Cys Leu Phe Lys Ala Lys Glu Val Phe Thr Phe Cys Gln
625                 630                 635                 640

Asp Asp Leu Ala Thr Glu Glu Thr Leu Ile Leu Asp Cys Gly Glu Glu
            645                 650                 655

Ile Tyr Val Trp Val Gly Leu His Ser Gly Val Thr Ser Lys Glu His
            660                 665                 670

Ala Leu Asp Ile Gly Lys Met Phe Leu Gln Ala Gly Asn Ala Glu Asp
            675                 680                 685

Gly Arg Arg Ser Ile Phe Asp Thr Thr Val Tyr Ala Val Ala Glu Gly
            690                 695                 700

Asp Glu Pro Ala Phe Phe Thr Ser Phe Phe Asn Trp Asp Asn Ser Lys
705                 710                 715                 720

Gln Val Ala Ser Val Leu Gly Asn Ser Phe Glu Arg Lys Leu Ala Ile
            725                 730                 735

Leu Lys Gly Ile Ser Pro Lys Leu Glu Ala Pro Asp Arg Ser Leu Arg
            740                 745                 750

Arg Ser Ser Arg Arg Pro Gly Thr Ser Ser Glu Pro Thr Thr Pro
            755                 760                 765

Glu Gln His Gln Pro Ala Ala Arg Arg Thr Phe Gly Pro Ala Ser Ala
            770                 775                 780

Ser Val Gly Arg Val Ala Lys Glu Arg Ser Gly Ala Ser Pro Ala Leu
785                 790                 795                 800

Ser Pro Ser Pro Val Thr Pro Ser Trp Ser Cys Glu Glu Pro Arg Leu
            805                 810                 815

Val Leu Ala Val Val Ala Ile His Thr Val Gly Ser Ala Ala Ala Leu
            820                 825                 830

Pro Val His Ala Ala Arg Pro Leu Arg Tyr Ser His Cys Glu Pro Arg
            835                 840                 845

Ser Thr Thr
    850

<210> SEQ ID NO 112
<211> LENGTH: 626
<212> TYPE: PRT
<213> ORGANISM: Lolium perenne

<400> SEQUENCE: 112

Met Asp Tyr Thr Ser Asp Gly Asp Ser Glu Leu Glu Ala Tyr Gly Ser
1               5                   10                  15

Asp Thr Tyr Ala Leu Leu Leu Ser Gly Asp Ile Gln Val Met Asn Asp
            20                  25                  30

Glu Gly Leu Tyr Lys Cys Pro Phe Cys Ser Asp Glu Lys Asp Asp Tyr
            35                  40                  45

Asn Lys Tyr Asp Leu Leu Gln His Ala Leu Gly Val Gly Ala Ala His
            50                  55                  60

Asp Gln Gln Val Lys Glu Lys Val Asp His Arg Ala Leu Ala Lys His
65                  70                  75                  80

```
Leu Lys Asp Asp Glu Pro Ala Lys Ser His Ser Pro Leu Leu Gln Pro
                85                  90                  95

Ile Val Ile Asp Pro Gln Pro Gln His Asn Arg Asp Asp Leu Phe
            100                 105                 110

Val Trp Pro Trp Met Gly Ile Ile Val Asn Met Pro Ser Glu Tyr Val
            115                 120                 125

Gly Lys Ser Ala Asn Arg Leu Lys Glu His Phe Ser Arg Phe Tyr Pro
            130                 135                 140

Val Lys Val His His Val Tyr Ser Lys Gly Arg Pro Thr Gly Asn Ala
145                 150                 155                 160

Ile Val Glu Phe Gly Lys Asp Leu Val Gly Phe Arg Asn Ala Leu Thr
            165                 170                 175

Phe Glu Asn Gln Phe Glu Lys Glu Gly His Gly Lys Ile Gly Trp Gln
            180                 185                 190

Glu Lys Gln His Gly Gly Pro Glu Pro Phe Gly Trp Ile Ala Arg Ala
            195                 200                 205

Asp Asp Tyr Asn Ala Pro Gly Ala Ile Gly Asp Phe Leu Arg Lys Asn
            210                 215                 220

Gly Asp Leu Lys Thr Ala Asp Gly Val Glu Asp Glu Thr Met Lys
225                 230                 235                 240

Asn Asn Lys Leu Val Ala Ser Leu Ser Phe Lys Val Ile Glu Thr Asp
            245                 250                 255

Met His Ile Gln Glu Leu Lys Ser Val Tyr Gln Glu Arg Thr Ala Ser
            260                 265                 270

Leu Lys Arg Met Met Glu Gln Arg Glu Gln Leu Gln Ser Tyr Asn
            275                 280                 285

Gln Glu Ile Gln Lys Met Gln Gln Leu Ser Val Glu His Thr Lys Thr
            290                 295                 300

Ile Val Asp Glu Asn Lys Lys Leu Ser Leu Asp Leu Gln Ser Met Thr
305                 310                 315                 320

His Glu Leu Asp Ala Arg Ser Lys Gln Ile Asp Glu Leu Ala Ala Gln
            325                 330                 335

Thr Asp Cys Asp Arg Lys Asn Leu Glu Leu Glu Lys Gln Arg Asn Ala
            340                 345                 350

Met Lys Phe Asn His Leu Thr Leu Ala Glu Arg Glu Tyr Gln Lys Ala
            355                 360                 365

Asp Glu Asn Val Leu Lys Leu Val Glu Gln His Lys Arg Glu Lys Glu
            370                 375                 380

Thr Ala Leu Asn Asn Ile Lys Lys Leu Asn Glu Lys Leu His Leu Thr
385                 390                 395                 400

His Lys Leu Gln Leu Asp Ile Lys His Leu Thr Gly Lys Leu Glu Val
            405                 410                 415

Ile Lys Leu Thr Pro Gly Asn Glu Thr Ser Glu Ser Gly Lys Arg Ile
            420                 425                 430

Ala Glu Leu Thr Glu Glu Leu Arg Asp Lys Ile Glu Met Asp Tyr
            435                 440                 445

Thr Glu Asn Tyr Asn Gln Asp Leu Ile Val Gln Glu Lys Lys Thr Ala
            450                 455                 460

Val Glu Leu Gln Glu Ala Arg Lys Leu Ala Ile Asp Ala Ile Gln Arg
465                 470                 475                 480

Phe Pro Gly Gln Thr Ile Asp Lys Ala His Ile Gly Ile Lys Met Ile
            485                 490                 495
```

```
Gly Glu Leu Asp Leu Lys Ala Phe Ser Asn Val Cys Arg Gln Lys Phe
                500                 505                 510

Pro Lys Asp Asp Ala Glu Val Glu Ser Val Lys Leu Cys Ser Lys Trp
            515                 520                 525

Gln Asn Glu Ile Ser Asn Pro Asn Trp His Pro Phe Val Ala Ala Met
        530                 535                 540

Leu Asn Gly Lys Glu Ser Glu Val Ile Arg Glu Asp Asp Lys Lys Leu
545                 550                 555                 560

Gln Glu Leu Lys Glu Glu Tyr Gly Glu Ala Tyr Ala Ala Val Thr
                565                 570                 575

Thr Ala Leu Thr Glu Leu Asn Glu His Ser Ser Gly Ser Arg Val
                580                 585                 590

Pro Phe Pro Glu Met Trp Asn Tyr Lys Glu Gly Arg Lys Ala Lys Thr
            595                 600                 605

Lys Glu Ile Val Gln His Val Ile Lys Leu Ala Lys Ala Ser Lys Arg
            610                 615                 620

Gly Arg
625

<210> SEQ ID NO 113
<211> LENGTH: 84
<212> TYPE: PRT
<213> ORGANISM: Lolium perenne

<400> SEQUENCE: 113

Met Ile Gly Met Ile Asp Gly Arg Thr Glu Leu Lys Pro Ala Pro Glu
1               5                   10                  15

Thr Ser Ala Gly Asp Met Arg Gln Leu Gln Val Leu Asn Val Leu Val
            20                  25                  30

Ser Gly Glu Val Ala Asp Leu Glu Ser Gly Tyr Val Thr Asp Gly Thr
        35                  40                  45

Pro Leu Ile Val Arg Thr Tyr Leu Ile Leu Glu Ile Thr Val Met Ala
    50                  55                  60

Ala Lys Ile Ala Tyr Glu Asn Ala Ala Phe Val Glu Asn Val Val Asn
65                  70                  75                  80

Asn Val Trp Lys

<210> SEQ ID NO 114
<211> LENGTH: 431
<212> TYPE: PRT
<213> ORGANISM: Lolium perenne

<400> SEQUENCE: 114

Met Ala Glu Leu Asn Tyr Ile Pro Asn Arg Val Ala Gln Gln Leu Ala
1               5                   10                  15

Gly Lys Gln Ser Leu Leu Ile Gly Val Ala Thr Ser Ser Leu Ala Leu
            20                  25                  30

His Ala Pro Ser Gln Ile Val Ala Ile Lys Ser Arg Ala Asp Gln
        35                  40                  45

Leu Gly Ala Ser Val Val Val Ser Met Val Glu Arg Ser Gly Val Glu
    50                  55                  60

Ala Cys Lys Ala Ala Val His Asn Leu Leu Gln Arg Val Ser Gly
65                  70                  75                  80

Leu Ile Ile Asn Tyr Pro Leu Asp Asp Gln Asp Ala Ile Ala Val Glu
                85                  90                  95

Ala Ala Cys Thr Asn Val Pro Ala Leu Phe Leu Asp Val Ser Asp Gln
```

```
                  100                 105                 110
Thr Pro Ile Asn Ser Ile Ile Phe Ser His Glu Asp Glu His Arg His
            115                 120                 125
Ala Leu Gly Arg Arg Leu Glu Thr Trp Lys Asp Val Val Ala Val Leu
130                 135                 140
Ala Ala Val Glu Val Val Glu Arg Arg Val Pro Leu Val Ala Glu Val
145                 150                 155                 160
Arg Ala Asp Val Ala Leu His Leu Val Glu Gln Val Gln Val Val His
                165                 170                 175
Gln Phe Val Glu Asn Val Ala Ala Ala Leu Asn Glu Asp Gly Ala
            180                 185                 190
Val Gly Val Gly Val Arg Val Asp Gly Ala Gly Ala Leu Pro Ala
        195                 200                 205
His Val Ala Gly Arg Cys Val Arg Gly Ala Gly Ile Val Glu Ala Gly
        210                 215                 220
Asp Ala Ala Glu Leu Val Phe Lys Ala Ala Thr Ser Leu Asp Ser Val
225                 230                 235                 240
Leu Trp Thr Thr Met Ile Ser Ala Tyr Gly Lys Ser Gly Arg Ala Gln
                245                 250                 255
Asp Ala Val Ser Met Phe Asp Arg Met Ala His Leu Gly Ile Lys Arg
                260                 265                 270
Asp Gly Val Ala Tyr Leu Ala Val Leu Ser Ala Cys Ser His Gly Gly
            275                 280                 285
Leu Val Arg Glu Gly Trp His Tyr Phe Lys Val Leu Phe Asp Gly Gln
        290                 295                 300
Ser Ser Val Lys Leu Gln Pro Glu His Tyr Gly Cys Met Ala Asp Leu
305                 310                 315                 320
Ile Cys Arg Arg Gly Cys Leu Gln Asp Ala Leu Glu Phe Ile Glu Ser
                325                 330                 335
Met Pro Phe Asp Ser Ser Val Ala Ala Trp Ser Ala Leu Leu Asn Ser
                340                 345                 350
Cys Arg Ile Tyr Arg Asp Ala Lys Leu Gly Gln Leu Ala Ala Ser Arg
            355                 360                 365
Leu Leu Lys Leu Asp Pro Gly Asn His Ser Asn Trp Val Ala Leu Ser
370                 375                 380
Ser Ile His Ala Leu Glu Gly Asp Trp His Glu Thr Trp Met Ile Arg
385                 390                 395                 400
Glu Asn Met Asn Lys Glu Trp Val Asn Phe Phe Ile Ile Ile
                405                 410                 415
Ser Phe Tyr Ser Thr Ala Met Val Ile Thr Tyr Met Ala Ala Arg
            420                 425                 430

<210> SEQ ID NO 115
<211> LENGTH: 664
<212> TYPE: PRT
<213> ORGANISM: Lolium perenne
<220> FEATURE:
<221> NAME/KEY: misc_feature
<222> LOCATION: (128)..(152)
<223> OTHER INFORMATION: Xaa can be any naturally occurring amino acid
<220> FEATURE:
<221> NAME/KEY: misc_feature
<222> LOCATION: (193)..(205)
<223> OTHER INFORMATION: Xaa can be any naturally occurring amino acid
<220> FEATURE:
<221> NAME/KEY: misc_feature
<222> LOCATION: (344)..(363)
<223> OTHER INFORMATION: Xaa can be any naturally occurring amino acid
```

```
<220> FEATURE:
<221> NAME/KEY: misc_feature
<222> LOCATION: (401)..(407)
<223> OTHER INFORMATION: Xaa can be any naturally occurring amino acid
<220> FEATURE:
<221> NAME/KEY: misc_feature
<222> LOCATION: (492)..(492)
<223> OTHER INFORMATION: Xaa can be any naturally occurring amino acid
<220> FEATURE:
<221> NAME/KEY: misc_feature
<222> LOCATION: (533)..(543)
<223> OTHER INFORMATION: Xaa can be any naturally occurring amino acid
<220> FEATURE:
<221> NAME/KEY: misc_feature
<222> LOCATION: (610)..(610)
<223> OTHER INFORMATION: Xaa can be any naturally occurring amino acid

<400> SEQUENCE: 115
```

Pro Pro His Glu Pro Pro Thr Gly Pro Val Ala Val Ala Val Ala
1               5                   10                  15

Ala Ser Asn Ile Arg Pro Gln Asn Pro Ser Pro Ala Thr Ser Thr Ala
            20                  25                  30

Ala Pro Arg His Gly His Gln Arg Gln Leu Pro Glu Gly Arg Arg Gly
        35                  40                  45

Glu Gln Pro Gly Gln Gly Glu Ala Ala Val His Gly Val Arg Glu
    50                  55                  60

Val Pro Ala Ala Gly Ser Pro Ala Glu Thr Ile Asp Ala Thr Glu Met
65                  70                  75                  80

Glu Lys Met Asp Asn Ile Gly Pro Asn Ile Trp Lys Asp Gly Ile Gln
                85                  90                  95

Thr Ser Glu Glu Asn Cys Cys Glu Gly Ile His Phe Ile Cys Cys Lys
            100                 105                 110

His His Tyr Phe Val Ser Cys Lys Phe Ser Arg Asn Ala Lys Val Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Ser Leu Asn Thr Asn Phe Asp Leu
145                 150                 155                 160

His Ile Leu Ser Lys Phe Ser Leu Phe Asn His Phe Lys Pro Arg Ser
                165                 170                 175

Gly Met Pro Lys Tyr Asp Gly Cys Cys Phe Tyr Ile Gly Thr Pro Gln
            180                 185                 190

Xaa Xaa Xaa Xaa Xaa Xaa Xaa Xaa Xaa Xaa Xaa Ile Thr Phe
    195                 200                 205

Phe Ala Leu Lys Leu Leu Val Leu Pro Lys Leu Gly Tyr Leu His Cys
210                 215                 220

Met Gln His Ser Tyr Tyr Lys His Ile Lys Arg Gln Ile Arg Trp Leu
225                 230                 235                 240

Gly Met Ala Leu Leu Leu His Ala Arg Leu Arg Arg Gln Leu Leu Met
            245                 250                 255

Leu Thr Gln Leu Leu Trp Arg Pro Arg Met Leu His Arg Phe Gln
            260                 265                 270

Gly Gln Leu Leu Gly Trp Val Gln Ile Ile Gln Met Arg Val Asn Leu
    275                 280                 285

Met Ile Pro Ser Arg Arg Ser Glu Lys Met Arg Ser Cys Ser Ile
    290                 295                 300

Trp Leu Arg Thr Ser Val Leu Gly Thr Leu Gln Phe Gly Lys Gln Thr
305                 310                 315                 320

Asn Gln Arg Leu Gln Arg Leu Gln Arg Gln Gln Leu Leu Gln Leu Ile
               325                 330                 335

His Trp Met Asn Arg Asp Asp Xaa Xaa Xaa Xaa Xaa Xaa Xaa Xaa Xaa
           340                 345                 350

Xaa Xaa Xaa Xaa Xaa Xaa Xaa Xaa Xaa Xaa Glu Ala His Met Trp
       355                 360                 365

Arg Thr Glu Leu Gly Lys Ala Arg Glu Gln Ala Val Ile Gln Glu Ala
370                 375                 380

Thr Ile Ala Arg Ala Glu Glu Lys Val Arg Val Ser Glu Ala Asp Ala
385                 390                 395                 400

Xaa Xaa Xaa Xaa Xaa Xaa Xaa Val Arg Ile Lys Glu Ala Ala Glu Asn
               405                 410                 415

Leu His Ala Val Glu Lys Glu Lys Glu Glu Leu Leu Ala Leu Ile Gly
           420                 425                 430

Val Leu Gln Ser Gln Val Gln Arg Asp Gln Ser Ser Thr Lys Gln Val
       435                 440                 445

Cys Glu Glu Arg Ser Glu Ser Cys Ser Gly Ala Asp Asn Ser Pro Pro
450                 455                 460

Leu Thr Lys His Val Asp Ala Ser Asp Asp Val Asp Lys Ala Cys
465                 470                 475                 480

Val Ser Asp Ser Arg Ser Val Leu Val Ser Ser Xaa His Arg Ser Pro
               485                 490                 495

Ala Cys Cys Gly Trp Gly Gly His Pro Ser Asn Trp Arg Cys Arg Met
           500                 505                 510

Gly Leu Pro Ala Ala Arg Ser Ile Asp Arg Cys Pro Gly Ser Leu Pro
       515                 520                 525

Gly Arg Arg Arg Xaa Xaa Xaa Xaa Xaa Xaa Xaa Xaa Xaa Xaa Thr
530                 535                 540

Ser Pro Ser Tyr Ala Gly Arg Gly Asn Thr Ser Leu Lys Val Leu Glu
545                 550                 555                 560

Leu Pro His Thr Phe Leu Gly Gly Cys Asp Tyr Gly Asn Cys Gln Gly
               565                 570                 575

Phe Glu Ser Ser Arg Glu Leu Leu Ser Gln Val Phe Ala Leu Leu Pro
           580                 585                 590

Gly Cys Met Ser Ile Val Phe Lys Tyr Ala Thr Gln Lys Met Leu Arg
       595                 600                 605

Val Xaa Leu Cys Asp Cys Lys Leu Phe Thr Ser Ser Pro Ser Ala Ile
610                 615                 620

Ile Trp Leu Ser Val His Asp Asn Cys Asp Val Lys Val Cys Leu Glu
625                 630                 635                 640

Val Gln Gln Leu Asp Ile Ser Leu Trp Asn Lys Arg Lys Ser Lys Ser
               645                 650                 655

Cys Ala Cys Leu Val Trp Met Leu
           660

<210> SEQ ID NO 116
<211> LENGTH: 718
<212> TYPE: PRT
<213> ORGANISM: Lolium perenne

<400> SEQUENCE: 116

Met Leu His Glu Leu Leu Leu Ala Leu Leu Gly Phe Thr Gly Asp Phe
1               5                   10                  15

Val Ile Asp Asn Ser Ser Ser Ser Ala Arg Arg Arg Pro Ser Pro
            20                  25                  30

```
Ala Glu Ser Val Ala Ala Gly Asp Ala Asp Ala Gly Pro Ala Phe Arg
        35                  40                  45

Leu Ala Pro Asp Leu Thr Phe Leu Gln Pro Ser Glu Arg Ser Ala Ile
 50                  55                  60

Glu Arg Leu Ile Ser Leu Gly Phe Tyr Arg Glu Leu Asn Arg Phe
 65              70                  75                  80

Ala Thr Glu Ser Arg Asp Leu Ser Trp Ile Gln Ser Ser Val Asp Val
                 85                  90                  95

Ser Ser Pro Asn Ala Asp Ile Thr Leu Lys Gly Lys Val Arg Lys Gly
            100                 105                 110

Ser Ala Tyr Arg Arg Ala Ile Gly Asn Gly Ile Ala Glu Ile Leu Ser
            115                 120                 125

Val Tyr Arg Ser Ala Val Leu Gln Val Glu Gln Asn Leu Leu Ser Asp
        130                 135                 140

Pro Leu Pro Ile Leu Ala Thr Val Thr His Gly Leu Asn Lys Phe Glu
145                 150                 155                 160

Val Leu Leu Pro Pro Leu Tyr Glu Leu Val Met Glu Ile Glu Gln Lys
                165                 170                 175

Asp Ile Lys Gly Gly Gln Leu Leu Asn Leu Leu His Lys Arg Cys His
            180                 185                 190

Cys Gly Val Pro Glu Leu Gln Ser Cys Ile Gln Arg Gln Val Asp Arg
        195                 200                 205

Asp Glu Glu Asn Glu Ser Ala Gln Ser Asp Val Ala Asp Lys Phe Ala
    210                 215                 220

Gln Lys Leu Ala Lys Asp Thr Ser Leu Thr Ser Trp His Ser Gly Phe
225                 230                 235                 240

His Val Ser Leu Asp Met Leu Pro Glu Tyr Ile His Met Arg Val Ala
                245                 250                 255

Glu Ser Ile Leu Phe Ala Gly Lys Ala Ile Arg Val Leu Arg Asn Pro
            260                 265                 270

Ser Pro Gly Ala Thr Leu Gln Glu Pro Ala Asn Gln Ser Gln Ile Leu
        275                 280                 285

Lys Gly Ser His Arg Met Gln Thr Phe Thr Gly Ser Gly Ala Leu
            290                 295                 300

Lys Glu Leu Pro Asn Phe Ser Asn Ile Ser Ala Glu Glu Leu Leu Pro
305                 310                 315                 320

Gln Val Glu Ala Asp Lys Val Asp Ala Met Leu Lys Gln Leu Lys His
                325                 330                 335

Ser Ser Glu Phe His Lys Arg Leu Phe Glu Ser Ala Val Ser Ser Ile
            340                 345                 350

Arg Thr Ile Ala Ala Asn His Leu Trp Gln Leu Val Val Arg Ala
        355                 360                 365

Asp Leu Asn Gly His Leu Lys Ala Leu Lys Asp Tyr Phe Leu Leu Ala
    370                 375                 380

Lys Gly Asp Phe Phe Gln Cys Phe Leu Glu Glu Ser Arg Gln Leu Met
385                 390                 395                 400

Arg Leu Pro Pro Arg Gln Ser Thr Ala Glu Ala Asp Leu Ile Val Pro
                405                 410                 415

Phe Gln Leu Ala Ala Leu Lys Thr Ile Gly Asp Glu Asp Lys Tyr Phe
            420                 425                 430

Thr Arg Val Ser Leu Arg Met Pro Leu Phe Gly Met Lys Ser Ser Thr
        435                 440                 445
```

```
Ser Gln Lys Asp Leu Gln Lys Ser Asn Thr Pro Asp Leu Ser Ser Gln
        450                 455                 460

Gly Lys Ala Ser Ser Glu Leu Ala Leu Asp Gly Trp His Ser Ile Ala
465                 470                 475                 480

Leu Glu Tyr Ser Val Asp Trp Pro Leu Gln Leu Phe Phe Thr Pro Asp
                485                 490                 495

Val Leu Ser Lys Tyr Arg Lys Val Phe Gln Tyr Leu Ile Arg Leu Lys
            500                 505                 510

Arg Thr Gln Met Glu Leu Glu Lys Ser Trp Thr Ala Val Met His Gln
                515                 520                 525

Asp His Val Asp Phe Ser Asp Tyr Cys Lys Asp Arg Lys Asn Ser Ser
530                 535                 540

Ala Thr Gln Leu Arg Arg Leu Arg Thr Lys Pro Phe Trp Arg Val Arg
545                 550                 555                 560

Glu His Met Ala Phe Leu Ile Arg Asn Leu Gln Phe Tyr Ile Gln Val
                565                 570                 575

Asp Val Ile Glu Ser Gln Trp Asn Val Leu Gln Thr His Val Gln Asp
            580                 585                 590

Ser His Asp Phe Thr Glu Leu Val Thr Phe His Gln Asp Tyr Leu Ser
        595                 600                 605

Ala Leu Ile Ser Gln Ser Phe Leu Asp Ile Gly Ser Val Ser Arg Ile
        610                 615                 620

Leu Asp Ser Ile Met Lys Leu Cys Leu Gln Phe Cys Trp Ser Ile Glu
625                 630                 635                 640

His Tyr Glu Thr Gly Ala Asn Met Phe Glu Ile Asp His Ile Thr Glu
                645                 650                 655

Glu Phe Asn Lys Lys Ser Asn Ser Leu Tyr Thr Ile Leu Arg Ser Ser
                660                 665                 670

Arg Leu Ala Gly Ser Gln Arg Ala Pro Phe Leu Arg Gln Phe Leu Met
            675                 680                 685

Arg Leu Asn Phe Asn Ser Phe Phe Glu Thr Thr Ala Arg Gly Val Met
            690                 695                 700

Asn Ser Gly Arg Leu Arg Pro Asn Thr Ala Gly Thr Gln Leu
705                 710                 715

<210> SEQ ID NO 117
<211> LENGTH: 818
<212> TYPE: PRT
<213> ORGANISM: Lolium perenne

<400> SEQUENCE: 117

Met Gly Gln Gln Val Phe Ala Glu His Pro Val Ser Ala Pro
1               5                   10                  15

Gly Ala His Pro Cys Pro Tyr Val Ala Tyr Leu Gln Pro Leu Pro Ser
                20                  25                  30

Leu Ala Ser Ser Ser Ser Ala His Val Pro Glu Arg Thr Met Asp Gly
            35                  40                  45

Ser Val Tyr His Asp His Trp Asn His Leu Ala Gly Pro Ser Asp Gly
        50                  55                  60

Arg Pro Leu His Thr Val Pro Pro Thr Asp Phe His Asn His Trp
65                  70                  75                  80

Ala His Leu Pro His Ser Tyr Ala Gln Pro Asn Ser Asn Asn Gly Leu
                85                  90                  95

Thr Glu Gln Pro Gly Val Pro Phe Gly Thr Met Arg Ala Ala Arg Ala
                100                 105                 110
```

```
Asp Gly Asp Ile Gln Arg Arg Gly Ser Val Ile Ser Pro Ser Tyr Phe
            115                 120                 125

Ser Asn Gly Ser Gly Ser Arg Ser Arg Ala Pro Asn Val Pro Pro Leu
    130                 135                 140

Val Pro Gln Phe Met Arg Gly His Gly Asn Ile Asn Glu Gln Tyr Gln
145                 150                 155                 160

Gln Asn Pro Ser Ser Leu Phe Ala Gly Ala His Arg Ser Gly Gly
            165                 170                 175

Met Arg Ser Ala Pro Pro Gln Pro Glu Asn Pro Thr Phe Cys Leu
            180                 185                 190

Phe Pro Pro Gly Ser Ser Gly His Ser Ser Met Glu Thr Asp Asp Ala
            195                 200                 205

Gly Gly Ser Arg Phe Tyr Ala Trp Glu Arg Asp Arg Phe Ala Pro Tyr
            210                 215                 220

Pro Leu Met Pro Val Asp Cys Glu Thr Ser Trp Trp Ser Ser Gln Gln
225                 230                 235                 240

Ser His Gly Ala Ser Glu Ser Thr Ala Ala Pro Ala Pro Ala Pro Ala
            245                 250                 255

Pro Arg Arg Leu Phe Gly Gln Trp Ile Gly Leu Gly Arg Gly Ala Ala
            260                 265                 270

Thr Leu Gly Ile Leu Gln Gln Leu His Pro Trp Arg Met Ile Pro Met
            275                 280                 285

Ile Ser Ile Tyr Ala Glu Asp Ile Met Ala Ile Lys Glu Ile Leu Asn
            290                 295                 300

Leu Phe Trp Arg Thr Ser Gly Leu Gln Val Asn Phe Ser Lys Ser Ser
305                 310                 315                 320

Ala Thr Leu Ile His Cys Ser Glu Glu Asp Thr Asp Ala Ile Gly Gln
            325                 330                 335

His Phe Arg Cys Pro Ser Val Gln Phe Pro Ile Ile Tyr Leu Gly Ile
            340                 345                 350

Ser Leu Thr Ala Arg Lys Ser Thr Ala Ala Gln Met Gln Pro Leu Ile
            355                 360                 365

Glu Lys Ala Arg Asp Asn Leu Pro Thr Trp Lys Ala Arg Leu Met Asn
            370                 375                 380

Lys Ser Gly Arg Leu Glu Leu Ile Lys Ser Val Leu Ser Ala Ile Pro
385                 390                 395                 400

Met His Gln Leu Leu Val Leu Ala Pro Pro Lys Lys Ser Thr Lys Gln
            405                 410                 415

Leu Glu Lys Asn Arg Ala Trp Ile Ser Leu Asp Cys Asp Leu Glu Arg
            420                 425                 430

Ala Gly Leu Thr Leu Arg Leu Arg Trp Leu Trp Tyr Ser His Thr Asp
            435                 440                 445

Met Asn Arg Ala Trp Ser Asn Leu Glu Leu Gln Phe Ser Ala Glu Glu
            450                 455                 460

His Thr Leu Phe Phe Thr Ser Thr Ser Met Ser Ala Gly Asn Gly Gln
465                 470                 475                 480

Thr Ala Leu Phe Trp Asp Asp Arg Trp Ile Ser Gly Arg Ser Ile Ser
            485                 490                 495

Glu Ile Ala Pro Gln Leu His Ala Cys Arg Pro Lys Arg Arg Trp Lys
            500                 505                 510

Ala Pro Glu Thr Met Leu Arg Leu Thr Leu Pro Cys Pro Ser Thr Leu
            515                 520                 525
```

```
Leu Ile Trp Gln Glu Ile Leu Ser Trp His Arg Met Thr Cys Arg Pro
            530                 535                 540

Pro Ala Gln Glu Ile Ser Leu Thr Glu Trp Trp Ile Glu Ala Arg Gln
545                 550                 555                 560

Arg Leu Ala Pro Ala Thr Leu Leu Ile Leu Trp Met Thr Trp Lys His
                565                 570                 575

Arg Asn Ser Cys Val Phe Glu Gly Ala Gln Pro Leu Ile Asn Gly Leu
            580                 585                 590

Ile Ser Ser Ile Lys Asp Glu Thr Ile Leu Trp Ala Lys Ala Ser Ala
        595                 600                 605

Thr Gly Leu Gly Val Val Thr Asp Asp Leu Gly Cys Thr Leu Val Ser
    610                 615                 620

Phe Pro Leu Phe Phe Ser Arg Thr Arg Arg Lys Ser Pro Ser His Phe
625                 630                 635                 640

Ile Lys Leu Glu Lys Glu Gly Ser Pro Trp Val Ile Leu Asn Arg Arg
                645                 650                 655

Phe Ile Glu Tyr Cys Ile Leu Gly Trp Glu Asn Leu Pro Arg Val Leu
            660                 665                 670

Leu Met Tyr Phe Asn Asn Val Val Leu Pro Gln Glu Gly Tyr Phe His
        675                 680                 685

Ser Val Ile Cys Asn Ser Val Asp Phe Arg Asn Ser Thr Val Asn Asn
    690                 695                 700

Asp Leu Arg Tyr Lys Val Trp Asp Glu Pro Gln Thr Glu Pro Leu
705                 710                 715                 720

Phe Leu Asn Met Ala His Tyr Asp Glu Met Val Asn Ser Gly Gln Pro
                725                 730                 735

Phe Ala Arg Arg Phe Gln Lys Lys Glu Pro Leu Leu Asp Lys Ile Asp
            740                 745                 750

Asp Lys Leu Leu Arg Arg Pro Gly His Gly Pro Val Pro Gly Ala Trp
        755                 760                 765

Cys Ser Gly Arg Lys Gly Trp Phe Val Asp Ser Cys Ser Gln Trp Ser
    770                 775                 780

Asp Val Asn Val Val Lys Pro Gly Pro Gln Ala Leu Lys Leu Gln Gln
785                 790                 795                 800

Tyr Ile Asn Arg Thr Leu Glu Glu Ala Asn Ser Gly Ala Lys Ser Cys
                805                 810                 815

Arg Arg

<210> SEQ ID NO 118
<211> LENGTH: 407
<212> TYPE: PRT
<213> ORGANISM: Lolium perenne

<400> SEQUENCE: 118

Met Lys Val His Phe Ser Ala Lys Leu Leu Ser Gly Pro Val Pro Val
1               5                   10                  15

Tyr Leu Leu Ala Leu Ala Val Leu Ile Leu Leu Thr His Ala His Tyr
                20                  25                  30

Met Gly His Val Gly Val Gly Val Pro Pro Ala Ala Lys Leu Glu Glu
            35                  40                  45

Pro Val Val Ser Val Met Lys Gln Cys Asp Ile Phe Arg Gly Glu Trp
        50                  55                  60

Val Pro Asp Thr Ala Ala Pro Ala Tyr Ser His Lys Thr Cys Gly Met
65                  70                  75                  80
```

Ile Gln Glu His Gln Asn Cys Leu Lys Tyr Gly Arg Pro Asp Leu Gly
            85                  90                  95

Phe Leu Lys Trp Arg Trp Arg Pro Ser Gly Cys Glu Leu Pro Arg Phe
        100                 105                 110

Asp Pro Ala Gln Phe Leu Arg Phe Ala Arg His Arg Ser Leu Ala Phe
    115                 120                 125

Val Gly Asp Ser Leu Ala Arg Asn His Met Gln Ser Leu Leu Cys Leu
130                 135                 140

Leu Ala Gln Val Ala Ser Pro Lys Asp Ile Ser Pro Asp Pro Ser Asp
145                 150                 155                 160

Gln Gln Asn Lys Val Tyr His Tyr Arg Ala Tyr Asn Phe Thr Val Ala
                165                 170                 175

Met Phe Trp Ser Pro Phe Leu Val Arg Ala Arg Glu Pro Ala His Asp
            180                 185                 190

Asp Pro Ala His Thr Ala His Tyr Ser Leu Tyr Leu Asp Glu Pro Asp
        195                 200                 205

Glu Arg Trp Val Ser Gln Val Pro Arg Phe Asp Tyr Val Leu Val Ser
    210                 215                 220

Ala Ala Asn Trp Phe Ser Arg Pro Ser Leu Phe Tyr Glu Lys Arg Arg
225                 230                 235                 240

Leu Val Gly Cys Ser Phe Cys Ser Arg Gln Tyr Gly Val Pro Asp Leu
                245                 250                 255

Thr Leu His Tyr Ser His Arg Lys Ala Trp Arg Val Ala Leu Arg Ala
            260                 265                 270

Ile Asn Ala Leu Asp Asn Val Thr Gly Arg Val Ile Val Arg Thr Leu
        275                 280                 285

Ser Pro Met Ser His Phe Asp Asn Gly Thr Trp Asp Gln Gly Gly Asp
    290                 295                 300

Cys Arg Arg Thr Glu Pro Leu Arg Ser Asn Gln Thr Ser Met Met Asp
305                 310                 315                 320

Gly Arg Gly Pro Asp His Arg Phe Tyr Ala Ala Gln Met Glu Glu Tyr
                325                 330                 335

Arg Ala Ala Glu Lys Ala Ala Arg Ala Lys Gly Thr Met Arg Leu Met
            340                 345                 350

Leu Met Asp Ala Thr Ala Ala Met Leu Met Arg Pro Asp Gly His Pro
        355                 360                 365

Ser Arg Tyr Gly His Arg Pro Asn Asp Lys Val Gln Leu Tyr Asn Asp
    370                 375                 380

Cys Val His Trp Cys Leu Pro Gly Pro Ile Asp Ile Trp Asn Asp Met
385                 390                 395                 400

Leu Phe Gln Met Ile Leu Val
                405

<210> SEQ ID NO 119
<211> LENGTH: 1687
<212> TYPE: PRT
<213> ORGANISM: Lolium perenne

<400> SEQUENCE: 119

Met Ala Pro Lys Ala Gly Arg Gly Lys Gly Arg Gly Gly Gly Lys
1               5                   10                  15

Gly Asp Arg Lys Lys Lys Glu Glu Lys Val Val Pro Thr Val Val Asp
            20                  25                  30

Leu Thr Val Thr Thr Pro Tyr Asp Ser Gln Val Thr Leu Lys Gly Ile
        35                  40                  45

Ser Thr Asp Arg Val Leu Asp Val Arg Arg Leu Leu Gly Ser Asn Val
    50                  55                  60

Glu Thr Cys His Leu Thr Asn Tyr Ser Leu Ser His Val Val Arg Gly
 65                  70                  75                  80

His Arg Leu Asp Asp Gly Val Glu Ile Val Ala Leu Lys Pro Cys Ala
                 85                  90                  95

Leu Thr Ile Ala Glu Glu Tyr Ala Thr Glu Glu Ala Ala Val Ala
            100                 105                 110

His Val Arg Arg Leu Leu Asp Ile Val Ala Cys Thr Thr Ala Phe Ala
            115                 120                 125

Lys His Lys His Lys Ser Ser Pro Lys His Ala Arg Pro Ala Thr Pro
            130                 135                 140

Pro Ser Pro Pro Ala Thr Ala Ser Ser Pro Ala Ala Asn Gly Gly Lys
145                 150                 155                 160

Gly Asp Gly Ala Glu Ala Pro Ala Ile Ser Glu Ala His Asp Met Ala
                165                 170                 175

Ala Ile Gly Pro Pro Lys Leu Gly Glu Phe Tyr Asp Phe Phe Ser
            180                 185                 190

Phe Ala His Leu Thr Pro Pro Leu His Phe Ile Arg Arg Lys Glu Lys
            195                 200                 205

Asn Gly Ala Ala Gln Glu Gly Asp Tyr Phe Glu Ile Glu Val Lys Val
210                 215                 220

Cys Asn Gly Lys Leu Leu His Ile Val Ala Ser Val Lys Gly Phe Tyr
225                 230                 235                 240

Leu Val Gly Lys Pro His Thr Ala Tyr Glu Ala Leu Met Lys Ala Phe
            245                 250                 255

Val Asp His Asn Lys Phe Gly Asn Leu Pro Phe Gly Phe Arg Ala Asn
            260                 265                 270

Thr Trp Leu Val Pro Pro Val Tyr Met Asp Ser Ala Ala Lys Gly Pro
    275                 280                 285

Ala Leu Pro Val Glu Asp Glu Ser Trp Gly His Gly Gly Gly Arg
    290                 295                 300

Gly Arg Asp Gly Lys His Asp Arg Arg Arg Trp Ala Lys Glu Phe Ser
305                 310                 315                 320

Ile Leu Ala Arg Met Pro Cys Lys Thr Glu Glu Glu Arg Val Val Arg
            325                 330                 335

Asp Arg Lys Ala Phe Leu Leu His Asn Leu Phe Val Asp Thr Ala Ile
            340                 345                 350

Phe Arg Ala Ala Ser Thr Ile Arg Arg Leu Ile Asp Thr Ser Val Arg
            355                 360                 365

Thr Gly Ser Asp Gly Ser Leu Val Phe Glu Glu Arg Val Gly Asp Met
    370                 375                 380

His Val Thr Val Lys Lys Asp Asp Ala Asp Ala Ser Val Lys Leu Gly
385                 390                 395                 400

Asp Lys Val Asp Ala Ala Val Tyr Gln Thr Asp Ala Met Asp Ile
            405                 410                 415

Ser Gln Arg Asn Leu Leu Lys Gly Leu Thr Ser Asp Glu Ser Val Val
            420                 425                 430

Ala Lys Asp Ser Ser Thr Leu Gly Val Val Ile Val Lys His Cys Gly
            435                 440                 445

Tyr Thr Ala Thr Val Lys Val Ser Gly Arg Thr Lys Asn Ser Thr Asp
    450                 455                 460

```
Ser Lys Gln Pro Ser Asp Ile Ser Asp His Leu Asp Gly Val Leu Asn
465                 470                 475                 480

Ile Asp Val Asp His Pro Asp Gly Gly Ser Asn Ala Leu Asn Val
            485                 490                 495

His Ser Leu Arg Ile Pro Leu Pro Lys Ile Ile Asn Pro Glu Val Ala
            500                 505                 510

Ala Ser Asn Gln His Leu Ser Ser Lys Thr His Val Asp Asn Tyr Ala
            515                 520                 525

Arg Lys Leu Ala Arg Thr Val Leu Glu Ala Ser Leu Met Lys Leu Glu
            530                 535                 540

Asn Met Gln Lys Glu Asn Pro Arg Leu Ile Arg Trp Glu Leu Gly Ser
545                 550                 555                 560

Ser Trp Leu Gln His Leu Gln Lys Lys Asp Ser Ser Ala Ser Gly Asp
                565                 570                 575

Ser Glu Lys Ser Thr Lys Lys Val Glu Lys Asp Ser Ser Val Lys Gly
                580                 585                 590

Leu Gly Lys His Phe Glu Gln Leu Arg Lys Leu Lys Lys Asn Val Glu
            595                 600                 605

Gly Ala Lys Thr Glu Lys Glu Asp Ser Asp Ser Asn Cys Ser Leu Thr
            610                 615                 620

Asn Gly Met Glu Glu Ser Asp Asn Lys Ala Phe Asp Glu Thr Ser Glu
625                 630                 635                 640

Ala Glu Leu Arg Lys Leu Met Thr Glu Asp Ala Phe Cys Arg Leu Lys
                645                 650                 655

Ser Leu Glu Ala Gly Leu His Gln Lys Ser Leu Glu Glu Leu Thr Lys
                660                 665                 670

Met Ala His Lys Phe Tyr Asp Asp Thr Ala Leu Pro Lys Leu Val Ala
            675                 680                 685

Asp Phe Ala Ser Leu Glu Leu Ser Pro Val Asp Gly Arg Thr Met Thr
            690                 695                 700

Asp Phe Met His Thr Arg Gly Leu Asn Met Cys Ser Leu Gly Arg Val
705                 710                 715                 720

Val Asp Leu Ala Glu Lys Leu Pro His Ile Gln Ser Ile Cys Ile His
            725                 730                 735

Glu Met Val Ile Arg Ser Phe Lys His Val Ile Arg Ala Val Ile Ala
            740                 745                 750

Ser Val Asp Asp Met Gln Asn Met Ser Ala Val Ile Ala Glu Thr Leu
            755                 760                 765

Asn Ile Leu Leu Gly Ser Pro Arg Leu Asp Asn Asp Leu Asp Thr Asp
770                 775                 780

Ala His Asn Glu His Asn Leu Arg Leu Lys Trp Ile Glu Ser Phe Leu
785                 790                 795                 800

Ser Lys Arg Tyr Cys Trp Lys Leu Lys Asp Glu Tyr Glu His Leu Arg
                805                 810                 815

Lys Ser Ile Ile Leu Arg Gly Leu Cys Ser Lys Val Gly Leu Glu Leu
            820                 825                 830

Val Ala Arg Asp Tyr Asp Met Asn Ser Pro Asn Pro Phe Asp Lys Ser
            835                 840                 845

Asp Ile Val Asn Ile Val Pro Ile Cys Lys His Val Val Tyr Ser Ser
            850                 855                 860

Ile Asp Ser Arg Asn Leu Leu Glu Ser Ser Lys Met Ala Leu Asp Lys
865                 870                 875                 880

Gly Lys Leu Asp Asp Ala Val Asn Tyr Gly Ala Lys Ala Leu Ser Lys
```

```
            885                 890                 895
Val Ile Ala Val Cys Gly Pro Tyr His Arg Leu Thr Ala Asn Ala Tyr
            900                 905                 910

Ser Leu Leu Ala Val Val Leu Tyr His Thr Gly Asp Phe Asn Gln Ala
            915                 920                 925

Thr Ile Tyr Gln Gln Lys Ala Leu Asp Ile Asn Glu Arg Glu Leu Gly
            930                 935                 940

Leu Asp His Pro Glu Thr Met Lys Ser Tyr Gly Asp Leu Ser Val Phe
945                 950                 955                 960

Tyr Tyr Arg Leu Gln His Ile Glu Met Ala Leu Lys Tyr Val Asn Arg
            965                 970                 975

Ala Leu Tyr Leu Leu Gln Phe Ser Cys Gly Leu Ser His Pro Asn Ser
            980                 985                 990

Ala Ala Thr Tyr Ile Asn Val Ala Met Met Glu Glu Gly Met Gly Asn
            995                 1000                1005

Val His Val Ala Leu Arg Tyr Leu His Glu Ala Leu Lys Cys Asn
        1010                1015                1020

Lys Arg Leu Leu Gly Ala Asp His Ile Gln Thr Ala Ala Ser Tyr
        1025                1030                1035

His Ala Ile Ala Ile Ala Leu Ser Met Met Asp Ala Tyr Ser Leu
        1040                1045                1050

Ser Val Gln His Glu Gln Thr Thr Leu Gln Ile Leu Gln Glu Lys
        1055                1060                1065

Leu Gly Glu Asp Asp Leu Arg Thr Gln Asp Ala Ala Ala Trp Leu
        1070                1075                1080

Glu Tyr Phe Asp Ser Lys Ala Leu Glu Gln Gln Glu Ala Ala Arg
        1085                1090                1095

Arg Gly Ile Pro Lys Pro Asp Ser Ser Ile Ala Ser Lys Gly His
        1100                1105                1110

Leu Ser Val Ser Asp Leu Leu Asp Tyr Ile Ser Pro Asp Gln Glu
        1115                1120                1125

Arg Lys Glu Arg Asp Met Gln Arg Lys Cys Arg Arg Ala Lys Asn
        1130                1135                1140

Asn Thr Arg Ala Gln Gln Gly Glu Ser Val Glu Glu Lys Glu Asn
        1145                1150                1155

Phe Gln Asp Asp Ser Gly Ser Leu Leu Glu Ala Val Lys Asn Asp
        1160                1165                1170

Phe Gln Glu Ala Lys Leu Glu Pro Gln Ala Pro Val Val Ser Val
        1175                1180                1185

Val Thr Glu Glu Ile Cys Ala Val His Asp Glu Leu Lys Gln Val
        1190                1195                1200

Glu Ala Leu Ser Pro Glu Glu Tyr Ser Asp Glu Gly Trp Gln Ala
        1205                1210                1215

Ala Thr Leu Arg Gly Arg Ser Ala Asn Val Arg Lys Lys Ser Ile
        1220                1225                1230

Arg Arg Arg Pro Ala Leu Thr Lys Leu Ala Val Gly Arg Ile Glu
        1235                1240                1245

Asp Gly Arg Thr Ala Ser Ala Gln Arg Thr Asp Val Gln Pro Gln
        1250                1255                1260

Thr Lys Glu His Lys Glu Glu Ala Thr Tyr Ser Pro Ser Gln Leu
        1265                1270                1275

Ser Phe Gly Asn Phe Phe Asn Ser Asp Lys Leu Asn Gly Asp Pro
        1280                1285                1290
```

```
Val Leu Thr Glu Asp Lys Ser Cys Asn Ala Thr Ser Lys Ser Glu
    1295                1300                1305

Gln Ser Ile Lys Pro Thr Gly Ile Asn Arg Pro Thr Ser Ile Ala
    1310                1315                1320

Ser Lys Leu Val Ser Tyr Lys Asp Val Ala Ala Ser Pro Pro Gly
    1325                1330                1335

Thr Val Trp Lys Pro Ile Leu Glu Gln Lys Glu Ala Lys Glu Lys
    1340                1345                1350

Asp Thr Glu Glu Val Ile Asp Val Thr Pro Ser Ser Glu Glu Asp
    1355                1360                1365

Gly Lys Val Thr Asp Glu Val Glu Lys Ser Ser Asp Glu Gly Ser
    1370                1375                1380

Lys Glu Ile Val Ser Ser Gln Pro Glu Gly Gly Ser His Ser Glu
    1385                1390                1395

Lys Ala Ser Asp Ser Asp Gly Ser Thr Ser Pro Asn Lys Lys Thr
    1400                1405                1410

Ser Gly Ser Lys Leu Ser Ala Ser Ala Pro Pro Phe Asn Pro Gly
    1415                1420                1425

Ser Leu Leu Ser Val Ser His Pro Tyr Ser Thr Val Ala Ile Tyr
    1430                1435                1440

Asp Ala Ser Val Val Leu Gln Thr Ile Pro Ser Gln Ala Met Glu
    1445                1450                1455

Ile Phe Pro His Ala Val Asp Thr Arg Val Pro Arg Gly Pro Arg
    1460                1465                1470

Ser Thr Leu Tyr Tyr Arg Thr Gly His Ser Phe Gln Arg Lys Gln
    1475                1480                1485

Gly Tyr Thr Gln Ser Gln Ser Thr Ile Val Arg Gly Ser Thr Ser
    1490                1495                1500

Pro Pro Ala Met Asn Pro His Ala Ala Glu Phe Val Pro Gly Lys
    1505                1510                1515

Ala Val Gln Gln Thr Asp Leu Ala Asn Gly Lys His Val Ala Asp
    1520                1525                1530

Ser Ala Asp Gln Gln Leu Thr Pro Gln Thr Ser Asp Glu Val Lys
    1535                1540                1545

Ala Asp Ile His Ala Ala Asp Lys Ala Gly Gln Val Glu Lys Ile
    1550                1555                1560

Thr Pro Gly Lys Gly Lys Glu Asn Arg Gly Lys Asp Ala Met Arg
    1565                1570                1575

Asp Ser Tyr Lys Ala Glu Leu Ala Arg Gln Ile Leu Leu Ser Phe
    1580                1585                1590

Ile Val Lys Ser Val His Asp Ser Leu Gly Ser Thr Arg Ala Gln
    1595                1600                1605

Pro Asp Arg Lys Pro Ser Ala Pro Asp Glu Pro Ser Asn Glu Gln
    1610                1615                1620

Ser Ser Asn Ile Thr Lys Pro Ala Ser Ala Arg Lys Glu Phe Asp
    1625                1630                1635

Lys Gln Pro Lys Ala Ala Glu Val Leu Lys Ser Glu Lys Asp Thr
    1640                1645                1650

Glu Gly Phe Thr Val Val Ser Lys Arg Arg Ser Lys Gln His
    1655                1660                1665

Phe Met Asn Pro Ile Asn Gly Leu Tyr Ser Gln Gln Ser Ile Cys
    1670                1675                1680
```

```
Thr Ser  Val Ser
    1685

<210> SEQ ID NO 120
<211> LENGTH: 206
<212> TYPE: PRT
<213> ORGANISM: Lolium perenne

<400> SEQUENCE: 120

Met Ser Ser Ser Ser Arg Pro Pro Thr Thr Pro Arg Gly Ala Ala
1               5                   10                  15

Ala Ala Ala Ala Gly Cys Ala Asp Pro Asn Thr Thr Phe Val Gln Ala
            20                  25                  30

Asp Pro Ala Thr Phe Arg Ala Leu Val Gln Lys Leu Thr Gly Ala Pro
        35                  40                  45

Gly Gly Ala Pro Ala Ala Ser Val Glu Lys Gln Gln Val Ser Gly Thr
    50                  55                  60

Ile Phe Pro Ala Val Pro Leu Pro Leu Arg Arg Pro Lys Leu Gln Glu
65                  70                  75                  80

Arg Arg Arg Ala Ala Pro Ala Arg Leu Glu Leu Ala Arg Pro Gln Pro
                85                  90                  95

Phe Tyr Tyr His Pro His His Asn His His His His His His His His
            100                 105                 110

His Gly Ile Met Gln Tyr Ser Pro Val Ser Thr Met Asp Tyr Ala His
        115                 120                 125

Ala Leu Ala Ala Ser Ser Ala Ser Ser Pro Ser Pro Ser Pro His
    130                 135                 140

Ser Ser Cys Ser Cys Gly Val Val Ile Ser Lys Glu Glu Glu Arg
145                 150                 155                 160

Glu Glu Lys Ala Ile Ala Ser Lys Ala Phe Tyr Leu His Ser Ser Pro
                165                 170                 175

Arg Ser Ser Ala Val Ala Gly Gly Asp Ser Glu Arg Pro Lys Leu Leu
            180                 185                 190

Pro Leu Phe Pro Val His Ser Pro Arg Ser Ser Ser Phe Ala
        195                 200                 205

<210> SEQ ID NO 121
<211> LENGTH: 226
<212> TYPE: PRT
<213> ORGANISM: Lolium perenne

<400> SEQUENCE: 121

Met Ser Ser Ala Pro Pro Pro Ala Pro Ser Arg Ser Asn
1               5                   10                  15

Pro Glu Ala Pro Pro Arg Val Val Arg Pro Pro Arg Pro Pro
            20                  25                  30

Arg Ala Pro Gly Pro Pro Pro Trp Ala Glu Arg Arg Pro Ser Val Ser
        35                  40                  45

Val Asp Tyr Asp Arg Gly Arg Arg Thr Ala Arg Val Glu Val Asp Gly
    50                  55                  60

Val Gly Ala Asp Ala Leu Pro Ser Arg His Arg Leu Arg Val Glu Gly
65                  70                  75                  80

Ser Arg Trp Gln Arg Asp Trp Lys Val Ser Gln Val Ala Ala Arg Val
                85                  90                  95

Leu Ala Leu Pro Pro Ala Asp Ala His Ala Val Asp Ala Val Leu Asn
            100                 105                 110
```

Cys Trp Ala Gly Arg Phe Ala Arg Arg Asn Phe Pro Leu Leu Ile Arg
            115                 120                 125

Glu Ile Thr Phe Thr Gly Ser Leu Gln His Ala Val His Val Phe Arg
        130                 135                 140

Trp Met Lys Asn Gln Glu Asn Tyr Cys Ala Arg Asn Asp Ile Tyr Gly
145                 150                 155                 160

Met Met Ile Arg Leu His Gly Arg His Asn Leu Val Asp Gln Ala Arg
                165                 170                 175

Gly Leu Phe Phe Glu Met Gln Glu Trp Arg Cys Thr Pro Asp Ala Asp
            180                 185                 190

Ile Phe Asn Ser Leu Ile His Val His Ala Arg Ala Gly Gln Trp Arg
        195                 200                 205

Trp Ala Ile Asn Ile Met Asp Asp Met Leu Arg Ala Ala Val Ser Ile
210                 215                 220

Val Leu
225

<210> SEQ ID NO 122
<211> LENGTH: 287
<212> TYPE: PRT
<213> ORGANISM: Lolium perenne

<400> SEQUENCE: 122

Met Asp Arg Gly Arg Gly Ser Asp Glu Met Ile Pro Gly Val Phe Phe
1               5                   10                  15

Val Gly His Ala Cys Leu Glu Val Ala Ala Pro Ala Gly Arg Thr Phe
            20                  25                  30

Asp Leu Gly Thr Pro Asp Leu Glu Ala Thr Asp Arg Ile Leu Arg Thr
        35                  40                  45

Ala Pro Pro Glu Pro Glu Ala Thr Gly Arg Thr Cys Arg Gly Asp
50                  55                  60

Ala Gly Pro Glu Ala Asp Val Asp Val Ala Gly Arg Ala Leu Ala Val
65                  70                  75                  80

Val Glu Arg Asp Gly Ala His Asp Pro Ala Thr Gly Arg Ala Leu Thr
                85                  90                  95

Gly Ser Trp Leu Trp Asp Ser Ala Leu Val Leu Thr Asn His Leu Ala
            100                 105                 110

Ser Ala Glu Pro Ser Gln Leu Leu Gly Ala Thr Val Leu Glu Leu Gly
        115                 120                 125

Ala Gly Thr Gly Leu Pro Gly Ile Ala Ala Val Ala Cys Leu Gly Ala
    130                 135                 140

Ala Arg Cys Val Leu Thr Asp Val Arg Pro Leu Leu Pro Gly Leu Arg
145                 150                 155                 160

Ala Asn Ala Glu Ala Asn Gly Leu Asp Leu Asp Thr Ala Gln Ala Asp
                165                 170                 175

Val Arg Glu Leu Arg Trp Gly Glu Glu Tyr Asp Leu Val Met Leu Asp
            180                 185                 190

Arg Glu Val Pro Cys Val Asp Val Leu Met Ser Asp Val Phe Tyr
        195                 200                 205

Asp Pro Glu Glu Met Pro Ala Met Ala Thr Thr Leu Arg Arg Leu Trp
    210                 215                 220

Arg Asp Gly Thr Val Cys Trp Ala Ala Ser Glu Val Arg Cys Gly Val
225                 230                 235                 240

Gln Asp Cys Val Asp Val Leu Arg Glu Glu Gly Phe Asp Val Ala Glu
                245                 250                 255

-continued

Val Asp Arg Val Thr Arg Pro Leu Leu Arg Ala Pro Ser Gln Asn Ala
                260                 265                 270

Asp Phe Ala Val Tyr Arg Ile Glu Leu Arg Arg Ser Arg Glu Gly
            275                 280                 285

<210> SEQ ID NO 123
<211> LENGTH: 414
<212> TYPE: PRT
<213> ORGANISM: Lolium perenne

<400> SEQUENCE: 123

Met Gly Ser Ser Leu Lys Tyr Arg Ala Gly Leu Val Leu Ile Gly Ala
1               5                   10                  15

Val Val Leu Ile Trp Val Thr Ser Ala Glu Val Thr Gln Glu Ile Phe
                20                  25                  30

Ala Asp Tyr Lys Gln Pro Phe Ala Ile Thr Tyr Phe Gly Ala Ser Leu
            35                  40                  45

Met Val Ile Tyr Ile Pro Leu Ala Phe Leu Lys Asp Phe Ile Tyr Lys
        50                  55                  60

Leu Leu Arg Arg His Ser Gly Ser Ser Arg Ala Ser Lys Val Val Ser
65                  70                  75                  80

Lys Ser Ser Phe Gly Gly Ser Ala Pro Leu Lys Asn Gly Glu Phe Glu
                85                  90                  95

Lys Met Leu Glu Met Glu Pro Gln Lys Thr Val Val Ile Asp Phe Thr
            100                 105                 110

Asp Val Asp Ile Pro Val Leu Glu Glu Ala Lys Pro Leu Ile Cys Gly
        115                 120                 125

Ile Gly Glu Phe Gly Asp Asp Val Leu Lys Glu Gln Gln Leu Ser Thr
130                 135                 140

Lys Glu Ile Ala Ile Tyr Gly Leu Tyr Leu Cys Pro Ile Trp Phe Val
145                 150                 155                 160

Thr Glu Tyr Leu Ser Asn Ala Ala Leu Ala Arg Thr Ser Val Ala Ser
                165                 170                 175

Thr Thr Val Leu Ser Ser Thr Ser Gly Leu Phe Thr Leu Phe Ile Ser
            180                 185                 190

Val Leu Leu Gly Gln Asp Ser Ile Asn Ala Ala Lys Val Ile Ala Val
        195                 200                 205

Phe Val Ser Met Ala Gly Val Ala Met Thr Thr Met Gly Gln Thr Trp
210                 215                 220

Ala Thr Asp Glu Ser Glu Val Ser Asn Ser Gly Thr Tyr Arg Leu Ala
225                 230                 235                 240

Asn His Leu Ile Leu Lys Pro Tyr Tyr Cys Arg Ala Thr Gln Arg Thr
                245                 250                 255

Leu Leu Gly Asp Met Phe Gly Leu Leu Ser Ala Val Ser Tyr Gly Leu
            260                 265                 270

Phe Thr Val Leu Leu Lys Phe Ala Gly Gly Glu Gly Ser Glu Lys
        275                 280                 285

Val Asp Val Gln Lys Leu Phe Gly Phe Leu Gly Leu Phe Thr Leu Cys
        290                 295                 300

Leu Leu Trp Trp Leu Val Trp Pro Leu Thr Ala Leu Gly Ile Glu Pro
305                 310                 315                 320

Lys Phe Thr Met Pro His Ser Ala Lys Val Asp Glu Val Val Leu Ala
                325                 330                 335

Asn Gly Leu Ile Gly Ser Val Leu Ser Asp Tyr Phe Trp Ala Leu Ser

```
            340                 345                 350
Val Val Trp Thr Asn Pro Leu Val Ala Thr Leu Gly Met Ser Leu Thr
        355                 360                 365

Ile Pro Leu Ala Met Val Ala Asp Met Val Ile His Gly Arg His Tyr
    370                 375                 380

Ser Ala Val Tyr Ile Ile Gly Ser Leu Gln Val Phe Ser Gly Phe Val
385                 390                 395                 400

Ile Ala Asn Leu Ala Asp Arg Phe Ser Arg Phe Leu Gly Leu
                405                 410

<210> SEQ ID NO 124
<211> LENGTH: 582
<212> TYPE: PRT
<213> ORGANISM: Lolium perenne

<400> SEQUENCE: 124

Met Thr Ser Pro Ser Ala Pro Pro Cys Pro His Leu Ala Ala His
1               5                   10                  15

Arg Leu Thr Ser Arg Pro Leu Arg Phe Pro Arg Arg Cys Leu Arg Val
            20                  25                  30

Arg Pro Leu Gly Arg Pro Glu Ile Arg Arg Asp Ala Arg Glu Val Pro
        35                  40                  45

Arg Cys Ser Pro Cys Ala Ser Ser Pro Pro Ala Arg Leu Tyr
    50                  55                  60

Ala Cys Leu Ser Cys Ala Ser Val Phe Cys Pro Ser His Ala Ala Ser
65                  70                  75                  80

His Ala Ser Ser Ser Pro Gly His Gln Ile Ala Val Asp Val Asp Arg
                85                  90                  95

Ala Glu Leu Phe Cys Ala Ala Cys Gly Asp Gln Val Tyr Asp Pro Asp
            100                 105                 110

Phe Asp His Ala Val Val Leu Ala Gln Ser Thr Ala Leu Ser Pro Pro
        115                 120                 125

Ser Thr Ser Thr Pro Ser Pro Ala Pro Arg Lys Arg Arg Arg Val Asp
130                 135                 140

Tyr Arg Ala Trp Ala Pro Asp Pro Ala Glu Ser Ala Leu Val Ser Ala
145                 150                 155                 160

Ala Ala Asp Pro Thr Thr Ser Ala Ser Thr Thr Asp Pro Ala Gly Leu
                165                 170                 175

Arg Gly Leu Asn Asn Leu Gly Asn Thr Cys Phe Met Asn Ser Val Leu
            180                 185                 190

Gln Ala Leu Leu His Ala Pro Pro Leu Arg Asn Tyr Phe Leu Gly Asp
        195                 200                 205

Arg His Asn Arg Phe Leu Cys Pro Arg Arg Thr Pro Met Arg His Arg
    210                 215                 220

Ala Thr Asp Ala Asp Ala Lys Ala Ala Cys Leu Ala Cys Asp Leu Asp
225                 230                 235                 240

Glu Ile Tyr Ser Ala Thr Phe Ser Gly Glu Arg Thr Pro Tyr Ser Pro
                245                 250                 255

Ala Lys Phe Leu Tyr Arg Ser Gly Ser Gln Ala Leu Phe Ala Leu Val
            260                 265                 270

His Val Ala Leu Ser Phe Gln Gln Pro Ala Val Leu Phe Tyr Ala Gly
        275                 280                 285

Trp Trp Gln His Ala Thr Asn Leu Ala Ser Tyr Glu Gln Gln Asp Ala
    290                 295                 300
```

```
His Glu Phe Phe Ile Ser Ile Leu Asp His Ile His Glu Asn Ile Lys
305                 310                 315                 320

Asp Asp Glu His Lys Ser His Glu Gln Gly His Gly Asp Cys Cys Ile
            325                 330                 335

Ala His Arg Val Phe Ser Gly Ile Leu Arg Ser Asp Val Ile Cys Thr
                340                 345                 350

Asn Cys Gly Phe Ser Ser Thr Thr Phe Glu Pro Cys Met Asp Phe Ser
            355                 360                 365

Leu Asp Leu Asp Ala Gly Cys Asn Gly Ser Arg Gly Val Ala Asn Pro
370                 375                 380

Lys Ala Arg Asn Gly Glu Arg Asn Leu Ala Gly Met Asn Pro Lys Val
385                 390                 395                 400

Ser Ser Thr Leu Met Arg Cys Leu Glu Arg Phe Thr Arg Ala Glu Arg
                405                 410                 415

Leu Asp Ala Asp Gln Lys Phe Phe Cys Glu Arg Cys Lys Glu Arg Gln
            420                 425                 430

Glu Ser Leu Lys Gln Met Ser Ile Arg Arg Leu Pro Leu Val Ser Cys
            435                 440                 445

Phe His Ile Lys Arg Phe Glu His Ser Thr Val Lys Lys Met Ser Arg
450                 455                 460

Lys Val Asp His Ser Leu Gln Phe Pro Phe Ser Leu Asp Met Ala Pro
465                 470                 475                 480

Tyr Leu Ser Ser Ser Ile Leu Arg Ser Arg Tyr Gly Asn Arg Ile Phe
                485                 490                 495

Pro Ser Glu Ser Ile Asp Ser Glu Ala Val Ser Glu Leu Ser Ser Glu
            500                 505                 510

Phe Glu Ile Phe Ala Val Ile Thr His Ser Gly Lys Leu Asp Ala Gly
            515                 520                 525

His Tyr Val Thr Tyr Leu Arg Leu Asn Asn Gln Trp Tyr Arg Cys Asp
530                 535                 540

Asp Ala Trp Val Thr Arg Val Asp Glu His Thr Val Arg Thr Ser Gln
545                 550                 555                 560

Ala Tyr Met Leu Phe Tyr Val Gln Lys Thr Leu Tyr Tyr Lys Ala Cys
                565                 570                 575

Glu Lys Pro Ala Ala Val
            580

<210> SEQ ID NO 125
<211> LENGTH: 295
<212> TYPE: PRT
<213> ORGANISM: Lolium perenne

<400> SEQUENCE: 125

Met Val Arg Ala Leu Ser Ser Pro Val Ser Ser Phe Ala Asn Ala
1               5                   10                  15

Leu Pro Gly Val Pro Ala Arg Arg Ser Arg His Gly Leu Gly His Pro
                20                  25                  30

Glu Ser Gln Met Pro Asn Ile Asn Asp Glu Asp Glu Asp Thr Gly Pro
            35                  40                  45

Phe Val Pro Thr Ala Pro Arg His Pro Pro Asp Arg Ser Met Gln Pro
50                  55                  60

Pro Thr Pro Leu Lys Ser Ala Pro Leu Gly Arg Gly Arg Gly His Pro
65                  70                  75                  80

Ile Met Pro Ala Ala Pro Arg His Ser Pro Ile Ile Leu Ser Leu Thr
                85                  90                  95
```

```
Glu Ser Pro Asn Gly Glu Leu Glu Pro Arg Arg Arg Cys Ser Val
            100                 105                 110

Ser Pro Arg Phe Arg Ala Gly Glu Ala Asn His Arg Leu Thr Val Asp
        115                 120                 125

Arg Glu Phe Glu Asp Leu Glu Ala His Ser Gly Ala Thr Asp Leu Glu
    130                 135                 140

Ser Gly Ala Asp Glu Glu Asp Gln Asp Gln Ala Ala His Arg Arg Gly
145                 150                 155                 160

Cys Cys Arg Cys Cys Met Val Pro Gly Ser Ala Ser Ser Ser Trp Ala
                165                 170                 175

Ala Gly Glu Ala Lys Asn Ser Thr Tyr Gly Thr Gly Gly Phe Ile Leu
            180                 185                 190

Leu Asn Thr Arg Asp Glu Val Thr Gln Pro Ser His Gly Leu Leu Ser
        195                 200                 205

Thr Ile Ala Tyr Lys Ile Gly Pro Tyr Val Thr Thr Asn Tyr Val Leu
    210                 215                 220

Glu Ser Ser Ile Ala Ile Ala Gly Pro Val Val Lys Trp Leu Arg Asp
225                 230                 235                 240

Ser Leu Glu Ile Ile Ser Ala Ala Val Glu Ile Glu Ile Leu Ala Gly
                245                 250                 255

Ser Val Gln Asp Ser Asp Ser Gly Phe Ile Gly Asp Gly Leu Leu Gln
            260                 265                 270

Asp Ala Asn Arg Tyr Asn Ile Gln Glu Val Ile Asn Lys Gly Lys Leu
        275                 280                 285

Gln Cys Arg Leu Phe Arg His
    290                 295

<210> SEQ ID NO 126
<211> LENGTH: 521
<212> TYPE: PRT
<213> ORGANISM: Lolium perenne
<220> FEATURE:
<221> NAME/KEY: misc_feature
<222> LOCATION: (472)..(472)
<223> OTHER INFORMATION: Xaa can be any naturally occurring amino acid

<400> SEQUENCE: 126

Met Arg Cys Glu Leu Asp Tyr Tyr Trp Ser Leu Gly Glu Val Ser Asp
1               5                   10                  15

Asn Gly Gly Val Ser Cys Val Ile Tyr Lys Val Gln Glu His Ile Arg
            20                  25                  30

Met Ala Asp Lys Leu Ser Tyr Glu Pro Cys Val Leu Ser Ile Gly Pro
        35                  40                  45

Tyr His His Gly Ala Pro Ala Leu Gln Thr Leu Gln Lys Asp Lys Trp
    50                  55                  60

Ser Tyr Leu Asp Phe Ile Leu Asn Leu Asn Thr Asp Lys Thr Leu Gln
65                  70                  75                  80

Asp Tyr Leu Leu Ala Leu Glu Ser Leu Ser Lys Val Ala Arg Ser Cys
                85                  90                  95

Tyr Ser Glu Asp Ile Glu Met Asp Ala Glu Glu Phe Leu Gln Met Leu
            100                 105                 110

Leu Leu Asp Gly Cys Phe Val Leu Val Ala Leu Gly Gly Thr Lys Glu
        115                 120                 125

Ile Leu Ala Ala Ala Lys His Ile Lys Leu Asp Lys Leu Lys Ser Glu
    130                 135                 140
```

Asp Thr Pro Glu Asn Ile Ser Asn Pro Asn Asp Ala Phe Asn Gly Thr
145                 150                 155                 160

Asp Glu Thr Asn Asn Glu Ser Met Asn Gln Glu Gly Gly Glu Asp Gly
            165                 170                 175

Lys Leu Gln Ala Glu His Arg Thr Gln Tyr Gln Asp Glu Phe Gly Gln
        180                 185                 190

Trp Phe Tyr Arg Phe Leu Val His Asp Leu Phe Leu Glu Asn Gln
    195                 200                 205

Ile Pro Phe Phe Ile Val Lys Lys Ile Phe Asn Val Ala Ser Asp
210                 215                 220

Asn Ile Leu Asp Asp Ser Pro Phe Thr His Glu Ile Ser Arg Tyr Val
225                 230                 235                 240

Asp Ala Ala Leu Arg Trp Phe Pro Lys Ser Ile Gln Glu Ser Asp Met
            245                 250                 255

Pro Lys Asp Phe Asp Asn Leu Leu Gln Leu Cys His Met Tyr Phe Arg
        260                 265                 270

Pro Ser Arg Thr Ala Glu Asp Tyr Ser Tyr Gln Leu Gly Lys Gln Tyr
    275                 280                 285

Phe Asn Arg Phe Leu Ser Phe Gly Leu Lys Tyr Leu Lys Ile Gly Gln
290                 295                 300

Tyr His Asp Asp Thr Glu Glu Tyr Ser Ser Tyr Asn Leu Glu Ile Pro
305                 310                 315                 320

Tyr Leu Gln Asp Gly Gln Leu Ser Arg Trp Arg Ala Ala Gln
            325                 330                 335

Tyr Leu Glu Ala Gly Val Lys Phe Lys Lys Arg Glu His Asp Gln Leu
        340                 345                 350

His Pro His Ser Leu Leu Asp Val Lys Phe Ser Asn Gly Thr Met Glu
    355                 360                 365

Val Pro Cys Ile Val Leu Asp Glu Phe Thr Gly Ala Leu Phe Arg Asn
370                 375                 380

Leu Ile Ala Phe Glu Gln Thr Cys Pro Gln Phe Gly Asp Asp Phe Thr
385                 390                 395                 400

Ala Tyr Ile Val Phe Leu Ser Gln Leu Ile Ser Met Pro Glu Asp Val
            405                 410                 415

Thr Leu Leu Ala Arg Arg Glu Ile Ile Val His His Leu Asp Ser Asp
        420                 425                 430

Glu Thr Val Ser Asp Leu Phe Thr Met Leu Ser Lys Asp Val Val Phe
    435                 440                 445

Asp Phe Asn Gly Gln Tyr Tyr Leu Lys Ser Leu Cys Gln Met Met Glu
450                 455                 460

Thr Tyr Tyr Gln Ser Arg Leu Xaa Arg Trp Met Ala Trp Leu Trp Leu
465                 470                 475                 480

Asn His Phe Arg Asn Pro Trp Leu Val Leu Ala Ala Phe Ala Thr Ala
            485                 490                 495

Val Val Leu Val Cys Thr Val Val Gln Thr Val Tyr Gly Val Leu Ala
        500                 505                 510

Tyr Ile His Pro Pro Gly Ser Asn Lys
    515                 520

<210> SEQ ID NO 127
<211> LENGTH: 390
<212> TYPE: PRT
<213> ORGANISM: Lolium perenne

<400> SEQUENCE: 127

```
Met Gly Arg Arg Gly Val Leu Phe Val Gly Gly Asp Gly
 1               5                  10                  15

Val Ala Arg Arg Arg Asp Gly Glu Ala Pro Arg Gly Gly Asp
                 20                  25                  30

Gly Gly Ala Gly Asp Gly Cys Val Leu Gly Arg Gly Ser Asp Gly Phe
                 35                  40                  45

Leu Arg Glu Glu Asn Ser Gly Gly Ile Ala Asn Tyr Met Val Val
     50                  55                  60

Asp Tyr Tyr Leu Tyr Asp Tyr Glu Tyr Ala Glu Pro Pro Arg Val Thr
 65                  70                  75                  80

Ser Leu Gln Asn Ala Val Pro Gln Arg Thr Phe Ser Asp Phe Gly Asp
                 85                  90                  95

Asp Val Tyr Phe Val Ala Asp Lys Arg Gly Tyr Glu Ser Val Val His
                100                 105                 110

Tyr Leu Ala Gly Gln Tyr Leu Asn Thr Asp Asp Ser Gly Asn Val Ala
            115                 120                 125

Asp Pro Arg Leu Gln Leu Asn Lys Val Val Arg Glu Ile Ser Tyr Ser
            130                 135                 140

Ser Ser Gly Val Thr Val Lys Thr Glu Asp Gly Ser Val Tyr Gln Ala
145                 150                 155                 160

Asp Tyr Arg His Gly Leu Cys Gln Leu Ala Ile Ser His Pro Thr His
                165                 170                 175

His Ser Ala Asn Tyr Ser Ile Ile Leu Leu Thr Phe Ala Met Ser Ile
            180                 185                 190

Asp Leu Gln Ala Trp Lys Ile Ala Ile Tyr Arg Phe Asp Met Ala
            195                 200                 205

Val Tyr Thr Lys Ile Phe Leu Lys Phe Pro Arg Lys Phe Trp Pro Thr
            210                 215                 220

Gly Glu Gly Lys Gln Phe Phe Val Tyr Ala Ser Ser Arg Arg Gly Tyr
225                 230                 235                 240

Tyr Gly Met Trp Gln Ser Phe Glu Glu Glu Tyr Pro Gly Ala Asn Val
                245                 250                 255

Leu Leu Val Thr Val Thr Asp Gln Glu Ser Arg Arg Ile Glu Gln Gln
            260                 265                 270

Pro Asp Asn Thr Thr Met Ala Glu Ala Val Ala Val Leu Arg Arg Met
            275                 280                 285

Phe Pro Asp Glu Asp Val Pro Asp Ala Thr Asp Ile Tyr Val Pro Arg
            290                 295                 300

Trp Trp Ser Asn Arg Phe Lys Gly Ser Tyr Ser Asn Trp Pro Ile
305                 310                 315                 320

Gly Val Asn Arg Tyr Glu Tyr Asp Gln Leu Arg Ala Pro Val Gly Arg
                325                 330                 335

Val Tyr Phe Thr Gly Glu His Thr Ser Glu His Tyr Asn Gly Tyr Val
            340                 345                 350

His Gly Gly Tyr Leu Ala Gly Thr Asp Ser Ala Asp Ile Leu Met Asn
            355                 360                 365

Ser Ile Phe Asn Asn Val Glu Phe Lys Val Arg Gly Lys Tyr His Asp
            370                 375                 380

Gln Thr Ala Glu Ala Lys
385                 390

<210> SEQ ID NO 128
<211> LENGTH: 264
```

```
<212> TYPE: PRT
<213> ORGANISM: Lolium perenne

<400> SEQUENCE: 128

Met Ala Glu Ala Asp Ala Ala Ala Arg Arg Thr Val Val
1               5                   10                  15

Thr Asp Tyr Arg Asn Lys Leu Leu Asn Cys Arg Glu Leu Glu Thr Arg
                20                  25                  30

Val Arg Thr Glu Leu Glu Leu Asp Arg Gly Lys Lys Ser Asp Tyr Pro
            35                  40                  45

Val Ser Arg Ser Ala Arg Glu Asn Leu Lys Lys Ala Lys Lys Asp Tyr
    50                  55                  60

Asp Lys Thr Glu Asp Asp Leu Lys Ser Leu Gln Ser Val Gly Gln Ile
65                  70                  75                  80

Ile Gly Glu Val Leu Arg Pro Leu Asp Thr Arg Phe Ile Val Lys
                85                  90                  95

Ala Ser Ser Gly Pro Arg Tyr Val Val Gly Cys Arg Ser Lys Val Asp
            100                 105                 110

Lys Glu Lys Leu Thr Ala Gly Thr Arg Val Val Leu Asp Met Thr Thr
        115                 120                 125

Leu Thr Ile Met Arg Thr Leu Pro Arg Glu Ile Val Ser Ser Ala Ile
130                 135                 140

Ile Asp Lys Tyr Ile Gly Glu Ser Ala Arg Leu Ile Arg Glu Met Phe
145                 150                 155                 160

Asn Tyr Ala Arg Glu His Gln Val Lys Met Ile Met Ala Thr Asn Arg
                165                 170                 175

Pro Asp Val Leu Asp Pro Ala Leu Leu Arg Pro Gly Arg Leu Asp Arg
            180                 185                 190

Lys Ile Glu Ile Pro Leu Pro Asn Glu Gln Ser Arg Met Glu Gly Phe
        195                 200                 205

Asn Gly Ala Asp Leu Arg Asn Val Cys Thr Glu Ala Gly Met Ala Ala
    210                 215                 220

Ile Arg Ala Glu Arg Asp Tyr Val Ile His Glu Asp Phe Met Lys Ala
225                 230                 235                 240

Ala Val Arg Lys Leu Asn Asp Ala Lys Lys Leu Glu Ser Ser Ala His
                245                 250                 255

Tyr Ser Asp Phe Gly Lys Glu
            260

<210> SEQ ID NO 129
<211> LENGTH: 1087
<212> TYPE: PRT
<213> ORGANISM: Lolium perenne

<400> SEQUENCE: 129

Met Thr Lys Leu Lys Ser Val Ala Ser Thr Val Gly Ala Ala Glu Glu
1               5                   10                  15

Cys Ala Gly Ser Ala Arg Gln Ile Ala Pro Ser Pro Met Lys Leu Leu
                20                  25                  30

Val Arg Val Val Glu Ala Arg Gly Leu Leu Ala Val His Val Asn Gly
            35                  40                  45

Thr Ser Asp Pro Phe Val Lys Leu Gln Leu Gly Lys Arg Arg Ala Lys
        50                  55                  60

Thr Ala Val Val Lys Lys Asn Leu Ala Pro Val Trp Asp Glu Glu Phe
65                  70                  75                  80
```

-continued

```
Ser Phe Leu Val Gly Asp Val Thr Glu Leu Ala Val Ser Val Leu
                85                  90                  95

Asn Glu Asp Lys Tyr Phe Ser Asn Asp His Leu Gly Arg Val Lys Val
            100                 105                 110

Pro Leu Ser Gln Val Met Asp Thr Asp Gly Leu Ser Leu Gly Thr Ala
            115                 120                 125

Trp Tyr Gln Leu Gln Pro Lys Ser Ser Lys Ser Lys Arg Lys Cys Arg
130                 135                 140

Gly Glu Ile Cys Leu Arg Ile Ser Leu Ser Thr Arg Thr His Val Ser
145                 150                 155                 160

Glu Glu Leu His Pro Leu Pro Arg Pro Thr Ser Asp Gly Val Ser Ser
                165                 170                 175

Ser Ser Asp Arg Ser Ile Gly Thr Lys Arg Gly Ala Leu Ser Thr Thr
            180                 185                 190

Asn Ser Tyr Ile Asp Leu Ser Ala Val Ala Ser Leu Asp Arg Gly Ser
            195                 200                 205

Gln Ser Ser Phe Glu Arg Ser Ala Asp Ser Phe Val Glu Gln Pro Pro
            210                 215                 220

Arg Ser Ser Ile Glu Gln Ala Val Thr Glu Pro Gly Thr Ala Ala Glu
225                 230                 235                 240

Thr Asp Ala Met Ala Asn Thr Ser Ser Met Val Glu Val Leu Ser Arg
                245                 250                 255

Tyr Phe Phe Arg Lys Pro Val Asp Ala Val Ala Ala Val Val Ser
                260                 265                 270

Asp Ala Glu Ser Val Val Asp Gln Ser Pro Glu Pro Lys Ala Cys Ser
            275                 280                 285

Glu Glu Arg Glu Gly Pro Glu Asn Arg Thr Pro Pro Glu Ser Ser Leu
290                 295                 300

Asp Glu Leu Leu Lys Ile Met Glu Ser Lys Asp Gln Gly Ala Glu Met
305                 310                 315                 320

Pro Ala Lys Leu Ser Asn Gly Val Leu Val Asp Glu Ser Tyr Val Thr
                325                 330                 335

Ala Pro Ala Gly Leu Asn Thr Leu Leu Phe Ser Pro Asn Ser Asp Phe
            340                 345                 350

Trp Pro Ala Val Ala Glu Leu Gln Gly Thr Ser Gly Phe Gln Ile Glu
            355                 360                 365

Ser Trp Lys Ile Asp Ser Asn Asp Gly Cys Leu Arg Arg Thr Leu Ser
            370                 375                 380

Tyr Ile Lys Ala Ala Ser Lys Leu Val Lys Ala Cys Lys Ala Thr Glu
385                 390                 395                 400

Glu Gln Lys Tyr Leu Lys Ala Ala Gly Asn Ser Phe Ala Val Leu Ser
                405                 410                 415

Ile Val Ser Thr Pro Asp Val Pro Cys Gly Thr Cys Phe Lys Ile Glu
            420                 425                 430

Ile Leu Tyr Ser Ile Thr Pro Gly Pro Gln Leu Ser Ser Glu Glu Gln
            435                 440                 445

Thr Ala His Leu Thr Val Ser Trp Arg Ile Asn Phe Val Gln Ser Thr
            450                 455                 460

Met Ile Lys Gly Met Ile Glu Asn Gly Ala Lys Gly Met Ser Glu
465                 470                 475                 480

Gly Tyr Ala Gln Phe Ser Glu Val Leu Ser Gln Lys Phe Lys Val Ala
                485                 490                 495

Glu Leu Asp Asp Ala Asn Ala Ser Lys Ala Lys Ile Leu Ala Ser Leu
```

```
            500                 505                 510
His Thr Gln Lys Glu Pro Ser Trp Arg Leu Ile Val Arg Phe Leu Gly
            515                 520                 525

Asn Phe Thr Phe Ile Val Ser Val Ile Val Gly Ile Tyr Ile Ile Ala
            530                 535                 540

His Leu His Leu Ser Lys Pro Lys Ala Met Asn Gly Leu Glu Tyr Phe
545                 550                 555                 560

Gly Ile Asp Leu Pro Asp Ser Ile Gly Glu Val Val Cys Ala Val
                565                 570                 575

Leu Ile Leu Gln Gly Gln Asn Ile Met Lys Val Met Lys Arg Phe Ser
            580                 585                 590

Asn Ala Trp Lys Gln Arg Gly Ser Asp His Gly Val Lys Ala His Gly
            595                 600                 605

Asp Gly Trp Ile Leu Thr Val Ala Leu Ile Glu Gly Ser Gly Ile Val
            610                 615                 620

Ala Gly Asp Ser Ser Gly Leu Phe Asp Leu Tyr Ala Val Phe Thr Cys
625                 630                 635                 640

Asn Ala Lys Arg Lys Thr Ser Ser Ile Lys Phe His Thr Ser Asp Pro
                645                 650                 655

Lys Trp Asn Glu Ile Phe Glu Phe Asp Ala Met Asp Asp Pro Pro Ser
                660                 665                 670

Arg Met Asp Val Ala Ile His Asp Ser Asn Arg Ser Asp Gly Asp Pro
                675                 680                 685

Ile Gly His Ala Glu Val Asn Phe Leu Thr Ser Ser Leu Ser Asp Leu
            690                 695                 700

Thr Asp Ile Trp Val Pro Leu Asp Gly Lys Cys Asp Pro Ala Ser Asn
705                 710                 715                 720

Pro Lys Leu His Leu Arg Ile Phe Leu Asn Asn Ser Arg Gly Thr Glu
                725                 730                 735

Val Val Met Asn Tyr Leu Ser Lys Met Gly Lys Glu Val Gly Lys Lys
                740                 745                 750

Ile Asn Leu Arg Ser Ala Gln Thr Asn Ser Ala Phe Arg Lys Leu Phe
            755                 760                 765

Asn Leu Pro Pro Glu Glu Phe Leu Ile Asp Asp Phe Thr Cys His Leu
770                 775                 780

Lys Arg Lys Met Pro Leu Gln Val Ile Pro Pro Thr Leu Ser Ile Gly
785                 790                 795                 800

Ser Pro Ser Leu Met Val Ile Leu Arg Lys Asp Arg Gly Ser Glu Ala
                805                 810                 815

Lys His Gly Ala Lys Gly Thr Asp Asn Asn Gly Arg Leu Lys Phe His
                820                 825                 830

Phe Gln Ser Phe Val Ser Phe Gly Asp Ala His Arg Ile Ile Met Gly
            835                 840                 845

Ile Trp Lys Met Arg Ser Pro Gly Pro Glu Gln Lys Gly Glu Ile Met
850                 855                 860

Glu Glu Ser Glu Leu Lys Glu Leu Pro Ala Glu Ser Gly Ser Leu
865                 870                 875                 880

Phe Ser His Glu Asp Val Lys Met Ser Glu Ile Phe Ser Ser Val Leu
                885                 890                 895

Ser Val Asp Lys Tyr Ile Pro Ala Ala Asn Gln Ile Asn Tyr Lys Phe
                900                 905                 910

Asp Lys Ala Leu Ser Arg Ser Gly Gly Glu Ala Ser Thr Thr Gln Gln
            915                 920                 925
```

-continued

Lys Tyr Ala Leu Val Asn Gln Asp Gly Trp Ala Ile Glu Glu Val Met
    930                 935                 940

Thr Leu Gln Gly Val Leu Leu Gly Asp Tyr Phe Ser Phe Asp Lys Pro
945                 950                 955                 960

Phe Ser Arg Tyr Gly Gly Glu Ala Thr Thr Thr Gln Gln Thr Tyr Ala
                965                 970                 975

Leu Val Asn Gln Asp Gly Trp Ala Ile Glu Glu Val Met Thr Leu Gln
            980                 985                 990

Gly Val Leu Leu Gly Asp Cys Phe Thr Leu Gln Leu Gln Leu Lys Tyr
        995                 1000                1005

His Met Ala Asn Val Pro Pro Lys Pro Asn Thr Cys Ser Val Gln
    1010                1015                1020

Val Leu Leu Gly Ile Ala Trp Leu Lys Ser Thr Lys Gln Gln Lys
    1025                1030                1035

Lys Val Thr Lys Asn Ile Met Ser Asn Thr Ser Asn Arg Leu Lys
    1040                1045                1050

Glu Leu Phe Ser Glu Val Glu Lys Asp Leu Thr Ser Arg Asn Gly
    1055                1060                1065

Thr Leu Phe Ser Ala Ser Ile Asp Pro Tyr Arg Ser Leu His Asp
    1070                1075                1080

Pro Asn Ile Thr
    1085

<210> SEQ ID NO 130
<211> LENGTH: 272
<212> TYPE: PRT
<213> ORGANISM: Lolium perenne

<400> SEQUENCE: 130

Met Ala Ala Ile Thr Thr Thr Ala Pro Ser Ser Phe Arg Ile Ser
1               5                   10                  15

Ser Ser Pro Pro Pro Thr Thr Ser Thr Pro Arg Ser Asn Leu Thr Phe
            20                  25                  30

His Ala Arg Asn Arg Cys His Ser Arg Leu Ala Cys Arg Ala Thr Asp
        35                  40                  45

Val Ser Gly Ala Glu Pro Ser Ala Pro Pro Glu Ala Gly Gly Gly Arg
    50                  55                  60

Thr Trp Val Pro Val Val Pro Leu Ala Ala Leu Pro Arg Gly Glu Arg
65                  70                  75                  80

Arg Val Ile Val Gln Asp Gly Asp Glu Ile Leu Leu Leu Trp Tyr Lys
                85                  90                  95

Asp Glu Val Phe Ala Ile Glu Asn Arg Ser Pro Ala Glu Gly Ala Tyr
            100                 105                 110

Ser Glu Gly Leu Leu Asn Ala Lys Leu Thr Gln Asp Gly Cys Ile Met
        115                 120                 125

Cys Pro Ser Thr Asp Ser Thr Phe Asp Leu Arg Thr Gly Glu Ile Lys
    130                 135                 140

Glu Trp Tyr Pro Lys Asn Pro Val Leu Arg Ala Leu Thr Pro Val Leu
145                 150                 155                 160

Arg Lys Leu Phe Val Tyr Pro Ala Lys Thr Asp Gly Glu Asn Ile Tyr
                165                 170                 175

Ile Ser Ile Arg Gly Asp Gly Ala Ser Val Gly Ser Ala Glu Ile Leu
            180                 185                 190

Phe Ser Gly Lys Ala Gln Pro Gly Ser Thr Ala Ser Asp Val Asn Ile

```
            195                 200                 205
Glu Glu Val Arg Met Val Val Asp Glu Gly Val Gly Gly Phe Gly Phe
210                 215                 220

Thr Pro Tyr Asn Glu Leu Ile Asn Gly Arg Ala Ala Ile Ile Gly Phe
225                 230                 235                 240

Leu Leu Leu Ile Asp Phe Glu Leu Leu Thr Gly Lys Gly Leu Leu Arg
                    245                 250                 255

Gly Thr Gly Leu Leu Asp Phe Ile Tyr Ala Ile Ser Arg Ala Phe Ser
                260                 265                 270

<210> SEQ ID NO 131
<211> LENGTH: 1014
<212> TYPE: PRT
<213> ORGANISM: Lolium perenne

<400> SEQUENCE: 131

Met Gly Ser Leu Ser Pro Trp Gly Gln Phe Ser Leu Val Pro Phe Leu
1               5                   10                  15

Leu Leu Gln Phe Met Leu His Val Ser Tyr Gly Cys Ser Val Glu Glu
                20                  25                  30

Arg Ala Ala Leu Leu Glu Ile Arg Ser Ser Leu Met Arg Ala His Ser
            35                  40                  45

Leu Glu Val Pro Asp Ser Trp Arg Lys Asp His Asp Cys Cys Ser
50                  55                  60

Trp Lys His Val Lys Cys Asn Asn Lys Thr Gln Arg Val Ser His Leu
65                  70                  75                  80

Asp Leu Ser Ser Val Tyr Ala Thr Thr Glu Gly Asp Gly His Trp Phe
                85                  90                  95

Leu Asn Ser Thr Val Phe Ser Val Phe His Glu Leu Gln Tyr Leu Asp
                100                 105                 110

Leu Ser Tyr Asn Ser Pro Cys Ser Leu Ser Leu Lys Gly Leu Val Gly
            115                 120                 125

Leu Ala Lys Leu Arg Tyr Leu Asp Leu Ser Gly Thr Met Trp Gly Val
130                 135                 140

Gly Phe Pro Glu Phe Ile Gly Glu Ile Val Ser Leu Glu Val Leu Ala
145                 150                 155                 160

Leu Asn Asp Asn Asn Ile Thr Gly Gly Leu Pro Gly Thr Ala Val Lys
                165                 170                 175

Asn Leu Arg Asn Leu Arg Gln Leu Asn Met Thr Ser Asn Ser Cys Asp
            180                 185                 190

Gly Asn Leu Pro Glu Ser Leu Phe Ser Leu Pro His Leu Lys Ile Leu
        195                 200                 205

Asp Leu Ser Ala Asn Ile Phe Gly Gly His Ile Pro Ile Ser Ser Ala
210                 215                 220

Ser Gln Pro Ile Ser Leu Glu Val Leu Asp Leu Ser Ser Asn His Leu
225                 230                 235                 240

Asn Gly Thr Leu Pro Val Ala Ala Phe Gln Asn Ile Arg Asn Leu Asn
                245                 250                 255

Leu Ser Gly Asn Gln Phe Arg Gly Ser Leu His Val Ser Leu Phe Ala
            260                 265                 270

Leu Pro His Leu Lys Phe Leu Asp Leu Ser Tyr Asn Asn Phe Glu Gly
        275                 280                 285

Arg Phe Pro Val Ser Leu Ser Pro Glu Pro Val Pro Leu Glu Val Leu
    290                 295                 300
```

```
Asn Leu His Tyr Asn Asn Met Ser Gly Ala Leu Pro Ser Glu Gln Ala
305                 310                 315                 320

Phe Glu Asn Phe Lys Lys Leu Arg Gly Leu Tyr Leu Ser Ser Asn Gln
            325                 330                 335

Phe Ser Gly Asn Ile Pro Ala Phe Leu Phe Tyr Leu Pro His Ile Glu
            340                 345                 350

Arg Leu Asn Leu Ser Thr Asn Ile Phe Ser Gly Pro Ile Pro Ile Asn
            355                 360                 365

Pro Ser Leu Asn Leu Pro Leu Ser Leu Lys Ser Leu Arg Phe Ser Gln
370                 375                 380

Asn Asn Leu Ser Gly Arg Ile Ser Phe Ile Trp Leu Gly Asn Leu Thr
385                 390                 395                 400

Lys Leu Glu Val Ile Asp Leu Ser Gly Asn Ala Asn Leu Val Val Asp
                405                 410                 415

Val Asn Ile Pro Gly Trp Thr Pro Gln Phe Gln Leu Lys Gln Leu Leu
                420                 425                 430

Leu Ser Gly Cys Asp Leu Asp Lys Ser Ile Ile Ala Glu Pro Arg Phe
            435                 440                 445

Leu His Thr Gln His His Leu Glu Val Val Asp Leu Ser Asn Asn Asn
            450                 455                 460

Leu Ser Gly Ser Met Pro Asn Trp Leu Phe Thr Lys Glu Ala Thr Leu
465                 470                 475                 480

Gln Tyr Leu Asn Leu Gly Asn Asn Ser Leu Thr Gly Leu Leu Asp Pro
                485                 490                 495

Ile Trp His Thr Gln Ser Phe Leu Tyr Val Ile Asn Ile His Met Asn
                500                 505                 510

His Ile Ala Gly Gln Leu Pro Ala Asn Ile Ser Ser Met Phe Pro Cys
            515                 520                 525

Leu Ser Val Leu Asp Phe Ser Asn Asn Asn Leu Leu Gly His Ile Pro
            530                 535                 540

Ser Ser Leu Cys Glu Ile Ser Leu Met Gln His Leu Asp Leu Ser Asn
545                 550                 555                 560

Asn Lys Leu Ser Gly Glu Val Pro Ala Cys Val Phe Thr Asn Tyr Pro
                565                 570                 575

Met Leu Met Thr Leu Lys Val Ser Asn Asn Lys Leu Gly Gly Val Ile
                580                 585                 590

Phe Gly Gly Met Asn Asn Leu Ser Ile Met Ser Glu Leu Cys Leu Asp
            595                 600                 605

Gly Asn Lys Phe Glu Gly Thr Ile Ser His Asp Leu Ser Gly Val Leu
            610                 615                 620

Glu Ile Met Asp Leu His Asp Asn Glu Leu Ser Gly Arg Leu Asp Thr
625                 630                 635                 640

Ser Leu Trp Asn Leu Ser Ser Leu Val Val Leu Asn Leu Ser Gly Asn
                645                 650                 655

Arg Leu Thr Gly Lys Ile Tyr Pro Gln Ile Cys Gly Leu Ala Gly Ile
            660                 665                 670

Arg Leu Leu Asp Leu Ser Ser Asn Asn Leu Ala Gly Ser Val Pro Asn
            675                 680                 685

Cys Ser Phe Leu Leu Leu Asn Phe Leu Asn Leu Ser Gly Asn Ser Leu
            690                 695                 700

Ser Gly Asp Ile Ser Tyr Ser Phe Phe Asn Thr Ser Ser Leu Val Ala
705                 710                 715                 720

Leu Asp Ile Arg His Asn Gln Phe Thr Gly Asn Leu His Trp Val Arg
```

```
                            725                 730                 735
Tyr Val Gly Asn Thr Arg Leu Leu Phe Leu Ser Gly Asn Lys Phe Glu
                740                 745                 750
Gly Gln Ile Ser Pro Asn Leu Cys Lys Leu Leu Tyr Leu Arg Ile Ile
                755                 760                 765
Asp Leu Ser His Asn Lys Leu Ser Gly Ser Leu Pro Ala Cys Ile Gly
                770                 775                 780
Asn Ile Ser Phe Lys Gly Glu Thr Asp Asp Gln Ile Phe Gln Pro Val
785                 790                 795                 800
His Arg Phe Ile Ser Tyr Phe Tyr Arg Asn Phe Tyr Ala Pro Gln Lys
                805                 810                 815
Tyr Ser Asn Ser Tyr Asp Phe Lys Ser Phe Ala Phe Ala Thr Lys Gly
                820                 825                 830
Asn Leu Tyr Ile Tyr Gly Arg Ser Phe Phe Leu Ser Met Ser Gly Ile
                835                 840                 845
Asp Leu Ser Ala Asn Met Leu Asp Gly Glu Ile Pro Trp Glu Leu Gly
                850                 855                 860
Asn Leu Ser Arg Ile Lys Ser Leu Asn Leu Ser Tyr Asn Phe Phe Val
865                 870                 875                 880
Gly Pro Ile Pro Ala Thr Phe Gly Gly Met Lys Glu Ile Glu Ser Leu
                885                 890                 895
Asp Leu Ser His Asn Glu Leu Ser Gly Leu Ile Pro Gln Gln Leu Thr
                900                 905                 910
Gln Leu Ser Ser Leu Gly Val Phe Ser Val Ala Tyr Asn Asn Leu Ser
                915                 920                 925
Gly Cys Ile Pro Asn Ser Gly Gln Leu Gly Ser Phe Gly Ile Gln Ser
                930                 935                 940
Tyr Leu Ala Asn Thr Asn Leu His Lys Ile Thr His Gly Asn Met Cys
945                 950                 955                 960
Thr Ala Pro Gly Leu Asp Pro Ala Pro Glu Glu Asp Val Gly Glu Met
                965                 970                 975
Phe Gly Asp Pro Val Leu Tyr Val Val Thr Ala Ala Thr Phe Val Leu
                980                 985                 990
Ala Phe Trp Ala Thr Ile Gly Phe Ser Phe Cys His Pro Tyr Gly Arg
                995                 1000                1005
Ser Val Met Leu Lys Leu
                1010

<210> SEQ ID NO 132
<211> LENGTH: 673
<212> TYPE: PRT
<213> ORGANISM: Lolium perenne

<400> SEQUENCE: 132

Met Lys Lys Leu Gly Gly Gly Ile Pro Gln Asp Ala Gly Leu Ser
1               5                   10                  15
Asp Phe Leu Lys Asn Arg Leu Gln Lys Ile Pro Arg Ile Ser Ala Pro
                20                  25                  30
Thr Gln Leu Phe Leu Gly Pro Pro Leu His Arg Ser Arg Thr Val Glu
                35                  40                  45
Thr Pro Cys Gly Gly Lys Ile Pro Ser Ser Glu Glu Phe Ser Leu Ile
                50                  55                  60
Leu Pro Leu Leu Ala Val Ser Arg Leu Ser Arg Thr Asn Ser Leu Arg
65                  70                  75                  80
```

-continued

```
Thr Glu Ser Val Glu Ser Pro Val Pro Asp Ala Phe Ala Ala Leu Pro
             85                  90                  95

Thr Ala Asp Ala Asp Glu Val Gly Thr Ser Ser Thr Ala Gly Gly
        100                 105                 110

Gly Ala Thr Ala Ser Asn Pro Ile Ser Pro Arg Ser Ser Asn Pro Leu
            115                 120                 125

Pro Ser Thr Thr Ser Ala Thr Thr Pro Leu Glu Leu Pro Gly Val Pro
    130                 135                 140

Pro Ala Ala Ser Ala Arg Asn Pro Lys Ile His His Thr Arg Gly Val
145                 150                 155                 160

Leu His Leu Tyr Arg Ser Ser Pro Ser Leu Pro Ala Ser Ser Tyr Ala
                165                 170                 175

Ser Ala Val Ala Val Ala Ala Thr Pro Ser Ser Ser Ser Gly Pro
            180                 185                 190

Thr Ala Pro Pro Leu Gln Cys Asp Ser Leu Leu Pro Ser Trp Arg Gly
        195                 200                 205

Thr Arg Leu Leu Val Leu Ala Val Pro Thr Arg Val Ser Pro Glu Asp
    210                 215                 220

Phe Val Arg Phe Cys Gly Pro Tyr Val Glu His Ala Ser Glu Ile Arg
225                 230                 235                 240

Val Ile Ser Asp Asp Gly Val Glu Asp Arg Tyr Ser Val Leu Val Glu
                245                 250                 255

Phe Glu Asp Gln Lys Ser Ala Asp Gly Phe Tyr Leu Asp Leu Asn Gly
            260                 265                 270

Trp Arg Phe Ser Ser Ser Glu Val Val Ile Leu Pro Ile Trp Cys Gln
        275                 280                 285

Leu Val Glu Val Cys His Val Leu Phe Ile Val Ala Val Gln Tyr Met
    290                 295                 300

Pro Ser Ala Val Pro Pro Val Gly Ser Thr Glu Leu Pro Thr Cys Pro
305                 310                 315                 320

Val Cys Ile Glu Arg Leu Asp Gln Asp Ile Ser Gly Ile Val Ala Thr
                325                 330                 335

Asn Cys Asp His Ser Phe Gln Cys Ser Cys Val Ser Met Trp Val Ser
            340                 345                 350

Ser Ser Cys Pro Val Cys Gln Phe Cys Gln Lys Gln Ser Glu Thr Pro
        355                 360                 365

Thr Asn Pro Thr Cys Ser Val Cys Gln Thr Ser Glu Asn Leu Trp Ile
    370                 375                 380

Cys Val Ile Cys Gly Phe Val Gly Cys Gly Arg Tyr Lys Glu Gly His
385                 390                 395                 400

Ser Ile Arg His Trp Lys Asp Thr Gln His Cys Tyr Ser Leu Asp Leu
                405                 410                 415

Glu Thr Gln Arg Val Trp Asp Tyr Val Gly Asp Ser Tyr Val His Arg
            420                 425                 430

Leu Asn His Ser Lys Ser Asp Ala Lys His Ser Lys Leu Arg Ser Lys
        435                 440                 445

Cys Glu Phe Ser Gly Asp Asn Asp Leu Asp Met Gly Gly Val Met
    450                 455                 460

Phe Ser Ser Lys Thr Asp Thr Ile Val Asp Glu Tyr Asn Arg Leu Leu
465                 470                 475                 480

Ala Ser Gln Leu Glu Thr Gln Arg Glu Tyr Tyr Glu Ala Leu Leu Ser
                485                 490                 495

Asp Ala Lys Lys Asp Arg Glu His Ile Ser Val Ala Val Asp Lys Ala
```

-continued

```
                500                 505                 510
Val Asn Asp Lys Leu Gln Glu Met Gln Leu Lys Leu Glu Asn Thr Met
            515                 520                 525

Leu Glu Lys Lys Lys Val Ala Glu Met Asn Glu Lys Leu Met Lys Ser
            530                 535             540

Gln Asp Ile Trp Ser Lys Thr Val Lys Gly Ile Glu Glu Arg Glu Arg
545                 550                 555                 560

Ala Gln Leu Arg Leu Lys Asp Asp Thr Ile Leu Asp Leu Glu Glu Gln
                565                 570                 575

Ile Lys Asp Phe Lys Tyr Ser Ile Lys Leu Gln Lys Ser Ile Glu Lys
            580                 585                 590

Ser Thr His Ala Asp Asp Leu Lys Gly Gly Met Leu Val Pro Leu Ala
            595                 600                 605

Met Glu Ser Glu Ser Gly Lys Gly Ala Glu Phe Glu His Tyr Val Asn
            610                 615                 620

Met Cys Lys Lys Asp His Glu Ala Pro Tyr Gln Lys Asn Leu Leu Pro
625                 630                 635                 640

Ser Arg Lys Asn Ser Asp Ser Met Glu Lys Leu Leu Ile Pro Pro Lys
                645                 650                 655

Thr Thr Pro Pro Ser Leu Leu Phe Asp Thr Leu Lys Val Lys Ser Met
            660                 665                 670

Gly

<210> SEQ ID NO 133
<211> LENGTH: 204
<212> TYPE: PRT
<213> ORGANISM: Lolium perenne

<400> SEQUENCE: 133

Met Ser Lys Leu Thr Val Gly Val Cys Ile Met Val Ala Leu Ser Leu
1               5                   10                  15

Ala Val Phe Leu Thr Ile Val Val Leu Leu Ala Asp Leu Phe Cys
                20                  25                  30

Ser His Leu Arg Leu Arg Arg Leu Arg Ala Asp Ala Glu Met Ala Pro
            35                  40                  45

His Lys Arg Pro Lys Leu Gly Val Pro Ala Ser Ser Pro Pro His Thr
        50                  55                  60

Ala Asp Asp Ala Ser Val Ala Thr Thr Thr Thr Ala Thr His Glu
65                  70                  75                  80

Ala Leu Ser Ser Thr Pro Pro Phe Tyr Tyr Ala His Gly Val Met Cys
                85                  90                  95

Ala Pro Thr Arg Lys Asp Leu Leu Ala Ile Pro Lys Leu Glu Ala
            100                 105                 110

Ala Val Trp Lys Trp Ser Pro Ala Arg Arg Ser Ser Pro Ser Pro Ser
        115                 120                 125

Pro Pro Arg Ser Glu Pro Thr Ala Arg Glu Ser Ser Ser Ala Tyr
    130                 135                 140

Ser Asp Gly Phe Leu Arg Ile Ser Asn Pro Val Tyr Glu Arg Gly Ala
145                 150                 155                 160

Thr Ala Ala Pro Gly Gly Tyr Glu Glu Asp Thr Pro Phe Asp Thr Pro
                165                 170                 175

Asp Ala Ser Pro Ser Pro Asn Gly Ile Thr Glu Glu Glu Gly Ala Phe
            180                 185                 190

Gly Arg Val Asn His Thr His Gln Gly Ala Arg Ser
        195                 200
```

195                 200

<210> SEQ ID NO 134
<211> LENGTH: 192
<212> TYPE: PRT
<213> ORGANISM: Lolium perenne

<400> SEQUENCE: 134

Met Arg Gly Ser Leu Ser Tyr Gln Val Ser Ile Ser Gly His Ser Arg
1               5                   10                  15

Gly Gly Lys Val Ala Phe Ala Leu Ala Leu Gly His Ala Lys Thr Ser
            20                  25                  30

Leu Pro Leu Ala Ala Leu Ile Ala Val Asp Pro Val Asp Gly Thr Gly
        35                  40                  45

Leu Gly Asn Gln Thr Pro Pro Pro Ile Leu Thr Tyr Lys Glu Thr Pro
    50                  55                  60

Leu His Val Pro Ala Pro Ile Met Val Ile Gly Thr Gly Leu Gly Glu
65                  70                  75                  80

Val Pro Arg Asn Phe Leu Cys Pro Pro Cys Ala Pro Leu Gly Val Ser
                85                  90                  95

His Ala Ala Phe Tyr Arg Glu Cys Ala Ala Pro Ala Cys His Leu Val
            100                 105                 110

Ala Arg Asp Tyr Gly His Thr Asp Met Met Asp Val Thr Thr Gly
        115                 120                 125

Ala Lys Gly Leu Ala Thr Arg Ala Val Cys Lys Ser Gly Glu Ala Arg
    130                 135                 140

Glu Pro Met Arg Arg Phe Val Gly Gly Ala Met Val Ala Phe Leu Lys
145                 150                 155                 160

Lys Trp Val Glu Gly Arg Pro Glu Trp Leu Asp Gly Ile Arg Glu Arg
                165                 170                 175

Pro Glu Val Ala Pro Val Val Leu Ser Val Val Glu Phe Arg Asp Glu
            180                 185                 190

<210> SEQ ID NO 135
<211> LENGTH: 80
<212> TYPE: PRT
<213> ORGANISM: Lolium perenne

<400> SEQUENCE: 135

Glu Arg Thr Gln Tyr Arg Asn Pro Ser Cys Ser Asn Ser Trp Lys Arg
1               5                   10                  15

Pro Pro Val Glu Glu Val Phe Cys Lys Leu Val Thr His Tyr Ala Arg
            20                  25                  30

Val His Ser Arg Gln Cys Leu Asp Glu Ala Glu Val Ala Glu His Val
        35                  40                  45

Val Gly Leu Thr Ser Ser Leu Ala Asn Cys Lys Phe Ser Tyr Ser Val
    50                  55                  60

Pro Ser Leu Leu Phe Arg His Leu Asn His Phe Tyr His Ser Arg Val
65                  70                  75                  80

<210> SEQ ID NO 136
<211> LENGTH: 101
<212> TYPE: PRT
<213> ORGANISM: Lolium perenne

<400> SEQUENCE: 136

Met Ala Phe Lys Lys Val Gln Met Ala Asp Lys Tyr Pro Lys Gly Gln
1               5                   10                  15

```
Ser Arg Gly Arg Gln Trp Lys His Leu Arg Phe Leu Leu Gln Ala Ala
         20                  25                  30

Asp Ala Thr Ser Leu Pro Pro Asp Arg Pro Asn Tyr Leu Asn Ile Gln
             35                  40                  45

Ser Pro Pro Ser Ile Tyr Pro Pro Lys Arg Tyr Cys Asp Val Thr Gly
 50                  55                  60

Phe Glu Gly Cys Ile Leu Gly Thr Lys Gly Ile Gln Asp Gly Arg Gly
 65                  70                  75                  80

Phe Val Glu Phe Leu Leu Phe Thr Gln Ser Pro Leu Tyr Lys Cys Gly
                 85                  90                  95

Leu Val Ile Arg Asp
            100

<210> SEQ ID NO 137
<211> LENGTH: 1981
<212> TYPE: PRT
<213> ORGANISM: Lolium perenne

<400> SEQUENCE: 137

Met Ala Leu Glu Lys Glu Ser Ile Arg Lys Asp Ser Phe Ser Lys Glu
 1               5                  10                  15

Gln Ile Gln Tyr Thr Arg Glu Gly Thr Gly Thr Pro Ser Thr His
             20                  25                  30

Leu Asp Leu Gln Ala His Leu Glu Lys Ile Ala Arg Leu Glu Arg Ser
             35                  40                  45

Leu Gln Gly Leu Gln Glu Gln Leu Ser Phe Ala Gln Ala Glu Cys Phe
 50                  55                  60

Asp Lys Asp Val Ile Leu Ala Lys Gln Ala Lys Val Ala Glu Glu Ala
 65                  70                  75                  80

Ile Leu Gly Trp Glu Lys Ala Glu Ala Glu Ala Ile Ala Thr Lys Thr
                 85                  90                  95

Glu Leu Asp Asp Thr Leu His Gln Lys Ala Thr Val Glu Gln Arg Ile
            100                 105                 110

Cys Gln Leu Asp Glu Ala Leu Asn Val Thr Met Val Glu Arg Glu Leu
            115                 120                 125

Leu Ile Lys Asp Thr Ala Lys Ile Ile Ser Cys Glu Lys Asp Lys Val
        130                 135                 140

His Lys Leu Glu Glu Asn Leu Glu Glu Lys Gln Asn Ile Ile Ala Ser
145                 150                 155                 160

Leu Asp Asp Glu Tyr Ser Arg Leu Ser Glu Ile Leu Leu Ala Lys Glu
                165                 170                 175

Lys Val Ile Leu Asp Leu Thr Glu Leu Asn Ala Val Lys Glu Ser Asp
            180                 185                 190

Leu Lys Asp Leu Val Val Lys Leu Glu Ser Thr Glu Arg Ser Asn Ser
        195                 200                 205

Ser Leu Arg Tyr Glu Val Cys Met Leu Gln Lys Gln Leu Asp Ile Arg
    210                 215                 220

Ser Glu Glu Arg Lys Cys Asn Leu Lys Ser Ala Asp Ala Ser His Lys
225                 230                 235                 240

Gln His Leu Glu Asn Val Arg Lys Ile Thr Lys Leu Glu Glu Glu Cys
                245                 250                 255

Lys Arg Leu Arg Ser Met Val Arg Lys Arg Leu Pro Gly Pro Ala Ala
            260                 265                 270

Ile Ala Lys Met Arg Ser Glu Val Glu Thr Leu Gly Asn Asn Ile Ala
```

-continued

|     |     |     |     |     | 275 |     |     |     |     | 280 |     |     |     |     | 285 |     |     |
| --- | --- | --- | --- | --- | --- | --- | --- | --- | --- | --- | --- | --- | --- | --- | --- | --- | --- |

Gln Thr Arg Met Gly Lys Leu Asn Ser Pro Ala Ser Ser Asn Ser Tyr
290 295 300

Asp Pro Val Gln Asn Phe Ser Asp Ala Ser His Ser Ser Ser Ser Leu
305 310 315 320

Leu Ala Arg Leu His Val Met Glu Asp Gln Asn Lys Ser Met Lys Glu
325 330 335

Ser Leu Ser Arg Lys Asp Gly Glu Leu Gln Phe Ser Arg Thr Met Leu
340 345 350

Ala Arg Ala Asn Ser Lys Leu Ser Gln Val Glu Ala Gln Leu Glu Glu
355 360 365

Leu Ser Gly Asp Gln Ala Ala Thr Glu Leu Val Lys Arg Ser Pro Ala
370 375 380

Leu Ala Glu Asn Pro Leu Ser Ser Ile Ser Glu Asn Gly Cys Asn Glu
385 390 395 400

Asp Asn Val Ser Cys Ser Gly Ser Trp Ala Ser Ala Leu Ile Ser Glu
405 410 415

Leu Glu His Phe Lys Lys Gly Lys Leu Thr Thr Pro Ser Cys Gln Ser
420 425 430

Thr Gly Val Ser Asp Met Ser Phe Met Asp Asp Phe Glu Glu Ile Glu
435 440 445

Arg Leu Ala Met Val Cys Asp Asn Lys Pro Ser Lys Leu Tyr Asp Ala
450 455 460

Lys Arg Glu Ala Ile Glu Ser Ala Gly Lys Glu Leu Val Pro Val Asp
465 470 475 480

Gly Pro Asn Glu Thr Asn Asp Gln Val His Gln Tyr Lys Ile Gln Lys
485 490 495

Gly Leu Val Lys Leu Ile Glu Leu Val Glu Gly Val Ile Gln Arg Ser
500 505 510

Ser Lys Asp His Asn Ser Lys Phe Val Gln Ser Gly Asp Asn Met Gly
515 520 525

Asp Gln Ser Thr Ala Ile Asp Gly Tyr Phe Ala His Ala Phe Leu Trp
530 535 540

Lys Thr Ser Glu Leu Thr Cys Val Leu Arg His Phe Ile Val Val Cys
545 550 555 560

Asn Glu Leu Met Tyr Gly Asn Thr Asp Ala Glu Arg Phe Val Leu Glu
565 570 575

Val Asn Leu Thr Leu Asp Trp Ile Ile Asn His Cys Phe Ser Leu Gln
580 585 590

Asp Val Pro Asp Met Arg Glu Thr Ile Ile Asn His Leu Glu Leu Asp
595 600 605

Ser Ser Asp Gly Leu Asp Ala Val Ala Lys Gln Ile Ala Ile Gln
610 615 620

Thr Thr Lys Gly Val His Glu Pro Ser Thr Pro Asn Ser Val Gln Met
625 630 635 640

Ser Leu Ile Ser Val Ser Ser His Val Asp Ile Gly Leu Lys Ala Asp
645 650 655

Asn Asp Thr Arg Ser Ile Thr Asn Glu Val Pro Val Ser Asn Pro His
660 665 670

Glu Leu Glu Gly Lys Ser Ser Leu Arg Ala Glu Leu Asn Ala Leu
675 680 685

Lys Glu Thr Gly Lys Ile Asn Ala Gln Ser Val Asn Cys Glu Ser Thr
690 695 700

```
Val Ser Asp Leu Asp Lys His Lys Pro Ile Cys Asn Ser Glu Glu Gly
705                 710                 715                 720

Lys Pro Tyr Phe Glu Phe Thr Ile Ile Leu Gln Pro Val Gly Ile Asp
            725                 730                 735

Lys Leu Ile Pro Cys Gln Leu Ala Pro Phe Val Gly Thr Arg Gly Val
            740                 745                 750

Lys Asp Pro Ile Ser Met Ala Arg Leu Arg Ser Ser Thr Ser Ser Thr
            755                 760                 765

Ala Ser Asn Ala Met Asp Arg Gly Lys Gln Ile Ala Thr Gly Leu Val
770                 775                 780

Asp Phe Val Pro His Pro Pro Ser Arg Leu Asp Ala Tyr Ala Tyr Leu
785                 790                 795                 800

Glu Glu Pro Met Glu Met Thr Phe Gly Arg Phe His Phe Arg Val Glu
                805                 810                 815

Lys Glu Gly Ser Tyr Arg Val Glu Ile Pro Ile Ser Ser Gly Ser Ser
                820                 825                 830

Ala Val Asp Ser Asp Phe Ser Ser Tyr Thr Ser Ser Thr Glu Ser Gly
            835                 840                 845

Glu Glu Glu Thr Ser Ser Ser Arg Phe Ile Ser Thr Arg Ala Arg Glu
850                 855                 860

Lys Leu Ala Lys Ile Phe Ser Asp Met Ser Phe Glu Ser Ser Ala Asp
865                 870                 875                 880

Ser Tyr Ile Ser Asp Gly Ser Ser Ser Val Asn Ser Tyr Asp Phe Ile
                885                 890                 895

Asp Lys Ser Thr Thr Val Gly Lys Val Phe Ala Asn Leu His Asp Gly
                900                 905                 910

Val Thr Lys Pro Asn Ile Asp Leu Asn Thr Lys Tyr His His Ile Tyr
            915                 920                 925

Val Ile Gly Glu Pro Ser Arg Asp Gln Glu Glu Thr Ser Glu Ala Phe
930                 935                 940

Asp Asp Leu Gly Asn Pro Tyr Val Asp Pro Ser Asp Leu Arg Arg Gly
945                 950                 955                 960

Leu Gly Asn Lys Tyr Ile Gly Pro Gln Pro Arg Asp Arg Val Gln Leu
                965                 970                 975

Pro Gln Ala Ala Trp Asp Arg Ala Ala Arg Ala Met Asp Gly Ser Glu
            980                 985                 990

Pro Met Ala Thr Thr Ala Thr Pro Glu Glu Leu Gln Ala Tyr Gln Tyr
            995                 1000                1005

Arg Leu Ala Arg Ala Ala Arg Glu Leu Glu Lys Gln Thr Ala Glu
    1010                1015                1020

Leu Asn Arg Arg Lys Glu Ala Ser Ala Ser Asn Lys Thr Leu
    1025                1030                1035

Leu Asp Thr Ser Cys Ser Gly Ser Phe Thr Arg Asn Lys Glu Glu
    1040                1045                1050

Phe Lys Arg Asp Leu Leu Asp Arg Ile Gln Glu Asn Thr Glu Gly
    1055                1060                1065

Trp Glu Asn Asp Lys Asp Arg Glu Ser Gly Phe Met Asp Thr Asp
    1070                1075                1080

Lys Phe Arg Asn Met Ser Ala Thr Tyr Gly Leu Asp Ser Gln Val
    1085                1090                1095

Ala Ala Asn Leu Tyr Lys Ala Phe Ala Ser His Tyr Glu Leu Pro
    1100                1105                1110
```

-continued

| | | | | | | | | | | | | |
|---|---|---|---|---|---|---|---|---|---|---|---|---|
|Lys|Lys|Asn|Phe|Asp|Lys|Tyr|His|Glu|Pro|Tyr|Lys|Asp Lys Ile|
|1115| | | | |1120| | | | |1125| | |
|Asp|Ser|Ser|Ile|Asn|Lys|Cys|Val|Val|Glu|Thr|Ala|Asp His|
|1130| | | | |1135| | | | |1140| | |
|Val|Ile|Pro|Glu|Ala|Tyr|Ile|Glu|Lys|Thr|Pro|Phe|Pro Ala Lys|
|1145| | | | |1150| | | | |1155| | |
|Met|Lys|Glu|Tyr|Ser|Val|Ile|Asn|Ser|Ala|Val|His|Lys Ser Glu|
|1160| | | | |1165| | | | |1170| | |
|Lys|Lys|Pro|Val|Glu|Pro|Glu|Gln|Ile|Lys|Val|Glu|Pro Ala|
|1175| | | | |1180| | | | |1185| | |
|Val|Ala|Ile|Val|Lys|Asp|Leu|Val|Thr|Glu|Asn|Val|Glu Asp Gly|
|1190| | | | |1195| | | | |1200| | |
|His|Ile|Ile|Phe|Cys|Glu|Asp|Ala|Ser|Asn|Ile|Val|Ser His Pro|
|1205| | | | |1210| | | | |1215| | |
|Asn|Lys|Pro|Lys|Gln|Val|Ser|Val|Pro|Met|Leu|Ser|Val Arg Ile|
|1220| | | | |1225| | | | |1230| | |
|Gly|Asp|His|Cys|Tyr|Tyr|Gly|Leu|Cys|Asp|Ile|Gly|Ala Ser Val|
|1235| | | | |1240| | | | |1245| | |
|Ser|Ala|Ile|Pro|Tyr|Glu|Leu|Tyr|Thr|Glu|Ile|Met|His Glu Ile|
|1250| | | | |1255| | | | |1260| | |
|Asp|Ser|Cys|Glu|Leu|Glu|Asp|Ile|Asp|Val|Val|Ile|Gln Leu Ala|
|1265| | | | |1270| | | | |1275| | |
|Asn|Arg|Glu|Thr|Ile|Ser|Pro|Ile|Gly|Ile|Val|Arg|Asp Val Glu|
|1280| | | | |1285| | | | |1290| | |
|Val|Leu|Cys|Gly|Lys|Ile|Lys|Tyr|Pro|Ala|Asp|Phe|Leu Val Leu|
|1295| | | | |1300| | | | |1305| | |
|Gly|Ser|Ala|Ala|Ser|Asp|Tyr|Cys|Pro|Ile|Ile|Phe|Gly Arg Pro|
|1310| | | | |1315| | | | |1320| | |
|Phe|Leu|Asn|Thr|Cys|Gly|Ala|Ile|Ile|Asp|Cys|Lys|Lys Glu Lys|
|1325| | | | |1330| | | | |1335| | |
|Ile|Leu|Thr|Lys|Phe|Ala|Gly|Glu|Ser|Tyr|Glu|Phe|Asn Phe Ser|
|1340| | | | |1345| | | | |1350| | |
|Lys|Phe|Thr|Lys|Thr|Pro|Tyr|Lys|Ala|Asp|Leu|Pro|Ser Asp Asp|
|1355| | | | |1360| | | | |1365| | |
|Phe|Lys|Met|Glu|Gln|Cys|Ala|Ser|Ile|Ile|Leu|Val|Pro Asn Asn|
|1370| | | | |1375| | | | |1380| | |
|Pro|Leu|Gln|Gln|His|Leu|Glu|Asn|Ser|Glu|Ser|Glu|Val Phe Arg|
|1385| | | | |1390| | | | |1395| | |
|Lys|Glu|Arg|Asp|Glu|Leu|Glu|Glu|Ile|Phe|Leu|Arg|Gln Pro Ile|
|1400| | | | |1405| | | | |1410| | |
|Leu|Lys|His|Asp|Leu|Pro|Val|Glu|Asp|Leu|Gly|Thr|Thr Pro Pro|
|1415| | | | |1420| | | | |1425| | |
|Pro|Lys|Glu|Asp|Pro|Val|Phe|Asp|Leu|Lys|Pro|Leu|Pro Asp Asn|
|1430| | | | |1435| | | | |1440| | |
|Leu|Lys|Tyr|Ala|His|Ile|Asp|Asp|Lys|Lys|Ile|Tyr|Pro Val Ile|
|1445| | | | |1450| | | | |1455| | |
|Ile|Ser|Ser|Lys|Leu|Ser|Glu|Ile|Glu|Glu|Arg|Leu|Leu Glu|
|1460| | | | |1465| | | | |1470| | |
|Ile|Leu|Lys|Lys|His|Arg|Gly|Ala|Ile|Gly|Tyr|Thr|Leu Asp Asp|
|1475| | | | |1480| | | | |1485| | |
|Leu|Lys|Gly|Ile|Ser|Pro|Ser|Ile|Cys|Gln|His|Ala|Ile Asn Met|
|1490| | | | |1495| | | | |1500| | |
|Glu|Asp|Asp|Ala|Lys|Pro|Val|Val|Glu|His|Gln|Arg|Arg Leu Ile|

-continued

```
              1505                1510                1515
Pro Lys Met Lys Glu Val Val Arg Asn Glu Val Leu Lys Leu Leu
         1520                1525                1530
Glu Ala Gly Ile Ile Tyr Pro Ile Ala Asp Ser Arg Trp Val Ser
         1535                1540                1545
Pro Val His Cys Val Pro Lys Lys Gly Gly Met Thr Val Val Pro
         1550                1555                1560
Asn Asp Asn Asp Glu Leu Ile Pro Gln Arg Val Val Gly Cys
         1565                1570                1575
Leu Arg Asn Leu Asp Lys Val Leu Gln Arg Cys Glu Glu Thr Asn
         1580                1585                1590
Leu Val Leu Asn Cys Glu Lys Cys His Phe Met Val Asn Glu Gly
         1595                1600                1605
Ile Val Leu Gly His Lys Ile Ser Glu Arg Ala Ile Glu Val Asp
         1610                1615                1620
Arg Ala Lys Val Glu Ala Ile Glu Lys Met Pro Tyr Pro Arg Asp
         1625                1630                1635
Val Lys Gly Ile Arg Ser Val Leu Gly His Ala Glu Phe Tyr Arg
         1640                1645                1650
Arg Phe Ile Lys Asp Phe Ser Lys Ile Ser Lys Pro Leu Thr Asn
         1655                1660                1665
Leu Leu Gln Lys Gly Val Pro Phe Val Phe Asp Asp Asp Cys Lys
         1670                1675                1680
Glu Ala Phe Glu Thr Leu Lys Lys Ala Leu Thr Thr Ala Pro Ile
         1685                1690                1695
Val Glu Pro Pro Asp Trp Asn Leu Pro Phe Glu Ile Met Cys Asp
         1700                1705                1710
Ala Ser Asp Phe Ala Val Gly Ala Val Leu Gly Gln Arg Val Asp
         1715                1720                1725
Lys Lys Leu Asn Val Ile His Tyr Ala Ser Lys Thr Leu Asp Ala
         1730                1735                1740
Ala Gln Arg Asn Tyr Ala Thr Thr Glu Lys Glu Leu Leu Ala Val
         1745                1750                1755
Val Phe Ala Cys Asp Lys Phe Arg Ser Tyr Ile Val Asp Ser Lys
         1760                1765                1770
Val Thr Ile His Thr Asp His Ala Ala Ile Arg Tyr Leu Met Thr
         1775                1780                1785
Lys Lys Asp Ala Lys Pro Arg Leu Ile Arg Trp Val Leu Leu Leu
         1790                1795                1800
Gln Glu Phe Asp Leu His Ile Val Asp Arg Lys Gly Ala Asp Asn
         1805                1810                1815
Pro Val Ala Asp Asn Leu Ser Arg Leu Glu Asn Ile Ala Tyr Asp
         1820                1825                1830
Pro Val Pro Val Asn Asp Ser Phe Pro Asn Lys Gln Leu Ala Val
         1835                1840                1845
Ile Lys Val Ser Ser Arg Asp Ser Pro Trp Tyr Ala Asp Tyr Ala
         1850                1855                1860
Asn Phe Ile Val Ser Lys Tyr Leu Pro Pro Thr Phe Ser Ala Gln
         1865                1870                1875
Gln Arg Arg Lys Phe Phe Tyr Asp Leu Arg His Tyr Phe Trp Asp
         1880                1885                1890
Asp Pro His Leu Tyr Lys Glu Gly Val Asp Gly Ile Leu Arg Ser
         1895                1900                1905
```

```
Ser Arg Leu Arg Val Gly Leu Phe Met His Val Ile Met Val Lys
    1910                1915                    1920

Trp Thr Asp Arg Ser Ala Met Leu Arg Ala Asp Arg Arg Ser Arg
    1925                1930                    1935

Glu Thr Thr Ser Cys Glu Tyr Met Leu Tyr Ser Val Lys Ser Tyr
    1940                1945                    1950

Thr Ser Leu Ser Pro Pro Ser Val His Val Ala Lys Asp Leu Tyr
    1955                1960                    1965

Val Gly Arg Ala Glu Arg Leu Ala Leu Tyr Glu Leu Ser
    1970                1975                    1980

<210> SEQ ID NO 138
<211> LENGTH: 511
<212> TYPE: PRT
<213> ORGANISM: Lolium perenne

<400> SEQUENCE: 138

Met Asp Met Asp Arg Ile Arg Tyr Thr Asn Asn Ile Asp Asp Gly Gly
1               5                   10                  15

Glu Ile Lys Ala Pro Ile Pro Tyr Asp Glu Gln Pro Glu Ser Phe Pro
                20                  25                  30

Ser Leu Asn Ala Ser Leu Gly Asn Phe Pro Leu Met Pro Glu Asp Ile
            35                  40                  45

Asp Gln Arg Ser Gly Ser Ser Leu Asp Gly Arg Arg Leu Ala Cys Lys
        50                  55                  60

Arg Lys Thr Ile Glu Gly Ala His Gly Ile Phe Ser Ala Gly Ala Ser
65                  70                  75                  80

Thr Ser Phe Ser His Arg Asn Asp Asn Val Phe His Asn Ile Pro Ser
                85                  90                  95

Thr Ser Phe Ser Pro Ala Pro Thr Met Asn Val Pro Ser His Asn Phe
            100                 105                 110

Leu Leu Pro Pro Ser Ser Ile Glu Glu Gln Leu Pro His Tyr Gly Ala
        115                 120                 125

Thr Thr Gly Leu Pro Ser Ser Ser Tyr Asn His Pro Ser Gly Gly Asn
    130                 135                 140

Tyr Asn Ser Gly Asn Ser Gln Arg Ser Phe Arg Val Arg Thr Thr Thr
145                 150                 155                 160

Ala Gln Gln Val Asn Pro Tyr Gly Val Trp Pro Ser Ser Ser Thr Met
                165                 170                 175

Ser His Ser Ser Ser Trp Asn His Gln Ala Pro Ala Leu Gln Ser Ala
            180                 185                 190

Phe Asp Glu Met Gln Glu Gly Ile Pro Met Val Ser Gly Ile Asn Leu
        195                 200                 205

Gln Tyr Gln His Pro Ala Asn Val Val Pro Gly Ile Pro Gln Ile Ala
    210                 215                 220

His Arg Phe Ala Cys His Gly Ala Ser Ser Arg Ala Gly Ser Leu
225                 230                 235                 240

Asp Asn Arg Ile Leu Gly Ser Glu Asp Val Thr Gly Arg Ser Val Ala
                245                 250                 255

Ala Pro Asn Phe Ser Asn Ala Ala Pro Leu Ala Gly Ile Asp Met Arg
            260                 265                 270

Pro Leu Val Pro Glu Pro Ser Thr Trp Asn Ser Asp Leu Arg Gly Thr
        275                 280                 285

Ala Ile Pro Gly Asn Val Ser Ser Val Ser Arg Ala Asn Pro Ser Ser
```

290                 295                 300
Ile Val Asn Arg Pro Ala Gly Ser Pro Ser Val Ala His Pro Thr Leu
305                 310                 315                 320

His Arg Arg His Pro Arg Asn Leu Ser Glu Glu Ile Gly Arg Leu Ser
                325                 330                 335

Gly Ala Leu Arg Gly Gln Gln Gln Pro Arg Leu Arg Ser Gly Phe Leu
                340                 345                 350

Leu Glu Arg Gln Gly Asp Gly Val Trp Gly Val Pro Leu Pro Met Arg
                355                 360                 365

Ser Ser Arg Glu Gly Arg Arg Leu Ile Glu Ile Arg Asn Ala Leu Glu
                370                 375                 380

Met Ile Gln Arg Gly Glu Asn Val Arg Phe Glu Ser Ile Phe Tyr Gly
385                 390                 395                 400

Gly Val Asp Ile His Asp Arg His Arg Asp Met Arg Leu Asp Ile Asp
                405                 410                 415

Asn Met Ser Tyr Glu Glu Leu Leu Ala Leu Glu Glu Arg Ile Gly Asn
                420                 425                 430

Val Ser Thr Gly Ile Ser Glu Asp Asp Val Met Lys Leu Leu Lys Gln
                435                 440                 445

Arg Lys Phe Ser Ser Trp Arg Leu Ala Ser Met Glu Tyr Glu Pro Cys
                450                 455                 460

Cys Ile Cys Gln Glu Glu Tyr Val Asp Gly Asp Asp Leu Gly Thr Leu
465                 470                 475                 480

His Cys Gly His Asp Phe His Ala Gly Cys Ile Arg Gln Trp Leu Val
                485                 490                 495

Val Lys Asn Leu Cys Pro Ile Cys Lys Asn Thr Ala Leu Lys Thr
                500                 505                 510

<210> SEQ ID NO 139
<211> LENGTH: 209
<212> TYPE: PRT
<213> ORGANISM: Lolium perenne

<400> SEQUENCE: 139

Met Ala Pro Leu Ala Ala Ala Ala Ala Val Ala Ala Lys Glu Glu
1               5                   10                  15

Leu Gly Val Thr Val Ala Val Ala Pro Pro Met Ala Leu Ala Pro Leu
                20                  25                  30

Ser Gln Gln Gln Pro Arg Arg Gln Tyr Arg Gly Val Arg Met Arg Lys
                35                  40                  45

Trp Gly Lys Trp Val Ala Glu Ile Arg Glu Pro His Lys Arg Thr Arg
50                  55                  60

Ile Trp Leu Gly Ser Tyr Ala Thr Pro Val Ala Ala Arg Ala Tyr
65                  70                  75                  80

Asp Thr Ala Val Phe Tyr Leu Arg Gly Arg Ser Ala Arg Leu Asn Phe
                85                  90                  95

Pro Asp Glu Ile Ser Ala Leu Ala Pro Leu Ser Pro Pro Glu Glu
                100                 105                 110

Leu Glu Ala Asp Gly Gly Ala Leu Ser Ala Ser Ile Arg Lys Lys
                115                 120                 125

Ala Ile Glu Val Gly Ser Arg Val Asp Ala Leu Gln Thr Gly Met Thr
                130                 135                 140

Met Val Ala Thr Ala Ala Ala Pro Ala Thr Asn His Arg Glu Arg Gln
145                 150                 155                 160

-continued

```
Arg Gln His His Ala Gln Gln Ala Ala Arg Asp Glu Glu Leu Leu
                165                 170                 175
Gln Leu His His Gln Lys Gln Arg Thr Ala Trp Asn Gly Arg Ala
                180                 185                 190
Lys Asn Pro Asp Leu Asn Gln Ala Pro Asp Pro Asp Ser Ser Asp Ala
            195                 200                 205
Glu

<210> SEQ ID NO 140
<211> LENGTH: 649
<212> TYPE: PRT
<213> ORGANISM: Lolium perenne

<400> SEQUENCE: 140

Met Arg Lys Ser Asn Trp Cys Trp Pro Arg Arg Phe Cys Met Phe Val
1               5                   10                  15
Ala Lys Lys Lys His Cys Gln Ala Leu Lys Leu Glu Asn Pro Ala Gly
                20                  25                  30
Asn Asp Ser Pro Val Gly Pro Met Gln Gly Glu His Thr Glu Thr Phe
            35                  40                  45
Val Ala Ile Phe Ala Ala Lys Lys Glu His Tyr Val Cys Ser Ile Val
    50                  55                  60
Val His Phe Val Val Thr Val Val Pro Ala Ala Gly Cys Val Val
65                  70                  75                  80
Lys His Leu His Ala His His Leu Asp Ala Leu Val Gly Glu Cys Glu
                85                  90                  95
Tyr Ala Ala Ser Arg Leu Gly Gly Arg Gly Thr Gly Arg Thr Ser Pro
                100                 105                 110
Gly Arg Cys Gly Val Glu Pro Glu Glu Val Gly Glu Arg Pro Arg His
            115                 120                 125
Gln Thr Arg Gln Glu Pro Glu Glu Gly Gly Ser Ser Pro Ala Met Trp
        130                 135                 140
Asp Leu Asn Asp Ser Pro Ala Ala Asp Ala Pro His Ala Pro Pro Leu
145                 150                 155                 160
Ser Pro Ser Val Asp Asp Ser Gly Ala Ser Ser Ser Ala Ala Ala
                165                 170                 175
Val Val Glu Ile His Asp Asp Gly Asp Asp Ala Ser Ala Ala Ala
                180                 185                 190
Ala Glu Glu Pro Met Phe Thr Arg Gln Phe Phe Pro Pro Ala Val Pro
        195                 200                 205
Gly Asp Pro Ala Pro Gly Asn Gly Arg Ala Ala Trp Leu Arg Leu Ala
210                 215                 220
Gly Ala Pro Pro Ala Ala Ala Ala Ser Ala Ala Ala Pro Gly
225                 230                 235                 240
Ala Gly Ala Gly Pro Ala Ala Ala Ala Ser Ala Ala Asn Lys Lys
                245                 250                 255
Ser Arg Arg Gly Pro Arg Ser Arg Ser Ser Gln Tyr Arg Gly Val Thr
                260                 265                 270
Phe Tyr Arg Arg Thr Gly Arg Trp Glu Ser His Ile Trp Asp Cys Gly
            275                 280                 285
Lys Gln Val Tyr Leu Gly Gly Phe Asp Thr Ala His Ala Ala Ala Arg
        290                 295                 300
Ala Tyr Asp Arg Ala Ala Ile Lys Phe Arg Gly Met Glu Ala Asp Ile
305                 310                 315                 320
```

Asn Phe Ser Leu Glu Asp Tyr Glu Asp Ile Lys Gln Met Gly Asn Leu
                325                 330                 335

Thr Lys Glu Glu Phe Val His Val Leu Arg Arg Gln Ser Thr Gly Phe
            340                 345                 350

Pro Arg Gly Ser Ser Lys Tyr Arg Gly Val Thr Leu His Lys Cys Gly
        355                 360                 365

Arg Trp Glu Ala Arg Met Gly Gln Phe Leu Gly Lys Lys Tyr Val Tyr
    370                 375                 380

Leu Gly Leu Phe Asp Thr Glu Glu Ala Ala Arg Ser Tyr Asp Arg
385                 390                 395                 400

Ala Ala Ile Lys Cys Asn Gly Lys Asp Ala Val Thr Asn Phe Asp Pro
                405                 410                 415

Ser Thr Tyr Ala Glu Glu Phe Glu Leu Pro Ala Ala Ser Thr Gly
            420                 425                 430

Asp Asp Gly Glu Gln Asn Leu Asp Leu Ser Leu Gly Ser Ser Ala Gly
        435                 440                 445

Ser Asn Lys Arg Gly Ser Leu Asp Gly Gly Asp Asp Gly Thr Ala
    450                 455                 460

Gly Ser Asp Gln Arg Val Pro Met Ala Phe Glu Leu Asp Trp Gln Thr
465                 470                 475                 480

Ala Ala Arg Ser Thr Lys Ala Lys Phe Asp Gln Asn Ser Thr His His
                485                 490                 495

Gln Met Pro Pro Val Leu Gln Ala Ser His Leu Pro Phe Ser Pro
            500                 505                 510

Arg His Ser Gln Val Gly Thr Phe Ala Met Pro Phe Ser Arg Glu Phe
        515                 520                 525

Ser Arg Ile Ser Ser Leu Phe Leu Phe Ala Ser Asn Gly Asp Pro Gly
    530                 535                 540

Thr Ala Gly Gly Leu Ser Leu Thr Val Gly Gly Ala Ser Gly Gly Gly
545                 550                 555                 560

Gly Gly His Trp Leu Pro His Gln Tyr His His Gln Pro Pro Gln
                565                 570                 575

Gln Gln Gln Gln Arg Leu His His Gly Gly Trp Gly Asn Gly Ala Pro
            580                 585                 590

Gly Thr Ser Trp Pro Pro Pro Gln Pro His Leu Pro Thr Ala Pro
        595                 600                 605

Pro Ser Asn Ala Ala Val Ala Ala Ala Ala Ala Ala Ser Ser Arg
    610                 615                 620

Phe Pro Pro Tyr Val Ala Thr Gln Ala His Ser Trp Leu Gln Lys Asn
625                 630                 635                 640

Gly Phe His Ser Leu Ala Arg Pro Thr
                645

<210> SEQ ID NO 141
<211> LENGTH: 3765
<212> TYPE: DNA
<213> ORGANISM: Artificial Sequence
<220> FEATURE:
<223> OTHER INFORMATION: genetic construct

<400> SEQUENCE: 141
ggggacaagt ttgtacaaaa aagcaggctg tgcagcgtga cccggtcgtg cccctctcta     60
gagataatga gcattgcatg tctaagttat aaaaaattac cacatatttt ttttgtcaca    120
cttgtttgaa gtgcagttta tctatcttta tacatatatt taaactttac tctacgaata    180

-continued

| | |
|---|---|
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggtttag ggttaatggt ttttatagac taattttttt | 420 |
| agtacatcta ttttattcta ttttagcctc taaattaaga aaactaaaac tctattttag | 480 |
| ttttttttatt taataattta gatataaaat agaataaaat aaagtgacta aaaattaaac | 540 |
| aaatacccctt taagaaatta aaaaaactaa ggaaacattt ttcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttcctttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctcccccccc cccctctct accttctcta gatcggcgtt ccggtccatg gttagggccc | 1080 |
| ggtagttcta cttctgttca tgtttgtgtt agatccgtgt tgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttt tgtttcgttg catagggttt ggtttgccct tttcctttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |
| atatgcagca tctattcata tgctctaacc ttgagtacct atctattata ataaacaagt | 1860 |
| atgttttata attattttga tcttgatata cttggatgat ggcatatgca gcagctatat | 1920 |
| gtggattttt ttagccctgc cttcatacgc tatttatttg cttggtactg tttcttttgt | 1980 |
| cgatgctcac cctgttgttt ggtgttactt ctgcaggtca tggtgttttgc ggttttgtct | 2040 |
| cgctggggcc gggtggcatg gctcatcact ggaggggtga tcctgctcgt caccaatggg | 2100 |
| gtcaattcgc gcattctggt cttcagcgag gatatattct tcatctactt gctcccgccc | 2160 |
| atcatcttta acgctgggtt tcaagtaaag aaaaagcaat tcttccgcaa ttttgcaaca | 2220 |
| attactttgt ttggggctat tgggacattg atatcctttg taataatcag ccttggtgcc | 2280 |
| atgggattgt tcagcaaact tgatgttgat ccactccagc ttggggacta tcttgcaatt | 2340 |
| ggtgctatct tctcagcaac agattctgtt tgcaccttac aggtgcttaa ccaggatgaa | 2400 |
| acaccccctac tctatagtct ggttttttggt gaaggtgttg ttaatgatgc tacatctgtt | 2460 |
| gtgctattca atgcaattca aaacattgat cttgatcatt tcgatgcgtt tgttctacta | 2520 |
| caacttattg gaaaattcct ctacctactt ttcaccagta ctgttcttgg aatagctaaa | 2580 |

```
ggtatggata gtgtatcttc atactgcatt tgtttaattt gaaaatggtt atctagttgc    2640
ctaacaaaat atagctggga tatcttataa cacatgtgca ggtgacatgg aaaaaaatgc    2700
ctattttcct atgcactaac tattcatcat gtgacatact tccccaaaaa actaaataag    2760
ccaaattttc cagcttccga gtcctgaaaa agagtagtgt acctgataca atttatagag    2820
tttttttttt cgaaaagaag ggatagccct catagataga gtactaacta aaagtctact    2880
tttaccaatt tcaggttttt gagctattcc aagaacagta ctggtgaaaa gtaggtagag    2940
gaattttcca ataagttgta gtagaacaaa cgcatcgaaa tgatcaagat caatgttttg    3000
aattgcattg aatagcacaa cagatgtagc atcattaaca acaccttcac caaaaaccag    3060
actatagagt aggggtgttt catcctggtt aagcacctgt aaggtgcaaa cagaatctgt    3120
tgctgagaag atagcaccaa ttgcaagata gtccccaagc tggagtggat caacatcaag    3180
tttgctgaac aatcccatgg caccaaggct gattattaca aaggatatca atgtcccaat    3240
agccccaaac aaagtaattg ttgcaaaatt gcggaagaat tgcttttttct ttacttgaaa    3300 cccagcgtta aagatgatgg gcgggagcaa gtagatgaag aatatatcct cgctgaagac    3360
cagaatgcgc gaattgaccc cattggtgac gagcaggatc acccctccag tgatgagcca    3420
tgccacccgg ccccagcgag acaaaaccgc aaacaccatg aagaaggagt gcgtcgaagc    3480
agatcgttca aacatttggc aataaagttt cttaagattg aatcctgttg ccggtcttgc    3540
gatgattatc atataatttc tgttgaatta cgttaagcat gtaataatta acatgtaatg    3600
catgacgtta tttatgagat gggttttat gattagagtc ccgcaattat acatttaata    3660
cgcgatagaa aacaaaatat agcgcgcaaa ctaggataaa ttatcgcgcg cggtgtcatc    3720
tatgttacta gatcgaaccc agctttcttg tacaaagtgg tcccc                   3765

<210> SEQ ID NO 142
<211> LENGTH: 3627
<212> TYPE: DNA
<213> ORGANISM: Artificial Sequence
<220> FEATURE:
<223> OTHER INFORMATION: genetic construct

<400> SEQUENCE: 142
ggggacaagt ttgtacaaaa aagcaggctg tgcagcgtga cccggtcgtg cccctctcta      60
gagataatga gcattgcatg tctaagttat aaaaaattac cacatatttt ttttgtcaca     120
cttgtttgaa gtgcagttta tctatcttta tacatatatt taaactttac tctacgaata     180
atataatcta tagtactaca ataatatcag tgttttagag aatcatataa atgaacagtt     240
agacatggtc taaaggacaa ttgagtattt tgacaacagg actctacagt tttatctttt     300
tagtgtgcat gtgttctcct ttttttttgc aaatagcttc acctatataa tacttcatcc     360
attttattag tacatccatt tagggtttag ggttaatggt ttttatagac taattttttt     420
agtacatcta ttttattcta ttttagcctc taaattaaga aaactaaaac tctattttag     480
tttttttatt taataattta gatataaaat agaataaaat aaagtgacta aaattaaac     540 aaatacccctt taagaaatta aaaaaactaa ggaaacattt ttcttgtttc gagtagataa     600
tgccagcctg ttaaacgccg tcgacgagtc taacggacac caaccagcga accagcagcg     660
tcgcgtcggg ccaagcgaag cagacggcac ggcatctctg tcgctgcctc tggaccctc      720 tcgagagttc cgctccaccg ttggacttgc tccgctgtcg gcatccagaa attgcgtggc     780
ggagcggcag acgtgagccg gcacggcagg cggcctcctc ctcctctcac ggcacggcag     840
```

-continued

| | |
|---|---|
| ctacggggga ttcctttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctcccccccc cccccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttttt tgtttcgttg catagggttt ggtttgccct tttcctttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |
| atatgcagca tctattcata tgctctaacc ttgagtacct atctattata ataaacaagt | 1860 |
| atgttttata attattttga tcttgatata cttggatgat ggcatatgca gcagctatat | 1920 |
| gtggattttt ttagccctgc cttcatacgc tatttatttg cttggtactg tttcttttgt | 1980 |
| cgatgctcac cctgttgttt ggtgttactt ctgcagggcg attgtgaggg tgccggtgag | 2040 |
| atgttccaag tcacctcctt gttcagccag gctgaaaagg ttgacaagga gcttaaggag | 2100 |
| aaccctgcac catctgaagc tgatgttgag gctgctaagc ttgttgtcaa gggaaaagga | 2160 |
| gatgcagttg cgcaacttaa agcagcaaaa gctagcaagc aagagataac tgctgctgtt | 2220 |
| tcggagctta caaaggcaaa agaggttgtc ttaaggctgg aagagaggtc taagttgaaa | 2280 |
| cctggaattc cccacaaaga tgatgggtcc attgcgtttg agaatgactt cttcaagcgt | 2340 |
| gcagcctttc tgactgtttc aggccaactt caggttgaga cttatgcttg tgctctcagc | 2400 |
| agtgtctata ccttttggacc cacattccgg gcagagaact cacatacgtc aagcatttg | 2460 |
| gcagaatttt ggatggttga accagaaatt gcatatgcaa acttgcataa aggtatggat | 2520 |
| agtgtatctt catactgcat tgtttaatt tgaaaatggt tatctagttg cctaacaaaa | 2580 |
| tatagctggg atatcttata acacatgtgc aggtgacatg gaaaaaaatg cctattttc | 2640 |
| tatgcactaa ctattcatca tgtgacatac ttccccaaaa aactaaataa gccaaatttt | 2700 |
| ccagcttccg agtcctgaaa aagagtagtg tacctgatac aatttataga gttttttttt | 2760 |
| tcgaaaagaa gggatagccc tcatagatag agtactaact aaaagtctac ttttaccaat | 2820 |
| ttcaggtttt tgatgcaagt ttgcatatgc aatttctggt tcaaccatcc aaaattctgc | 2880 |
| caaatgtctt gacgtatgtg agttctctgc ccggaatgtg ggtccaaagg tatagacact | 2940 |
| gctgagagca caagcataag tctcaacctg aagttggcct gaaacagtca gaaggctgc | 3000 |
| acgcttgaag aagtcattct caaacgcaat ggacccatca tctttgtggg gaattccagg | 3060 |
| tttcaactta gacctctctt ccagccttaa gacaacctct tttgccttg taagctccga | 3120 |
| aacagcagca gttatctctt gcttgctagc ttttgctgct ttaagttgcg caactgcatc | 3180 |
| tccttttccc ttgacaacaa gcttagcagc ctcaacatca gcttcagatg gtgcagggtt | 3240 |

```
ctccttaagc tccttgtcaa ccttttcagc ctggctgaac aaggaggtga cttggaacat    3300
ctcaccggca ccctcacaat cgcagaagga gtgcgtcgaa gcagatcgtt caaacatttg    3360
gcaataaagt ttcttaagat tgaatcctgt tgccggtctt gcgatgatta tcatataatt    3420
tctgttgaat tacgttaagc atgtaataat taacatgtaa tgcatgacgt tatttatgag    3480
atgggttttt atgattagag tcccgcaatt atacatttaa tacgcgatag aaaacaaaat    3540
atagcgcgca aactaggata aattatcgcg cgcggtgtca tctatgttac tagatcgaac    3600
ccagctttct tgtacaaagt ggtcccc                                        3627

<210> SEQ ID NO 143
<211> LENGTH: 3601
<212> TYPE: DNA
<213> ORGANISM: Artificial Sequence
<220> FEATURE:
<223> OTHER INFORMATION: genetic construct

<400> SEQUENCE: 143
ggggacaagt ttgtacaaaa aagcaggctg tgcagcgtga cccggtcgtg ccctctctcta    60 gagataatga gcattgcatg tctaagttat aaaaaattac cacatatttt ttttgtcaca   120
cttgtttgaa gtgcagttta tctatcttta tacatatatt taaactttac tctacgaata   180
atataatcta tagtactaca ataatatcag tgttttagag aatcatataa atgaacagtt   240
agacatggtc taaaggacaa ttgagtattt tgacaacagg actctacagt tttatctttt   300
tagtgtgcat gtgttctcct tttttttttgc aaatagcttc acctatataa tacttcatcc   360
attttattag tacatccatt tagggtttag ggttaatggt tttatagac taattttttt   420 agtacatcta ttttattcta ttttagcctc taaattaaga aaactaaaac tctatttag   480 tttttttatt taataattta gatataaaat agaataaaat aaagtgacta aaaattaaac   540
aaatacccct taagaaatta aaaaaactaa ggaaacattt ttcttgtttc gagtagataa   600
tgccagcctg ttaaacgccg tcgacgagtc taacggacac caaccagcga accagcagcg   660
tcgcgtcggg ccaagcgaag cagacggcac ggcatctctg tcgctgcctc tggacccctc   720
tcgagagttc cgctccaccg ttggacttgc tccgctgtcg gcatccagaa attgcgtggc   780
ggagcggcag acgtgagccg gcacggcagg cggcctcctc ctcctctcac ggcacggcag   840
ctacggggga ttcctttccc accgctcctt cgctttccct tcctcgcccg ccgtaataaa   900
tagacacccc ctccacaccc tctttcccca acctcgtgtt gttcggagcg cacacacaca   960
caaccagatc tcccccaaat ccacccgtcg gcacctccgc ttcaaggtac gccgctcgtc   1020 ctccccccc cccctctct accttctcta gatcggcgtt ccggtccatg gttagggccc   1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260 tgatttttt tgtttcgttg catagggttt ggtttgccct tttcctttat ttcaatatat   1320
gccgtgcact tgtttgtcgg gtcatctttt catgcttttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
```

-continued

```
ttcattcgtt ctagatcgga gtagaatact gtttcaaact acctggtgta tttattaatt    1680
ttggaactgt atgtgtgtgt catacatctt catagttacg agtttaagat ggatggaaat    1740
atcgatctag ataggtata catgttgatg tgggttttac tgatgcatat acatgatggc    1800
atatgcagca tctattcata tgctctaacc ttgagtacct atctattata ataaacaagt    1860
atgttttata attattttga tcttgatata cttggatgat ggcatatgca gcagctatat    1920
gtggattttt ttagccctgc cttcatacgc tatttatttg cttggtactg tttcttttgt    1980
cgatgctcac cctgttgttt ggtgttactt ctgcaggtct cgggaaacac gcattggcaa    2040
taccggccga tcgatcgaca gatcggcacg gggtccggcg aggcgcgatg gcgtatcggg    2100
tgctggaggt gacgctgatc tcggccaagg acctgaagaa ggtgacggtg ttctccaaga    2160
tgcgggtgta cgcggtggcg tccatctccg gcggcgaccc gcgcacgccg acgcaccgga    2220
cgcactcgga ccggcacggc gggccgctgc ggttcccaat accgatcgcc gccgaccccc    2280
gcgggctcgc actgcacgtg ctcctccgct ccgagcgctc cttcggcgac cgcgacgtcg    2340
gcgaggtgct cgtccccgtc caggaccttt tcgccgcagc gcctctcgcc ggcgagcatc    2400
gccacctcag ctaccaggtg cgacgcccca tgagcggccg gaagcgcggg gtgctccaca    2460
tctcctacag cctcacggac gcgccggcga tagggaaagg tatggatagt gtatcttcat    2520
actgcatttg tttaatttga aaatggttat ctagttgcct aacaaaatat agctgggata    2580
tcttataaca catgtgcagg tgacatggaa aaaaatgcct atttttctat gcactaacta    2640
ttcatcatgt gacatacttc cccaaaaaac taaataagcc aaattttcca gcttccgagt    2700
cctgaaaaag agtagtgtac ctgatacaat ttatagagtt ttttttttcg aaaagaaggg    2760
atagccctca tagatagagt actaactaaa agtctacttt taccaatttc aggttttttgc    2820 cctatcgccg gcgcgtccgt gaggctgtag gagatgtgga gcaccccgcg cttccggccg    2880
ctcatggggc gtcgcacctg gtagctgagg tggcgatgct cgccggcgag aggcgctgcg    2940
gcgaaaaggt cctggacggg gacgagcacc tcgccgacgt cgcggtcgcc gaaggagcgc    3000
tcggagcgga ggagcacgtg cagtgcgagc ccgcgggggt cggcggcgat cggtattggg    3060
aaccgcagcg gccgccgtg ccggtccgag tgcgtccggt gcgtcggcgt gcgcgggtcg    3120
ccgccggaga tggacgccac cgcgtacacc cgcatcttgg agaacaccgt caccttcttc    3180
aggtccttgg ccgagatcag cgtcacctcc agcacccgat acgccatcgc gcctcgccgg    3240
accccgtgcc gatctgtcga tcgatcggcc ggtattgcca atgcgtgttt cccgagaaga    3300
aggagtgcgc cgaagcagat cgttcaaaca tttggcaata agtttcttta agattgaatc    3360
ctgttgccgg tcttgcgatg attatcatat aatttctgtt gaattacgtt aagcatgtaa    3420
taattaacat gtaatgcatg acgttattta tgagatgggt ttttatgatt agagtcccgc    3480
aattatacat ttaatacgcg atagaaaaca aaatatagcg cgcaaactag gataaattat    3540
cgcgcgcggt gtcatctatg ttactagatc gaacccagct ttcttgtaca aagtggtccc    3600
c                                                                    3601
```

<210> SEQ ID NO 144
<211> LENGTH: 4013
<212> TYPE: DNA
<213> ORGANISM: Artificial Sequence
<220> FEATURE:
<223> OTHER INFORMATION: genetic construct

<400> SEQUENCE: 144

```
ggggacaagt ttgtacaaaa aagcaggctg tgcagcgtga cccggtcgtg cccctctcta      60
```

-continued

```
gagataatga gcattgcatg tctaagttat aaaaaattac cacatatttt ttttgtcaca    120
cttgtttgaa gtgcagttta tctatcttta tacatatatt taaactttac tctacgaata    180
atataatcta tagtactaca ataatatcag tgttttagag aatcatataa atgaacagtt    240
agacatggtc taaaggacaa ttgagtattt tgacaacagg actctacagt tttatctttt    300
tagtgtgcat gtgttctcct tttttttgc aaatagcttc acctatataa tacttcatcc     360
attttattag tacatccatt tagggtttag ggttaatggt tttatagac taattttttt     420 agtacatcta ttttattcta ttttagcctc taaattaaga aaactaaaac tctattttag    480
tttttttatt taataattta gatataaaat agaataaaat aaagtgacta aaaattaaac    540 aaatacccctt taagaaatta aaaaaactaa ggaaacattt ttcttgtttc gagtagataa   600
tgccagcctg ttaaacgccg tcgacgagtc taacggacac caaccagcga accagcagcg    660
tcgcgtcggg ccaagcgaag cagacggcac ggcatctctg tcgctgcctc tggaccccctc   720 tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840 ctacgggggga ttccttttccc accgctcctt cgctttccct tcctcgcccg ccgtaataaa  900 tagacaccccc ctccacaccc tctttcccca acctcgtgtt gttcggagcg cacacacaca   960
caaccagatc tcccccaaat ccacccgtcg gcacctccgc ttcaaggtac gccgctcgtc   1020 ctccccccccc ccccctctct accttctcta gatcggcgtt ccggtccatg gttagggccc  1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260 tgatttttttt tgtttcgttg catagggttt ggtttgccct tttcctttat ttcaatatat  1320
gccgtgcact tgtttgtcgg gtcatctttt catgcttttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcaggatg cgcgtcacca tcaccggcgg   2040
cgggacgagg ctgcacgtgg acctctacta cgcgtgcgtg cagagccgcg cgctcttcac   2100
ggtgtggagc ctcctgcagc tgatgcggcg gcaccgcggc cgcgtccccg acgtggacct   2160
catgttcgac tgcatggacc ggcccgccat caaccgcacc gagcacagcg gcgagggcgc   2220 gcccctccg ccgccgctgt tccggtactg caccactcgc gaccacttcg acatcccgtt    2280
cccggactgg tccttctggg gctggccgga gacgcacctc gagccctgga gccgcgagtt   2340
caagagcatc cggcagggcg ccaagaagaa ctgggacgag gaggcgaggt ccgggtacca   2400
```

```
gaactcgaag ctgtcgagcc agtgcacgca ccggtacaag atctacgcgg aggggttcgc   2460
gtggtcggtg agcctgaaat acatcctctc ctgcggctcc acggcgctcc tgatcgaccc   2520
gctgtaccag gacttcttca gccgggggct ggagccgcgg gtgaaccacc tgccggtgag   2580
caccgtgggg atgtgcgagt ccatcaggga cgccgtggag tggggcaacg cgcacccgga   2640
cgaggcggag cgcgtcgggc ggcgcgggca gcggctgatg caggacctgg ccatggacgc   2700
caaaggtatg gatagtgtat cttcatactg catttgttta atttgaaaat ggttatctag   2760
ttgcctaaca aaatatagct gggatatctt ataacacatg tgcaggtgac atggaaaaaa   2820
atgcctattt ttctatgcac taactattca tcatgtgaca tacttcccca aaaaactaaa   2880
taagccaaat tttccagctt ccgagtcctg aaaaagagta gtgtacctga tacaatttat   2940
agagtttttt ttttcgaaaa gaagggatag ccctcataga tagagtacta actaaaagtc   3000
tacttttacc aatttcaggt ttttgggcgt ccatggccag gtcctgcatc agccgctgcc   3060
cgcgccgccc gacgcgctcc gcctcgtccg ggtgcgcgtt gccccactcc acggcgtccc   3120
tgatggactc gcacatcccc acggtgctca ccggcaggtg gttcacccgc ggctccagcc   3180
cccggctgaa gaagtcctgg tacagcgggt cgatcaggag cgccgtggag ccgcaggaga   3240
ggatgtattt caggctcacc gaccacgcga accctccgc gtagatcttg taccggtgcg   3300
tgcactggct cgacagcttc gagttctggt acccggacct cgcctcctcg tcccagttct   3360
tcttggcgcc ctgccggatg ctcttgaact cgcggctcca gggctcgagg tgcgtctccg   3420
gccagcccca gaaggaccag tccgggaacg ggatgtcgaa gtggtcgcga gtggtgcagt   3480
accggaacag cggcggcgga gggggcgcgc cctcgccgct gtgctcggtg cggttgatgg   3540
cgggccggtc catgcagtcg aacatgaggt ccacgtcggg gacgcggccg cggtgccgcc   3600
gcatcagctg caggaggctc cacaccgtga gagcgcgcg gctctgcacg cacgcgtagt   3660
agaggtccac gtgcagcctc gtcccgccgc cggtgatggt gacgcgcata aaggagtgc   3720 gtcgaagcag atcgttcaaa catttggcaa taaagtttct taagattgaa tcctgttgcc   3780
ggtcttgcga tgattatcat ataatttctg ttgaattacg ttaagcatgt aataattaac   3840
atgtaatgca tgacgttatt tatgagatgg gtttttatga ttagagtccc gcaattatac   3900
atttaatacg cgatagaaaa caaaatatag cgcgcaaact aggataaatt atcgcgcgcg   3960
gtgtcatcta tgttactaga tcgaacccag ctttcttgta caaagtggtc ccc          4013
```

<210> SEQ ID NO 145  
<211> LENGTH: 3615  
<212> TYPE: DNA  
<213> ORGANISM: Artificial Sequence  
<220> FEATURE:  
<223> OTHER INFORMATION: genetic construct

<400> SEQUENCE: 145

```
ggggacaagt ttgtacaaaa aagcaggctg tgcagcgtga cccggtcgtg ccctctctcta    60 gagataatga gcattgcatg tctaagttat aaaaaattac cacatatttt ttttgtcaca   120
cttgtttgaa gtgcagttta tctatcttta tacatatatt taaactttac tctacgaata   180
atataatcta tagtactaca ataatatcag tgttttagag aatcatataa atgaacagtt   240
agacatggtc taaaggacaa ttgagtattt tgacaacagg actctacagt tttatctttt   300
tagtgtgcat gtgttctcct tttttttgc aaatagcttc acctatataa tacttcatcc   360
attttattag tacatccatt tagggtttag ggttaatggt tttatagac taattttttt   420 agtacatcta ttttattcta ttttagcctc taaattaaga aaactaaaac tctatttag   480
```

```
ttttttttatt taataattta gatataaaat agaataaaat aaagtgacta aaaattaaac    540
aaatacccct taagaaatta aaaaaactaa ggaaacattt tcttgttc gagtagataa      600
tgccagcctg ttaaacgccg tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840
ctacggggga ttccttcccc accgctcctt cgctttccct tcctcgcccg ccgtaataaa    900
tagcaccccc ctccacaccc tctttcccca acctcgtgtt gttcggagcg cacacacaca    960
caaccagatc tcccccaaat ccacccgtcg gcacctccgc ttcaaggtac gccgctcgtc   1020
ctccccccccc ccccctctct accttctcta gatcggcgtt ccggtccatg ttagggccc   1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260
tgatttttt tgtttcgttg catagggttt ggtttgccct tttcctttat ttcaatatat    1320
gccgtgcact tgtttgtcgg gtcatctttt catgcttttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attatttga tcttgatata cttggatgat ggcatatgca gcagctatat    1920
gtggattttt ttagccctgc cttcatacgc tatttatttg cttggtactg tttcttttgt   1980
cgatgctcac cctgttgttt ggtgttactt ctgcagggga aaggaacat tctggatgtt    2040
atgcattgct tcgggatgac aaggtggatg atcttaaaag gatgttttcg ctcttctcaa   2100
aaatcacccg tggtctggaa cctgtttcta acatgttcaa atcgcatgtt acgaatgagg   2160
gtacagcttt ggtcaagcaa gcagaagatt ctgctagtaa taaaaagcca gagaagaagg   2220
agatggttgg aatgcaggaa caggttttg tctggaaaat cattgcactg catgataagt    2280
atgtagcata tgtgacagat tgtttccacg gccatacact cttccacaag gcacttaaag   2340
aagcctttga ggtcttctgc aataagggtg tctctggcag ttcgagtgct gaattgctcg   2400
ccaccttctg tgacaacatt ctgaagaaag gctgcagtga aaagctcagt gatgaagcca   2460
ttgaagatgc ccttgagaag gtggtgcgcc tgcttgcata cataagtgat aaagaccaaa   2520
ggtatggata tgtatcttc atactgcatt tgtttaattt gaaatggtt atctagttgc     2580
ctaacaaaat atagctggga tatcttataa cacatgtgca ggtgacatgg aaaaaaatgc   2640
ctatttttct atgcactaac tattcatcat gtgacatact tccccaaaaa actaaataag   2700
ccaaattttc cagcttccga gtcctgaaaa agagtagtgt acctgataca atttatagag   2760
tttttttttt gtactaacta aaagtctact tttaccaatt tcaggttttt gggtctttat   2820
```

| | |
|---|---|
| cacttatgta tgcaagcagg cgcaccacct tctcaagggc atcttcaatg gcttcatcac | 2880 |
| tgagctttc actgcagcct ttcttcagaa tgttgtcaca gaaggtggcg agcaattcag | 2940 |
| cactcgaact gccagagaca cccttattgc agaagacctc aaaggcttct ttaagtgcct | 3000 |
| tgtggaagag tgtatggccg tggaaacaat ctgtcacata tgctacatac ttatcatgca | 3060 |
| gtgcaatgat tttccagaca aaaacctgtt cctgcattcc aaccatctcc ttcttctctg | 3120 |
| gctttttatt actagcagaa tcttctgctt gcttgaccaa agctgtaccc tcattcgtaa | 3180 |
| catgcgattt gaacatgtta gaaacaggtt ccagaccacg ggtgattttt gagaagagcg | 3240 |
| aaaacatcct tttaagatca tccaccttgt catcccgaag caatgcataa catccagaat | 3300 |
| gttccttctc cagaaggagt gcgtcgaagc agatcgttca acatttggc aataaagttt | 3360 |
| cttaagattg aatcctgttg ccggtcttgc gatgattatc atataatttc tgttgaatta | 3420 |
| cgttaagcat gtaataatta acatgtaatg catgacgtta tttatgagat gggtttttat | 3480 |
| gattagagtc ccgcaattat acatttaata cgcgatagaa acaaaatat agcgcgcaaa | 3540 |
| ctaggataaa ttatcgcgcg cggtgtcatc tatgttacta gatcgaaccc agctttcttg | 3600 |
| tacaaagtgg tcccc | 3615 |

<210> SEQ ID NO 146
<211> LENGTH: 3845
<212> TYPE: DNA
<213> ORGANISM: Artificial Sequence
<220> FEATURE:
<223> OTHER INFORMATION: genetic construct

<400> SEQUENCE: 146

| | |
|---|---|
| ggggacaagt ttgtacaaaa aagcaggctg tgcagcgtga cccggtcgtg cccctctcta | 60 |
| gagataatga gcattgcatg tctaagttat aaaaaattac cacatatttt ttttgtcaca | 120 |
| cttgtttgaa gtgcagttta tctatcttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggtttag ggttaatggt tttatagac taattttttt | 420 |
| agtacatcta ttttattcta ttttagcctc taaattaaga aaactaaaac tctattttag | 480 |
| ttttttatt taataattta gatataaaat agaataaaat aaagtgacta aaattaaac | 540 |
| aaatacccct taagaaatta aaaaaactaa ggaaacattt ttcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttcctttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccaccgctcg gcacctccgc ttcaaggtac gccgctcgtc | 1020 |
| ctcccccccc ccccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |

```
tgattttttt tgtttcgttg catagggttt ggtttgccct tttccttat ttcaatatat    1320
gccgtgcact tgtttgtcgg gtcatctttt catgctttt tttgtcttgg ttgtgatgat    1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtaccct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcaggtgc ctcgagtagg tgaggtagca   2040
tcttcatctt ctccatccga tcatgacaat gaggagcagg aacaggtcac agttgtccgc   2100
actcttgaaa gcttgaacca gaaaaatgaa ggcaaggcac cacatcaaaa ggaaaagcag   2160
caacgcaata accgcccgca acctcggaga tcttatccta aaccaagtgc gtcattttac   2220
ggatcacgct tacaaaatca gacatacccca aatgttgcac aagagcaagc aatgtaccat   2280
atgtggcacc aggtgcaacc aacacagcag aagcccccatt ttcggatggt tccaactatg   2340
ggcaacacaa ggtttccacc gccaccaact atactctcca tgtaccctcc acctagagga   2400
cagttcgccg tgccagccag ccaagatgct ttggctctaa ttccatgttt tcctgaagct   2460
gctcctgccc ttccacggta cttctcgcct taccctgcct catacgtacc agcaagtcca   2520
ctgccagctg cagttaacat gatgcatggg agaaggcaag ggtgtgctga acggttgag    2580
cttcctgatg caccagtttt cgccagatac actgctcaaa ggtatggata gtgtatcttc   2640
atactgcatt tgtttaattt gaaaatggtt atcagttgc ctaacaaaat atagctggga    2700
tatcttataa cacatgtgca ggtgacatgg aaaaaaatgc ctattttct atgcactaac    2760
tattcatcat gtgacatact tcccccaaaaa actaaataag ccaaattttc cagcttccga   2820
gtcctgaaaa agagtagtgt acctgataca atttatagag ttttttttt cgaaaagaag    2880
ggatagccct catagataga gtactaacta aaagtctact tttaccaatt tcaggttttt    2940
ggagcagtgt atctggcgaa aactggtgca tcaggaagct caaccgtttc agcacaccct   3000
tgccttctcc catgcatcat gttaactgca gctggcagtg gacttgctgg tacgtatgag   3060
gcagggtaag gcgagaagta ccgtggaagg gcaggagcag cttcaggaaa acatggaatt   3120
agagccaaag catcttggct ggctggcacg gcgaactgtc ctctaggtgg agggtacatg   3180
gagagtatag ttggtggcgg tggaaaacctt gtgttgccca tagttggaac catccgaaaa   3240
tggggcttct gctgtgttgg ttgcacctgg tgccacatat ggtacattgc ttgctcttgt   3300
gcaacatttg ggtatgtctg attttgtaag cgtgatccgt aaaatgacgc acttggttta   3360
ggataagatc tccgaggttg cgggcggtta ttgcgttgct gcttttcctt ttgatgtggt   3420
gccttgcctt catttttctg gttcaagctt tcaagagtgc ggacaactgt gacctgttcc   3480
tgctcctcat tgtcatgatc ggatgggaga atgaagatg ctacctcacc tactcgaggc    3540
aagaaggagt gcgtcgaagc agatcgttca aacatttggc aataaagttt cttaagattg   3600
```

| aatcctgttg ccggtcttgc gatgattatc atataatttc tgttgaatta cgttaagcat | 3660 |
| gtaataatta acatgtaatg catgacgtta tttatgagat gggttttttat gattagagtc | 3720 |
| ccgcaattat acatttaata cgcgatagaa acaaaatat agcgcgcaaa ctaggataaa | 3780 |
| ttatcgcgcg cggtgtcatc tatgttacta gatcgaaccc agctttcttg tacaaagtgg | 3840 |
| tcccc | 3845 |

<210> SEQ ID NO 147
<211> LENGTH: 3645
<212> TYPE: DNA
<213> ORGANISM: Artificial Sequence
<220> FEATURE:
<223> OTHER INFORMATION: genetic construct

<400> SEQUENCE: 147

| ggggacaagt ttgtacaaaa aagcaggctg tgcagcgtga cccggtcgtg cccctctcta | 60 |
| gagataatga gcattgcatg tctaagttat aaaaaattac cacatatttt ttttgtcaca | 120 |
| cttgtttgaa gtgcagttta tctatctttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggttag ggttaatggt tttatagac taattttttt | 420 |
| agtacatcta ttttattcta ttttagcctc taaattaaga aaactaaaac tctattttag | 480 |
| tttttttatt taataattta gatataaaat agaataaaat aaagtgacta aaaattaaac | 540 |
| aaatacccctt taagaaatta aaaaaactaa ggaaacattt ttcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttcctttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctccccccccc cccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttttt tgtttcgttg catagggttt ggtttgccct tttccttat ttcaatatat | 1320 |
| gccgtgcact tgtttgtcgg gtcatccttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |

```
atatgcagca tctattcata tgctctaacc ttgagtacct atctattata ataaacaagt    1860
atgttttata attattttga tcttgatata cttggatgat ggcatatgca gcagctatat    1920
gtggattttt ttagccctgc cttcatacgc tatttatttg cttggtactg tttcttttgt    1980
cgatgctcac cctgttgttt ggtgttactt ctgcaggttt cactgtactt gagaggctag    2040
taagcagatg ccgcaacctc aagactctga agctcaacaa tgcaatccct cttgacaatg    2100
ttgctagcct gcttcgtaag gctccgcaaa taatagaact cggaactggc aaattctctg    2160
ctgactatca tccagatctt tttgcaaagg ttgaagcagc atttgcaggt tgtacaagcc    2220
taagaaggct ttctgggact tgggacgctg ttccagatta cctgccagca ttctattgtg    2280
tatgtgaagg cctcacatct cttaatctga gttatgccac cgtgcaaggc cctgagctca    2340
tcaaattcat tagcagatgc aagaatctgc tgcagttatg ggtgatggac ctcattgagg    2400
accatggtct atctgttgtg gcatcaagtt gcagtaaact gcaagagttg cgggtcttcc    2460
cttccgatcc ttttggtcat aacggcgggc aagttttctt gacagaaaga ggtcttgaaa    2520
ggtatggata gtgtatcttc atactgcatt tgtttaattt gaaaatggtt atctagttgc    2580
ctaacaaaat atagctggga tatcttataa cacatgtgca ggtgacatgg aaaaaaatgc    2640
ctatttttct atgcactaac tattcatcat gtgacatact tccccaaaaa actaaataag    2700
ccaaattttc cagcttccga gtcctgaaaa agagtagtgt acctgataca atttatagag    2760
tttttttttt cgaaaagaag ggatagccct catagataga gtactaacta aaagtctact    2820
tttaccaatt tcaggttttt gcaagacctc tttctgtcaa gaaaacttgc ccgccgttat    2880
gaccaaaagg atcggaaggg aagacccgca actcttgcag tttactgcaa cttgatgcca    2940
caacagatag accatggtcc tcaatgaggt ccatcaccca taactgcagc agattcttgc    3000
atctgctaat gaatttgatg agctcagggc cttgcacggt ggcataactc agattaagag    3060
atgtgaggcc ttcacataca aatagaatg ctggcaggta atctggaaca gcgtcccaag    3120
tcccagaaag ccttcttagg cttgtacaac ctgcaaatgc tgcttcaacc tttgcaaaaa    3180
gatctggatg atagtcagca gagaatttgc cagttccgag ttctattatt tgcggagcct    3240
tacgaagcag gctagcaaca ttgtcaagag ggattgcatt gttgagcttc agagtcttga    3300
ggttgcggca tctgcttact agcctctcaa gtacagtgaa agaaggagt gcgtcgaagc    3360 agatcgttca aacatttggc aataaagttt cttaagattg aatcctgttg ccggtcttgc    3420
gatgattatc atataatttc tgttgaatta cgttaagcat gtaataatta acatgtaatg    3480
catgacgtta tttatgagat gggttttat gattagagtc ccgcaattat acatttaata    3540
cgcgatagaa aacaaaatat agcgcgcaaa ctaggataaa ttatcgcgcg cggtgtcatc    3600
tatgttacta gatcgaaccc agctttcttg tacaaagtgg tcccc               3645
```

<210> SEQ ID NO 148
<211> LENGTH: 3251
<212> TYPE: DNA
<213> ORGANISM: Artificial Sequence
<220> FEATURE:
<223> OTHER INFORMATION: genetic construct

<400> SEQUENCE: 148

```
ggggacaagt ttgtacaaaa aagcaggctg tgcagcgtga cccggtcgtg cccctctcta      60
gagataatga gcattgcatg tctaagttat aaaaaattac cacatatttt ttttgtcaca     120
cttgtttgaa gtgcagttta tctatcttta tacatatatt taaactttac tctacgaata     180
```

```
atataatcta tagtactaca ataatatcag tgttttagag aatcatataa atgaacagtt    240
agacatggtc taaaggacaa ttgagtattt tgacaacagg actctacagt tttatctttt    300
tagtgtgcat gtgttctcct tttttttgc aaatagcttc acctatataa tacttcatcc    360
attttattag tacatccatt tagggtttag ggttaatggt ttttatagac taatttttt    420 agtacatcta ttttattcta ttttagcctc taaattaaga aaactaaaac tctattttag    480 ttttttatt taataattta gatataaaat agaataaaat aaagtgacta aaaattaaac    540
aaatacccct taagaaatta aaaaaactaa ggaaacattt ttcttgtttc gagtagataa    600
tgccagcctg ttaaacgccg tcgacgagtc taacggacac caaccagcga accagcagcg    660
tcgcgtcggg ccaagcgaag cagacggcac ggcatctctg tcgctgcctc tggaccccctc    720 tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840
ctacggggga ttcctttccc accgctcctt cgctttccct tcctcgcccg ccgtaataaa    900
tagacacccc ctccacaccc tctttcccca acctcgtgtt gttcggagcg cacacacaca    960
caaccagatc tcccccaaat ccacccgtcg gcacctccgc ttcaaggtac gccgctcgtc   1020
ctcccccccc cccctctct accttctcta gatcggcgtt ccggtccatg gttagggccc   1080
ggtagttcta cttctgttca tgtttgtgtt agatccgtgt tgtgttaga tccgtgctgc   1140 tagcgttcgt acacggatgc gacctgtacg tcagacacgt tctgattgct aacttgccag   1200
tgtttctctt tggggaatcc tgggatggct ctagccgttc cgcagacggg atcgatttca   1260
tgattttttt tgtttcgttg catagggttt ggtttgccct tttcctttat ttcaatatat   1320
gccgtgcact tgtttgtcgg gtcatctttt catgcttttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcaggatg gcgcagtccg gcagcgacgc   2040
cgcaccgatc agcacgcacc ccaccgagga ggaggaggtg acggtggaga ggacgccgga   2100
ggaggaggcg gccaggctca ggtacctcga gttcgtgcag caggcggcgg cgcaggcggt   2160
cgtgctggcc gccgcggcct acgcctacgc caagcagggc gcggggccgc tccgccccgg   2220
cgtcgaccac gtcgagggca ccgtcaaggc cgtcgtcggc cctgtgtatg atcggtacca   2280
cgccgtgccg ctcgacctcc tcaagttcct cgaccgcaag aaaggtatgg atagtgtatc   2340
ttcatactgc atttgtttaa tttgaaaatg gttatctagt tgcctaacaa aatatagctg   2400
ggatatctta taacacatgt gcaggtgaca tggaaaaaaa tgcctatttt tctatgcact   2460
aactattcat catgtgacat acttccccaa aaaactaaat aagccaaatt ttccagcttc   2520
cgagtcctga aaaagagtag tgtacctgat acaatttata gagttttttt tttcgaaaag   2580
```

| | |
|---|---|
| aagggatagc cctcatagat agagtactaa ctaaaagtct acttttacca atttcaggtt | 2640 |
| tttgcttgcg gtcgaggaac ttgaggaggt cgagcggcac ggcgtggtac cgatcataca | 2700 |
| cagggccgac gacggccttg acggtgccct cgacgtggtc gacgccgggg cggagcggcc | 2760 |
| ccgcgccctg cttggcgtag gcgtaggccg cggcggccag cacgaccgcc tgcgccgccg | 2820 |
| cctgctgcac gaactcgagg tacctgagcc tggccgcctc ctcctccggc gtcctctcca | 2880 |
| ccgtcacctc ctcctcctcg gtggggtgcg tgctgatcgg tgcggcgtcg ctgccggact | 2940 |
| gcgccataga aggagtgcgt cgaagcagat cgttcaaaca tttggcaata aagtttctta | 3000 |
| agattgaatc ctgttgccgg tcttgcgatg attatcatat aatttctgtt gaattacgtt | 3060 |
| aagcatgtaa taattaacat gtaatgcatg acgttattta tgagatgggt ttttatgatt | 3120 |
| agagtcccgc aattatacat ttaatacgcg atagaaaaca aaatatagcg cgcaaactag | 3180 |
| gataaattat cgcgcgcggt gtcatctatg ttactagatc gaacccagct tcttgtaca | 3240 |
| aagtggtccc c | 3251 |

<210> SEQ ID NO 149
<211> LENGTH: 3365
<212> TYPE: DNA
<213> ORGANISM: Artificial Sequence
<220> FEATURE:
<223> OTHER INFORMATION: genetic construct

<400> SEQUENCE: 149

| | |
|---|---|
| ggggacaagt ttgtacaaaa aagcaggctg tgcagcgtga cccggtcgtg cccctctcta | 60 |
| gagataatga gcattgcatg tctaagttat aaaaaattac cacatatttt ttttgtcaca | 120 |
| cttgtttgaa gtgcagttta tctatcttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggtttag ggttaatggt ttttatagac taattttttt | 420 |
| agtacatcta ttttattcta tttagcctc taaattaaga aaactaaaac tctattttag | 480 |
| tttttttatt taataattta gatataaaat agaataaaat aaagtgacta aaaattaaac | 540 |
| aaatacccct taagaaatta aaaaaactaa ggaaacattt ttcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttcctttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctccccccc cccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgattttttt tgtttcgttg catagggttt ggtttgccct tttccttat ttcaatatat | 1320 |

```
gccgtgcact tgtttgtcgg gtcatctttt catgctttt tttgtcttgg ttgtgatgat      1380
gtggtctggt tgggcggtcg ttctagatcg gagtagaatt ctgtttcaaa ctacctggtg      1440
gatttattaa ttttggatct gtatgtgtgt gccatacata ttcatagtta cgaattgaag      1500
atgatggatg gaaatatcga tctaggatag gtatacatgt tgatgcgggt tttactgatg      1560
catatacaga gatgcttttt gttcgcttgg ttgtgatgat gtggtgtggt tgggcggtcg      1620
ttcattcgtt ctagatcgga gtagaatact gtttcaaact acctggtgta tttattaatt      1680
ttggaactgt atgtgtgtgt catacatctt catagttacg agtttaagat ggatggaaat      1740
atcgatctag dataggtata catgttgatg tgggttttac tgatgcatat acatgatggc      1800
atatgcagca tctattcata tgctctaacc ttgagtacct atctattata ataaacaagt      1860
atgttttata attattttga tcttgatata cttggatgat ggcatatgca gcagctatat      1920
gtggattttt ttagccctgc cttcatacgc tatttatttg cttggtactg tttcttttgt      1980
cgatgctcac cctgttgttt ggtgttactt ctgcaggtct ccatgggtta ttctaaatcg      2040
gcggtttata gagtattgta ttcttggctg ggagaatctt cctcgggttc ttctcatgta      2100
cttcaacaac gtagtgctgc ctcaggaagg atacttccac tcagtcatat gcaactcggt      2160
tgatttccgt aattccactg tgaacaatga tttgaggtac aaggtgtggg atgaaccacc      2220
tcagacagag cccctatttc tgaacatggc acattatgat gagatggtga acagcggaca      2280
gccttttgca aggcgttttc agaagaagga accattgctg acaagatcg atgacaaact       2340
actcaggcgt cctgggcatg ggcctgttcc tggtgccaaa ggtatggata gtgtatcttc      2400
atactgcatt tgtttaattt gaaaatggtt atctagttgc ctaacaaaat atagctggga      2460
tatcttataa cacatgtgca ggtgacatgg aaaaaaatgc ctattttct atgcactaac       2520
tattcatcat gtgacatact tccccaaaaa actaaataag ccaaattttc cagcttccga      2580
gtcctgaaaa agagtagtgt acctgataca atttatagag ttttttttt cgaaaagaag      2640
ggatagccct catagataga gtactaacta aaagtctact tttaccaatt tcaggttttt      2700
gggcaccagg aacaggccca tgcccaggac gcctgagtag tttgtcatcg atcttgtcca      2760
gcaatggttc cttcttctga aaacgccttg caaaaggctg tccgctgttc accatctcat      2820
cataatgtgc catgttcaga ataggggct ctgtctgagg tggttcatcc cacaccttgt       2880
acctcaaatc attgttcaca gtggaattac ggaaatcaac cgagttgcat atgactgagt      2940
ggaagtatcc ttcctgaggc agcactacgt tgttgaagta catgagaaga acccgaggaa      3000
gattctccca gccaagaata caatactcta taaaccgccg atttagaata acccatggag      3060
aagaaggagt gcgtcgaagc agatcgttca aacatttggc aataaagttt cttaagattg      3120
aatcctgttg ccggtcttgc gatgattatc atataatttc tgttgaatta cgttaagcat      3180
gtaataatta acatgtaatg catgacgtta tttatgagat gggttttat gattagagtc       3240
ccgcaattat acatttaata cgcgatagaa aacaaaatat agcgcgcaaa ctaggataaa      3300
ttatcgcgcg cggtgtcatc tatgttacta gatcgaaccc agctttcttg tacaaagtgg      3360
tcccc                                                                3365
```

<210> SEQ ID NO 150
<211> LENGTH: 3613
<212> TYPE: DNA
<213> ORGANISM: Artificial Sequence
<220> FEATURE:
<223> OTHER INFORMATION: genetic construct

<400> SEQUENCE: 150

```
ggggacaagt tgtacaaaa aagcaggctg tgcagcgtga cccggtcgtg cccctctcta    60
gagataatga gcattgcatg tctaagttat aaaaaattac cacatatttt ttttgtcaca   120
cttgtttgaa gtgcagttta tctatcttta tacatatatt taaactttac tctacgaata   180
atataatcta tagtactaca ataatatcag tgttttagag aatcatataa atgaacagtt   240
agacatggtc taaaggacaa ttgagtattt tgacaacagg actctacagt tttatctttt   300
tagtgtgcat gtgttctcct ttttttttgc aaatagcttc acctatataa tacttcatcc   360
attttattag tacatccatt tagggtttag ggttaatggt ttttatagac taattttttt   420
agtcacatcta ttttattcta ttttagcctc taaattaaga aaactaaaac tctattttag   480
ttttttttatt taataattta gatataaaat agaataaaat aaagtgacta aaaattaaac   540
aaatacccctt taagaaatta aaaaaactaa ggaaacattt ttcttgtttc gagtagataa   600
tgccagcctg ttaaacgccg tcgacgagtc taacggacac caaccagcga accagcagcg   660
tcgcgtcggg ccaagcgaag cagacggcac ggcatctctg tcgctgcctc tggacccctc   720
tcgagagttc cgctccaccg ttggacttgc tccgctgtcg gcatccagaa attgcgtggc   780
ggagcggcag acgtgagccg gcacggcagg cggcctcctc ctcctctcac ggcacggcag   840
ctacggggga ttcctttccc accgctcctt cgctttccct tcctcgcccg ccgtaataaa   900
tagacacccc ctccacaccc tctttcccca acctcgtgtt gttcggagcg cacacacaca   960
caaccagatc tcccccaaat ccacccgtcg gcacctccgc ttcaaggtac gccgctcgtc  1020
ctcccccccc ccccctctct accttctcta gatcggcgtt ccggtccatg gttagggccc  1080
ggtagttcta cttctgttca tgtttgtgtt agatccgtgt ttgtgttaga tccgtgctgc  1140
tagcgttcgt acacggatgc gacctgtacg tcagacacgt tctgattgct aacttgccag  1200
tgtttctctt tggggaatcc tgggatggct ctagccgttc cgcagacggg atcgatttca  1260
tgattttttt tgtttcgttg catagggttt ggtttgccct tttcctttat ttcaatatat  1320
gccgtgcact tgtttgtcgg gtcatctttt catgcttttt tttgtcttgg ttgtgatgat  1380
gtggtctggt tgggcggtcg ttctagatcg gagtagaatt ctgtttcaaa ctacctggtg  1440
gatttattaa ttttggatct gtatgtgtgt gccatacata ttcatagtta cgaattgaag  1500
atgatggatg gaaatatcga tctaggatag gtatacatgt tgatgcgggt tttactgatg  1560
catatacaga gatgcttttt gttcgcttgg ttgtgatgat gtggtgtggt tgggcggtcg  1620
ttcattcgtt ctagatcgga gtagaatact gtttcaaact acctggtgta tttattaatt  1680
ttggaactgt atgtgtgtgt catacatctt catagttacg agtttaagat ggatggaaat  1740
atcgatctag ataggtata catgttgatg tgggttttac tgatgcatat acatgatggc  1800
atatgcagca tctattcata tgctctaacc ttgagtacct atctattata ataaacaagt  1860
atgttttata attattttga tcttgatata cttggatgat ggcatatgca gcagctatat  1920
gtggattttt ttagccctgc cttcatacgc tatttatttg cttggtactg tttcttttgt  1980
cgatgctcac cctgttgttt ggtgttactt ctgcaggcaa tccagacata gccaccggtc  2040
atcatctgga gctcgttagc tatagaaaat aatcgcagcc ctgtatcagg attgacatgc  2100
acaaccagaa cccttgattc catcatgtta actttaaaca gtatatcact gatcacatct  2160
ttgttcgcat ctggaggaat tactgcttta tatgaaattc tggcacgctt tgttgcaagg  2220
gcatcaccaa gggcagacac cccacctctc ccataatcat catcaacaaa tatagcagtt  2280
acctctttcc attgatagta gtaagcaatg ctagcaatcg cacgcatttg gaagtaatcg  2340
```

```
ctgacagtgc tccttaaaaa gtaagaatac tccgatgcag aaagagttgg atcagtggct    2400
gcgaatgata ggagcggaac atgcagctca ttaacaaaat gtgagatgac atggcctatc    2460
acagaggact gcgggccaac aactgcaacc acattttct caaaggtatg atagtgtat     2520 cttcatactg catttgttta atttgaaaat ggttatctag ttgcctaaca aaatatagct    2580
gggatatctt ataacacatg tgcaggtgac atggaaaaaa atgcctattt ttctatgcac    2640
taactattca tcatgtgaca tacttcccca aaaaactaaa taagccaaat tttccagctt    2700
ccgagtcctg aaaaagagta gtgtacctga tacaatttat agagtttttt ttttcgaaaa    2760
gaagggatag ccctcataga tagagtacta actaaaagtc tacttttacc aatttcaggt    2820
ttttggagaa aaatgtggtt gcagttgttg gcccgcagtc ctctgtgata ggccatgtca    2880
tctcacattt tgttaatgag ctgcatgttc cgctcctatc attcgcagcc actgatccaa    2940
ctctttctgc atcggagtat tcttactttt taaggagcac tgtcagcgat tacttccaaa    3000
tgcgtgcgat tgctagcatt gcttactact atcaatggaa agaggtaact gctatatttg    3060
ttgatgatga ttatgggaga ggtggggtgt ctgcccttgg tgatgccctt gcaacaaagc    3120
gtgccagaat tcatatataa gcagtaattc ctccagatgc gaacaaagat gtgatcagtg    3180
atatactgtt taaagttaac atgatggaat caagggttct ggttgtgcat gtcaatcctg    3240
atacagggct gcgattattt tctatagcta acgagctcca gatgatgacc ggtggctatg    3300
tctggattga gaaggagtgc gtcgaagcag atcgttcaaa catttggcaa taaagtttct    3360
taagattgaa tcctgttgcc ggtcttgcga tgattatcat ataatttctg ttgaattacg    3420
ttaagcatgt aataattaac atgtaatgca tgacgttatt tatgagatgg gttttttatga   3480 ttagagtccc gcaattatac atttaatacg cgatagaaaa caaaatatag cgcgcaaact    3540
aggataaatt atcgcgcgcg gtgtcatcta tgttactaga tcgaacccag ctttcttgta    3600
caaagtggtc ccc                                                       3613
```

<210> SEQ ID NO 151
<211> LENGTH: 3445
<212> TYPE: DNA
<213> ORGANISM: Artificial Sequence
<220> FEATURE:
<223> OTHER INFORMATION: genetic construct

<400> SEQUENCE: 151

```
ggggacaagt ttgtacaaaa aagcaggctg tgcagcgtga cccggtcgtg ccctctcta     60 gagataatga gcattgcatg tctaagttat aaaaaattac cacatatttt ttttgtcaca    120
cttgtttgaa gtgcagttta tctatctttta tacatatatt taaactttac tctacgaata   180
atataatcta tagtactaca ataatatcag tgttttagag aatcatataa atgaacagtt    240
agacatggtc taaaggacaa ttgagtattt tgacaacagg actctacagt tttatctttt    300
tagtgtgcat gtgttctcct tttttttgc aaatagcttc acctatataa tacttcatcc     360
attttattag tacatccatt tagggtttag ggttaatggt tttatagac taatttttt      420 agtacatcta ttttattcta ttttagcctc taaattaaga aaactaaaac tctatttag     480 tttttttatt taataattta gatataaat agaataaaat aaagtgacta aaaattaaac    540
aaataccctt taagaaatta aaaaaactaa ggaaacattt ttcttgtttc gagtagataa    600
tgccagcctg ttaaacgccg tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
```

```
ggagcggcag acgtgagccg gcacggcagg cggcctcctc ctcctctcac ggcacggcag    840
ctacggggga ttcctttccc accgctcctt cgctttccct tcctcgcccg ccgtaataaa    900
tagacacccc ctccacaccc tctttcccca acctcgtgtt gttcggagcg cacacacaca    960
caaccagatc tcccccaaat ccacccgtcg gcacctccgc ttcaaggtac gccgctcgtc   1020
ctcccccccc cccctctct accttctcta gatcggcgtt ccggtccatg gttagggccc   1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260 tgatttttt tgtttcgttg catagggttt ggtttgccct tttcctttat ttcaatatat   1320
gccgtgcact tgtttgtcgg gtcatctttt catgctttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcaggtca tagtagaccg gcttggcggc   2040
gcagccgtag gcggcgttgg agcaaggcac ccggatggac tccagcagct tctccatgtc   2100
gtggttccgg tggtatccgc cggaagtcgc cgtgcgacac acatggcacc tccgagccgc   2160
ccccagcttg tctcggcacg tcgagcacac cacgtgcccc accttacact gcaagcgcgg   2220
agacatgaga cgatgagccc ttgttcgcat ggttgacatc attttgcata tgttaattac   2280
ctggaagatg ggcggcttga gtggtaggca gcaaggcgg cagtcgaggg cgtcggtgtt   2340
gtctaaagtc acgccgtgga gtgccgctgc cgcgcgtgta gacgccggtg ccattgtttc   2400
tacttgactg tccaggaaaa ggtatggata gtgtatcttc atactgcatt tgtttaattt   2460
gaaaatggtt atctagttgc ctaacaaaat atagctggga tatcttataa cacatgtgca   2520
ggtgacatgg aaaaaaatgc ctattttct atgcactaac tattcatcat gtgacatact   2580
tccccaaaaa actaaataag ccaaattttc cagcttccga gtcctgaaaa agagtagtgt   2640
acctgataca attttatagag tttttttttt cgaaagaag ggatagccct catagataga   2700
gtactaacta aaagtctact tttaccaatt tcaggttttt gtcctggaca gtcaagtaga   2760
aacaatggca ccggcgtcta cacgcgcggc agcggcactc cacggcgtga ctttagacaa   2820
caccgacgcc ctcgactgcc gcctttgctg cctaccactc aagccgccca tcttccaggt   2880
aattaacata tgcaaaatga tgtcaaccat gcgaacaagg gctcatcgtc tcatgtctcc   2940
gcgcttgcag tgtaaggtgg ggcacgtggt gtgctcgacg tgccgagaca agctgggggc   3000
ggctcggagg tgccatgtgt gtcgcacggc gacttccggc ggataccacc ggaaccacga   3060
catggagaag ctgctggagt ccatccgggt gccttgctcc aacgccgcct acggctgcgc   3120
```

| | |
|---|---|
| cgccaagccg gtctactatg aagaaggagt gcgtcgaagc agatcgttca acatttggc | 3180 |
| aataaagttt cttaagattg aatcctgttg ccggtcttgc gatgattatc atataatttc | 3240 |
| tgttgaatta cgttaagcat gtaataatta acatgtaatg catgacgtta tttatgagat | 3300 |
| gggttttat gattagagtc ccgcaattat acatttaata cgcgatagaa aacaaaatat | 3360 |
| agcgcgcaaa ctaggataaa ttatcgcgcg cggtgtcatc tatgttacta gatcgaaccc | 3420 |
| agctttcttg tacaaagtgg tcccc | 3445 |

```
<210> SEQ ID NO 152
<211> LENGTH: 3717
<212> TYPE: DNA
<213> ORGANISM: Artificial Sequence
<220> FEATURE:
<223> OTHER INFORMATION: genetic construct

<400> SEQUENCE: 152
```

| | |
|---|---|
| ggggacaagt ttgtacaaaa aagcaggctg tgcagcgtga cccggtcgtg ccctctctcta | 60 |
| gagataatga gcattgcatg tctaagttat aaaaaattac acatatttt ttttgtcaca | 120 |
| cttgtttgaa gtgcagttta tctatcttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggtttag ggttaatggt ttttatagac taatttttt | 420 |
| agtacatcta ttttattcta ttttagcctc taaattaaga aaactaaaac tctattttag | 480 |
| ttttttatt taataattta gatataaaat agaataaaat aaagtgacta aaaattaaac | 540 |
| aaatacccct taagaaatta aaaaaactaa ggaaacattt tcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttcctttccc accgctcctt cgctttccct tcctcgcccg ccgtaataaa | 900 |
| tagacaccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctccccccc cccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttt tgtttcgttg catagggttt ggtttgccct tttccttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |

```
atcgatctag gataggtata catgttgatg tgggttttac tgatgcatat acatgatggc    1800
atatgcagca tctattcata tgctctaacc ttgagtacct atctattata ataaacaagt    1860
atgttttata attattttga tcttgatata cttggatgat ggcatatgca gcagctatat    1920
gtggattttt ttagccctgc cttcatacgc tatttatttg cttggtactg tttcttttgt    1980
cgatgctcac cctgttgttt ggtgttactt ctgcaggatg ggtatcatag tcaatatgcc    2040
ttctgaatat gttggaaaaa gtgcaaaccg gctgaaggag catttctcac gttttatcc     2100
tgtgaaagtg caccatgtgt acagtaaagg tcgccctaca ggaaatgcta ttgttgagtt    2160
tgggaaggac ttggttggtt ttagaaatgc actaacattt gagaatcaat ttgagaagga    2220
agggcatggg aaataggct ggcaggaaaa acagcatgga gggccagagc cttttggatg     2280
gatcgctaga gcagacgatt acaatgctcc aggagcaata ggggactttc taagaaaaaa    2340
tggtgatctg aagacggctg acggtgttga ggatgaagaa acaatgaaaa ataacaaact    2400
tgtggccagt ttatctttta aagttattga aactgatatg catataccag aacttaaatc    2460
tgtgtatcag gagagaactg cctcactgaa aagaatgatg gagcagaggg aacagcagct    2520
acagtcatac aatcaagtgc gtcctaatct tctaaaggta tggatagtgt atcttcatac    2580
tgcatttgtt taatttgaaa atggttatct agttgcctaa caaaatatag ctgggatatc    2640
ttataacaca tgtgcaggtg acatggaaaa aaatgcctat ttttctatgc actaactatt    2700
catcatgtga catacttccc caaaaaacta ataagccaa attttccagc ttccgagtcc     2760
tgaaaaagag tagtgtacct gatacaattt atagagtttt ttttttcgaa agaagggat    2820
agccctcata gatagagtac taactaaaag tctacttta ccaatttcag gttttttgaga   2880
agattaggac gcacttgatt gtatgactgt agctgctgtt ccctctgctc catcattctt    2940
ttcagtgagg cagttctctc ctgatacaca gatttaagtt ctggtatatg catatcagtt    3000
tcaataactt taaagataa actgccaca agtttgttat ttttcattgt ttcttcatcc      3060
tcaacaccgt cagccgtctt cagatcacca ttttttctta gaaagtcccc tattgctcct    3120
ggagcattgt aatcgtctgc tctagcgatc catccaaaag gctctggccc tccatgctgt    3180
ttttcctgcc agcctatttt cccatgccct tccttctcaa attgattctc aaatgttagt    3240
gcatttctaa aaccaaccaa gtccttccca aactcaacaa tagcatttcc tgtagggcga    3300
cctttactgt acacatggtg cactttcaca ggataaaaac gtgagaaatg ctccttcagc    3360
cggtttgcac tttttccaac atattcagaa ggcatattga ctatgatacc catagaagga    3420
gtgcgtcgaa gcagatcgtt caaacatttg gcaataaagt ttcttaagat tgaatcctgt    3480
tgccggtctt gcgatgatta tcatataatt tctgttgaat tacgttaagc atgtaataat    3540
taacatgtaa tgcatgacgt tatttatgag atgggttttt atgattagag tcccgcaatt    3600
atacatttaa tacgcgatag aaaacaaaat atagcgcgca aactaggata aattatcgcg    3660
cgcggtgtca tctatgttac tagatcgaac ccagctttct tgtacaaagt ggtcccc       3717
```

<210> SEQ ID NO 153
<211> LENGTH: 3589
<212> TYPE: DNA
<213> ORGANISM: Artificial Sequence
<220> FEATURE:
<223> OTHER INFORMATION: genetic construct

<400> SEQUENCE: 153

```
ggggacaagt ttgtacaaaa aagcaggctg tgcagcgtga cccggtcgtg cccctctcta    60
```

-continued

| | |
|---|---|
| gagataatga gcattgcatg tctaagttat aaaaaattac cacatatttt ttttgtcaca | 120 |
| cttgtttgaa gtgcagttta tctatcttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggtttag ggttaatggt ttttatagac taattttttt | 420 |
| agtacatcta ttttattcta ttttagcctc taaattaaga aaactaaaac tctattttag | 480 |
| tttttttatt taataattta gatataaaat agaataaaat aaagtgacta aaaattaaac | 540 |
| aaatacccct taagaaatta aaaaaactaa ggaaacattt tcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggacccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttccttttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctccccccc cccctctct accttctcta gatcggcgtt ccggtccatg gttagggccc | 1080 |
| ggtagttcta cttctgttca tgtttgtgtt agatccgtgt tgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttt tgtttcgttg catagggttt ggtttgccct tttcctttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |
| atatgcagca tctattcata tgctctaacc ttgagtacct atctattata ataaacaagt | 1860 |
| atgttttata attattttga tcttgatata cttggatgat ggcatatgca gcagctatat | 1920 |
| gtggattttt ttagccctgc cttcatacgc tatttatttg cttggtactg tttcttttgt | 1980 |
| cgatgctcac cctgttgttt ggtgttactt ctgcagggtc gtgagcaaat cttcctttgg | 2040 |
| cggcagcgct cctctgaaga atggtgaatt tgagaagatg ctggaaatgg aaccgcagaa | 2100 |
| aaccgtggtc atagatttta ctgatgtgga catccctgtg ctagaagagg caaaaccgct | 2160 |
| tatttgtgga atcggtgagt ttggtgatga tgttctgaag gagcaacagc tttccaccaa | 2220 |
| ggagattgca atttacggat tatatctttg ccccatttgg tttgtcacag agtatttatc | 2280 |
| aaatgcagcc cttgcaagaa caagtgttgc cagtactacg gtactatctt caacttcggg | 2340 |
| actcttcaca ctcttcatta gtgtgctcct tggccaagat tccataaatg ctgccaaagt | 2400 |
| tattgctgtt tttgttagca tggctggtgt agcaatgaca actatgggcc agacttgggc | 2460 |

```
aacagatgaa tctgaagtaa gcaattcaga aaggtatgga tagtgtatct tcatactgca    2520 tttgttaat ttgaaaatgg ttatctagtt gcctaacaaa atatagctgg gatatcttat     2580
aacacatgtg caggtgacat ggaaaaaaat gcctattttt ctatgcacta actattcatc    2640
atgtgacata cttccccaaa aaactaaata agccaaattt tccagcttcc gagtcctgaa    2700
aaagagtagt gtacctgata caatttatag agttttttt ttcgaaaaga agggatagcc     2760
ctcatagata gagtactaac taaaagtcta cttttaccaa tttcaggttt ttgctgaatt    2820
gcttacttca gattcatctg ttgcccaagt ctggcccata gttgtcattg ctacaccagc    2880
catgctaaca aaaacagcaa taactttggc agcatttatg gaatcttggc caaggagcac    2940
actaatgaag agtgtgaaga gtcccgaagt tgaagatagt accgtagtac tggcaacact    3000
tgttcttgca agggctgcat ttgataaata ctctgtgaca aaccaaatgg ggcaaagata    3060
taatccgtaa attgcaatct ccttggtgga aagctgttgc tccttcagaa catcatcacc    3120
aaactcaccg attccacaaa taagcggttt tgcctcttct agcacaggga tgtccacatc    3180
agtaaaatct atgaccacgg ttttctgcgg ttccatttcc agcatcttct caaattcacc    3240
attcttcaga ggagcgctgc cgccaaagga agatttgctc acgacagaag gagtgcgtcg    3300
aagcagatcg ttcaaacatt tggcaataaa gtttcttaag attgaatcct gttgccggtc    3360
ttgcgatgat tatcatataa tttctgttga attacgttaa gcatgtaata attaacatgt    3420
aatgcatgac gttatttatg agatgggttt ttatgattag agtcccgcaa ttatacattt    3480
aatacgcgat agaaaacaaa atatagcgcg caaactagga taaattatcg cgcgcggtgt    3540
catctatgtt actagatcga acccagcttt cttgtacaaa gtggtcccc                3589
```

<210> SEQ ID NO 154
<211> LENGTH: 3645
<212> TYPE: DNA
<213> ORGANISM: Artificial Sequence
<220> FEATURE:
<223> OTHER INFORMATION: genetic construct

<400> SEQUENCE: 154

```
ggggacaagt tgtacaaaa aagcaggctg tgcagcgtga cccggtcgtg cccctctcta     60
gagataatga gcattgcatg tctaagttat aaaaaattac cacatatttt ttttgtcaca   120
cttgtttgaa gtgcagttta tctatcttta tacatatatt taaactttac tctacgaata   180
atataatcta tagtactaca ataatatcag tgttttagag aatcatataa atgaacagtt   240
agacatggtc taaaggacaa ttgagtattt tgacaacagg actctacagt tttatctttt   300
tagtgtgcat gtgttctcct ttttttttgc aaatagcttc acctatataa tacttcatcc   360
attttattag tacatccatt tagggtttag ggttaatggt tttatagac taatttttt     420 agtacatcta ttttattcta ttttagcctc taaattaaga aaactaaaac tctatttag    480 ttttttatt taataattta gatataaaat agaataaaat aaagtgacta aaaattaaac    540
aaataccctt taagaaatta aaaaaactaa ggaaacattt tcttgtttc gagtagataa    600 tgccagcctg ttaaacgccg tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840
ctacggggga ttcctttccc accgctcctt cgctttccct tcctcgcccg ccgtaataaa    900
```

```
tagacacccc ctccacaccc tctttcccca acctcgtgtt gttcggagcg cacacacaca    960
caaccagatc tccccccaaat ccacccgtcg gcacctccgc ttcaaggtac gccgctcgtc   1020
ctcccccccc cccctctct accttctcta gatcggcgtt ccggtccatg gttagggccc    1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260
tgatttttt tgtttcgttg catagggttt ggtttgccct tttcctttat ttcaatatat    1320
gccgtgcact tgtttgtcgg gtcatctttt catgctttt tttgtcttgg ttgtgatgat    1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggatttt ttagccctgc cttcatacgc tatttatttg cttggtactg tttcttttgt    1980
cgatgctcac cctgttgttt ggtgttactt ctgcaggcac actcttcatt agtgtgctcc   2040
ttggccaaga ttccataaat gctgccaaag ttattgctgt ttttgttagc atggctggtg   2100
tagcaatgac aactatgggc cagacttggg caacagatga atctgaagta agcaattcag   2160
gaacttatcg ccttgctaac catctaattc ttaagcctta ctactgcagg gccacacaga   2220
ggactcttct aggtgatatg tttggtcttc tgtcagctgt gtcatatggt ctcttcactg   2280
tgcttctcaa aaagtttgct ggaggagaag gatctgaaaa ggttgatgtc caaaaactgt   2340
tcggcttttct cggacttttc actctttgtc ttctctggtg gcttgtctgg ccattaactg   2400
cgctaggcat tgagccaaag tttacaatgc cccactcagc taaagtggat gaagttgttc   2460
tggcaaatgg ccttattggg agtgtgctat cagactattt ctgggctcta tctgttgaaa   2520
ggtatggata gtgtatcttc atactgcatt tgtttaattt gaaaatggtt atctagttgc   2580
ctaacaaaat atagctggga tatcttataa cacatgtgca ggtgacatgg aaaaaaatgc   2640
ctattttct atgcactaac tattcatcat gtgacatact tccccaaaaa actaaataag    2700
ccaaattttc cagcttccga gtcctgaaaa agagtagtgt acctgataca atttatagag   2760
tttttttttt cgaaaagaag ggatagccct catagataga gtactaacta aaagtctact   2820
tttaccaatt tcaggttttt gcaacagata gagcccagaa atagtctgat agcacactcc   2880
caataaggcc atttgccaga acaacttcat ccactttagc tgagtggggc attgtaaact   2940
ttggctcaat gcctagcgca gttaatggcc agacaagcca ccagagaaga caaagagtga   3000
aaagtccgag aaagccgaac agtttttgga catcaacctt ttcagatcct tctcctccag   3060
caaactttt gagaagcaca gtgaagagac catatgacac agctgacaga agaccaaaca   3120
tatcacctag aagagtcctc tgtgtggccc tgcagtagta aggcttaaga attagatggt   3180
tagcaaggcg ataagttcct gaattgctta cttcagattc atctgttgcc caagtctggc   3240
ccatagttgt cattgctaca ccagccatgc taacaaaaac agcaataact ttggcagcat   3300
```

```
ttatggaatc ttggccaagg agcacactaa tgaagagtgt gagaaggagt gcgtcgaagc      3360
agatcgttca aacatttggc aataaagttt cttaagattg aatcctgttg ccggtcttgc      3420
gatgattatc atataatttc tgttgaatta cgttaagcat gtaataatta acatgtaatg      3480
catgacgtta tttatgagat gggtttttat gattagagtc ccgcaattat acatttaata      3540
cgcgatagaa aacaaaatat agcgcgcaaa ctaggataaa ttatcgcgcg cggtgtcatc      3600
tatgttacta gatcgaaccc agctttcttg tacaaagtgg tcccc                      3645
```

<210> SEQ ID NO 155
<211> LENGTH: 3629
<212> TYPE: DNA
<213> ORGANISM: Artificial Sequence
<220> FEATURE:
<223> OTHER INFORMATION: genetic construct

<400> SEQUENCE: 155

```
ggggacaagt ttgtacaaaa aagcaggctg tgcagcgtga cccggtcgtg ccctctcta       60 gagataatga gcattgcatg tctaagttat aaaaaattac cacatatttt ttttgtcaca     120
cttgtttgaa gtgcagttta tctatcttta tacatatatt taaactttac tctacgaata     180
atataatcta tagtactaca ataatatcag tgttttagag aatcatataa atgaacagtt     240
agacatggtc taaaggacaa ttgagtattt tgacaacagg actctacagt tttatctttt     300
tagtgtgcat gtgttctcct tttttttttgc aaatagcttc acctatataa tacttcatcc    360
attttattag tacatccatt tagggtttag ggttaatggt ttttatagac taatttttttt    420 agtacatcta ttttattcta ttttagcctc taaattaaga aaactaaaac tctattttag     480
tttttttatt taataattta gatataaaat agaataaaat aaagtgacta aaaattaaac     540
aaatacccct taagaaatta aaaaaactaa ggaaacattt ttcttgtttc gagtagataa     600
tgccagcctg ttaaacgccg tcgacgagtc taacggacac caaccagcga accagcagcg     660
tcgcgtcggg ccaagcgaag cagacggcac ggcatctctg tcgctgcctc tggaccctc      720 tcgagagttc cgctccaccg ttggacttgc tccgctgtcg gcatccagaa attgcgtggc     780
ggagcggcag acgtgagccg gcacggcagg cggcctcctc ctcctctcac ggcacggcag     840
ctacggggga ttccttttccc accgctcctt cgctttccct tcctcgcccg ccgtaataaa    900
tagacacccc ctccacaccc tctttcccca acctcgtgtt gttcggagcg cacacacaca     960
caaccagatc tcccccaaat ccaccccgtcg gcacctccgc ttcaaggtac gccgctcgtc   1020
ctcccccccc cccctctct accttctcta gatcggcgtt ccggtccatg gttagggccc      1080
ggtagttcta cttctgttca tgtttgtgtt agatccgtgt ttgtgttaga tccgtgctgc    1140
tagcgttcgt acacggatgc gacctgtacg tcagacacgt tctgattgct aacttgccag   1200
tgtttctctt tggggaatcc tgggatggct ctagccgttc cgcagacggg atcgatttca    1260 tgatttttttt tgtttcgttg catagggttt ggtttgccct tttccttat ttcaatatat    1320 gccgtgcact tgtttgtcgg gtcatctttt catgcttttt tttgtcttgg ttgtgatgat    1380
gtggtctggt tgggcggtcg ttctagatcg gagtagaatt ctgtttcaaa ctacctggtg    1440
gatttattaa ttttggatct gtatgtgtgt gccatacata ttcatagtta cgaattgaag    1500
atgatggatg gaaatatcga tctaggatag gtatacatgt tgatgcgggt tttactgatg    1560
catatacaga gatgcttttt gttcgcttgg ttgtgatgat gtggtgtggt tgggcggtcg    1620
ttcattcgtt ctagatcgga gtagaatact gtttcaaact acctggtgta tttattaatt   1680
```

| | |
|---|---|
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |
| atatgcagca tctattcata tgctctaacc ttgagtacct atctattata ataaacaagt | 1860 |
| atgttttata attattttga tcttgatata cttggatgat ggcatatgca gcagctatat | 1920 |
| gtggattttt ttagccctgc cttcatacgc tatttatttg cttggtactg tttcttttgt | 1980 |
| cgatgctcac cctgttgttt ggtgttactt ctgcagggga gcgcacgcca tacagccccg | 2040 |
| ccaagttcct ctataggtcc ggatctcaag ctctatttgc attggttgat gcagcgctgt | 2100 |
| gatttcagca acgtgctgtt ttttttttcaa tgctgggttc gttgcgtatt agggaagtta | 2160 |
| gccgttagtt aaatggctgt gtcaagtatt gtaactgtgg gaagcaggtc ttgtttgaga | 2220 |
| cagtatactg tatattctct cctgcaaaag atagagtaat cttctatgc tattccatgg | 2280 |
| aactaagtta gatcatgcag attgcaagtc tacttaacat gatatggaat gatgtgaaca | 2340 |
| gagatatatc actaaaaggg gcaaggtttg cttagtggga gctgctactg ggggaaatg | 2400 |
| gttgcacgtt tgcatttcta tggcctgttt gaggaaatcc cctcgtatat aaagcatgta | 2460 |
| tagagttaag ttcttatgtt ttcatttgat tctgcaagta ctcttggcaa aaggtatgga | 2520 |
| tagtgtatct tcatactgca tttgtttaat ttgaaaatgg ttatctagtt gcctaacaaa | 2580 |
| atatagctgg gatatcttat aacacatgtg caggtgacat ggaaaaaaat gcctattttt | 2640 |
| ctatgcacta actattcatc atgtgacata cttccccaaa aaactaaata agccaaattt | 2700 |
| tccagcttcc gagtcctgaa aaagagtagt gtacctgata caatttatag agttttttt | 2760 |
| ttcgaaaaga agggatagcc ctcatagata gagtactaac taaaagtcta cttttaccaa | 2820 |
| tttcaggttt ttgtgccaag agtacttgca gaatcaaatg aaaacataag aacttaactc | 2880 |
| tatacatgct ttatatacga ggggatttcc tcaaacaggc catagaaatg caaacgtgca | 2940 |
| accatttccc cccagtagca gctcccacta agcaaacctt gccccttta gtgatatatc | 3000 |
| tctgttcaca tcattccata tcatgttaag tagacttgca atctgcatga tctaacttag | 3060 |
| ttccatggaa tagcatagaa agattactct atcttttgca ggagagaata tacagtatac | 3120 |
| tgtctcaaac aagacctgct tcccacagtt acaatacttg acacagccat ttaactaacg | 3180 |
| gctaacttcc ctaatacgca acgaacccag cattgaaaaa aaaacagcac gttgctgaaa | 3240 |
| tcacagcgct gcatcaacca atgcaaatag agcttgagat ccggacctat agaggaactt | 3300 |
| ggcggggctg tatggcgtgc gctccagaag gagtgcgtcg aagcagatcg ttcaaacatt | 3360 |
| tggcaataaa gtttcttaag attgaatcct gttgccggtc ttgcgatgat tatcatataa | 3420 |
| tttctgttga attacgttaa gcatgtaata attaacatgt aatgcatgac gttatttatg | 3480 |
| agatgggttt ttatgattag agtcccgcaa ttatacatttt aatacgcgat agaaaacaaa | 3540 |
| atatagcgcg caaactagga taaattatcg cgcgcggtgt catctatgtt actagatcga | 3600 |
| acccagcttt cttgtacaaa gtggtcccc | 3629 |

<210> SEQ ID NO 156
<211> LENGTH: 4445
<212> TYPE: DNA
<213> ORGANISM: Artificial Sequence
<220> FEATURE:
<223> OTHER INFORMATION: genetic construct

<400> SEQUENCE: 156

| | |
|---|---|
| ggggacaagt ttgtacaaaa aagcaggctg tgcagcgtga cccggtcgtg cccctctcta | 60 |
| gagataatga gcattgcatg tctaagttat aaaaaattac cacatatttt ttttgtcaca | 120 |

-continued

```
cttgtttgaa gtgcagttta tctatcttta tacatatatt taaactttac tctacgaata    180 ataatcta tagtactaca ataatatcag tgttttagag aatcatataa atgaacagtt      240
agacatggtc taaaggacaa ttgagtattt tgacaacagg actctacagt tttatctttt    300
tagtgtgcat gtgttctcct ttttttttgc aaatagcttc acctatataa tacttcatcc    360
attttattag tacatccatt tagggtttag ggttaatggt ttttatagac taattttttt    420
agtacatcta ttttattcta ttttagcctc taaattaaga aaactaaaac tctattttag    480 ttttttatt taataattta gatataaaat agaataaaat aaagtgacta aaaattaaac     540 aaatacccctt taagaaatta aaaaaactaa ggaaacattt ttcttgtttc gagtagataa   600
tgccagcctg ttaaacgccg tcgacgagtc taacggacac caaccagcga accagcagcg   660
tcgcgtcggg ccaagcgaag cagacggcac ggcatctctg tcgctgcctc tggacccctc   720
tcgagagttc cgctccaccg ttggacttgc tccgctgtcg gcatccagaa attgcgtggc   780
ggagcggcag acgtgagccg gcacggcagg cggcctcctc ctcctctcac ggcacggcag   840
ctacggggga ttcctttccc accgctcctt cgctttccct tcctcgcccg ccgtaataaa   900
tagacacccc ctccacaccc tctttcccca acctcgtgtt gttcggagcg cacacacaca   960
caaccagatc tcccccaaat ccacccgtcg gcacctccgc ttcaaggtac gccgctcgtc  1020 ctccccccc ccccctctct accttctcta gatcggcgtt ccggtccatg ttagggccc    1080 ggtagttcta cttctgttca tgtttgtgtt agatccgtgt ttgtgttaga tccgtgctgc  1140
tagcgttcgt acacggatgc gacctgtacg tcagacacgt tctgattgct aacttgccag  1200
tgtttctctt tggggaatcc tgggatggct ctagccgttc cgcagacggg atcgatttca  1260 tgatttttt tgtttcgttg catagggttt ggtttgccct tttcctttat ttcaatatat   1320
gccgtgcact tgtttgtcgg gtcatctttt catgcttttt tttgtcttgg ttgtgatgat  1380
gtggtctggt tgggcggtcg ttctagatcg gagtagaatt ctgtttcaaa ctacctggtg  1440
gatttattaa ttttggatct gtatgtgtgt gccatacata ttcatagtta cgaattgaag  1500
atgatggatg gaaatatcga tctaggatag gtatacatgt tgatgcgggt tttactgatg  1560
catatacaga gatgcttttt gttcgcttgg ttgtgatgat gtggtgtggt tgggcggtcg  1620
ttcattcgtt ctagatcgga gtagaatact gtttcaaact acctggtgta tttattaatt  1680
ttggaactgt atgtgtgtgt catacatctt catagttacg agtttaagat ggatggaaat  1740
atcgatctag gataggtata catgttgatg tgggttttac tgatgcatat acatgatggc  1800
atatgcagca tctattcata tgctctaacc ttgagtacct atctattata ataaacaagt  1860
atgttttata attattttga tcttgatata cttggatgat ggcatatgca gcagctatat  1920
gtggattttt ttagccctgc cttcatacgc tatttatttg cttggtactg tttcttttgt  1980
cgatgctcac cctgttgttt ggtgttactt ctgcaggatg ggcaggcgag gcggcgtgtt  2040
gtttgtggtg gggggaggag acggcgtggc gaggaggcgg gatggggagg cggcgccgcg  2100
aggaggaggg gatgggggcg ccggggacgg atgcgtgctg gggagggga gcgatgggtt    2160 tctgcgagag gagaatagtg gaggcggat cgctaattac atggtggtag actactacct   2220
gtatgactac gagtacgccg agccgccgcg cgtgaccagc ctgcagaacg ccgttcccca  2280
gaggaccttc agcgacttcg gagatgacgt ctacttcgtc gccgacaaac ggggctacga  2340
gtccgtcgtc cactacctcg ccggccagta cctcaacacc gacgactccg gcaacgtcgc  2400 cgaccccccgc ctgcagctca caaggtggt gcgagagatc tcctactcct cgagcggagt  2460
```

| | |
|---|---|
| caccgtcaag acggaggacg gctcagtgta ccaggcagac tatcgtcatg catggaaaat | 2520 |
| catcgccatc taccggttcg acatggcagt gtacaccaag atcttcctca agttccctcg | 2580 |
| gaagttctgg cccacgggcg aaggcaagca gttcttcgtc tacgccagct ccaggcgagg | 2640 |
| ctactacggg atgtggcagt ccttcgagga ggagtacccg ggggccaacg tgctcctcgt | 2700 |
| gacggtgacg gaccaggagt cgcggcggat cgagcagcag ccggacaaca ccaccatggc | 2760 |
| ggaggctgtg gcggtgctgc ggaggatgtt ccccgacgag gacgtccccg acgccaccga | 2820 |
| tatctacgtg cccaggtggt ggtccaaccg cttcttcaag ggctcctact ccaactggcc | 2880 |
| catcggcgtc aaccgctacg aatacgacca gcttcggaaa ggtatggata gtgtatcttc | 2940 |
| atactgcatt tgtttaattt gaaaatggtt atctagttgc ctaacaaaat atagctggga | 3000 |
| tatcttataa cacatgtgca ggtgacatgg aaaaaaatgc ctattttttct atgcactaac | 3060 |
| tattcatcat gtgacatact tccccaaaaa actaaataag ccaaattttc cagcttccga | 3120 |
| gtcctgaaaa agagtagtgt acctgataca atttatagag tttttttttt cgaaaagaag | 3180 |
| ggatagccct catagataga gtactaacta aaagtctact tttaccaatt tcaggttttt | 3240 |
| gccgaagctg gtcgtattcg tagcggttga cgccgatggg ccagttggag taggagccct | 3300 |
| tgaagaagcg gttggaccac cacctgggca cgtagatatc ggtggcgtcg ggacgtcct | 3360 |
| cgtcggggaa catcctccgc agcaccgcca cagcctccgc catggtggtg ttgtccggct | 3420 |
| gctgctcgat ccgccgcgac tcctggtccg tcaccgtcac gaggagcacg ttggcccccg | 3480 |
| ggtactcctc ctcgaaggac tgccacatcc cgtagtagcc tcgcctggag ctggcgtaga | 3540 |
| cgaagaactg cttgccttcg cccgtgggcc agaacttccg agggaacttg aggaagatct | 3600 |
| tggtgtacac tgccatgtcg aaccggtaga tggcgatgat tttccatgca tgacgatagt | 3660 |
| ctgcctggta cactgagccg tcctccgtct tgacggtgac tccgctcgag gagtaggaga | 3720 |
| tctctcgcac caccttgttg agctgcaggc ggggtcggc gacgttgccg gagtcgtcgg | 3780 |
| tgttgaggta ctggccggcg aggtagtgga cgacggactc gtagcccgt ttgtcggcga | 3840 |
| cgaagtagac gtcatctccg aagtcgctga aggtcctctg gggaacggcg ttctgcaggc | 3900 |
| tggtcacgcg cggcggctcg gcgtactcgt agtcatacag gtagtagtct accaccatgt | 3960 |
| aattagcgat cccgcctcca ctattctcct ctcgcagaaa cccatcgctc cccctcccca | 4020 |
| gcacgcatcc gtccccggcg ccccccatccc ctcctcctcg cggcgccgcc tcccatccc | 4080 |
| gcctcctcgc cacgccgtct cctcccccca ccacaaacaa cacgccgcct cgcctgccca | 4140 |
| tagaaggagt gcgtcgaagc agatcgttca aacatttggc aataaagttt cttaagattg | 4200 |
| aatcctgttg ccggtcttgc gatgattatc atataatttc tgttgaatta cgttaagcat | 4260 |
| gtaataatta acatgtaatg catgacgtta tttatgagat gggtttttat gattagagtc | 4320 |
| ccgcaattat acatttaata cgcgatagaa aacaaaatat agcgcgcaaa ctaggataaa | 4380 |
| ttatcgcgcg cggtgtcatc tatgttacta gatcgaaccc agctttcttg tacaaagtgg | 4440 |
| tcccc | 4445 |

<210> SEQ ID NO 157
<211> LENGTH: 3645
<212> TYPE: DNA
<213> ORGANISM: Artificial Sequence
<220> FEATURE:
<223> OTHER INFORMATION: genetic construct

<400> SEQUENCE: 157

| | |
|---|---|
| ggggacaagt ttgtacaaaa aagcaggctg tgcagcgtga cccggtcgtg ccctctcta | 60 |

```
gagataatga gcattgcatg tctaagttat aaaaaattac cacatatttt ttttgtcaca    120
cttgtttgaa gtgcagttta tctatcttta tacatatatt taaactttac tctacgaata    180
atataatcta tagtactaca ataatatcag tgttttagag aatcatataa atgaacagtt    240
agacatggtc taaaggacaa ttgagtattt tgacaacagg actctacagt tttatctttt    300
tagtgtgcat gtgttctcct ttttttttgc aaatagcttc acctatataa tacttcatcc    360
attttattag tacatccatt tagggtttag ggttaatggt tttatagac taatttttt     420 agtacatcta ttttattcta ttttagcctc taaattaaga aaactaaaac tctattttag    480 ttttttatt taataattta gatataaaat agaataaaat aaagtgacta aaaattaaac     540
aaataccctt taagaaatta aaaaaactaa ggaaacattt ttcttgtttc gagtagataa    600
tgccagcctg ttaaacgccg tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840
ctacggggga ttccttttccc accgctcctt cgctttccct tcctcgcccg ccgtaataaa    900
tagacacccc ctccacaccc tctttcccca acctcgtgtt gttcggagcg cacacacaca    960
caaccagatc tcccccaaat ccacccgtcg gcacctccgc ttcaaggtac gccgctcgtc   1020
ctcccccccc ccccctctct accttctcta gatcggcgtt ccggtccatg gttagggccc   1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260 tgatttttt tgtttcgttg catagggttt ggtttgccct tttcctttat ttcaatatat   1320
gccgtgcact tgtttgtcgg gtcatctttt catgctttt tttgtcttgg ttgtgatgat    1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcaggcca atggcatcga tttcatccat   2040
gaaaataata catggttgat gctcacgtgc atagttgaac atttctctta taagacgggc   2100
actttcacca atatatttgt caatgatagc acttgaaaca atctttaaaa agtttgcatc   2160
gatgttgcta gcaatagctc tagcaagcaa tgtcttcccc gttccaggtg gccatagag    2220 cagaacaccc tttggcggtt tgattccaac acggagaaac agttcaggat tcataagcgg   2280
taactcgatg gactcccgca gttcccttat ttgatctgat aatccaccta cagctgagta   2340
actgacgttg cctgggtctt catgtagcat gttatagacc accggatcaa cctcacgcgg   2400
```

```
tagagttctc ataatggtta aagttgtcat gtcaagaaca acccgcgttc cagctgtcag    2460
cttttctttg tcaactttac tcctgcagcc aaccacataa cgtggcccac tactggcaaa    2520
ggtatggata gtgtatcttc atactgcatt tgtttaattt gaaaatggtt atctagttgc    2580
ctaacaaaat atagctggga tatcttataa cacatgtgca ggtgacatgg aaaaaaatgc    2640 ctattttttct atgcactaac tattcatcat gtgacatact tccccaaaaa actaaataag    2700
ccaaattttc cagcttccga gtcctgaaaa agagtagtgt acctgataca atttatagag    2760
tttttttttt cgaaaagaag ggatagccct catagataga gtactaacta aaagtctact    2820
tttaccaatt tcaggttttt ggccagtagt gggccacgtt atgtggttgg ctgcaggagt    2880
aaagttgaca agaaaagct gacagctgga acgcgggttg ttcttgacat gacaacttta    2940
accattatga aactctacc gcgtgaggtt gatccgtgg tctataacat gctacatgaa    3000
gacccaggca acgtcagtta ctcagctgta ggtggattat cagatcaaat aagggaactg    3060
cgggagtcca tcgagttacc gcttatgaat cctgaactgt ttctccgtgt tggaatcaaa    3120
ccgccaaagg gtgttctgct ctatggccca cctggaacgg ggaagacatt gcttgctaga    3180
gctattgcta gcaacatcga tgcaaacttt ttaaagattg tttcaagtgc tatcattgac    3240
aaatatattg gtgaaagtgc ccgtcttata agagaaatgt caactatgc acgtgagcat    3300 caaccatgta ttattttcat ggatgaaatc gatgccattg gagaaggagt gcgtcgaagc    3360
agatcgttca acatttggc aataaagttt cttaagattg aatcctgttg ccggtcttgc    3420
gatgattatc atataatttc tgttgaatta cgttaagcat gtaataatta acatgtaatg    3480
catgacgtta tttatgagat gggtttttat gattagagtc ccgcaattat acatttaata    3540
cgcgatagaa aacaaaatat agcgcgcaaa ctaggataaa ttatcgcgcg cggtgtcatc    3600
tatgttacta gatcgaaccc agctttcttg tacaaagtgg tcccc              3645

<210> SEQ ID NO 158
<211> LENGTH: 3445
<212> TYPE: DNA
<213> ORGANISM: Artificial Sequence
<220> FEATURE:
<223> OTHER INFORMATION: genetic construct

<400> SEQUENCE: 158
ggggacaagt tgtacaaaaa aagcaggctg tgcagcgtga cccggtcgtg cccctctcta     60
gagataatga gcattgcatg tctaagttat aaaaaattac cacatatttt ttttgtcaca    120
cttgtttgaa gtgcagttta tctatctttta tacatatatt taaactttac tctacgaata    180 atataatccta tagtactaca ataatatcag tgttttagag aatcatataa atgaacagtt    240
agacatggtc taaaggacaa ttgagtattt tgacaacagg actctacagt tttatctttt    300
tagtgtgcat gtgttctcct ttttttttgc aaatagcttc acctatataa tacttcatcc    360
attttattag tacatccatt tagggttag ggttaatggt tttatagac taatttttt     420 agtacatcta ttttattcta ttttagcctc taaattaaga aaactaaaac tctattttag    480
tttttttatt taataattta gatataaaat agaataaaat aaagtgacta aaaattaaac    540
aaataccctt taagaaatta aaaaactaa ggaaacattt tctttgttc gagtagataa    600 tgccagcctg ttaaacgccg tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcacggcag    840
```

```
ctacggggga ttcctttccc accgctcctt cgctttccct tcctcgcccg ccgtaataaa    900
tagacacccc ctccacaccc tctttcccca acctcgtgtt gttcggagcg cacacacaca    960
caaccagatc tcccccaaat ccacccgtcg gcacctccgc ttcaaggtac gccgctcgtc   1020
ctcccccccc cccctctct accttctcta gatcggcgtt ccggtccatg gttagggccc   1080
ggtagttcta cttctgttca tgtttgtgtt agatccgtgt tgtgttaga tccgtgctgc   1140 tagcgttcgt acacggatgc gacctgtacg tcagacacgt tctgattgct aacttgccag   1200
tgtttctctt tggggaatcc tgggatggct ctagccgttc cgcagacggg atcgatttca   1260
tgattttttt tgtttcgttg catagggttt ggtttgccct tttcctttat ttcaatatat   1320
gccgtgcact tgtttgtcgg gtcatctttt catgcttttt tttgtcttgg ttgtgatgat   1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcagggcc aactggccca caacctcagg   2040
cccagcatac acacagcgac gtaggcctcc aaggcggact gagggcaaga tgcacggctc   2100
actgtgacag acaccagcct agacgagaag aacagccaag gcgtcctcgc ggcaggccca   2160
agcacgcaac tcccgaactc gaattggtca aaaccgaaaa ccctagcctg caaccctcct   2220
aaataatcac ggaaaaccag atcttctcgt ccagtagcca gcaaccctag ccaggacccg   2280
cggatagctc ggagcgagtc aactagcctg aaccctgtgc ggaccctcgt ctccagctcg   2340
cggcagttga ggagcttgtt gcggtagtcg gtgaccacgg tgcggcggcg ggcggccgcg   2400
gcatcgtcgg cctcggcaaa ggtatggata gtgtatcttc atactgcatt tgtttaatt    2460 gaaaatggtt atctagttgc ctaacaaaat atagctggga tatcttataa cacatgtgca   2520
ggtgacatgg aaaaaaatgc ctatttttct atgcactaac tattcatcat gtgacatact   2580
tccccaaaaa actaaataag ccaaattttc cagcttccga gtcctgaaaa agagtagtgt   2640
acctgataca atttatagag ttttttttt cgaaaagaag ggatagccct catagataga   2700
gtactaacta aaagtctact tttaccaatt tcaggttttt ggccgaggcc gacgatgccg   2760
cggccgcccg ccgccgcacc gtggtcaccg actaccgcaa caagctcctc aactgccgcg   2820
agctggagac gagggtccgc acagggttca ggctagttga ctcgctccga gctatccgcg   2880
ggtcctggct agggttgctg gctactggac gagaagatct ggttttccgt gattatttag   2940
gagggttgca ggctagggtt ttcggttttg accaattcga gttcgggagt tgcgtgcttg   3000
ggcctgccgc gaggacgcct tggctgttct tctcgtctag ctggtgtct gtcacagtga    3060 gccgtgcatc ttgccctcag tccgccttgg aggcctacgt cgctgtgtgt atgctgggcc   3120
tgaggttgtg ggccagttgg cagaaggagt gcgtcgaagc agatcgttca aacatttggc   3180
```

-continued

| | |
|---|---|
| aataaagtttt cttaagattg aatcctgttg ccggtcttgc gatgattatc atataatttc | 3240 |
| tgttgaatta cgttaagcat gtaataatta acatgtaatg catgacgtta tttatgagat | 3300 |
| gggtttttat gattagagtc ccgcaattat acatttaata cgcgatagaa aacaaaatat | 3360 |
| agcgcgcaaa ctaggataaa ttatcgcgcg cggtgtcatc tatgttacta gatcgaaccc | 3420 |
| agctttcttg tacaaagtgg tcccc | 3445 |

<210> SEQ ID NO 159
<211> LENGTH: 3801
<212> TYPE: DNA
<213> ORGANISM: Artificial Sequence
<220> FEATURE:
<223> OTHER INFORMATION: genetic construct

<400> SEQUENCE: 159

| | |
|---|---|
| ggggacaagt ttgtacaaaa aagcaggctg tgcagcgtga cccggtcgtg ccctctcta | 60 |
| gagataatga gcattgcatg tctaagttat aaaaaattac cacatatttt ttttgtcaca | 120 |
| cttgtttgaa gtgcagttta tctatcttta tacatatatt taaactttac tctacgaata | 180 |
| atataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct ttttttttgc aaatagcttc acctatataa tacttcatcc | 360 |
| attttattag tacatccatt tagggttag ggttaatggt tttatagac taatttttttt | 420 |
| agtacatcta ttttattcta ttttagcctc taaattaaga aaactaaaac tctattttag | 480 |
| tttttttatt taataattta gatataaaat agaataaaat aaagtgacta aaaattaaac | 540 |
| aaatacccctt taagaaatta aaaaaactaa ggaaacattt tcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggaccccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacggggga ttccttttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tcccccaaat ccacccgtcg gcacctccgc ttcaaggtac gccgctcgtc | 1020 |
| ctccccccccc ccccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgatttttttt tgtttcgttg catagggttt ggtttgccct tttccttttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |

```
atatgcagca tctattcata tgctctaacc ttgagtacct atctattata ataaacaagt    1860
atgttttata attattttga tcttgatata cttggatgat ggcatatgca gcagctatat    1920
gtggatttt  ttagccctgc cttcatacgc tatttatttg cttggtactg tttcttttgt    1980
cgatgctcac cctgttgttt ggtgttactt ctgcaggcct ttcctctatt ccttttactg    2040
tcttggacca tatatcctgg ctcttcatga gttttcatt  catttctgca actttctttt    2100
tctccaacat agtattttca agcttaagtt gcatctcttg aagcttatca tttacagctt    2160
tatccacagc aacagaaatg tgttccctat cttctttagc gtctgacaga aagcctcgta    2220
atactctctc tgagtttcaa gttggcttgc aagaagacgg ttgtactcat ccacgattgt    2280
atcagttttg ctgctaaaca taactccacc catatccgag tcatcgttgt ccccagaaaa    2340
ttcacacttt gacctgagct tagaatgttt tgcatcgctt ttcgagtgat taagacgatg    2400
aacataactg tcaccgacat aatcccaaac acgttgagtt tccaaatcaa gagaatagca    2460
gtgctgagtg tctttccagt gcctaattga gtggccttct ttataccttc cgcatccaac    2520
aaaaccacat atcacacaga tccagaggtt ttcagaggtc tgacaaacag aacatgtagg    2580
atttgtagga gtttcaaagg tatggatagt gtatcttcat actgcatttg tttaatttga    2640
aaatggttat ctagttgcct aacaaaatat agctgggata tcttataaca catgtgcagg    2700
tgacatggaa aaaatgcct  attttctat  gcactaacta ttcatcatgt gacatacttc    2760
cccaaaaaac taaataagcc aaattttcca gcttccgagt cctgaaaaag agtagtgtac    2820
ctgatacaat ttatagagtt ttttttttcg aaaagaaggg atagccctca tagatagagt    2880
actaactaaa agtctacttt taccaatttc aggttttgg  aaactcctac aaatcctaca    2940
tgttctgttt gtcagacctc tgaaaacctc tggatctgtg tgatatgtgg ttttgttgga    3000
tgcggaaggt ataagaagg  ccactcaatt aggcactgga aagacactca gcactgctat    3060
tctcttgatt tggaaactca acgtgtttgg gattatgtcg gtgacagtta tgttcatcgt    3120
cttaatcact cgaaaagcga tgcaaaacat tctaagctca ggtcaaagtg tgaattttct    3180
ggggacaacg atgactcgga tatgggtgga gttatgttta gcagcaaaac tgatacaatc    3240
gtggatgagt acaaccgtct tcttgcaagc caacttgaaa ctcagagaga gtattacgag    3300
gctttctgtc agacgctaag aaagataggg aacacatttc tgttgctgtg gataaagctg    3360
taaatgataa gcttcaagag atgcaactta agcttgaaaa tactatgttg gagaaaaaga    3420
aagttgcaga atgaatgaa  aaactcatga agagccagga tatatggtcc aagacagtaa    3480
aaggaataga ggaaaggaga aggagtgcgt cgaagcagat cgttcaaaca tttggcaata    3540
aagtttctta agattgaatc ctgttgccgg tcttgcgatg attatcatat aatttctgtt    3600
gaattacgtt aagcatgtaa taattaacat gtaatgcatg acgttattta tgagatgggt    3660
ttttatgatt agagtcccgc aattatacat ttaatacgcg atagaaaaca aaatatagcg    3720
cgcaaactag gataaattat cgcgcgcggt gtcatctatg ttactagatc gaacccagct    3780
ttcttgtaca aagtggtccc c                                              3801
```

<210> SEQ ID NO 160
<211> LENGTH: 3645
<212> TYPE: DNA
<213> ORGANISM: Artificial Sequence
<220> FEATURE:
<223> OTHER INFORMATION: genetic construct

<400> SEQUENCE: 160

| | |
|---|---|
| ggggacaagt tgtacaaaa aagcaggctg tgcagcgtga cccggtcgtg ccctctcta | 60 |
| gagataatga gcattgcatg tctaagttat aaaaaattac cacatatttt ttttgtcaca | 120 |
| cttgtttgaa gtgcagttta tctatcttta tacatatatt taaactttac tctacgaata | 180 |
| ataatcta tagtactaca ataatatcag tgttttagag aatcatataa atgaacagtt | 240 |
| agacatggtc taaaggacaa ttgagtattt tgacaacagg actctacagt tttatctttt | 300 |
| tagtgtgcat gtgttctcct tttttttgc aaatagcttc acctatataa tacttcatcc | 360 |
| attttattag tacatccatt tagggtttag ggttaatggt tttatagac taattttttt | 420 |
| agtacatcta ttttattcta ttttagcctc taaattaaga aaactaaaac tctattttag | 480 |
| tttttttatt taataattta gatataaaat agaataaaat aaagtgacta aaattaaac | 540 |
| aaataccctt taagaaatta aaaaaactaa ggaaacattt ttcttgtttc gagtagataa | 600 |
| tgccagcctg ttaaacgccg tcgacgagtc taacggacac caaccagcga accagcagcg | 660 |
| tcgcgtcggg ccaagcgaag cagacggcac ggcatctctg tcgctgcctc tggaccctc | 720 |
| tcgagagttc cgctccaccg ttggacttgc tccgctgtcg gcatccagaa attgcgtggc | 780 |
| ggagcggcag acgtgagccg gcacggcagg cggcctcctc ctcctctcac ggcacggcag | 840 |
| ctacgggga ttccttttccc accgctcctt cgctttccct tcctcgcccg ccgtaataaa | 900 |
| tagacacccc ctccacaccc tctttcccca acctcgtgtt gttcggagcg cacacacaca | 960 |
| caaccagatc tccccaaat ccacccgtcg gcacctccgc ttcaaggtac gccgctcgtc | 1020 |
| ctcccccccc ccccctctct accttctcta gatcggcgtt ccggtccatg gttagggccc | 1080 |
| ggtagttcta cttctgttca tgtttgtgtt agatccgtgt ttgtgttaga tccgtgctgc | 1140 |
| tagcgttcgt acacggatgc gacctgtacg tcagacacgt tctgattgct aacttgccag | 1200 |
| tgtttctctt tggggaatcc tgggatggct ctagccgttc cgcagacggg atcgatttca | 1260 |
| tgattttttt tgtttcgttg catagggttt ggtttgccct tttcctttat ttcaatatat | 1320 |
| gccgtgcact tgtttgtcgg gtcatctttt catgcttttt tttgtcttgg ttgtgatgat | 1380 |
| gtggtctggt tgggcggtcg ttctagatcg gagtagaatt ctgtttcaaa ctacctggtg | 1440 |
| gatttattaa ttttggatct gtatgtgtgt gccatacata ttcatagtta cgaattgaag | 1500 |
| atgatggatg gaaatatcga tctaggatag gtatacatgt tgatgcgggt tttactgatg | 1560 |
| catatacaga gatgcttttt gttcgcttgg ttgtgatgat gtggtgtggt tgggcggtcg | 1620 |
| ttcattcgtt ctagatcgga gtagaatact gtttcaaact acctggtgta tttattaatt | 1680 |
| ttggaactgt atgtgtgtgt catacatctt catagttacg agtttaagat ggatggaaat | 1740 |
| atcgatctag gataggtata catgttgatg tgggttttac tgatgcatat acatgatggc | 1800 |
| atatgcagca tctattcata tgctctaacc ttgagtacct atctattata ataaacaagt | 1860 |
| atgttttata attattttga tcttgatata cttggatgat ggcatatgca gcagctatat | 1920 |
| gtggattttt ttagccctgc cttcatacgc tatttatttg cttggtactg tttcttttgt | 1980 |
| cgatgctcac cctgttgttt ggtgttactt ctgcaggtca gcctggccgt cttcctcacc | 2040 |
| atcgtcgtcc tcctcctggc cgacctcttc tgctcccacc tccgcctccg ccgcctccgc | 2100 |
| gctgacgccg agatggcgcc gcacaagagg ccgaagcttg gcgtcccggc gtcgtccccg | 2160 |
| ccgcacaccg ccgacgacgc gtcggtggcc accaccacca ccacggcgac gcacgaggcg | 2220 |
| ctctccagca ccccgccctt ctactacgcg cacggcgtca tgtgcgcgcc cacccgcaag | 2280 |
| gacctcctcc tcgccatccc caagctggag gccgccgtgt ggaagtggtc tcccgcgcgc | 2340 |
| cgctcctcgc cgtcgccttc gccgccgcgg tccgagccca ccgcccgcga gtcctcctcc | 2400 |

```
tccgcgtaca gcgacggctt cctgcgcatc tccaacccc  gtgtacgagcg gggcgccacg      2460 gccgcgccgg gcgggtacga agaagacacg ccgttcgaca cgcctgacgc atcgccgaaa      2520
ggtatggata gtgtatcttc atactgcatt tgtttaattt gaaaatggtt atctagttgc      2580
ctaacaaaat atagctggga tatcttataa cacatgtgca ggtgacatgg aaaaaaatgc      2640 ctattttttct atgcactaac tattcatcat gtgacatact tccccaaaaa actaaataag      2700
ccaaattttc cagcttccga gtcctgaaaa agagtagtgt acctgataca atttatagag      2760 ttttttttt  cgaaaagaag ggatagccct catagataga gtactaacta aaagtctact       2820
tttaccaatt tcaggttttt gcggcgatgc gtcaggcgtg tcgaacgcg  tgtcttcttc       2880 gtacccgccc ggcgcggccg tggcgccccg ctcgtacacg gggttggaga tgcgcaggaa      2940
gccgtcgctg tacgcggagg aggaggactc gcggggcggtg ggctcggacc gcggcggcga    3000
aggcgacggc gaggagcggc gcgcgggaga ccacttccac acggcggcct ccagcttggg     3060
gatggcgagg aggaggtcct tgcgggtggg cgcgcacatg acgccgtgcg cgtagtagaa      3120
gggcggggtg ctggagagcg cctcgtgcgt cgccgtggtg gtggtggtgg ccaccgacgc     3180
gtcgtcggcg gtgtgcggcg gggacgacgc cgggacgcca agcttcggcc tcttgtgcgg      3240
cgccatctcg gcgtcagcgc ggaggcggcg gaggcggagg tgggagcaga agaggtcggc     3300
caggaggagg acgacgatgg tgaggaagac ggccaggctg aagaaggagt gcgtcgaagc     3360
agatcgttca acatttggc  aataaagttt cttaagattg aatcctgttg ccggtcttgc       3420
gatgattatc atataatttc tgttgaatta cgttaagcat gtaataatta acatgtaatg      3480
catgacgtta tttatgagat gggttttttat gattagagtc ccgcaattat acatttaata     3540
cgcgatagaa aacaaaatat agcgcgcaaa ctaggataaa ttatcgcgcg cggtgtcatc     3600
tatgttacta gatcgaaccc agctttcttg tacaaagtgg tcccc                      3645
```

<210> SEQ ID NO 161
<211> LENGTH: 3905
<212> TYPE: DNA
<213> ORGANISM: Artificial Sequence
<220> FEATURE:
<223> OTHER INFORMATION: genetic construct

<400> SEQUENCE: 161

```
ggggacaagt ttgtacaaaa aagcaggctg tgcagcgtga cccggtcgtg ccctctctc      60 gagataatga gcattgcatg tctaagttat aaaaaattac cacatatttt ttttgtcaca      120
cttgtttgaa gtgcagttta tctatcttta tacatatatt taaactttac tctacgaata     180
atataatcta tagtactaca ataatatcag tgttttagag aatcatataa atgaacagtt     240
agacatggtc taaaggacaa ttgagtattt tgacaacagg actctacagt tttatctttt     300
tagtgtgcat gtgttctcct tttttttgc  aaatagcttc acctatataa tacttcatcc       360
attttattag tacatccatt tagggtttag ggttaatggt ttttatagac taattttttt      420
agtacatcta ttttattcta ttttagcctc taaattaaga aaactaaaac tctattttag     480 ttttttttatt  taataattta gatataaaat agaataaaat aaagtgactta aaaattaaac    540 aaatacccctt taagaaatta aaaaaactaa ggaaacattt ttcttgtttc gagtagataa    600
tgccagcctg ttaaacgccg tcgacgagtc taacggacac caaccagcga accagcagcg     660
tcgcgtcggg ccaagcgaag cagacggcac ggcatctctg tcgctgcctc tggacccctc     720
tcgagagttc cgctccaccg ttggacttgc tccgctgtcg gcatccagaa attgcgtggc    780
```

```
ggagcggcag acgtgagccg gcacggcagg cggcctcctc ctcctctcac ggcacggcag    840
ctacggggga ttcctttccc accgctcctt cgctttccct tcctcgcccg ccgtaataaa    900
tagacacccc ctccacaccc tctttcccca acctcgtgtt gttcggagcg cacacacaca    960
caaccagatc tcccccaaat ccacccgtcg gcacctccgc ttcaaggtac gccgctcgtc   1020
ctcccccccc cccctctct accttctcta gatcggcgtt ccggtccatg gttagggccc    1080
ggtagttcta cttctgttca tgtttgtgtt agatccgtgt ttgtgttaga tccgtgctgc   1140
tagcgttcgt acacggatgc gacctgtacg tcagacacgt tctgattgct aacttgccag   1200
tgtttctctt tggggaatcc tgggatggct ctagccgttc cgcagacggg atcgatttca   1260
tgatttttt tgtttcgttg catagggttt ggtttgccct tttcctttat ttcaatatat    1320
gccgtgcact tgtttgtcgg gtcatctttt catgctttt tttgtcttgg ttgtgatgat    1380
gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgcttttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attatttga tcttgatata cttggatgat ggcatatgca gcagctatat    1920
gtggattttt ttagccctgc cttcatacgc tatttatttg cttggtactg tttcttttgt   1980
cgatgctcac cctgttgttt ggtgttactt ctgcaggatg cgcctcttg ccgccgcggc    2040
cgcggcggtg gcggcgaagg aggagctggg cgtgacggtg gccgtggcgc cgccgatggc   2100
gctgccccg ctgagccagc agcagccgcg cggcagtac cgcggcgtgc gcatgcggaa     2160
gtggggcaag tgggtggcgg agatccggga gccgcacaag cgcacgcgca tctggctcgg   2220
ctcctacgcc acgcccgtcg ccgccgcgcg cgcctacgac acggccgtct tctacctgcg   2280
cggccggtcg gccaggctca acttccccga cgagatctcc gcgctggcgc gctgtccc     2340
gccgcccgag gagctggagg ccgacggcgg cgcgctgtcg gcggcgtcga tccggaagaa   2400
ggccatcgag gtcgggtccc gcgtcgacgc gctccagacc gggatgacca tggtcgccac   2460
cgccgccgcg ccgccgacaa accaccggga gcggcagagg cagcaccacg cgcagcagca   2520
ggctgcgcgc gacgaggagc tgctccagct ccaccaccag aagcagcagc ggacggcgtg   2580
gaacgggcgg gccaagaacc cggatctcaa ccaggcgccc gaccccgaca gctccgacgc   2640
cgagtgaaaa ggtatggata gtgtatcttc atactgcatt tgtttaattt gaaaatggtt   2700
atctagttgc ctaacaaaat atagctggga tatcttataa cacatgtgca ggtgacatgg   2760
aaaaaaatgc ctatttttct atgcactaac tattcatcat gtgacatact tccccaaaaa   2820
actaaataag ccaaattttc cagcttccga gtcctgaaaa agagtagtgt acctgataca   2880
atttatagag ttttttttt cgaaaagaag ggatagccct catagataga gtactaacta   2940
aaagtctact tttaccaatt tcaggttttt gtcactcggc gtcggagctg tcggggtcgg   3000
gcgcctggtt gagatccggg ttcttggccc gcccgttcca cgccgtccgc tgctgcttct   3060
ggtggtggag ctggagcagc tcctcgtcgc gcgcagcctg ctgctgcgcg tggtgctgcc   3120
tctgccgctc ccggtggttt gtcgccggcg cggcggcggt ggcgaccatg gtcatcccgg   3180
```

```
tctggagcgc gtcgacgcgg gacccgacct cgatggcctt cttccggatc gacgccgccg    3240
acagcgcgcc gccgtcggcc tccagctcct cgggcggcgg ggacagcggc gccagcgcgg    3300
agatctcgtc ggggaagttg agcctggccg accggccgcg caggtagaag acggccgtgt    3360
cgtaggcgcg cgcggcggcg acgggcgtgg cgtaggagcc gagccagatg cgcgtgcgct    3420
tgtgcggctc ccggatctcc gccacccact tgccccactt ccgcatgcgc acgccgcggt    3480
actgccgccg cggctgctgc tggctcagcg gggccagcgc catcggcggc gccacgcca    3540 ccgtcacgcc cagctcctcc ttcgccgcca ccgccgcggc cgcggcggca agaggcgcca    3600
tagaaggagt gcgtcgaagc agatcgttca aacatttggc aataaagttt cttaagattg    3660
aatcctgttg ccggtcttgc gatgattatc atataatttc tgttgaatta cgttaagcat    3720
gtaataatta acatgtaatg catgacgtta tttatgagat gggtttttat gattagagtc    3780
ccgcaattat acatttaata cgcgatagaa aacaaaatat agcgcgcaaa ctaggataaa    3840
ttatcgcgcg cggtgtcatc tatgttacta gatcgaaccc agctttcttg tacaaagtgg    3900
tcccc                                                                3905
```

MANIPULATION OF SELF-INCOMPATIBILITY IN PLANTS

This application is a divisional of U.S. patent application Ser. No. 14/769,423, filed on Aug. 20, 2015, which is a 371 of PCT/AU2014/000146, filed on Feb. 19, 2014, which claims the benefit of foreign priority to Australian Patent Application Ser. No. 2013900597, filed Feb. 22, 2013, Australian Patent Application Ser. No.: 2013900601, filed Feb. 22, 2013, Australian Patent Application Ser. No.: 2013900602, filed Feb. 22, 2013, Australian Patent Application Ser. No.: 2013900603, filed Feb. 22, 2013, Australian Patent Application Ser. No.: 2013900604, filed Feb. 22, 2013, Australian Patent Application Serial No.: 2013900606, filed Feb. 22, 2013 and Australian Patent Application Serial No.: 2013900608, filed Feb. 22, 2013, all of which are incorporated by reference herein for all purposes.

FIELD OF THE INVENTION

The present invention relates to methods for controlling hybridization in plants and methods for producing hybrid plants. The present invention also relates to nucleic acids and nucleic acid fragments encoding amino acid sequences for self-incompatibility proteins in plants, in particular through self-gamete recognition in plants of grass and cereal species, and the use thereof for the manipulation of SI, including seed production, in plants. The present invention also relates to kits, compositions, constructs and vectors including such nucleic acids, and related polypeptides, regulatory elements and methods.

The present invention also relates to expression of self-gamete recognition genes in plants and to related nucleic acids, constructs, molecular markers derived from nucleic acids and related methods.

BACKGROUND OF THE INVENTION

The phenomenon through which some flowering plant species are unable to successfully reproduce through self-pollination has been termed 'self-incompatibility' (SI). A definition of SI was accepted as proposed by Lundqvist, being 'the inability of a fertile hermaphrodite seed-plant to produce zygotes after self-pollination'. This phraseology was in order to distinguish between SI and the effect of post-fertilisation barriers. SI has been described in about 30% of all flowering plants, and is the most important system for prevention of self-fertilization. The key part of this system is self-recognition, in which the pistil discriminates between self- or non-self-pollen to either inhibit or permit pollen tube germination and/or elongation and resulting fertilisation.

There are multiple genetic mechanisms that regulate and enable the system, SI does not represent a unique system. The molecular basis of the plant SI mechanism has been well studied in several groups of dicotyledonous plant species. Self-incompatibility locus (S locus) genes were identified in winged tobacco (*Nicotiana alata*) and *Brassica rapa* L. (syn. *campestris*) in the late 1980s. Subsequent biological investigations using multiple approaches have identified SI factors, to help elucidate the molecular basis of SI mechanisms in these species.

Plant species within the Poaceae (grass and cereal) family, can display an obligate outbreeding reproductive habit controlled by a two-locus (termed S and 2) gametophytic SI system, in which the pollen genotype is autonomously controlled by its own genetic constitution. This system is conserved between allogamous Poaceae species, such as wild barley (*Hordeum bulbosum* L.) and cereal rye (*Secale cereale* L.) and has been found to be widely conserved within the family, but is expected to be genetically and mechanistically distinct from the well-characterised single-locus SI mechanisms of dicotyledonous plants.

The Poaceae-specific mechanism prevents self-fertilisation through arrest of self-generated gamete pollen tube elongation at the stigmatic surface. Although several of the key molecular signals involved in dicot-specific SI systems have been identified, the molecular basis of the Poaceae system remains unknown.

Free calcium concentrations are essential for directed cell growth in pollen tubes in many species. The role calcium plays was initially identified as increasing cell wall rigidity and regulating permeability. However, the specific concentration of calcium in the cell is critical, as free calcium is typically kept at c. 100 nm due to cellular metabolism being based on free phosphates, and if free cytosolic calcium levels elevate over this concentration, interference with the energy status of the cell will result due to the formation of calcium salts. Studies of calcium gradients within the pollen tube have identified an increased gradient at the active growing tip, and the increase has been postulated to be absorbed by the cellular growth.

Previously, calcium has been identified to play a role in regulation of the SI system in the Poaceae family. Treatment with calcium channel blockers (lanthanum and verapamil) has been demonstrated to inhibit the perennial ryegrass SI mechanism. By treating excised stigmas with the chemical blocking agents self pollen was able to germinate.

The S and Z loci of perennial ryegrass (*Lolium perenne* L.) have been assigned to linkage groups (LGs) 1 and 2 respectively, in regions of known macrosynteny with the genomes of the inbreeding cereal species rice (*Oryza sativa* L.) and wheat (*Triticum aestivum* L.). Fine-structure mapping of the Poaceae SI loci was performed for blue canary grass (*Phalaris coerulescens* L.) and cereal rye (*Secale cereale* L.), and the candidate gene-containing regions were delimited to 0.26 cM and 1.5 cM intervals for the S and Z loci, respectively. The presence of gene-associated (cDNA-based) markers in these studies permitted comparative analysis to define map colinearity around the SI loci for related self-incompatible and self-compatible Poaceae species. The proposed 1.5 cM Z-containing region exhibited microsynteny with a BAC clone (OSJNBa0070011: GenBank Acc. No. AL606445) from rice chromosome 4 c. 125 kb in length, to which 12 predicted genes have been assigned.

For outbreeding crops, understanding and regulation of SI mechanisms can simplify and accelerate breeding procedures. For example, knowledge of the Solanaceae S-RNase-based SI system informed a method for almond cultivar development through use of a previously-characterised self-compatible ($S_c$) mutant line. The program involved introduction of the $S_c$ allele into existing almond varieties for enhanced fixation of genes for favourable oil content and fatty acid composition. Inbreeding also enables simpler maintenance of agronomically elite lines.

In the standard semi-hybrid breeding scheme for outbreeding pasture crop species, two cultivar groups are intercrossed to generate a progeny population with increased yield owing to heterosis. However, around half the progeny are derived from an intracross within each parental group and do not receive the benefit of heterosis. Heterosis in forage mass has been also reported in perennial ryegrass and other grass crop species using the standard semi-hybrid breeding system.

In a new scheme with SI genotyping technology, an SI-allele restricted population is established, and intercrossing between the restricted population and a cultivar group generates a progeny population with a higher ratio of hybrid progeny. An experiment with red clover proved higher hybrid ratios in progenies and improved seed yields when the restricted populations were used.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

It is an object of the present invention to overcome, or at least alleviate, one or more of the difficulties or deficiencies associated with the prior art.

SUMMARY OF THE INVENTION

Applicants have used an extensive and inclusive approach involving both genomics and transgenic modification for molecular dissection of the SI pathway in monocots. Spatiotemporal profiles of gene expression, comparative genomics, BAC clone sequencing and whole-exome sequencing suggests that the components of the SI pathway (the S and Z genes) may be encoded by a collection of genes from within the Poaceae family that have not been previously characterised as having these functions in ryegrass.

Applicants have found that modification or selection of the genes located at the S and Z loci of outbreeding plants of the Poaceae family is an attractive strategy for controlling pollination and fertilization by repression or activation of the SI mechanism. Applicants have also found that modification or selection of the genes located at the S and Z loci of plants of the Poaceae family may be used to control hybridization or to produce hybrid plants in higher numbers than conventional breeding approaches. By identifying the nucleic acid sequences of the genes, transgenic modification through down-regulation or through inducible expression enables hybrid breeding schemes to be enabled. Modification of the nucleic acids through targeted gene disruption, by the use of transcription activator-like effector nucleases (TALENs) or zinc-finger nucleases (ZFNs), mediating cleavage of specific target sites in the nucleic acid, leading to micro-deletions and insertions within the endogenous nucleic acid sequence, also enables control of fertilisation. The use of molecular markers derived from inherent variation originating from within the nucleic acid sequences may also provide a predictive means for control of fertilisation.

A perennial ryegrass BAC-based genomic library composed of 50,304 (131×384-well plates) BAC clones (average insert size=113 kb) has been constructed to support contig assembly, and estimated to correspond to c. 3.4 genome equivalents (Spangenberg et al. 2005; Forster et al. 2008). A combination of fine-structure genetic linkage mapping and physical genome characterisation enables implementation of map-based cloning to isolate perennial ryegrass SI genes.

In addition, whole-genome sequencing has been performed to generate genic contigs from the perennial ryegrass genome that can assist with gene identification and nucleic acid characterisation. These efforts have been undertaken on a single plant genotype that has been clonally propagated to provide sufficient source material (Cogan et al. 2012a, Forster et al. 2012). A global gene expression (transcriptome) profile has also been extensively generated and characterised through sequencing of RNA nucleic acids from the same plant as was used for the genome sequence (Cogan et al. 2012b, Forster et al. 2012).

Identification and characterisation of the S and Z genes may enable establishment of novel breeding methodology for perennial ryegrass.

For example, plants of the Poaceae family may be transformed with a gametophytic Z gene nucleic acid wherein (1) transformation with said Z gene specific nucleic acid transforms a self incompatible plant of the Poaceae family into a self compatible plant or (2) transformation with said Z gene specific nucleic acid transforms a self compatible plant of the Poaceae family into a self incompatible plant. In a preferred embodiment, the gametophytic Z gene may encode a 26S proteasome subunit, a zinc finger protease, a no-pollen (NOP) polypeptide, or an ubiquitin-specific protease, such as an ubiquitin-specific protease 22.

For example, plants of the Poaceae family may be transformed with a gametophytic S gene nucleic acid wherein (1) transformation with said S gene specific nucleic acid transforms a self incompatible plant of the Poaceae family into a self compatible plant or (2) transformation with said S gene specific nucleic acid transforms a self compatible plant of the Poaceae family into a self incompatible plant. In a preferred embodiment, the gametophytic S gene may encode a Cullin, a glutamate receptor or precursor thereof, or a seven-in-absentia homologue (SIAH).

Accordingly, in a first aspect, the present invention provides a composition or kit for hybridization or self-incompatibility (SI) control in plants, said composition or kit including:
  a first nucleic acid or nucleic acid fragment encoding a SI polypeptide, wherein said first nucleic acid or nucleic acid fragment is isolated from or corresponds to a gene from the Z locus of a plant of the Poaceae family; and
  a second nucleic acid or nucleic acid fragment encoding a SI polypeptide, wherein said second nucleic acid or nucleic acid fragment is isolated from or corresponds to a gene from the S locus of a plant of the Poaceae family.

Preferably said first and second nucleic acids are substantially purified or isolated.

In a preferred embodiment, the first nucleic acid or nucleic acid fragment may be a gametophytic Z gene.

In a preferred embodiment, the second nucleic acid or nucleic acid fragment may be a gametophytic S gene.

In a particularly preferred embodiment the first and second nucleic acids or nucleic acid fragments may be selected from the group of nucleic acids and nucleic acid fragments as hereinafter described.

For example, the Z gene may encode a 26S proteasome subunit, a zinc finger protease, a no-pollen (NOP) polypeptide, or an ubiquitin-specific protease, such as an ubiquitin-specific protease 22, as hereinafter described.

For example, the S gene may encode a Cullin, a glutamate receptor or precursor thereof, or a seven-in-absentia homologue (SIAH), as hereinafter described.

In a further preferred embodiment, the first and second nucleic acids or nucleic acid fragments may be included in a construct or vector, as hereinafter described.

In a further aspect of the present invention there is provided a method for controlling hybridization in a plant or for producing hybrid plants, said method including:
  establishing or identifying a first plant strain with a first Z locus haplotype and a first S locus haplotype;

establishing or identifying a second plant strain with a second Z locus haplotype and a second S locus haplotype; and crossing said plant strains to produce hybrid plants;

wherein said haplotypes are selected so that the first plant strain is heterozygous at both the S and Z loci and said second plant strain is homozygous at one of the S and Z loci and heterozygous at the other of the S and Z loci.

Preferably the first and second plant strains are plants of the Poaceae family. More preferably they are grass species, particularly pasture grasses such as ryegrass (*Lolium*) or fescue (*Festuca*), more particularly perennial ryegrass (*Lolium perenne* L.) or tall fescue (*Festuca arundinaceum*, otherwise known as *Lolium arundinaceum*).

Preferably the haplotypes are from genes according to the present invention, as hereinafter described.

In a further aspect of the present invention there is provided a method of manipulating self-incompatibility in a plant, said method including introducing into said plant an effective amount of a nucleic acid, construct and/or vector according to the present invention.

In a preferred embodiment the method involves altering the SI status of the plant.

In a preferred embodiment, the method may include introducing into said plant:

a first nucleic acid or nucleic acid fragment encoding a SI polypeptide, wherein said first nucleic acid or nucleic acid fragment is isolated from or corresponds to a gene from the Z locus of a plant of the Poaceae family; and a second nucleic acid or nucleic acid fragment encoding a SI polypeptide, wherein said second nucleic acid or nucleic acid fragment is isolated from or corresponds to a gene from the S locus of a plant of the Poaceae family.

For example, the Z gene may encode a 26S proteasome subunit, a zinc finger protease, a no-pollen (NOP) polypeptide, or an ubiquitin-specific protease, such as an ubiquitin-specific protease 22, as hereinafter described.

For example, the S gene may encode a Cullin, a glutamate receptor or precursor thereof, or a seven-in-absentia homologue (SIAH), as hereinafter described.

The present invention also contemplates co-expressing a nucleic acid of the present invention with a gene encoding a mediator or modulator of SI activity.

By SI status is meant the ability or inability of a fertile hermaphrodite seed-plant to produce zygotes after self-pollination.

By a 'mediator or modulator of SI activity' is meant a molecule that enhances or otherwise modifies expression, activity or function of SI in a plant cell, plant callus, plant, seed or other plant part. For example, the mediator or modulator of SI activity may improve pollen tube growth, or enhance action or activity of the SI mechanisms.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, self-incompatibility may be induced, increased, decreased, repressed or otherwise altered, in a transformed plant relative to an untransformed control plant, for example by incorporating additional copies of a sense nucleic acid of the present invention, preferably to overexpress the polypeptide or in sense suppression. They may be decreased or otherwise altered, for example by incorporating an antisense nucleic acid of the present invention.

In a further aspect, the present invention provides a method for altering the SI status of a plant, said method including identifying a gene encoding a polypeptide which is active in the SI pathway of the plant and up-regulating or down-regulating expression of said gene to repress or induce the SI mechanism in said plant. Preferably said gene is a nucleic acid according to the present invention. Preferably the plant is as hereinbefore described.

By 'up-regulating' expression of said gene is meant increasing expression of said gene and, as a result, the protein encoded by the gene, in a plant relative to a control plant.

By 'down-regulating' expression of said gene is meant decreasing expression of said gene and, as a result, the protein encoded by the gene, in a plant relative to a control plant.

The up-regulation or down-regulation may be carried out by methods known to those skilled in the art. For example, a gene may be up-regulated by incorporating additional copies of a sense copy of the gene. A gene may be down-regulated, for example, by incorporating an antisense nucleic acid, a frame-shifted or otherwise modified sense copy of the gene, or nucleic acid encoding interfering RNA (RNAi). Up or down regulation may also be achieved through the use of transcription activator-like effector nucleases or zinc-finger nucleases, mediating cleavage of specific target sites in the nucleic acid, leading to micro-deletions and insertions within the endogenous nucleic acid sequence.

Techniques for incorporating the genetic constructs of the present invention into plant cells are known to those skilled in the art. Such techniques include high velocity projectile introduction to cells, tissues, calli, immature and mature embryos. Cells incorporating the genetic constructs of the present invention may be selected, as described above, and then cultured in an appropriate medium to regenerate transformed plants, using techniques well know in the art. The culture conditions, such as temperature, pH and the like, will be apparent to the person skilled in the art. The resulting plants may be reproduced either sexually or asexually, using methods well known in the art.

By 'repressing the SI mechanism' of a plant is meant reducing the tendency of the plant to inhibit pollen tube elongation and resulting fertilisation of self-pollen.

By 'activating the SI mechanism' of a plant is meant introducing the tendency of the plant to inhibit pollen tube elongation and resulting fertilisation of self-pollen.

In a further aspect, the present invention provides a substantially purified or isolated nucleic acid or nucleic acid fragment encoding a plant self-incompatibility (SI) protein, complements thereof, sequences antisense thereto, and functionally active fragments and variants thereof. Preferably, the nucleic acid or nucleic acid fragment encodes a polypeptide selected from the group consisting of a proteasome subunit, more particularly a 26S proteasome subunit, a Cullin (Cullins are molecular scaffolds responsible for assembling ubiquitin E3 ligases, more particularly RING-based E3 ubiquitin ligases), a glutamate receptor or precursor thereof, a zinc finger protease, a no-pollen (NOP) polypeptide, a seven-in-absentia homologue (SIAH), and a ubiquitin-specific protease, more particularly a ubiquitin-specific protease 22.

The nucleic acid or nucleic acid fragment may be isolated from or correspond to a gene from a plant of the Poaceae family. In a preferred embodiment the nucleic acid or nucleic acid fragment may be isolated from or correspond to a gene from a grass species, particularly a pasture grass such as ryegrass (*Lolium*) or fescue (*Festuca*), more particularly perennial ryegrass (*Lolium perenne* L.) or tall fescue (*Festuca arundinaceum*, otherwise known as *Lolium arundinaceum*).

By 'nucleic acid' is meant a chain of nucleotides capable of genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double stranded, optionally containing synthetic, non-natural or altered nucleotide bases, synthetic nucleic acids and combinations thereof.

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

By 'substantially purified' is meant that the nucleic acid is free of the genes, which, in the naturally-occurring genome of the organism from which the nucleic acid of the invention is derived, flank the nucleic acid. The term therefore includes, for example, a nucleic acid which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a nucleic acid which is part of a hybrid gene encoding additional polypeptide sequence. Preferably, the substantially purified nucleic acid is 90%, more preferably 95%, even more preferably 98% pure.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

Such nucleic acids or nucleic acid fragments could be assembled to form a consensus contig. As used herein, the term "consensus contig" refers to a nucleotide sequence that is assembled from two or more constituent nucleotide sequences that share common or overlapping regions of sequence homology. For example, the nucleotide sequence of two or more nucleic acids or nucleic acid fragments can be compared and aligned in order to identify common or overlapping sequences. Where common or overlapping sequences exist between two or more nucleic acids or nucleic acid fragments, the sequences (and thus their corresponding nucleic acids or nucleic acid fragments) can be assembled into a single contiguous nucleotide sequence.

In a preferred embodiment, the present invention provides a substantially purified or isolated nucleic acid or nucleic acid fragment encoding a plant self-incompatibility (SI) protein, or complementary or antisense to a sequence encoding a plant SI protein, said nucleic acid or nucleic acid fragment including a nucleotide sequence selected from the group consisting of:

(a) the sequences shown in SEQ ID NOS: 1 to 70;
(b) a nucleotide sequence encoding the polypeptide shown SEQ ID NOS: 71 to 140;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

Preferably, the SI protein is selected from the group consisting of a proteasome subunit, more preferably a 26S proteasome subunit, a Cullin, a glutamate receptor or precursor thereof, a zinc finger protease, a protein containing C2 and GRAM amino acid domains, more preferably a protein involved in signal transduction, membrane trafficking, and/or membrane-coupled processes, more preferably a protein encoded by a NOP gene, a SIAH, and a ubiquitin-specific protease, more preferably a ubiquitin-specific protease 22.

In a preferred embodiment, the present invention provides a substantially purified or isolated nucleic acid or nucleic acid fragment encoding a proteasome subunit, more preferably a 26S proteasome subunit, or complementary or antisense to a sequence encoding a proteasome subunit, more preferably a 26S proteasome subunit, said nucleic acid or nucleic acid fragment including a nucleotide sequence selected from the group consisting of:

(a) the sequences shown in SEQ ID NO: 58 and FIG. 3;
(b) a nucleotide sequence encoding the polypeptide shown SEQ ID NO: 128;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a Cullin, or complementary or antisense to a sequence encoding a Cullin, said nucleic acid or nucleic acid fragment including a nucleotide sequence selected from the group consisting of:

(a) the sequences shown in SEQ ID NO: 20 and FIG. 5;
(b) a nucleotide sequence encoding the polypeptide shown SEQ ID NO: 90;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a glutamate receptor or precursor thereof, or complementary or antisense to a sequence encoding a glutamate receptor or precursor thereof, said nucleic acid or nucleic acid fragment including a nucleotide sequence selected from the group consisting of:

(a) the sequences shown in SEQ ID NO: 39 and FIG. 7;
(b) a nucleotide sequence encoding the polypeptide shown SEQ ID NO: 109;
(c) complements of the sequences recited in (a) and (b);
(d) sequences antisense to the sequences recited in (a) and (b);

(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a zinc finger protease, or complementary or antisense to a sequence encoding a zinc finger protease, said nucleic acid or nucleic acid fragment including a nucleotide sequence selected from the group consisting of:

(a) the sequences shown in SEQ ID NO: 62 and FIG. 9;
(b) a nucleotide sequence encoding the polypeptide shown SEQ ID NO: 132;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a C2 and GRAM domain containing polypeptide, preferably a no pollen (NOP) polypeptide, or complementary or antisense to a sequence encoding a C2 and GRAM domain containing polypeptide, preferably a no pollen (NOP) polypeptide, said nucleic acid or nucleic acid fragment including a nucleotide sequence selected from the group consisting of:

(a) the sequences shown in SEQ ID NO: 59 and FIG. 11;
(b) a nucleotide sequence encoding the polypeptide shown SEQ ID NO: 129;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a seven-in-absentia homologue, or complementary or antisense to a sequence encoding a seven-in-absentia homologue, said nucleic acid or nucleic acid fragment including a nucleotide sequence selected from the group consisting of:

(a) the sequences shown in SEQ ID NO: 40 and FIG. 13;
(b) a nucleotide sequence encoding the polypeptide shown SEQ ID NO: 110;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

In a preferred embodiment, the present invention provides a substantially purified or isolated nucleic acid or nucleic acid fragment encoding a ubiquitin-specific protease, more preferably a ubiquitin-specific protease 22, or complementary or antisense to a sequence encoding a ubiquitin-specific protease, more preferably a ubiquitin-specific protease 22, said nucleic acid or nucleic acid fragment including a nucleotide sequence selected from the group consisting of:

(a) the sequences shown in SEQ ID NO: 54 and FIG. 15;
(b) a nucleotide sequence encoding the polypeptide shown SEQ ID NO: 124;
(c) complements of the sequences recited in (a) and (b);
(d) sequences antisense to the sequences recited in (a) and (b);
(e) functionally active fragments of the sequences recited in (a), (b), (c) and (d); and
(f) functionally active variants of the sequences recited in (a), (b), (c), (d) and (e).

The present invention encompasses functionally active fragments and variants of the nucleic acids of the present invention. By 'functionally active' in relation to the nucleic acid is meant that the fragment or variant (such as an analogue, derivative or mutant) is capable of manipulating SI in a plant. For example, it may be capable of manipulating a proteasome in a plant, more particularly a proteasome subunit, even more particularly a 26S proteasome subunit. For example, it may be capable of manipulating an E3 ubiquitin ligase in a plant, more particularly a Cullin. For example, it may be capable of manipulating influx channels in a plant, more particularly glutamate receptors. For example, it may be capable of manipulating ubiquitin-specific protease activity in a plant, more particularly zinc finger protease activity. For example, it may be capable of manipulating signal transduction, membrane trafficking, and/or membrane-coupled processes in a plant. For example, it may be capable of manipulating SIAH in a plant. For example it may be capable of manipulating a ubiquitin-specific protease in a plant, more particularly a ubiquitin-specific protease 22.

Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

Particularly preferred fragments include fragments of the nucleic acid sequences which include hypervariable regions of the gametophytic gene in sense or anti sense orientation, and functionally active variants of these fragments, see FIGS. 17 to 37.

Preferably the fragment has a size of at least 20 nucleotides, more preferably at least 50 nucleotides, more preferably at least 100 nucleotides, more preferably at least 200 nucleotides, more preferably at least 500 nucleotides.

In a particularly preferred embodiment, the fragment or variant may include a sequence shown in FIGS. 17 to 37 hereto.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His
Other conservative amino acid substitutions may also be made as follows:
Aromatic: Phe, Tyr, His
Proton Donor: Asn, Gln, Lys, Arg, His, Trp
Proton Acceptor: Glu, Asp, Thr, Ser, Tyr, Asn, Gln In a further aspect of the present invention, there is provided a genetic construct including one or more nucleic acids according to the present invention.

In a preferred embodiment the genetic construct may include a chimeric sequence comprising a nucleic acid according to the present invention and a gene encoding a mediator or modulator of SI activity.

In another preferred embodiment, the genetic construct may include:
  a first nucleic acid or nucleic acid fragment encoding a SI polypeptide, wherein said first nucleic acid or nucleic acid fragment is isolated from or corresponds to a gene from the Z locus of a plant of the Poaceae family; and
  a second nucleic acid or nucleic acid fragment encoding a SI polypeptide, wherein said second nucleic acid or nucleic acid fragment is isolated from or corresponds to a gene from the S locus of a plant of the Poaceae family.

The term "genetic construct" as used herein refers to an artificially assembled or isolated nucleic acid molecule which includes the gene of interest. Preferably the genetic construct is a recombinant nucleic acid molecule. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

By a 'chimeric sequence' is meant a hybrid produced by recombinant means through expression of a fusion gene including two or more linked nucleic acids which originally encoded separate proteins, or functionally active fragments or variants thereof.

By a 'fusion gene' is meant that two or more nucleic acids are linked in such a way as to permit expression of the fusion protein, preferably as a translational fusion. This typically involves removal of the stop codon from a nucleic acid sequence coding for a first protein, then appending the nucleic acid sequence of a second protein in frame. The fusion gene is then expressed by a cell as a single protein. The protein may be engineered to include the full sequence of both original proteins, or a functionally active fragment or variant of either or both.

In a preferred embodiment, the genetic construct according to the present invention may be a vector.

By a 'vector' is meant a genetic construct used to transfer genetic material to a target cell. The term vector encompasses both cloning and expression vectors. Vectors are often recombinant molecules containing nucleic acid molecules from several sources.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'->5' direction along the nucleic acid.

The promoter and terminator may be of any suitable type and may be endogenous to the target cell or may be exogenous, provided that they are functional in the target cell.

The promoter used in the constructs and methods of the present invention may be a constitutive, tissue specific or inducible promoter. For example, the promoter may be a constitutive cauliflower mosaic virus (CaMV35S) promoter for expression in many plant tissues, an inducible 'photosynthetic promoter' (e.g. ribulose 1,5-bisphosphate), capable of mediating expression of a gene in photosynthetic tissue in plants under light conditions, or a tissue specific promoter such as a seed specific promoter, for example from a gene selected from the group consisting of *Brassica napus* napin gene, *Zea mays* zein 4 gene, Orysa *sativa* PR602 gene and *Triticum aestivum* glutelin gene.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptll) gene, the hygromycin phosphotransferase (hph) gene, the phosphinothricin acetyltransferase (bar or pat) gene], and reporter genes (such as beta-glucuronidase (GUS) gene (gusA)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

In a still further aspect, the present invention provides a substantially purified or isolated regulatory element capable of causing expression of an exogenous gene in plant cells. Preferably the regulatory element is isolated from a nucleic acid or nucleic acid fragment encoding a plant self-incompatibility (SI) protein and functionally active fragments and variants thereof. Preferably, the regulatory element is isolated from a nucleic acid or nucleic acid fragment encoding a proteasome subunit, more particularly a 26S proteasome subunit, a Cullin, a glutamate receptor or precursor thereof, a zinc finger protease, a polypeptide with both C2 and GRAM amino acid domains, more preferably a no-pollen (NOP) gene, a SIAH, or a ubiquitin-specific protease, more preferably a ubiquitin-specific protease 22.

The regulatory element may be a nucleic acid molecule, including DNA (such as cDNA or genomic DNA) and RNA (such as mRNA) that is single- or double-stranded, optionally containing synthetic, non-natural or altered nucleotide bases, and combinations thereof.

Preferably the regulatory element includes a promoter. In a preferred embodiment, the regulatory element includes a proteasome subunit gene promoter, more preferably a 26S proteasome subunit gene promoter. In another preferred embodiment the regulatory element includes a Cullin gene promoter. In another preferred embodiment the regulatory element includes a glutamate receptor or precursor gene promoter. In another preferred embodiment the regulatory element includes a zinc finger protease gene promoter. In another preferred embodiment the regulatory element includes a promoter from a polypeptide with both C2 and GRAM amino acid domains, more preferably a promoter from a no-pollen (NOP) gene. In another preferred embodiment the regulatory element includes a SIAH gene promoter. In another preferred embodiment the regulatory element includes a ubiquitin-specific protease gene promoter, more preferably a ubiquitin-specific protease 22 gene promoter.

Preferably the regulatory element may be isolated from or correspond to a regulatory element from a plant of the Poaceae family. In a preferred embodiment the regulatory element may be isolated from or correspond to a regulatory element from a grass species, particularly a pasture grass such as ryegrass (*Lolium*) or fescue (*Festuca*), more particularly perennial ryegrass (*Lolium perenne* L.) or tall fescue (*Festuca arundinaceum*, otherwise known as *Lolium arundinaceum*).

In a particularly preferred embodiment of this aspect of the invention, the regulatory element includes a promoter from a 26S proteasome subunit gene from perennial ryegrass.

Preferably the regulatory element includes a promoter element of the sequence shown in FIG. 3; or a functionally active fragment or variant thereof, including hypervariable regions. The person skilled in the art will understand that the promoter element is located upstream of the ATG start codon shown at position 2335 of FIG. 3.

In another particularly preferred embodiment of this aspect of the invention, the regulatory element includes a promoter from a Cullin gene from perennial ryegrass.

Preferably the regulatory element includes a promoter element of the sequence shown in FIG. 5; or a functionally active fragment or variant thereof, including hypervariable regions. The person skilled in the art will understand that the promoter element is located upstream of the ATG start codon shown at position 294 of FIG. 5.

In another particularly preferred embodiment of this aspect of the invention, the regulatory element includes a promoter from glutamate receptor or precursor gene from perennial ryegrass.

Preferably the regulatory element includes a promoter element of the sequence shown in FIG. 7; or a functionally active fragment or variant thereof, including hypervariable regions. The person skilled in the art will understand that the promoter element is located upstream of the ATG start codon shown at position 788 of FIG. 7.

In another particularly preferred embodiment of this aspect of the invention, the regulatory element includes a promoter from zinc finger protease gene from perennial ryegrass.

Preferably the regulatory element includes a promoter element of the sequence shown in FIG. 9; or a functionally active fragment or variant thereof, including hypervariable regions. The person skilled in the art will understand that the promoter element is located upstream of the ATG start codon shown at position 625 of FIG. 9.

In another particularly preferred embodiment of this aspect of the invention, the regulatory element includes a promoter from a NOP gene from perennial ryegrass.

Preferably the regulatory element includes a promoter element of the sequence shown in FIG. 11; or a functionally active fragment or variant thereof, including hypervariable regions. The person skilled in the art will understand that the promoter element is located upstream of the ATG start codon shown at position 7924 of FIG. 11.

In another particularly preferred embodiment of this aspect of the invention, the regulatory element includes a promoter from a SIAH gene from perennial ryegrass.

Preferably the regulatory element includes a promoter element of the sequence shown in FIG. 13; or a functionally active fragment or variant thereof, including hypervariable regions. The person skilled in the art will understand that the promoter element is located upstream of the ATG start codon shown at position 124 of FIG. 13.

In another particularly preferred embodiment of this aspect of the invention, the regulatory element includes a promoter from a ubiquitin-specific protease gene from perennial ryegrass.

Preferably the regulatory element includes a promoter element of the sequence shown in FIG. 15; or a functionally active fragment or variant thereof, including hypervariable regions. The person skilled in the art will understand that the promoter element is located upstream of the ATG start codon shown at position 6784 of FIG. 15.

By "functionally active" in this context is meant that the fragment or variant (such as an analogue, derivative or mutant) is capable of causing expression of a transgene in plant cells, particularly of the reproductive tissues. Such variants include naturally occurring allelic variants and non-naturally occurring variants. Additions, deletions, substitutions and derivatizations of one or more of the nucleotides are contemplated so long as the modifications do not result in loss of functional activity of the regulatory element. Preferably the functionally active fragment or variant has at least approximately 80% identity to the relevant part of the above mentioned sequence to which the fragment or variant corresponds, more preferably at least approximately 90% identity, even preferably at least approximately 95% identity, most preferably at least approximately 98% identity. Preferably the fragment has a size of at least 100 nucleotides, more preferably at least 150 nucleotides, most preferably at least 200 nucleotides.

In a particularly preferred embodiment of this aspect of the invention, the regulatory element includes a nucleotide sequence selected from the group consisting of:
Nucleotides 0 to 2334 of FIG. 3,
Nucleotides 500 to 2334 of FIG. 3, and
Nucleotides 1000 to 2334 of FIG. 3;
or a functionally active fragment or variant thereof.

In a particularly preferred embodiment of this aspect of the invention, the regulatory element includes a nucleotide sequence selected from the group consisting of: Nucleotides 0 to 293 of FIG. 5, and functionally active fragments and variants thereof.

In a particularly preferred embodiment of this aspect of the invention, the regulatory element includes a nucleotide sequence selected from the group consisting of: Nucleotides 0 to 787 of FIG. 7, and functionally active fragments and variants thereof.

In a particularly preferred embodiment of this aspect of the invention, the regulatory element includes a nucleotide sequence selected from the group consisting of: Nucleotides 0 to 624 of FIG. 9, and functionally active fragments and variants thereof.

In a particularly preferred embodiment of this aspect of the invention, the regulatory element includes a nucleotide sequence selected from the group consisting of:
Nucleotides 0 to 7923 of FIG. 11,
Nucleotides 6968 to 7923 of FIG. 11, and
Nucleotides 7468 to 7923 of FIG. 11,
or a functionally active fragment or variant thereof.

In a particularly preferred embodiment of this aspect of the invention, the regulatory element includes a nucleotide sequence selected from the group consisting of: Nucleotides 0 to 123 of FIG. 13, and functionally active fragments and variants thereof.

In a particularly preferred embodiment of this aspect of the invention, the regulatory element includes a nucleotide sequence selected from the group consisting of:
Nucleotides 0 to 6783 of FIG. 15,
Nucleotides 5087 to 6783 of FIG. 15,
Nucleotides 5587 to 6783 of FIG. 15, and
Nucleotides 6087 to 6783 of FIG. 15;
or a functionally active fragment or variant thereof.

By an "exogenous gene" is meant a gene not natively linked to said regulatory element. In certain embodiments of the present invention the exogenous gene is also not natively found in the relevant plant or plant cell.

The exogenous gene may be of any suitable type. The exogenous gene may be a nucleic acid such as DNA (e.g. cDNA or genomic DNA) or RNA (e.g. mRNA), and combinations thereof. The exogenous gene may be a gene capable of manipulating SI in a plant, or be a fragment or variant (such as an analogue, derivative or mutant) thereof which is capable of manipulating SI in a plant. Such variants include nucleic acid sequences which are antisense to said target gene or an analogue, derivative, mutant or fragment thereof. The transgene may code for a protein or RNA sequence depending on the target condition and whether down or up-regulation of gene expression is required.

The regulatory element according to the present invention may be used to express exogenous genes to which it is operatively linked in the production of transgenic plants. Preferably the regulatory element is used for gene expression in reproductive tissues of the plant.

Preferably, the genetic constructs of the present invention are substantially purified or isolated, as hereinbefore described. By 'substantially purified', in the current context, is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

The genetic constructs and vectors of the present invention may be incorporated into a variety of plants, preferably monocotyledons, preferably of the Poaceae family, such as grasses from the genera *Lolium, Festuca, Paspalum, Pennisetum, Panicum* and other forage and turfgrasses, corn, oat, sugarcane, wheat and barley.

The genetic constructs of the present invention may be introduced into plants by any suitable technique. Techniques for incorporating the genetic constructs of the present invention into plant cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of protoplasts, PEG-mediated transformation is particularly preferred.

Cells incorporating the genetic constructs of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector or construct, nucleic acid or nucleic acid fragment of the present invention. Preferably the plant cell is a transformed plant cell.

By a 'transformed plant cell' is meant a plant cell which has undergone transformation.

By 'transformation' is meant the transfer of nucleic acid into a plant cell.

By a 'transgene' is meant a nucleic acid suitable for transforming a plant cell.

The plant cell, plant, plant seed or other plant part may be from any suitable species. In a preferred embodiment the plant cell, plant, plant seed or other plant part may be from a monocotyledon, preferably of the Poaceae family, such as grasses from the genera *Lolium, Festuca, Paspalum, Pennisetum, Panicum* and other forage and turfgrasses, corn, oat, sugarcane, wheat and barley.

The present invention also provides a plant, plant seed or other plant part, or a plant extract derived from a plant cell or plant of the present invention and preferably including e.g. transformed with, a vector or construct, nucleic acid or nucleic acid fragment, or regulatory element of the present invention.

The nucleic acids or nucleic acid fragments of the present invention may be used to isolate cDNAs and genes encoding homologous SI proteins from the same or other plant species, using sequence-dependent protocols, such as methods of nucleic acid hybridisation, and methods of DNA and RNA amplification as exemplified by various uses of nucleic acid amplification technologies (e.g. polymerase chain reaction, ligase chain reaction).

For example, other 26S proteasome subunit genes, Cullin genes, glutamate receptor or precursor genes, zinc finger protease genes, NOP genes, SIAH genes, or ubiquitin-specific protease genes may be isolated directly by using all or a portion of the nucleic acids or nucleic acid fragments of the present invention as hybridisation probes to screen libraries from the desired plant employing the methodology well known to those skilled in the art. Specific oligonucleotide probes based upon the nucleic acid sequences of the present invention may be designed and synthesized by methods known in the art. Moreover, the entire sequences may be used directly to synthesize DNA probes by methods known to the skilled artisan such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full-length cDNA or genomic fragments under conditions of appropriate stringency.

In addition, short segments of the nucleic acids or nucleic acid fragments of the present invention may be used in protocols to amplify longer nucleic acids or nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad Sci. USA* 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments may be isolated (Ohara et al. (1989) *Proc. Natl. Acad Sci USA* 86:5673; Loh et al. (1989) *Science* 243:217, the entire disclosures of which are incorporated herein by reference). Products generated by the 3' and 5' RACE procedures may be combined to generate full-length cDNAs.

In a further aspect of the present invention there is provided a substantially purified or isolated SI polypeptide. Preferably, the SI polypeptide is selected from the group consisting of a proteasome subunit, more particularly a 26S proteasome subunit, a Cullin, a glutamate receptor or precursor thereof, a zinc finger protease, a polypeptide including both C2 and GRAM amino acid domains, more preferably a polypeptide encoded by a no-pollen (NOP) gene, a SIAH, and a ubiquitin-specific protease, more preferably a ubiquitin-specific protease 22.

The SI polypeptide may be isolated from or correspond to a polypeptide from a plant of the Poaceae family. In a preferred embodiment the SI polypeptide may be isolated from or correspond to a polypeptide from a grass species, particularly a pasture grass such as ryegrass (*Lolium*) or fescue (*Festuca*), more particularly perennial ryegrass (*Lolium perenne* L.) or tall fescue (*Festuca arundinaceum*, otherwise known as *Lolium arundinaceum*).

In a preferred embodiment, the present invention provides a substantially purified or isolated SI polypeptide, said polypeptide including an amino acid sequence selected from the group consisting of:
  (a) sequences shown in SEQ ID NOS: 71 to 140 hereto;
  (b) polypeptides encoded by the sequences shown in SEQ ID NOS: 1 to 70 hereto;
  (c) functionally active fragments of the sequences recited in (a) and (b); and
  (d) functionally active variants of the sequences recited in (a), (b) and (c).

In a preferred embodiment, the present invention provides a substantially purified or isolated proteasome subunit polypeptide, more particularly a 26S proteasome subunit polypeptide, said polypeptide including an amino acid sequence selected from the group consisting of:
  (a) sequence shown in SEQ ID NO: 128 hereto;
  (b) polypeptides encoded by the sequences shown in SEQ ID NO: 58 and FIG. 3 hereto;
  (c) functionally active fragments of the sequences recited in (a) and (b); and
  (d) functionally active variants of the sequences recited in (a), (b) and (c).

In a preferred embodiment, the present invention provides a substantially purified or isolated Cullin polypeptide, said polypeptide including an amino acid sequence selected from the group consisting of:
  (a) sequence shown in SEQ ID NO: 90 hereto;
  (b) polypeptides encoded by the sequences shown in SEQ ID NO: 20 and FIG. 5 hereto;
  (c) functionally active fragments of the sequences recited in (a) and (b); and
  (d) functionally active variants of the sequences recited in (a), (b) and (c).

In a preferred embodiment, the present invention provides a substantially purified or isolated glutamate receptor polypeptide or precursor thereof, said polypeptide including an amino acid sequence selected from the group consisting of:
  (a) sequence shown in SEQ ID NO: 109 hereto;
  (b) polypeptides encoded by the sequences shown in SEQ ID NO: 39 and FIG. 7 hereto;
  (c) functionally active fragments of the sequences recited in (a) and (b); and
  (d) functionally active variants of the sequences recited in (a), (b) and (c).

In a preferred embodiment, the present invention provides a substantially purified or isolated zinc finger protease polypeptide, said polypeptide including an amino acid sequence selected from the group consisting of:
(a) sequence shown in SEQ ID NO: 132 hereto;
(b) polypeptides encoded by the sequences shown in SEQ ID NO: 62 and FIG. 9 hereto;
(c) functionally active fragments of the sequences recited in (a) and (b); and
(d) functionally active variants of the sequences recited in (a), (b) and (c).

In a preferred embodiment, the present invention provides a substantially purified or isolated NOP polypeptide, said polypeptide including an amino acid sequence selected from the group consisting of:
(a) sequence shown in SEQ ID NO: 129 hereto;
(b) polypeptides encoded by the sequences shown in SEQ ID NO: 59 and FIG. 11 hereto;
(c) functionally active fragments of the sequences recited in (a) and (b); and
(d) functionally active variants of the sequences recited in (a), (b) and (c).

In a preferred embodiment, the present invention provides a substantially purified or isolated SIAH polypeptide, said polypeptide including an amino acid sequence selected from the group consisting of:
(a) sequence shown in SEQ ID NO: 110 hereto;
(b) polypeptides encoded by the sequences shown in SEQ ID NO: 40 and FIG. 13 hereto;
(c) functionally active fragments of the sequences recited in (a) and (b); and
(d) functionally active variants of the sequences recited in (a), (b) and (c).

In a preferred embodiment, the present invention provides a substantially purified or isolated ubiquitin-specific protease polypeptide, said polypeptide including an amino acid sequence selected from the group consisting of:
(a) sequence shown in SEQ ID NO: 124 hereto;
(b) polypeptides encoded by the sequences shown in SEQ ID NO: 54 and FIG. 15 hereto;
(c) functionally active fragments of the sequences recited in (a) and (b); and
(d) functionally active variants of the sequences recited in (a), (b) and (c).

The present invention encompasses functionally active fragments and variants of the polypeptides of the present invention. By 'functionally active' in this context is meant that the fragment or variant has one or more of the biological properties of the corresponding protein from which the fragment or variant is derived. Additions, deletions, substitutions and derivatizations of one or more of the amino acids are contemplated so long as the modifications do not result in loss of functional activity of the fragment or variant. Preferably the fragment or variant has at least approximately 80% identity to the relevant part of the above mentioned sequence to which the fragment or variant corresponds, more preferably at least approximately 90% identity, more preferably at least approximately 95% identity, most preferably at least approximately 98% identity. Such functionally active variants and fragments include, for example, those having conservative amino acid substitutions of one or more residues in the corresponding amino acid sequence.

By 'conservative amino acid substitutions' is meant the substitution of an amino acid by another one of the same class, the classes being as follows:
Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His
Other conservative amino acid substitutions may also be made as follows:
Aromatic: Phe, Tyr, His
Proton Donor: Asn, Gln, Lys, Arg, His, Trp
Proton Acceptor: Glu, Asp, Thr, Ser, Tyr, Asn, Gln Preferably the fragment has a size of at least 10 amino acids, more preferably at least 20 amino acids, more preferably at least 50 amino acids, more preferably at least 100 amino acids, more preferably at least 200 amino acids.

In a particularly preferred embodiment, the fragment or variant may include a sequence shown in FIGS. 38 to 58 hereto.

In a further embodiment of this aspect of the invention, there is provided a polypeptide recombinantly produced from a nucleic acid or nucleic acid fragment according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

In a still further aspect of the present invention there is provided a method of isolating a nucleic acid or nucleic acid fragment of the present invention said method including sequencing nucleic acid fragments from a nucleic acid library.

The nucleic acid library may be of any suitable type and is preferably a cDNA library.

The nucleic acid or nucleic acid fragment may be isolated from a recombinant plasmid or may be amplified, for example using polymerase chain reaction.

The sequencing may be performed by techniques known to those skilled in the art.

In a still further aspect, the present invention involves identifying variation in the sequence of a gene encoding a polypeptide which is active in the SI pathway of a plant and deploying such variants as molecular markers. More particularly, the method includes determining the specific genetic constitution of a plant within the Poaceae family at the S and Z loci through analysis of genetic variation at the S and Z loci using methods known to those skilled in the art. This genetic variation may be in regions surrounding the SI genes and may be used in a proxy manner. Examples of sequence variation within the genes and their encoded polypeptides are shown in FIGS. 17 to 58.

Accordingly, the present invention provides use of a nucleic acid or nucleic acid fragment of the present invention or a SNP thereof as a molecular genetic marker.

More particularly, nucleic acids or nucleic acid fragments according to the present invention and/or nucleotide sequence information thereof may be used as a molecular genetic marker for quantitative trait loci (QTL) tagging, QTL mapping, DNA fingerprinting and in marker assisted selection, particularly in grasses such as *Lolium perenne*. Even more particularly, nucleic acids or nucleic acid fragments according to the present invention may be used as molecular genetic markers in plant improvement in relation to SI control or manipulation. Even more particularly, sequence information revealing SNPs in allelic variants of the nucleic acids or nucleic acid fragments of the present invention may be used as molecular genetic markers for QTL tagging and mapping and in marker assisted selection, particularly in grasses such as *Lolium perenne*.

As used herein, except where the context requires otherwise, the term "comprise" and variations of the term, such as "comprising", "comprises" and "comprised", are not intended to exclude further additives, components, integers or steps.

As used herein, except where the context requires otherwise, the singular forms "a", "an" and "the" include plural aspects.

DETAILED DESCRIPTION OF THE EMBODIMENTS

The present invention will now be more fully described with reference to the accompanying examples and figures. It should be understood, however, that the description following is illustrative only and should not be taken in any way as a restriction on the generality of the invention description above.

BRIEF DESCRIPTION OF THE DRAWINGS/FIGURES

In the figures:

FIG. 1. Comparative genetic ideogram of the S region delimited in *Lolium perenne* L. in comparison to the model genomes of *Oryza sativa* and *Brachypodium distachion*. Genes identified in common between *Oryza sativa* and *Brachypodium distachion* are indicated by joining lines. Assembled fragments of sequenced BAC clones from *Lolium perenne* L. are indicated along with their predicted location within the comparative genome map and their gene content. Gene content of the *Lolium perenne* L. nucleotide sequences are documented as orthologous genes based on the *Oryza* numerical numbering, with a Lp prefix.

Figure 2:
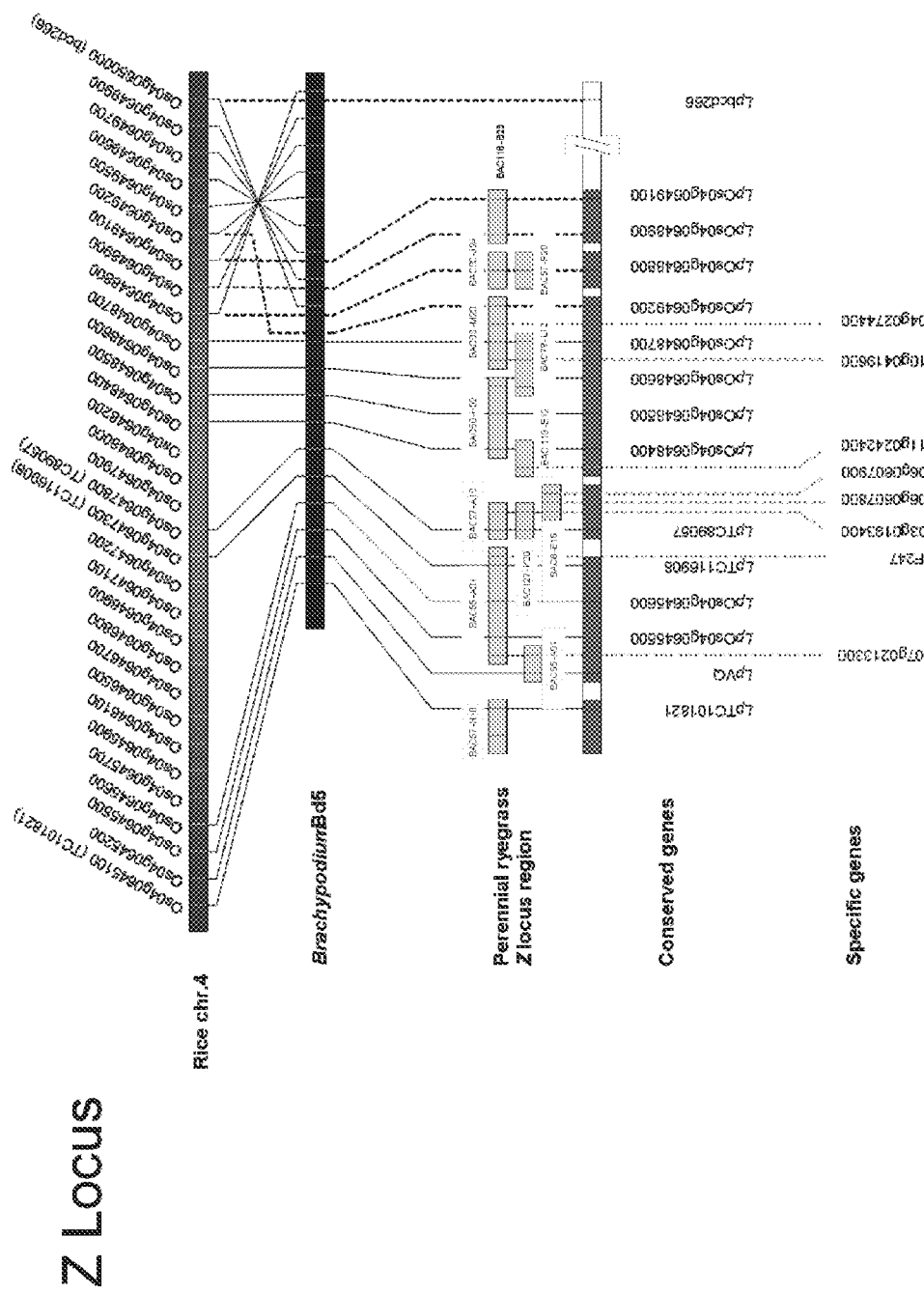

FIG. 2. Comparative genetic ideogram of the Z region delimited in *Lolium perenne* L. in comparison to the model genomes of *Oryza sativa* and *Brachypodium distachion*. Genes identified in common between *Oryza sativa* and *Brachypodium distachion* are indicated by joining lines. Assembled fragments of sequenced BAC clones from *Lolium perenne* L. are indicated along with their predicted location within the comparative genome map and their gene content. Gene content of the *Lolium perenne* L. nucleotide sequences are documented as orthologous genes based on the *Oryza* numerical numbering, with a Lp prefix.

Figure 3:
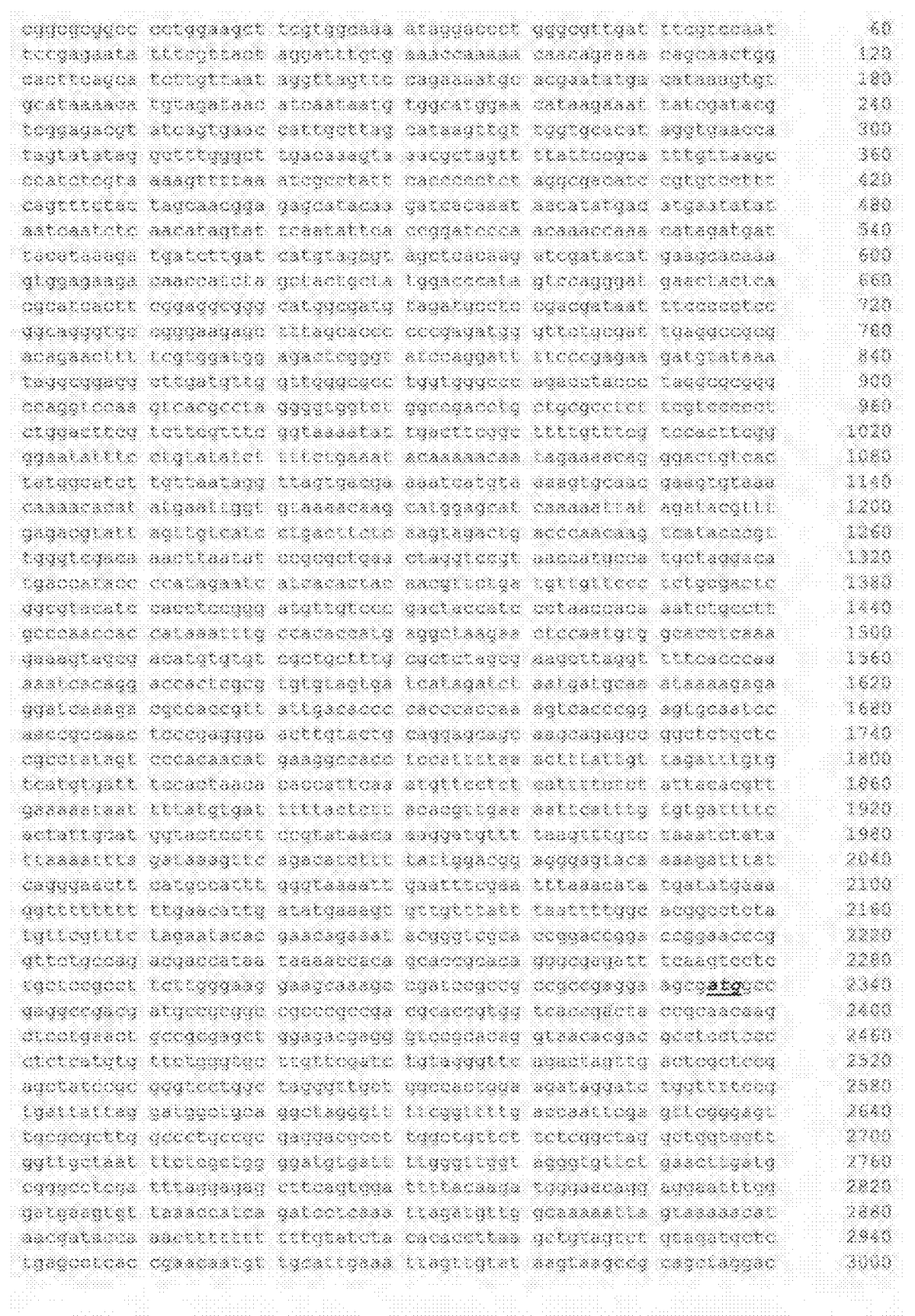
Figure 3:
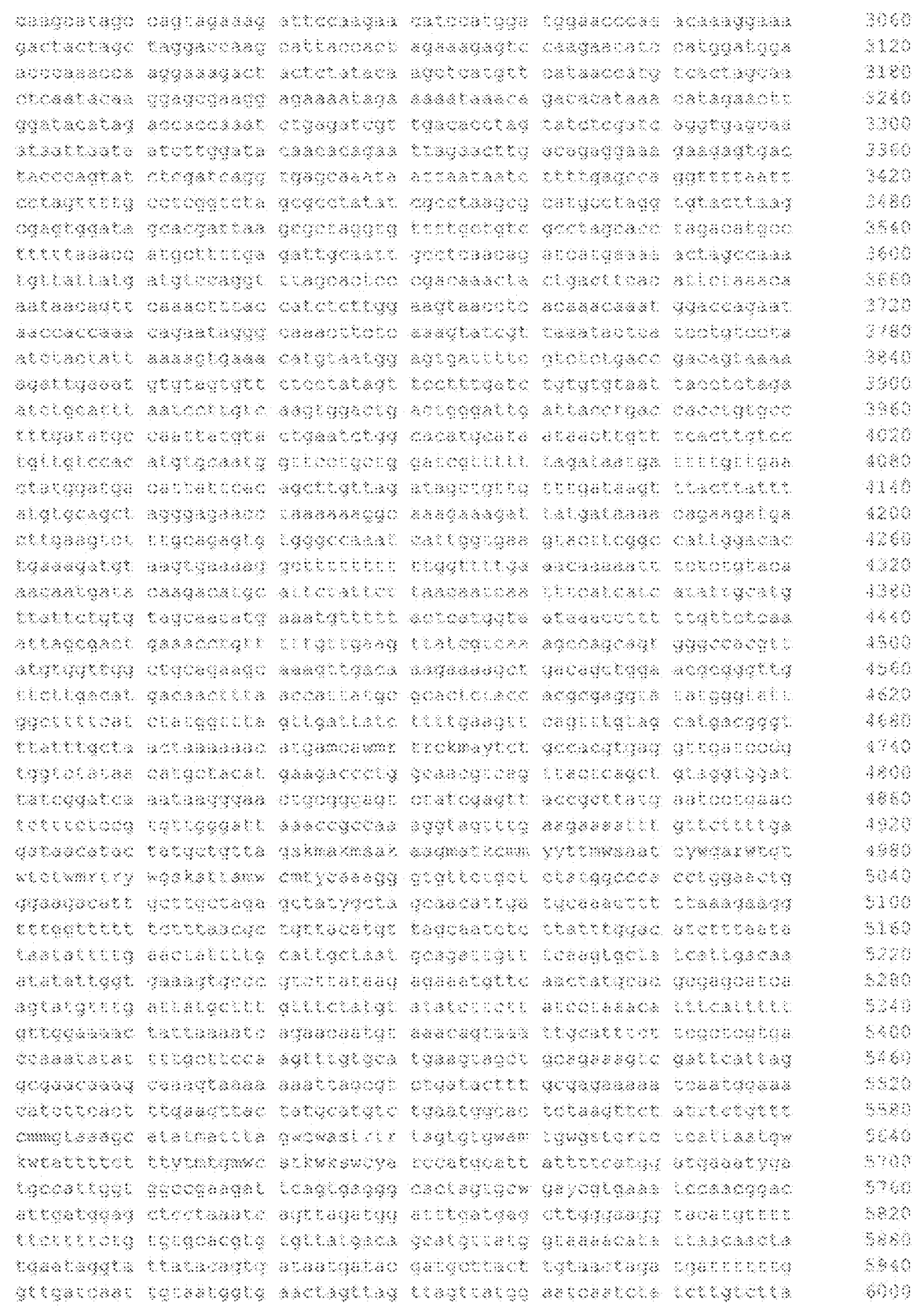
Figure 3:
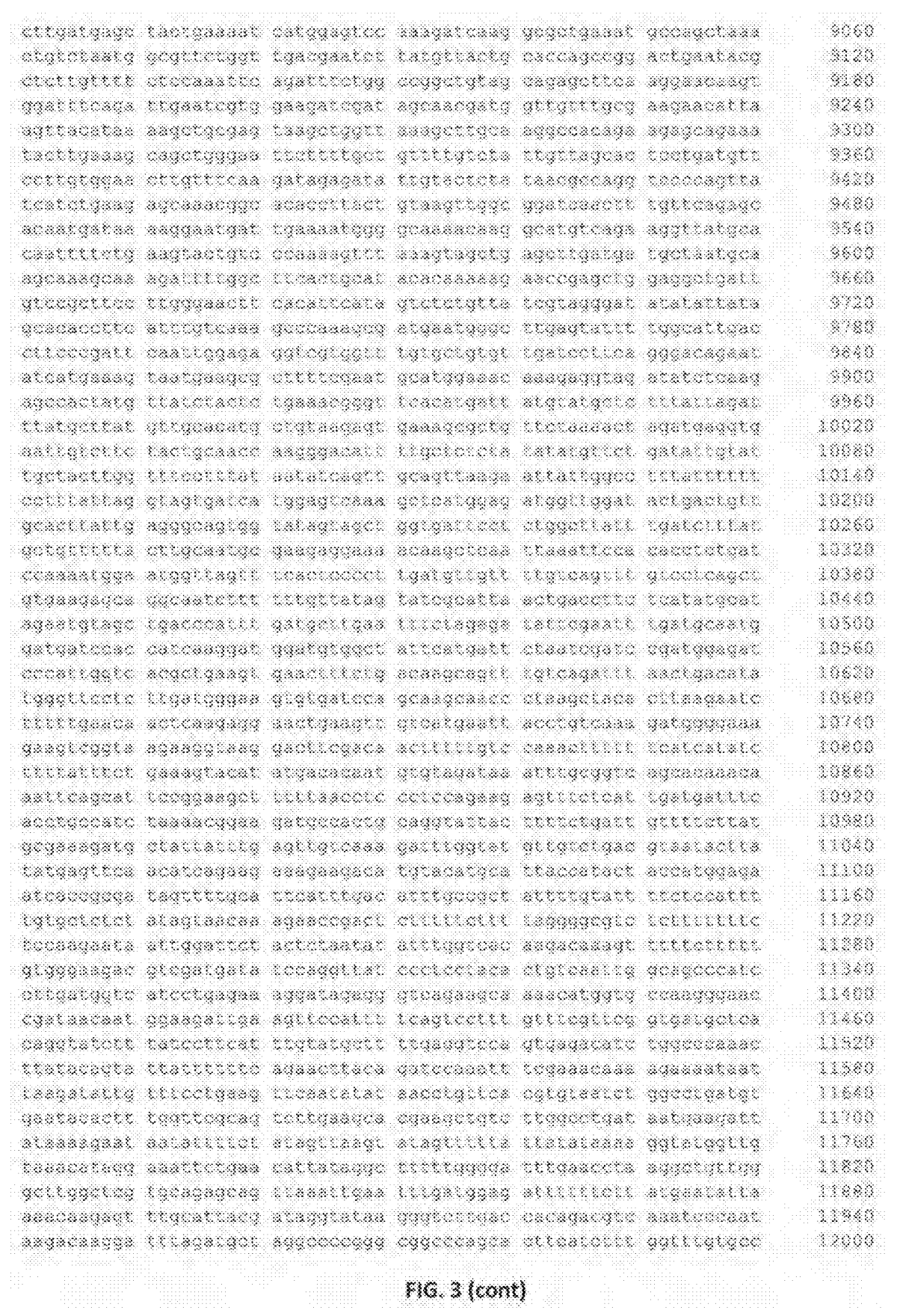
Figure 3:
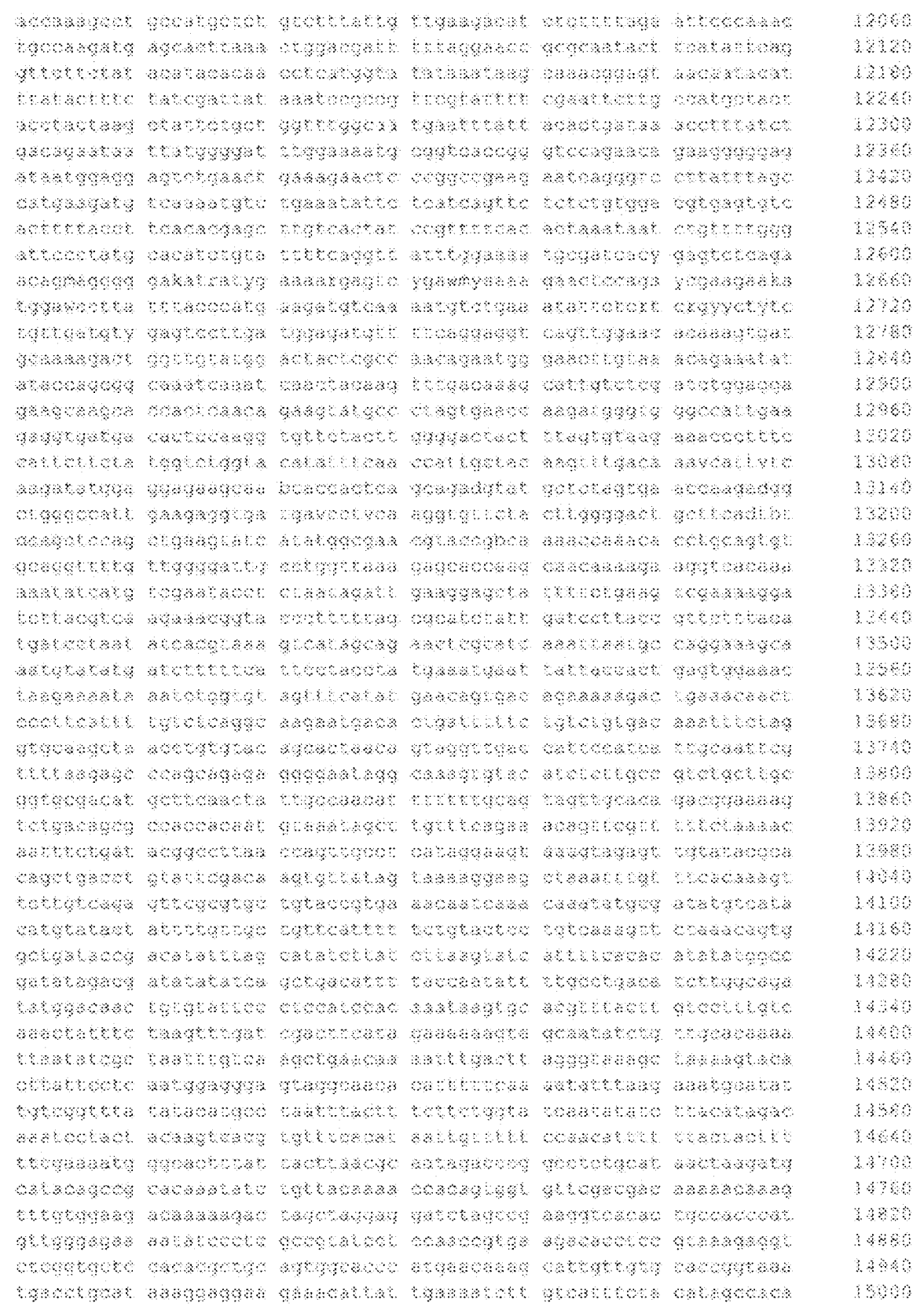
Figure 3:
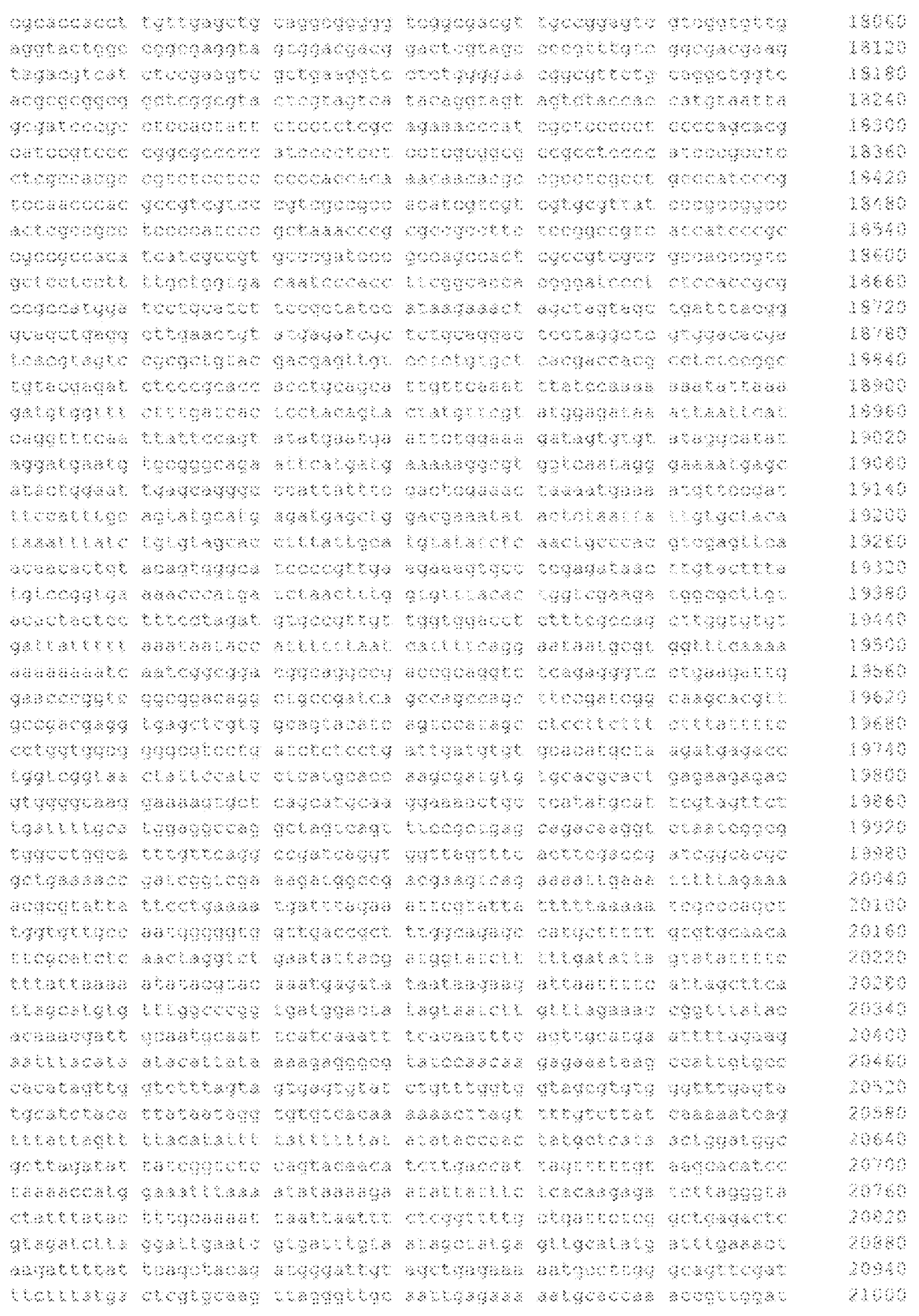
Figure 3:
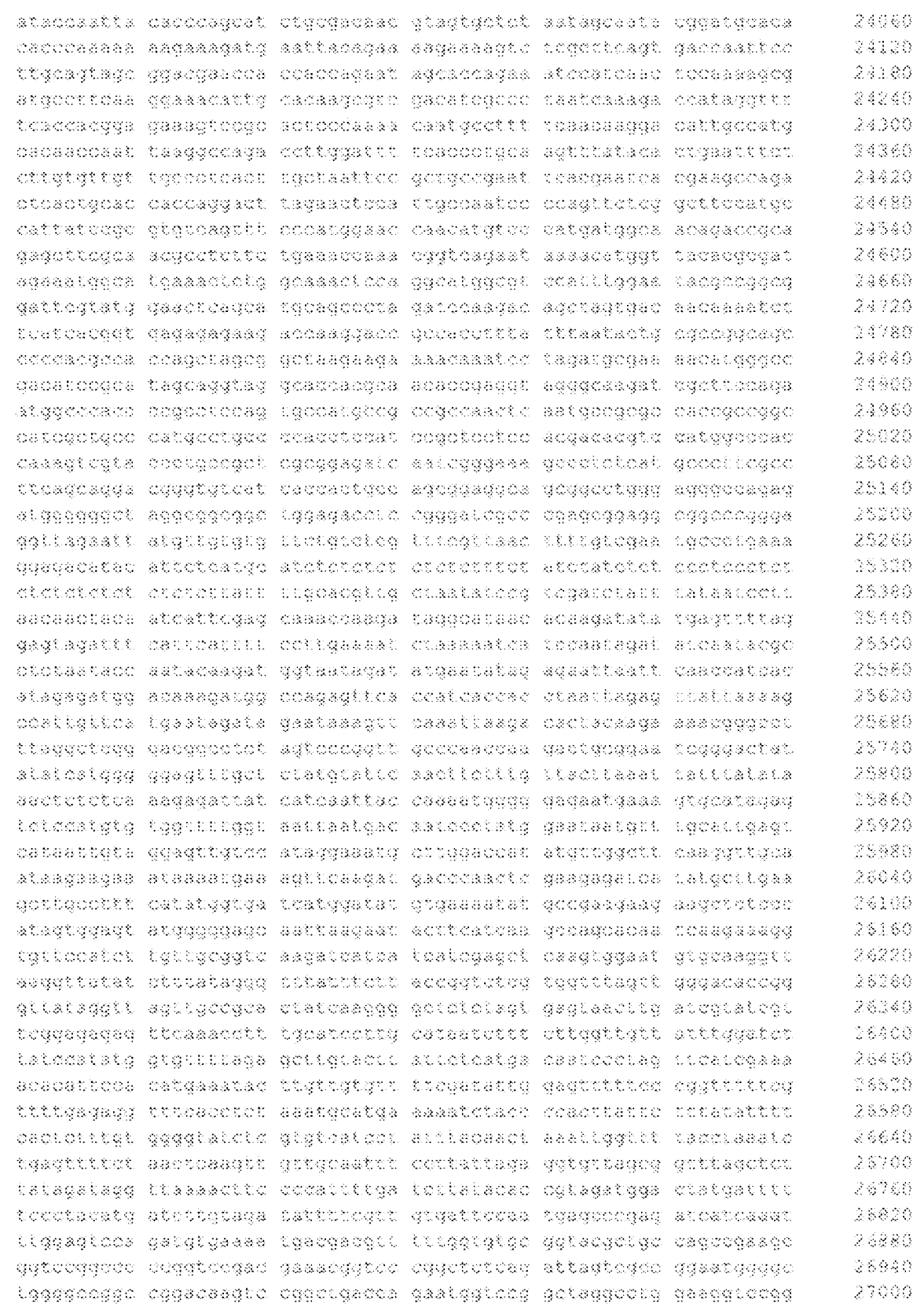

FIG. 3. Nucleic acid sequence of the genomic clone that contains the *Lolium perenne* LpOs06g0607800 26S proteasome subunit gene. The initial codon (ATG) of the LpOs06g0607800 gene is shown in bold italic underline.

Figure 4:
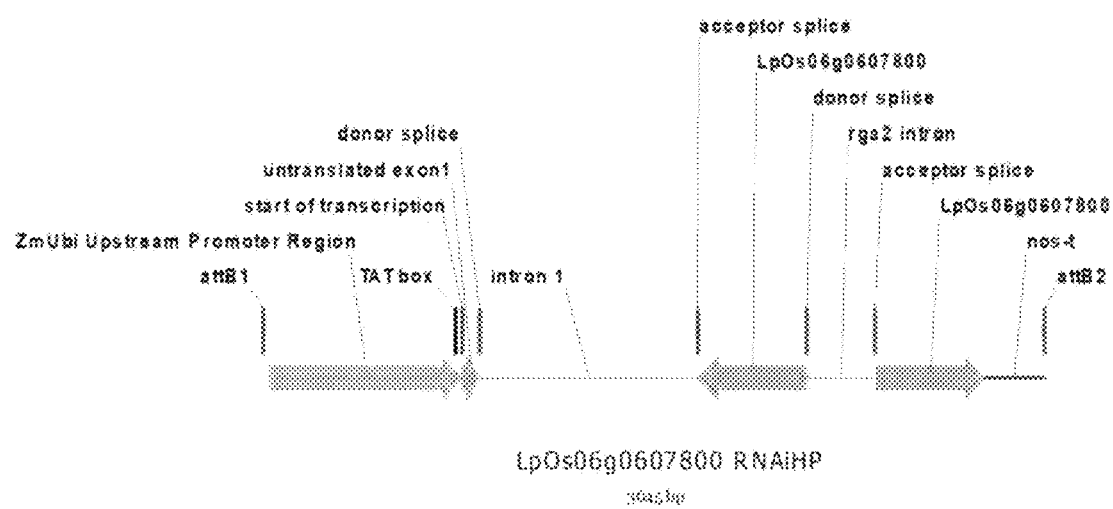

FIG. 4. Map of transformation vector containing the *Lolium perenne* ZmUbi_LpOs06g0607800_nos expression cassette used in biolistic mediated transformation of *Lolium perenne* L.

Figure 5:
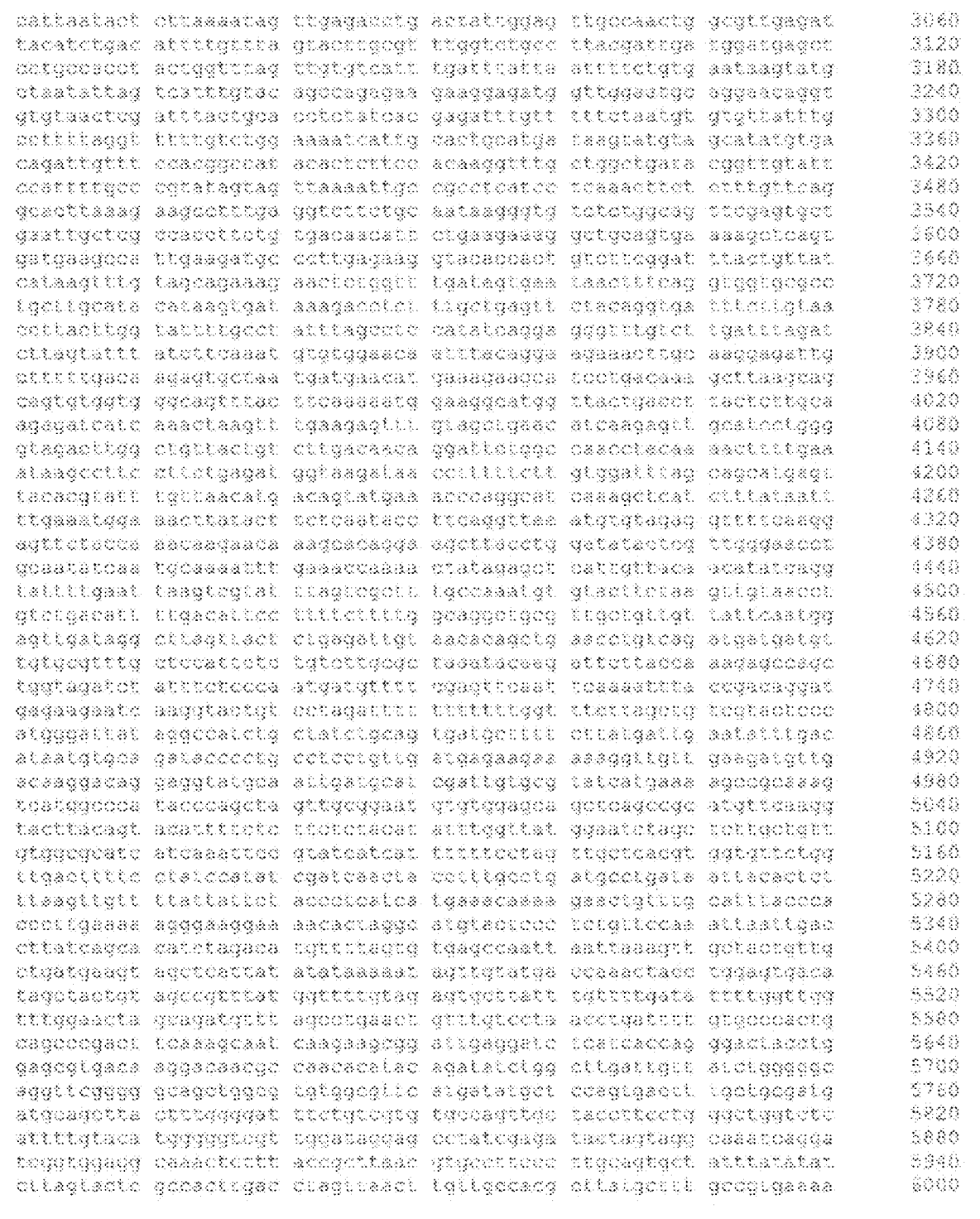
Figure 5:
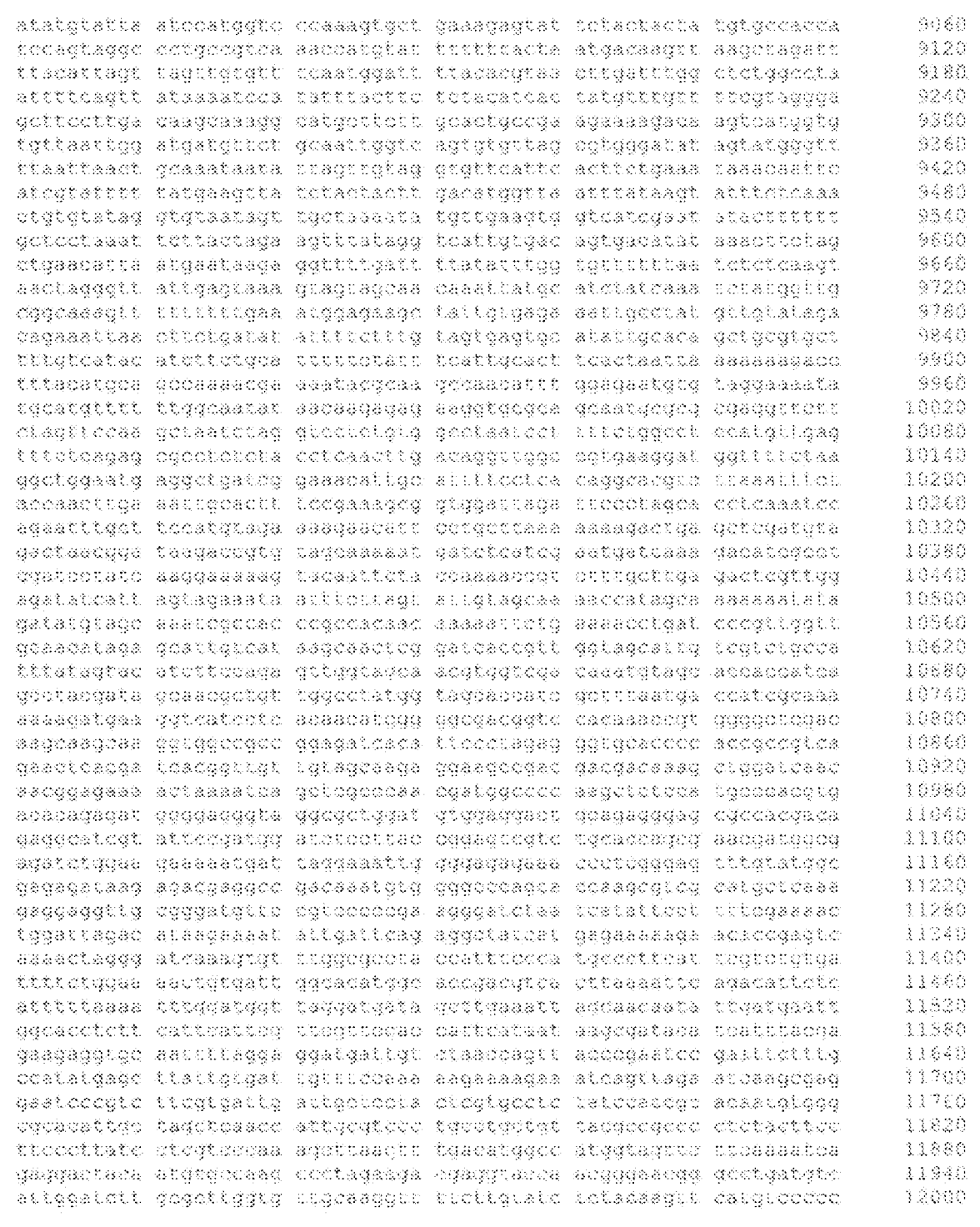

FIG. 5. Nucleic acid sequence of the genomic clone that contains the *Lolium perenne* LpOs05g0149600 Cullin gene. The initial codon (ATG) of the Cullin gene is shown in bold italic underline.

Figure 6:
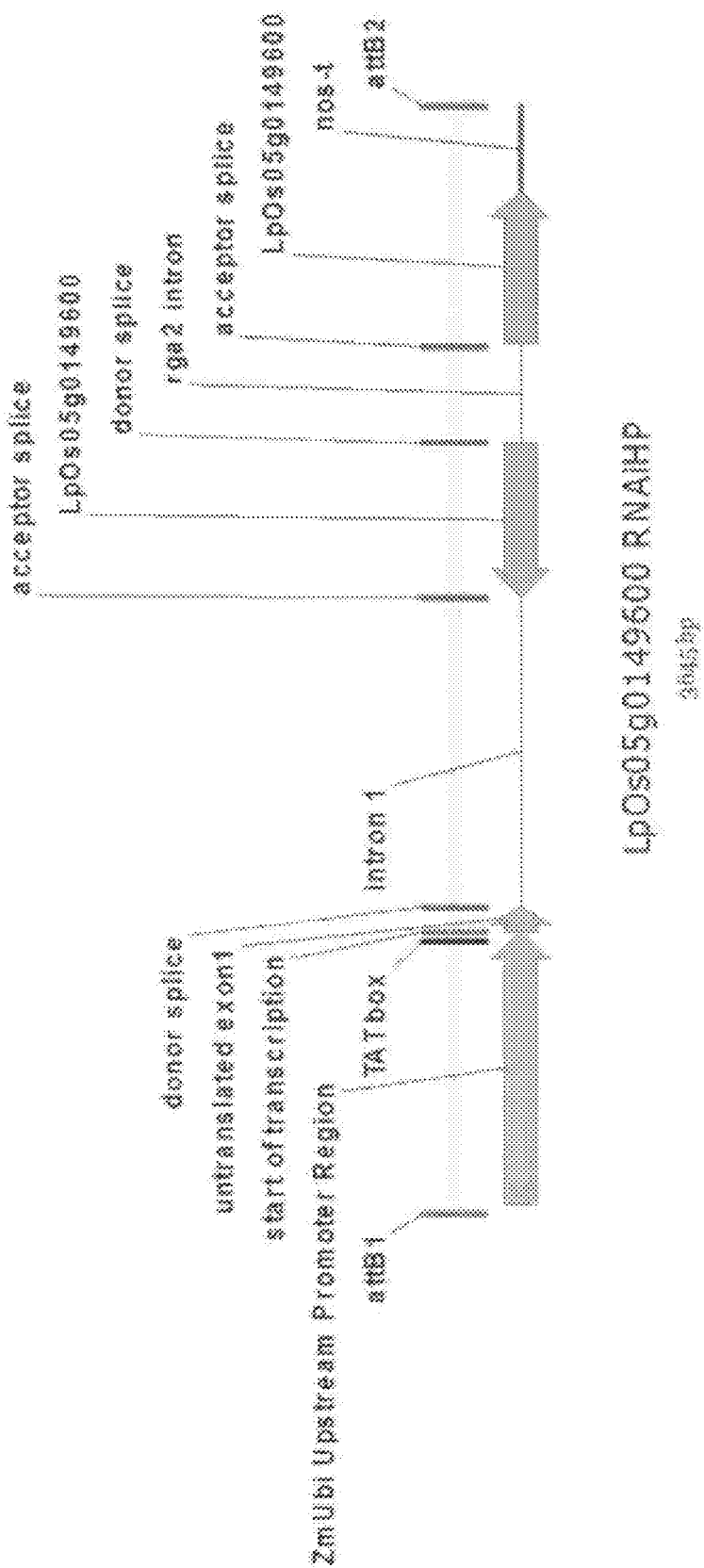

FIG. 6. Map of transformation vector containing the *Lolium perenne* ZmUbi_LpOs05g0149600_nos expression cassette used in biolistic mediated transformation of *Lolium perenne* L.

Figure 7:
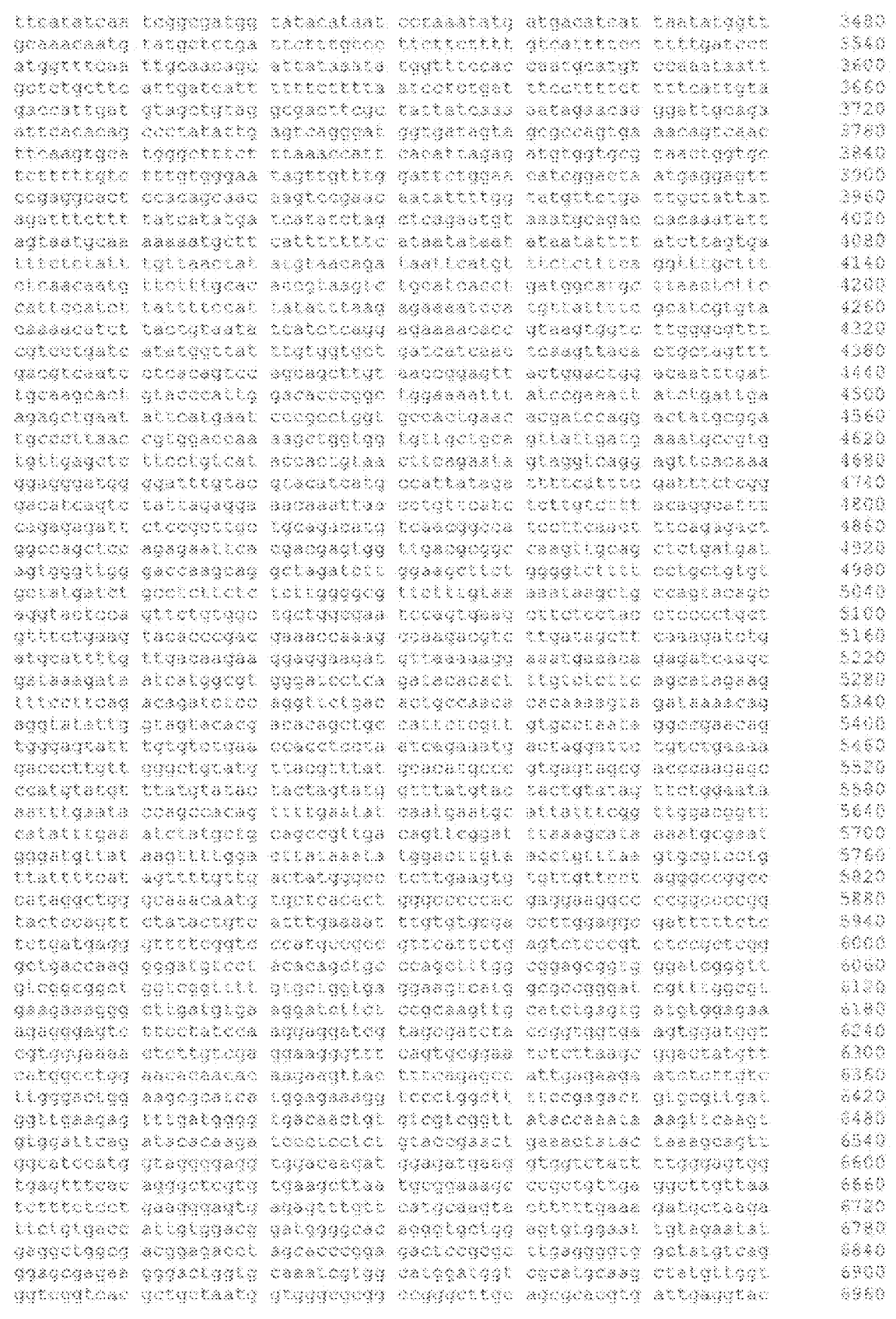

FIG. 7. Nucleic acid sequence of the genomic clone that contains the *Lolium perenne* LpOs06g0680500 Glutamate Receptor (LpGlu1) gene. The initial codon (ATG) of the glutamate receptor gene is shown in bold italic underline.

Figure 8:
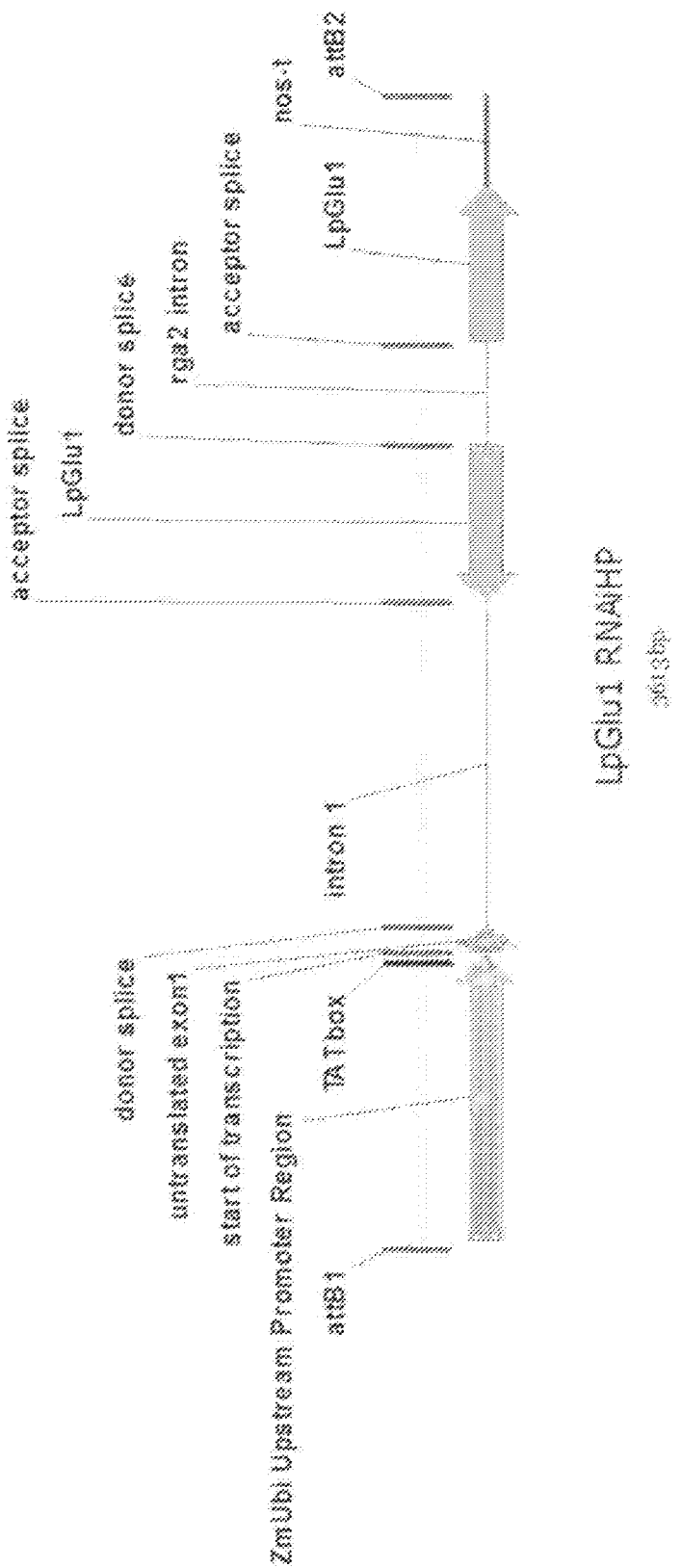

FIG. 8. Map of transformation vector containing the *Lolium perenne* ZmUbi_LpGlu1_nos expression cassette used in biolistic mediated transformation of *Lolium perenne* L.

Figure 9:
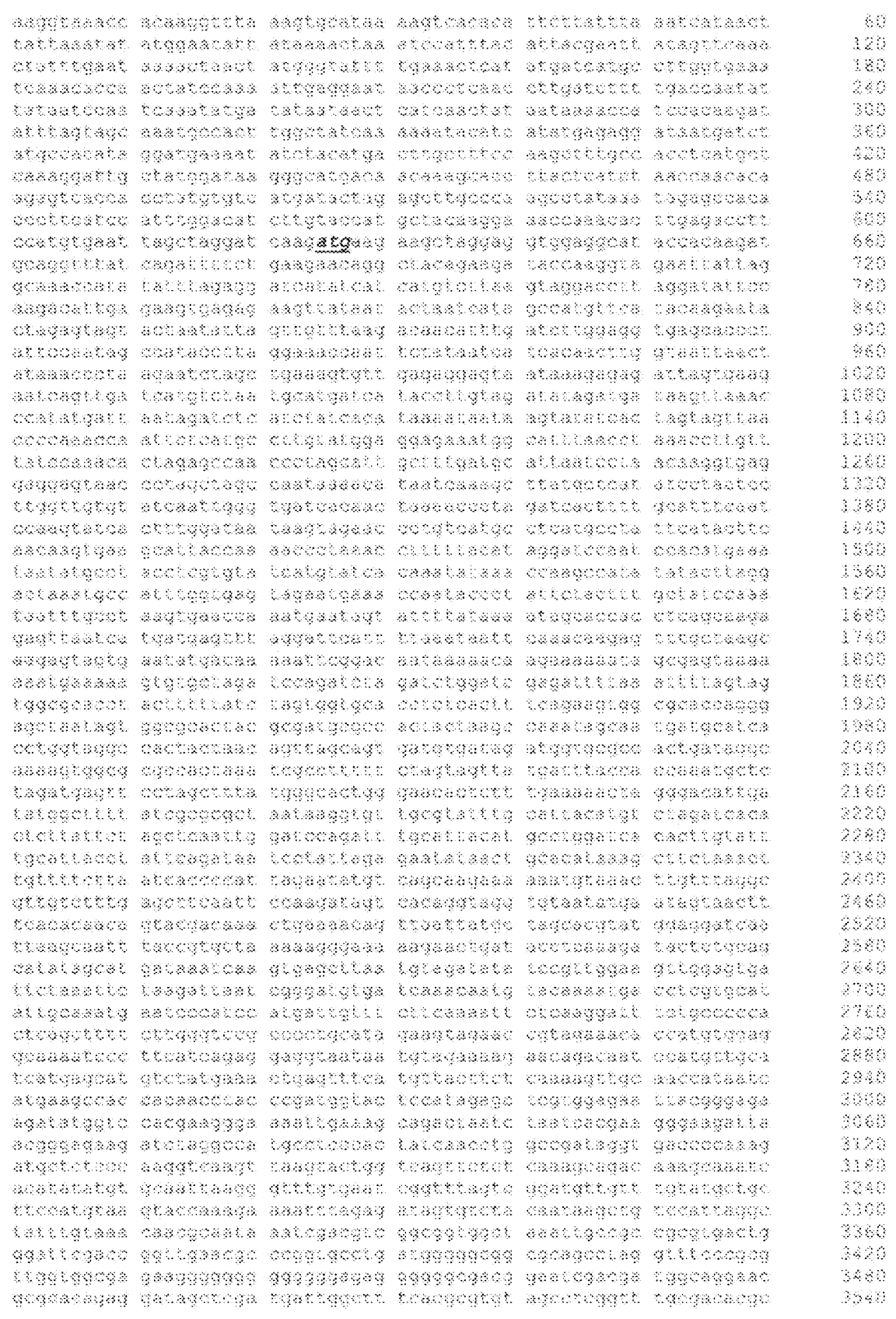
Figure 9:
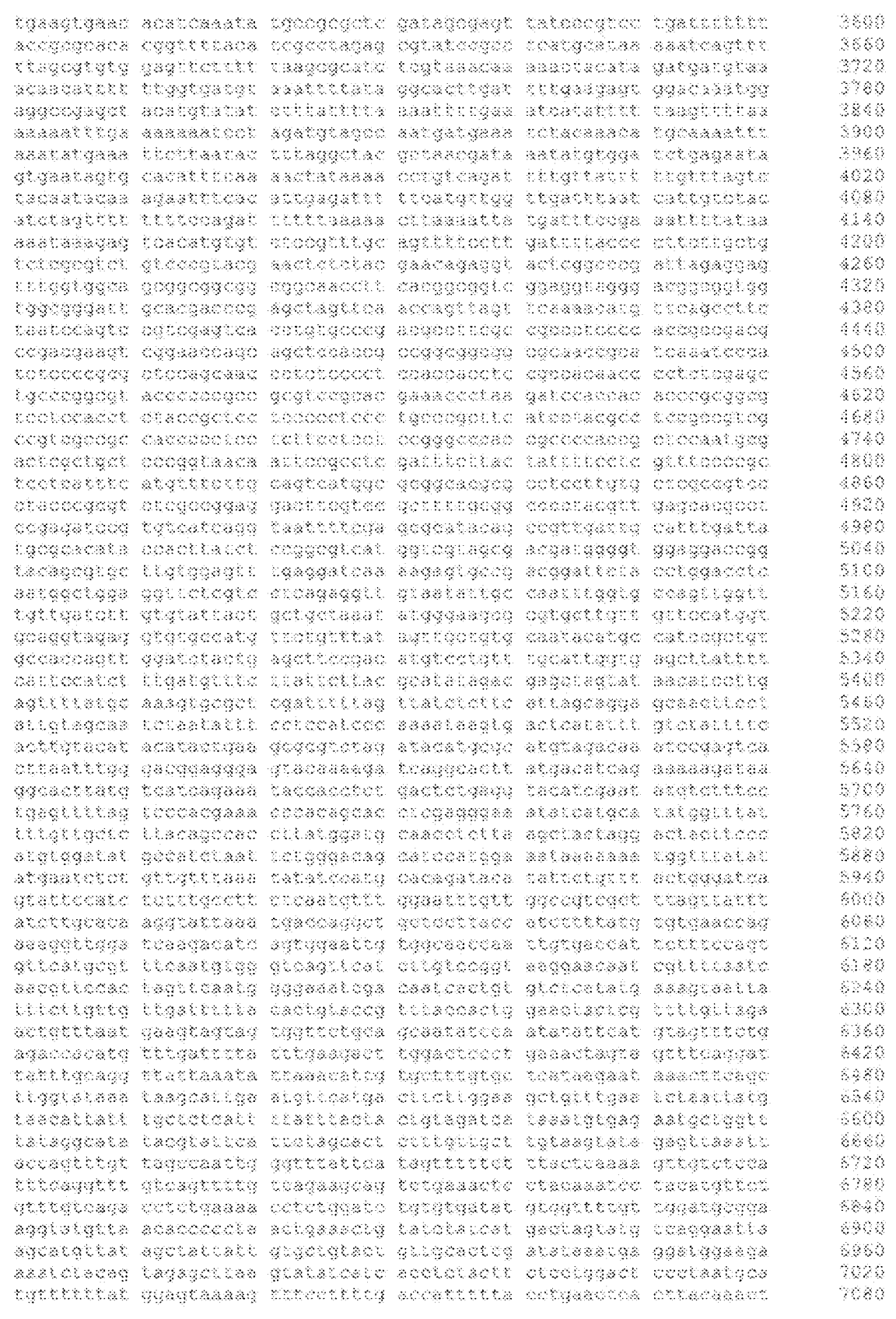

FIG. 9. Nucleic acid sequence of the genomic clone that contain the *Lolium perenne* LpOs04g0648500 zinc finger protease gene. (SEQ ID NO: 62). The initial codon (ATG) of the zinc finger protease gene is shown in bold italic underline.

Figure 10:
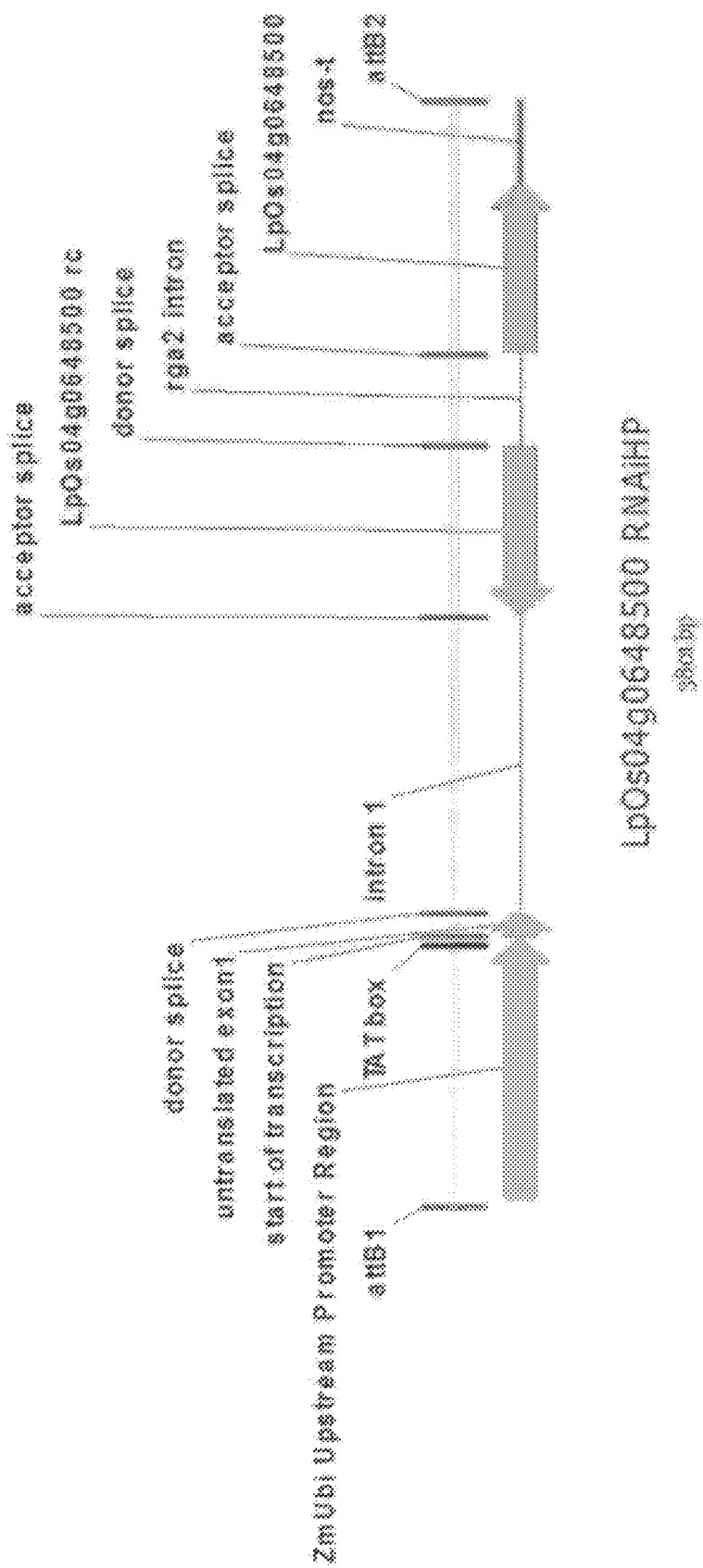

FIG. 10. Map of transformation vector containing the *Lolium perenne* ZmUbi_LpOs04g0648500_nos expression cassette used in biolistic mediated transformation of *Lolium perenne* L.

Figure 11:
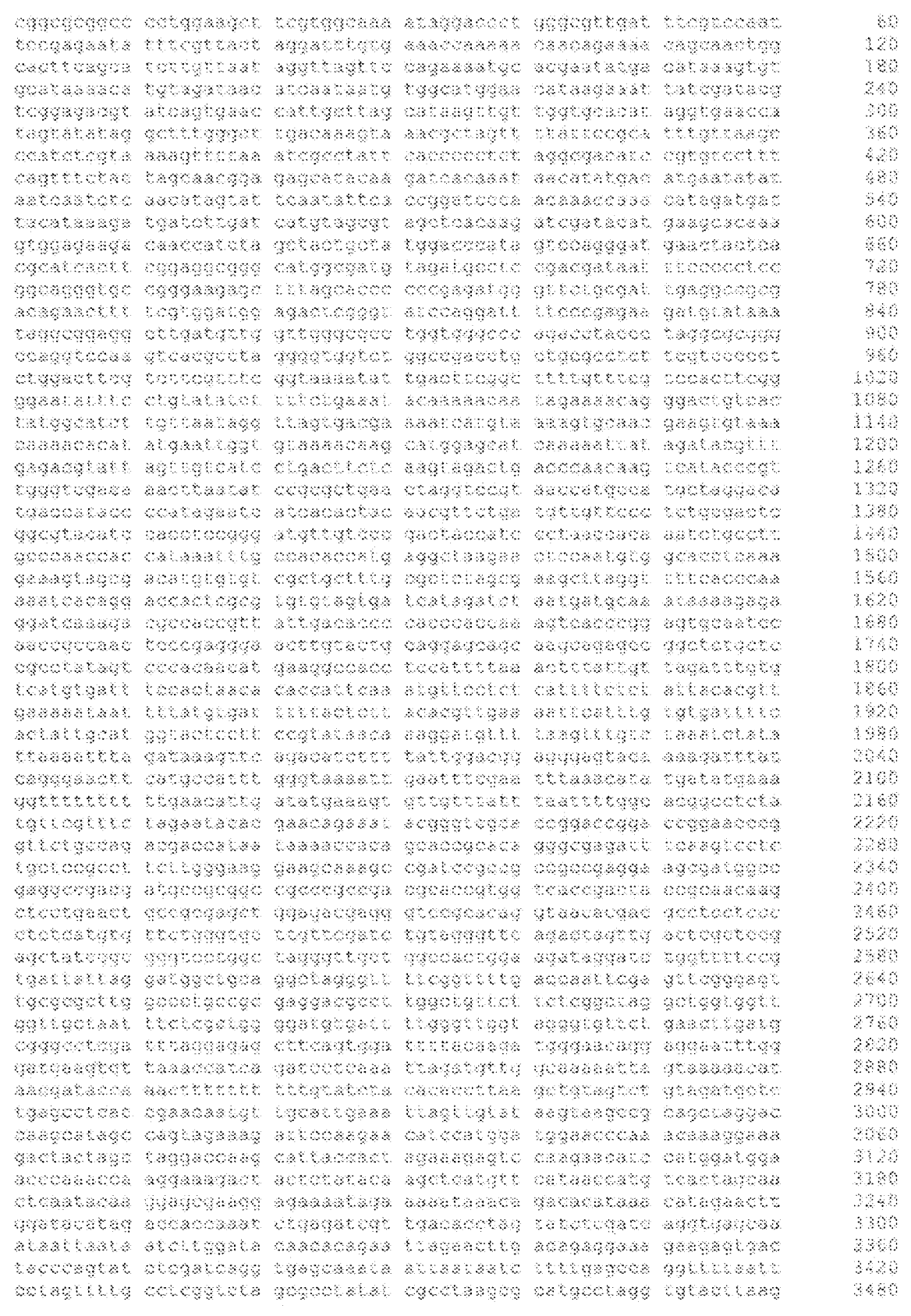
Figure 11:
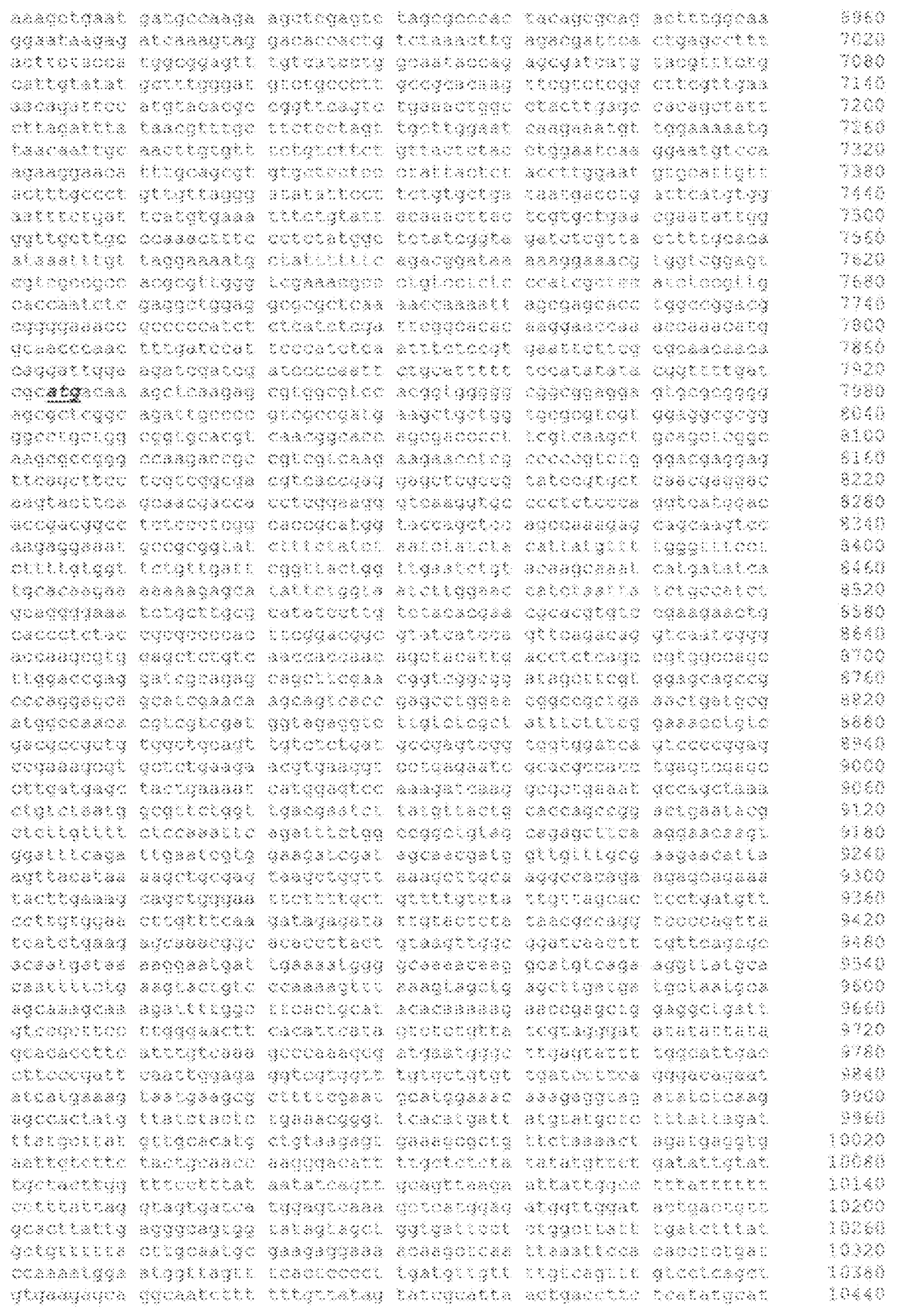
Figure 11:
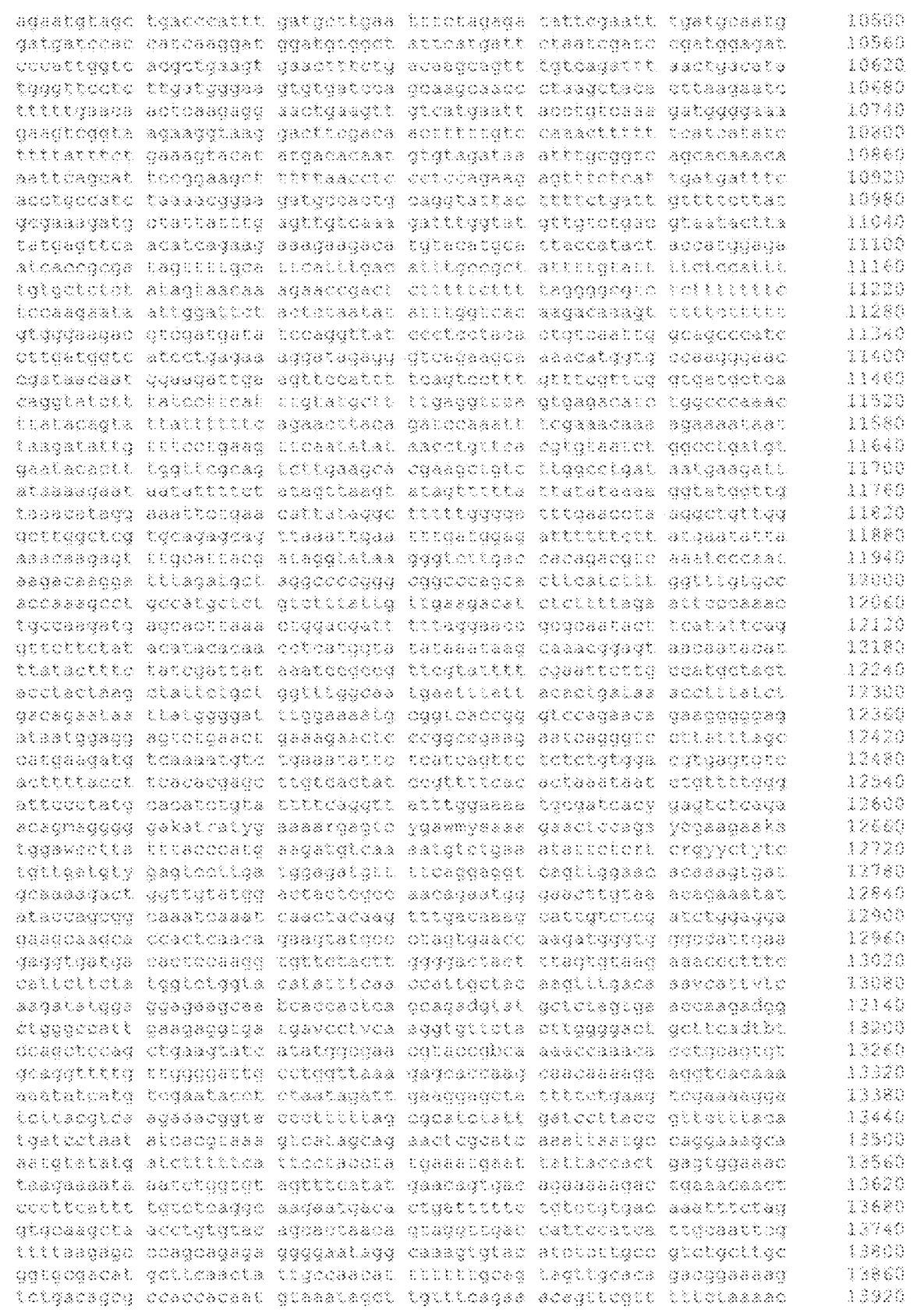
Figure 11:
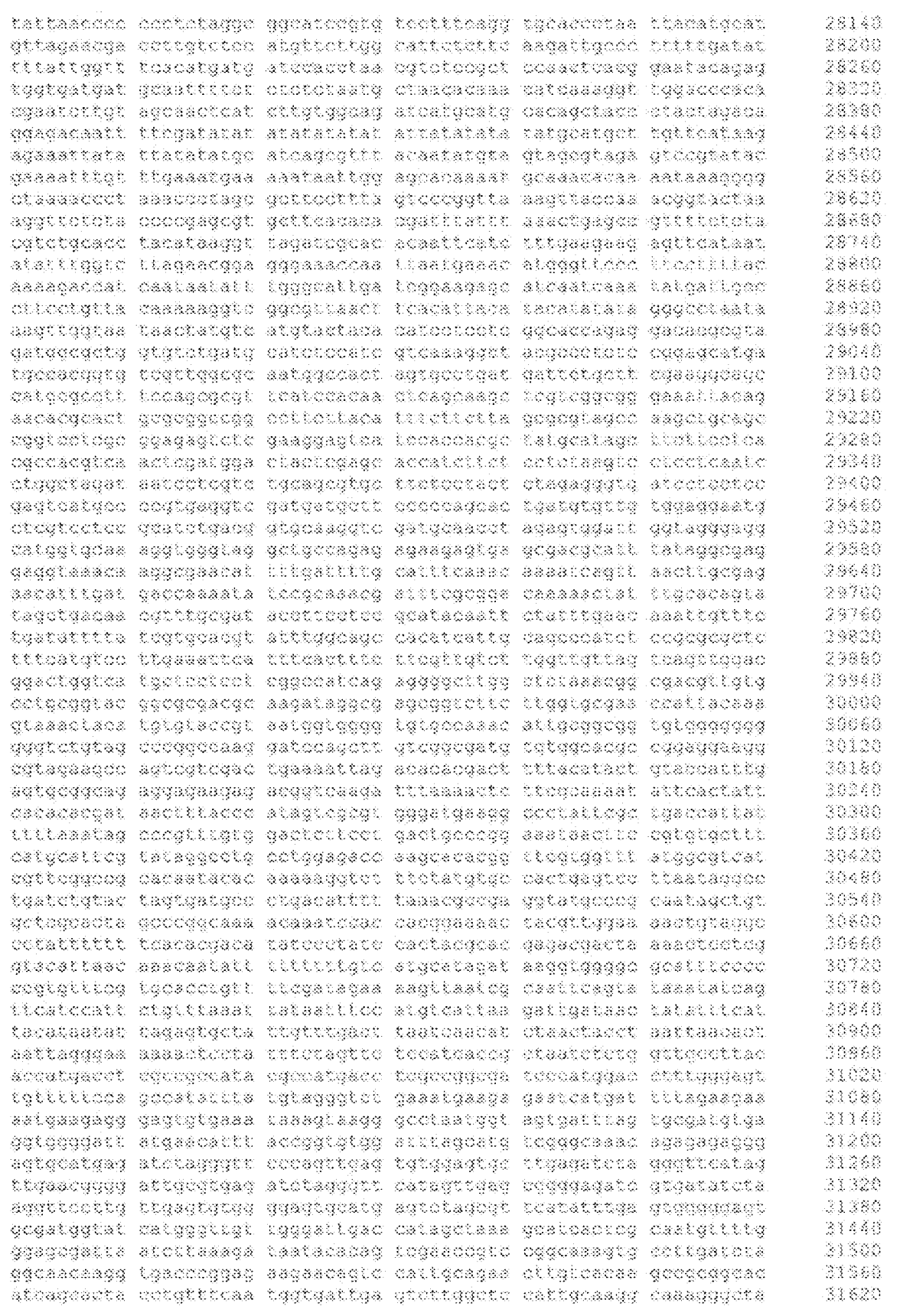

FIG. 11. Nucleic acid sequence of the genomic clone that contains the *Lolium perenne* LpOs06g0607900 No-Pollen (LpNOP) gene. (SEQ ID NO: 59). The initial codon (ATG) of the LpNOP gene is shown in bold italic underline.

Figure 12:
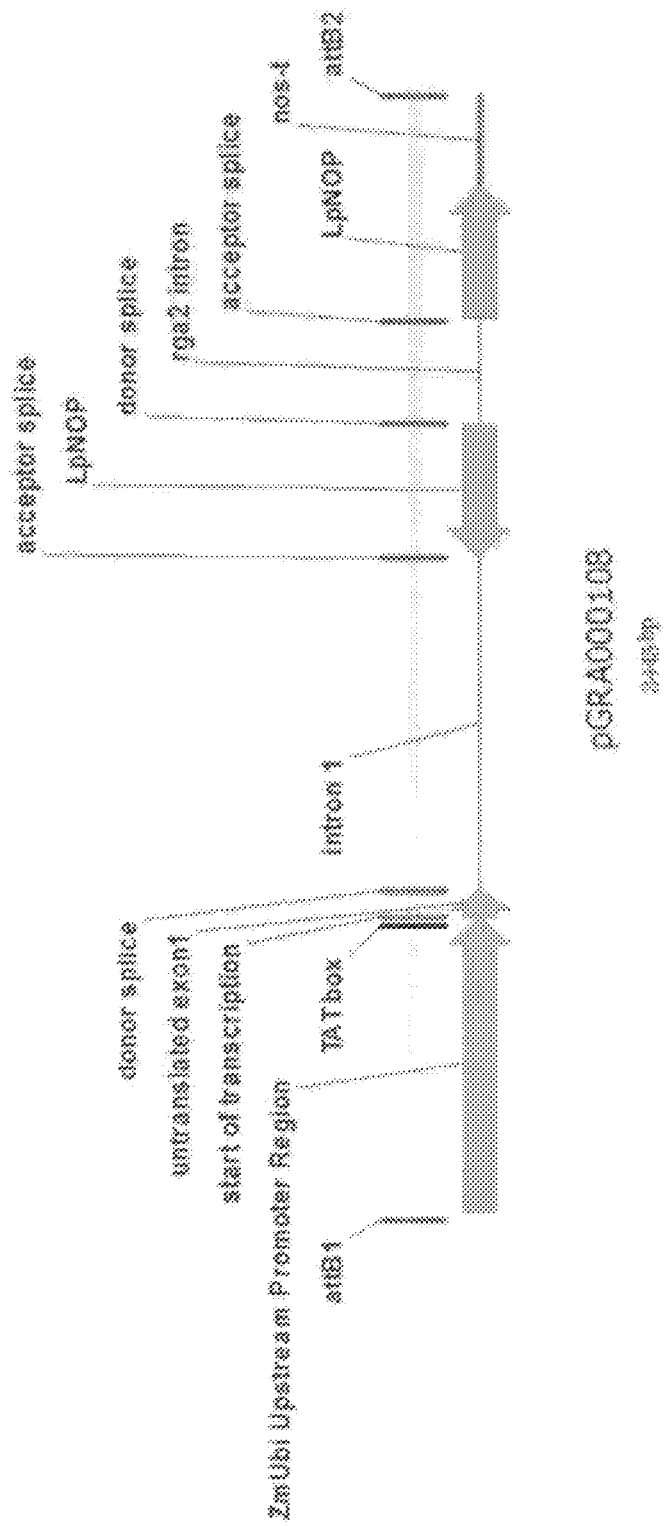

FIG. 12. Map of transformation vector containing the *Lolium perenne* ZmUbi_LpNOP_nos expression cassette used in biolistic mediated transformation of *Lolium perenne* L.

FIG. 13. Nucleic acid sequence of the genomic clone that contains the *Lolium perenne* LpOs05g0152900 Seven-In-Absentia Homolog (LpSIAH) gene. The initial codon (ATG) of the LpSIAH gene is shown in bold italic underline.

Figure 14:
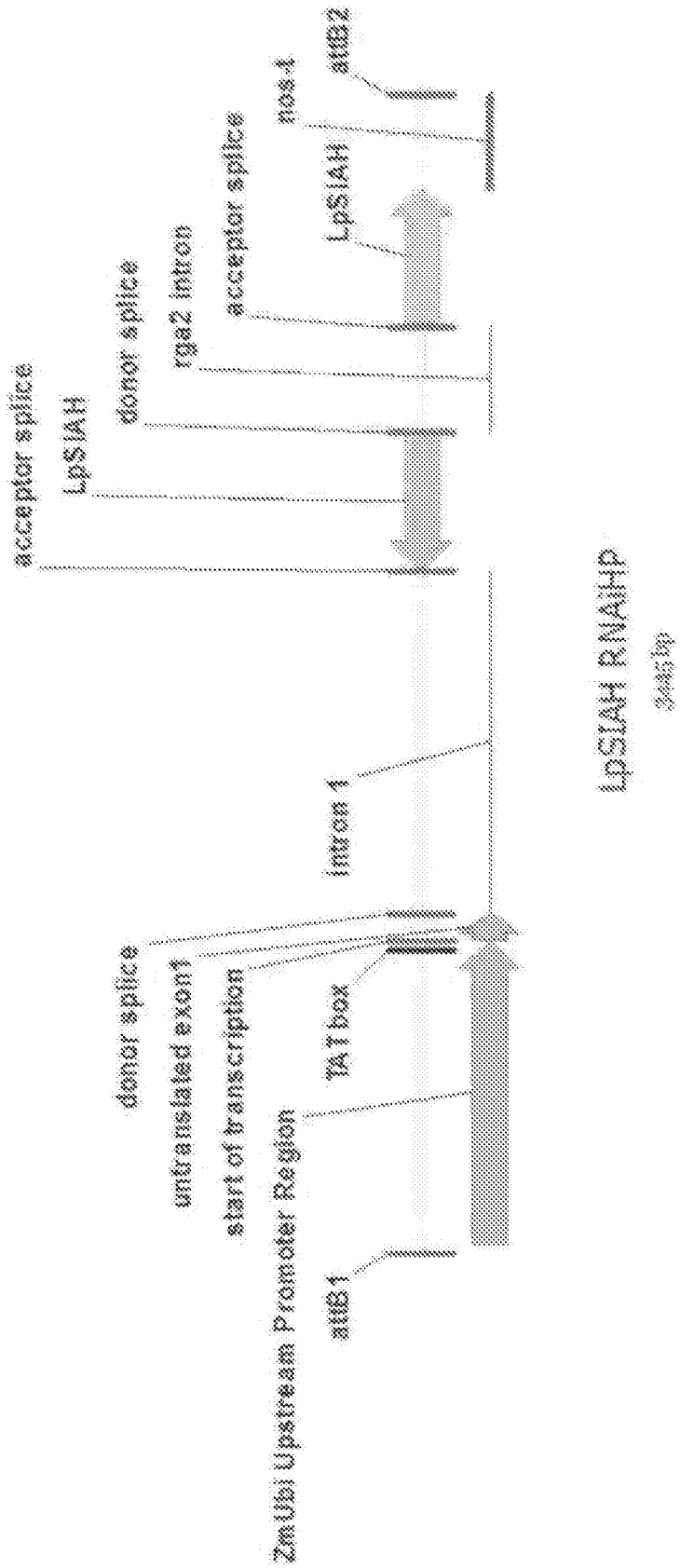

FIG. 14. Map of transformation vector containing the *Lolium perenne* ZmUbi_LpSIAH_nos expression cassette used in biolistic mediated transformation of *Lolium perenne* L.

Figure 15:
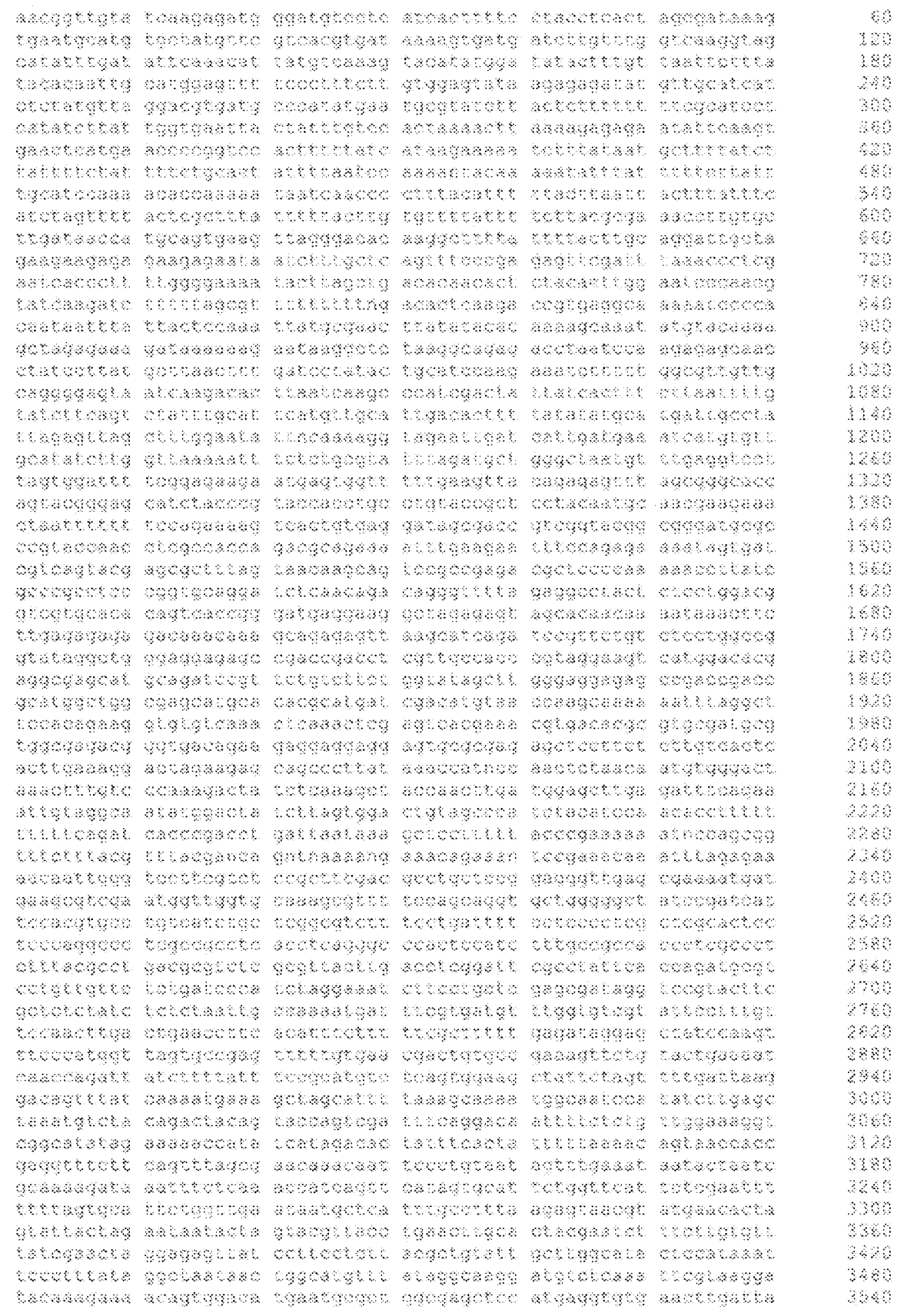
Figure 15:
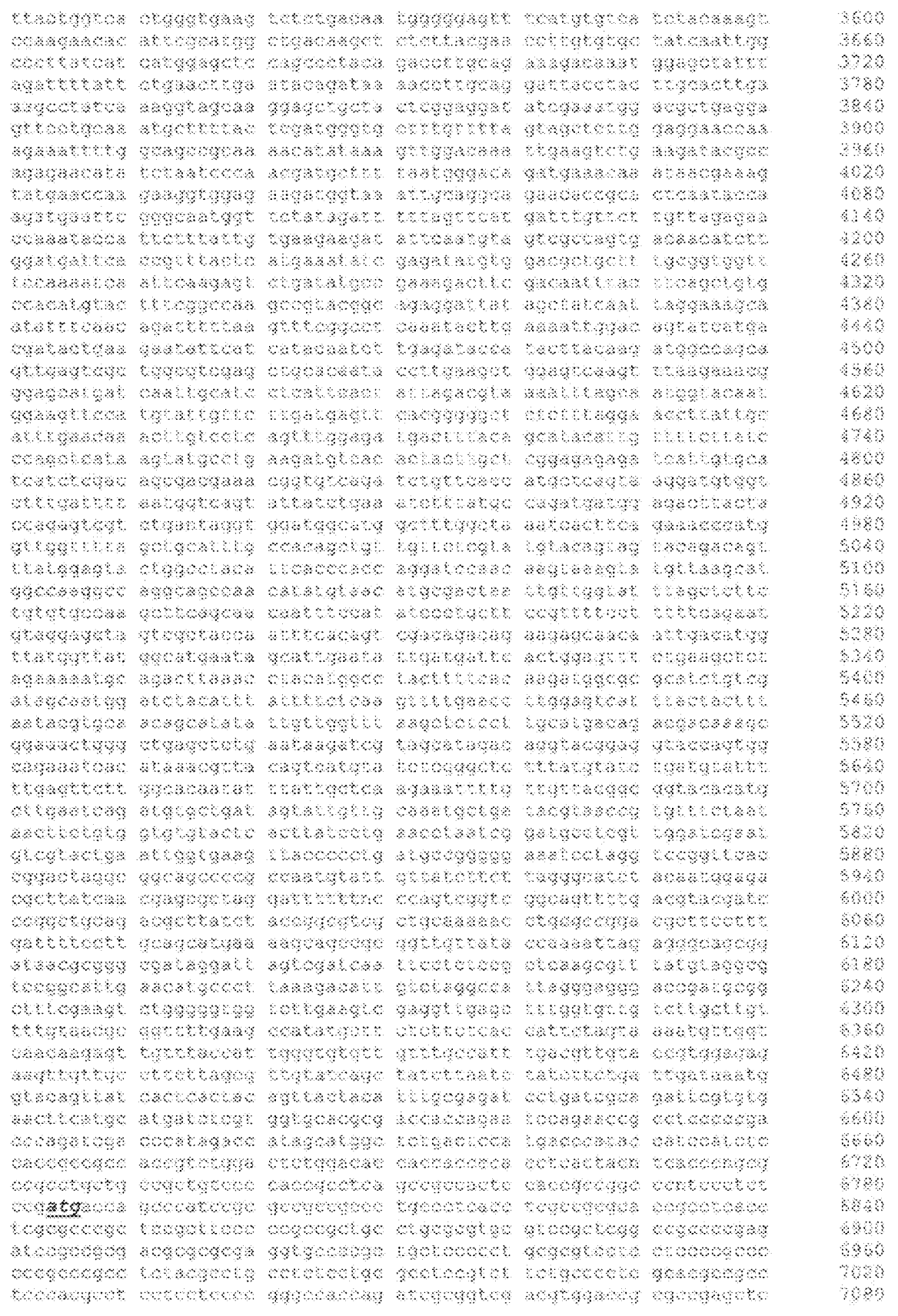
Figure 15:
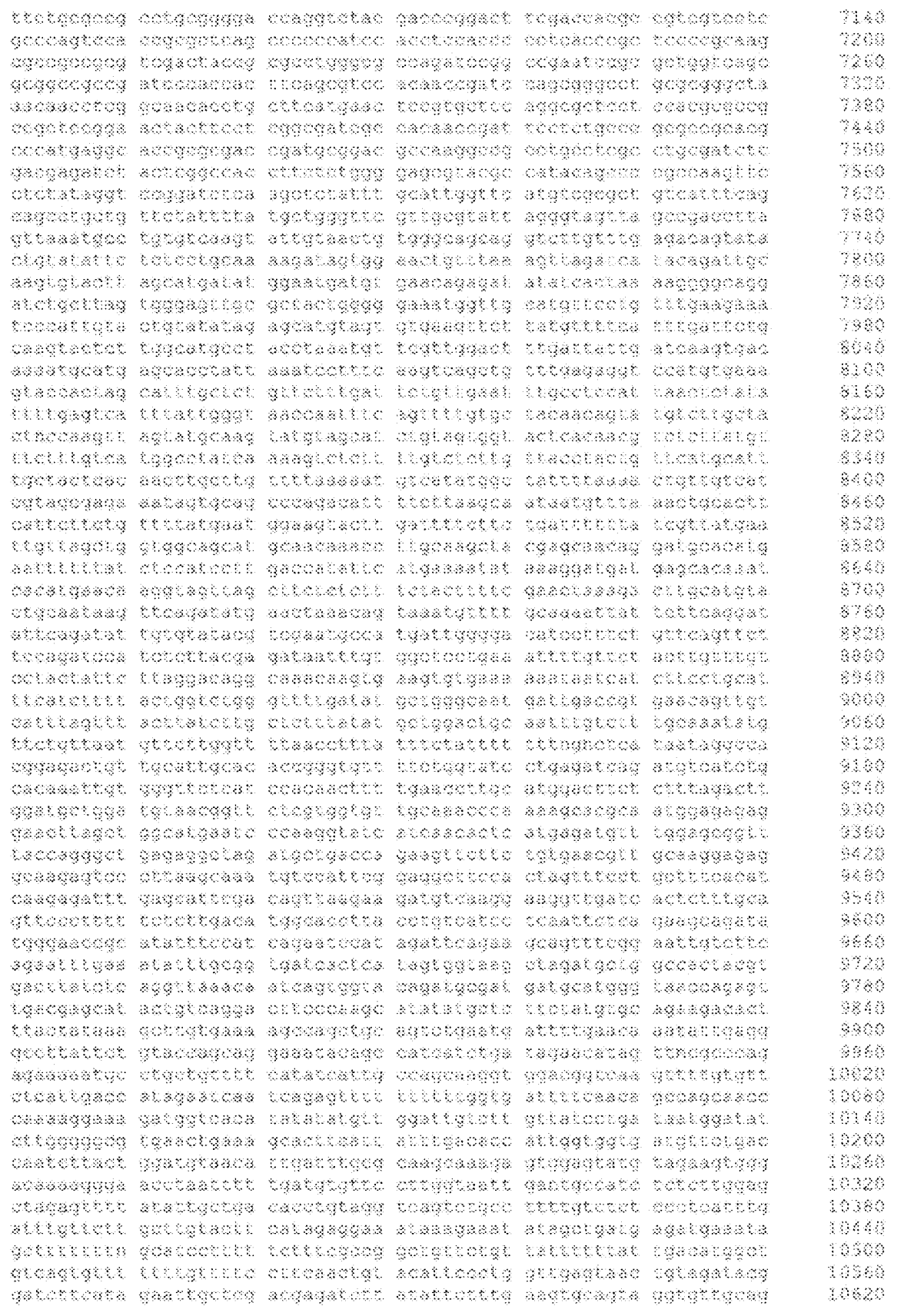
Figure 15:
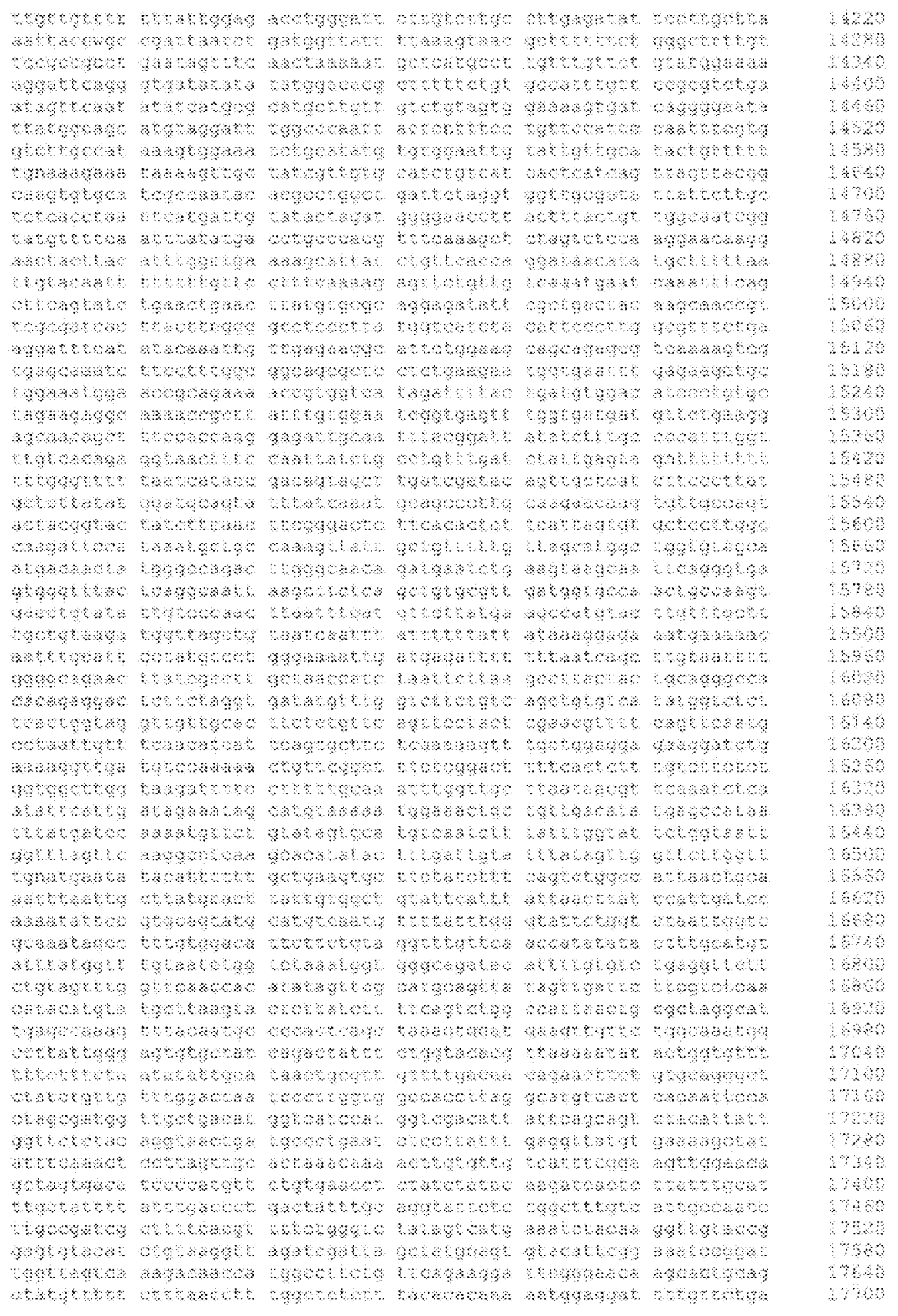
Figure 15:
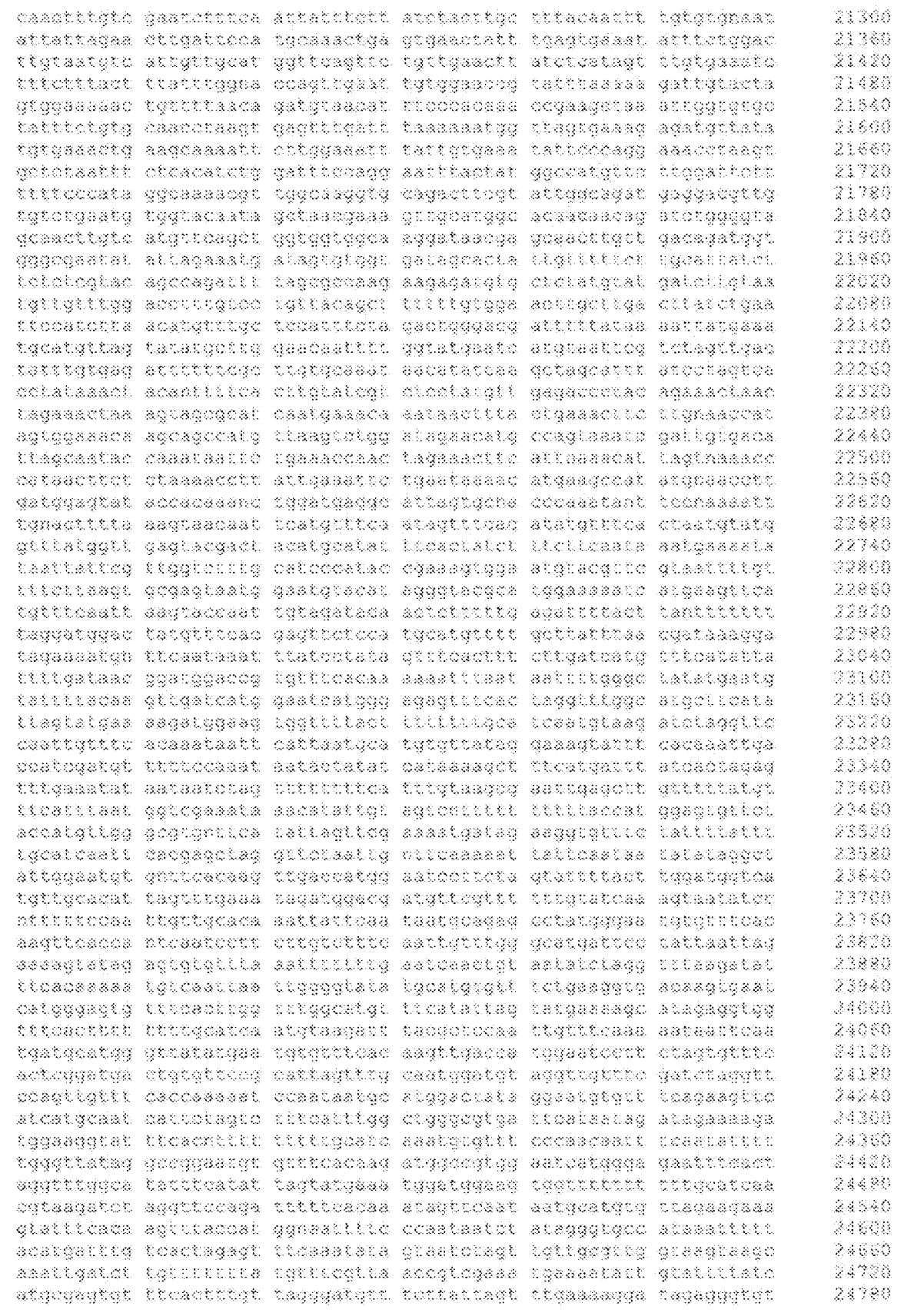

FIG. 15. Nucleic acid sequence of the genomic clone that contains the *Lolium perenne* LpTC116908 gene. (SEQ ID NO: 54). The initial codon (ATG) of the LpTC116908 gene is shown in bold italic underline.

Figure 16:
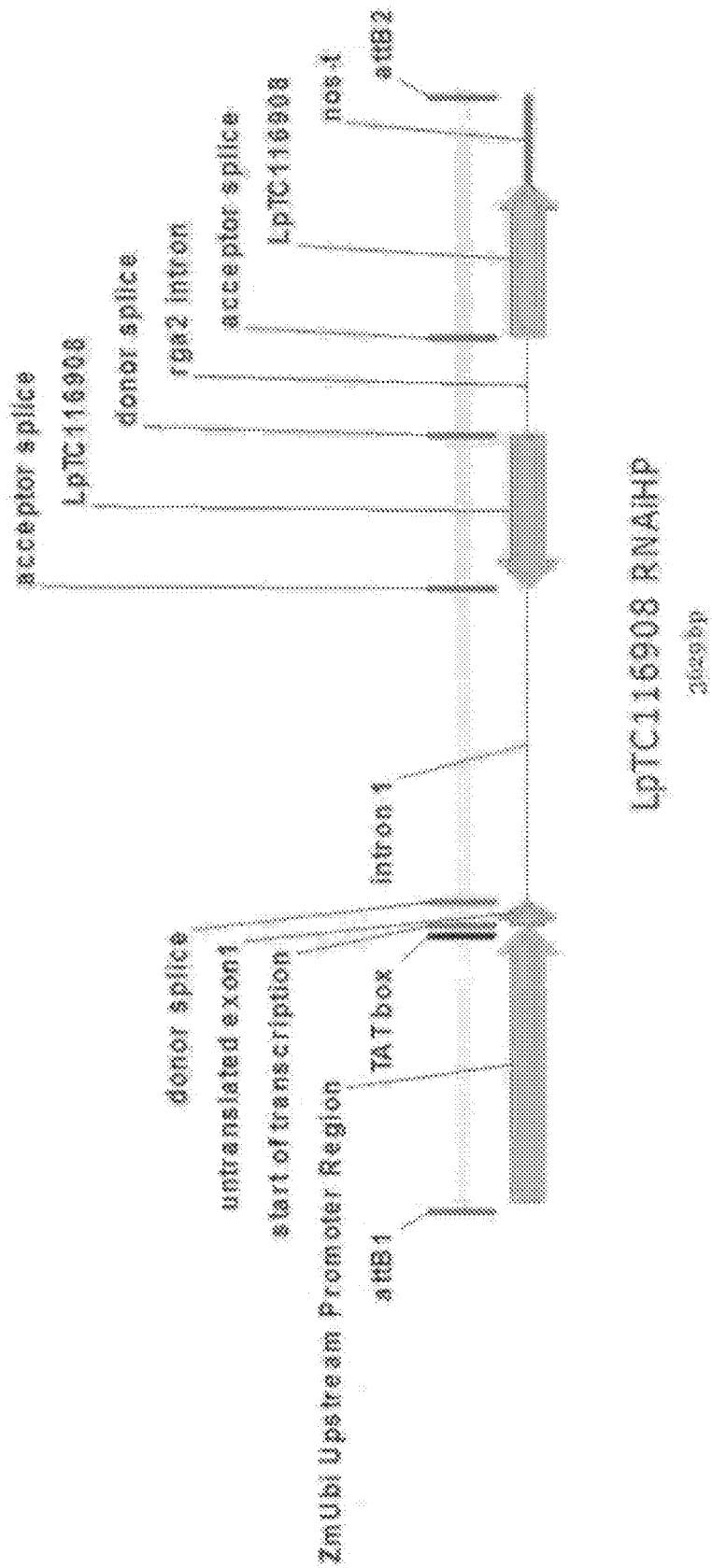

FIG. 16. Map of transformation vector containing the *Lolium perenne* ZmUbi_LpTC116908_nos expression cassette used in biolistic mediated transformation of *Lolium perenne* L.

FIGS. 17-28. S locus CDS variants. Detected sequence variation is identified within [ ] with both allelic forms described.

FIGS. 29-37. Z locus CDS variants. Detected sequence variation is identified within [ ] with both allelic forms described.

FIGS. 38-49. Predicted Amino Acid translation showing S locus amino acid variants.

FIGS. 50-58. Predicted Amino Acid translation showing Z locus amino acid variants.

FIGS. 59-79. Nucleic acid sequences of the ZmUbi_SI-_gene_nos expression cassettes used in biolistic mediated transformation of *Lolium perenne* L.

Legend: Gateway attB1 site (bold underline); *Zea mays* Ubi promoter (italics)+intron (underlined italics); *Lolium perenne* coding region in antisense and sense orientations (underline); rga2 intron (bold); Nopaline synthase (nos) terminator (bold italics); Gateway attB2 site (bold underline)

Figure 80:
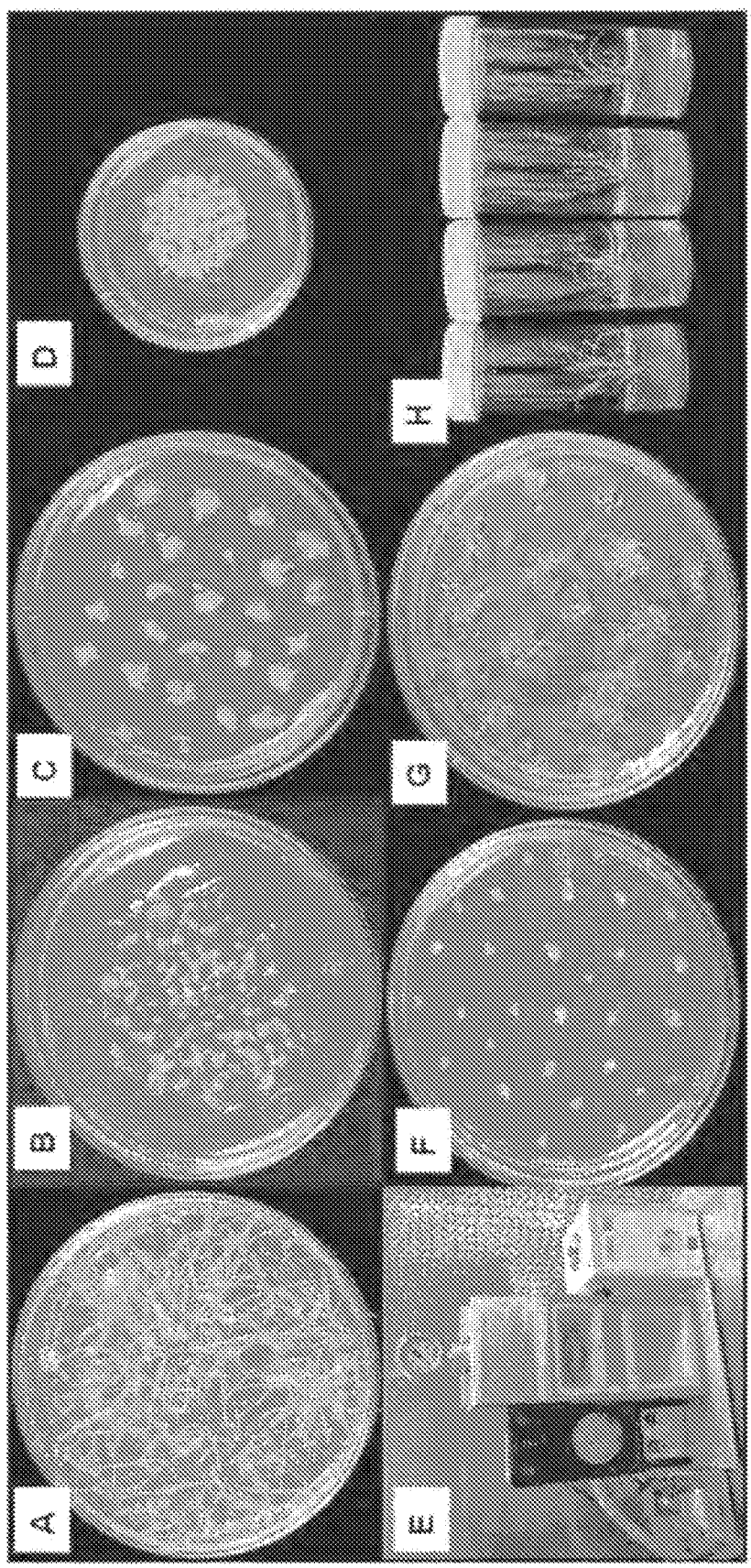

FIG. 80. Pictorial description of the transformation pipeline; A, preparation of donor ryegrass material; B, somatic embryo callus initiation; C, callus proliferation; D, osmotic treatment; E, biolistic delivery of transgene including expression cassette; F, callus growth on tissue culture medium including appropriate selection agent; G, regeneration of putative transgenic plant from callus; H, establishment of putative transgenic plant.

Figure 81:
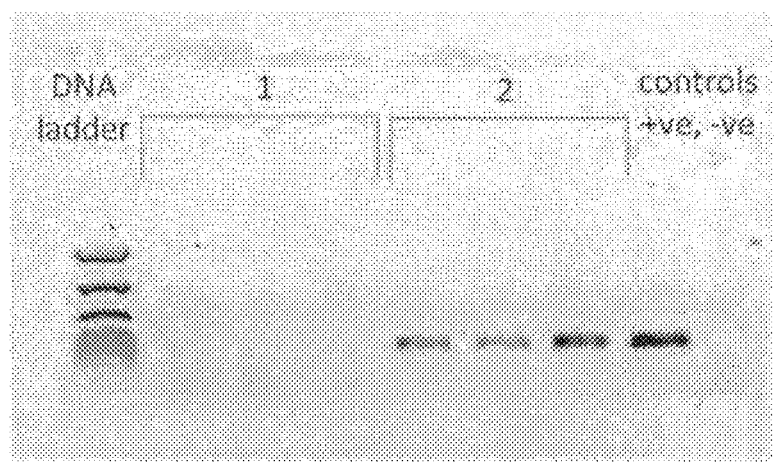

FIG. 81. PCR evaluation of transgenic status for individual tillers from regenerated transgenic events. Each transformation event was assessed through three individual tillers split from the regenerated plant. Only examples where all three tillers gave positive confirmation of the presence of the transgene, did the event get accepted for further evaluation. The brackets with numbers 1 and 2 in the figure identify 1, a transgenic event that would be discarded as all tillers are negative for the presence of the transgene and 2, a transgenic event where all three tillers have generated a positive result for the presence of the transgene.

FIGS. 82 A and B. FDA staining of viable pollen grains for example transgenic plants with SiRNA constructs for the down regulation of a candidate S and Z gene respectively. Both viable and non-viable pollen grains can be seen in both A and B.

Figure 83:
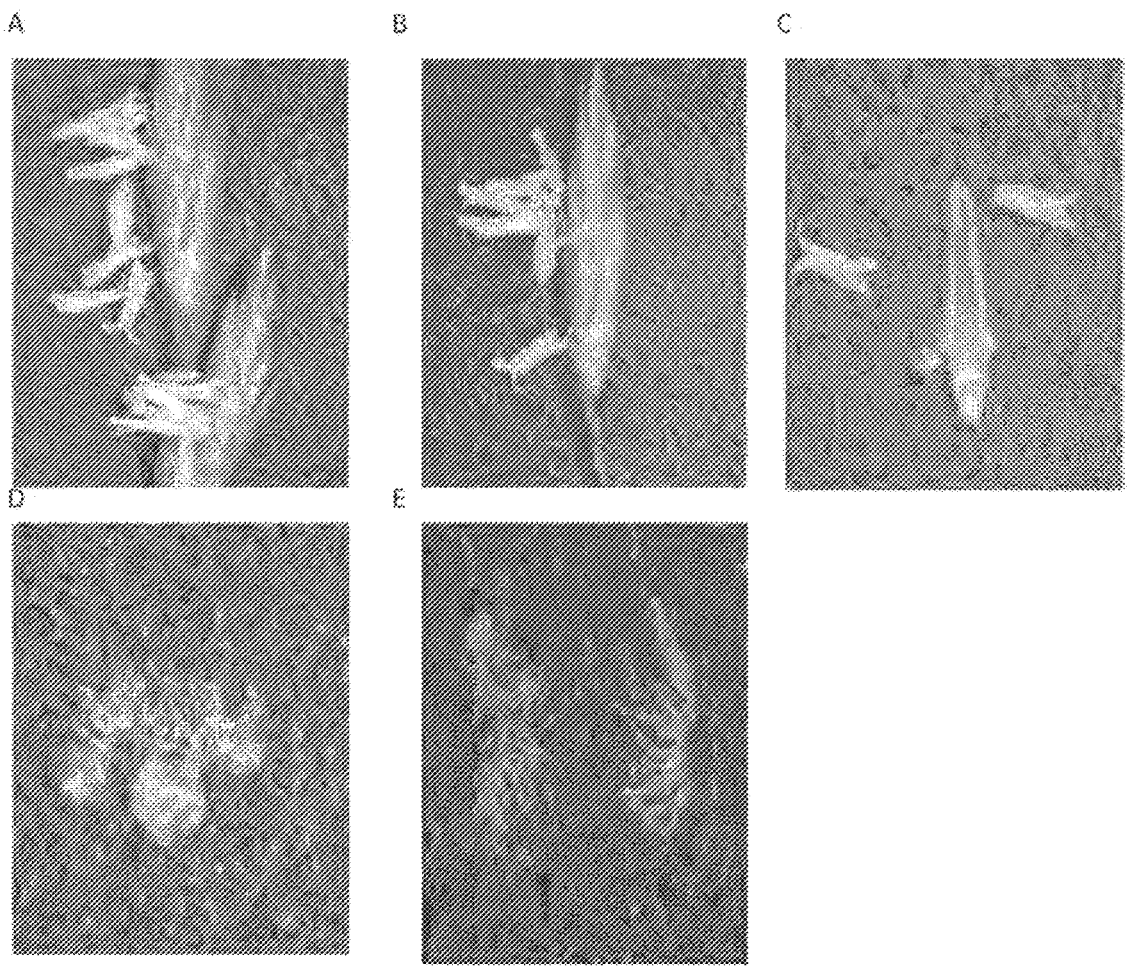

FIG. 83. Stages of ryegrass flower dissection. A—Intact flowers of ryegrass. Upon reaching reproductive maturity the anthers are released from the flower. The stigmatic papillae will then extend and become visible. B— individual spikelets were excised from a floral spike for further dissection. C—Both male and female reproductive tissues were excised from the spikelet. D and E—the female tissue was further excised to examine pollen tube growth on pollinated stigmas.

FIG. 84. Incompatible reaction of pollen tube growth. A and B, examples of single pollen grains germinating on stigmatic papillae and upon contact growth is arrested. The pollen tubes upon contact will often become swollen in shape through cytoplasmic pressure, indicated by arrows. C, An incompatible reaction of self pollination from a transgenic plant containing the SiRNA construct for LpOs05g0149600.

Figure 85:
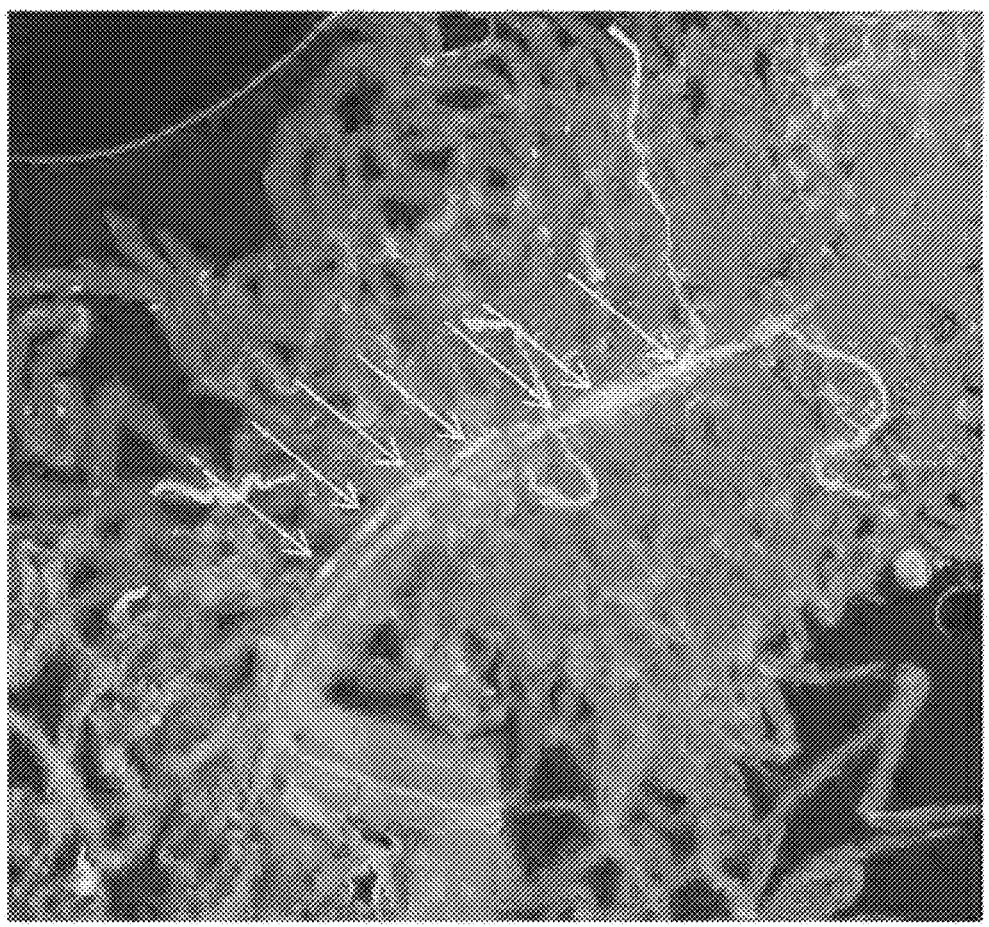

FIG. 85. Compatible pollen tube growth with untransformed plants. Pollen was taken from unrelated ryegrass plants and placed upon an untransformed flower. The pollen tube has made contact with the stigmatic papillae and has then continued to grow in a directed manner towards the ovary. The pollen tube upon growth will deposit callose plugs at regular intervals (indicated by arrows) to retain cytoplasmic pressure, allowing the sperm cells to successfully migrate towards the ovary. These vacated regions will become vacuolated.

Figure 86:
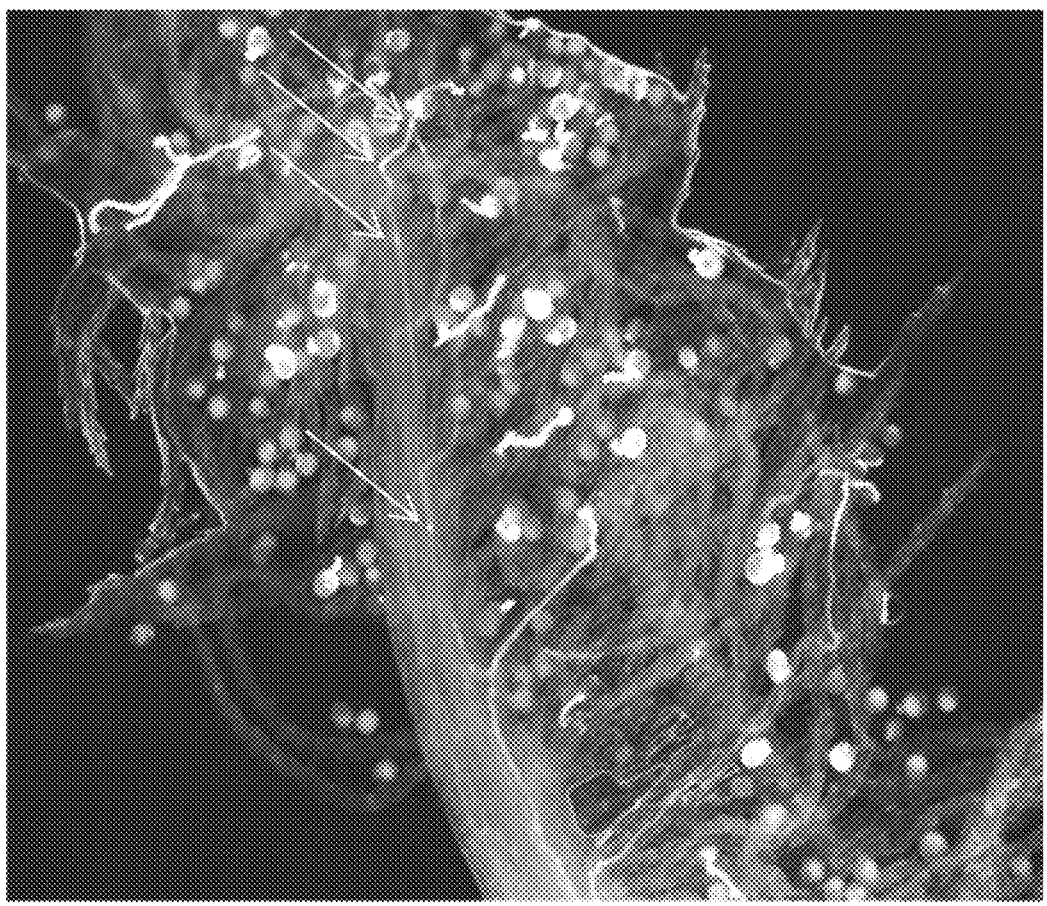

FIG. 86. Compatible pollen reaction. The pollen tube has made contact with the stigmatic papillae and has then continued to grow in a directed manner towards the ovary. The compatible pollen tube will deposit callose plugs at regular intervals (indicated by arrows). The reaction was observed on self-pollination of a transgenic plant containing the siRNA construct for the LpOs06g0680500.

Figure 87:
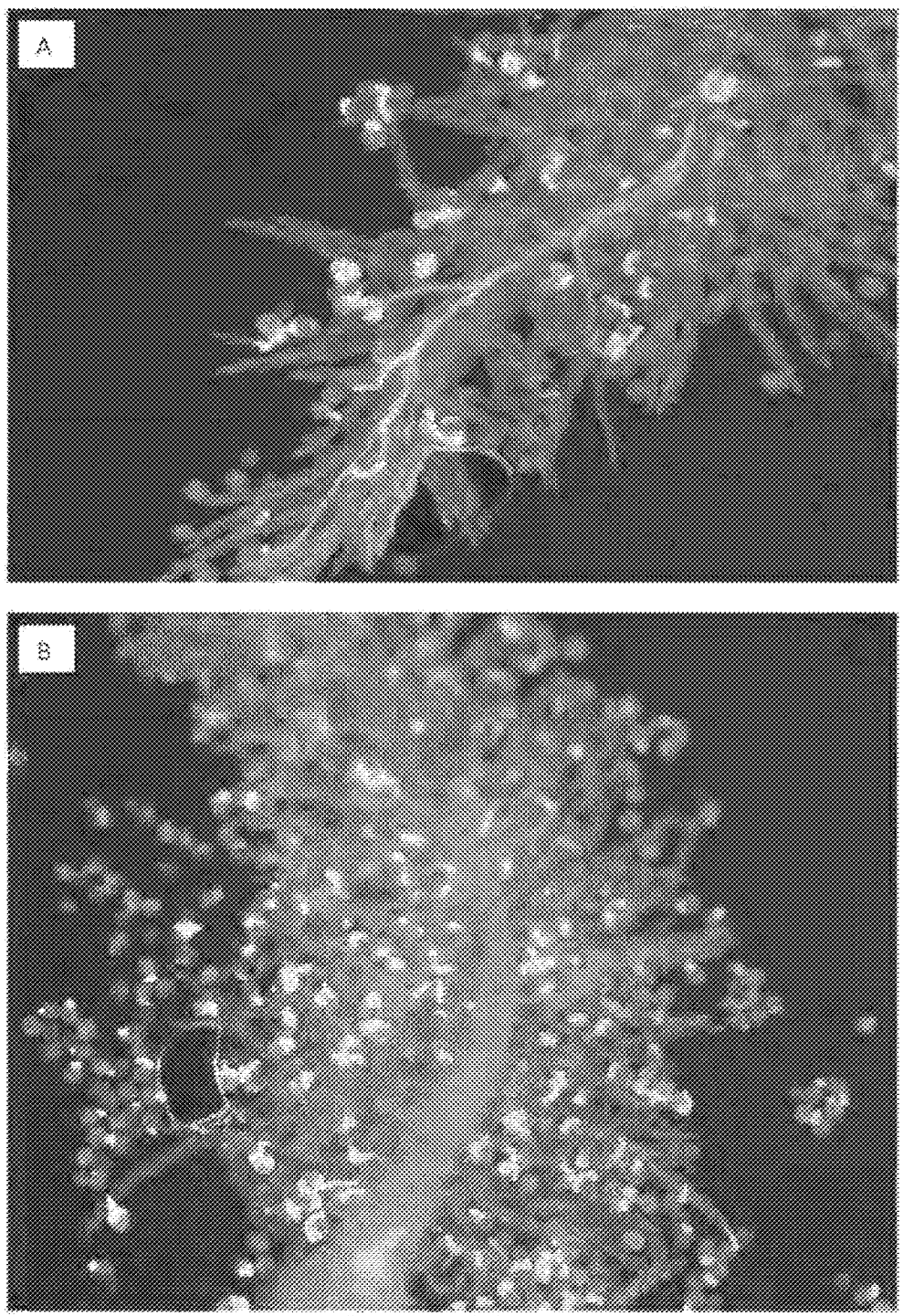
Figure 88:
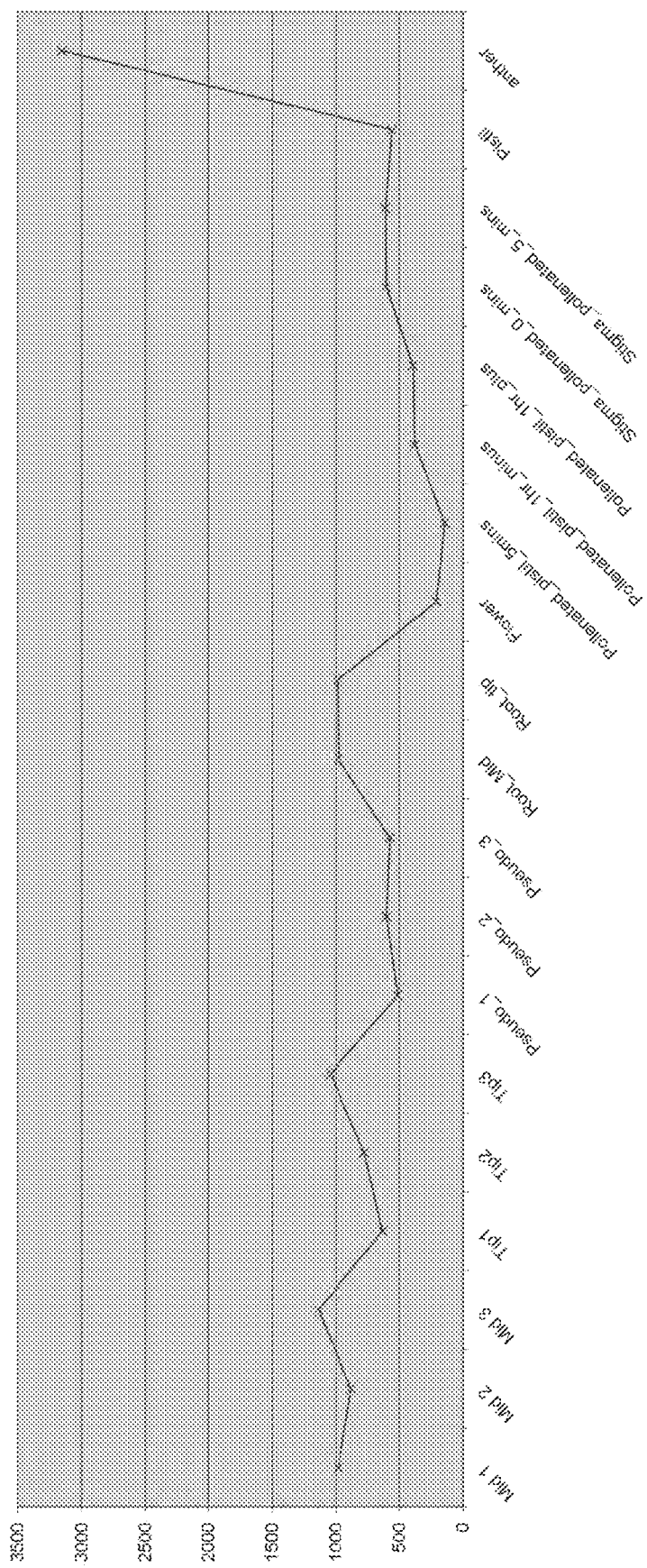
Figure 89:
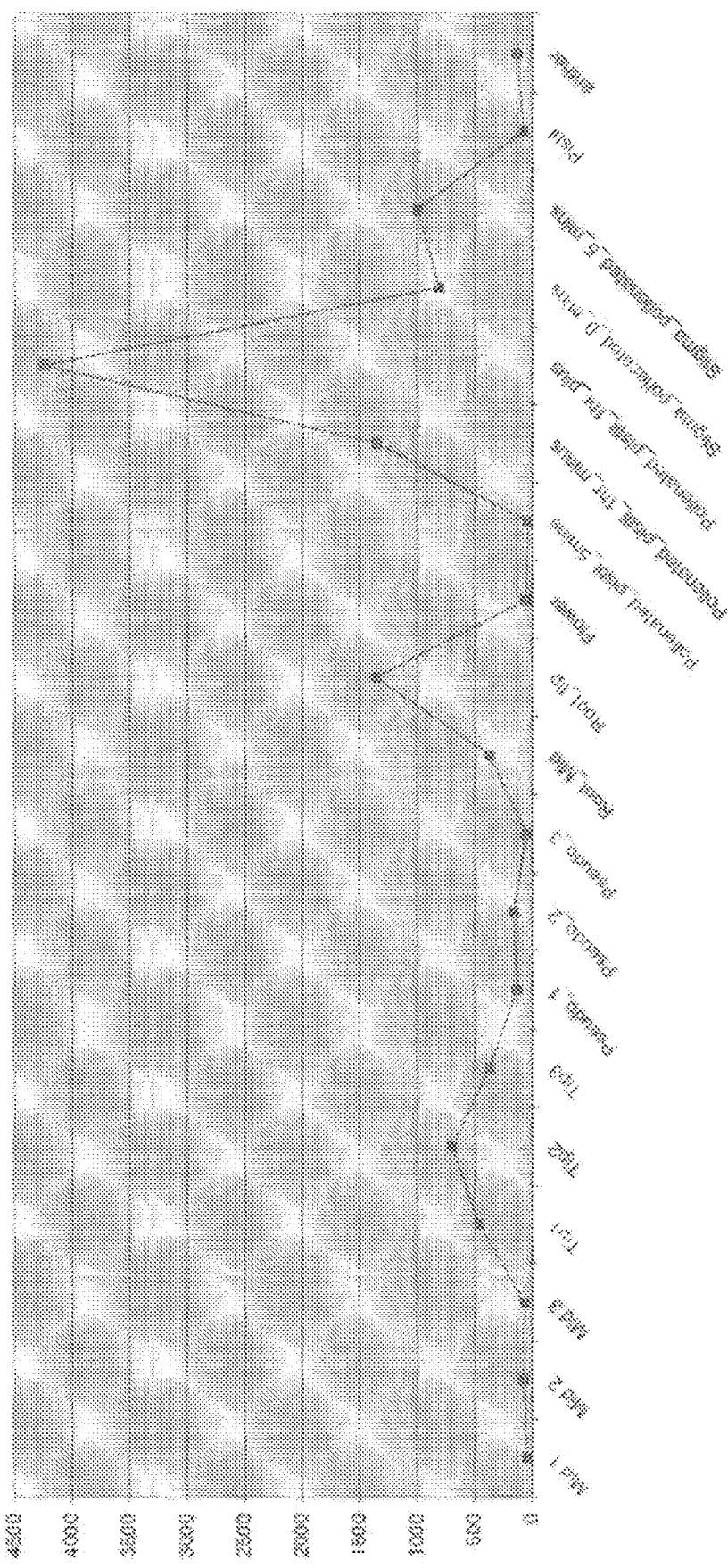
Figure 90:
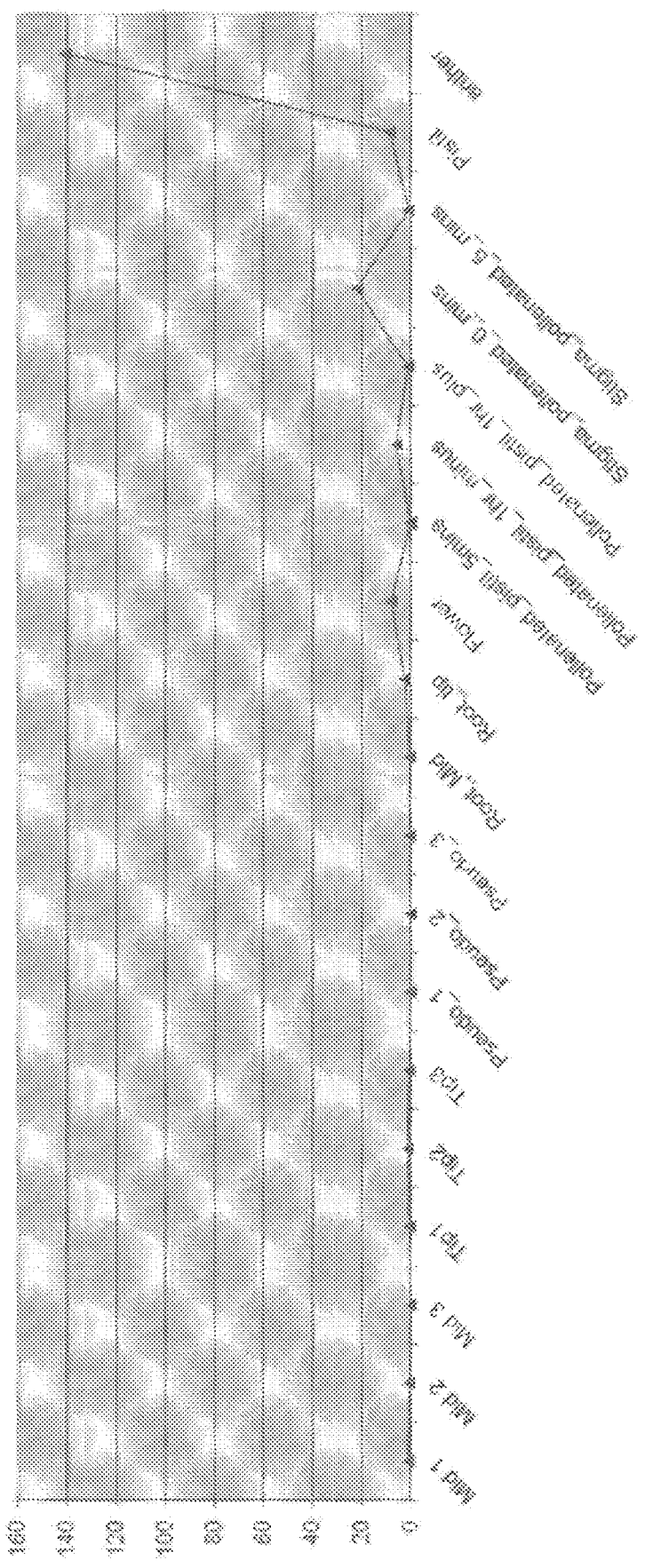
Figure 91:
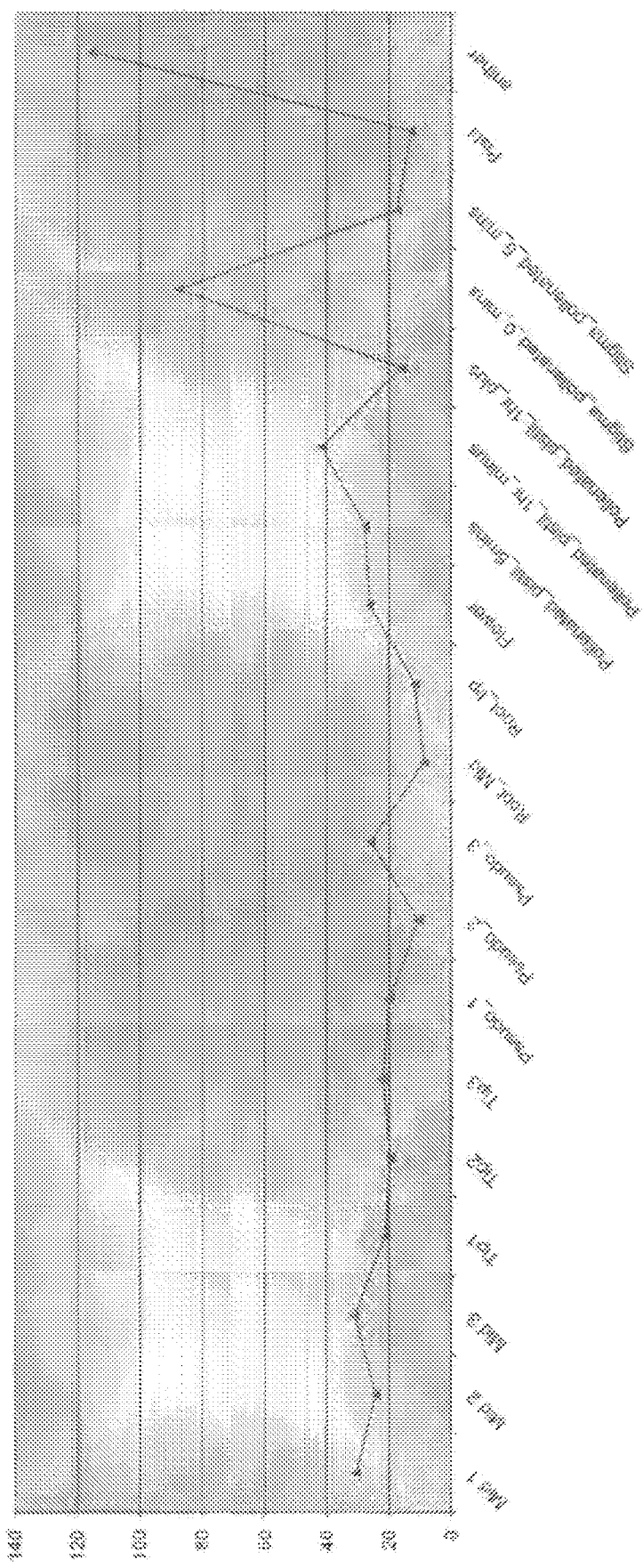

FIG. 87. Microscopic images of the pollen-stigma interaction of two different plants containing the siRNA construct for the LpOs05g0152900 gene. The two different transgenic events (A and B) show a range of phenotypes from incompatible to partially compatible.

FIGS. 88-108. Expression profiles of the *Lolium perenne* SI genes. Expression profiles were determined through BLAST analysis of sequence reads from multiple tissues of the *Lolium perenne* L. genotype Impact04, compared to the *Brachypodium distachion* CDS gene sequences used as orthologous templates.

Figure 109:
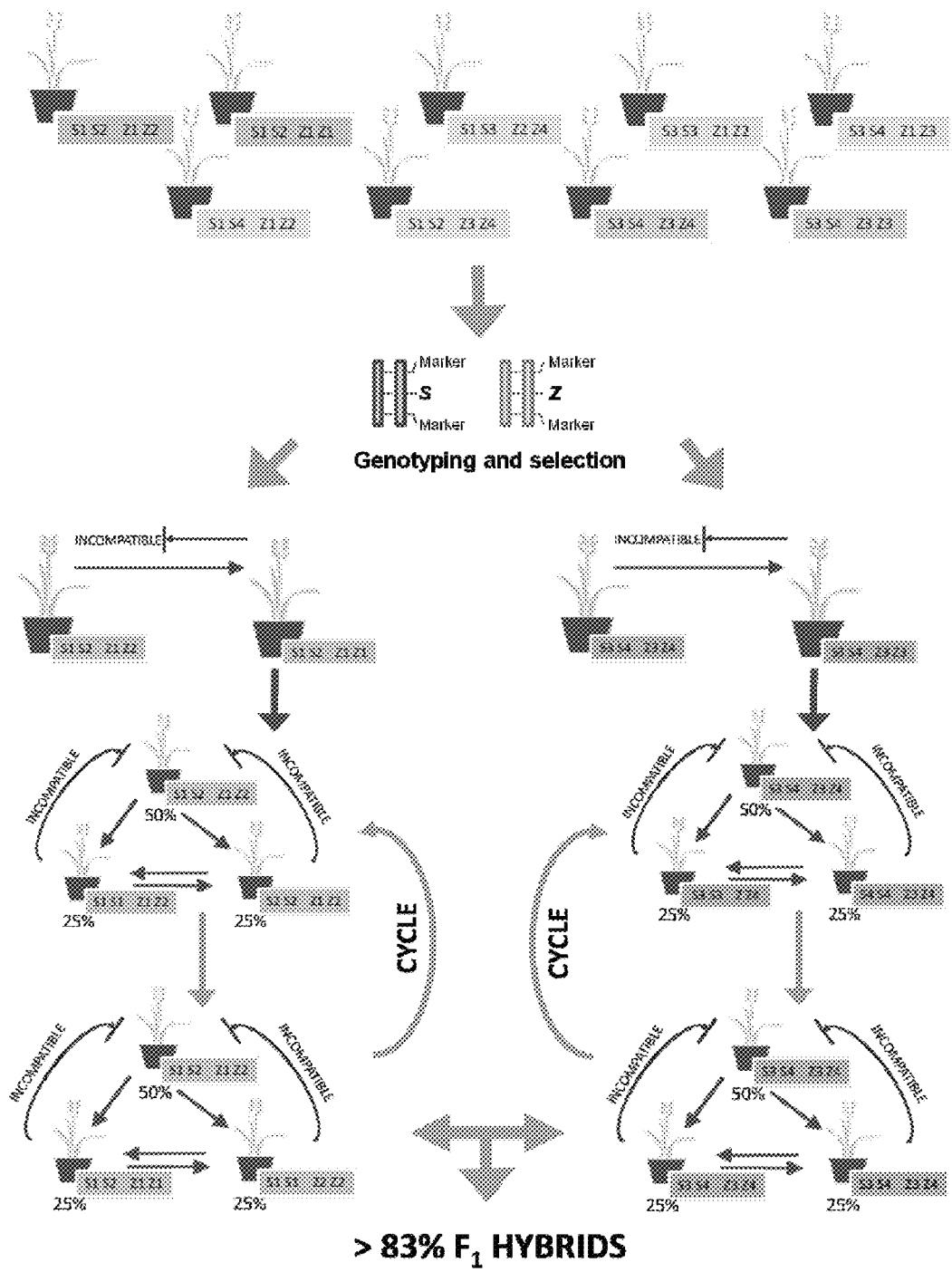

FIG. 109. Schematic diagram of F1 hybrid grass breeding. Plants are initially genotyped using markers on or around the S and Z loci. Two parental pools are then generated and multiplied, with testing of the degree of heterosis between pools once sufficient seed has been generated.

EXAMPLES

Example 1. Isolation of SI Genes

Both the S and Z locus was delimited through comparative genomics and BAC clone and genomic sequencing. All genes within the sequence data were identified (Tables 1 and 2). Sequences were determined through the FGENESH prediction software. Expression profiles were determined for each gene as described in Example 6. Expression profiles were determined through BLAST analysis of sequence reads from multiple tissues of the *Lolium perenne* L. genotype Impact04, compared to the *Brachypodium distachion* CDS gene sequences used as orthologous templates (See FIGS. 88-108).

TABLE 1

Genes identified within the S locus

| Ryegrass gene identified | Syn | Predicted Gene Function | Nucleic acid SEQ ID NO: | Polypeptide SEQ ID NO: |
|---|---|---|---|---|
| LpOs05g0481800 | | Protein prenyltransferase domain containing protein, pentatricopeptide repeat-containing protein | 1 | 71 |
| LpOs05g0147700 | | Cyclin-like F-box domain containing protein | 2 | 72 |
| LpOs05g0148300 | | Ribosomal protein S27, mitochondrial family protein | 3 | 73 |
| LpOs01g0254300 | | Similar to Pectinesterase-1 precursor (EC 3.1.1.11) (Pectin methylesterase 1) (PE 1) | 4 | 74 |
| LpOs08g0226800 | | TRAF-like domain containing protein, BTB/POZ and MATH domain-containing protein | 5 | 75 |
| LpOs05g0148400 | | Conserved hypothetical protein | 6 | 76 |
| LpOs05g0148500 | | Electron transport accessory protein domain containing protein | 7 | 77 |
| LpOs07g0118800 | | Conserved hypothetical protein | 8 | 78 |
| LpOs07g0118900 | | Cyclin-like F-box domain containing protein | 9 | 79 |

TABLE 1-continued

Genes identified within the S locus

| Ryegrass gene identified | Syn | Predicted Gene Function | Nucleic acid SEQ ID NO: | Polypeptide SEQ ID NO: |
|---|---|---|---|---|
| LpOs05g0148600 | | Na+/H+ antiporter | 10 | 80 |
| LpOs05g0148700 | | Armadillo-like helical domain containing protein, senescence associated protein | 11 | 81 |
| LpOs01g0372700 | | hypothetical protein, putative asparagine--tRNA ligase, cytoplasmic 1-like | 12 | 82 |
| LpOs05g0148900 | | Glutathione-S-transferase 19E50 | 13 | 83 |
| LpOs01g0369700 | | Similar to Glutathione S-transferase GST 8 | 14 | 84 |
| LpOs05g0149100 | | C2 calcium/lipid-binding region, CaLB domain containing protein | 15 | 85 |
| LpOs05g0149200 | | PWWP domain containing protein | 16 | 86 |
| LpOs05g0149300 | | 1-aminocyclopropane-1-carboxylate oxidase | 17 | 87 |
| LpOs05g0149400 | | 1-aminocyclopropane-1-carboxylic acid oxidase | 18 | 88 |
| LpOs05g0149500 | | Lipopolysaccharide-modifying protein family protein, predicted: O-glucosyltransferase rumi homolog | 19 | 89 |
| LpOs05g0149600 | | Cullin-1 | 20 | 90 |
| LpOs05g0149800 | | EF-Hand type domain containing protein, serine/threonine-protein phosphatase 2A regulatory subunit B" subunit gamma-like | 21 | 91 |
| LpOs05g0149900 | | Tetratricopeptide-like helical domain containing protein | 22 | 92 |
| LpOs05g0150000 | | putative proline synthetase associated protein | 23 | 93 |
| LpOs05g0150300 | | probable chromatin-remodelling complex ATPase chain-like protein | 24 | 94 |
| LpOs05g0150400 | | Double-stranded RNA binding domain containing protein | 25 | 95 |
| LpOs05g0150500 | | Conserved hypothetical protein, putative transport inhibitor response TIR1 | 26 | 96 |
| LpOs05g0150600 | | ATP-dependent DNA helicase RecQ family protein | 27 | 97 |
| LpOs10g0545800 | | Cytochrome biosynthesis CcmE/CycJ protein family protein | 28 | 98 |
| LpOs05g0150700 | | Heavy metal transport/detoxification protein domain containing protein | 29 | 99 |
| LpOs05g0150800 | | Similar to Plastid 5,10-methylene-tetrahydrofolate dehydrogenase, | 30 | 100 |
| LpOs05g0150900 | | Histidyl-tRNA synthetase | 31 | 101 |
| LpOs02g0508100 | | hypothetical protein containing DUF3339 | 32 | 102 |
| LpOs05g0151000 | Lpbcd762 | Similar to RNA polymerase II largest subunit | 33 | 103 |
| LpOs05g0151100 | | Conserved hypothetical protein, ferritin domain | 34 | 104 |
| LpOs05g0151300 | | Rubber elongation factor family protein | 35 | 105 |
| LpOs05g0151400 | | Chloroplast protein import component Toc86/159 family protein | 36 | 106 |
| LpSb07g026730 | | Putative uncharacterized protein | 37 | 107 |
| LpOs05g0152400 | | Glycosyl transferase, family 14 protein, xylosyltransferase-like | 38 | 108 |
| LpOs06g0680500 | | Glutamate receptor 3.4 precursor (Ligand-gated ion channel 3.4) | 39 | 109 |
| LpOs05g0152900 | | Seven in absentia protein family protein | 40 | 110 |
| LpOs05g0153000 | | Gelsolin family protein, villin-1-like | 41 | 111 |
| LpOs05g0153200 | | Region of unknown function, putative Zinc finger, XS and XH domain containing protein | 42 | 112 |

TABLE 1-continued

Genes identified within the S locus

| Ryegrass gene identified | Syn | Predicted Gene Function | Nucleic acid SEQ ID NO: | Polypeptide SEQ ID NO: |
|---|---|---|---|---|
| LpOs05g0153300 | | Lipase, class 3 family protein | 43 | 113 |
| LpOs05g0153400 | | predicted pentatricopeptide repeat-containing protein | 44 | 114 |
| LpOs05g0153600 | | FAR1 domain containing protein | 45 | 115 |
| LpOs05g0154500 | | Spc97/Spc98 family protein, gamma-tubulin complex | 46 | 116 |
| LpOs05g0154600 | | Similar to VIP2 protein, Hypothetical RING domain containing protein | 47 | 117 |
| LpOs01g0652800 | | Protein of unknown function DUF231, leaf senescence like protein, yellow leaf specific - like protein | 48 | 118 |
| LpOs07g0286100 | | Cyclin-like F-box domain containing protein; | | |

TABLE 2

Genes identified within the Z locus

| Ryegrass gene identified | Syn | Predicted Gene Function | Nucleic acid SEQ ID NO: | Polypeptide SEQ ID NO: |
|---|---|---|---|---|
| LpOs04g0645100 | LpTC101821 | Tetratricopeptide-like helical domain containing protein | 49 | 119 |
| LpOs04g0645200 | LpVQ | VQ domain containing protein | 50 | 120 |
| LpOs07g0213300 | | pentatricopeptide repeat-containing protein | 51 | 121 |
| LpOs04g0645500 | | methyltransferase-like protein 22-like | 52 | 122 |
| LpOs04g0645600 | | Protein of unknown function DUF6, transmembrane domain containing protein, vacuolar protein | 53 | 123 |
| LpOs04g0647300 | LpTC116908 | Ubiquitin-specific protease 22 | 54 | 124 |
| LpOs04g0647800 | LpTC89057 | Glycerol kinase 2 | 55 | 125 |
| LpOs04g0647701 | LpDUF247 | Protein of unknown function DUF247 | 56 | 126 |
| LpOs03g0193400 | | Polyamine oxidase precursor (EC1.5.3.11); | 57 | 127 |
| LpOs06g0607800 | | Similar to 26S proteasome regulatory complex subunit p42D | 58 | 128 |
| LpOs06g0607900 | | C2 and GRAM domain containing protein "No Pollen" | 59 | 129 |
| LpOs11g0242400 | | Rieske [2Fe—2S] region domain containing protein oxidoreductase | 60 | 130 |
| LpOs04g0648400 | | Leucine rich repeat, N-terminal domain containing protein | 61 | 131 |
| LpOs04g0648500 | | Zinc Finger Protease | 62 | 132 |
| LpOs04g0648600 | | Conserved hypothetical protein | 63 | 133 |
| LpOs10g0419600 | | Chlorophyllase family protein | 64 | 134 |
| LpOs04g0648700 | | Conserved hypothetical protein | 65 | 135 |
| LpOs04g0274400 | | YL1 nuclear, C-terminal domain containing protein | 66 | 136 |
| LpOs04g0649200 | | Protein of unknown function DUF869, filament-like plant protein 7-like | 67 | 137 |

TABLE 2-continued

Genes identified within the Z locus

| Ryegrass gene identified | Syn | Predicted Gene Function | Nucleic acid SEQ ID NO: | Polypeptide SEQ ID NO: |
|---|---|---|---|---|
| LpOs04g0648800 | | RING-type domain containing protein, zinc finger binding | 68 | 138 |
| LpOs04g0648900 | | Dehydration responsive element binding protein 2F, AP2 domain containing | 69 | 139 |
| LpOs04g0649100 | | Pathogenesis-related transcriptional factor and ERF domain containing protein, AP2 domain containing, Apetala 2 like | 70 | 140 |
| LpOs04g0650000 | Lpbcd266 | Oryzain alpha chain precursor (EC 3.4.22.-) | | |

Example 2. Resequencing Data Identified DNA Nucleotide Variance

A cohort of 21 genes were selected as key candidates of the S and Z loci. The genes were selected based on expression profile as well as sequence annotation.

The collection of 21 genes all had PCR primers designed to resequence the coding regions of the genes. The designed PCR amplicons were optimised to generate large genomic fragments. A total of 50 plant genotypes were used as the template DNA for resequencing. The 50 plants were chosen as a diverse spread of plants with a potential wide range of diversity to maximise allelic variation at the genic loci being resequenced.

The amplicons were generated, then pooled from each genotype and physically sheared to smaller fragments. DNA bar codes and sequencing adaptors were ligated onto the sheared fragments to identify each sample and then all samples were combined and sequenced using a next-generation Illumina MiSeq platform with 300 bp×2 reads.

The resulting sequence data was attributed back to the individual samples using the bar codes and was then checked for quality and low quality reads removed. The sequence reads were then reference aligned to the genes amplified and variant bases identified. The individual samples were then combined to give a dataset to identify all variant bases from the 50 samples, with potentially 100 different alleles.

The variant bases were recorded for each gene to identify if the variation was synonymous or non-synonymous in nature. A minimalistic requirement for each of the genes under investigation would be to have 5 or more variant amino acids identified within the transcript. A total of 5 variant amino acids would enable a maximum of 32 potential haplotypes from the data set allowing complete random mating maximal recombination.

As 100 haplotypes were resequenced, high levels of diversity are expected, however there could be a degree of overlap between the haplotypes from the plants chosen so the total number of unique haplotypes could be lower than the number sequenced.

Perennial ryegrass has been characterised as having a high degree of sequence variation within its genome, with estimates ranging from 1 SNP every 20-30 bases within a gene bases on resequencing 2-4 haplotypes. With two exceptions all of the genes resequenced contained sufficient variation in the coding regions of the genes that would generate a sufficient diversity of polypeptides that could deliver the required allelic variability (See FIGS. 17 to 58). Detected sequence variation is identified within [ ] with both allelic forms described.

The genes LpOs05g0151300 and LpOs05g0152400 did not have sufficient diversity, with only 3 and 2 variant amino acids respectively.

Example 3—Isolation of SI Genes: Cloning of the Ryegrass LpOs06g0607800 26S Proteasome Gene In order to develop novel genetic markers for fine-scale genetic and physical mapping of the perennial ryegrass SI loci, linked heterologous cDNA-derived RFLP markers were selected for the S locus and Z on the basis of ortholocus co-segregation in cereal rye and/or blue canary grass. Molecular marker development, genetic mapping and region dissection is described in Shinozuka et al (2010). As a result of the assembled data sets fine-scale comparative sequence synteny with the model Poaceae species, specifically *Oryza sativa* and *Brachypodium distachyon*, was achieved for the delimited S and Z regions. Using the defined gene complement from the model Poaceae species, a BAC library was screened with primer pairs specific to the genes described and 39 specific clones were identified. The identity of the selected BAC clones was verified through direct sequencing of locus-specific amplicons. The specific BAC clones were then sequenced using Sanger and/or GSFLX technology and the resulting data was sequence assembled using the Newbler software package. Following sequencing and assembly gene-like nucleotide sequences were identified using BLAST and gene prediction software tools. Based on the derived information the reiteration of the procedure was performed for the selection of additional clones to further enhance the resolution and sequence data to assemble physical maps for the SI locus regions (FIGS. 1 and 2).

Molecular markers were developed from resequencing of specific genic loci, identified from the BAC sequencing and genetically mapped in a segregating population of *Lolium perenne* L. to confirm the location of the generated sequence.

The genome of a single *Lolium perenne* L. genotype (the plant—Impact04) has been sequenced to approximately 70× coverage, generating c. 2 billion sequencing reads of 100 bp paired-end sequence reads on the Illumina GA2X and HiSeq2000 platform. The sequence data was filtered for high quality reads before being assembled using the SOAPdenovo v. 1.05 software package. The sequence assembly has been empirically optimised through iterative assessment of performance based on a range of input kmer sizes, in terms of number of bases assembled, and the average length of assembled contigs and scaffolds. An optimal assembly has generated 1.9 million scaffolds covering c. 1.7 Gb, while all contigs and singletons cover c. 3.5 Gb.

Comparison of contigs and scaffolds to the coding sequences of the model grass species *Brachypodium distachyon* L. permitted identification of putative perennial ryegrass orthologues to c. 86% of all predicted genes and alternate transcripts from the model grass species. A pipeline approach was implemented based on a highly parallel BLAST analysis method in order to group transcript and genomic sequences relevant to each individual *Brachypodium* gene sequence into individual local CAP3-based assemblies. This approach generated 23,285 genic files that were indexed to the corresponding *Brachypodium* gene. Development of the exome sequence library enabled identification of a large collection of genic contigs, along with the corresponding regulatory elements. The collection of contigs was then screened for the presence of the predicted genes within the S and Z loci that had not been identified through the BAC screening process.

A novel *Lolium perenne* L. gene was identified from BAC clone-related sequence that displayed sequence similarity with the rice gene Os06g0607800, hence the ryegrass gene was designated LpOs06g0607800 (SEQ ID NO: 58 and FIG. 3). The ryegrass gene was annotated as a 26S proteasome subunit gene through a BLASTx analysis (at e value=3e-65 compared to the rice amino acid sequence). The gene also contained an AAA ATPase domain (SEQ ID NO: 128).

In addition the ryegrass 26S proteasome subunit gene identified in the Z locus region through BAC sequencing, was compared through BLAST analysis to the genomic Impact04 sequence through BLAST analysis. The identification of the sequence from the BAC clones as well as the genomic sequence enabled the identification of variant sequence bases from the coding region of the gene (FIGS. 33 and 54).

Intracellular proteolysis is mainly regulated and enabled through the ubiquitin-proteasome pathway or the autophagy-lysozome/vacuole pathway. Proteolytic events play significant roles in SI through self-pollen rejection. Ubiquitin-mediated proteolysis is involved in the SI mechanism of the Brassicaceae and the Solanaceae.

The 26S proteasome consists of the 20S core proteasome (CP) element and the 19S regulatory particle (RP). Proteolysis occurs in the 20S compartment, while the 19S element confers ATP dependence and substrate specificity to the CP. The RP consists of two elements: a ring of six AAA-ATPase subunits (often abbreviated as RPT) that is expected to function in target unfolding and transport, and three non-ATPase subunits (often abbreviated as RPN). As the 26S Proteasome subunit gene LpOs06g0607800 contains the AAA-ATPase domain, it is of the class RPT.

*Arabidopsis thaliana* L. mutant lines, in which the RTP2 subunit of the 26S proteasome gene is disrupted, have demonstrated that male and female gamete transmission require a normal copy of the RPT2 gene to avoid abortion and failure in gametogenesis. In tobacco (*Nicotiana tabacum* L.) the NtRpn3 gene was found to physically interact with a calcium-dependent protein kinase and become phosphorylated in a calcium dependent manner.

While applicants do not wish to be restricted by theory, the LpOs06g0607800 26S Proteasome gene is hence proposed to be the female determinant of the Z locus.

Example 4—Generation of Transformation Vectors Containing an Inverted Hairpin Structure of the LpOs06g0607800 26S Proteasome Gene The LpOs06g0607800 expression cassette consists of the promoter, 5' untranslated region and intron from the Ubiquitin (Ubi) gene from *Zea mays* (Toki et al 1992) followed by 500 bp of coding sequence of the LpOs06g0607800 gene from *L. Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from *E. coli* (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized by a commercial gene synthesis vendor (GeneArt, Life Technologies) and cloned into a Gateway-enabled vector. The LpOs06g0607800 expression cassette was synthesized by a commercial gene synthesis vendor (GeneArt, Life Technologies) with flanking attB sites. For delivery in cis the LpOs06g0607800 expression cassette was sub-cloned into pDONR221 II (Invitrogen, Life Technologies) in a BP Clonase reaction. The resulting ENTRY clone was used in a LR Clonase II (Invitrogen, Life Technologies) reaction with the Gateway-enabled vector encoding the hph expression cassette. Colonies of all assembled plasmids were initially screened by restriction digestion of miniprep DNA. Restriction endonucleases were obtained from New England Bio-Labs (NEB; Ipswich, Mass.) and Promega (Promega Corporation, WI). Plasmid preparations were performed using the QlAprep Spin Miniprep Kit (Qiagen, Hilden) or the Pure Yield Plasmid Maxiprep System (Promega Corporation, WI) following the instructions of the suppliers. Plasmid DNA of selected clones was sequenced using ABI Sanger Sequencing and Big Dye Terminator v3.1 cycle sequencing protocol (Applied Biosystems, Life Technologies). Sequence data were assembled and analyzed using the SEQUENCHER™ software (Gene Codes Corporation, Ann Arbor, Mich.).

An ideogram of the gene expression cassette is shown in FIG. 4. The full sequence of the expression cassette is shown in FIG. 75.

Example 5—Biolistic Transformation of Perennial Ryegrass (*Lolium perenne*) for Expression of dsRNA Products of the LpOs06g0607800 26S Proteasome Gene for RNAi-Mediated Down-Regulation of SI Biolistic co-transformation of perennial ryegrass with the vectors containing the LpOs06g0607800 26S Proteasome gene sequence, driving the expression of the RNAi cassette and the synthetic version of hph gene from *E. coli* for hygromycin resistance was conducted on embryogenic calli for perennial ryegrass.

The vector used along with the transformation protocol has previously been used successfully in plant transformation experiments (Bilang, et al., 1991; Spangenberg, et al., 1995a; Spangenberg, et al., 1995b; Ye, et al., 1997; Bai, et al., 2001). The perennial ryegrass biolistic transformation method is outlined in FIG. 80.

Phenotypic evaluation of the resulting transgenic plants was performed by growing the plants to maturity, then following a vernalisation period of at 5° C. with 12 hour lighting for ten weeks, the plants were subjected to 22° C. with 24 hour lighting. The change in temperature and perceived day length initiated flowering in the plants, which then occurred 2-3 weeks later. Before the ryegrass flowers opened the flowering spike was checked for morphological alterations or deformities and was then contained within a paper bag to isolate the flowers from other potential pollen donors. The flowering spike may be maintained in its isolated state until flowering is complete, at which time seed set may be assessed. Multiple spikes may be bagged per plant and each spikelet and flower assessed visually for seed production.

Once a putative transgenic plant had regenerated on the selective medium, the plant was split into three single plant tillers. Each tiller was individually screened for the presence of the transgene through conventional PCR. Oligonucleotide primers had been designed to the promoter region that originated from the Ubiquitin (Ubi) gene from *Zea mays* as well as a second assay that targeted the RGA2 intron sequence from *Triticum turgidum* subsp, which interrupts the inverted ryegrass repeat of the target gene. These regions were chosen to minimise cross amplification from the endogenous ryegrass genome. The assays were developed and initially tested on untransformed ryegrass genomic DNA to confirm that cross amplification did not occur. Transgenic events were only selected when all three tillers returned a positive result for the presence of the transgene with both assays. If variable results were seen, the single tillers that were positive were returned to growth medium and grown further, until they could be resplit into three tillers and screened again.

FIG. 81 shows PCR evaluation of transgenic status for individual tillers from regenerated transgenic events. Each transformation event was assessed through three individual tillers split from the regenerated plant. Only examples where all three tillers gave positive confirmation of the presence of the transgene, did the event get accepted for further evaluation. The brackets with numbers 1 and 2 in the figure identify 1, a transgenic event that would be discarded as all tillers are negative for the presence of the transgene and 2, a transgenic event where all three tillers have generated a positive result for the presence of the transgene.

An average of 12 different transgenic events per construct were generated, with a range of 3-19. The plants were transferred to soil and were maintained in an appropriate containment glasshouse.

TABLE 3

Numbers of transgenic events generated for the seven candidate genes undergoing functional evaluation.

| Gene Number | Gene Name | Positive Transgenic Events Generated |
| --- | --- | --- |
| LpOs04g0648500 | Zinc Finger Protease | 3 |
| LpOs05g0149600 | Cullin | 15 |
| LpOs06g0607800 | 26S proteasome | 8 |

TABLE 3-continued

Numbers of transgenic events generated for the seven candidate genes undergoing functional evaluation.

| Gene Number | Gene Name | Positive Transgenic Events Generated |
| --- | --- | --- |
| LpOs06g0680500 | Glutamate receptor | 11 |
| LpOs06g0607900 | NoPollen Gram domain | 11 |
| LpOs05g0152900 | SlAHa | 18 |
| LpOs04g0647300 | TC116908 | 19 |

Phenotypic evaluation was performed upon the plant reaching reproductive maturity. Initially pollen grains were assessed for viability to ensure a response would be seen. A common effect on plant cells passing through a transformation and tissue culture process is reduced fertility of the resultant whole plant. The viability was confirmed through staining with fluorescein diacetate (FDA). FDA is a lipophilic compound and is membrane-permeable and non-fluorescent. Viable pollen grains will have intracellular esterase activity and will be able to perform enzymatic hydrolysis of FDA upon its entry into the cell. Once FDA has been hydrolyzed within the viable pollen grain it will be a highly fluorescent compound that is unable to diffuse out of the cell and will be retained, producing an intense green fluorescence within the cytoplasm.

FIG. 82 shows FDA staining of viable pollen grains for example transgenic plants with SiRNA constructs for the down regulation of a candidate S and Z gene respectively. Both viable and non-viable pollen grains can be seen in both A and B.

Once pollen viability was confirmed pollen-pistil interactions were assessed. Dissection of the floral tissues of flowering ryegrass plants were performed to microscopically assess pollen-pistil interactions.

FIG. 83 shows stages of ryegrass flower dissection. A—Intact flowers of ryegrass. Upon reaching reproductive maturity the anthers are released from the flower. The stigmatic papillae will then extend and become visible. B—individual spikelets were excised from a floral spike for further dissection. C—Both male and female reproductive tissues were excised from the spikelet. D and E—the female tissue was further excised to examine pollen tube growth on pollinated stigmas.

Each transgenic event was represented by three plants as described in the PCR screening process. Multiple transgenic events are required as the insertion of the transgene SiRNA construct is likely to result in a range of expression levels. This difference in expression between the transgenic events is likely to lead to a range of phenotypes for the reaction. The pollen-pistil compatible/incompatible reaction can be visualised through pollen tube abortion upon contact with the stigmatic tissue, or pollen tube directed growth towards the ovary. Multiple flowers per plant are required to be assessed for confidence over the observed phenotype. Once pollinated stigmatic tissues were isolated, aniline blue staining was performed and the tissue visualised under an inverted fluorescent microscope. A range of reactions were observed. Incidences of self-incompatibility was seen for many plants, while instances of partial compatibility was also seen.

FIG. 84 shows an incompatible reaction of pollen tube growth. A and B, examples of single pollen grains germinating on stigmatic papillae and upon contact growth is arrested. The pollen tubes upon contact will often become swollen in shape through cytoplasmic pressure, indicated by arrows. C, An incompatible reaction of self pollination from a transgenic plant containing the SiRNA construct for LpOs05g0149600.

FIG. 85 shows a compatible pollen tube growth with untransformed plants. Pollen was taken from unrelated ryegrass plants and placed upon an untransformed flower. The pollen tube has made contact with the stigmatic papillae and has then continued to grow in a directed manner towards the ovary. The pollen tube upon growth will deposit callose plugs at regular intervals (indicated by arrows) to retain cytoplasmic pressure, allowing the sperm cells to successfully migrate towards the ovary. These vacated regions will become vacuolated.

FIG. 86 shows a compatible pollen reaction. The pollen tube has made contact with the stigmatic papillae and has then continued to grow in a directed manner towards the ovary. The compatible pollen tube will deposit callose plugs at regular intervals (indicated by arrows). The reaction was observed on self-pollination of a transgenic plant containing the siRNA construct for the LpOs06g0680500.

FIG. 87 shows microscopic images of the pollen-stigma interaction of two different plants containing the siRNA construct for the LpOs05g0152900 gene. The two different transgenic events (A and B) show a range of phenotypes from incompatible to partially compatible.

Example 6—Expression Analysis of the LpOs06g0607800 26S Proteasome Gene

A single genotype of perennial ryegrass was subjected to transcriptome analysis through deep-sequencing of cDNA samples derived from multiple distinct tissue types. A total of 19 different RNA samples were generated from vegetative tissues, including leaf, pseudostem and root samples for both terrestrial and subterranean aspects of gene expression (Table 4). In addition a collection of reproductive libraries were generated from anthers, pistils, stigmas and pollinated pistils. The libraries were prepared for Illumina-based sequencing using the RNASeq preparation method. Each library was internally bar-coded to permit discrimination following the sequencing process.

A total of c. 0.6 billion sequencing reads were generated from the Illumina HiSeq2000 platform. Approximately 30 million sequence reads was generated from each tissue sample. The generated sequences were then filtered and quality trimmed to ensure <3 bases per sequence read were called as "N" and mean and local Phred quality was >30 in all instances.

The quality filtered reads were then BLASTn analysed against the coding sequences of the *Brachypodium distachion* genome. The number of BLASTn matches per gene were counted per tissue type and tabulated. As the number of reads generated per sample varied, the BLASTn mapped read count was normailsed on the 75th percentile to generate normalised values for comparative analysis. The *Brachypodium distachion* genome was used as a whole genome reference in this analysis to mitigate issues of gene absence or incomplete assemblies of any de novo generated gene catalogue.

TABLE 4

Gene expression analysis through RNA sequencing from different tissues of *Lolium perenne* L.

| Tissue name - library | Description of tissue source | Number of unique reads aligned to the *Brachypodium* CDS gene catalogue |
|---|---|---|
| Tip 1 | Tip of the youngest leaf from a single tiller | 22,752,873 |
| Tip 2 | Tip of the second youngest leaf from a single tiller | 18,298,951 |
| Tip 3 | Tip of the third youngest leaf from a single tiller | 14,929,714 |
| Mid 1 | Mid section of the youngest leaf from a single tiller | 17,729,494 |
| Mid 2 | Mid section of the second youngest leaf from a single tiller | 18,952,545 |
| Mid 3 | Mid section of the third youngest leaf from a single tiller | 13,934,280 |
| Pseudo 1 | Complete pseudostem from a single tiller | 9,887,218 |
| Pseudo 2 | Lower portion of the pseudostem of a single tiller | 12,245,297 |
| Pseudo 3 | Upper portion of the pseudostem of a single tiller | 12,594,959 |
| Root Mid | Mid section of root mass | 12,571,148 |
| Root Tip | Tip section of root mass | 12,239,578 |
| Flower | Complete flower, (un)opened | 9,920,235 |
| Pollinated Pistil 5 mins | Self pollen added to pistil, then after 5 minutes pistil excised and frozen | 10,840,818 |
| Pollinated Pistil 1 hour minus | Self pollen added to pistil, then after c. 1 hour pistil excised and frozen | 9,281,790 |
| Pollinated Pistil 1 hour plus | Self pollen already added to pistil, upon tissue harvest, for an undefined time greater than 1 hour prior to pistil being excised and frozen | 11,208,524 |
| Stigma pollinated 0 mins | Harvested following pollination at 0 minutes | 9,724,120 |
| Stigma pollinated 5 mins | Harvested following pollination at 5 minutes | 13,258,777 |
| Pistil | Complete pistil, without pollen | 13,714,389 |
| Anther | Complete anther without(out) pollen grains | 13,724,305 |

Figure 104:
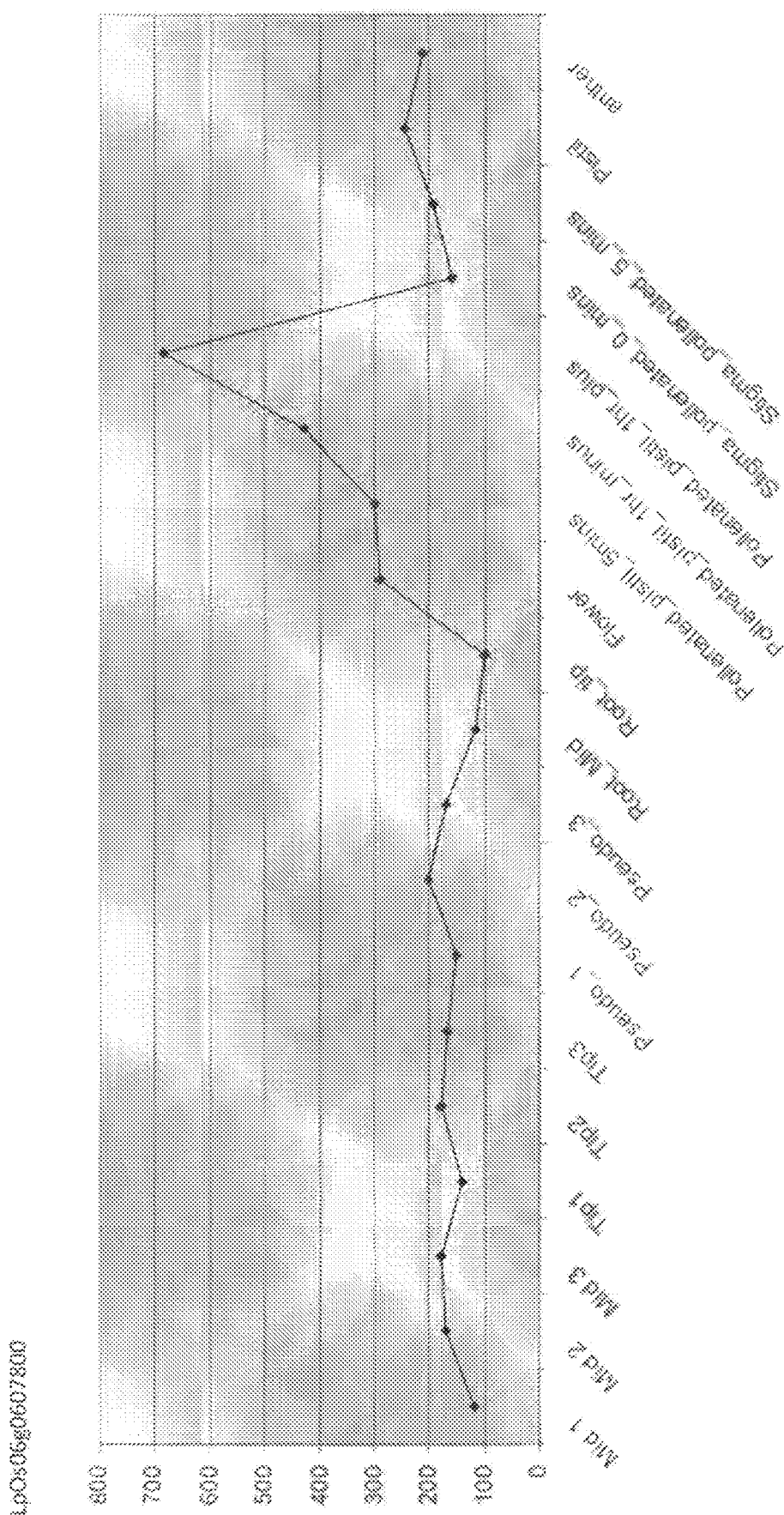
Figure 105:
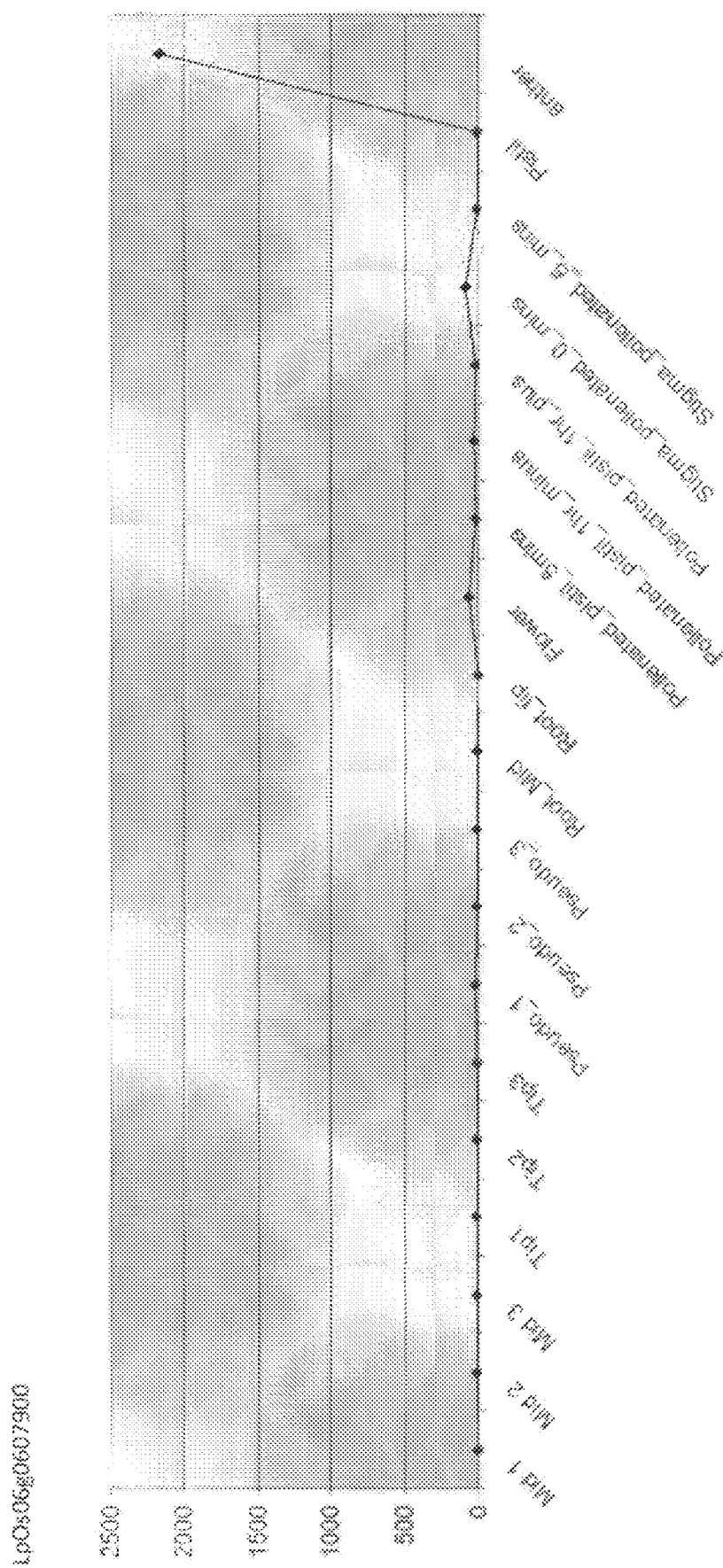
Figure 106:
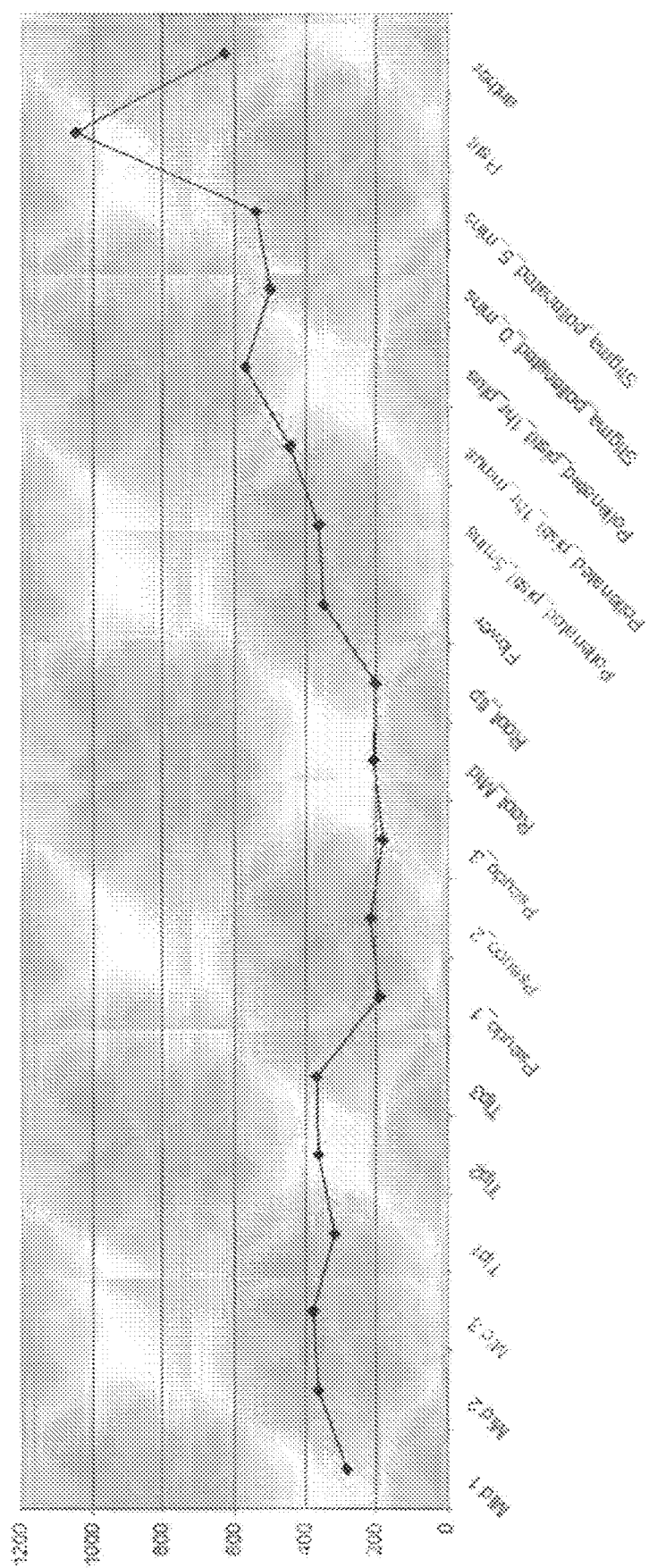
Figure 107:
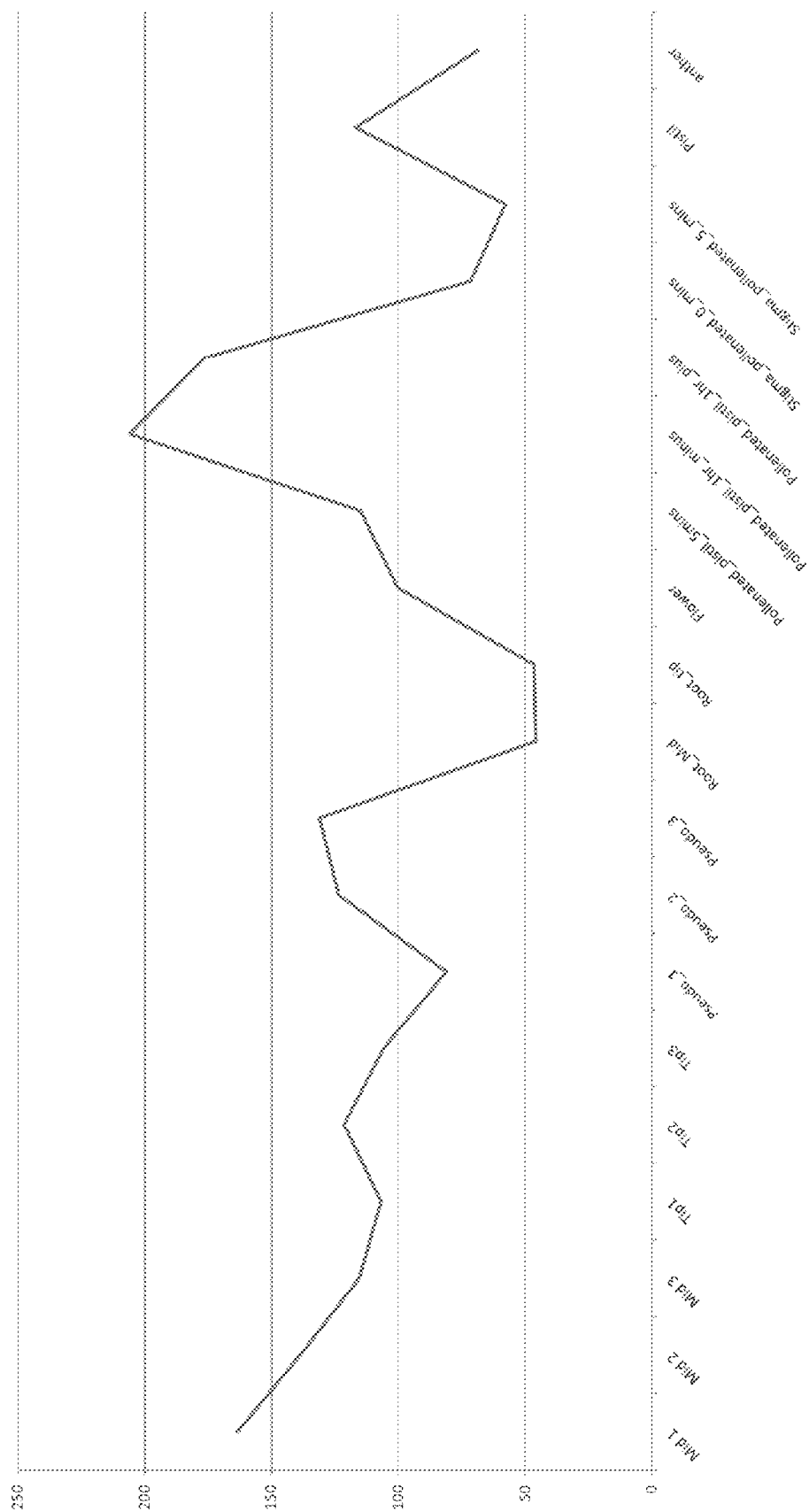
Figure 108:
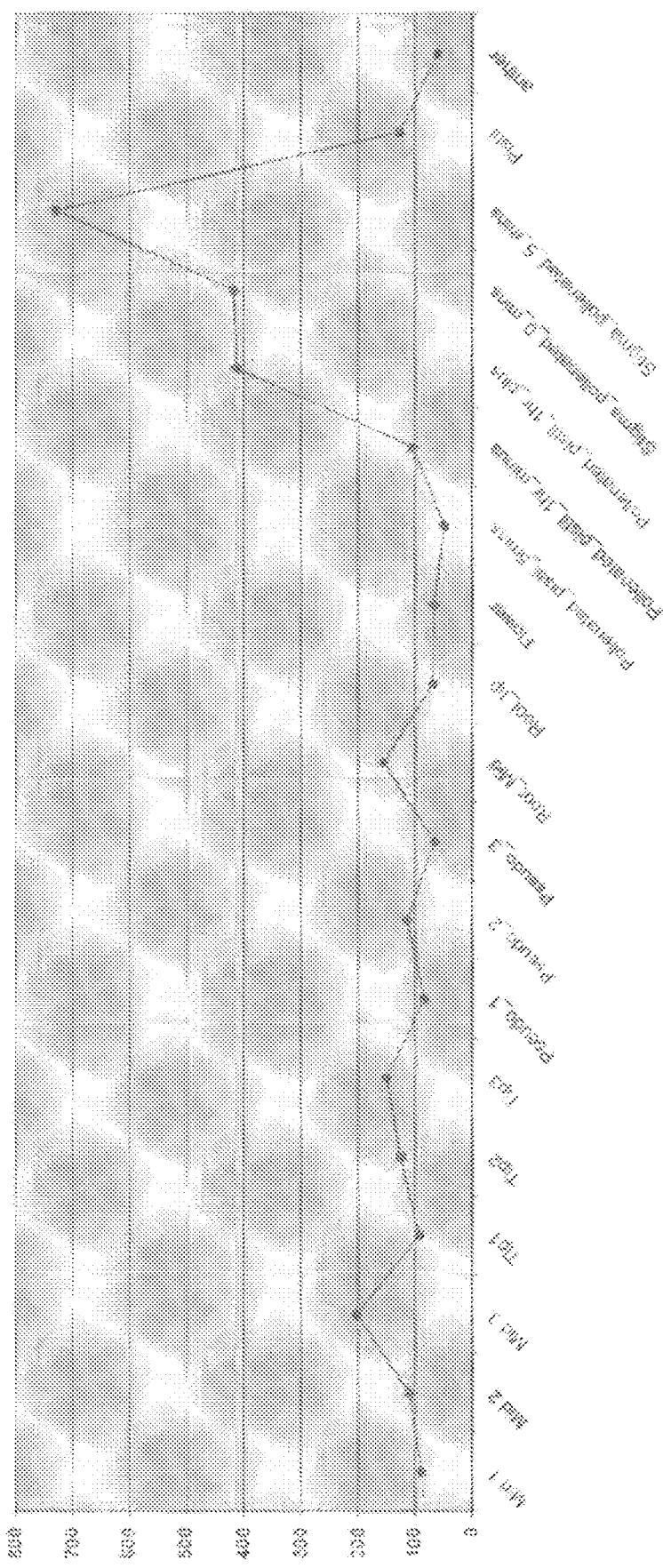

The nucleic acid sequence identified as the LpOs06g0607800 gene, when compared against the coding portion of the *Brachypodium distachion* genome sequence, identifies Bradi1g36400 as the closest matching gene sequence. The expression profile that has been generated from this analysis identifies a dramatic increase in gene expression over time in the pistil tissues upon self pollination (FIG. 104). A constant level of gene expression is detected across the entire plant, however some interference in the analysis from other gene family members is possible. Alternatively, the generic expression of the gene may have an alternative function across all tissues, or may demonstrate non-tissue specific gene expression as a result of particular promoter elements.

Example 7—Isolation of SI Genes: Cloning of the Ryegrass LpOs05g0149600 Cullin Gene Using the methods outlined in Example 3, a novel *Lolium perenne* L. gene was identified from BAC clone-related sequence that displayed sequence similarity with the rice gene Os05g0149600, hence the ryegrass gene was designated LpOs05g0149600 (SEQ ID NO: 20 and FIG. 5). The ryegrass gene was annotated as a Cullin gene through BLASTx analysis (SEQ ID NO: 90).

In addition the ryegrass Cullin gene identified in the S locus region through BAC sequencing, was compared through BLAST analysis to the genomic Impact04 sequence through BLAST analysis. The identification of the sequence from the BAC clones as well as the genomic sequence enabled the identification of variant sequence bases from the coding region of the gene (FIG. 21).

Cullins are molecular scaffolds responsible for assembling RING-based E3 ubiquitin ligases. Within the Solanaceae, Rosaceae and Plantaginaceae families the SI mechanism involves the formation of a complex consisting of a Cullin gene, an F-box gene along with a suppressor of kinetochore protein. The complex possesses the ubiquitin E3 ligase activity that attaches polyubiquitin chains to target proteins, such that ubiquitinated proteins are degraded by the 26S proteasome. The Cullin gene within the complex plays a role in assembling the other sub-units, and links to a further compound that recruits ubiquitin proteins to attach to the target proteins.

Example 8—Generation of Transformation Vectors Containing an Inverted Hairpin Structure of the LpOs05g0149600 Gene The LpOs05g0149600 expression cassette consists of the promoter, 5' untranslated region and intron from the Ubiquitin (Ubi) gene from *Zea mays* (Toki et al 1992) followed by 500 bp of coding sequence of the LpOs05g0149600 gene from *L. Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from *E. coli* (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized, delivered and sequenced as described in Example 4.

An ideogram of the gene expression cassette is shown in FIG. 6. The full sequence of the expression cassette is shown in FIG. 63.

Example 9—Biolistic Transformation of Perennial Ryegrass (*Lolium perenne*) for Expression of dsRNA Products of the LpOs05g0149600 Cullin Gene for RNAi-Mediated Down-Regulation of SI Biolistic co-transformation of perennial ryegrass with the vectors containing the LpOs05g0149600 gene sequence, driving the expression of the RNAi cassette and the synthetic version of hph gene from *E. coli* for hygromycin resistance was conducted on embryogenic calli for perennial ryegrass, as described in Example 5.

Example 10—Expression Analysis of LpOs05g0149600 Cullin Gene

Figure 92:
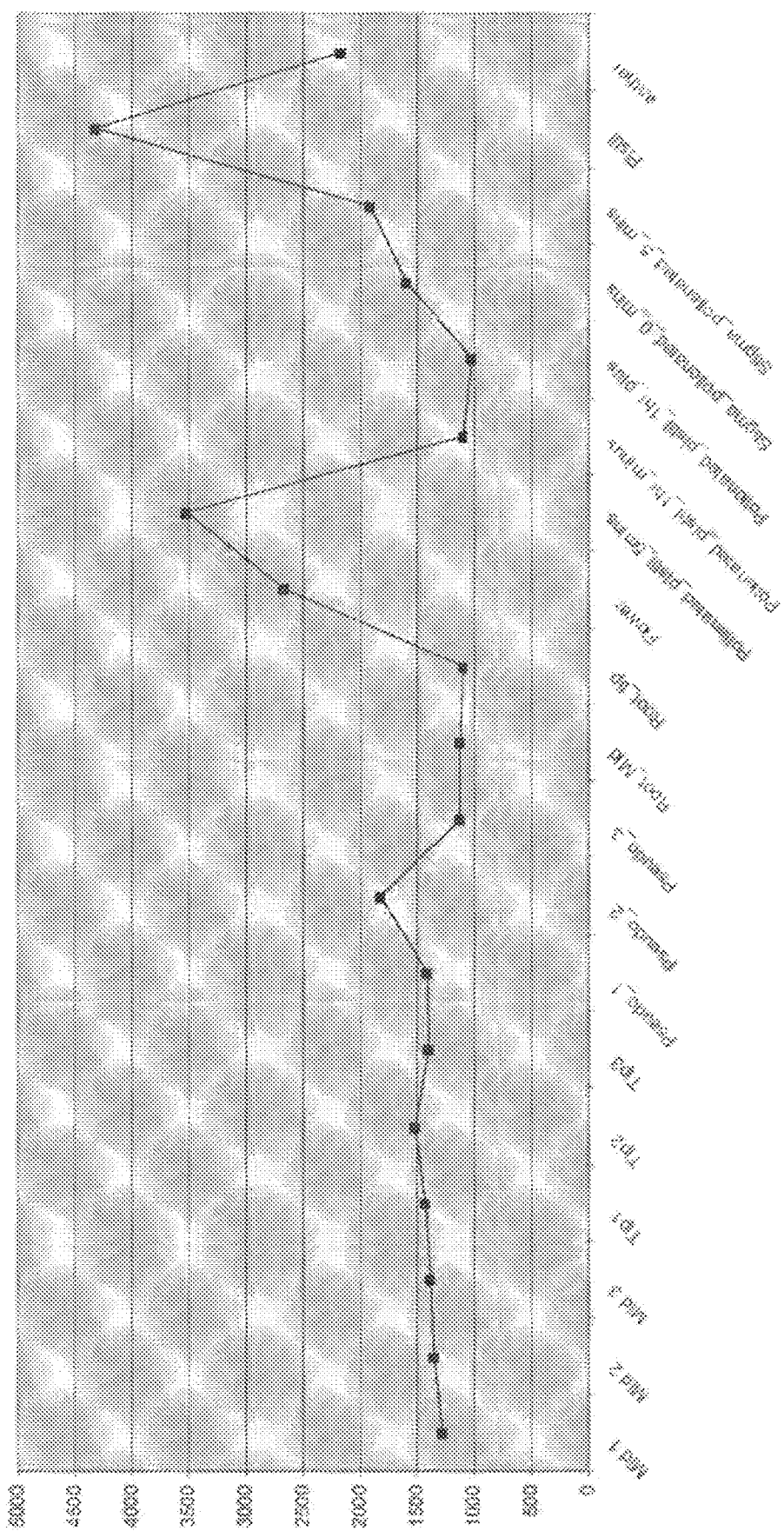
Figure 93:
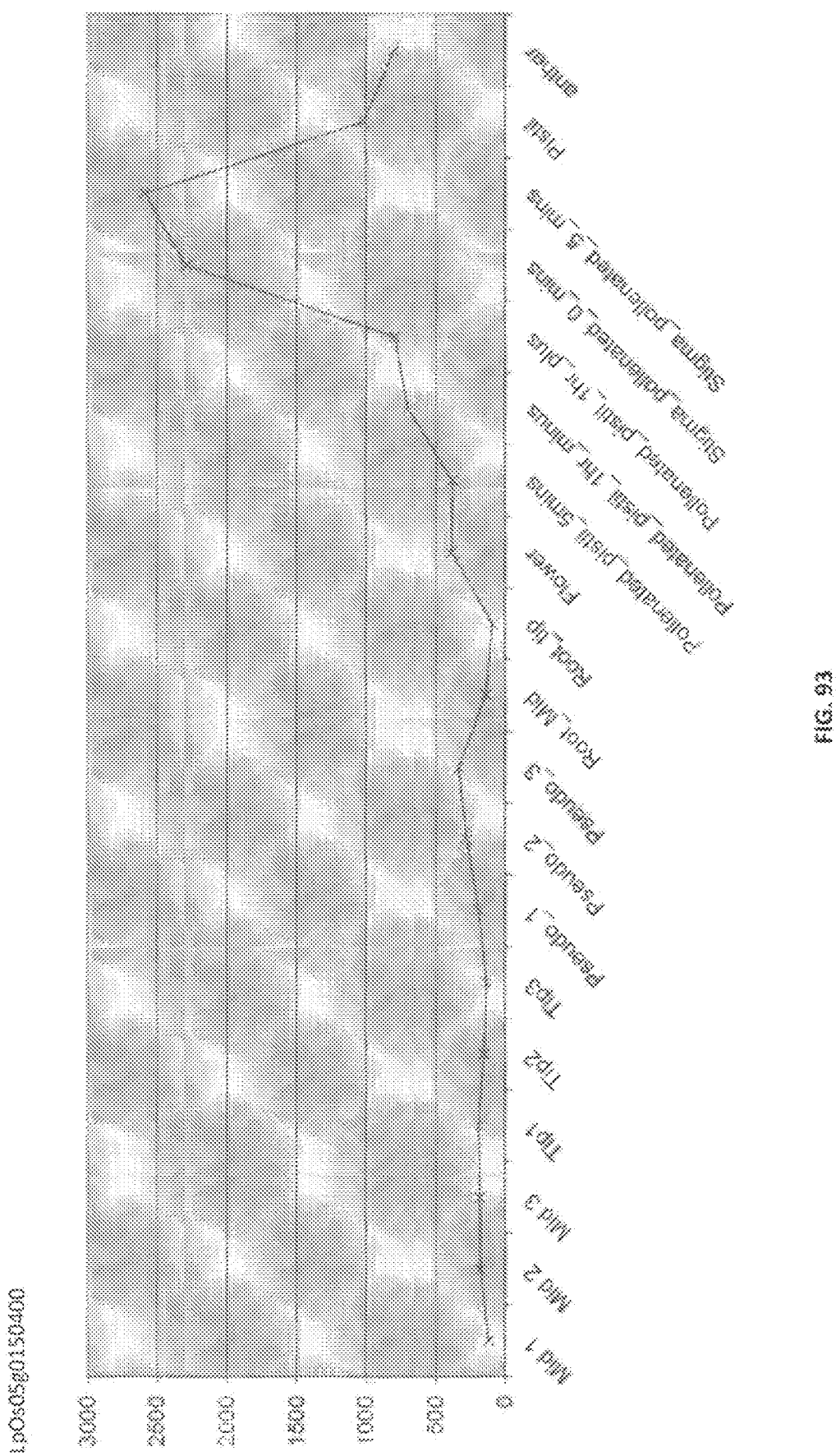
Figure 94:
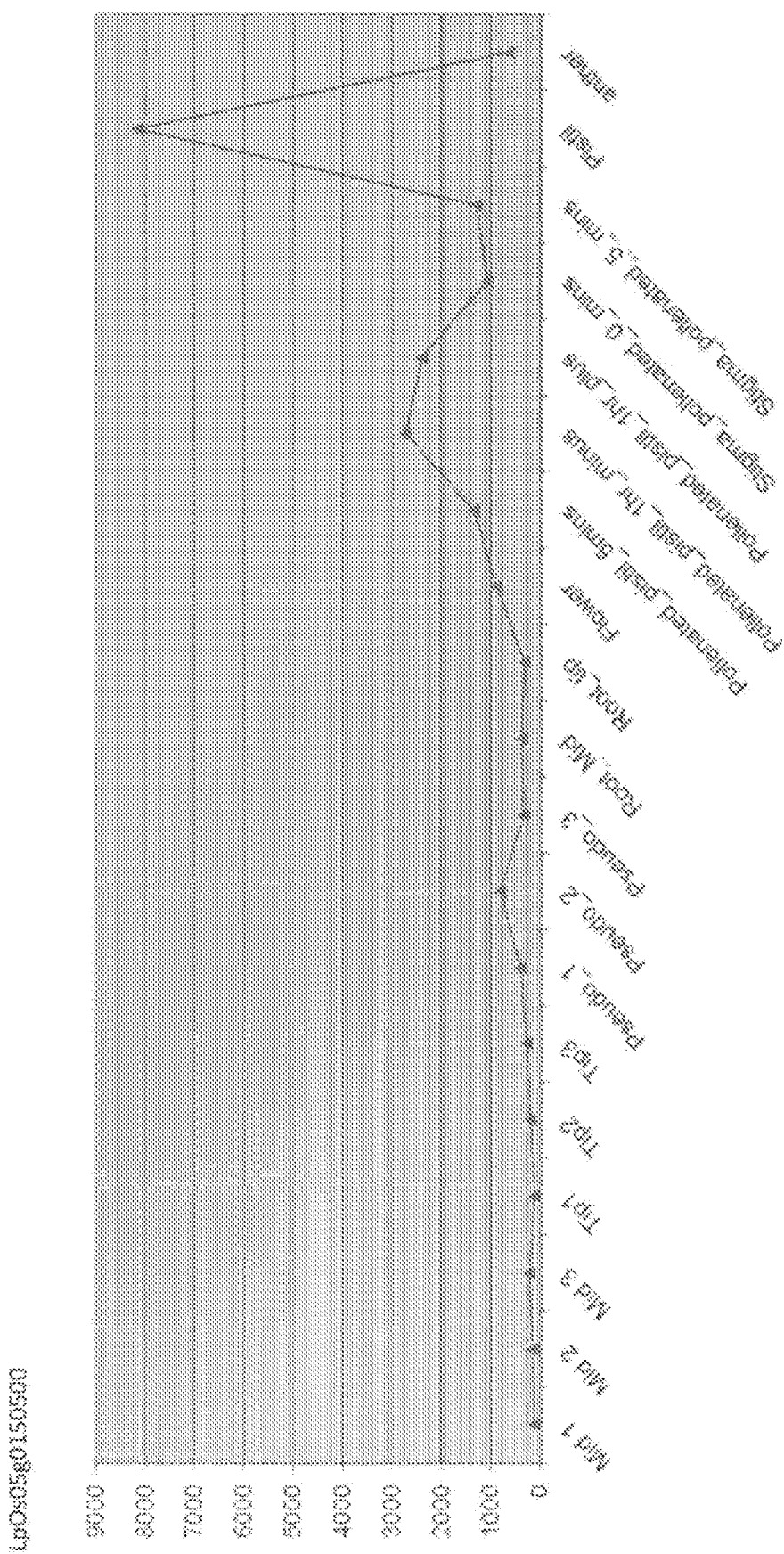
Figure 95:
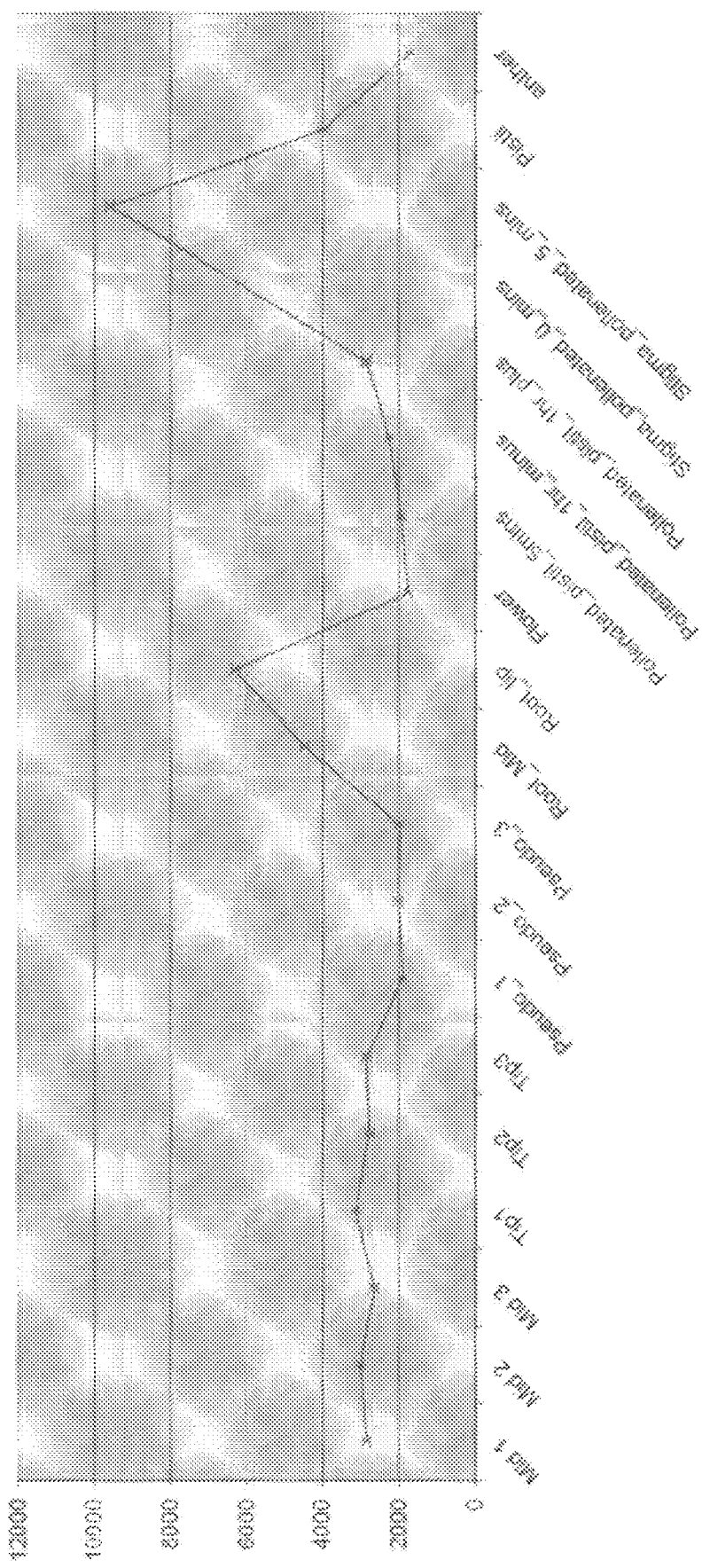
Figure 96:
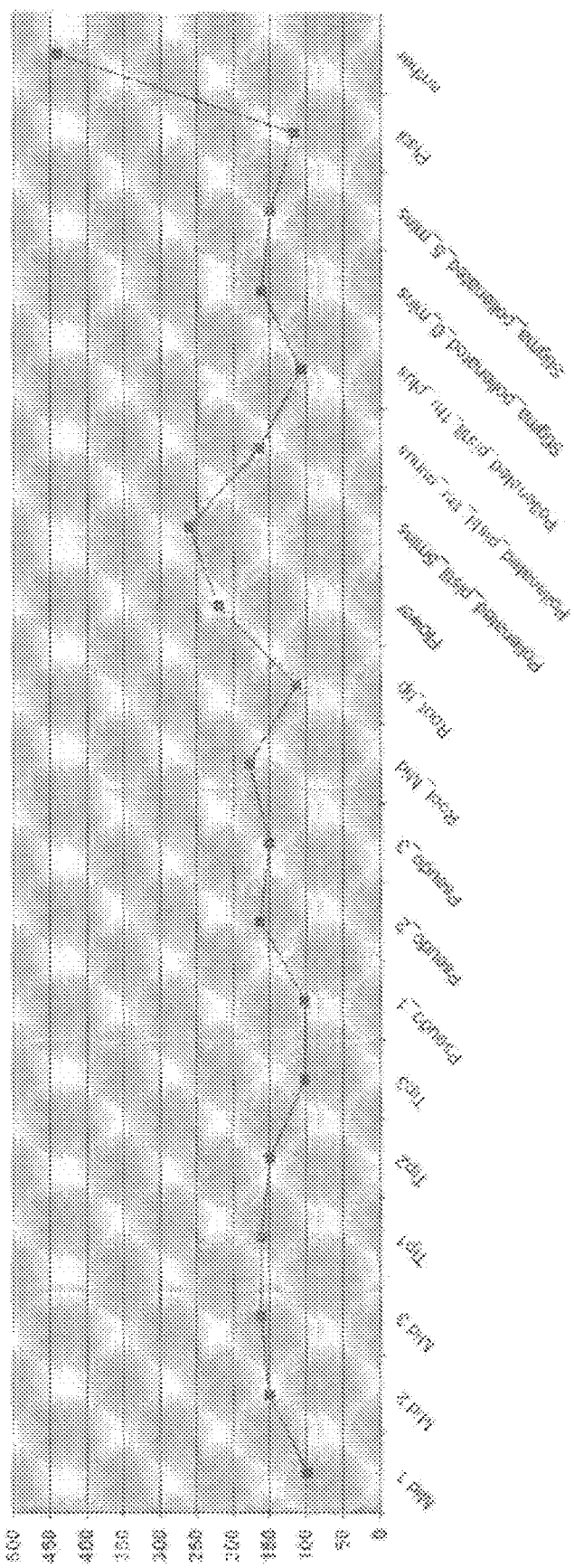

Using the methods outlined in Example 6, the nucleic acid sequence identified as the LpOs05g0149600 gene, when compared against the coding portion of the *Brachypodium distachion* genome sequence, identifies Bradi2g35830 as the closest matching gene sequence. The expression profile that has been generated from this analysis identifies a constitutive level of gene expression in all tissues (FIG. 92). However, significantly elevated levels of gene expression are seen in pistil and pollinated pistils at 5 minutes as well as whole flower and stigma at 0 and 5 minutes. The pattern of expression seen can be described as increasing in stigma from 0 to 5 minutes along with a corresponding increase in pistil at 5 minutes that then decreases to the constitutive level at a 1 hour time point.

Example 11—Isolation of SI Genes: Cloning of the Ryegrass LpOs06g0680500 Glutamate Receptor Gene Using the methods outlined in Example 3, a novel *Lolium perenne* L. gene was identified from BAC-clone related sequence that displayed sequence similarity with the rice gene Os06g0680500, hence the ryegrass gene was designated LpOs06g0680500 (FIG. 7 and SEQ ID NO:39). The ryegrass gene was annotated as a glutamate receptor gene through a BLASTx analysis (e value=0 compared to the rice amino acid sequence) and was identified as containing the requisite GABA domain (SEQ ID NO: 109).

Glutamate receptor genes have been identified in *Arabidopsis thaliana* and tobacco as forming influx channels in tip cell types that undergo directed patterns of growth such as those of pollen tubes, as well as root hairs. Studies on *Arabidopsis* root cells show that glutamate induces a sharp depolarization of the membrane potential, and a concomitant rise in intracellular calcium. Growth of tobacco pollen tubes in the presence of a glutamate receptor antagonist has been shown to be repressed, as is also the case for specific directed uptake of calcium. Gene knock-out experiments of pollen expressing glutamate receptor genes in *Arabidopsis* have documented reduction in growth rates as well as abnormal morphology of the tip and tube.

While applicants do not wish to be restricted by theory, LpOs06g0680500 LpGlu1 Glutamate receptor gene is hence proposed to be the male determinant of the S locus.

Example 12—Generation of Transformation Vectors Containing an Inverted Hairpin Structure of the LpOs06g0680500 LpGlu1 Gene The nucleic acid sequence identified as LpOs06g0680500 gene has a 484 bp fragment selected as a design element for expression cassette. The *Zea mays* ubiquitin gene promoter (Christensen et al. 1992) was used to drive expression and the nopaline synthase (nos) gene terminator (Bevan, 1984; Rogers et al., 1985) was selected to arrest transcription.

The LpGlu1 expression cassette consists of the promoter, 5' untranslated region and intron from the Ubiquitin (Ubi) gene from *Zea mays* (Toki et al 1992) followed by 484 bp of coding sequence of the LpGlu1 gene from L. *Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from E. coli (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized, delivered and sequenced as described in Example 4.

An ideogram of the gene expression cassette is shown in FIG. 8. The full sequence of the expression cassette is shown in FIG. 68.

Example 13—Biolistic Transformation of Perennial Ryegrass (Lolium perenne) for Expression of dsRNA Products of the LpOs06g0680500 Glutamate Receptor Gene for RNAi-Mediated Down-Regulation of SI Biolistic co-transformation of perennial ryegrass with the vectors containing the LpOs06g0680500 LpGlu1 gene sequence, driving the expression of the RNAi cassette and the synthetic version of hph gene from E. coli for hygromycin resistance was conducted on embryogenic calli for perennial ryegrass, as described in Example 5.

Figure 97:
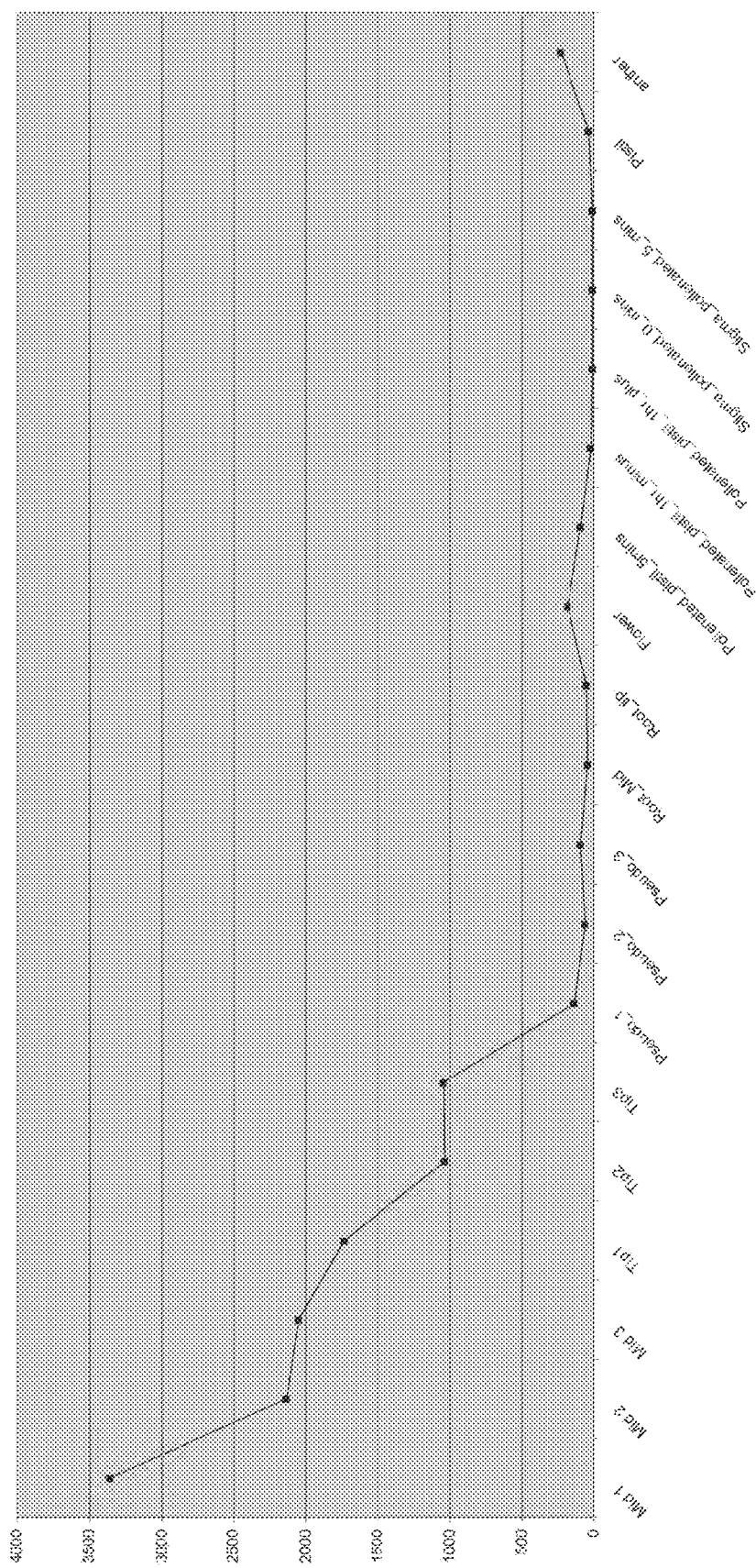
Figure 98:
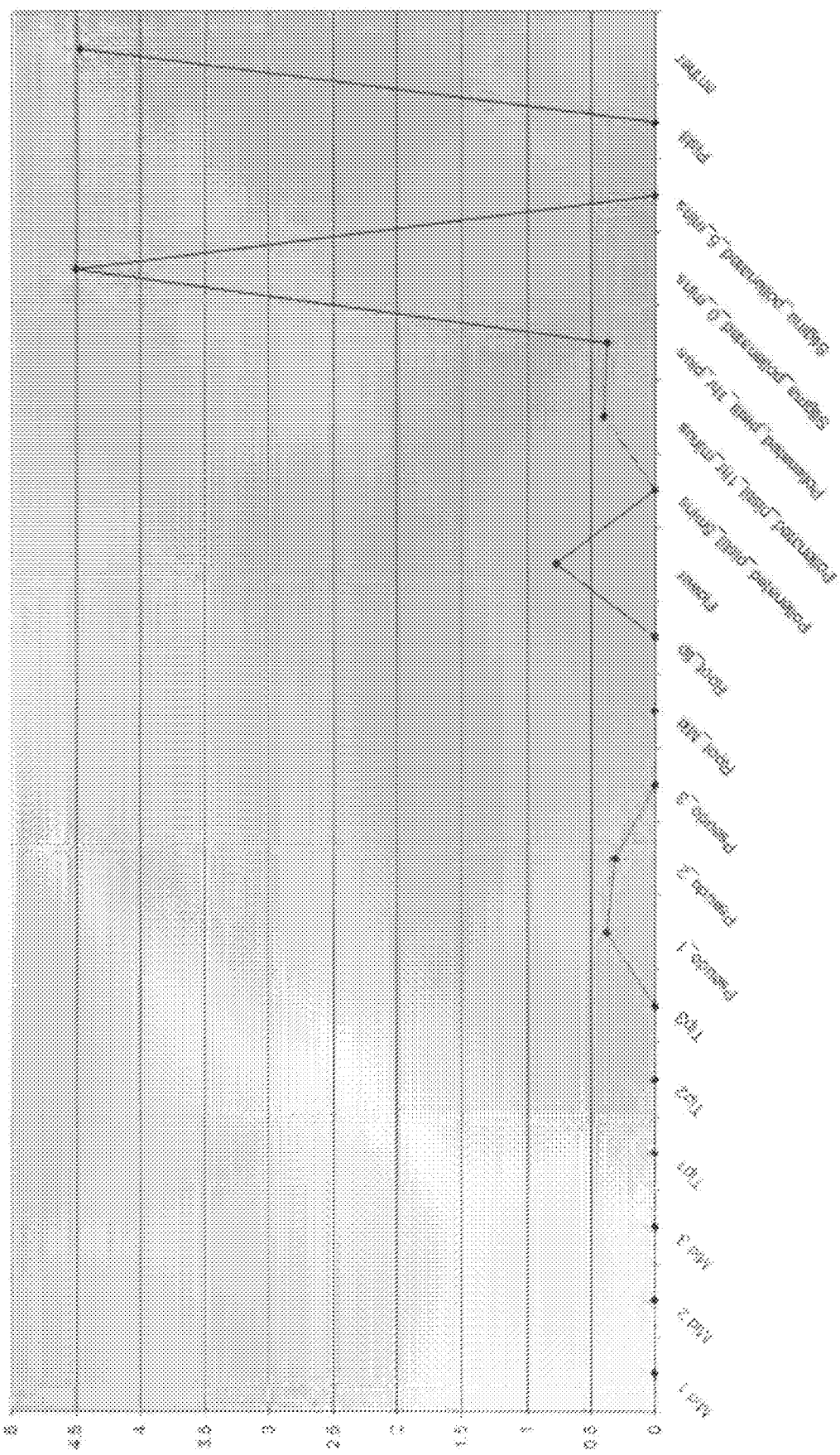
Figure 99:
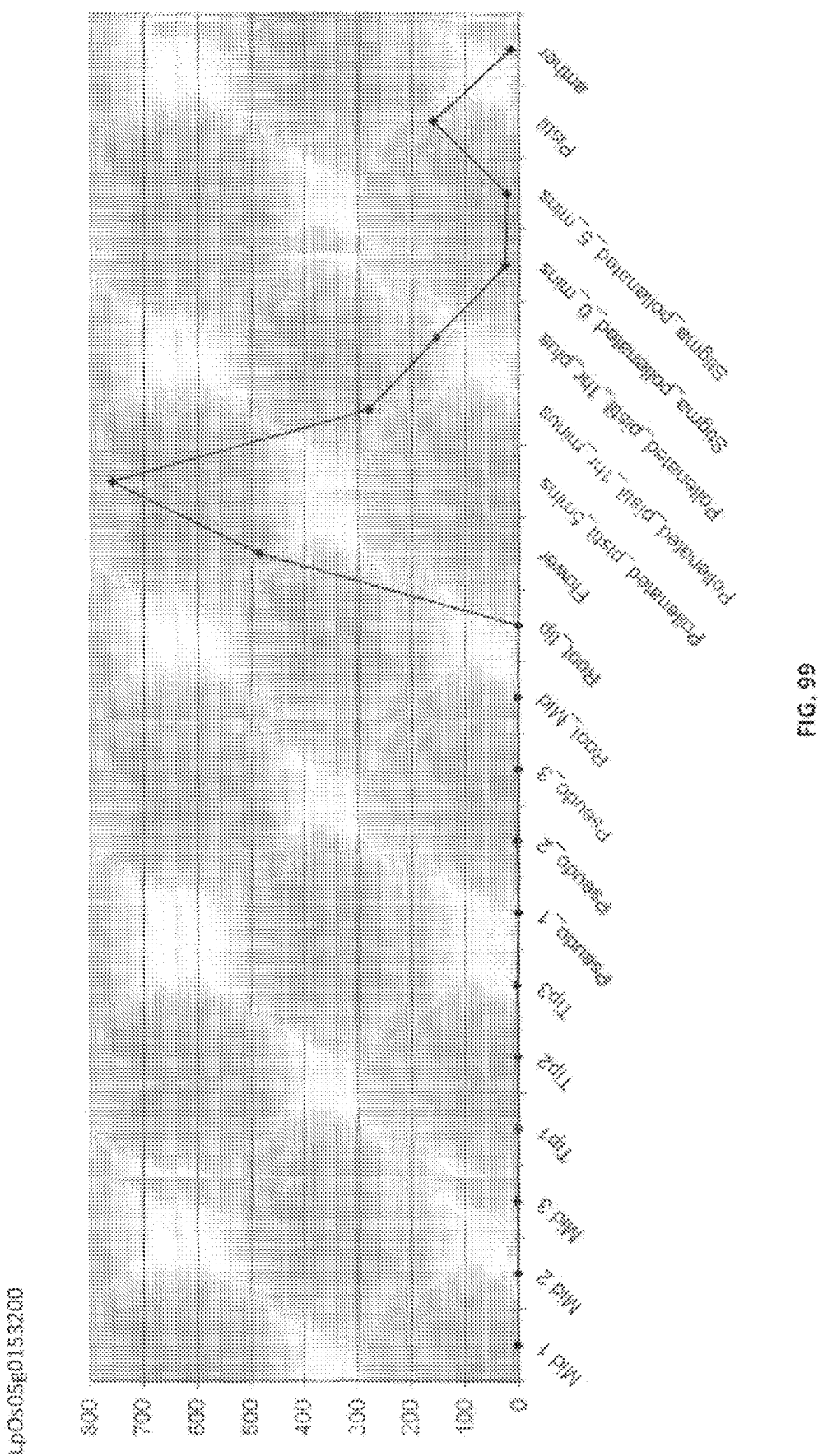
Figure 100:
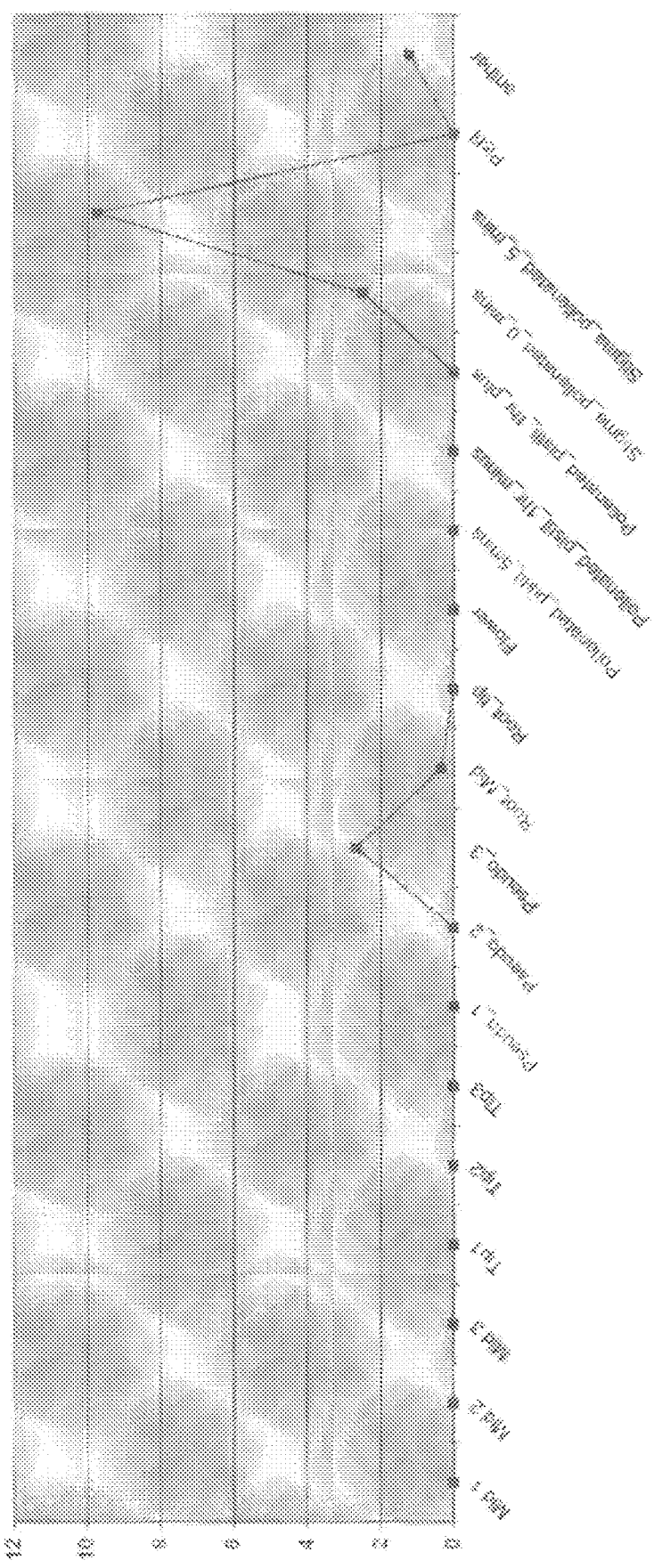
Figure 101:
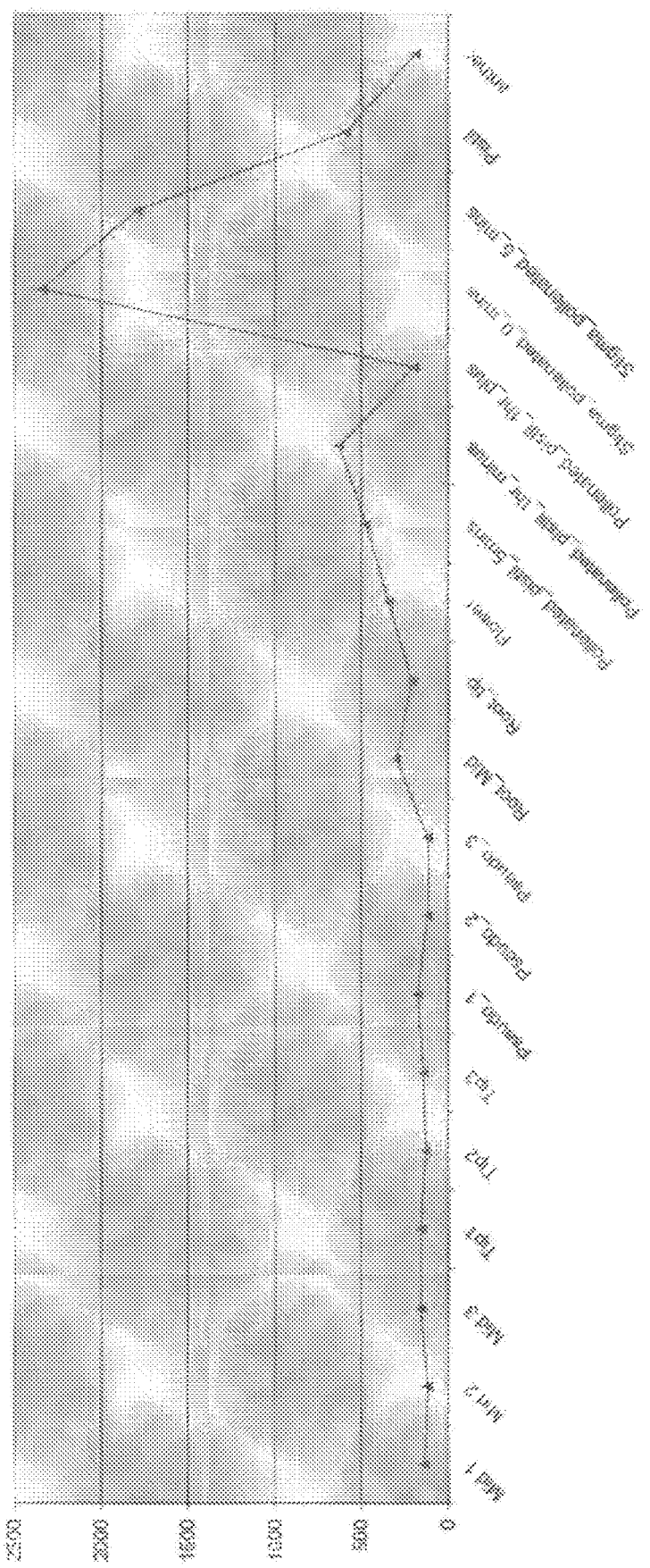

Example 14—Expression Analysis of the LpOs06g0680500 Glutamate Receptor Gene Using the methods outlined in Example 6, the nucleic acid sequence identified as the LpOs06g0680500 gene, when compared against the coding portion of the Brachypodium distachion genome sequence, identifies Bradi1g32800 as the closest matching gene sequence. The expression profile that has been generated from this analysis identifies high levels of gene expression in vegetative tissues and some gene expression in anthers (FIG. 97). The glutamate genes represent a gene family within the Brachypodium distachion genome that will be involved in many functions across the different plant tissues and consequently mapping of related sequences or alternative functions for glutamate genes is likely and could explain the constitutive expression. Nevertheless, a significant increase in expression is detected in anthers and not in the female pistil or stigma tissues.

Example 15—Isolation of SI Genes: Cloning of the Ryegrass LpOs04g0648500 Gene Using the methods outlined in Example 3, a novel Lolium perenne L. gene was identified from BAC clone-related sequence that displayed sequence similarity with the rice gene Os04g0648500, hence the ryegrass gene was designated LpOs04g0648500 (See FIG. 9 and SEQ ID NO: 62). The perennial ryegrass gene was identified as physically linked to the TC116908-related gene. The TC116908-derived genetic marker co-segregated with the Z locus in rye (Secale cereale L.) (Hackauf and Wehling 2005). In the perennial ryegrass BAC clone including the TC116908 orthologue, LpOs04g0648500 and other 2 genes were identified (Shinozuka et al. 2010).

The LpOs04g0648500 gene was annotated as an Ubiquitin-specific protease 22 gene through a BLASTx analysis (SEQ ID NO: 132). The gene contained a Znf-UBP and BRAP2 domains. The Znf-UBP domain exhibits the ubiquitin-specific protease activity and functions as protein stabiliser through target-specific de-ubiquitinylation. The human BRAP2 domain was originally identified as interacting with the BRCA1 (breast cancer 1) gene products. A sequence homology search indicated that this domain is also conserved in the Arabidopsis At2g26000 [zinc finger (ubiquitin-hydrolase) domain-containing protein] and At2g42160 [zinc finger (C3HC4-type RING finger) family protein] gene products, suggesting that this gene is involved in the ubiquitin-proteasome system.

In the S-RNase-based and Brassicaceae-type SI systems, involvement of the ubiquitin-proteasome system has been suggested. The 26S proteasome complex is bound with a UBP, and the 19S regulatory particle of the 26S proteasome complex is activated by the UBP. In the Z locus-linked BAC clones, 26S proteasome-related genes (LpTC116908 and LpOs06g0607800) were identified, of which products may interact with the LpOs04g0648500 gene product.

While applicants do not wish to be restricted by theory, the LpOs04g0648500 Ubiquitin-specific protease 22 gene is hence proposed to be one of the SI determinants in the Z locus

Example 16—Generation of Transformation Vectors Containing an Inverted Hairpin Structure of the LpOs04g0648500 Gene The nucleic acid sequence identified as LpOs04g0648500 gene has a 578 bp fragment selected as a design element for expression cassette. The Zea mays ubiquitin gene promoter (Christensen et al. 1992) was used to drive expression and the nopaline synthase (nos) gene terminator with (Bevan, 1984; Rogers et al., 1985) was selected to arrest transcription.

The LpOs04g0648500 expression cassette consists of the promoter, 5' untranslated region and intron from the Ubiquitin (Ubi) gene from Zea mays (Toki et al 1992) followed by 578 bp of coding sequence of the LpOs04g0648500 gene from L. Perenne in an inverted repeat interrupted by intron 2 of the RGA2 gene from Triticum turgidum subsp. durum (Douchkov et al 2005). The hairpin cassette was terminated with the 3' untranslated region (UTR) comprising the transcriptional terminator and polyadenylation site of the nopaline synthase gene (nos) from A. tumefaciens pTi15955 (Fraley et al 1983).

The selection cassette (delivered either in cis or trans) comprised of the promoter, 5' untranslated region and intron from the Actin (Act1) gene from Oryza sativa (McElroy et al 1990) followed by a synthetic, version of hph gene from E. coli (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized, delivered and sequenced as described in Example 4.

An ideogram of the gene expression cassette is shown in FIG. 10. The full sequence of the expression cassette is shown in FIG. 77.

Example 17—Biolistic Transformation of Perennial Ryegrass (Lolium perenne) for Expression of dsRNA Products of the LpOs04g0648500 Gene for RNAi-Mediated Down-Regulation of SI Biolistic co-transformation of perennial ryegrass with the vectors containing the LpOs04g0648500 gene sequence, driving the expression of the RNAi cassette and the synthetic version of hph gene from E. coli for hygromycin resistance was conducted on embryogenic calli for perennial ryegrass, as described in Example 5.

Example 18—Expression Analysis of the LpOs04g0648500 Gene

Using the methods outlined in Example 6, the nucleic acid sequence identified as the LpOs04g0648500 gene, when compared against the coding portion of the *Brachypodium distachion* genome sequence, identifies Bradi5g23970 as the closest matching gene sequence. The expression profile that has been generated from this analysis identifies a low level of constitutive expression in all tissues, with an increase in all of the reproductive samples. The highest level of gene expression was detected in the pistil samples (See FIG. 106).

Example 19—Isolation of SI Genes: Cloning of the Ryegrass LpOs06g0607900 Gene

Using the methods outlined in Example 3, a novel *Lolium perenne* L. gene was identified from BAC clone-related sequence that displayed sequence similarity with the rice gene Os06g0607900, and the ryegrass gene was hence designated LpOs06g0607900 (See FIG. 11 and SEQ ID NO: 59). The gene contained both the C2 and GRAM amino acid domains (SEQ ID NO: 129). The C2 domain is comprised of 2 highly conserved domains that are separated by a basic region. The C2 domain is a calcium-dependent membrane-targeting module that is found in proteins involved in signal transduction or membrane trafficking. The domain is often involved in calcium-dependent phospholipid binding and in membrane targeting processes. The GRAM domain is a glucosyltransferase, Rab-like GTPase activators and myotubularin domain. The domain is associated with membrane-coupled processes and signal transduction. The GRAM domain was first computationally identified in 2000 (Doerks et al.) and functional analysis of the domain has since elucidated roles in protein association with a target membrane.

The rice homologue of the novel gene identified from the BAC sequence characterisation has been partially described in its function and has been designated the "no-pollen" gene (Osnop). The rice Osnop gene was identified and characterised through a Ds transposon insertion strategy. The deleted gene displayed abnormal anthers and no pollen production. Through promoter fusions with the GUS reporter gene, the endogenous gene was characterised as showing gene expression late in pollen formation and in the germination of pollen tubes (Jiang et al. 2005).

While applicants do not wish to be restricted by theory, the LpOs06g0607900 No-Pollen (LpNOP) gene is hence proposed to be the male determinant of the Z locus.

Example 20—Generation of Transformation Vectors Containing an Inverted Hairpin Structure of the LpOs06g0607900 LpNOP1 Gene The LpOs06g0607900 expression cassette consists of the promoter, 5' untranslated region and intron from the Ubiquitin (Ubi) gene from *Zea mays* (Toki et al 1992) followed by 400 bp of coding sequence of the LpOs06g0607900 gene from *L. Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from *E. coli* (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized, delivered and sequenced as described in Example 4.

An ideogram of the gene expression cassette is shown in FIG. 12. The full sequence of the expression cassette is shown in FIG. 76.

Example 21—Biolistic Transformation of Perennial Ryegrass (*Lolium perenne*) for Expression of dsRNA Products of the LpOs06g0607900 Gene for RNAi-Mediated Down-Regulation of SI Biolistic co-transformation of perennial ryegrass with the vectors containing the LpOs06g0607900 gene sequence, driving the expression of the RNAi cassette and the synthetic version of hph gene from *E. coli* for hygromycin resistance was conducted on embryogenic calli for perennial ryegrass, as described in Example 5.

Example 22—Expression Analysis of the LpOs06g0607900 Gene

Using the methods outlined in Example 6, the nucleic acid sequence identified as the LpOs06g0607900 gene, when compared against the coding portion of the *Brachypodium distachion* genome sequence, identifies Bradi1g36390 as the closest matching gene sequence. The expression profile that has been generated from this analysis identifies high levels of gene expression almost exclusively in anthers. Limited expression has been detected in flowers and stigma pollinated at 0 minutes, which could result from anthers in the flower or initial germination of the pollen grain (See FIG. 105).

Example 23—Isolation of SI Genes: Cloning of the Ryegrass LpOs05g0152900 a Seven-in-Absentia Homologue Gene Using the methods outlined in Example 3, from the exome sequencing of the genotype Impact04, a *Lolium perenne* L. gene was identified that displayed sequence similarity with the rice gene Os05g0152900 (FIG. 13 and SEQ ID NO: 40). Due to sequence similarity with seven in absentia homologue (SIAH) genes, the identified gene was designated LpSIAH (SEQ ID NO: 110).

SIAH proteins consist of a RING finger domain at the N-terminus and a Sina domain at the C-terminus, and have an ubiquitin-E3 ligase activity when a homodimer is formed (Den Herder et al. 2008). Suppression of SIAH protein function in plant species results in increased root systems, enlarged leaves and increased shoot number, suggesting that SIAH protein is involved in a wide range of plant developmental processes.

Substrates of SIAH proteins are degraded in an ubiquitin-related pathway following interaction. Glutamate receptor proteins are substrates of SIAH proteins. The RING finger domain of SIAH protein and the Siah-interacting domain of glutamate receptor proteins are essential for interaction. Interaction of the SIAH and glutamate receptor proteins exerts effects on calcium current modulation. A glutamate receptor-like gene, LpGlu1, was identified as being located physically close to LpSIAH.

Example 24—Generation of Transformation Vectors Containing an Inverted Hairpin Structure of the LpOs05g0152900 LpSIAH Gene The LpSIAH expression cassette consists of the promoter, 5' untranslated region and intron from the Ubiquitin (Ubi) gene from *Zea mays* (Toki et al 1992) followed by 400 bp of coding sequence of the LpSIAH gene from *L. Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from *E. coli* (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault and Melcher 1993).

The selection cassette was synthesized, delivered and sequenced as described in Example 4.

An ideogram of the gene expression cassette is shown in FIG. 14. The full sequence of the expression cassette is shown in FIG. 69.

Example 25—Biolistic Transformation of Perennial Ryegrass (*Lolium perenne*) for Expression of dsRNA Products of the LpOs05g0152900 LpSIAH Gene for RNAi-Mediated Down-Regulation of SI Biolistic co-transformation of perennial ryegrass with the vectors containing the LpOs05g0152900 LpSIAH gene sequence, driving the expression of the RNAi cassette and the synthetic version of hph gene from *E. coli* for hygromycin resistance was conducted on embryogenic calli for perennial ryegrass, as described in Example 5.

Example 26—Expression Analysis of the LpOs05g0152900 LpSIAH Gene

Using the methods outlined in Example 6, the nucleic acid sequence identified as the LpOs05g0152900 gene, when compared against the coding portion of the *Brachypodium distachion* genome sequence, identifies Bradi2g35550 as the closest matching gene sequence. The expression profile that has been generated from this analysis identifies gene expression predominantly in anthers and the pollinated stigma at 0 minutes. Low or negligible expression in all other tissues was observed (See FIG. 98).

Example 27—Isolation of SI Genes: Cloning of the Ryegrass LpTC116908 Gene

Using the methods outlined in Example 3, a novel *Lolium perenne* L. gene was identified from BAC clone-related sequence that displayed sequence similarity with the rice gene Os04g0647300 and the barley gene TC116908, hence the ryegrass gene was designated LpTC116908. In rye (*Secale cereale* L.), a TC116908 derived genetic marker co-segregated with the rye Z locus. Close to the TC116908 derived marker, 4 genetic markers were located (Hackauf and Wehling 2005). The corresponding genetic markers were assigned to the lower part of LG2 of perennial ryegrass (Shinozuka et al. 2010). BAC clones containing the genetic marker-related sequences were sequenced to identify *Lolium perenne* L. genes encoded in the Z locus (See FIG. 15 and SEQ ID NO: 54).

The LpTC116908 gene was annotated as an Ubiquitin-specific protease 22 gene through a BLASTx analysis (SEQ ID NO: 124). The gene contained a Znf-UBP (Zinc finger ubiquitin-specific processing protease) and peptidase C19 domains. The Znf-UBP domain exhibits the ubiquitin-specific protease activity and functions as protein stabiliser through target-specific de-ubiquitinylation. The peptidase C19 domain shares sequence similarity to the Znf-UBP-like domain and possesses ubiquitin-specific peptidase activity. The LpTC116908 gene was expressed in perennial ryegrass reproduction organs (Shinozuka et al. 2010).

In the S-RNase-based and Brassicaceae-type SI systems, involvement of the ubiquitin-proteasome system has been suggested. The 26S proteasome complex is bound with a UBP, and the 19S regulatory particle of the 26S proteasome complex is activated by the UBP. In the Z locus-linked BAC clones, 26S proteasome-related genes (LpOs06g0607800 and LpOs04g0648800) were identified, of which products may interact with the LpTC116908 gene product.

While applicants do not wish to be restricted by theory, the LpTC116908 Ubiquitin-specific protease 22 gene is hence proposed to be one of SI determinants of the Z locus Example 28—Generation of Transformation Vectors Containing an Inverted Hairpin Structure of the LpTC116908 LpOs04g0647300 Gene The LpTC116908 expression cassette consists of the promoter, 5' untranslated region and intron from the Ubiquitin (Ubi) gene from *Zea mays* (Toki et al 1992) followed by 492 bp of coding sequence of the LpTC116908 gene from *L. Perenne* in an inverted repeat interrupted by intron 2 of the RGA2 gene from *Triticum turgidum* subsp. durum (Douchkov et al 2005). The hairpin cassette was terminated with the 3' untranslated region (UTR) comprising the transcriptional terminator and polyadenylation site of the nopaline synthase gene (nos) from *A. tumefaciens* pTi15955 (Fraley et al 1983).

The selection cassette (delivered either in cis or trans) comprised of the promoter, 5' untranslated region and intron from the Actin (Act1) gene from *Oryza sativa* (McElroy et al 1990) followed by a synthetic, version of hph gene from *E. coli* (Kaster et al 1983) codon-optimized for expression in monocots, which encodes a protein that confers resistance to the antibiotic hygromycin. This cassette was terminated with the 3' UTR comprising the transcriptional terminator and polyadenylation sites from the 35s gene of cauliflower mosaic virus (CaMV) (Chenault et al 1993).

The selection cassette was synthesized, delivered and sequenced as described in Example 4.

An ideogram of the gene expression cassette is shown in FIG. 16. The full sequence of the expression cassette is shown in FIG. 73.

Example 29—Biolistic Transformation of Perennial Ryegrass (*Lolium perenne*) for Expression of dsRNA Products of the LpTC116908 Gene for RNAi-Mediated Down-Regulation of SI Biolistic co-transformation of perennial ryegrass with the vectors containing the LpTC116908 gene sequence, driving the expression of the RNAi cassette and the synthetic version of hph gene from *E. coli* for hygromycin resistance was conducted on embryogenic calli for perennial ryegrass, as described in Example 5.

Example 30—Expression Analysis of the LpTC116908 Gene

Figure 102:
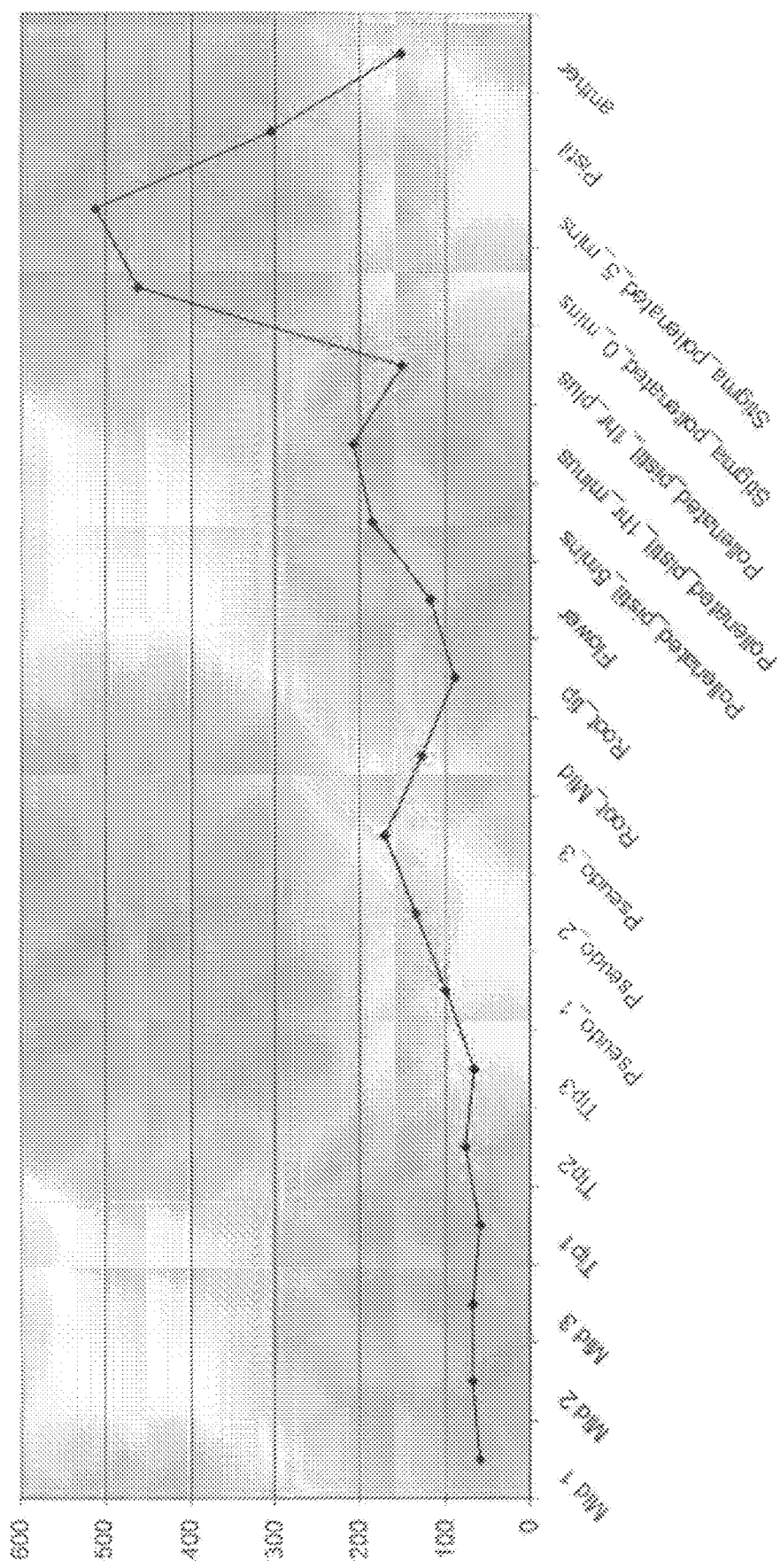
Figure 103:
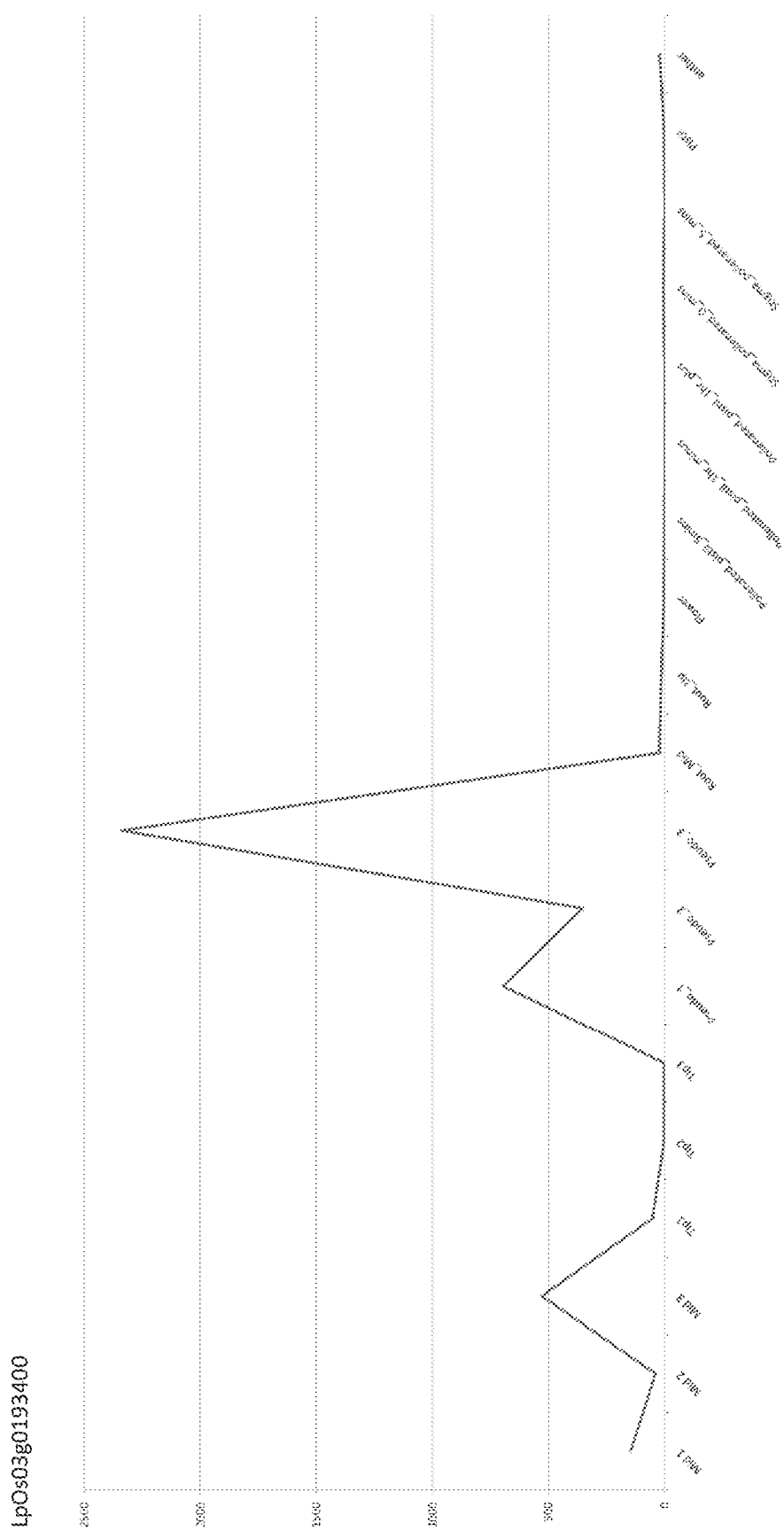

Using the methods outlined in Example 6, the nucleic acid sequence identified as the LpTC116908 gene, when compared against the coding portion of the *Brachypodium distachion* genome sequence, identifies Bradi5g23920 as the closest matching gene sequence. The expression profile that has been generated from this analysis identifies a low level of constitutive expression in all tissues, with a significant increase in both of the pollinated stigma samples. Slight increases in gene expression are also identified in pistil samples as well as pseudostems (FIG. 102).

Example 31. Generation of Transformation Vectors Containing an Inverted Hairpin Structure SiRNA constructs were prepared for all 21 candidate genes, using the methods outlined in Example 4. From the resequencing data the most conserved 300-500 bp region of the gene was chosen for the design.
S Locus
LpOs05g0148600
LpOs01g0369700
LpOs05g0149100
LpOs05g0149500
LpOs05g0149600
LpOs05g0150400
LpOs05g0150500
LpOs05g0151300
LpOs05g0152400
LpOs06g0680500
LpOs05g0152900
LpOs05g0153200
Z Locus
LpOs04g0645500
LpOs04g0645600
LpOs04g0647300
LpOs03g0193400
LpOs06g0607800
LpOs06g0607900
LpOs04g0648500
LpOs04g0648600
LpOs04g0648900

FIGS. 59 to 79 show nucleic acid sequence of the expression cassettes used in biolistic mediated transformation of *Lolium perenne* L. Legend: Gateway attB1 site (bold underline); *Zea mays* Ubi promoter (italics)+intron (underlined italics); *Lolium perenne* coding region in antisense and sense orientations (underline); rga2 intron (bold); Nopaline synthase (nos) terminator (bold italics); Gateway attB2 site (bold underline)

Example 30. Application of Genomic Data from the S and Z Interval in F1 Hybrid Grass Breeding Heterosis or hybrid vigour is the phenomenon where the performance of an $F_1$ hybrid is greater than that of the parents. Ryegrass cultivars today are commonly bred from a limited number of elite parents (4-12), polycrossed together and then further polycrossed to bulk up seed numbers suitable for commercial sale. There are no commercial activities or schemes to capture heterosis in ryegrass breeding currently.

The identification of genetic markers in linkage disequilibrium with S and Z loci enables haplotypic prediction. The ability to genotype individuals for S and Z haplotypes opens a new avenue for efficient $F_1$ hybrid ryegrass production by selectively bottlenecking and combining haplotypes. The production of $F_1$ hybrid ryegrass by selectively bottlenecking SI alleles using linked genetic markers displays the greatest potential for cost effective application to commercial ryegrass breeding in the near future. The application of SI genetic markers to bottleneck SI allows breeders to work with any germplasm at their disposal with no prior requirements. The haplotype defining SI markers will enable breeders to selectively bottleneck SI haplotypes (without self ing) within defined pools to reduce the within pool compatibility and then bring two pools together for random crossing, where the SI haplotypes ensure between pool compatibility is greater than within, resulting in an increased production of $F_1$ progeny.

For example, in the initial stages a breeding nursery of phenotypically elite plants would be genotyped with the SI linked molecular markers and haplotypic prediction would be performed. Pairs of individuals (termed parent pools) would then be identified where one individual is heterozygous at both S and Z and the other individual is homozygous at one locus, either S or Z, and heterozygous at the other locus (for the same haplotypes present in the heterozygous individual), for example:
Ind x s1s2-z1z2
Ind y s1s2-z1z1

Two parent pools where the S and Z haplotypes between pools are completely different are identified and taken forward to the next step. The two selected pools are referred to as pool A and B in the follow stages.

Following from the initial parental pool development the seeds are multiplied. During this seed bulk stage, pool A and B are maintained in isolation to ensure no foreign SI haplotypes are introduced through pollen flow or external seed.

One round of random mating within each pool will bring the S and Z haplotype frequencies to equilibrium, with 50% of individuals heterozygous at both the S and Z loci, 25% homozygous at S or Z for one of the haplotypes, and the remaining 25% of individuals homozygous at the same locus but for the opposing haplotype, for example:
25% inds—s1s1-z1z2
50% inds—s152-z1z2
25% inds—s2s2-z1z2

Continued unselected random mating within the two pools will maintain the homozygous and heterozygous frequencies whilst increasing seed numbers. In every round of mating, the heterozygous locus will alternate, for example:

| 25% - s1s1-z1z2 | | 25% - s1s2-z1z1 | | 25% - s1s1-z1z2 |
| 50% - s1s2-z1z2 | → | 50% - s1s2-z1z2 | → | 50% - s1s2-z1z2 |
| 25% - s2s2-z1z2 | | 25% - s1s2-z2z2 | | 25% - s2s2-z1z2 |

Pollen within pools will never be compatible with individuals heterozygous at both the S and Z loci. Consequently those individuals (which make up 50% of the plants) will only be pollen donors, not producing any seed, resulting in a 50% seed production rate within pools.

Once sufficient seed has been generated within pools, equal numbers of seed would be combined and sown out for $F_1$ seed production. As pollen from within pools is not compatible with the respective S and Z heterozygous individuals, only pollen from between the two pools will fertilize those individuals, resulting in those plants yielding 100% $F_1$ hybrid seed. The remaining individuals, which are compatible with pollen both from within and between pools will yield both $F_1$ hybrid and within-pool seed. However, as there is a greater number of compatible haplotypic combinations from between-pools, than from within-pools, a higher proportion of the seed will be $F_1$ hybrids.

From simulation of all the haplotypic combinations between and within-pools, and the proportion of compatible combinations, the theoretical percentage of $F_1$ hybrid seed produced following the described scheme is >83%. With hybrid individuals likely to be more vigorous and competitive than within-pool seed, the proportion of hybrids, >83%, is likely to increase on farm when grown under a competitive sward situation. In the proposed breeding design, pool A and B will reach haplotype frequency equilibrium after one round of crossing, meaning that breeders can bulk seed up within pools over as many generations as deemed necessary, as long as the pools are maintained in isolation from foreign pollen. This also allows breeders to perform small test crosses between pools with each seed bulk up to ensure heterosis still remains in the progeny. At no point during the breeding design is there a requirement for controlled pollination.

This breeding design could be applied to any outbreeding grass species belonging to the Poaceae that has the S and Z loci regulating self-incompatibility without limitation. More preferably the grass species would be of the Bambusoideae, Ehrhartoideae (formerly Oryzoideae) or Pooideae clade. More preferably the grass species would be of the tribe Poeae. More preferably the grass species would be of the genera *Lolium, Festuca, Poa, Dactylis, Bromus, Secale, Pennisetum* and *Panicum*. More preferably the grass species would be of the genera *Lolium* and *Festuca*. More preferably the species would be of the genus *Lolium*. More preferably the *Lolium* species would be *Lolium perenne* (perennial ryegrass), *Lolium multiflorum* (Italian ryegrass), *Lolium boucheanum* (hybrid ryegrass) *Lolium arundinaceum* (tall fescue) and *Lolium pratense* (meadow fescue).

FIG. 109 shows a schematic diagram of F1 hybrid grass breeding. Plants are initially genotyped using markers on or around the S and Z loci. Two parental pools are then generated and multiplied, with testing of the degree of heterosis between pools once sufficient seed has been generated.

REFERENCES

Bai, Y., et al. (2001) Genetic transformation of elite turf-type cultivars of Tall Fescue. *International Turfgrass Society Research Journal*, 9: 129-136.

Bevan, M. (1984) Binary *Agrobacterium* vectors for plant transformation. *Nucleic Acids Res.* 12: 8711-8721.

Bilang, R., et al. (1991) The 3'-terminal region of the hygromycin-B-resistance gene is important for its activity in *Escherichia coli* and *Nicotiana tabacum*. *Gene*, 100: 247-250.

Chenault K D and Melcher U (1993) Cauliflower mosaic virus isolate CMV-1. *Plant Physiology* 1993 101 (4), 1395-1396

Christensen, et al. (1992) Maize polyubiquitin genes: structure, thermal perturbation of expression and transcript splicing, and promoter activity following transfer to protoplasts by electroporation. *Plant Mol Biol* 18: 675-689

Cogan, N O I, Shinozuka, H., Sawbridge, T I, Spangenberg, G C., Forster, J W. (2012a) Whole genome sequencing of perennial ryegrass (*Lolium perenne* L.) supports exome assembly for gene and SNP catalogue development. Molecular Breeding of Forage and Turf 2012, Salt Lake City, Utah, USA, P-28.

Cogan, N O I, Shinozuka, H, Sawbridge, T I, Spangenberg, G C, Forster, J W. (2012b) Development of a transcriptome atlas for perennial ryegrass (*Lolium perenne* L.). Molecular Breeding of Forage and Turf 2012, Salt Lake City, Utah, USA, P-25.

Den Herder G, De Keyser A, De Rycke R, Rombauts S, Van de Velde W, Clemente M R, Verplancke C, Mergaert P, Kondorosi E, Holsters M, Goormachtig S: Seven in absentia proteins affect plant growth and nodulation in *Medicago truncatula*. *Plant Physiol* 2008, 148(1):369-382.

Doerks, T., Strauss, M., Brendel, M. and Bork, P. (2000) GRAM, a novel domain in glucosyltransferases, myotubularins and other putative membrane-associated proteins. *Trends Biochem. Sci.*, 25, 483-485

Douchkov D, Nowara D, Zierold U, Schweizer P (2005) A High-Throughput Gene-Silencing System for the Functional Assessment of Defense-Related Genes in Barley Epidermal Cells. *Molecular Plant Microbe Interactions* 2005 18 755-76

Forster J W, Cogan N O I, Dobrowolski M P, Francki M G, Spangenberg G C, Smith K F (2008) Functionally-associated molecular genetic markers for temperate pasture plant improvement. In Henry R J (ed.) Plant genotyping II: SNP technology. CABI Press, Wallingford, Oxford, UK, pp. 154-187

Forster, J. W., Cogan, N. O. I., Shinozuka, H., Pembleton, L. W., Wang, J., Sawbridge, T. I., Hayes, B. J., Spangenberg, G. C. Next-generation solutions for genomics-assisted breeding of outbreeding forage plant species. Molecular Breeding of Forage and Turf 2012, Salt Lake City, Utah, USA, Session 9 Invited Talk.

Fraley R T, Rogers S G, Horsch R B, Sanders P R, Flick J S, Adams S P, Bittner M L, Brand L A, Fink C L, Fry J S, Galluppi G R, Goldberg S B, Hoffmann N L, Woo S C Expression of bacterial genes in plant cells (1983) Proceedings of the National Academy of Sciences U.S.A. 80 (15) 4803-4807

Hackauf B, Wehling P (2005) Approaching the self-incompatibility locus Z in rye (*Secale cereale* L.) via comparative genetics. *Theor Appl Genet* 110: 832-845

Jiang S Y, Cai M, Ramachandran S. The *Oryza sativa* no pollen (Osnop) gene plays a role in male gametophyte development and most likely encodes a C2-GRAM domain containing protein. Plant Mol Biol 2005; 57:835-853.

Kaster K R, Burgett S G, Rao R N, Ingolia T D (1983) Analysis of a bacterial hygromycin B resistance gene by transcriptional and translational fusions and by DNA sequencing. Nucleic Acids Research 11(19), 6895-6911

McElroy D, Zhang W, Cao J, Wu R, Isolation of an efficient actin promoter for use in rice transformation (1990) The Plant Cell 1990 2(2) 163-171

Rogers S G, O'Connell K, Horsch R B and Fraley R T (1985) In: Biotechnology in Plant Science, eds, Zaitlin, M., Day, P., Hollaender, A. and Wilson, C. A., Academic Press, Inc., New York, N.Y., pp 219-226.

Shinozuka H, Cogan N O I, Smith K F, Spangenberg G C, Forster J W. (2010) Fine-scale comparative genetic and physical mapping supports map-based cloning strategies for the self-incompatibility loci of perennial ryegrass (*Lolium perenne* L.) *Plant Mol Biol* 72:343-355

Spangenberg, G., et al. (1995a). Transgenic tall fescue and red fescue plants from microprojectile bombardment of embryogenic suspension cells. *J Plant Physiol.*, 145: 693-701.

Spangenberg, G., et al. (1995b). Transgenic perennial ryegrass (*Lolium perenne*) plants from microprojectile bombardment of embryogenic suspension cells. Plant Sci., 108: 209-217.

Spangenberg G C, Forster J W, Edwards D, John U, Mouradov A, Emmerling M, Batley J, Felitti S, Cogan N O I, Smith K F, Dobrowolski M P (2005) Future directions in the molecular breeding of forage and turf. In: Humphreys M O (ed) Molecular breeding for the genetic improvement of forage crops and turf. Wageningen Academic Publishers, The Netherlands, pp 83-97

Toki S, Takamatsu S, Nojiri C, Ooba S, Anzai H, Iwata M, Christensen A H, Quail P H, Uchimiya H (1992) Expression of a maize ubiquitin gene promoter-bar chimeric gene in transgenic rice plants. *Plant Physiology*, 100 1503-07

Ye, X., et al. (1997) Transgenic Italian ryegrass (*Lolium multiflorum*) plants from microprojectile bombardment of embryogenic suspension cells. *Plant Cell Rep.*, 16: 379-384.

The claims defining the invention are as follows:

1. A kit for hybridization or self-incompatibility (SI) control in plants, said kit including:
 a first nucleic acid or nucleic acid fragment included in a vector encoding a SI polypeptide, wherein said first nucleic acid or nucleic acid fragment is isolated from or corresponds to a gene from the Z locus of a plant of the genera *Lolium* or *Festuca* of the Poaceae family; and
 a second nucleic acid or nucleic acid fragment included in a vector encoding a SI polypeptide, wherein said second nucleic acid or nucleic acid fragment is isolated from or corresponds to a gene from the S locus of a plant of the genera *Lolium* or *Festuca* of the Poaceae family;
 wherein said first nucleic acids or nucleic acid fragment includes a nucleotide sequence selected from the group consisting of:
 (a) the nucleotide sequence of SEQ ID NO: 39;
 (b) a nucleotide sequence encoding the polypeptide of SEQ ID NO: 109;
 (c) complements of the sequences recited in (a) and (b);
 (d) sequences antisense to the sequences recited in (a) and (b);
 (e) functionally active fragments of the sequences recited in (a), (b), (c) and (d); having a size of at least 100 nucleotides and
 (f) functionally active variants having at least 90% identity to any one of the sequences recited in (a), (b), (c), (d) and (e);
 wherein said second nucleic acids or nucleic acid fragments includes a nucleotide sequence selected from the group consisting of:
 (a) the nucleotide sequence of SEQ ID NO: 59;
 (b) a nucleotide sequence encoding the polypeptide of SEQ ID NO: 129;
 (c) complements of the sequences recited in (a) and (b);
 (d) sequences antisense to the sequences recited in (a) and (b);
 (e) functionally active fragments of the sequences recited in (a), (b), (c) and (d) having a size of at least 100 nucleotides; and
 (f) functionally active variants having at least 90% identity to any one of the sequences recited in (a), (b), (c), (d) and (e).

2. A vector comprising an isolated nucleic acid or nucleic acid fragment encoding a plant SI protein, selected from the group consisting of:
 (a) a polynucleotide comprising SEQ ID NO: 39 and SEQ ID NO: 59;
 (b) a nucleotide sequence encoding the polypeptide of SEQ ID NO: 109
 and SEQ ID NO: 129;
 (c) complements of the sequences recited in (a) and (b);
 (d) sequences antisense to the sequences recited in (a) and (b);
 (e) functionally active fragments of the sequences recited in (a), (b), (c) and (d); having a size of at least 100 nucleotides and
 (f) functionally active variants having at least 90% identity to any one of the sequences recited in (a), (b), (c), (d) and (e).

3. A plant cell, plant, plant seed or other plant part comprising the vector according to claim 2.

4. A method of manipulating self-incompatibility in a plant, said method including introducing into said plant an effective amount of the vector according to claim 2.

5. The method according to claim 4, wherein said method includes introducing into said plant said vector comprising;
 a first nucleic acid or nucleic acid fragment encoding a SI polypeptide, wherein said first nucleic acid or nucleic acid fragment is isolated from or corresponds to a gene from the Z locus of a plant of the Poaceae family; and
 a second nucleic acid or nucleic acid fragment encoding a SI polypeptide, wherein said second nucleic acid or nucleic acid fragment is isolated from or corresponds to a gene from the S locus of a plant of the Poaceae family, and wherein the plant of the Poaceae family is from the genera *Lolium* or *Festuca*.

6. The kit according to claim 1, wherein the plant of the Poaceae family is *Lolium perenne* L., *Lolium multiflorum*, or *Festuca arundinaceum*.

7. The vector comprising the isolated nucleic acid or nucleic acid fragment encoding a plant SI protein according to claim 2, wherein the plant is *Lolium perenne* L., *Lolium multiflorum*, or *Festuca arundinaceum*.

8. The method according to claim 5, wherein the method the plant of the Poaceae family is *Lolium perenne* L., *Lolium multiflorum*, or *Festuca arundinaceum*.

\* \* \* \* \*

UNITED STATES PATENT AND TRADEMARK OFFICE
CERTIFICATE OF CORRECTION

Page 1 of 1

PATENT NO. : 11,224,181 B2
APPLICATION NO. : 16/394796
DATED : January 18, 2022
INVENTOR(S) : Shinozuka et al.

It is certified that error appears in the above-identified patent and that said Letters Patent is hereby corrected as shown below:

In the Claims

Column 403, Claim 1, Line 41 should read - ...wherein said first nucleic acid or nucleic acid fragment ... -

Column 403, Claim 1, Line 51-52 should read - ... in (a), (b), (c) and (d) having a size of at least 100 nucleotides; and... -

Column 403, Claim 1, Lines 56-57 should read - ... wherein said second nucleic acid or nucleic acid fragment includes a nucleotide sequence selected from the ... -

Column 405, Claim 8, Lines 5-6 should read - The method according to claim 5, wherein the plant of the Poaceae family is Lolium perenne L., Lolium... -

Signed and Sealed this
Fourth Day of October, 2022

Katherine Kelly Vidal
*Director of the United States Patent and Trademark Office*